(12) United States Patent
Shirasaki et al.

(10) Patent No.: US 12,428,409 B2
(45) Date of Patent: Sep. 30, 2025

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Yoshinao Shirasaki, Chiba (JP); Tetsuya Masuda, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 1140 days.

(21) Appl. No.: 17/046,597

(22) PCT Filed: Apr. 12, 2019

(86) PCT No.: PCT/JP2019/015918
§ 371 (c)(1),
(2) Date: Oct. 9, 2020

(87) PCT Pub. No.: WO2019/198806
PCT Pub. Date: Oct. 17, 2019

(65) Prior Publication Data
US 2021/0130336 A1  May 6, 2021

(30) Foreign Application Priority Data
Apr. 13, 2018  (JP) ................. 2018-077802

(51) Int. Cl.
*H10K 85/60* (2023.01)
*C07D 405/04* (2006.01)
(Continued)

(52) U.S. Cl.
CPC ......... *C07D 409/10* (2013.01); *C07D 405/04* (2013.01); *C07D 409/04* (2013.01);
(Continued)

(58) Field of Classification Search
CPC .......................... C07D 409/04; H10K 85/6576
See application file for complete search history.

(56) References Cited

U.S. PATENT DOCUMENTS

2019/0067591 A1* 2/2019 Jang ................. H10K 99/00
2020/0227650 A1* 7/2020 Kim ................... C07D 251/24

FOREIGN PATENT DOCUMENTS

CN  108191842 A  6/2018
CN  108864068 A  11/2018
(Continued)

OTHER PUBLICATIONS

International Search Report issued on Jun. 25, 2019 in PCT/JP2019/015918 filed on Apr. 12, 2019, 2 pages.
(Continued)

*Primary Examiner* — Sean M DeGuire
(74) *Attorney, Agent, or Firm* — Oblon, McClelland, Maier &Neustadt, L.L.P.

(57) ABSTRACT

An organic electroluminescent element having a further improved life; and a compound which is a novel material
(Continued)

capable of providing the organic electroluminescent element and is represented by formula (1).

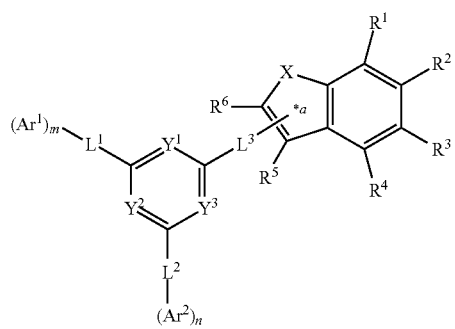

(In formula (1), $Y^1$ to $Y^3$, $L^1$, $L^2$, $L^3$, $Ar^1$, $Ar^2$, m, n, X, $R^1$ to $R^6$, and *a are as defined in the description).

41 Claims, 1 Drawing Sheet

(51) Int. Cl.
*C07D 409/04* (2006.01)
*C07D 409/10* (2006.01)
*C07D 409/14* (2006.01)
*H10K 50/16* (2023.01)
*H10K 50/18* (2023.01)

(52) U.S. Cl.
CPC ......... *C07D 409/14* (2013.01); *H10K 85/654* (2023.02); *H10K 85/6572* (2023.02); *H10K 85/6574* (2023.02); *H10K 85/6576* (2023.02); *H10K 50/166* (2023.02); *H10K 50/18* (2023.02)

(56) References Cited

FOREIGN PATENT DOCUMENTS

| | | |
|---|---|---|
| KR | 10-2014-0129454 A | 11/2014 |
| KR | 10-2015-0109111 A | 10/2015 |
| KR | 10-2017-0086211 A | 7/2017 |
| KR | 10-2018-0064861 A | 6/2018 |
| WO | WO 2010/126270 A1 | 11/2010 |

OTHER PUBLICATIONS

Irfan et al., "Tuning of optoelectronic and charge transport properties in star shaped anthracenothiophene-pyrimidine derivatives as multifunctional materials", Optik, 2017, vol. 149, pp. 321-331.

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

CROSS-REFERENCE TO RELATED APPLICATIONS

The present application is the national stage of international application PCT/JP2019/015918, fled on Apr. 12, 2019, and claims the benefit of the filing date of Japanese Appl. No. 2018-077802, filed on Apr. 13, 2018.

TECHNICAL FIELD

The present invention relates to a compound, a material for an organic electroluminescent element using the same, the organic electroluminescent element, and an electronic device.

BACKGROUND ART

In general, an organic electroluminescent element (an organic EL device) includes an anode, a cathode, and organic layers sandwiched between the anode and the cathode. When a voltage is applied between both electrodes, electrons from the cathode side, and holes from the anode side are injected into a light emitting region. The injected electrons and holes are recombined in the light emitting region to generate an excited state. When the excited state returns to a ground state, light is emitted. Thus, development of a compound which efficiently transports electrons or holes to a light emitting region, and promotes recombination of the electrons with the holes is important in obtaining a high-performance organic EL device. Also, in recent years, with the new spread of smart phones, organic EL TVs, organic EL lightings, and the like using organic EL devices, compound that satisfies both a high efficiency and a sufficient device life is demanded.

For example, Patent Literature 1 discloses a pyrimidine compound used in an organic EL device.

CITATION LIST

Patent Literature

PTL 1: KR 10-2017-086211 A

SUMMARY OF INVENTION

Technical Problem

Many compounds have conventionally been reported as a material for producing organic EL devices, but a demand for a compound that further improves characteristics of an organic EL device is still demanded.

The present invention has been made in order to solve the above problems, and an object thereof is to provide an organic EL device with a further improved lifetime, and a novel compound that realizes such an organic EL device.

Solution to Problem

The present inventors have conducted repetitive intensive studies in order to solve the above problem, and as a result, have found that the compound represented by formula (1) realizes an organic EL device with a further improved lifetime. Also, they have found that a compound having these characteristics allows to obtain an organic EL device with a long lifetime without significantly reducing the external quantum efficiency, and as a result, solve the above problem. Thus, they have completed the present invention.

In one aspect, the present invention provides a compound represented by formula (1) (hereinafter, also referred to as a compound (1)).

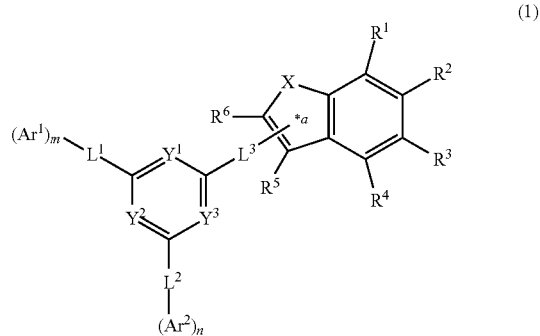

In the formula (1), two of $Y^1$ to $Y^3$ represent nitrogen atoms and the other one represents CR, or three of $Y^1$ to $Y^3$ represent nitrogen atoms. R represents a hydrogen atom or a substituent A. The substituent A is selected from a cyano group, a halogen atom, a phosphine oxide group substituted with an aryl group having 6 to 30 ring carbon atoms, a substituted or unsubstituted alkyl group having 1 to 30 carbon atoms, a substituted or unsubstituted cycloalkyl group having 3 to 30 ring carbon atoms, a substituted or unsubstituted aralkyl group having 7 to 36 carbon atoms, a substituted or unsubstituted alkoxy group having 1 to 30 carbon atoms, a substituted or unsubstituted aryloxy group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, a substituted or unsubstituted haloalkyl group having 1 to 30 carbon atoms, a substituted or unsubstituted haloalkoxy group having 1 to 30 carbon atoms, a substituted or unsubstituted aryl group having 6 to 30 ring carbon atoms, and a substituted or unsubstituted heteroaryl group having 5 to 30 ring atoms.

Each of $L^1$ and $L^2$ independently represents a single bond, or a divalent or trivalent residue of a compound selected from benzene, biphenyl, terphenyl, naphthalene, fluorene, carbazole, dibenzofuran, and dibenzothiophene. The residue is unsubstituted or has a substituent B. The substituent B is selected from the group from which the substituent A is selected, provided that the substituted or unsubstituted heteroaryl group having 5 to 30 ring atoms is excluded from the group.

$L^3$ represents a single bond or a p-phenylene group.

Each of $Ar^1$ and $Ar^2$ is independently a substituted or unsubstituted aryl group having 6 to 30 ring carbon atoms, or a substituted or unsubstituted heteroaryl group, and the heteroaryl group is selected from a pyridyl group, a quinolyl group, an isoquinolyl group, a phenanthrolinyl group, an acridinyl group, a phenazinyl group, a carbazolyl group, a benzocarbazolyl group, a phenoxazinyl group, a phenothiazinyl group, an azacarbazolyl group, a xanthenyl group, a dibenzofuranyl group, a naphthobenzofuranyl group, a dinaphthofuranyl group, an azadibenzofuranyl group, an azanaphthobenzofuranyl group, a dibenzothienyl group, a naphthobenzothienyl group, a dinaphthothienyl group, an azadibenzothienyl group, an azanaphthobenzothienyl group, a spiroxanthene-fluorenyl group, a spirofluorene-xanthenyl group, a spirofluorene-acridinyl group, and a spirofluorene-indoloacridinyl group.

When $Ar^1$ or $Ar^2$ is the aryl group having a substituent or the heteroaryl group having a substituent, the substituent is selected from the group from which the substituent B is selected.

Each of m and n independently represents an integer of 1 or 2. Meanwhile, when $L^1$ is a single bond, m is 1, and when $L^2$ is a single bond, n is 1.

X represents an oxygen atom or a sulfur atom.

Each of $R^1$ to $R^4$ independently represents a hydrogen atom or a group selected from the group from which the substituent A is selected.

One of $R^5$ and $R^6$ represents a single bond bonded to *a, and the other represents a hydrogen atom or a group selected from the group from which the substituent A is selected.

In another aspect, the present invention provides a material for an organic electroluminescent element, which contains the compound (1).

In a further aspect, the present invention provides an organic electroluminescent element including a cathode, an anode, and organic layers disposed between the cathode and the anode. The organic layers include a light emitting layer, and at least one layer in the organic layers contains the compound (1).

In a still further aspect, the present invention provides an electronic device including the organic electroluminescent element.

Advantageous Effects of Invention

The compound (1) realizes an organic EL device that has a further improved lifetime without significantly reducing the external quantum efficiency.

DESCRIPTION OF EMBODIMENTS

Figure 1:
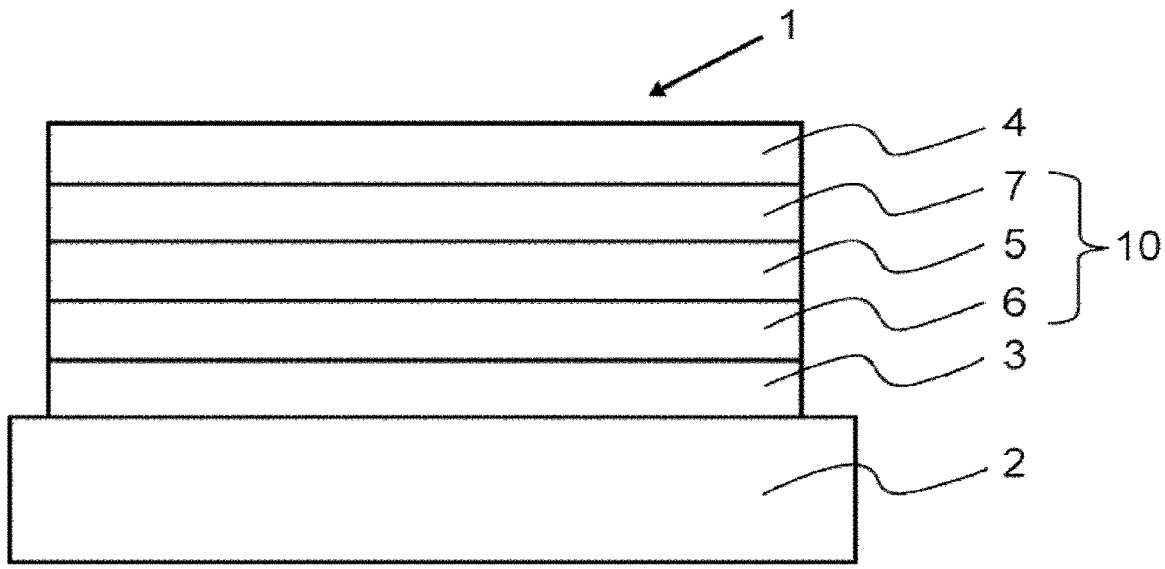
FIG. 1 is a schematic view illustrating the configuration of an example of an organic electroluminescent element according to an embodiment of the present invention.

In the present specification, the term of "XX to YY carbon atoms" referred to by "a substituted or unsubstituted group ZZ having XX to YY carbon atoms" indicates the number of carbon atoms of the unsubstituted group ZZ, and does not include any carbon atom in the substituent of the substituted group ZZ.

In the present specification, the term of "XX to YY atoms" referred to by "a substituted or unsubstituted group ZZ having XX to YY atoms" indicates the number of atoms of the unsubstituted group ZZ, and does not include any atom in the substituent of the substituted group ZZ.

In the present specification, the "unsubstituted group ZZ" in the case of the "substituted or unsubstituted group ZZ" indicates that a hydrogen atom in the group ZZ is not substituted with a substituent.

In the present specification, the "hydrogen atom" includes isotopes having different numbers of neutrons, that is, protium, deuterium, and tritium.

The number of "ring carbon atoms" referred to in the present specification indicates the number of carbon atoms among the atoms forming the ring itself of a compound with a structure in which the atoms are cyclically bonded (for example, a monocyclic compound, a fused ring compound, a cross-linked compound, a carbocyclic compound, and a heterocyclic compound). If the ring is substituted with a substituent, the carbon atom included in the substituent is not included in the ring carbon atom. The same applies to the number of "ring carbon atoms" described below unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Also, when the benzene ring or the naphthalene ring is substituted with, for example, an alkyl group as a substituent, the carbon atom in the alkyl group is not counted as the number of ring carbon atoms. Also, in a case of a fluorene ring to which, for example, a fluorene ring as a substituent is bonded (inclusive of a spirofluorene ring), the carbon atom in the fluorene ring as the substituent is not counted as the number of ring carbon atoms.

The number of "ring atoms" referred to in the present specification indicates the number of atoms forming the ring itself of a compound (for example, a monocyclic compound, a fused ring compound, a cross-linked compound, a carbocyclic compound, and a heterocyclic compound) with a structure in which the atoms are cyclically bonded (for example, a monocyclic ring, a fused ring, a ring assembly). The atom not forming the ring (for example, a hydrogen atom that terminates a bond of atoms forming the ring), and the atom included in a substituent if the ring is substituted with the substituent, are not counted as the number of ring atoms. The same applies to the number of "ring atoms" described below unless otherwise noted. For example, a pyridine ring has 6 ring atoms, a quinazoline ring has 10 ring atoms, and a furan ring has 5 ring atoms. The hydrogen atom bonded to each ring carbon atom in the pyridine ring or the quinazoline ring, and the atom constituting a substituent, are not counted as the number of ring atoms. Also, in a case of a fluorene ring to which, for example, a fluorene ring as a substituent is bonded (inclusive of a spirobifluorene ring), the atom in the fluorene ring as the substituent is not counted as the number of ring atoms.

In the present specification, it can be said that a preferred embodiment (for example, compounds, various groups, and numerical ranges) may be arbitrarily combined with any other embodiment (for example, compounds, various groups, and numerical ranges), and also, a combination of preferred embodiments (including a more preferable embodiment, a further preferable embodiment, and a particularly preferable embodiment) is more preferred.

A compound (1) according to one embodiment of the present invention is represented by formula (1).
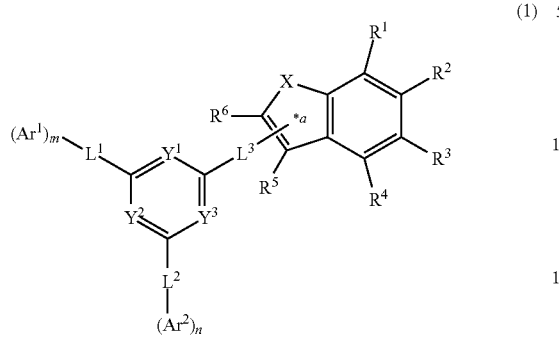
(1)
In one embodiment of the present invention, the compound (1) is preferably represented by formula (1-1).
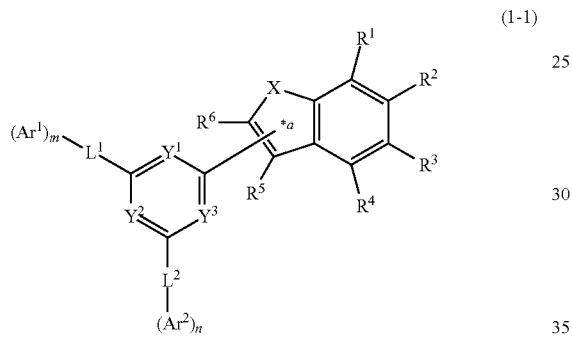
(1-1)
In one embodiment of the present invention, the compound (1) is represented by any of formulae (1-2a) to (1-5).
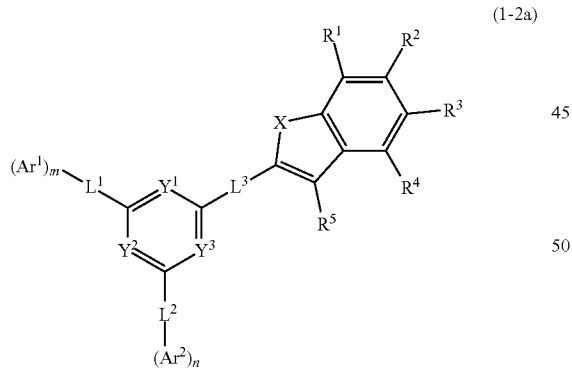
(1-2a)
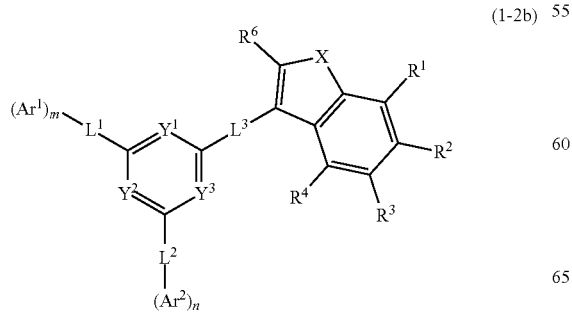
(1-2b)
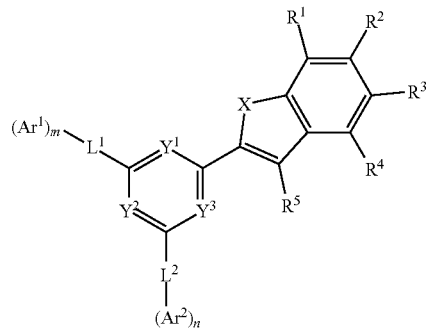
(1-3a)
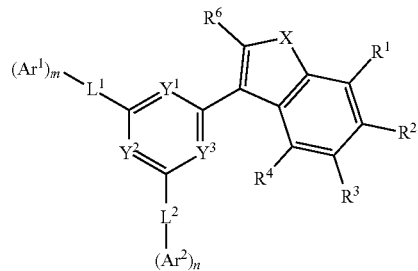
(1-3b)
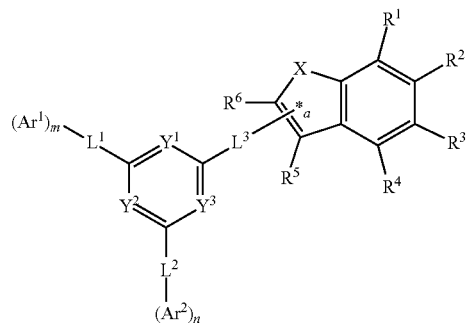
(1-4)
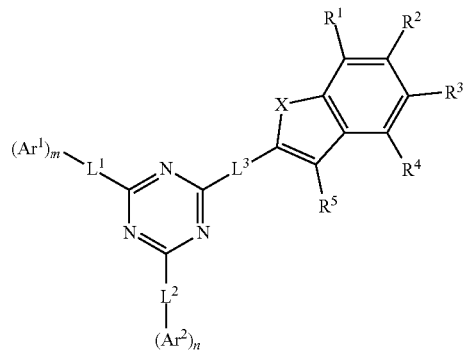
(1-4a)
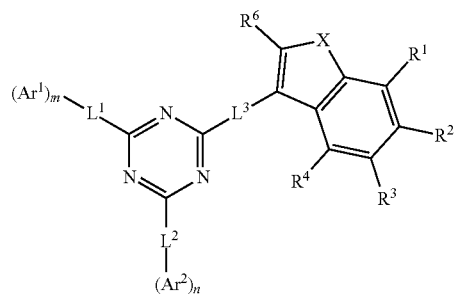
(1-4b)

-continued

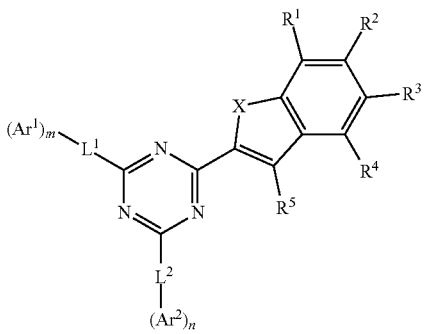

(1-5)

In formula (1), $R^6$ is preferably a single bond bonded to *a. More preferably, the compound (1) is represented by formula (1-2a), (1-3a), (1-4), (1-4a), or (1-5), and further preferably represented by formula (1-5).

Hereinafter, descriptions will be made on each symbol in formulae (1), (1-1), (1-2a), (1-2b), (1-3a), (1-3b), (1-4), (1-4a), (1-4b), and (1-5) (hereinafter, referred to as formulae (1) to (1-5)).

Two of $Y^1$ to $Y^3$ represent nitrogen atoms and the other one represents CR, or three of $Y^1$ to $Y^3$ represent nitrogen atoms. R represents a hydrogen atom or a substituent A. The substituent A is selected from a cyano group, a halogen atom, a phosphine oxide group substituted with an aryl group having 6 to 30 ring carbon atoms, a substituted or unsubstituted alkyl group having 1 to 30 carbon atoms, a substituted or unsubstituted cycloalkyl group having 3 to 30 ring carbon atoms, a substituted or unsubstituted aralkyl group having 7 to 36 carbon atoms, a substituted or unsubstituted alkoxy group having 1 to 30 carbon atoms, a substituted or unsubstituted aryloxy group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, a substituted or unsubstituted haloalkyl group having 1 to 30 carbon atoms, a substituted or unsubstituted haloalkoxy group having 1 to 30 carbon atoms, a substituted or unsubstituted aryl group having 6 to 30 ring carbon atoms, and a substituted or unsubstituted heteroaryl group having 5 to 30 ring atoms.

Examples of the halogen atom that may be the substituent A include a fluorine atom, a chlorine atom, a bromine atom, and an iodine atom.

In the substituted or unsubstituted alkyl group having 1 to 30 carbon atoms which may be the substituent A, the alkyl group is, for example, a methyl group, an ethyl group, an n-propyl group, an isopropyl group, an n-butyl group, an isobutyl group, an s-butyl group, a t-butyl group, a pentyl group, a hexyl group, a heptyl group, an octyl group, a nonyl group, a decyl group, an undecyl group, or a dodecyl group, preferably a methyl group, an ethyl group, an n-propyl group, an isopropyl group, an n-butyl group, an isobutyl group, an s-butyl group, a t-butyl group, or a pentyl group, more preferably a methyl group, an ethyl group, an n-propyl group, an isopropyl group, an n-butyl group, an isobutyl group, an s-butyl group, or a t-butyl group, and further preferably a methyl group or a t-butyl group.

The alkyl group having 1 to 30 carbon atoms includes an isomeric group when present.

In the substituted or unsubstituted cycloalkyl group having 3 to 30 ring carbon atoms which may be the substituent A, the cycloalkyl group is, for example, a cyclopropyl group, a cyclobutyl group, a cyclopentyl group, a cyclohexyl group, or a cycloheptyl group, and preferably a cyclopentyl group or a cyclohexyl group.

The cycloalkyl group having 3 to 30 ring carbon atoms includes an isomeric group when present.

In the substituted or unsubstituted aralkyl group having 7 to 36 carbon atoms which may be the substituent A, the aryl moiety of the aralkyl group having 7 to 36 carbon atoms is selected from aryl groups having 6 to 30, preferably 6 to 25, more preferably 6 to 18 ring carbon atoms, and the alkyl moiety is selected from alkyl groups having 1 to 30, preferably 1 to 18, more preferably 1 to 8 carbon atoms. The aralkyl group having 7 to 36 carbon atoms is, for example, a benzyl group, a phenethyl group, or a phenylpropyl group, and a benzyl group is preferred.

The aralkyl group having 7 to 36 carbon atoms includes an isomeric group when present.

In the substituted or unsubstituted alkoxy group having 1 to 30 carbon atoms which may be the substituent A, the alkyl moiety of the alkoxy group having 1 to 30 carbon atoms is selected from the substituted or unsubstituted alkyl groups having 1 to 30, preferably 1 to 18, more preferably 1 to 8 carbon atoms. The alkoxy group having 1 to 30 carbon atoms is, for example, a t-butoxy group, a propoxy group, an ethoxy group, or a methoxy group, preferably an ethoxy group or a methoxy group, and more preferably a methoxy group.

The alkoxy group having 1 to 30 carbon atoms includes an isomeric group when present.

In the substituted or unsubstituted aryloxy group having 6 to 30 ring carbon atoms which may be the substituent A, the aryl moiety of the aryloxy group having 6 to 30 ring carbon atoms is selected from aryl groups having 6 to 30, preferably 6 to 25, more preferably 6 to 18 ring carbon atoms. The aryloxy group having 6 to 30 ring carbon atoms is, for example, a terphenyloxy group, a biphenyloxy group, or a phenoxy group, preferably a biphenyloxy group or a phenoxy group, and more preferably a phenoxy group.

The aryloxy group having 6 to 30 ring carbon atoms includes an isomeric group when present.

The substituent included in the mono-, di-, or tri-substituted silyl group which may be the substituent A is selected from the alkyl group having 1 to 30, preferably 1 to 18, more preferably 1 to 8 carbon atoms, and the aryl group having 6 to 30, preferably 6 to 25, more preferably 6 to 18 ring carbon atoms. The tri-substituted silyl group is preferred. For example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group is more preferred.

The mono-, di-, or tri-substituted silyl group includes an isomeric group when present.

In the substituted or unsubstituted haloalkyl group having 1 to 30 carbon atoms which may be the substituent A, the haloalkyl group is a group obtained when at least one hydrogen atom, preferably 1 to 7 hydrogen atoms, or all hydrogen atoms in the alkyl group having 1 to 30, preferably 1 to 18, more preferably 1 to 8 carbon atoms is(are) replaced with halogen atom(s). The halogen atom is selected from a fluorine atom, a chlorine atom, a bromine atom, and an iodine atom, and is preferably a fluorine atom. The haloalkyl group is preferably a fluoroalkyl group having 1 to 30, preferably 1 to 18, more preferably 1 to 8 carbon atoms, more preferably a heptafluoropropyl group, a pentafluoroethyl group, a 2,2,2-trifluoroethyl group, or a trifluoromethyl group, further preferably a pentafluoroethyl group, a 2,2,2-trifluoroethyl group, or a trifluoromethyl group, and particularly preferably a trifluoromethyl group.

The haloalkyl group having 1 to 30 carbon atoms includes an isomeric group when present.

In the substituted or unsubstituted aryl group having 6 to 30 ring carbon atoms which may be the substituent A, the aryl group preferably has 6 to 18 (more preferably 6 to 10) ring carbon atoms, and is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, a triphenylenyl group, or a benzotriphenylenyl group.

A phenyl group, a biphenylyl group, a terphenylyl group, or a naphthyl group is preferred, and a phenyl group, or a naphthyl group is more preferred.

In the substituted or unsubstituted heteroaryl group having 5 to 30 ring atoms which may be the substituent A, the heteroaryl group includes 1 to 5, preferably 1 to 3, more preferably 1 to 2 ring hetero atoms. The ring hetero atom is selected from, for example, a nitrogen atom, a sulfur atom, and an oxygen atom. The free bond of the heteroaryl group is present on a ring carbon atom, or is present on a ring nitrogen atom if physically possible.

The heteroaryl group having 5 to 30 ring atoms is, for example, a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzoimidazolyl group, a benzoxazolyl group, a benzothiazolyl group, an indazolyl group, a benzoisoxazolyl group, a benzoisothiazolyl group, a phenathrizinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group (a benzothienyl group, hereinafter the same), an isobenzothiophenyl group (an isobenzothienyl group, hereinafter the same), a naphthobenzothiophenyl group (a naphthobenzothienyl group, hereinafter the same), a dibenzothiophenyl group (a dibenzothienyl group, hereinafter the same), or a carbazolyl group.

A benzofuranyl group, an isobenzofuranyl group, a naphthobenzofuranyl group, a dibenzofuranyl group, a benzothiophenyl group, an isobenzothiophenyl group, a naphthobenzothiophenyl group, a dibenzothiophenyl group, or a carbazolyl group (a 9-carbazolyl group, or a 1-, 2-, 3- or 4-carbazolyl group) is preferred.

The substituted heteroaryl group having 5 to 30 ring atoms is, for example, a 9-phenylcarbazolyl group, a 9-biphenylylcarbazolyl group, a 9-phenylphenylcarbazolyl group, a 9-naphthylcarbazolyl group, a phenyl dibenzofuranyl group, or a phenyl dibenzothiophenyl group (a phenyldibenzothienyl group, hereinafter the same).

The substituted or unsubstituted heteroaryl group having 5 to 30 ring atoms includes an isomeric group when present.

When the substituent A has a substituent, the substituent is selected from the group from which the substituent A is selected, provided that a group including a group to be substituted, i.e., the substituent A, is excluded from the group.

The phosphine oxide group substituted with an aryl group having 6 to 30 ring carbon atoms which may be the substituent A is a group represented by formula (2).

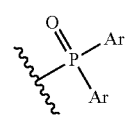

(2)

In formula (2), each Ar independently represents an aryl group having 6 to 30 ring carbon atoms. A more preferred phosphine oxide group has the structure of any of formulae (2-1) to (2-3).

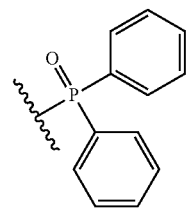

(2-1)

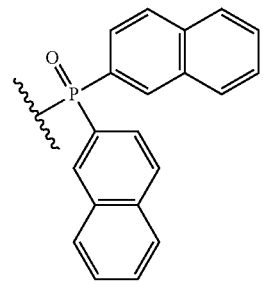

(2-2)

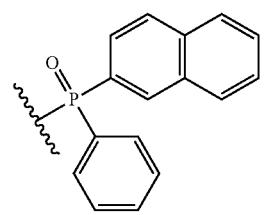

(2-3)

Each of $L^1$ and $L^2$ independently represents a single bond, or a divalent or trivalent residue of a compound selected from benzene, biphenyl, terphenyl, naphthalene, fluorene, carbazole, dibenzofuran, and dibenzothiophene. The residue is unsubstituted or has a substituent B. The substituent B is selected from the group from which the substituent A is selected, provided that the substituted or unsubstituted heteroaryl group having 5 to 30 ring atoms is excluded from the group.

$L^3$ represents a single bond or a p phenylene group.

Each of $Ar^1$ and $Ar^2$ is independently a substituted or unsubstituted aryl group having 6 to 30 ring carbon atoms, or a substituted or unsubstituted heteroaryl group. In the substituted or unsubstituted heteroaryl group, the heteroaryl group is selected from a pyridyl group, a quinolyl group, an isoquinolyl group, a phenanthrolinyl group, an acridinyl group, a phenazinyl group, a carbazolyl group, a benzocarbazolyl group, a phenoxazinyl group, a phenothiazinyl group, an azacarbazolyl group, a xanthenyl group, a dibenzofuranyl group, a naphthobenzofuranyl group, a dinaphthofuranyl group, an azadibenzofuranyl group, an azanaphthobenzofuranyl group, a dibenzothienyl group, a naphthobenzothienyl group, a dinaphthothienyl group, an azadibenzothienyl group, an azanaphthobenzothienyl group, a spiroxanthene-fluorenyl group, a spirofluorene-xanthenyl group, a spirofluorene-acridinyl group, and a spirofluorene-indoloacridinyl group. When $Ar^1$ or $Ar^2$ is the aryl group having a substituent or the heteroaryl group having a substituent, the substituent is selected from the group from which the substituent B is selected.

Each of m and n independently represents an integer of 1 or 2. Meanwhile, when $L^1$ is a single bond, m is 1, and when $L^2$ is a single bond, n is 1.

X represents an oxygen atom or a sulfur atom.

Each of $R^1$ to $R^4$ independently represents a hydrogen atom or a group selected from the group from which the substituent A is selected.

One of $R^5$ and $R^6$ represents a single bond bonded to *a, and the other represents a hydrogen atom or a group selected from the group from which the substituent A is selected.

In one preferred embodiment of the present invention, each of $L^1$ and $L^2$ independently represents a single bond, or a divalent or trivalent residue of a compound selected from benzene, biphenyl, terphenyl, naphthalene, fluorene, carbazole, dibenzofuran, and dibenzothiophene. The residue is unsubstituted. Also, each of $Ar^1$ and $Ar^2$ independently represents a substituted or unsubstituted aryl group having 6 to 30 ring carbon atoms. It is desirable that $Ar^1$ or $Ar^2$ represents a substituted or unsubstituted aryl group having 6 to 30 ring carbon atoms, because it is easy to adjust the electron affinity Af of the compound molecule.

In one preferred embodiment of the present invention, each of $L^1$ and $L^2$ independently represents a single bond, or a divalent or trivalent residue of a compound selected from benzene, biphenyl, terphenyl, naphthalene, fluorene, carbazole, dibenzofuran, and dibenzothiophene. The residue is unsubstituted. Also, each of $Ar^1$ and $Ar^2$ is independently each substituted or unsubstituted group selected from a phenyl group, a biphenyl group, a terphenyl group, a quaterphenyl group, a naphthyl group, an anthryl group, a phenanthryl group, a benzophenanthryl group, a pyrenyl group, a chrysenyl group, a benzochrysenyl group, a triphenylenyl group, a benzotriphenylenyl group, a fluorenyl group, a 9,9'-spirobifluorenyl group, a benzofluorenyl group, a dibenzofluorenyl group, a fluoranthenyl group, and a benzofluoranthenyl group.

In one preferred embodiment of the present invention, each of $L^1$ and $L^2$ independently represents a single bond, or a divalent or trivalent residue of a compound selected from benzene, biphenyl, and naphthalene. The residue is unsubstituted. Also, each of $Ar^1$ and $Ar^2$ is independently a group selected from a phenyl group, a biphenyl group, a naphthyl group, a phenanthryl group, a triphenylenyl group, a fluorenyl group, an anthryl group, a benzochrysenyl group, and a fluoranthenyl group.

In one preferred embodiment of the present invention, in formula (1), one of $-L^1-(Ar^1)_m$ and $-L^2-(Ar^2)_n$ is a phenyl group or a biphenyl group, and in the other, $Ar^1$ or $Ar^2$ is a naphthyl group, a phenanthryl group, a triphenylenyl group, a fluorenyl group, an anthryl group, a benzochrysenyl group or a fluoranthenyl group.

In one preferred embodiment of the present invention, each of the substituent A and the substituent B is independently selected from an unsubstituted alkyl group having 1 to 30 carbon atoms and an unsubstituted aryl group having 6 to 30 ring carbon atoms. Each of $R^1$ to $R^4$ and R is independently a hydrogen atom, an unsubstituted alkyl group having 1 to 30 carbon atoms, or an unsubstituted aryl group having 6 to 30 ring carbon atoms. One of $R^5$ and $R^6$ is a single bond bonded to *a, and the other is a hydrogen atom, an unsubstituted alkyl group having 1 to 30 carbon atoms, or an unsubstituted aryl group having 6 to 30 ring carbon atoms.

In one preferred embodiment of the present invention, $R^1$ to $R^4$ and R represent hydrogen atoms. One of $R^5$ and $R^6$ is a single bond bonded to *a, and the other is a hydrogen atom. Each of $L^1$ and $L^2$ is independently a single bond or the unsubstituted residue. Each of $Ar^1$ and $Ar^2$ is independently the unsubstituted aryl group having 6 to 30 carbon atoms, or the unsubstituted heteroaryl group.

In one preferred embodiment of the present invention, each of $L^1$ and $L^2$ is independently a single bond, or a group selected from a phenylene group, a biphenylene group, and a terphenylene group.

In one preferred embodiment of the present invention, $L^3$ is a single bond.

In one preferred embodiment of the present invention, in formulae (1) to (1-5), X is a sulfur atom. Also, in one preferred embodiment of the present invention, the compound (1) is represented by formula (1-6).

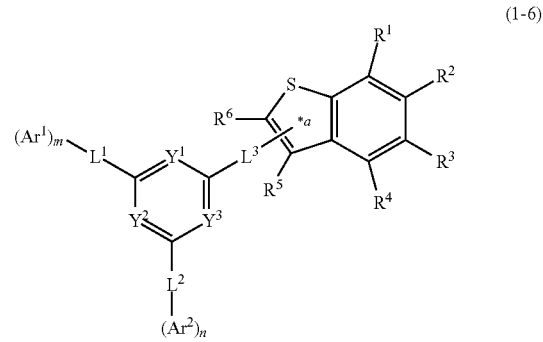

(1-6)

In formula (1-6),

Two of $Y^1$ to $Y^3$ represent nitrogen atoms and the other one represents CR, or three of $Y^1$ to $Y^3$ represent nitrogen atoms. Among $Y^1$ to $Y^3$, in the CR, not as a nitrogen atom, R is a hydrogen atom.

Each of $L^1$ and IA independently represents a divalent residue of a compound selected from benzene, biphenyl, terphenyl, naphthalene, and fluorene.

Each of $Ar^1$ and $Ar^2$ is independently a substituted or unsubstituted aryl group having 6 to 30 ring carbon atoms.

Each of $R^1$ to $R^4$ is independently a hydrogen atom, or a substituted or unsubstituted alkyl group having 1 to 30 carbon atoms, or a substituted or unsubstituted aryl group having 6 to 30 ring carbon atoms.

One of $R^5$ and $R^6$ is a single bond bonded to *a, and the other is a hydrogen atom, or a substituted or unsubstituted alkyl group having 1 to 30 carbon atoms, or a substituted or unsubstituted aryl group having 6 to 30 ring carbon atoms.

Each of the substituent A and the substituent B is independently a substituted or unsubstituted alkyl group having 1 to 30 carbon atoms, or a substituted or unsubstituted aryl group having 6 to 30 ring carbon atoms.

$L^3$, m, n and *a are the same as $L^3$, m, n and *a in formula (1).

In one preferred embodiment of the present invention, the compound (1) is represented by formula (1-7).

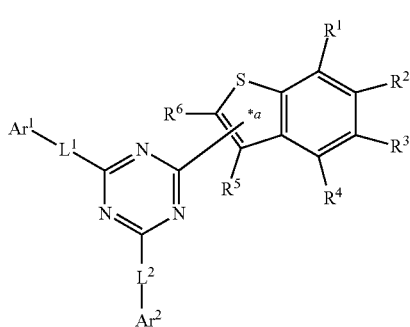

(1-7)

In formula (1-7),

Each of Ar¹ and Ar² is independently each substituted or unsubstituted group selected from a phenyl group, a biphenyl group, a naphthyl group, a phenanthryl group, a triphenylenyl group, a fluorenyl group, an anthryl group, a benzochrysenyl group, and a fluoranthenyl group.

Each of $L^1$ and $L^2$ is independently a single bond, or a divalent residue of a compound selected from benzene, biphenyl, and naphthalene.

Each of $R^1$ to $R^4$ is independently a hydrogen atom, an alkyl group having 1 to 30 carbon atoms, or an aryl group having 6 to 30 ring carbon atoms.

One of $R^5$ and $R^6$ is a single bond bonded to *a, and the other is a hydrogen atom, an alkyl group having 1 to 30 carbon atoms, or an aryl group having 6 to 30 ring carbon atoms.

Each of the substituent A and the substituent B is independently a substituted or unsubstituted alkyl group having 1 to 30 carbon atoms, or a substituted or unsubstituted aryl group having 6 to 30 ring carbon atoms.

*a is the same as *a in formula (1).

In one preferred embodiment of the present invention, each of $L^1$ and $L^2$ is independently a single bond, a phenylene group or a biphenylene group. Each of Ar¹ and Ar² is independently each substituted or unsubstituted group selected from a phenyl group, a biphenyl group, a naphthyl group, a phenanthryl group, a triphenylenyl group, a fluorenyl group, an anthryl group, a benzochrysenyl group, and a fluoranthenyl group.

In one preferred embodiment of the present invention, one of $-L^1-(Ar^1)_m$ and $-L^2-(Ar^2)_n$ is a phenyl group or a biphenyl group, and in the other, Ar¹ or Ar² is a naphthyl group, a phenanthryl group, a triphenylenyl group, a fluorenyl group, an anthryl group, a benzochrysenyl group, or a fluoranthenyl group.

In one embodiment of the present invention, the compound (1) is represented by formula (1-8a) or (1-8b).

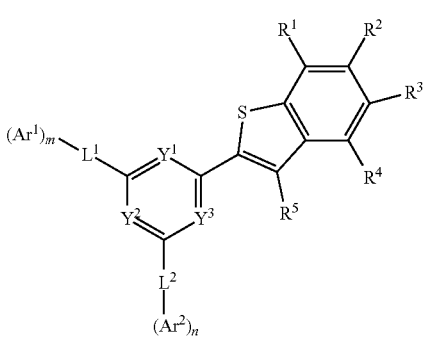

(1-8a)

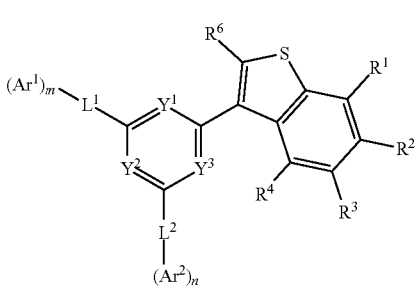

(1-8b)

In formulae (1-8a) and (1-8b), $Y^1$ to $Y^3$, Ar¹, Ar², $L^1$, $L^2$, $R^1$ to $R^4$, m and n are the same as X, $Y^1$ to $Y^3$, Ar¹, Ar², $L^1$, $L^2$, $R^1$ to $R^4$, m and n in formula (1). $R^5$ in formula (1-8a), or $R^6$ in formula (1-8b) represents a hydrogen atom or a group selected from the group from which the substituent A is selected.

In one embodiment of the present invention, in formulae (1), (1-1), (1-2a), (1-2b), (1-3a), (1-3b), (1-4), (1-4a), (1-4b), (1-5), (1-6), (1-7), (1-8a), and (1-8b) (hereinafter, referred to as formulae (1) to (1-8b)), each of Ar¹ and Ar² independently represents each substituted or unsubstituted heteroaryl group selected from a pyridyl group, a quinolyl group, an isoquinolyl group, a phenanthrolinyl group, a carbazolyl group, a benzocarbazolyl group, a dibenzofuranyl group, a naphthobenzofuranyl group, a dinaphthofuranyl group, a dibenzothienyl group, a naphthobenzothienyl group, a dinaphthothienyl group, a spirofluorene-xanthenyl group, a spirofluorene-acridinyl group, and a spirofluorene-indoloacridinyl group.

In one embodiment of the present invention, in formulae (1) to (1-8b), each of Ar¹ and Ar² independently represents each substituted or unsubstituted heteroaryl group selected from a pyridyl group, a quinolyl group, an isoquinolyl group, a phenanthrolinyl group, a carbazolyl group, a dibenzofuranyl group, and a dibenzothienyl group.

In one embodiment of the present invention, the compound (1) is represented by formula (1-9).

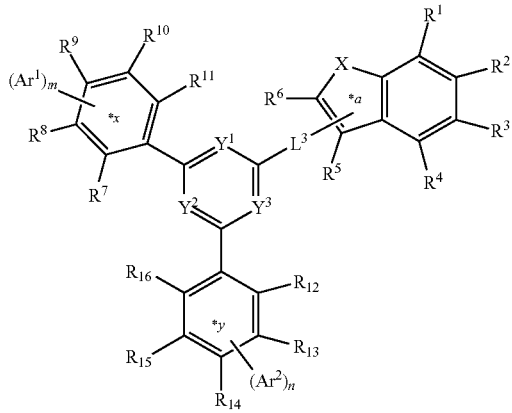

(1-9)

In formula (1-9),

X, $Y^1$ to $Y^3$, $Ar^1$, $Ar^2$, $L^3$, $R^1$ to $R^6$, *a, m and n are the same as X, $Y^1$ to $Y^3$, $Ar^1$, $Ar^2$, $L^3$, $R^1$ to $R^6$, *a, m and n in formula (1).

One of $R^7$ to $R^{11}$ is bonded to *x. Each of $R^7$ to $R^{11}$ not bonded to *x is independently a hydrogen atom, an alkyl group having 1 to 30 carbon atoms, or an aryl group having 6 to 30 ring carbon atoms.

One of $R^{12}$ to $R^{16}$ is bonded to *y. Each of $R^{12}$ to $R^{16}$ not bonded to *y is independently a hydrogen atom, an alkyl group having 1 to 30 carbon atoms, or an aryl group having 6 to 30 ring carbon atoms.

In one embodiment of the present invention, the compound (1) is represented by formula (1-10).

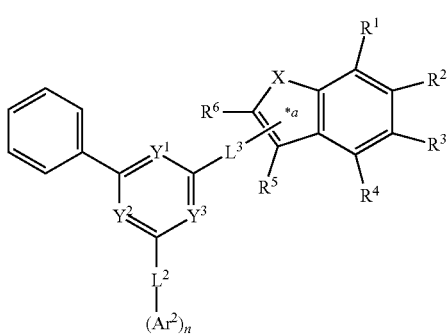

(1-10)

In formula (1-10),

X, $Y^1$ to $Y^3$, $Ar^2$, $L^2$, $L^3$, $R^1$ to $R^6$, *a, and n are the same as X, $Y^1$ to $Y^3$, $Ar^2$, $L^2$, $L^3$, $R^1$ to $R^6$, *a, and n in formula (1).

In one embodiment of the present invention, the compound (1) is represented by formula (1-11).

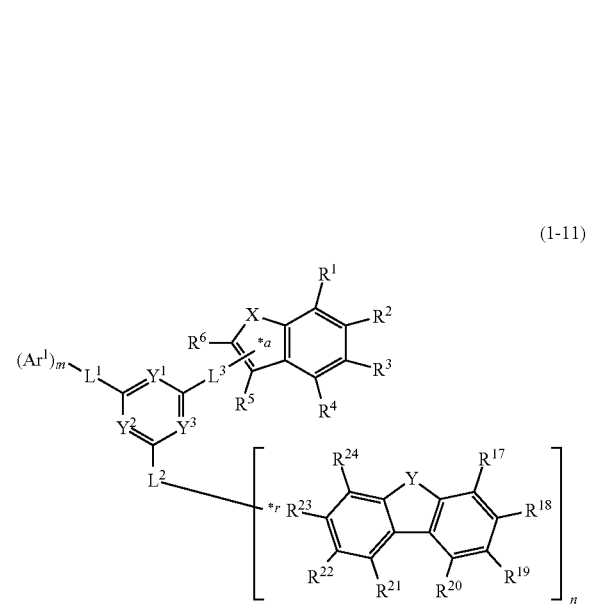

(1-11)

In formula (1-11),

X, $Y^1$ to $Y^3$, $Ar^1$, $L^1$ to $L^3$, $R^1$ to $R^6$, *a, m, and n are the same as X, $Y^1$ to $Y^3$, $Ar^1$, $L^1$ to $L^3$, $R^1$ to $R^6$, *a, m, and n in formula (1).

Y represents an oxygen atom, a sulfur atom, $CR^{50}R^{51}$, or $NR^{52}$.

Each of $R^{50}$ and $R^{51}$ is independently a hydrogen atom, an alkyl group having 1 to 30 carbon atoms, or an aryl group having 6 to 30 ring carbon atoms.

$R^{52}$ is a single bond bonded to *r, or an alkyl group having 1 to 30 carbon atoms, or an aryl group having 6 to 30 ring carbon atoms.

One of $R^{17}$ to $R^{24}$, and $R^{52}$ is bonded to *r. Each of $R^{17}$ to $R^{24}$ not bonded to *r is independently a hydrogen atom, an alkyl group having 1 to 30 carbon atoms, or an aryl group having 6 to 30 ring carbon atoms.

In one embodiment of the present invention, the compound (1) is represented by formula (1-12).

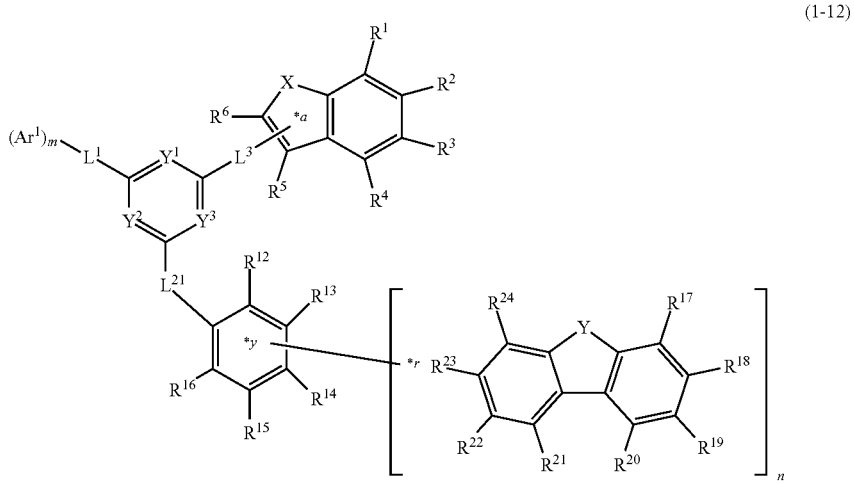

(1-12)

In formula (1-12),

X, $Y^1$ to $Y^3$, $Ar^1$, $L^1$, $L^3$, $R^1$ to $R^6$, *a, m, and n are the same as X, $Y^1$ to $Y^3$, $Ar^1$, $L^1$, $L^3$, $R^1$ to $R^6$, *a, m, and n in formula (1).

Y, $R^{17}$ to $R^{24}$, and *r are the same as Y, $R^{17}$ to $R^{24}$, and *r in formula (1-11).

$L^{21}$ represents a single bond or a phenylene group. The phenylene group may be any of an o-phenylene group, a p-phenylene group, and an m-phenylene group, and a p-phenylene group is preferred.

One of $R^{12}$ to $R^{16}$ is bonded to *y. Each of $R^{12}$ to $R^{16}$ not bonded to *y is independently a hydrogen atom, an alkyl group having 1 to 30 carbon atoms, or an aryl group having 6 to 30 ring carbon atoms.

In one preferred embodiment of the present invention, in formula (1-11) or (1-12), n is 2.

In one embodiment of the present invention, the compound (1) is represented by formula (1-13).

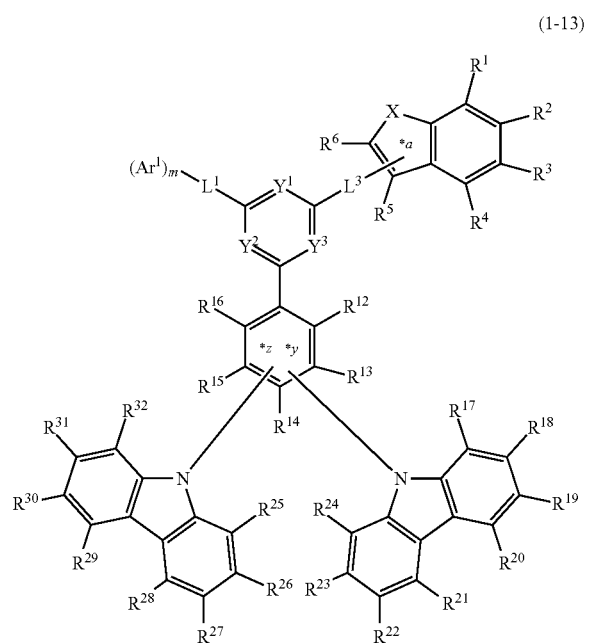

(1-13)

In formula (1-13),

X, $Y^1$ to $Y^3$, $Ar^1$, $L^3$, $R^1$ to $R^6$, *a, and m are the same as X, $Y^1$ to $Y^3$, $Ar^1$, $L^3$, $R^1$ to $R^6$, *a, and m in formula (1).

One of $R^{12}$ to $R^{1G}$ is bonded to *y, and another is bonded to *z. Each of $R^{12}$ to $R^{16}$ not bonded to *y and *z is independently a hydrogen atom, an alkyl group having 1 to 30 carbon atoms, or an aryl group having 6 to 30 ring carbon atoms.

Each of $R^{17}$ to $R^{32}$ is independently a hydrogen atom, an alkyl group having 1 to 30 carbon atoms, or an aryl group having 6 to 30 ring carbon atoms.

In one embodiment of the present invention, the compound (1) is represented by formula (1-14).

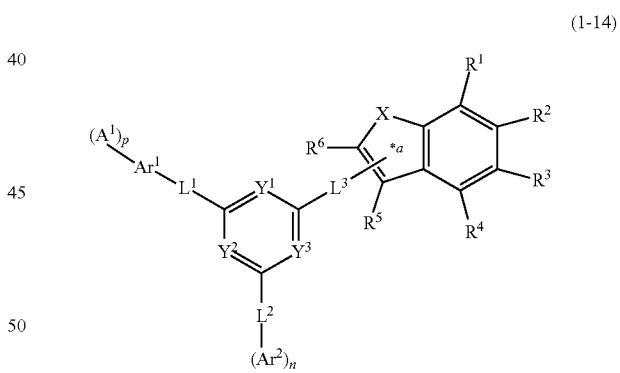

(1-14)

In formula (1-14), $L^1$ represents a divalent or trivalent residue of a compound selected from benzene, biphenyl, terphenyl, naphthalene, fluorene, carbazole, dibenzofuran, and dibenzothiophene. The residue is unsubstituted or has the substituent B.

X, $Y^1$ to $Y^3$, $Ar^1$, $Ar^2$, $L^2$, $L^3$, $R^1$ to $R^6$, *a, and n are the same as X, $Y^1$ to $Y^3$, $Ar^1$, $Ar^2$, $L^2$, $L^3$, $R^1$ to $R^6$, *a, and n in formula (1).

$A^1$ is selected from the group from which the substituent B is selected, p is an integer of 1 or more.

In one embodiment of the present invention, the compound (1) is represented by formula (1-15).

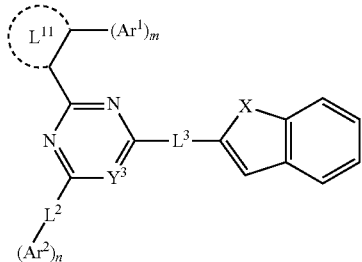

(1-15)

In formula (1-15), $L^{11}$ represents a divalent or trivalent residue of a compound selected from benzene, biphenyl, terphenyl, naphthalene, fluorene, carbazole, dibenzofuran, and dibenzothiophene, which includes a benzene ring to which $Ar^1$ is connected at least at an ortho position. The residue is unsubstituted or has the substituent B.

X, $Y^3$, $Ar^1$, $Ar^2$, $L^2$, $L^3$, m, and n are the same as X, $Y^3$, $Ar^1$, $Ar^2$, $L^2$, $L^3$, m, and n in formula (1).

In one embodiment of the present invention, the compound (1) is represented by formula (1-16).

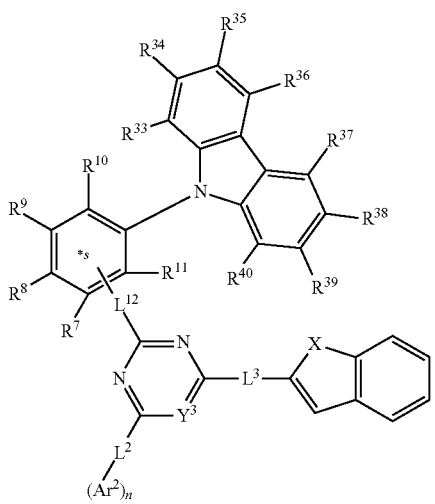

(1-16)

In formula (1-16), $L^{12}$ represents a single bond or a phenylene group. The phenylene group may be any of an o-phenylene group, a p-phenylene group, and an m-phenylene group.

One of $R^7$ to $R^{11}$ is bonded to *s. Each of $R^7$ to $R^{11}$ not bonded to *s is independently a hydrogen atom, an alkyl group having 1 to 30 carbon atoms, or an aryl group having 6 to 30 ring carbon atoms.

Each of $R^{33}$ to $R^{40}$ independently represents a hydrogen atom, or a group selected from the group from which the substituent A is selected.

X, $Y^3$, $Ar^2$, $L^2$, $L^3$, and n are the same as X, $Y^3$, $Ar^2$, $L^2$, $L^3$, and n in formula (1).

In one embodiment of the present invention, the compound (1) is represented by formula (1-17).

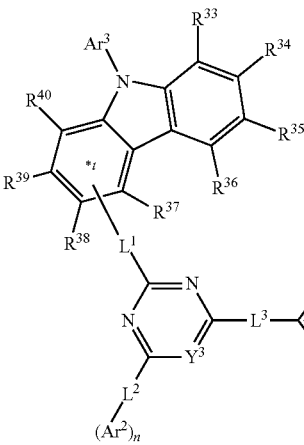

(1-17)

In formula (1-17),

X, $Y^3$, $Ar^2$, $L^1$ to $L^3$, and n are the same as X, $Y^3$, $Ar^2$, $L^1$ to $L^3$, and n in formula (1).

$Ar^3$ is a substituted or unsubstituted aryl group having 6 to 30 ring carbon atoms, or a substituted or unsubstituted heteroaryl group having 5 to 30 ring carbon atoms.

When $Ar^3$ is the aryl group having a substituent or the heteroaryl group having a substituent, the substituent represents a group selected from the group from which the substituent A is selected.

Each of $R^{33}$ to $R^{36}$ independently represents a hydrogen atom or a group selected from the group from which the substituent A is selected.

One of $R^{37}$ to $R^{40}$ is bonded to *t. Each of $R^{37}$ to $R^{40}$ not bonded to *t is independently a hydrogen atom, an alkyl group having 1 to 30 carbon atoms, or an aryl group having 6 to 30 ring carbon atoms.

In formulae (1-9), (1-11), (1-12), and (1-13), the alkyl group having 1 to 30 carbon atoms, which may be represented by $R^7$ to $R^{32}$, is, for example, a methyl group, an ethyl group, an n-propyl group, an isopropyl group, an n-butyl group, an isobutyl group, an s-butyl group, a t-butyl group, a pentyl group, a hexyl group, a heptyl group, an octyl group, a nonyl group, a decyl group, an undecyl group, or a dodecyl group.

Also, in formulae (1-9), (1-11), (1-12), and (1-13), the aryl group having 6 to 30 ring carbon atoms, which may be represented by $R^7$ to $R^{32}$, preferably has 6 to 18, more preferably 6 to 10, ring carbon atoms, and is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, a triphenylenyl group, or a benzotriphenylenyl group.

In formula (1-17), in the substituted or unsubstituted aryl group having 6 to 30 ring carbon atoms, which may be represented by $Ar^3$, the aryl group preferably has 6 to 18, more preferably 6 to 10, ring carbon atoms, and is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, a triphenylenyl group, or a benzotriphenylenyl group.

In formula (117), in the substituted or unsubstituted heteroaryl group having 5 to 30 ring carbon atoms, which may be represented by $Ar^3$, the heteroaryl group having 5 to 30 ring carbon atoms includes 1 to 5, preferably 1 to 3, more preferably 1 to 2 ring hetero atoms. The ring hetero atom is selected from, for example, a nitrogen atom, a sulfur atom, and an oxygen atom. The free bond of the heteroaryl group is present on a ring carbon atom, or is present on a ring nitrogen atom if physically possible.

The heteroaryl group having 5 to 30 ring atoms is, for example, a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzoimidazolyl group, a benzoxazolyl group, a benzothiazolyl group, an indazolyl group, a benzoisoxazolyl group, a benzoisothiazolyl group, a phenanthrizinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group, an isobenzothiophenyl group, a naphthobenzothiophenyl group, a dibenzothiophenyl group, or a carbazolyl group. When the $Ar^3$ has a substituent, the substituent is selected from the group from which the substituent A is selected, provided that a group including a group to be substituted, i.e., Ar, is excluded from the group.

In one embodiment of the present invention, $R^5$ or $R^6$ not bonded to *a is not bonded to a group including a nitrogen atom directly or via a linking group.

In one embodiment of the present invention, the structure of a group bonded to $R^5$ is different from the structure of a group bonded to $R^6$.

In one embodiment of the present invention, $R^5$ and $R^6$ not bonded to *a are unsubstituted.

In one embodiment of the present invention, at least one of $Ar^1$ and $Ar^2$ is an unsubstituted aryl group having 6 to 30 ring carbon atoms.

In one embodiment of the present invention, at least one of $-L^1-(Ar^1)_m$ and $-L^2-(Ar^2)_n$ does not include a pyridine ring.

In one embodiment of the present invention, $Ar^2$ is a substituted or unsubstituted heteroaryl group, and $Ar^1$ is a substituted or unsubstituted aryl group having 6 to 30 ring carbon atoms.

In one embodiment of the present invention, $Ar^2$ is a substituted or unsubstituted aryl group, and the aryl group is a fused ring in which three or more benzene rings are condensed.

In one embodiment of the present invention, $Ar^2$ is an aryl group having the substituent A, and the aryl group is a fused ring in which three or more benzene rings are condensed.

In one embodiment of the present invention, $Ar^2$ is a substituted or unsubstituted aryl group. The aryl group is a fused ring in which three or more benzene rings are continuously bonded, and a benzene ring other than both ends has a single bond bonded to $L^2$.

In one embodiment of the present invention, $Ar^2$ is a substituted or unsubstituted aryl group, and the aryl group is anthracene or phenanthrene.

In one embodiment of the present invention, $Ar^2$ is a substituted or unsubstituted aryl group, the aryl group is a fused ring in which three or more benzene rings are condensed, and $Ar^1$ is a substituted or unsubstituted aryl group having 6 to 30 ring carbon atoms.

In one embodiment of the present invention, $-L \cdot A-Ar^1$ and $-L^2-Ar^2$ have the same structure and do not include a hetero atom.

In one embodiment of the present invention, any one of $R^{21}$ to $R^{24}$ is bonded to *r, preferably, any one of $R^{22}$ to $R^{24}$ is bonded to *r, and more preferably, $R^{22}$ or $R^{24}$ is bonded to *r.

In one embodiment of the present invention, Y is $NR^{52}$, and $R^{52}$ is a single bond bonded to *r.

Specific examples of the compound according to the present invention are exemplified below, but there is no particular limitation to these.

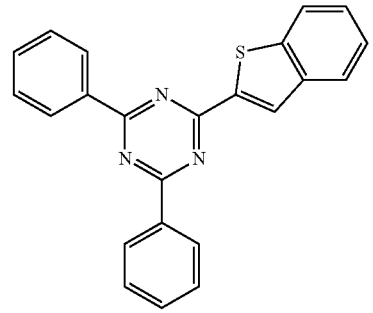

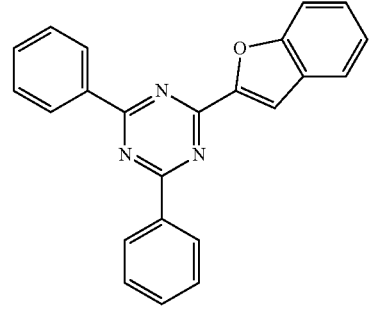

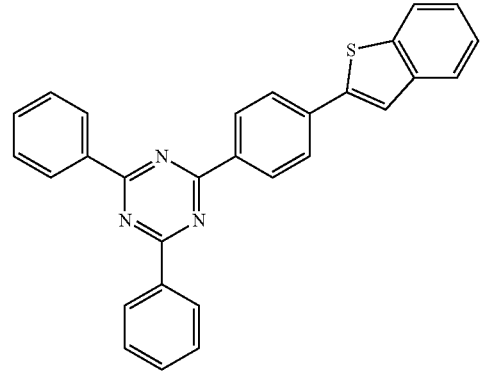

-continued
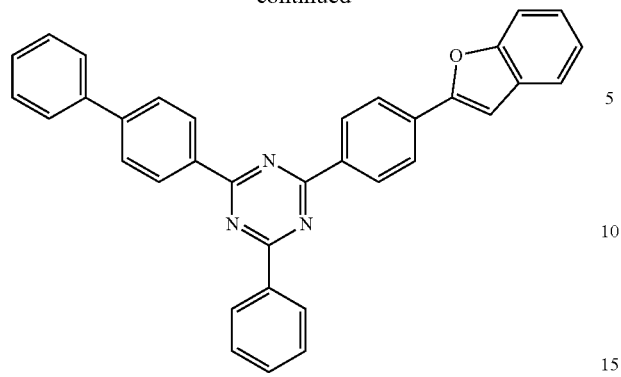
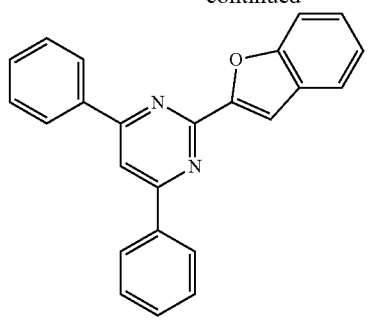
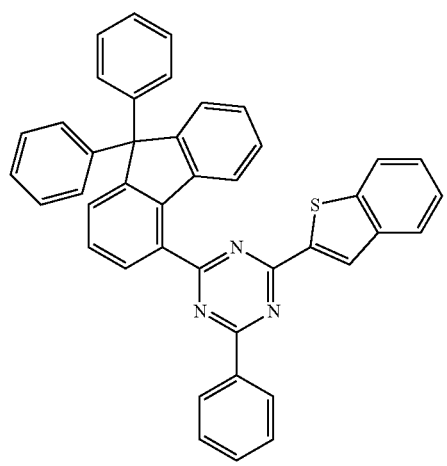
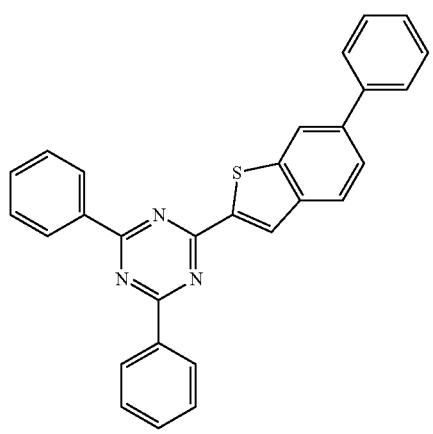
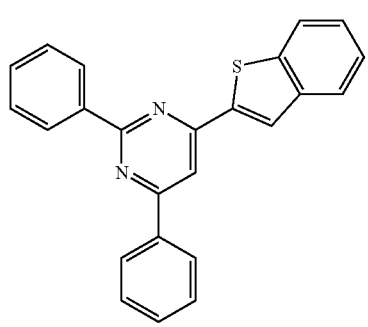
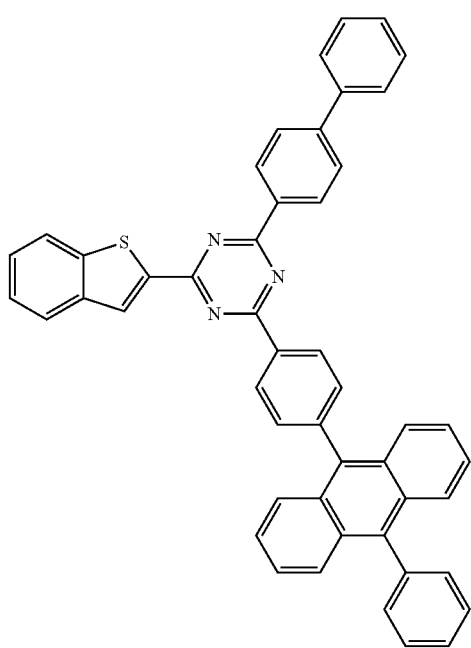

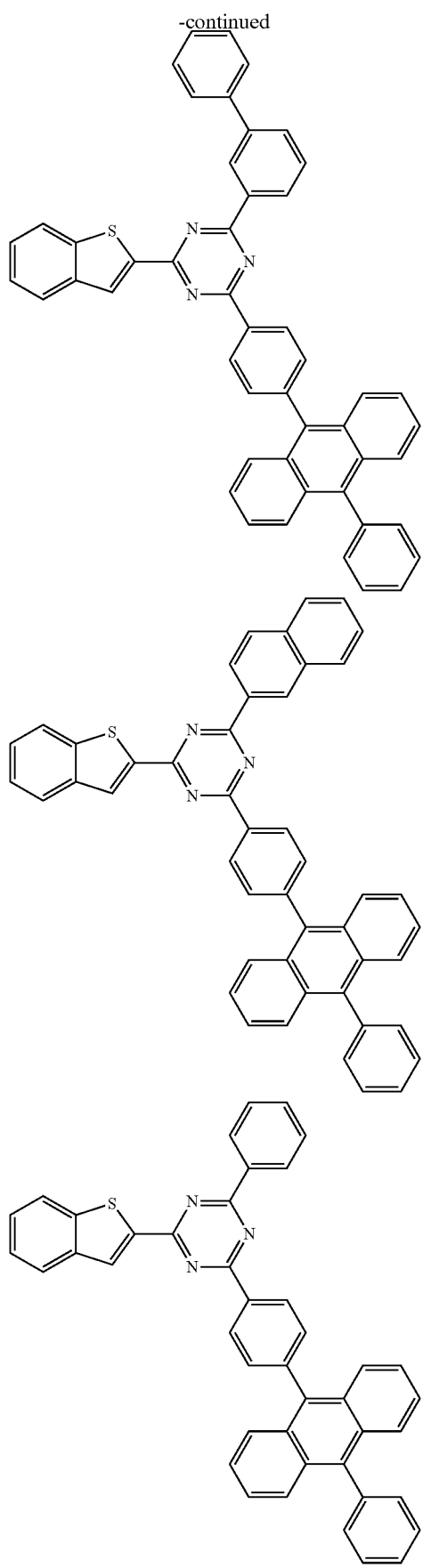
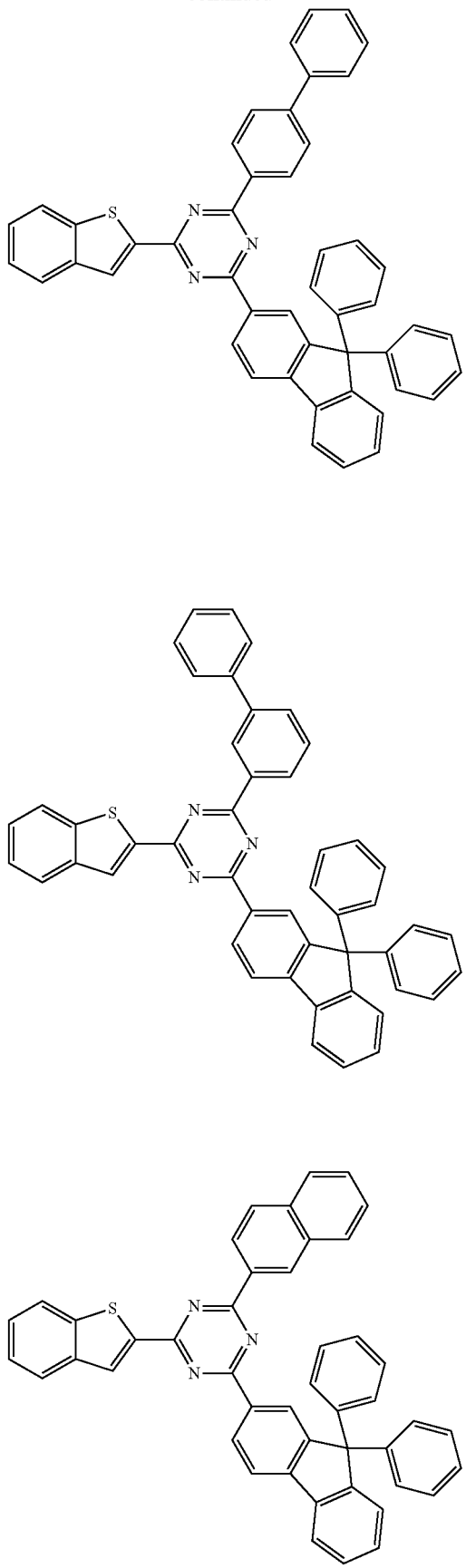

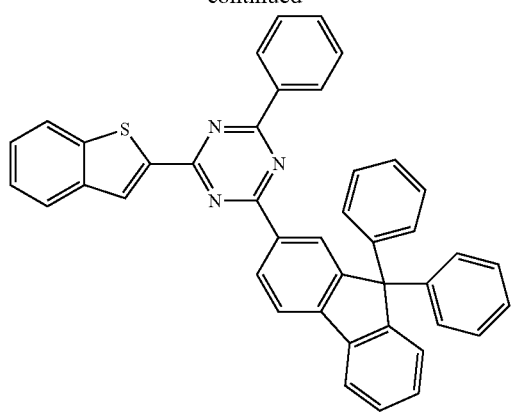
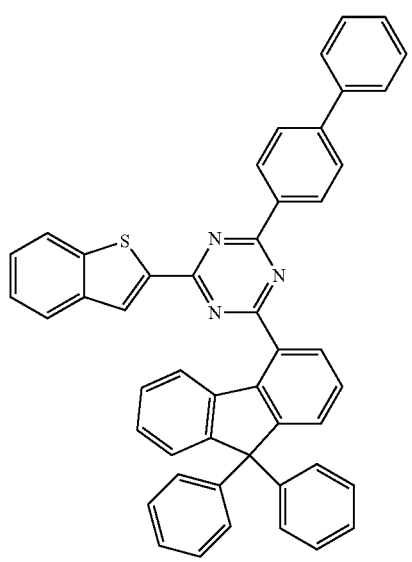
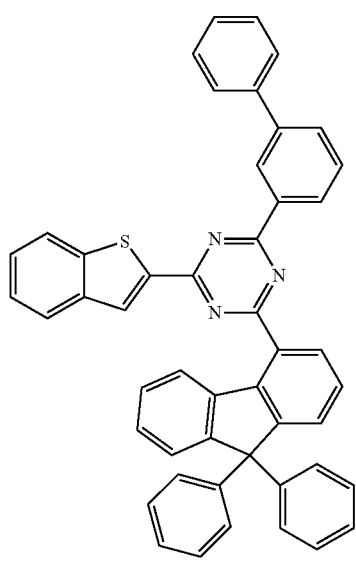
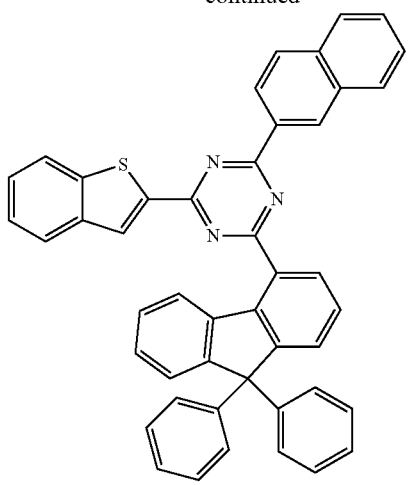
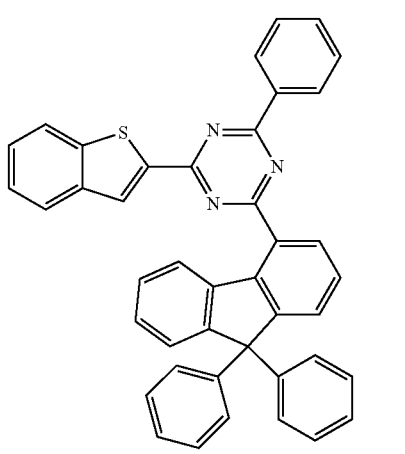
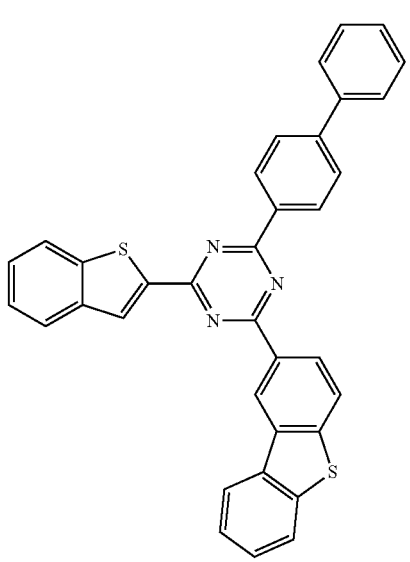

-continued
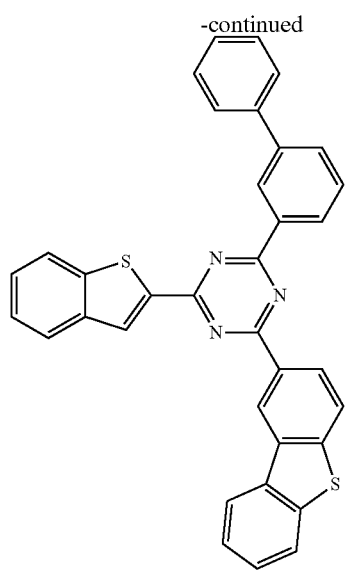
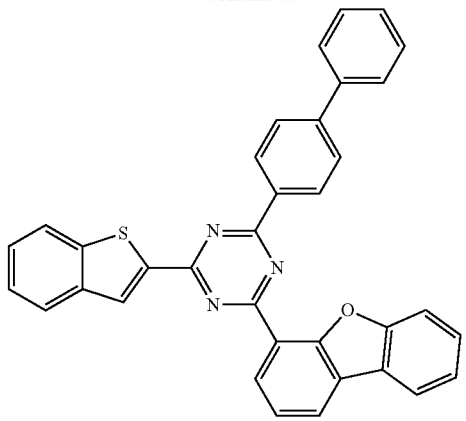
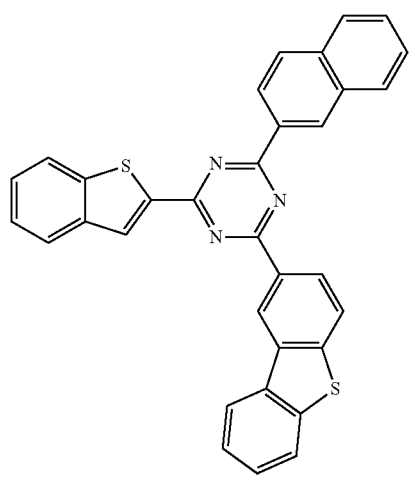
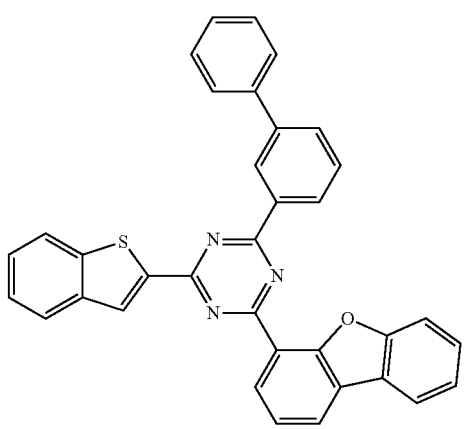
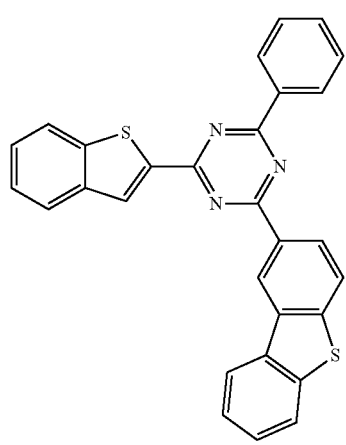
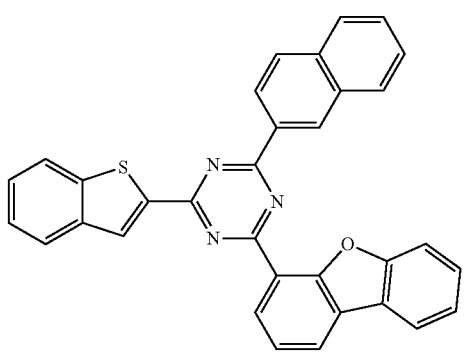
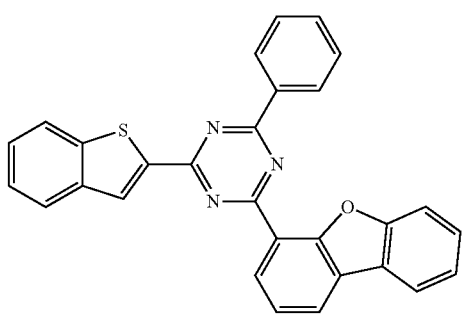

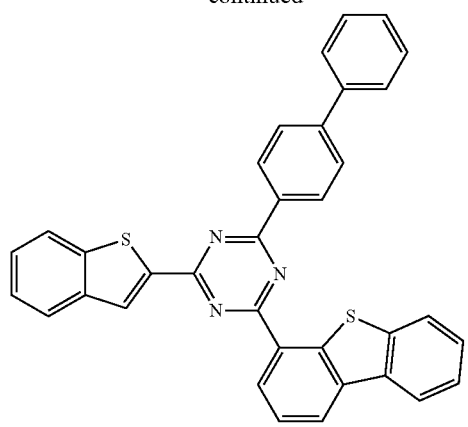
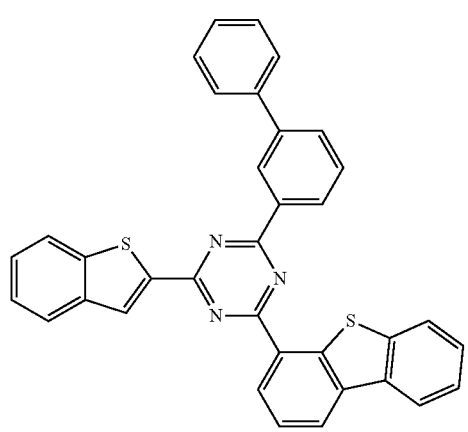
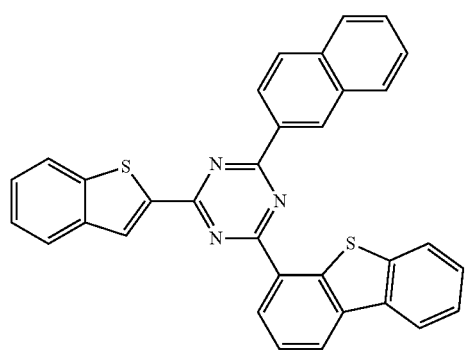
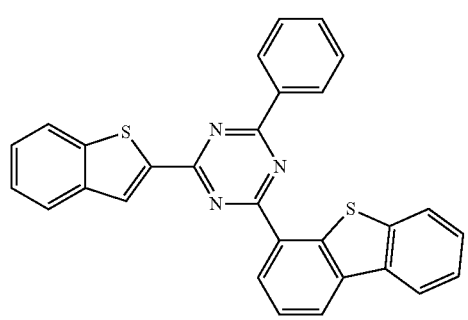
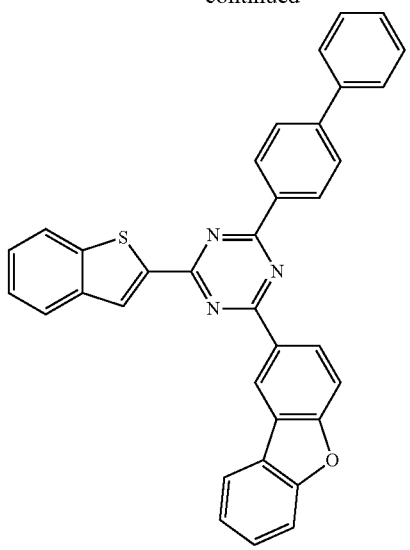
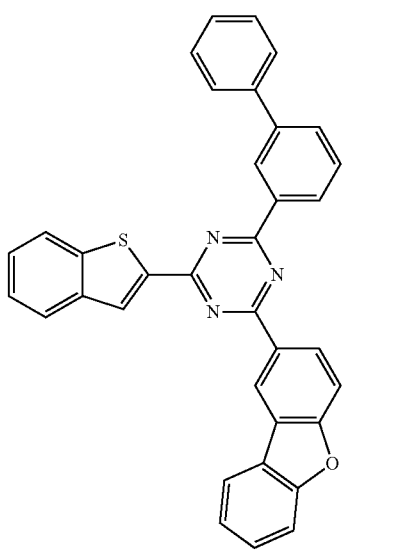
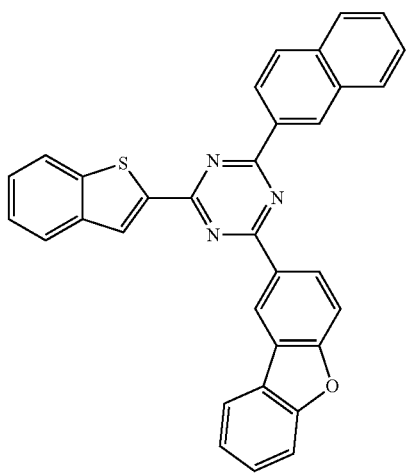

-continued
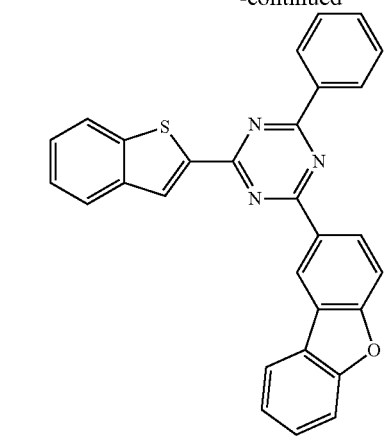
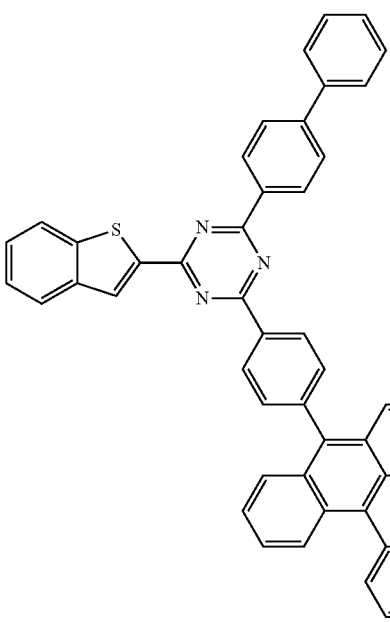
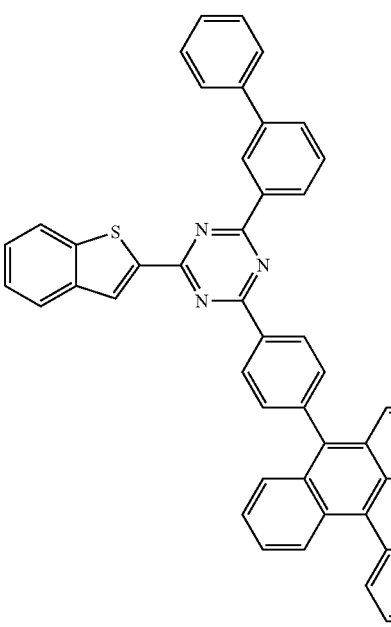
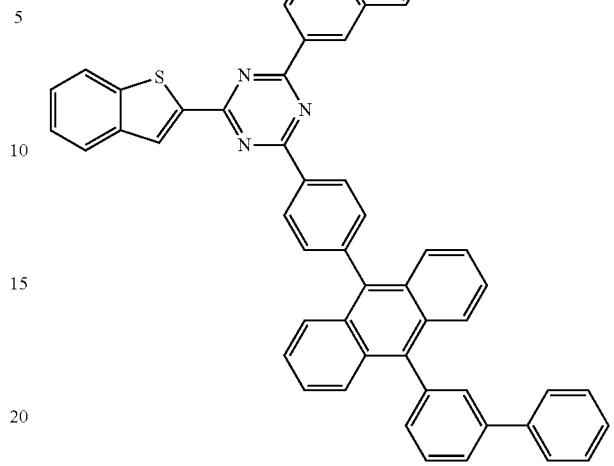
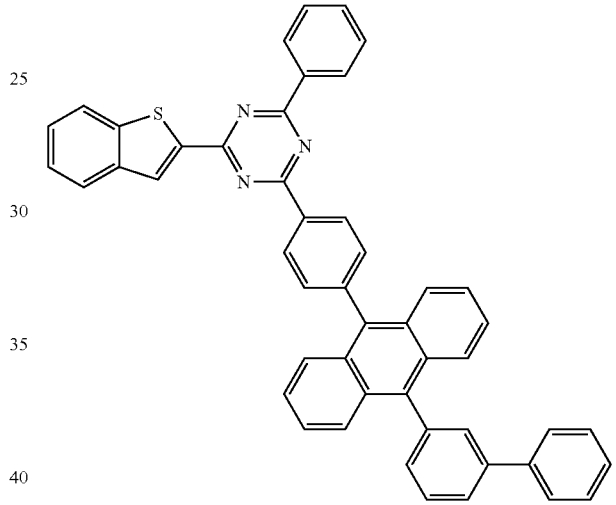
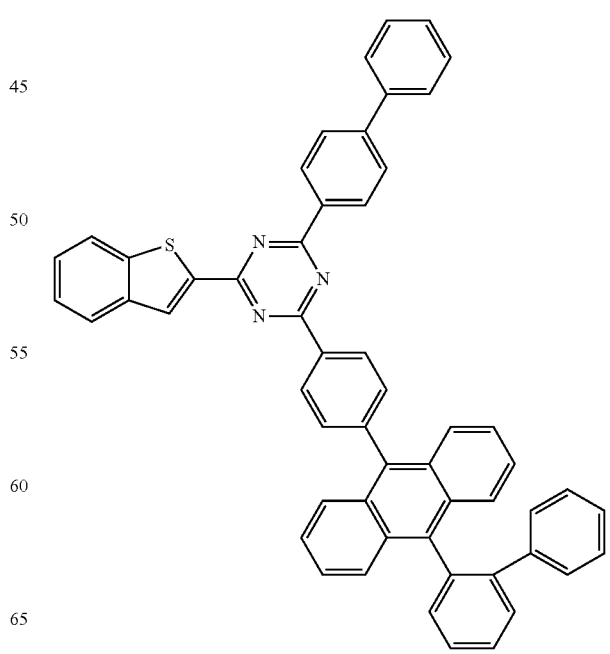

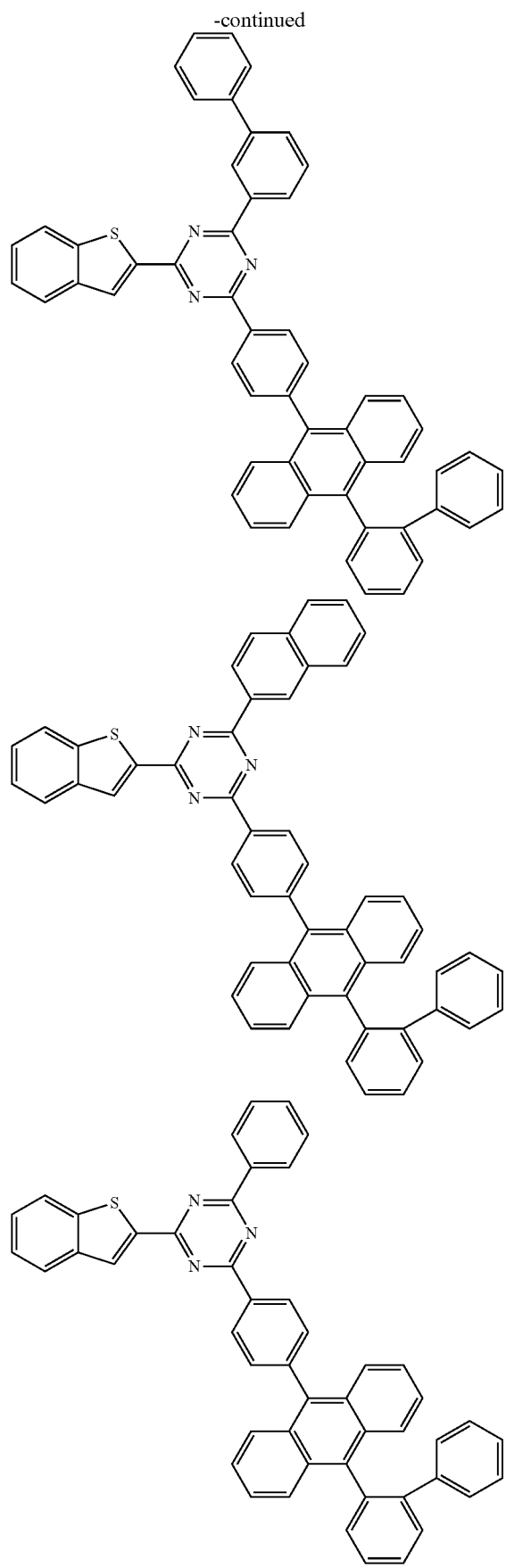
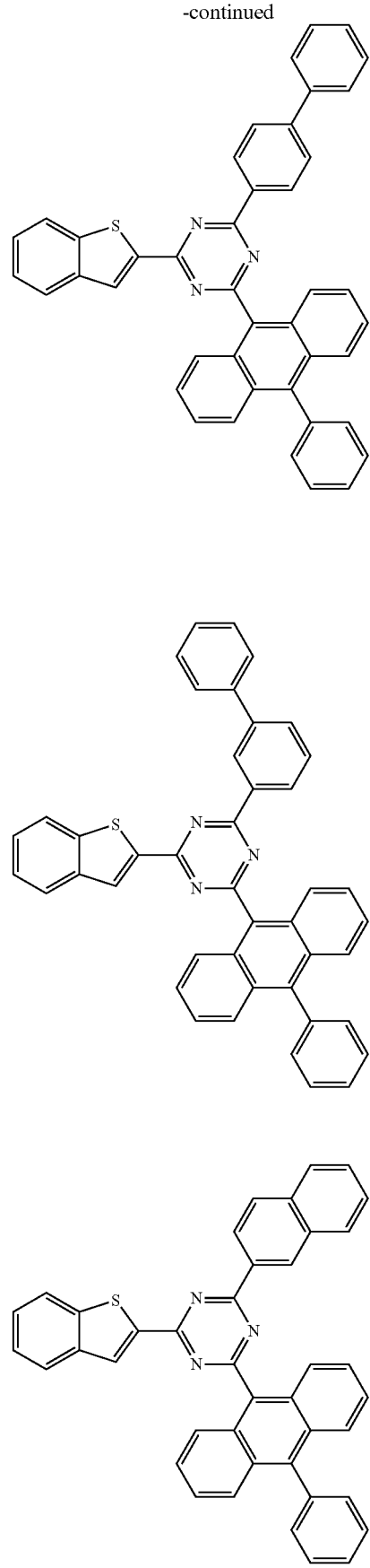

-continued
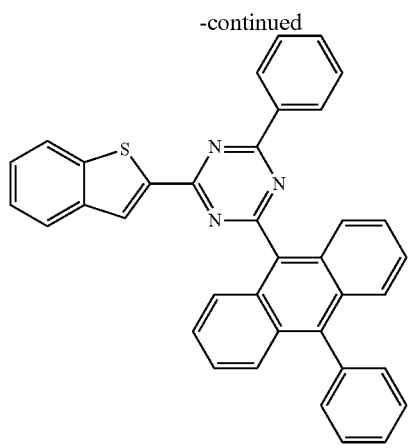
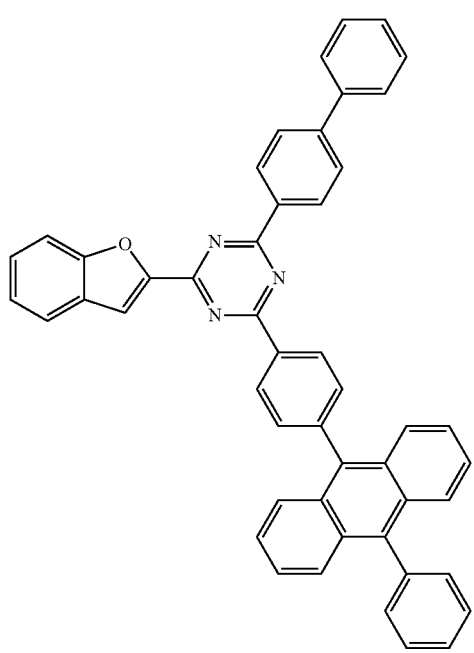
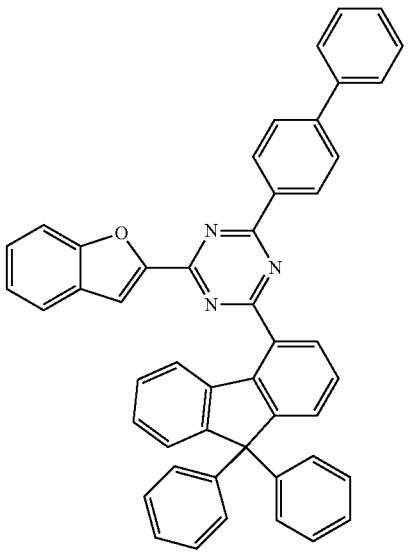
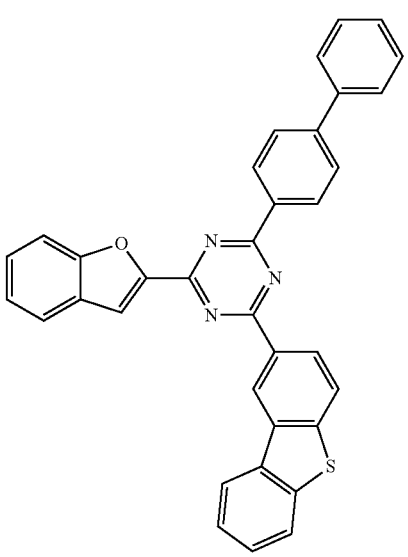
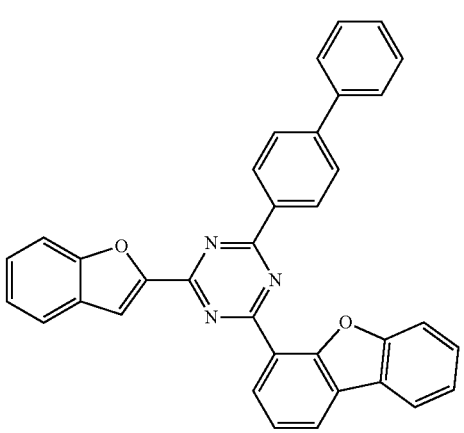

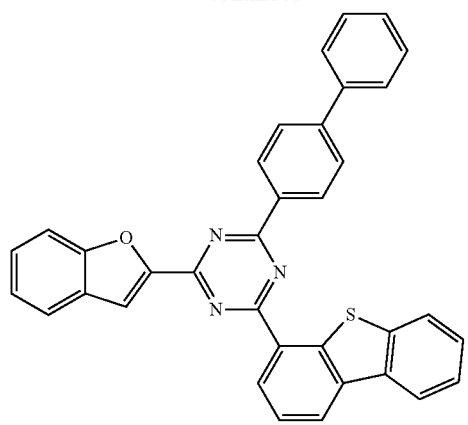
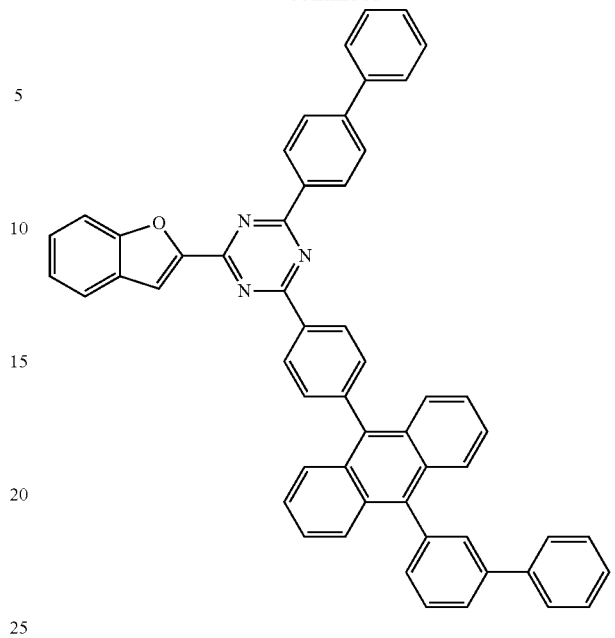
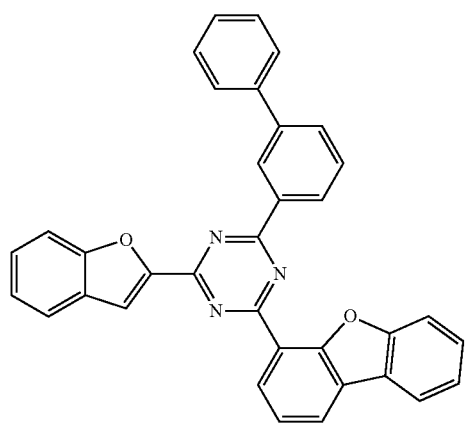
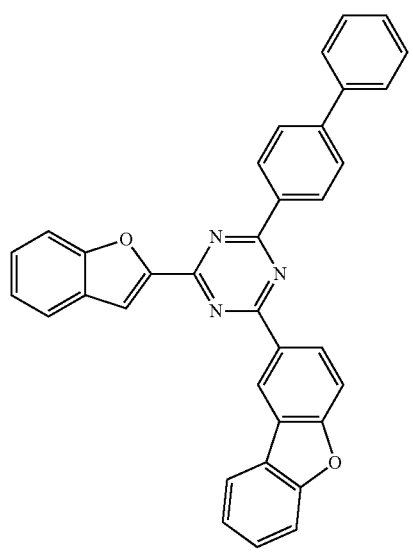
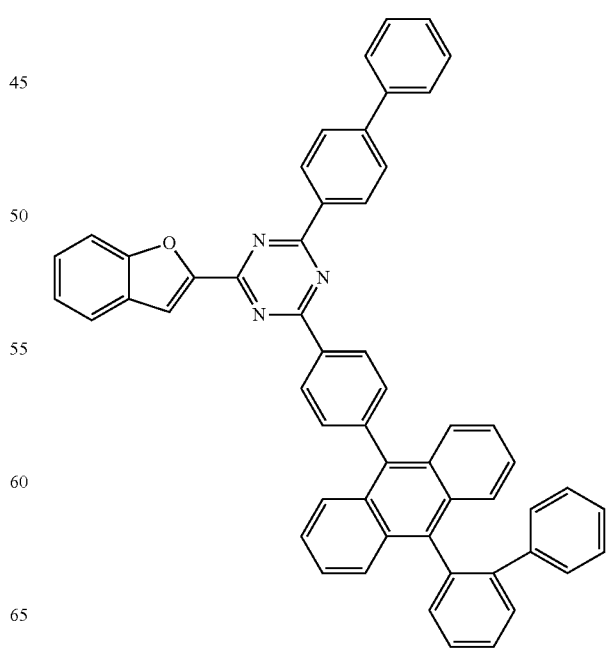

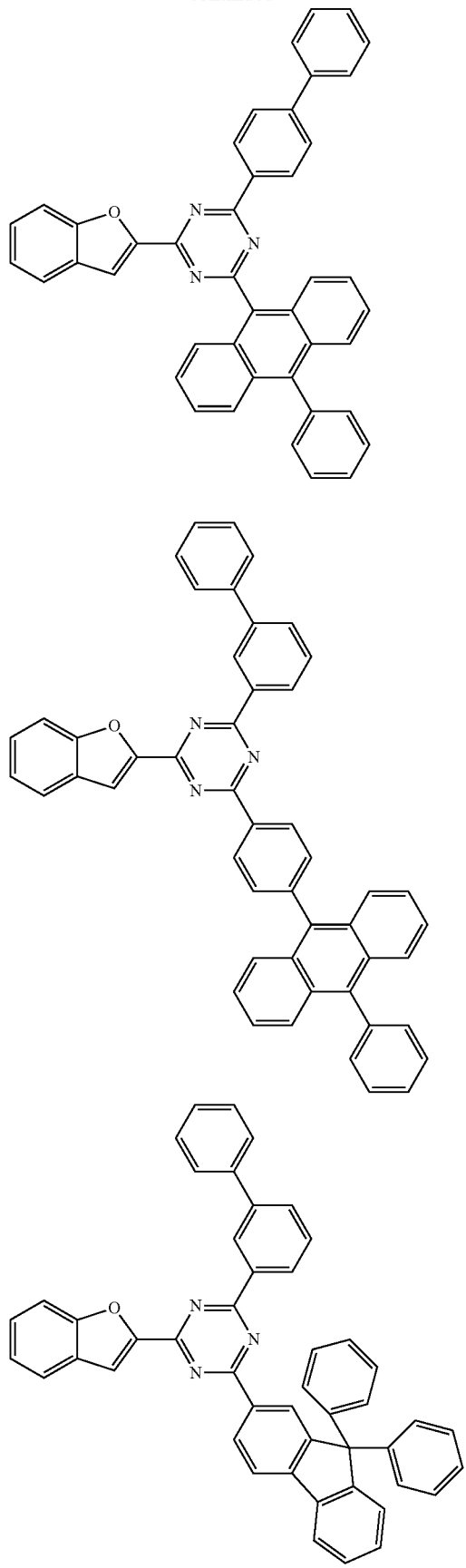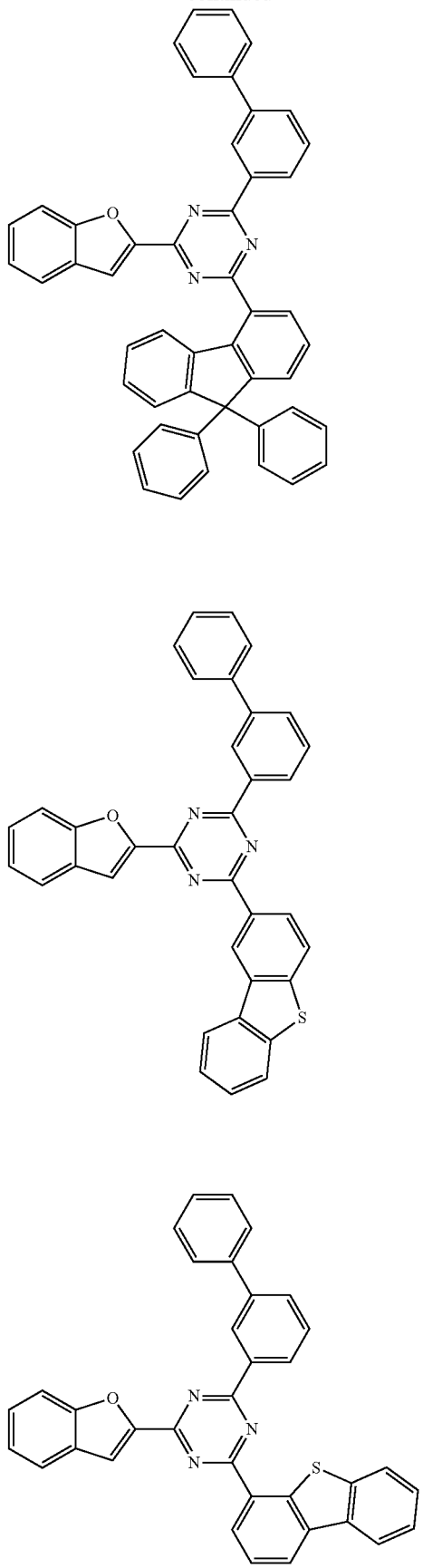

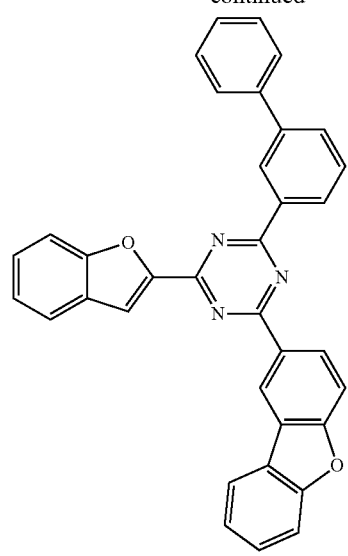
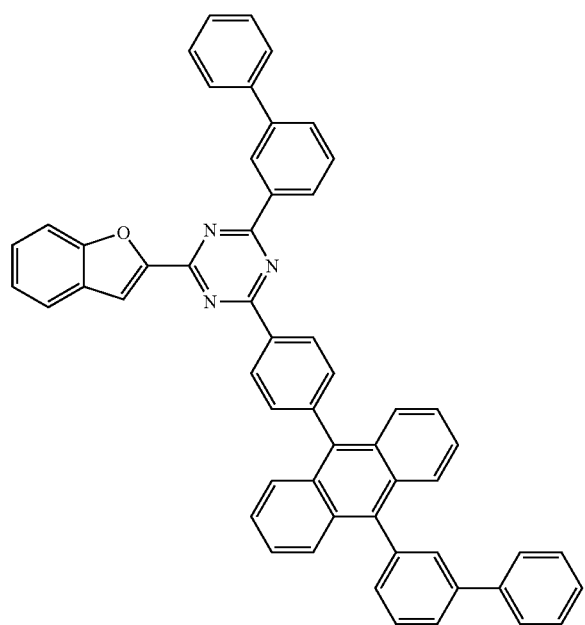
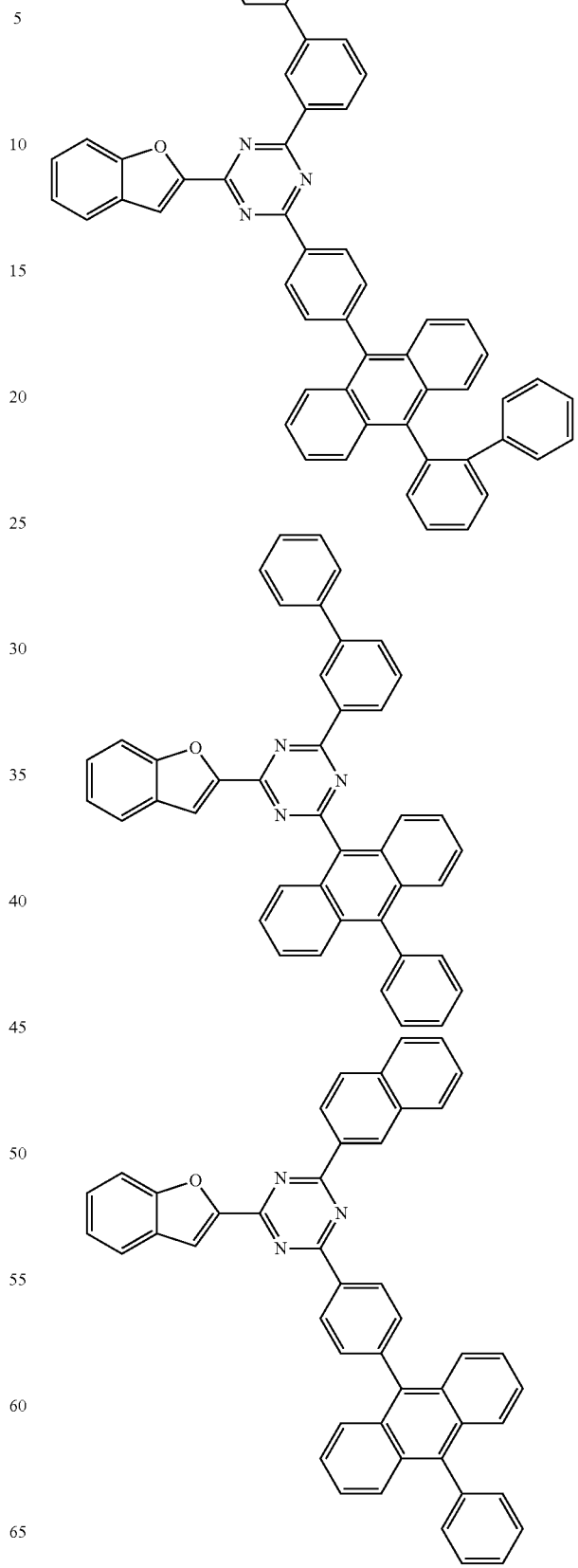

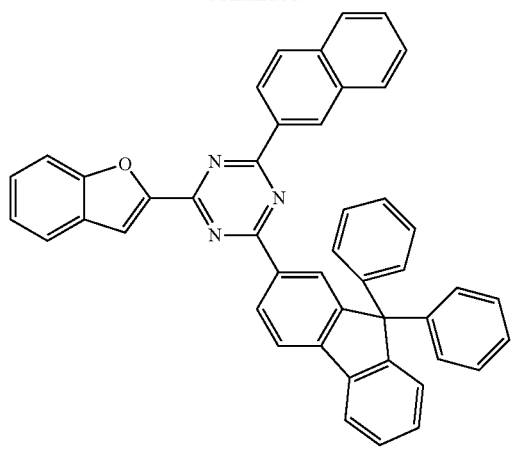
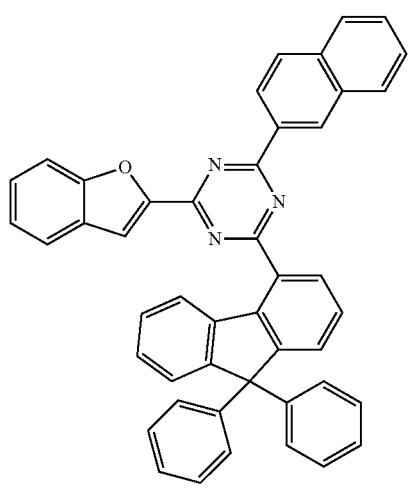
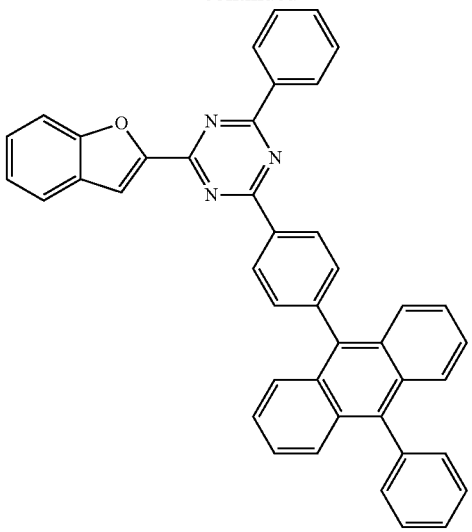
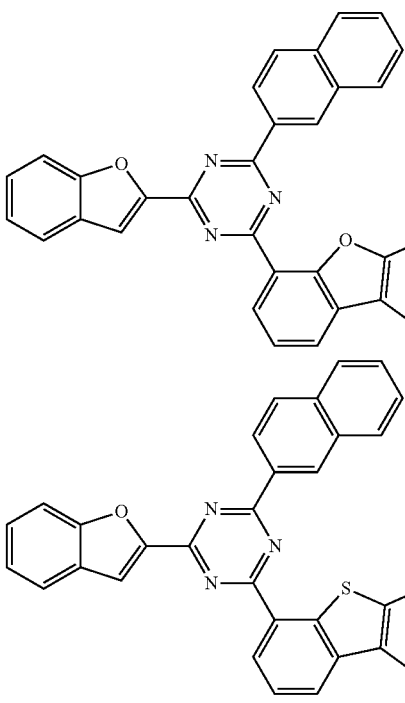
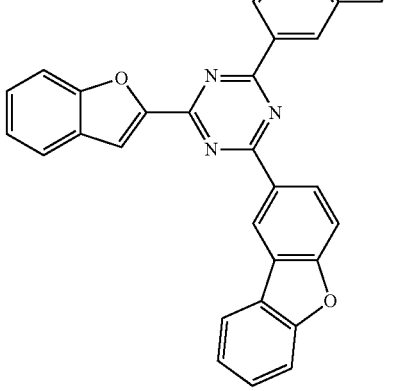

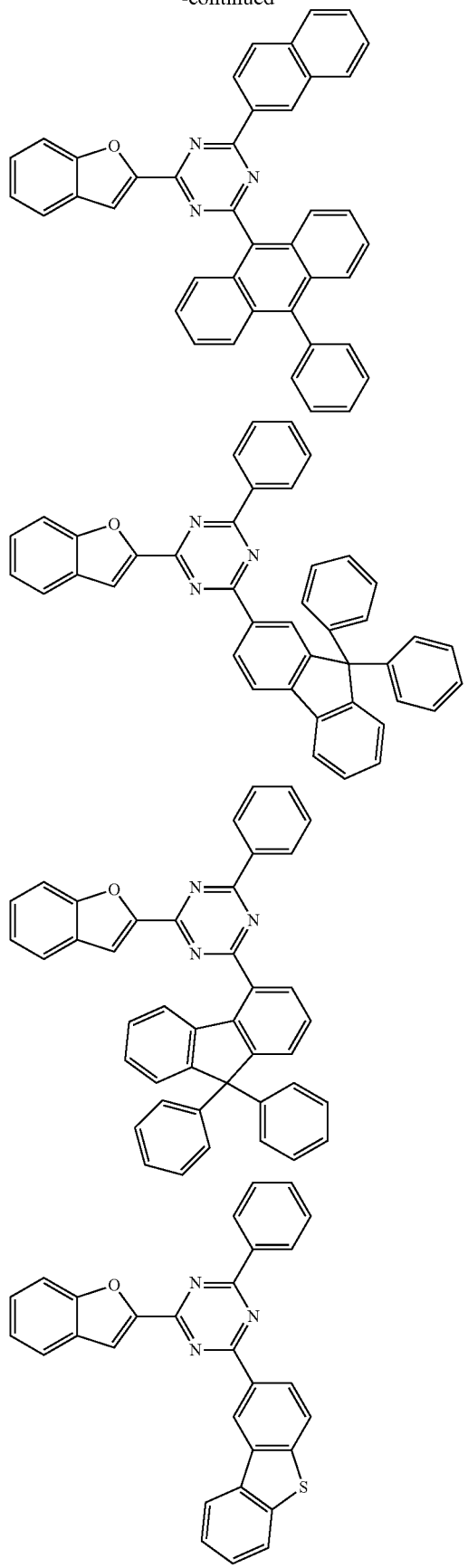
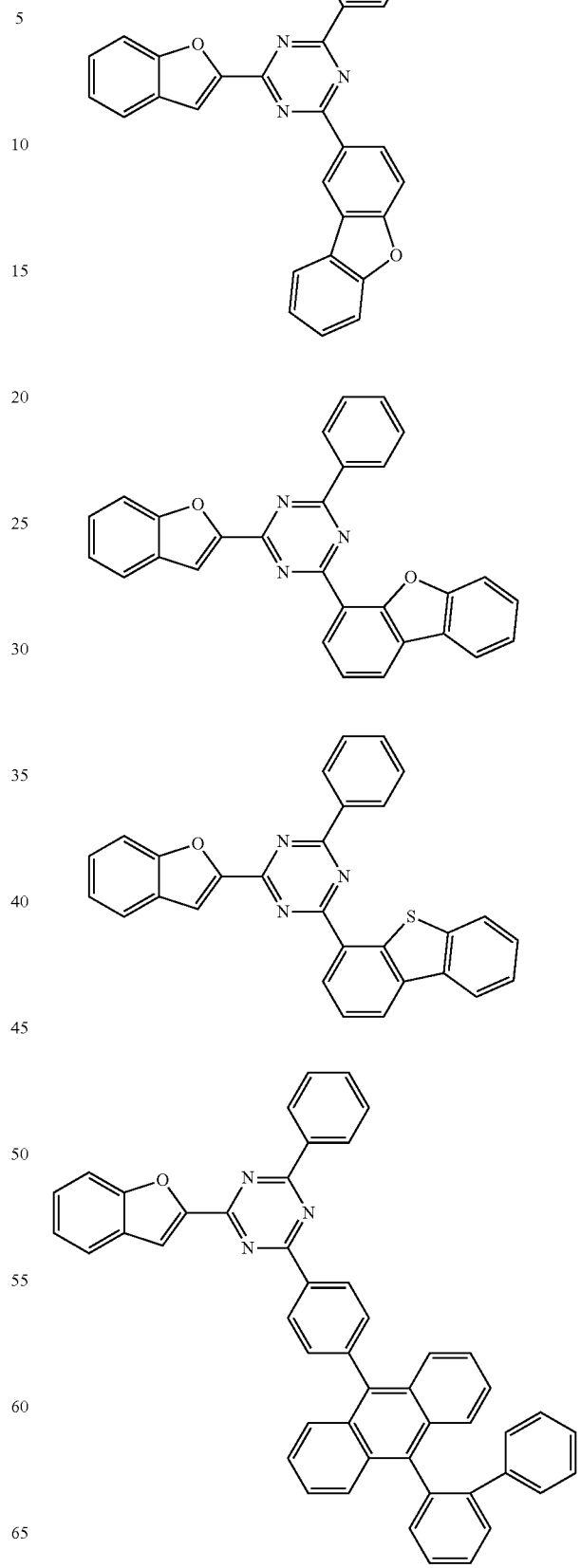

-continued
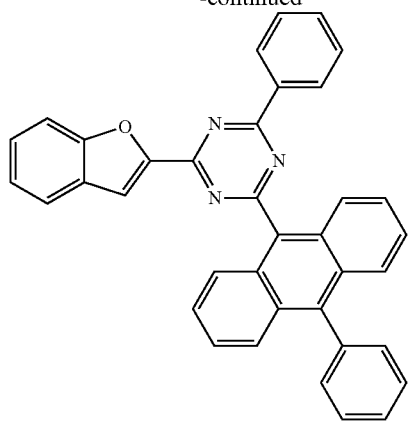
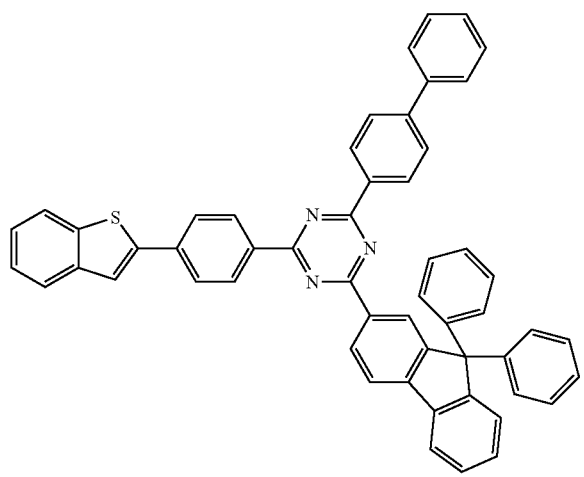
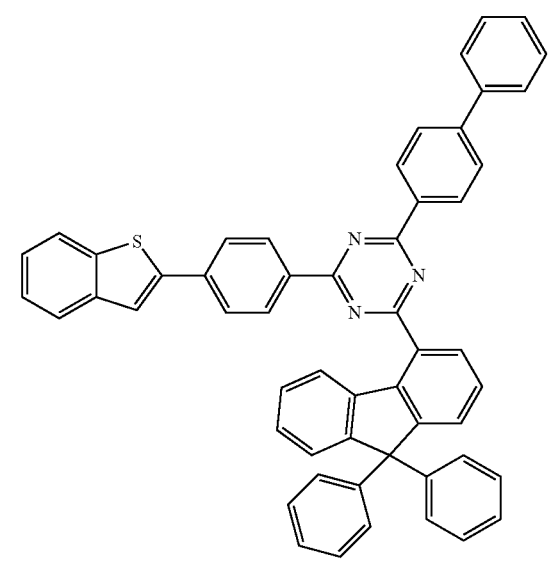
-continued
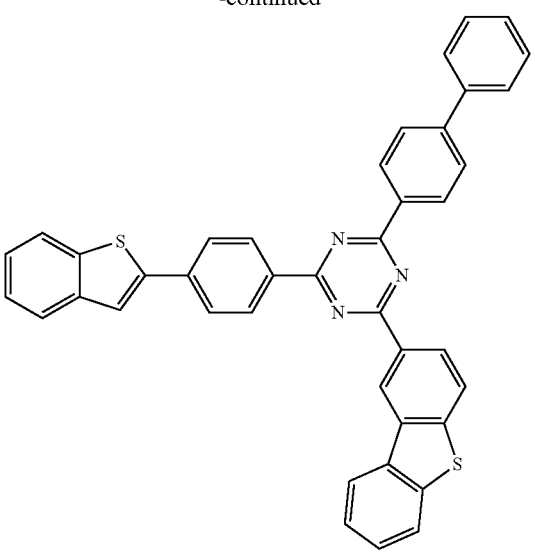
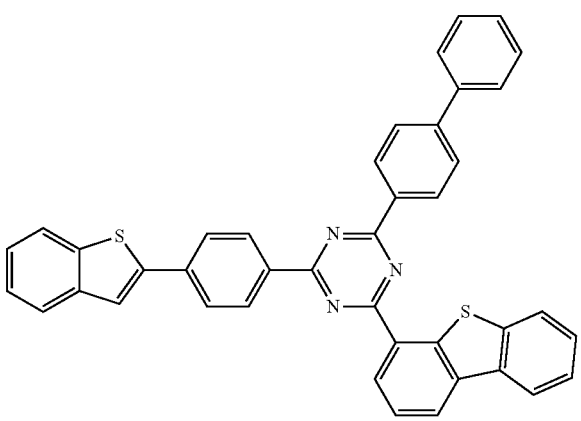

51
-continued
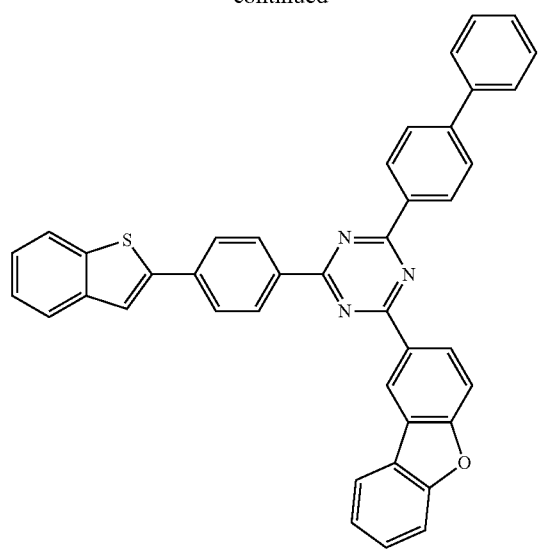
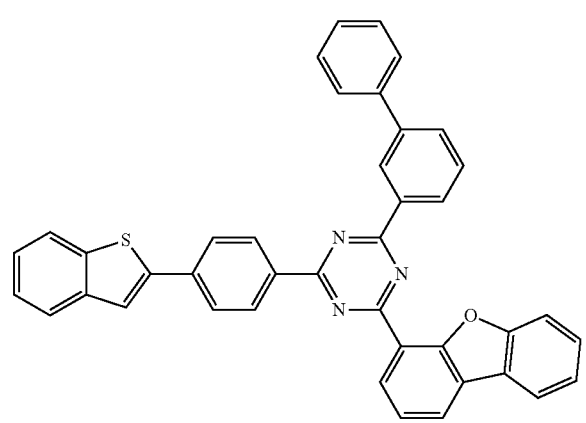
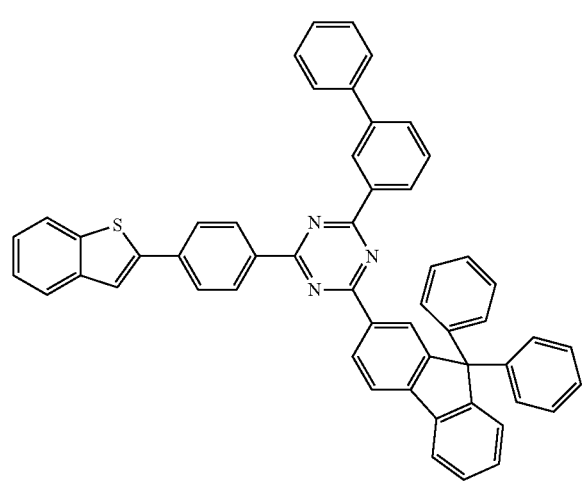
52
-continued
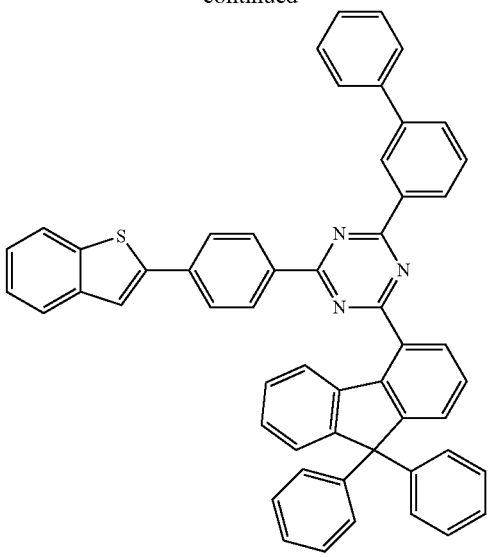
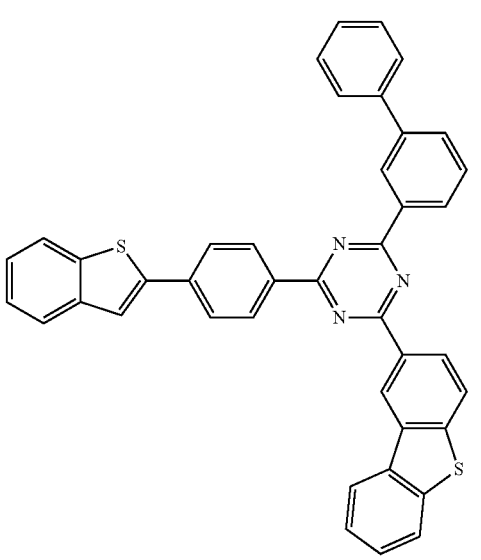

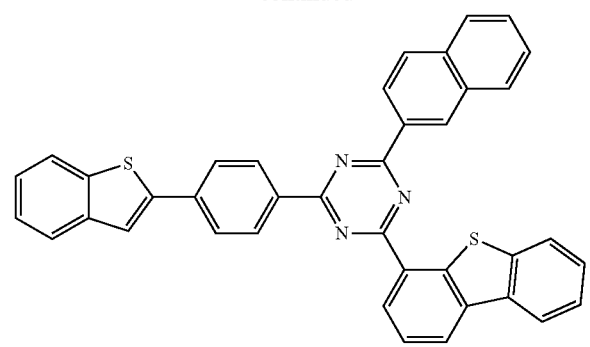
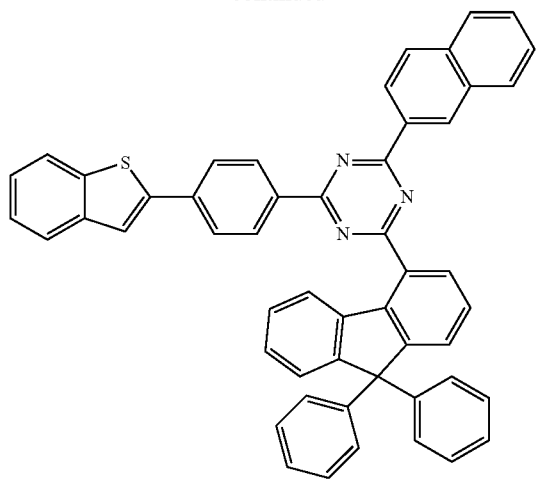
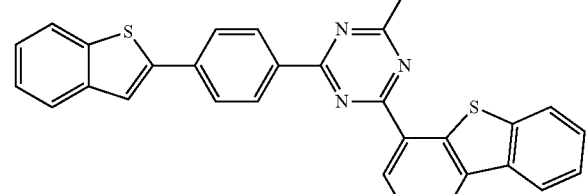
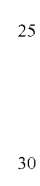
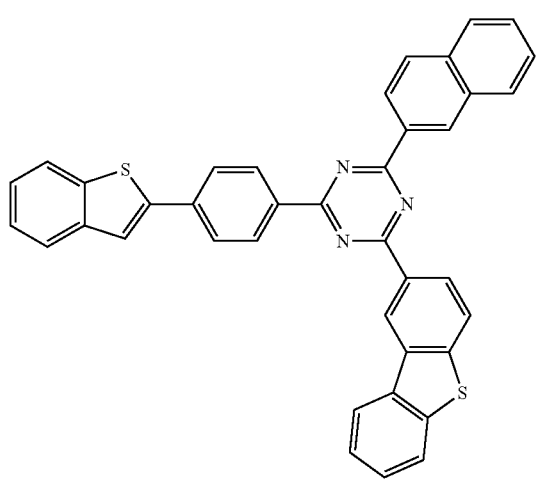
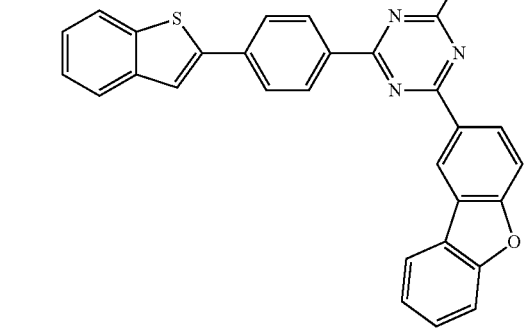
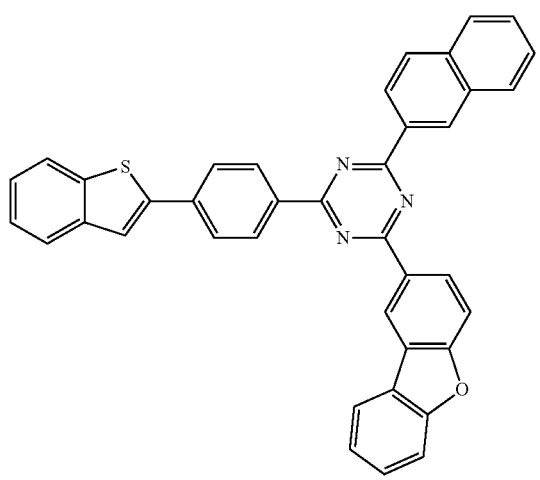
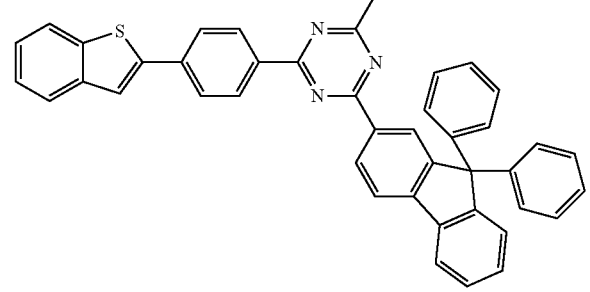

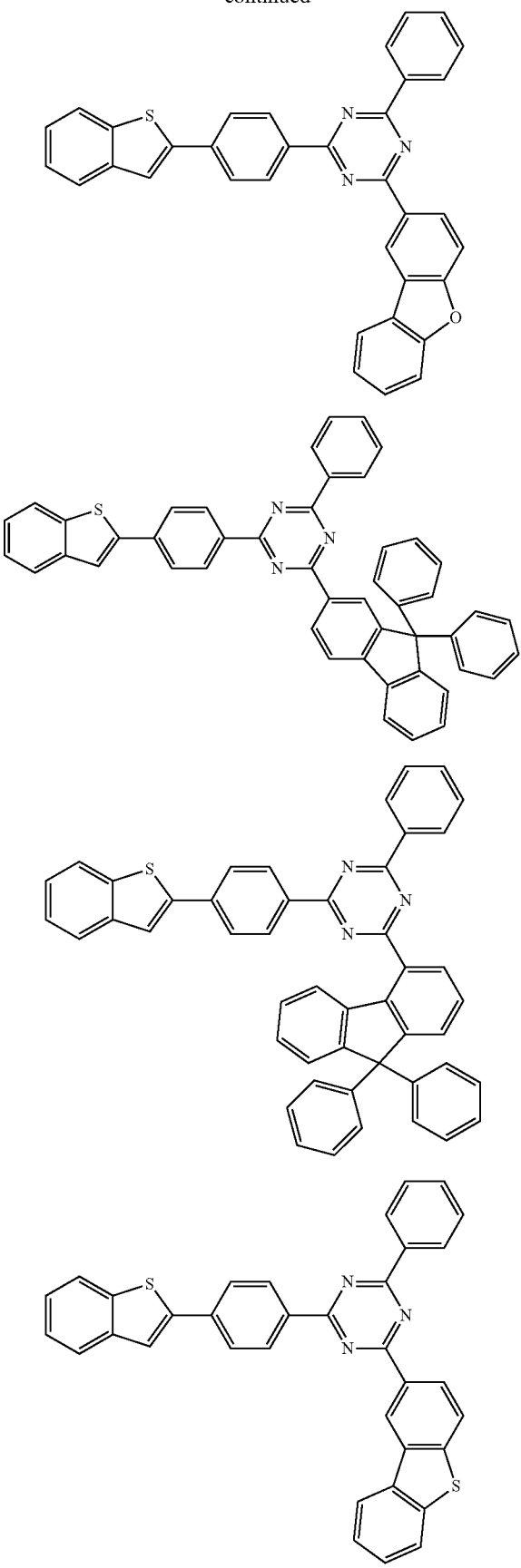
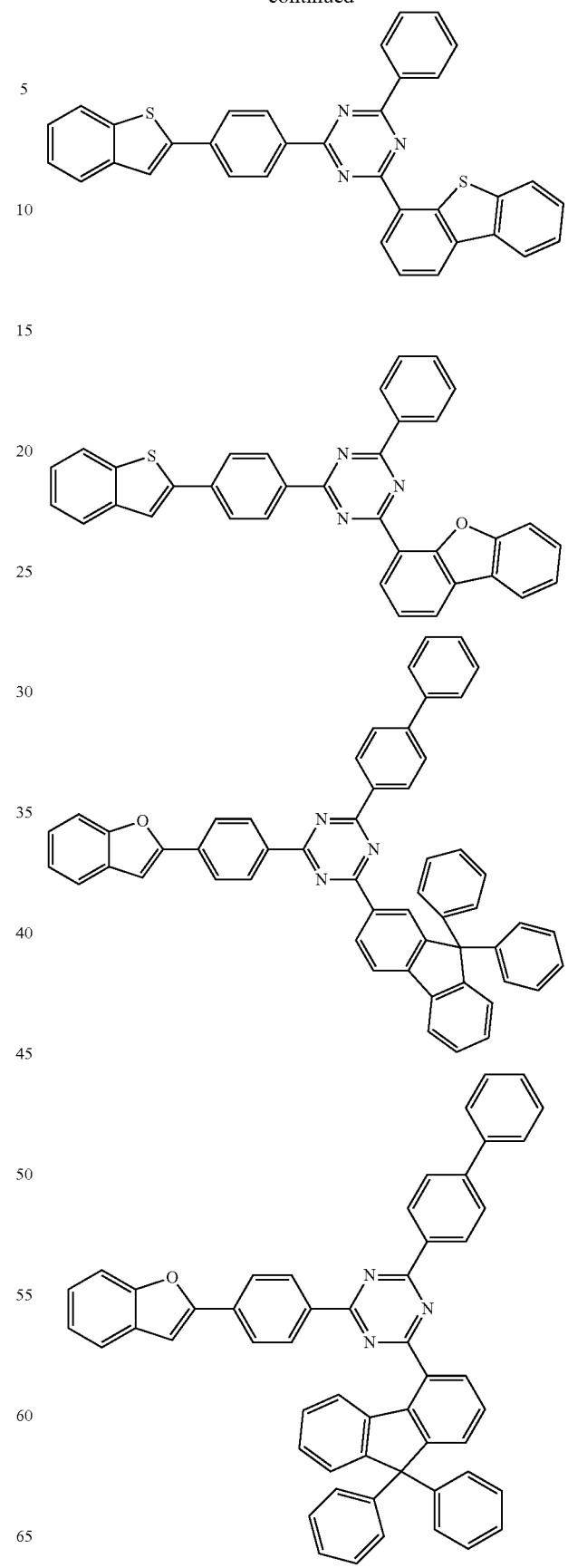

57
-continued
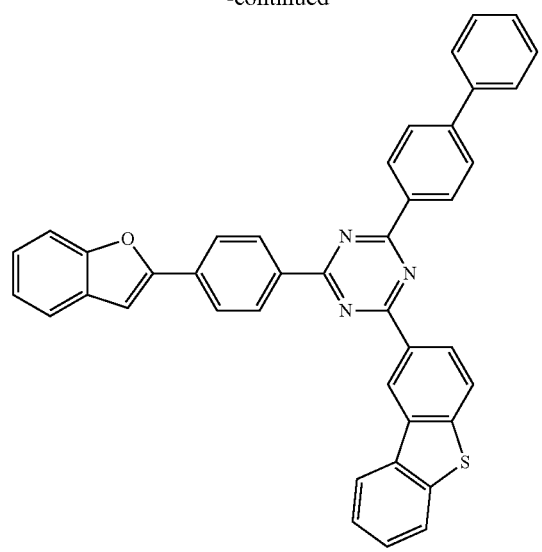
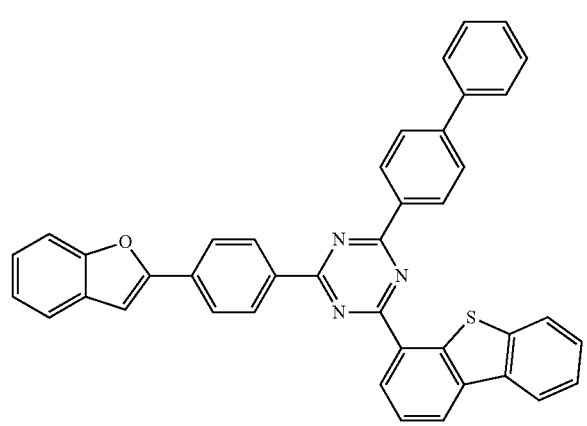
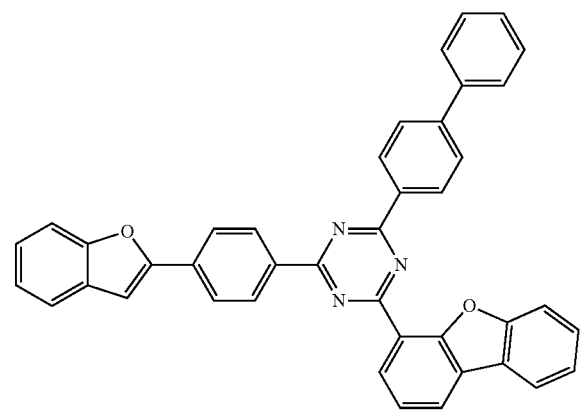
58
-continued
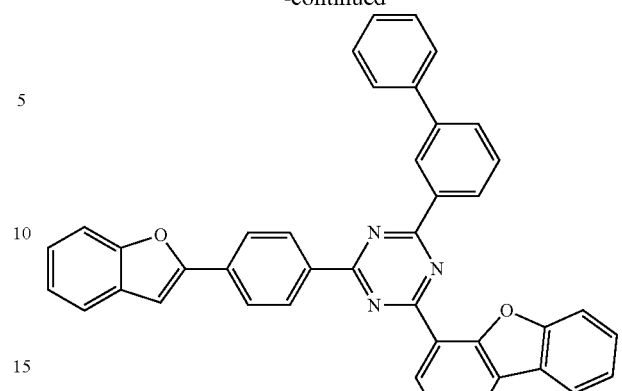
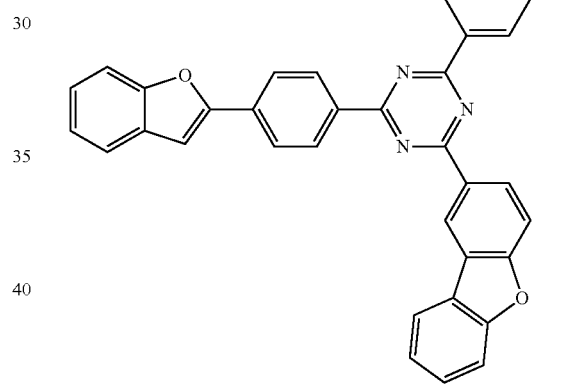
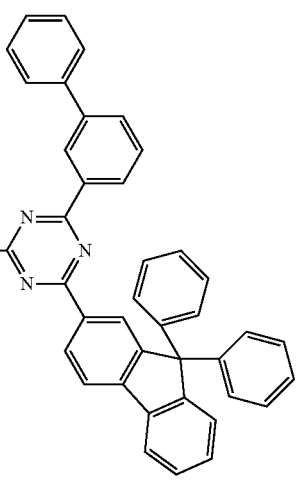

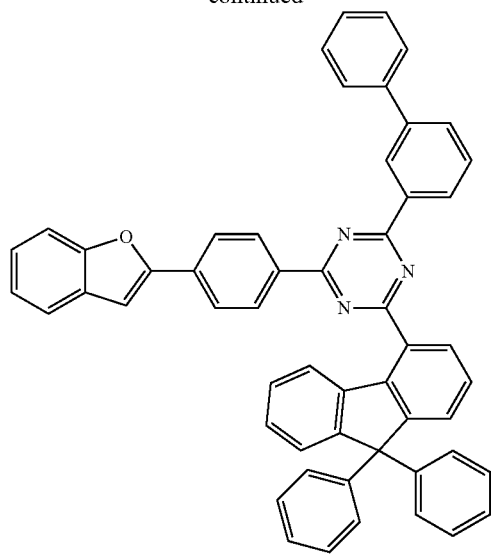
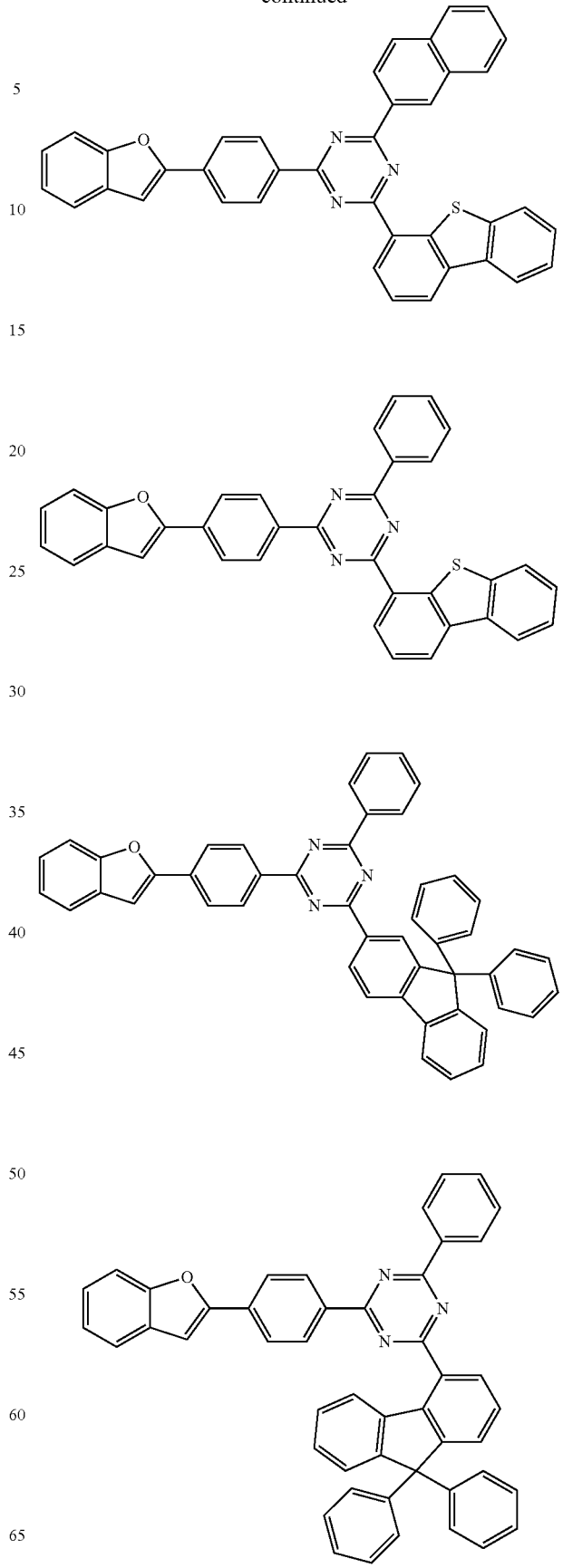

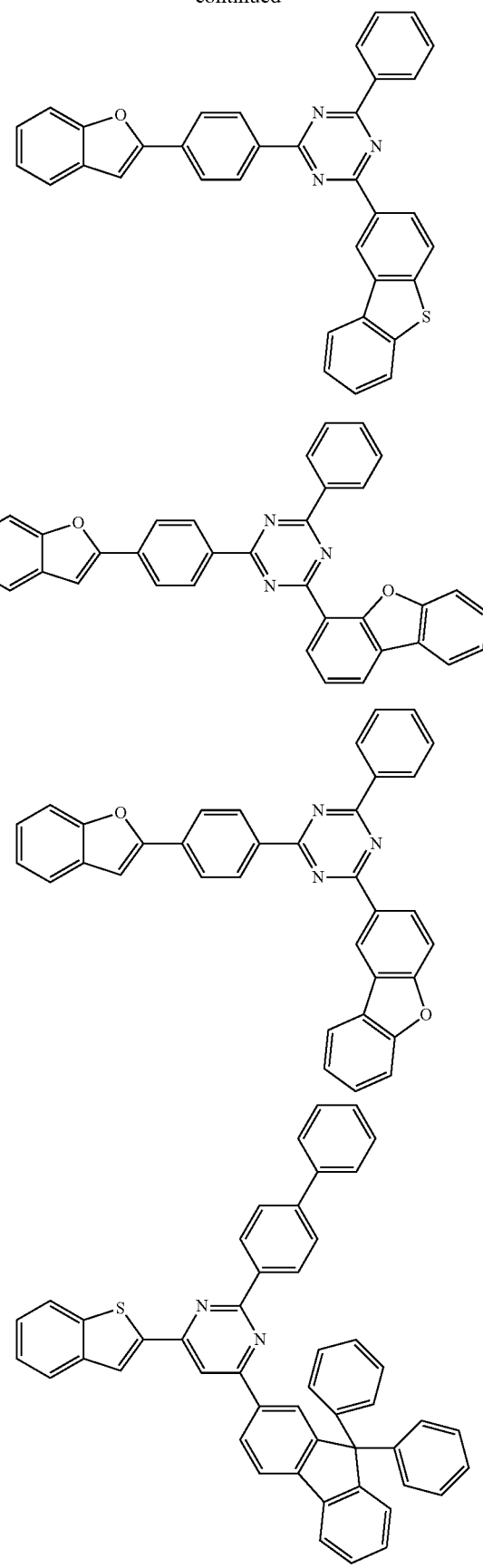
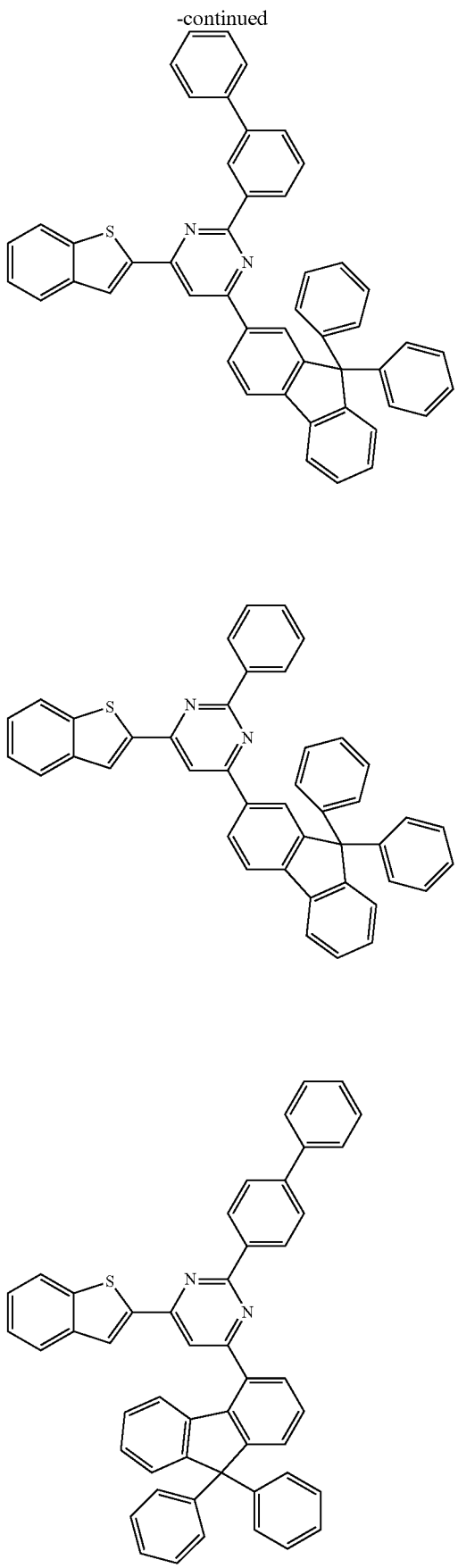

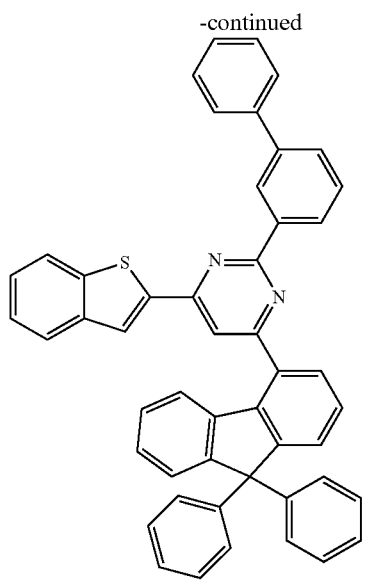
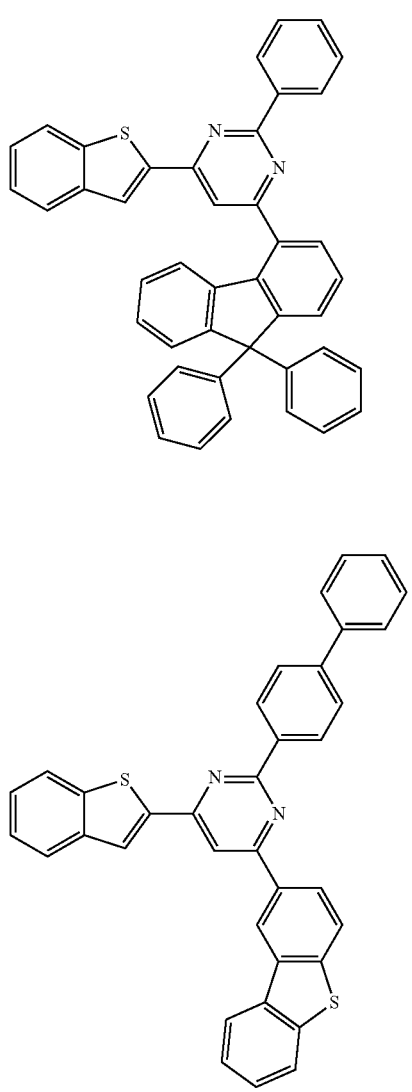
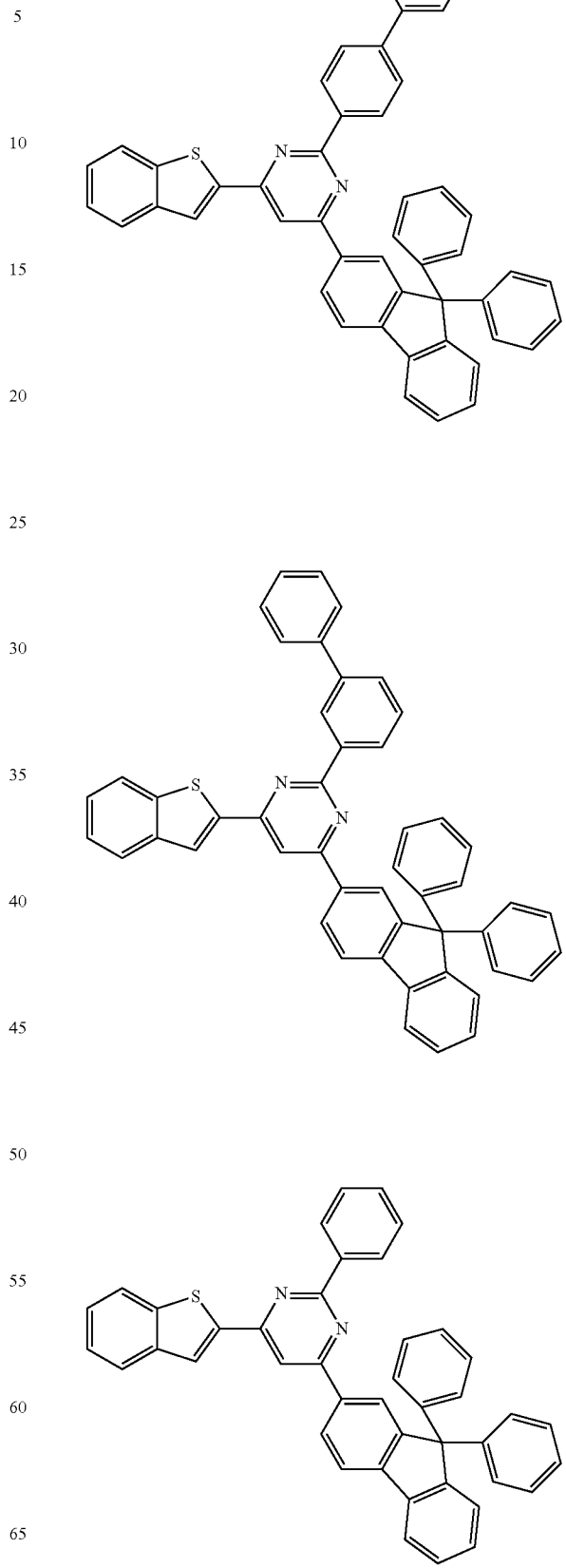

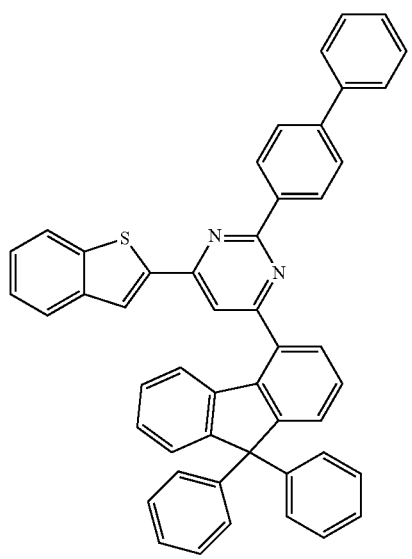
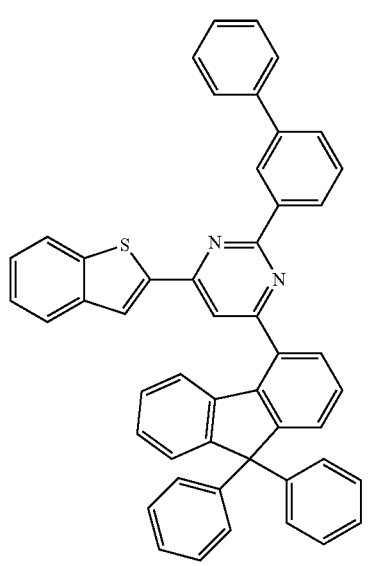
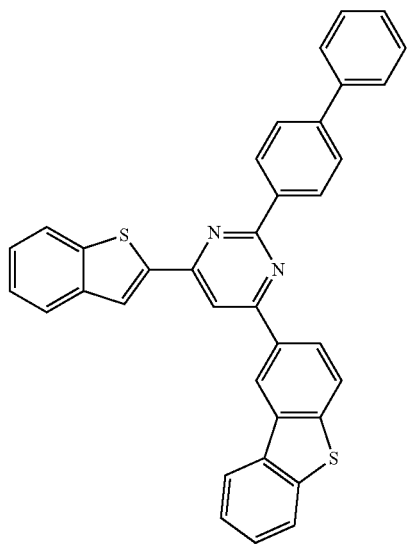
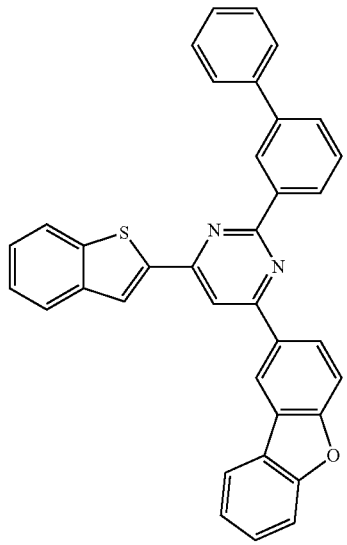
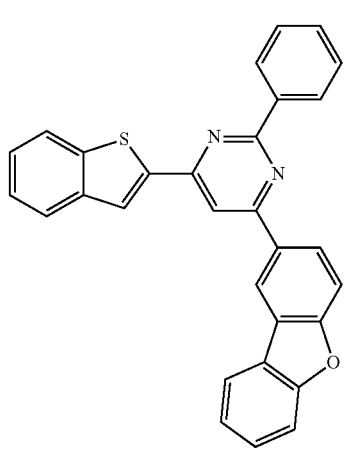

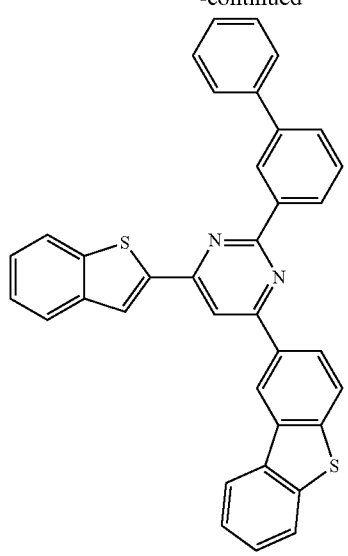
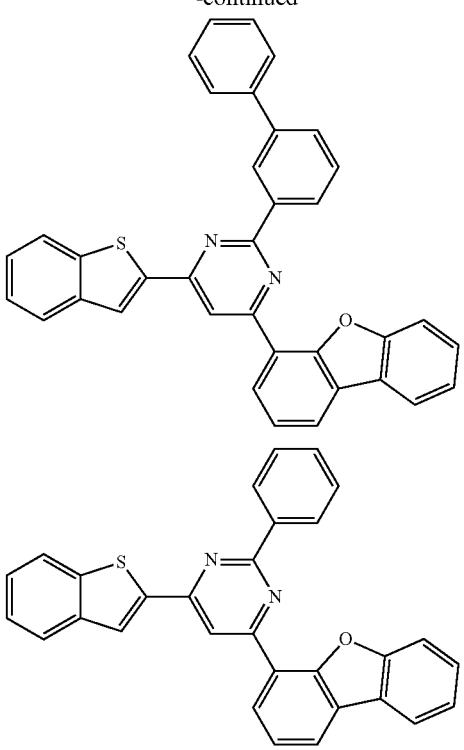
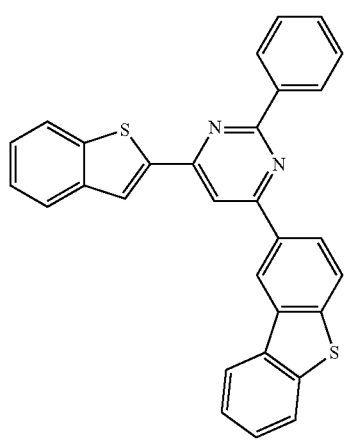
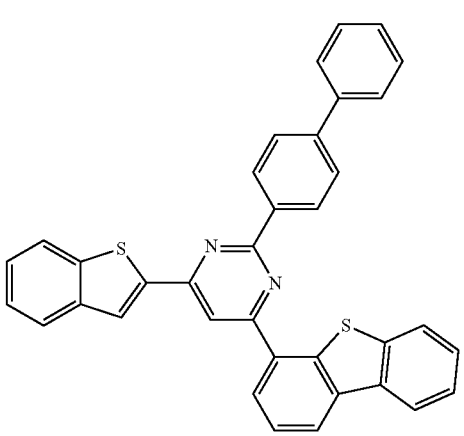
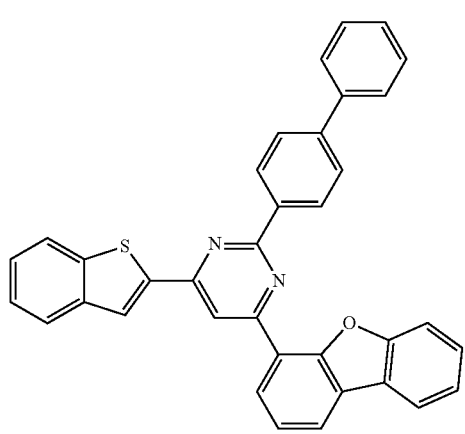
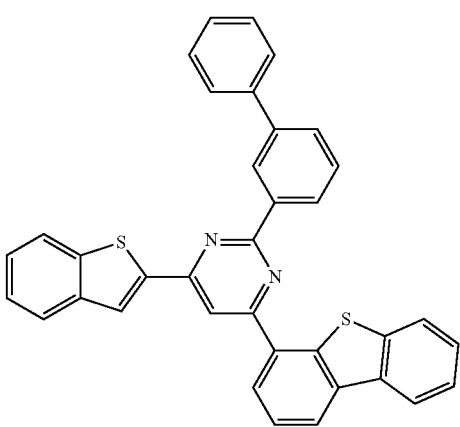

-continued

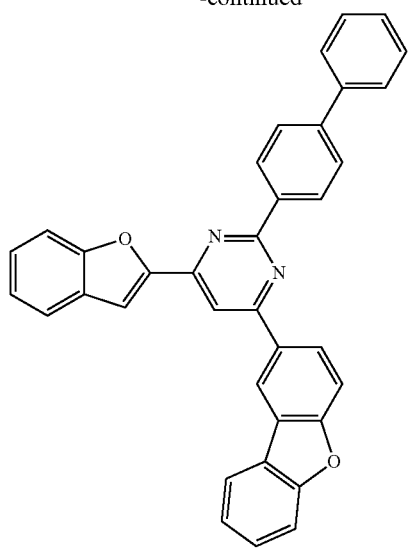
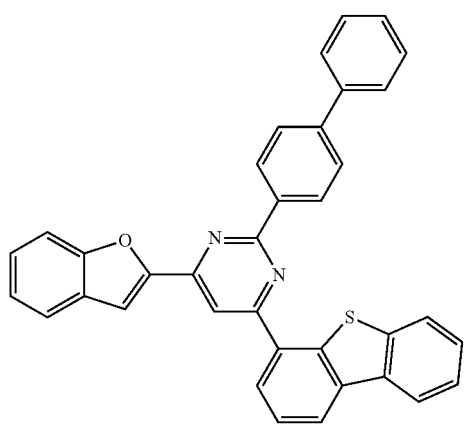
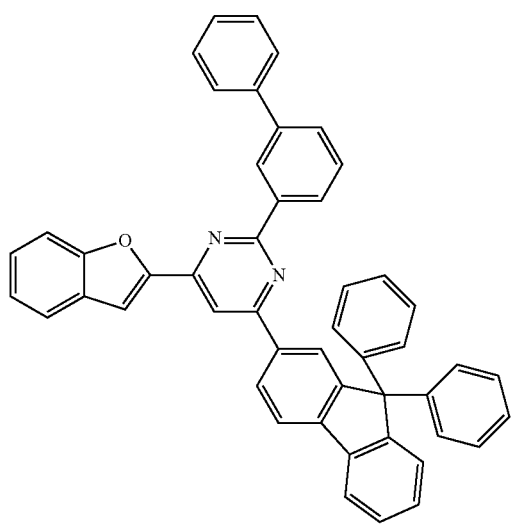
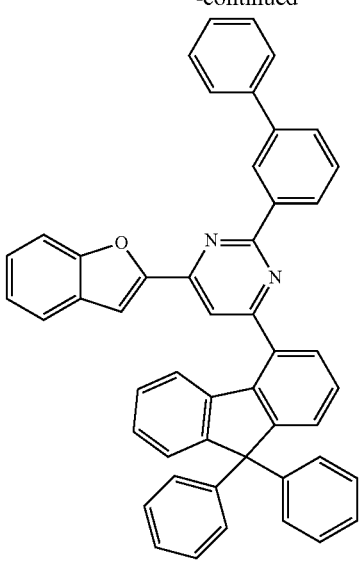
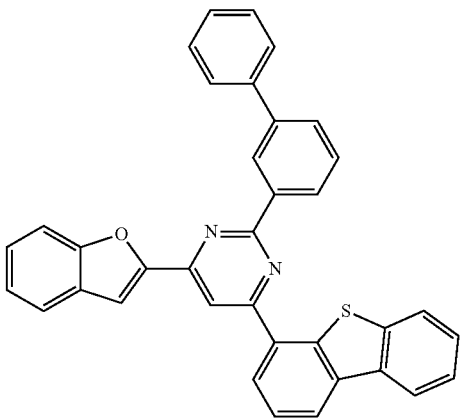
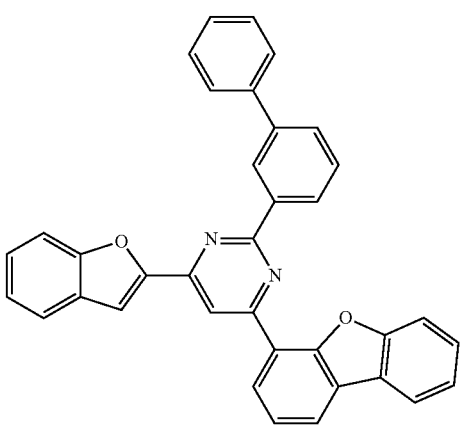

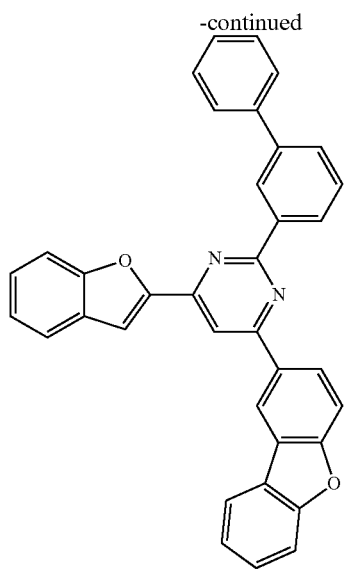
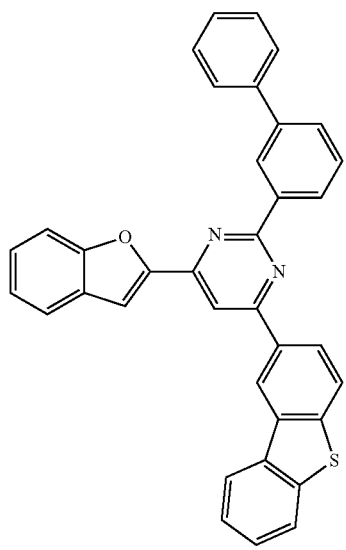
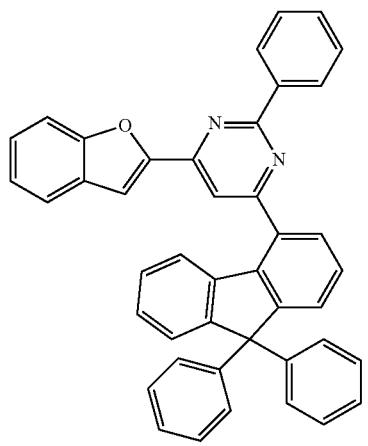
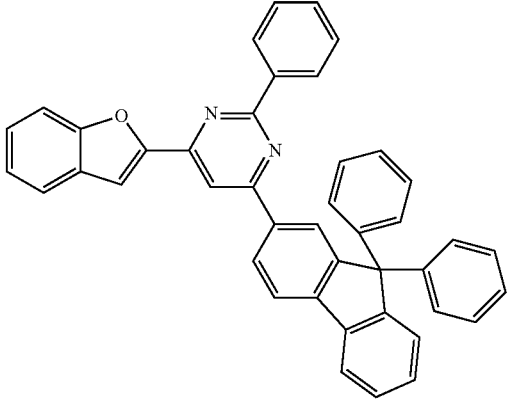
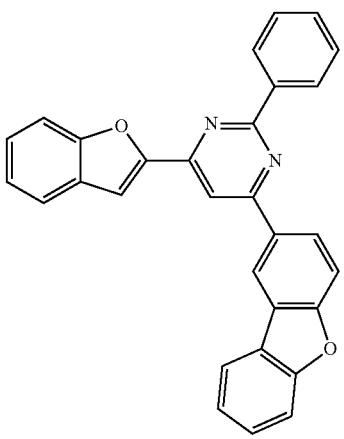
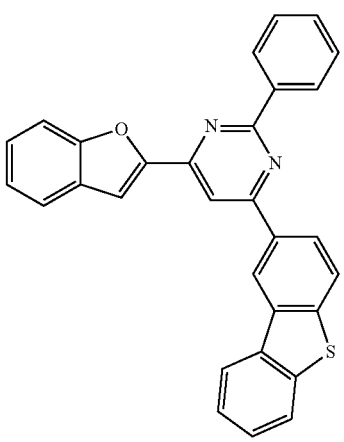
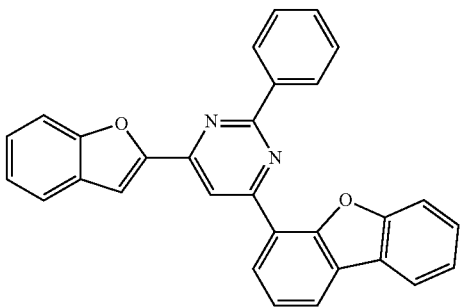

-continued
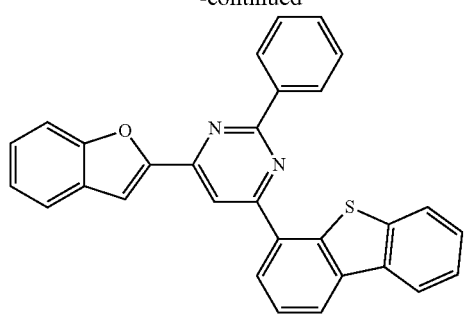
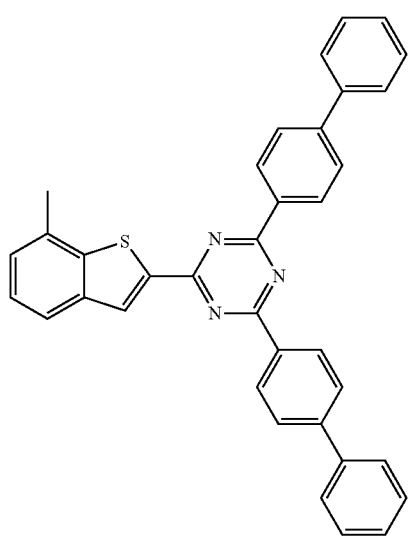
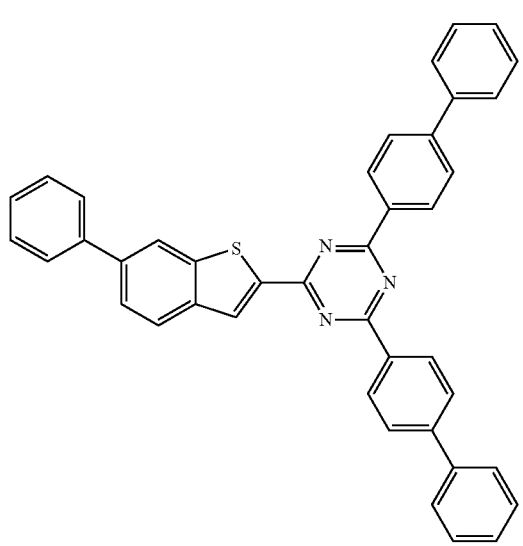
-continued
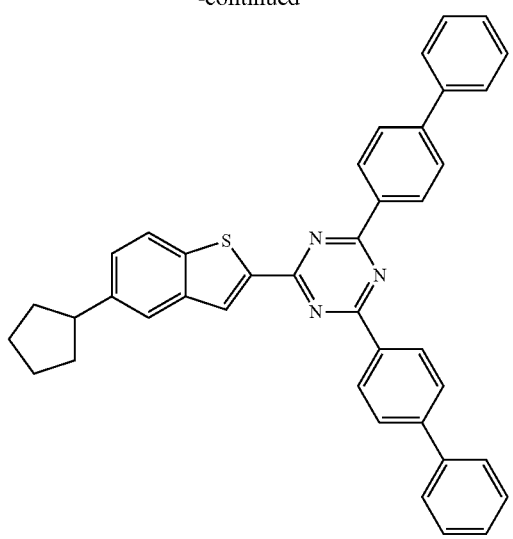
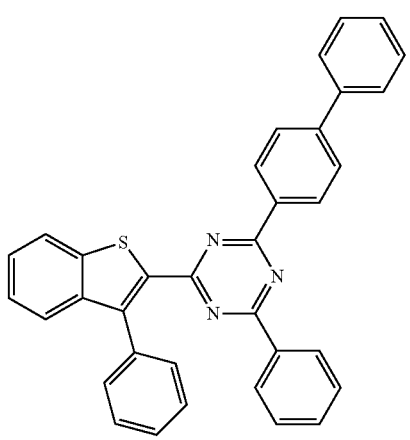
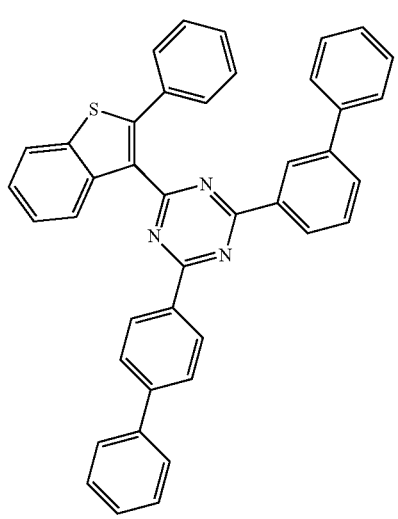

77
-continued
78
-continued
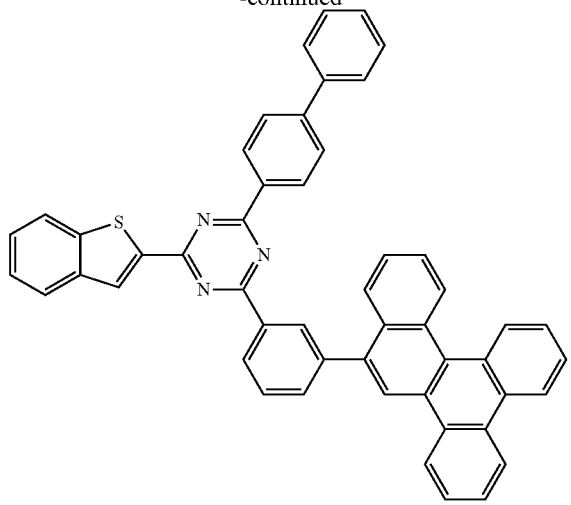
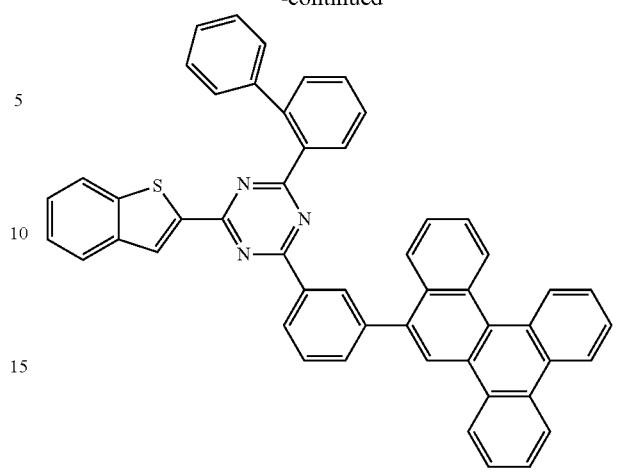
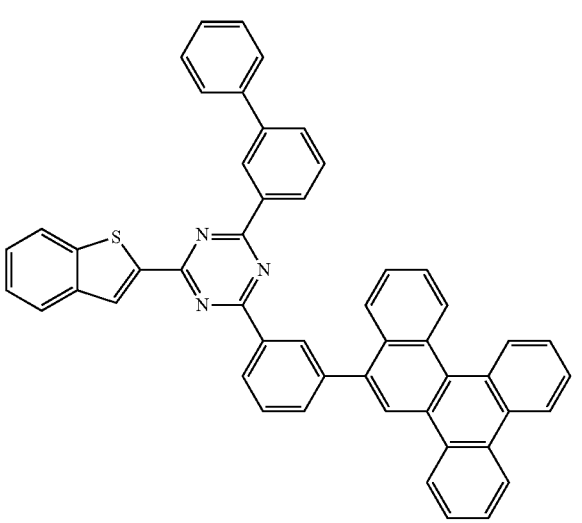
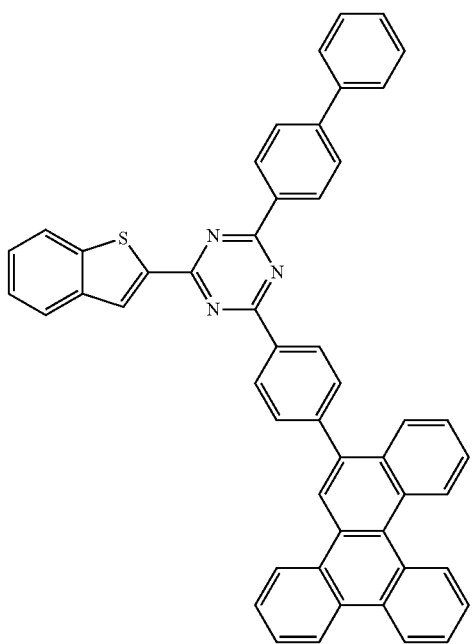

79
-continued
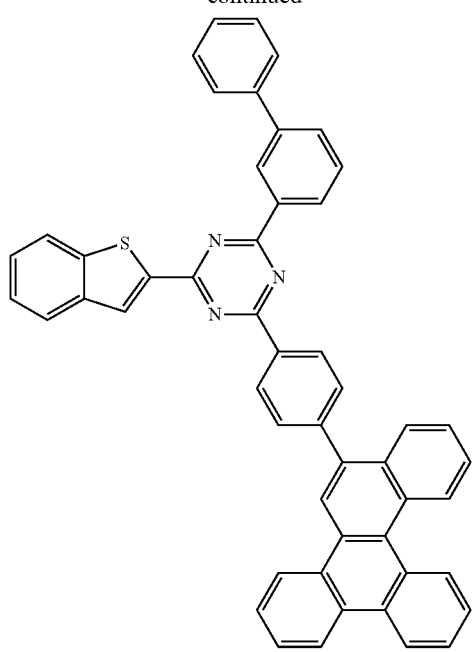
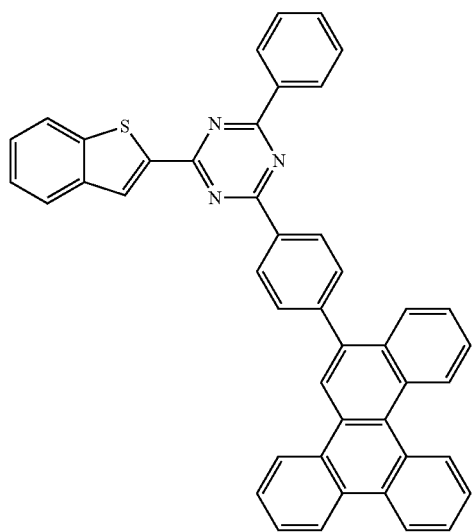
80
-continued
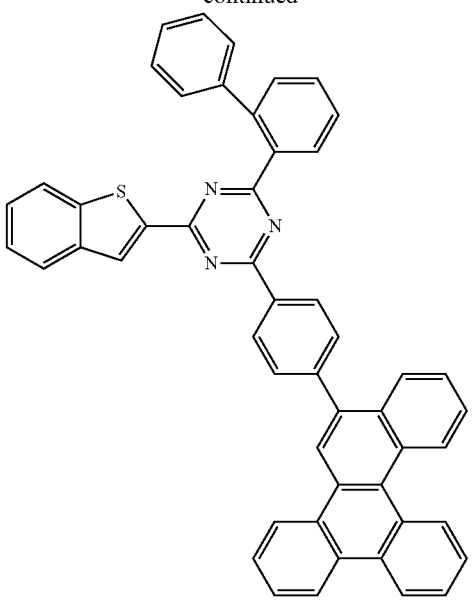
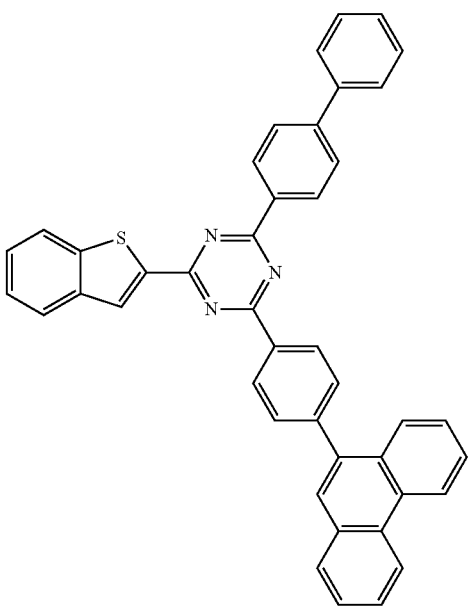

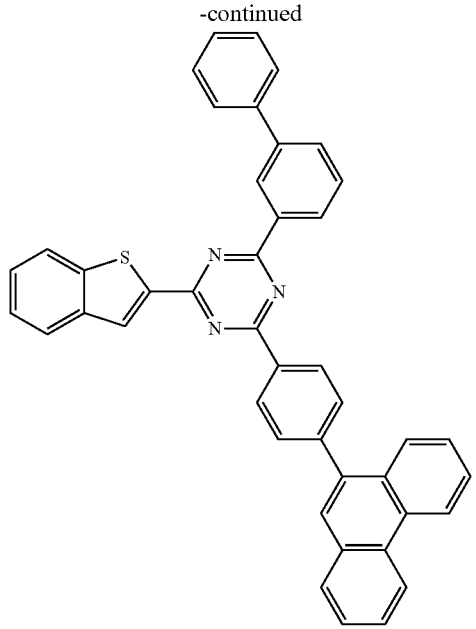
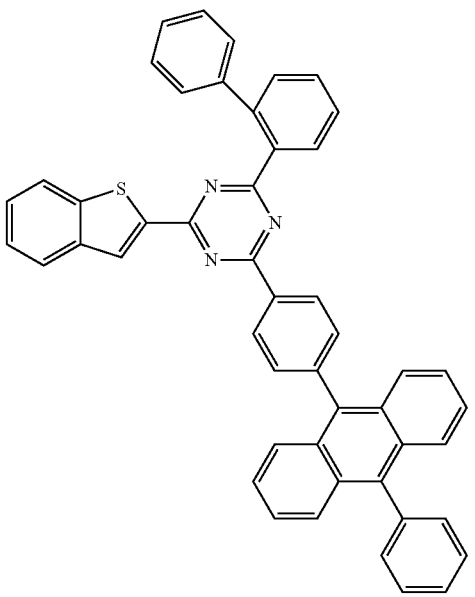
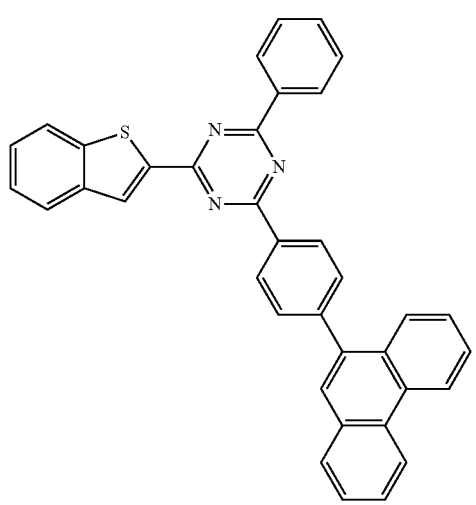
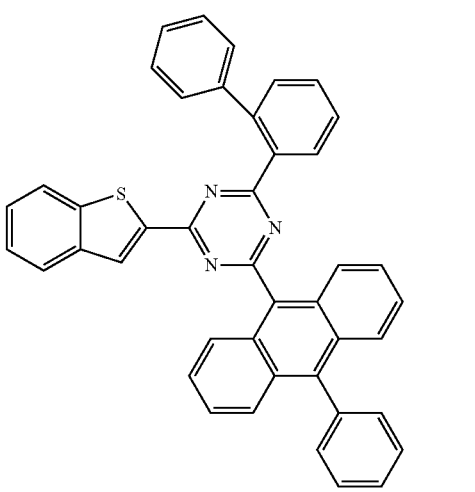
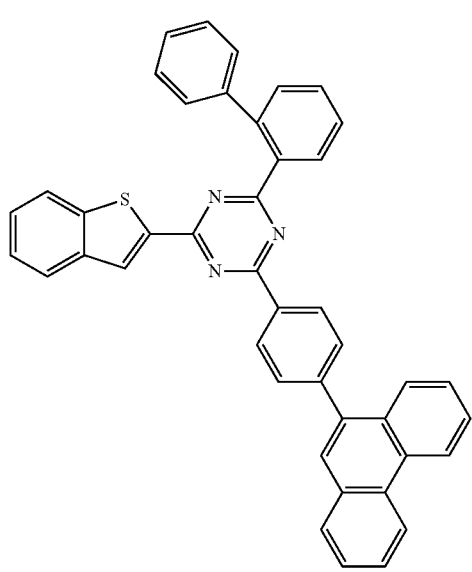
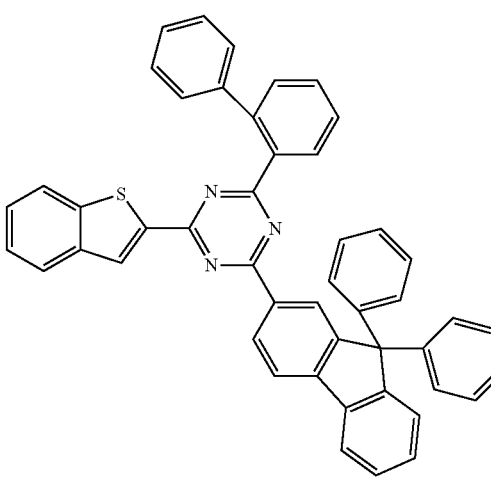

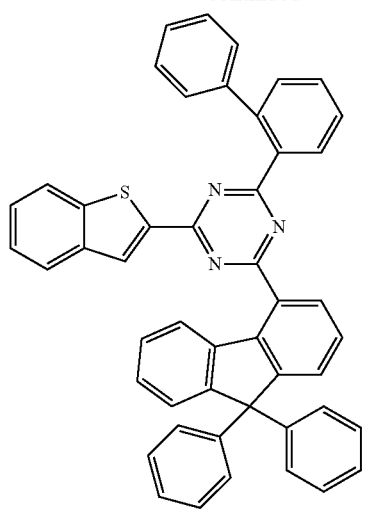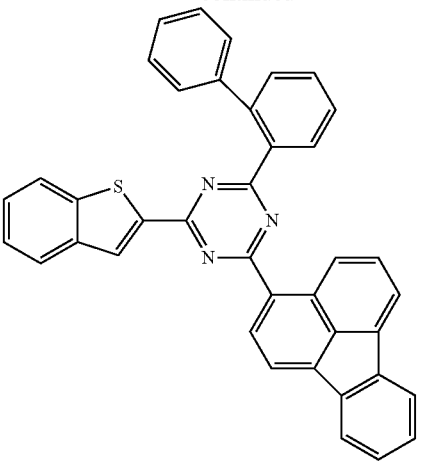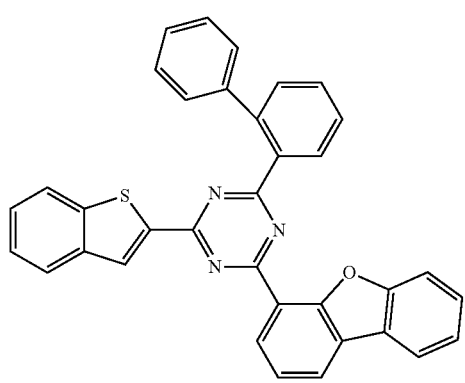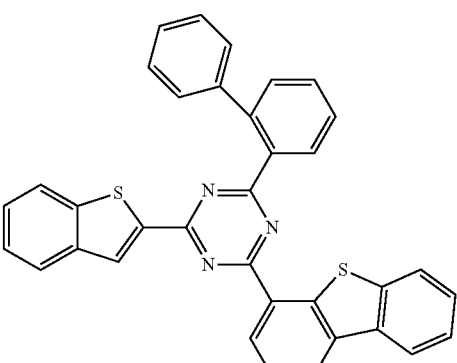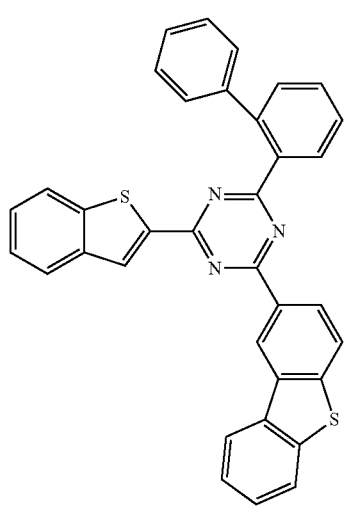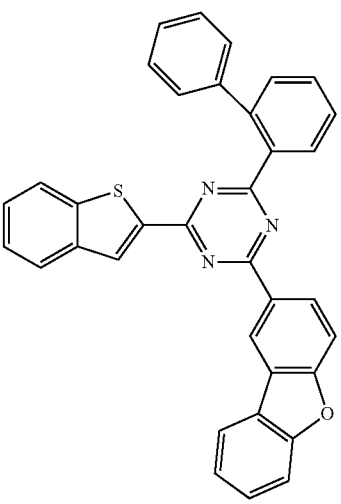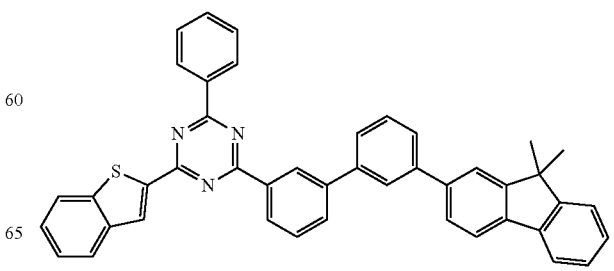

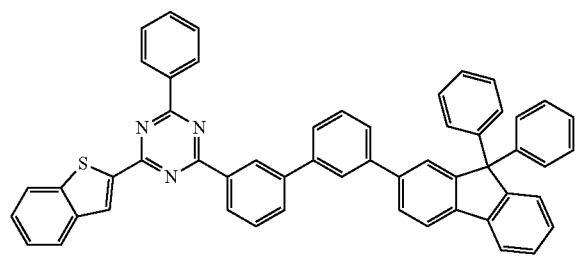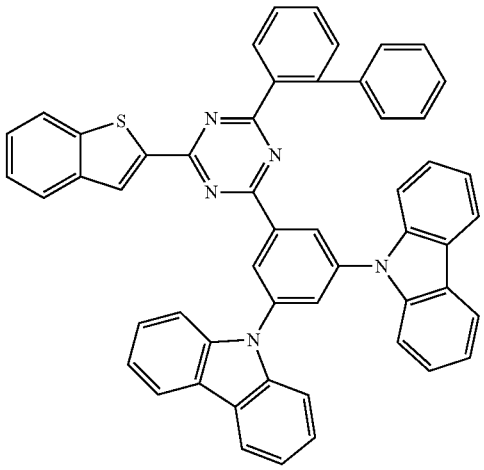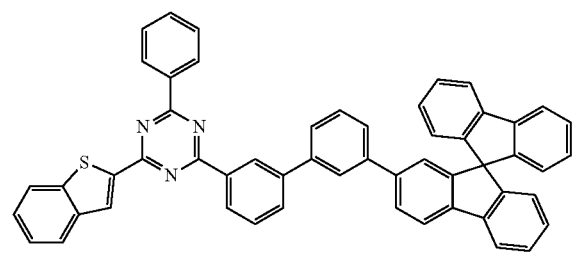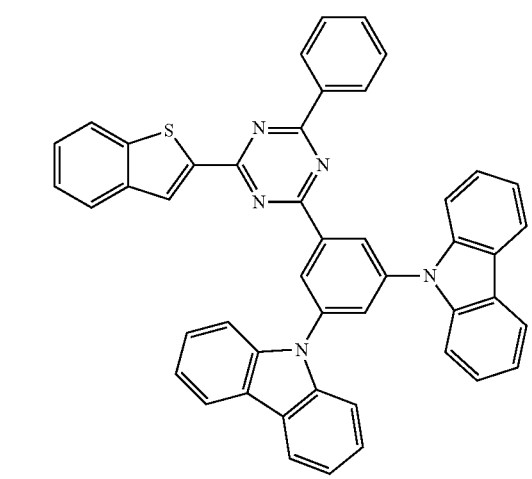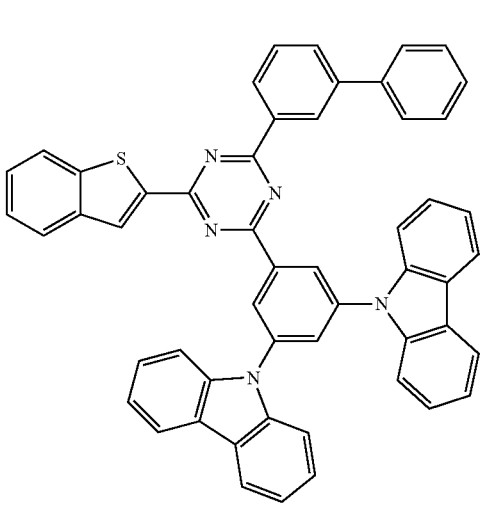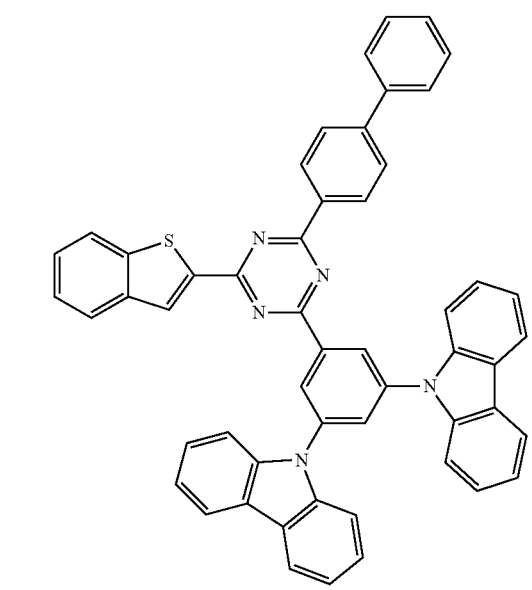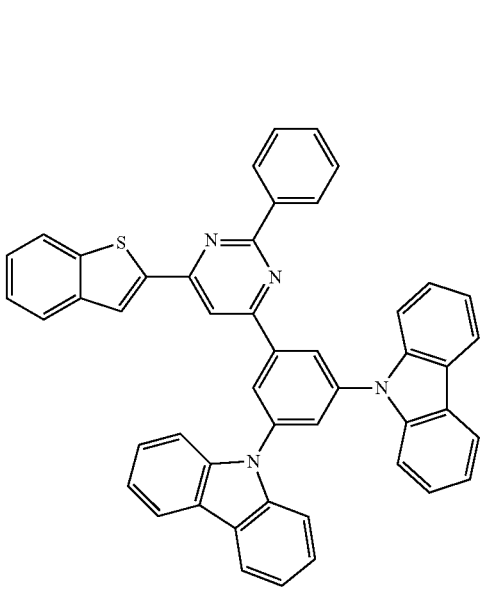

-continued
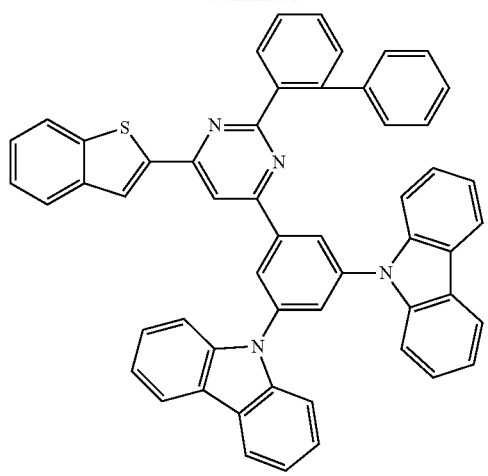
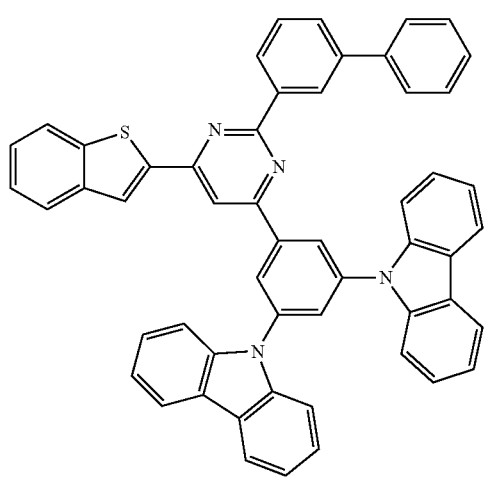
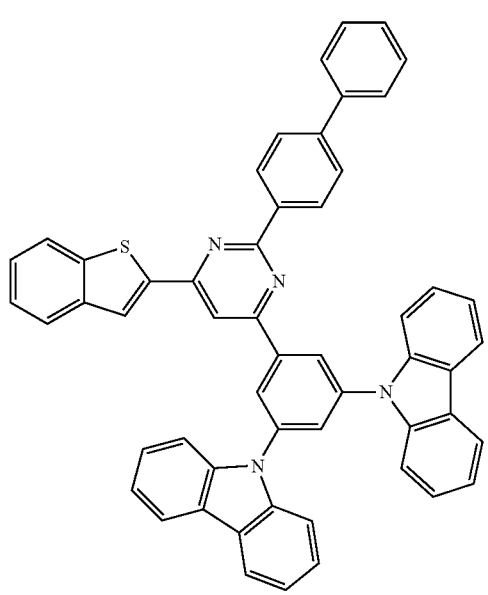
-continued
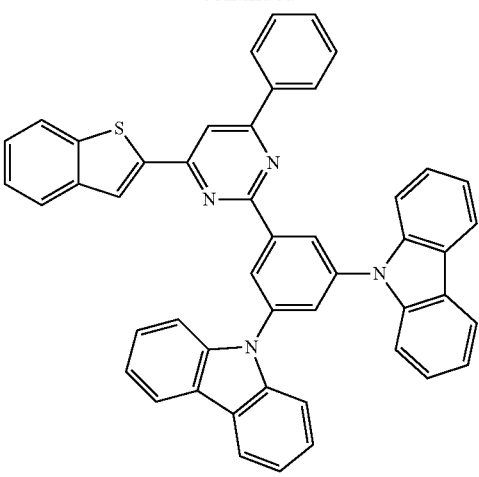
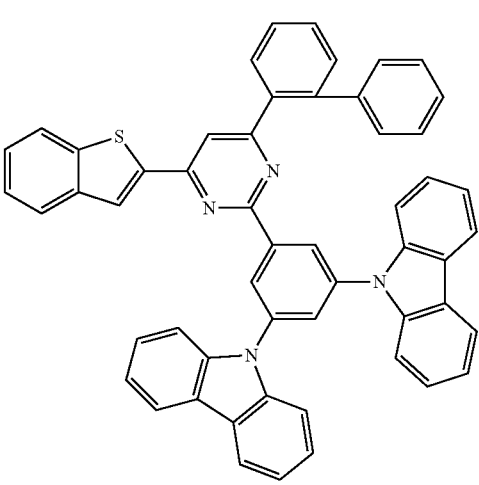
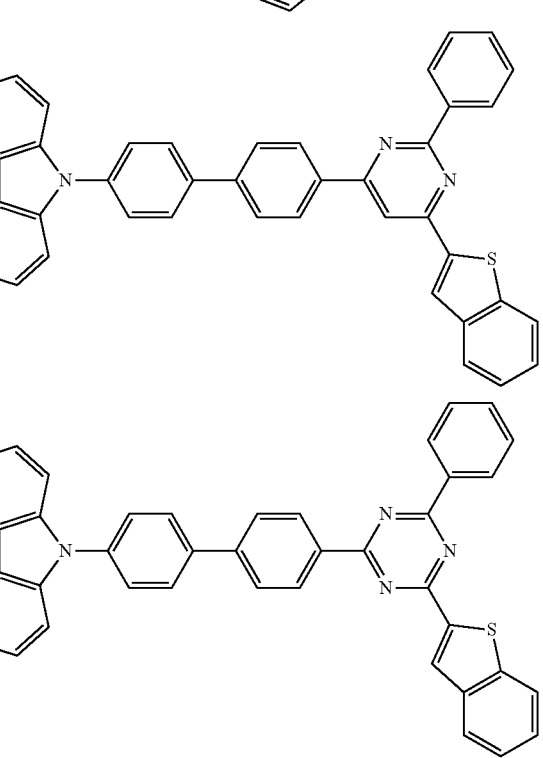

-continued
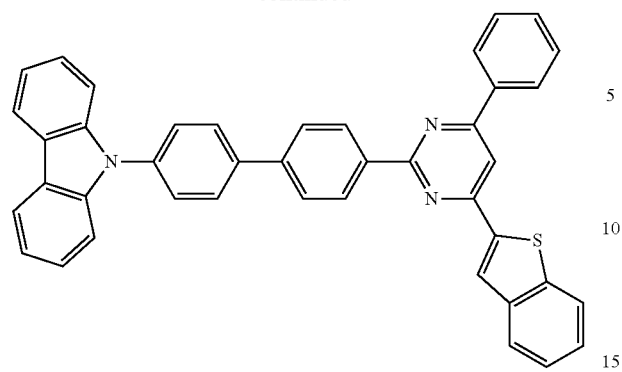
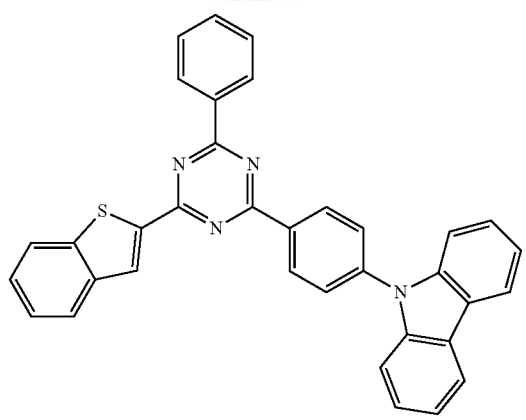
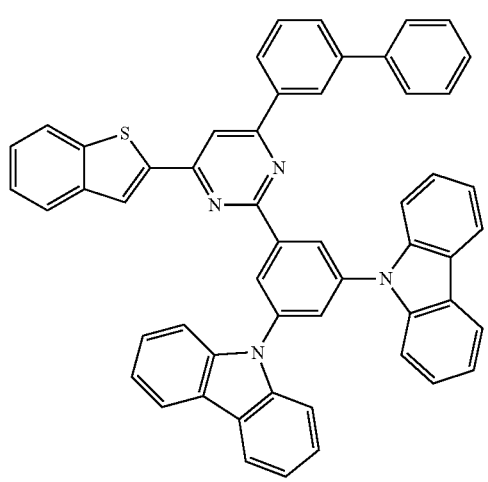
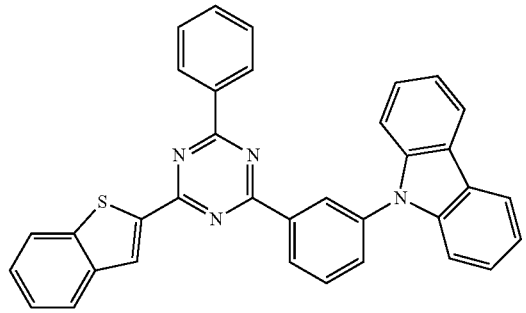
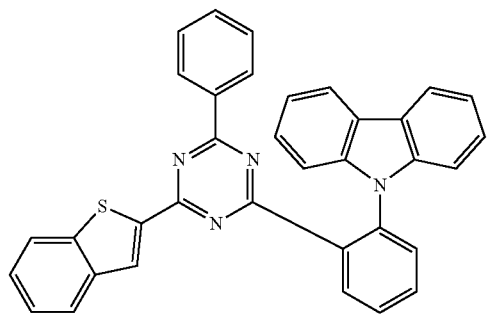
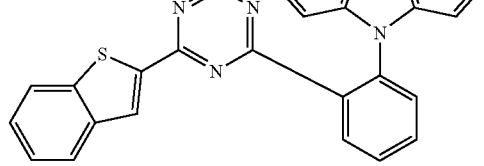
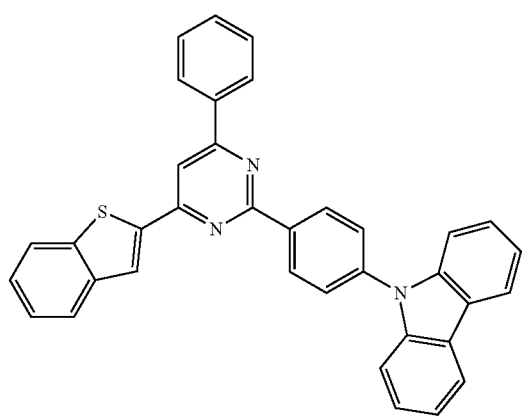

-continued
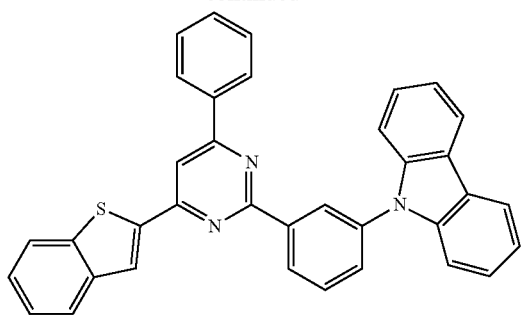
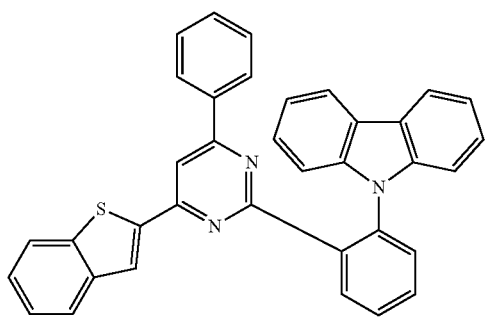
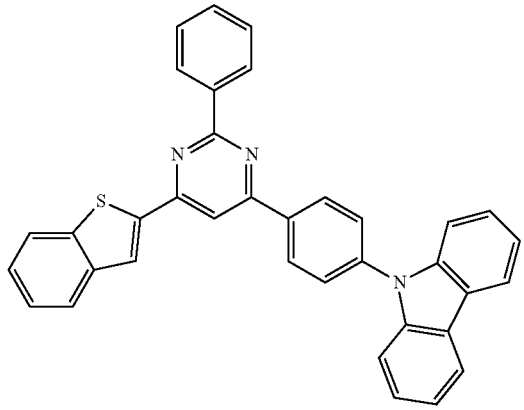
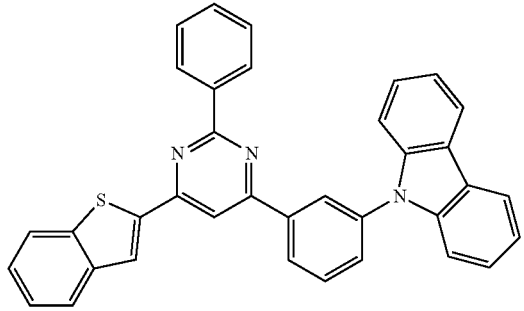
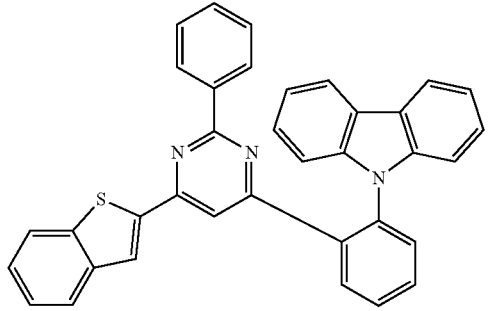
-continued
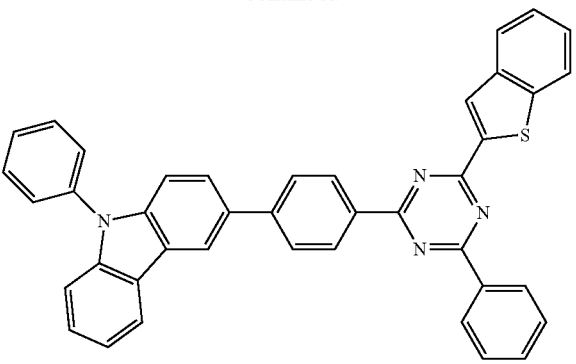
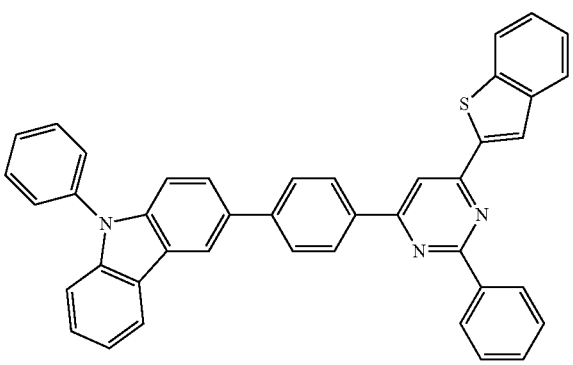
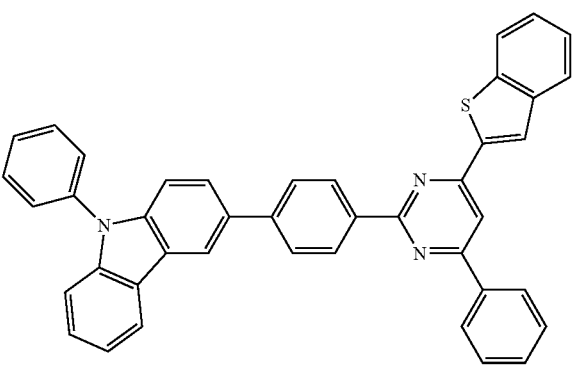
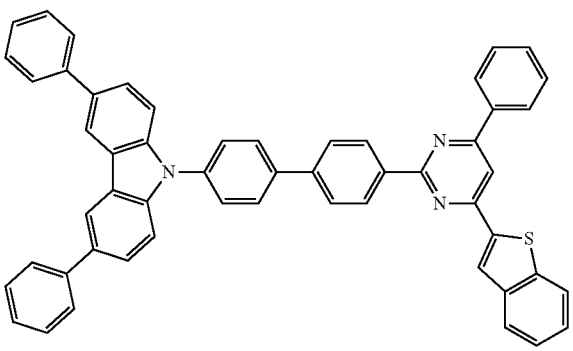

93
-continued
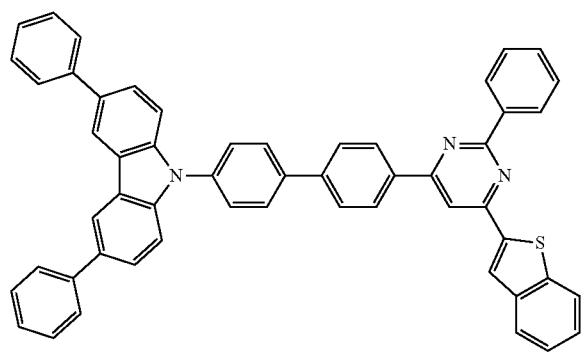
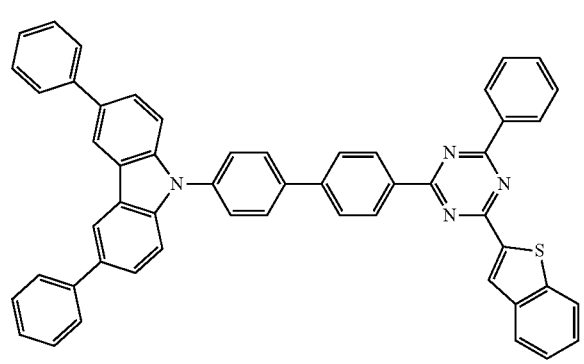
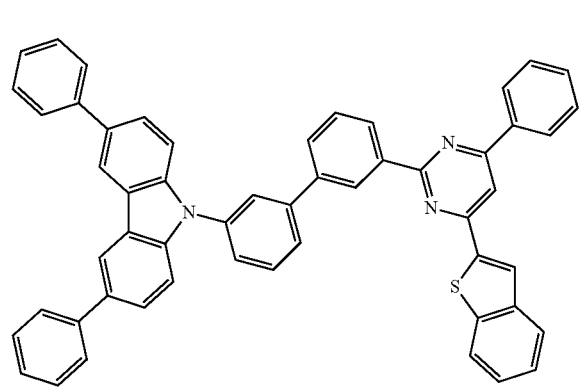
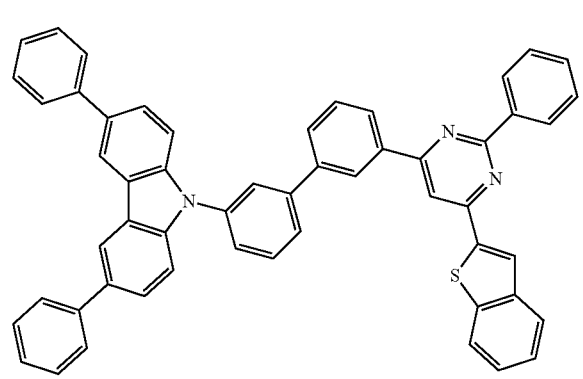
94
-continued
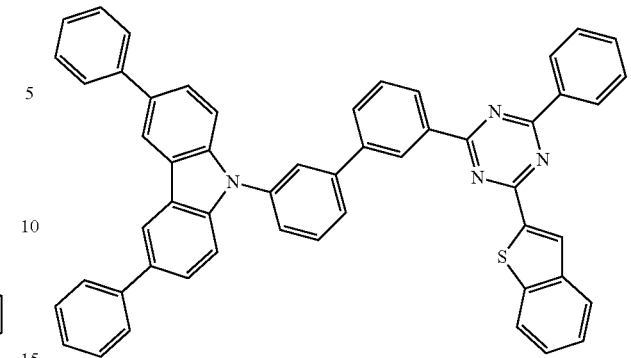
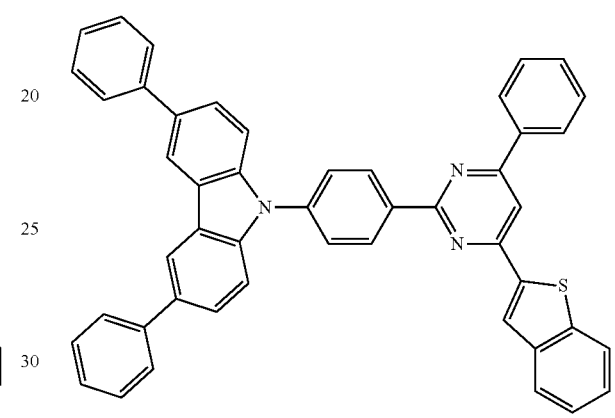
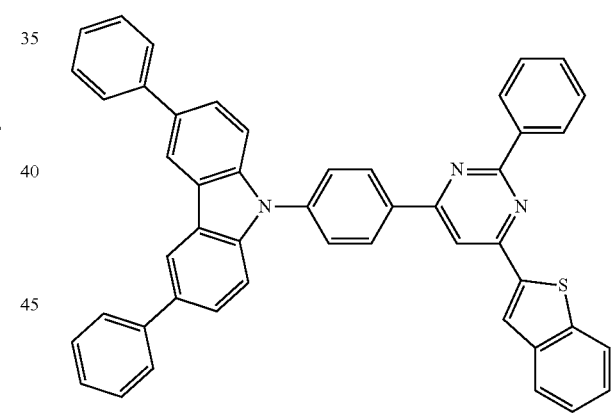
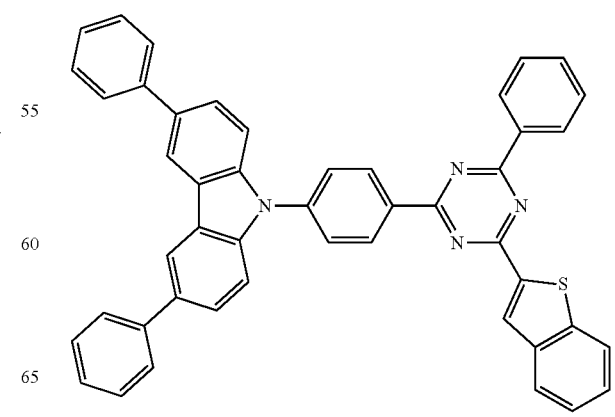

95
-continued
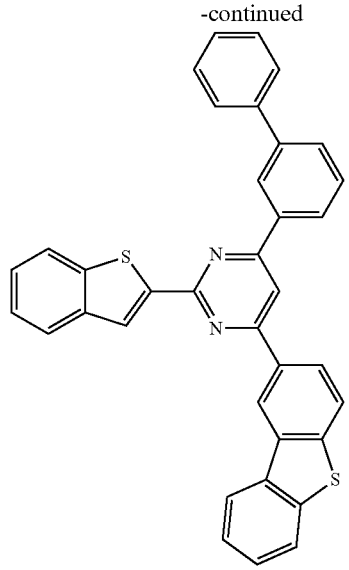
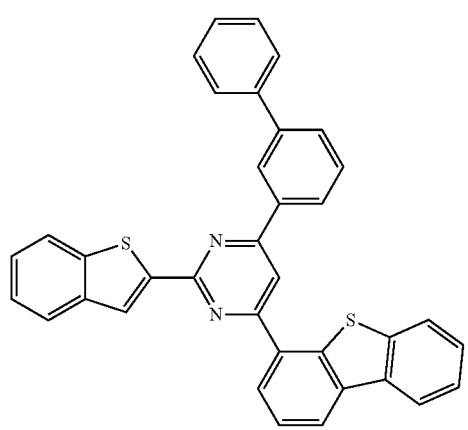
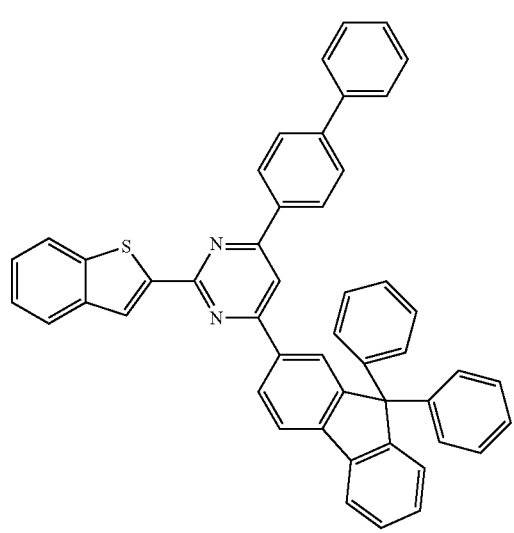
96
-continued
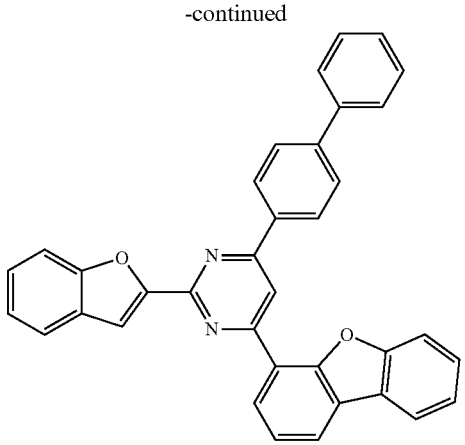
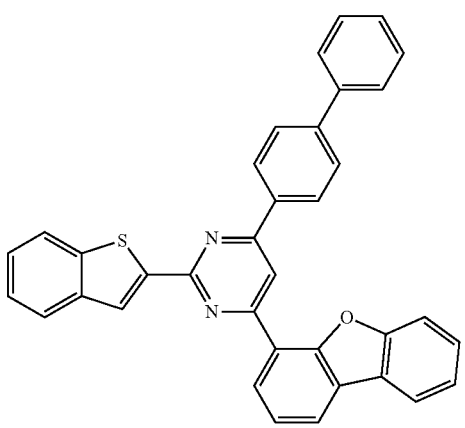
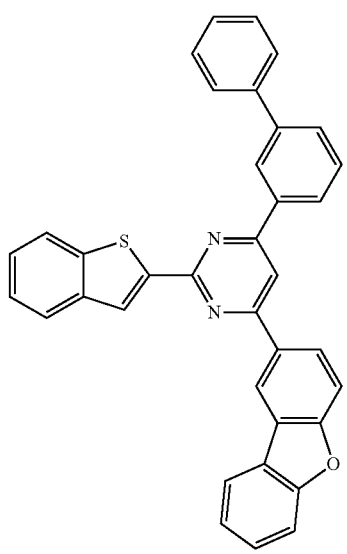

-continued
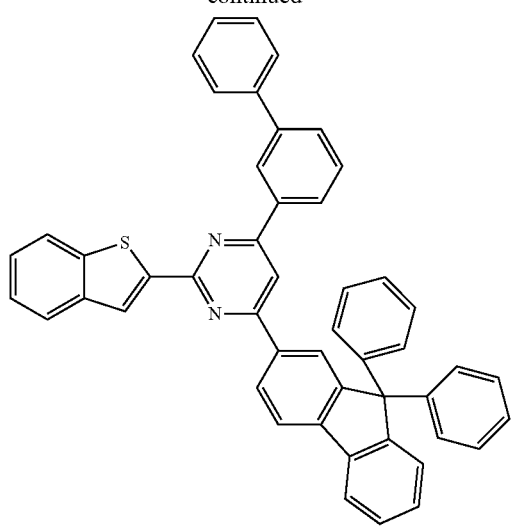
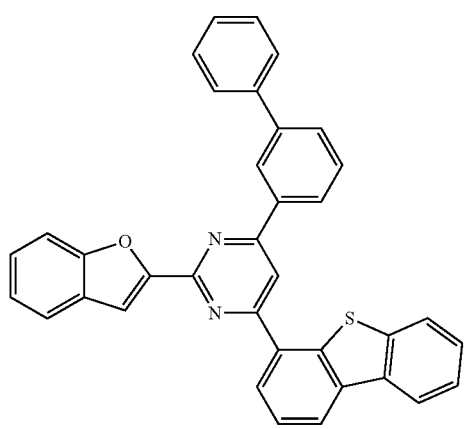
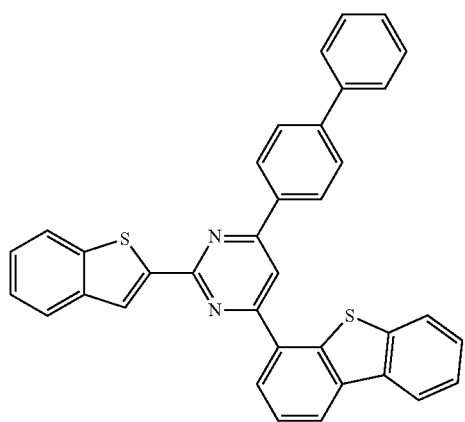
-continued
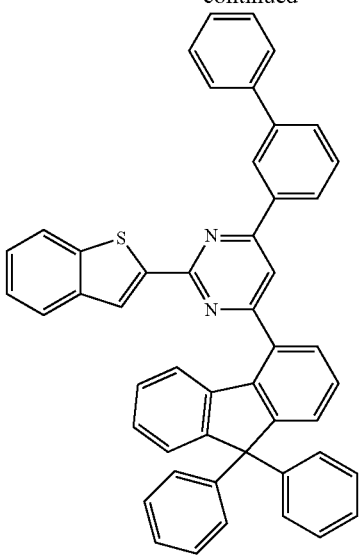
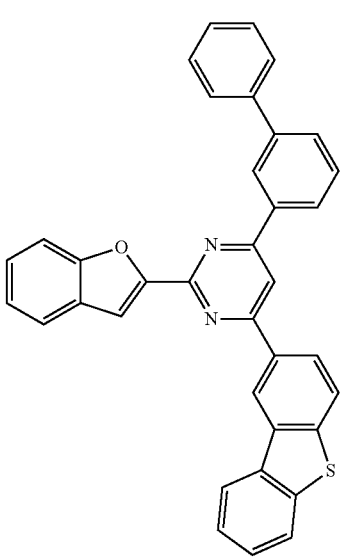
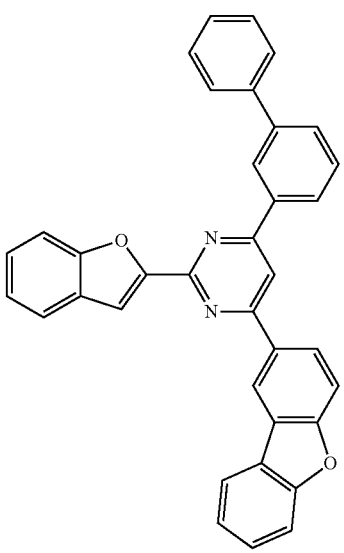

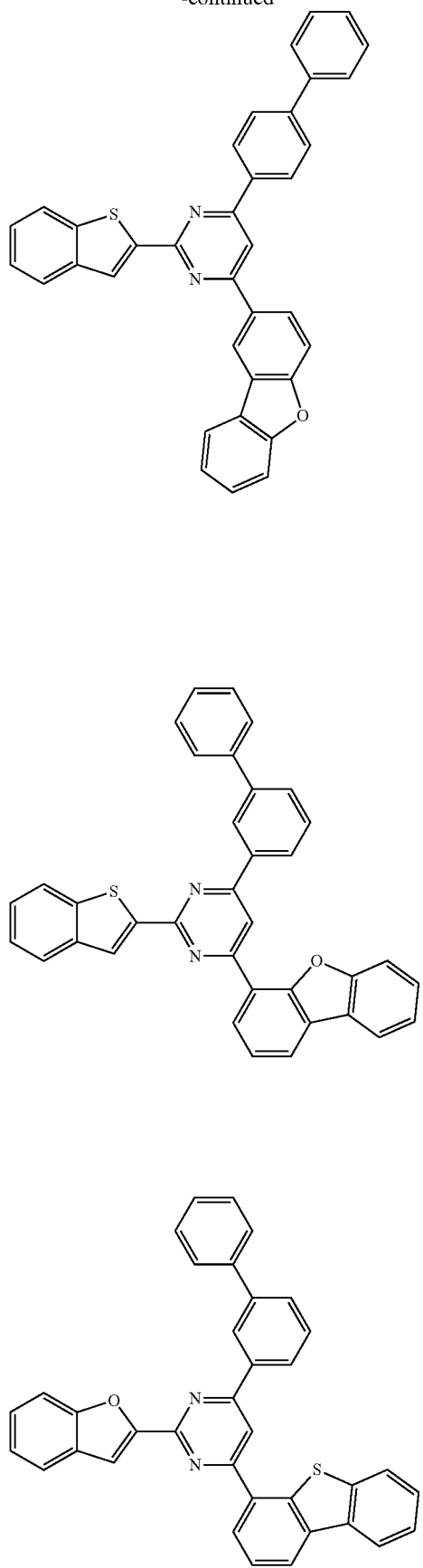

101
-continued
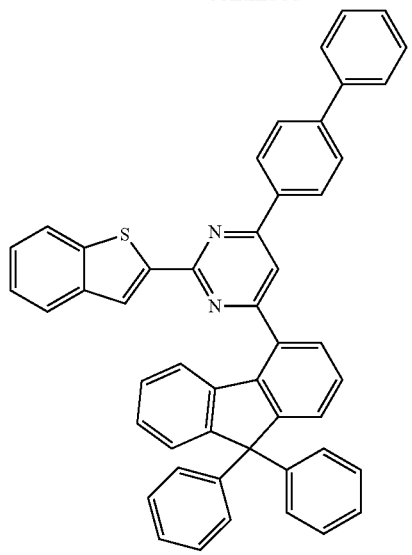
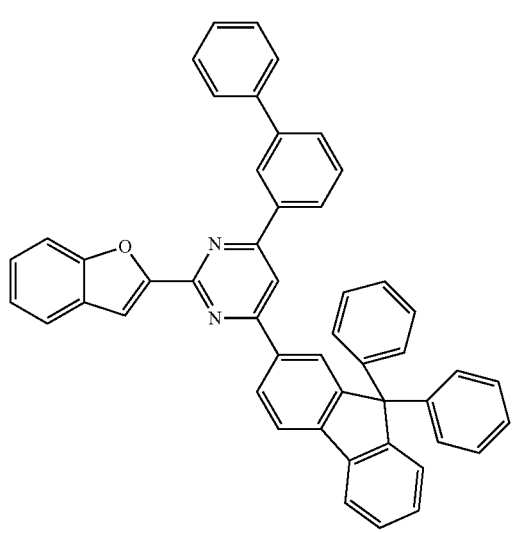
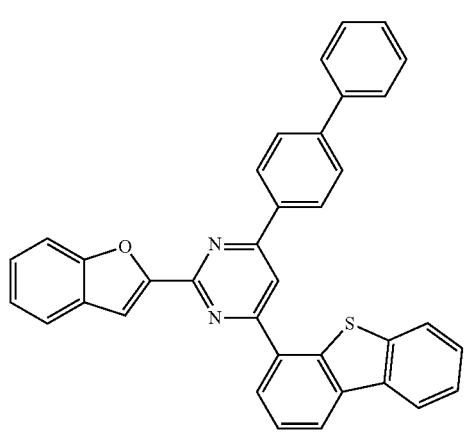
102
-continued
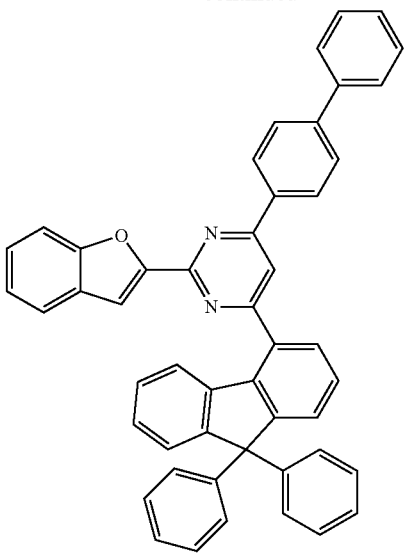
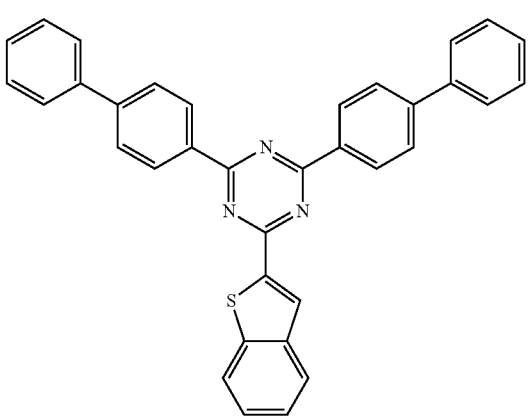
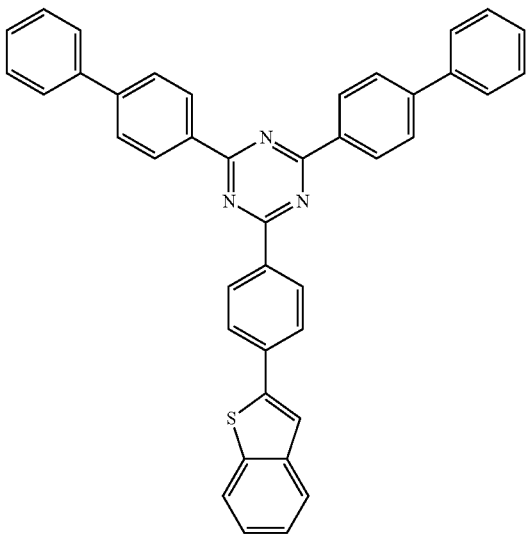

103
-continued
104
-continued
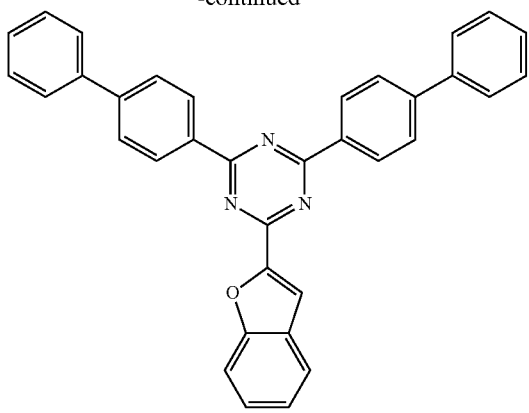
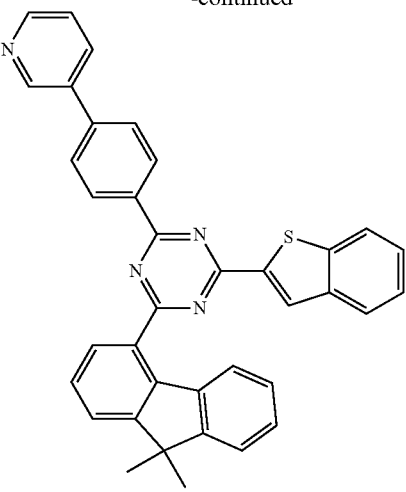
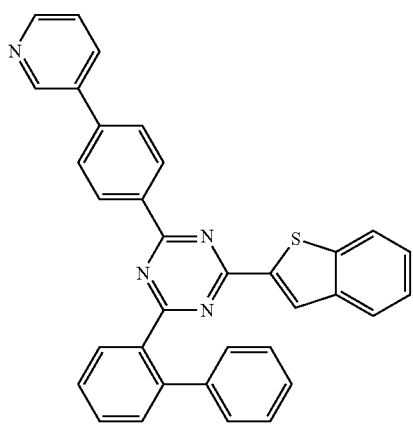
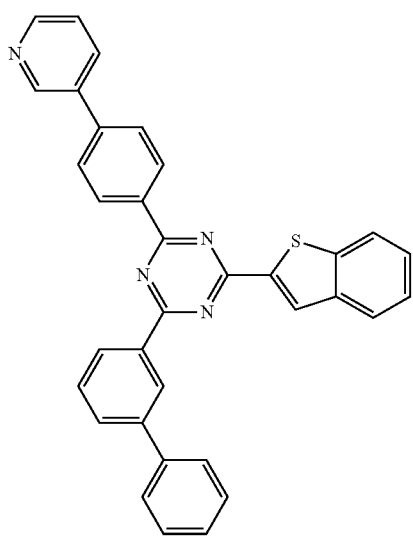
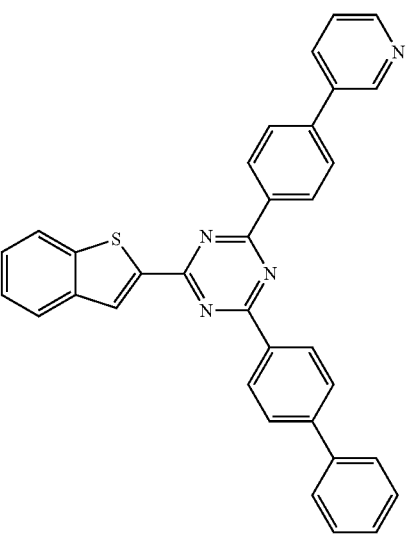

-continued
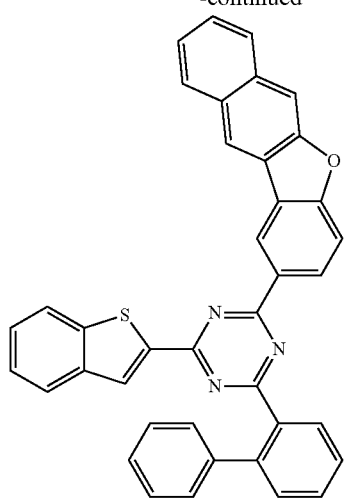
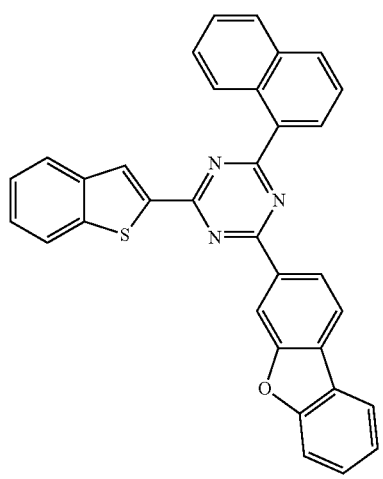
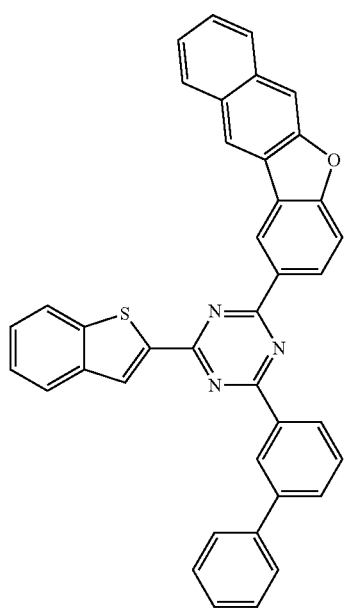
-continued
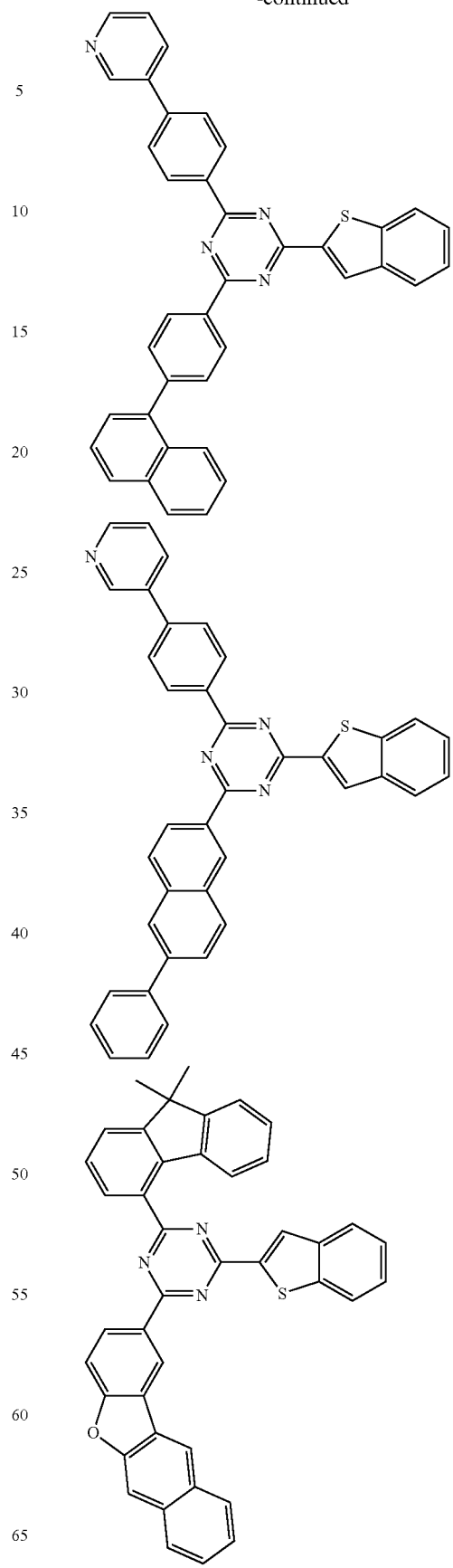

107
-continued
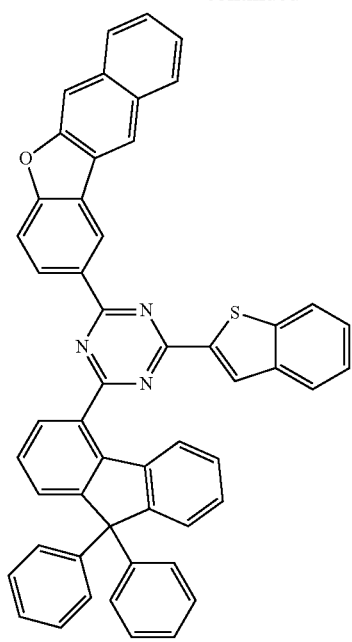
108
-continued
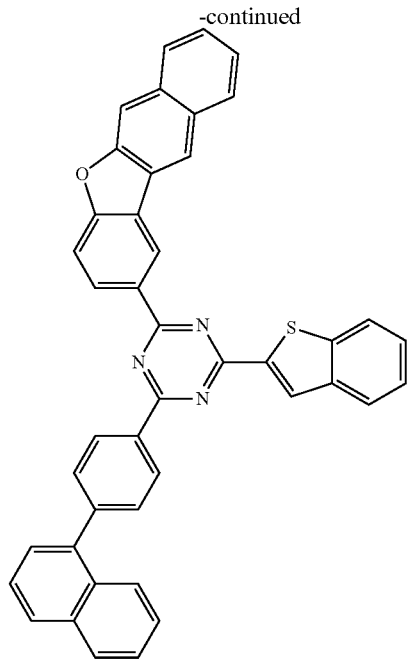
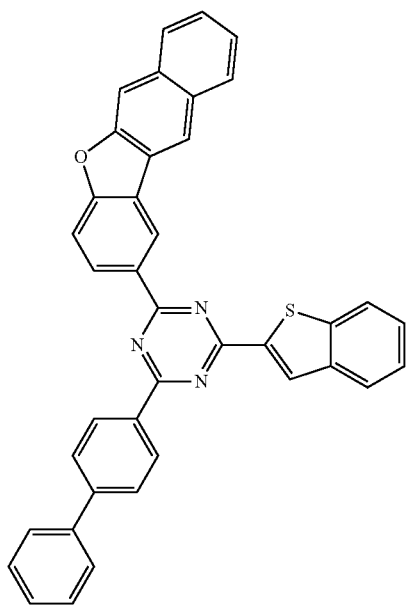
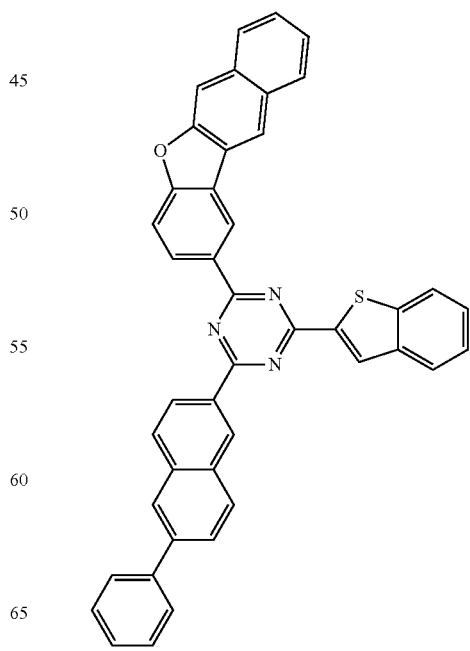

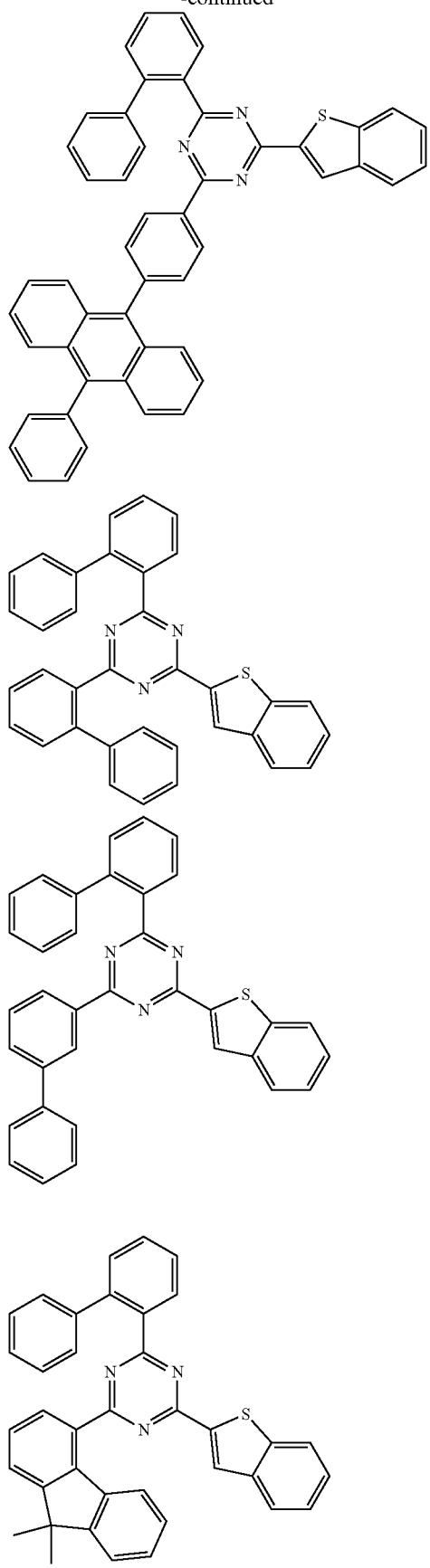
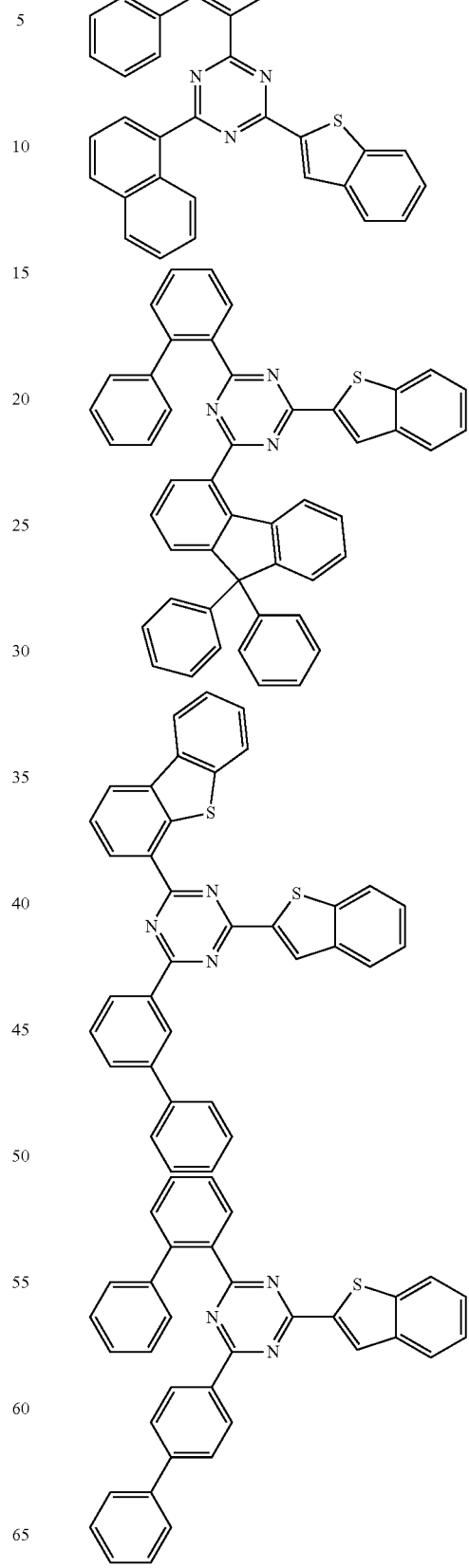

111
-continued
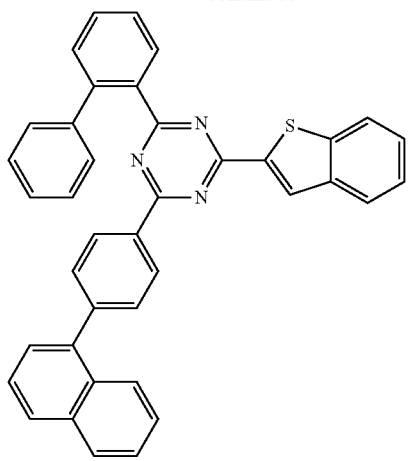
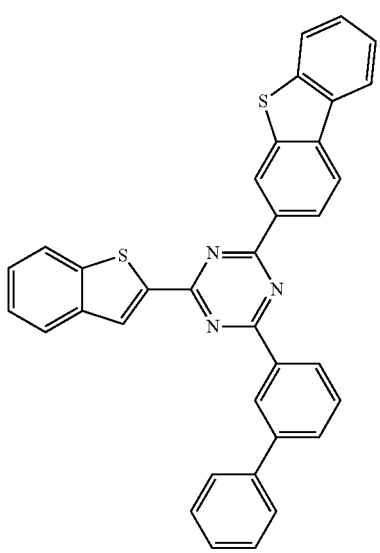
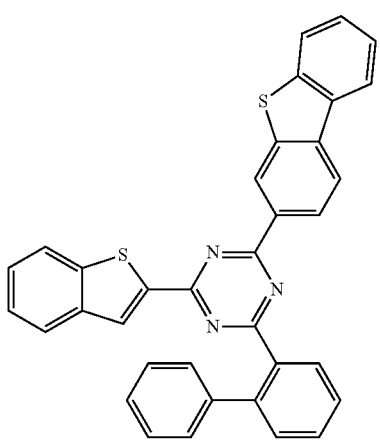
112
-continued
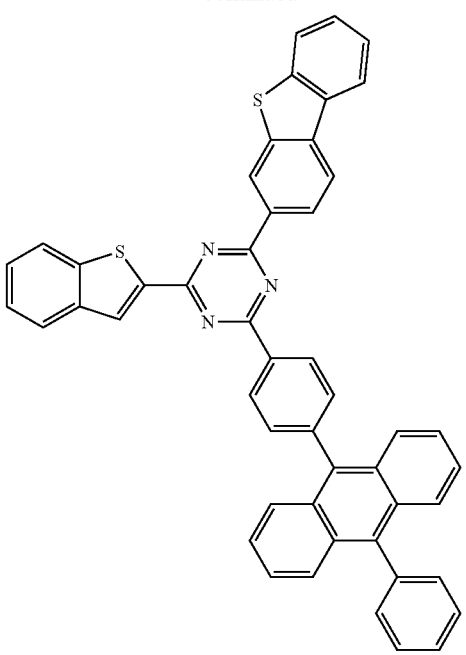
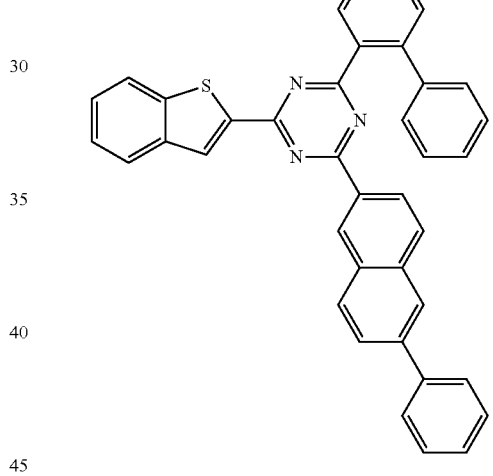
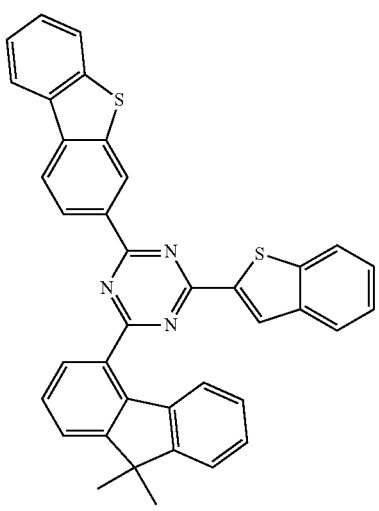

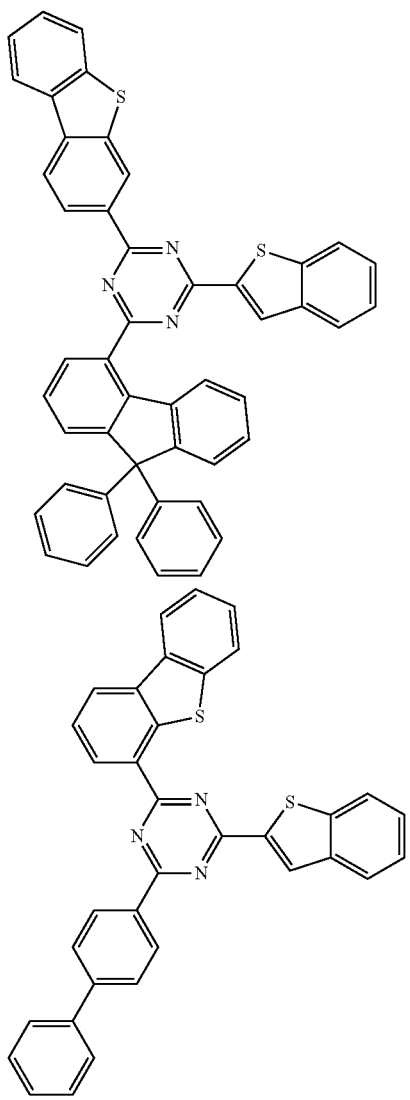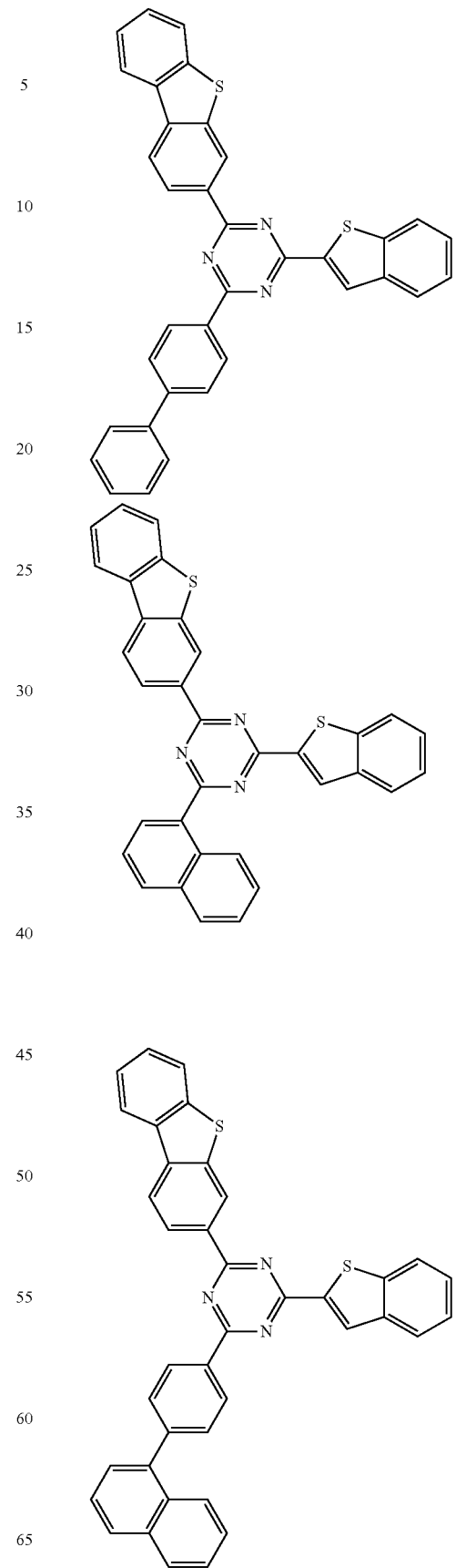

115
-continued
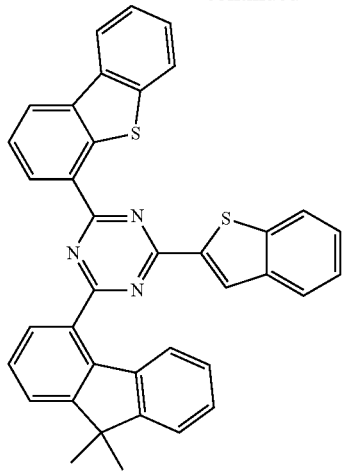
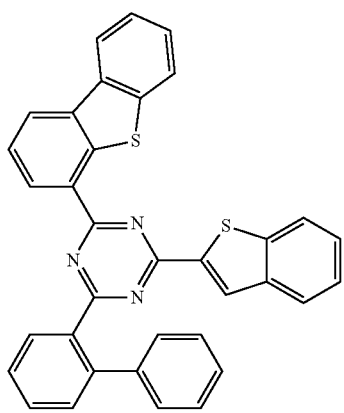
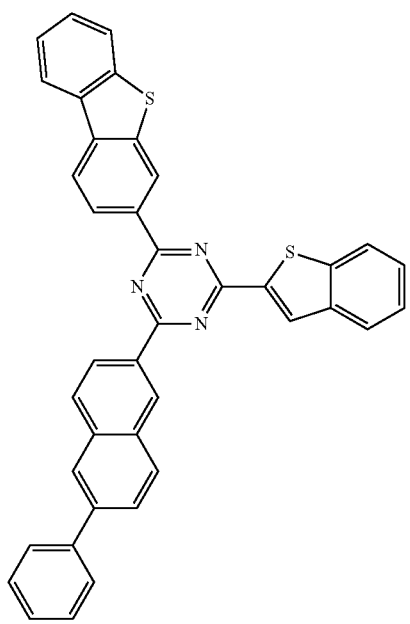
116
-continued
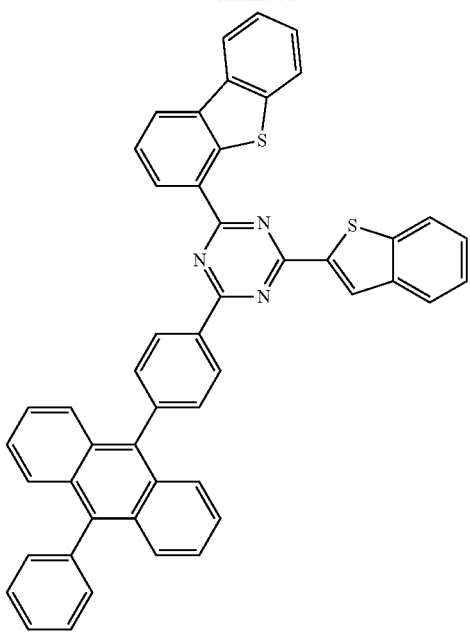
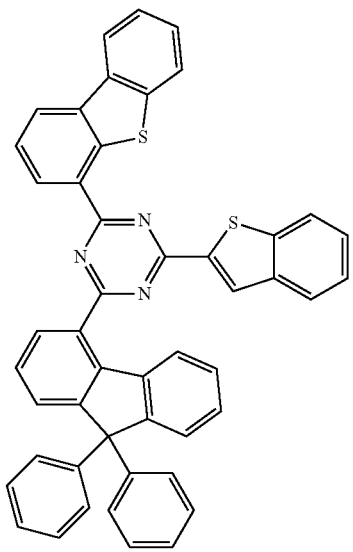

117
-continued
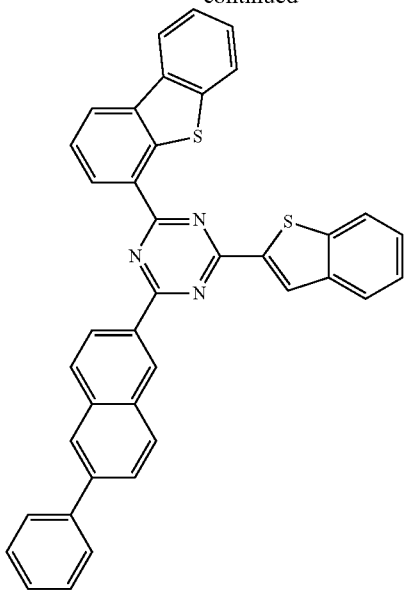
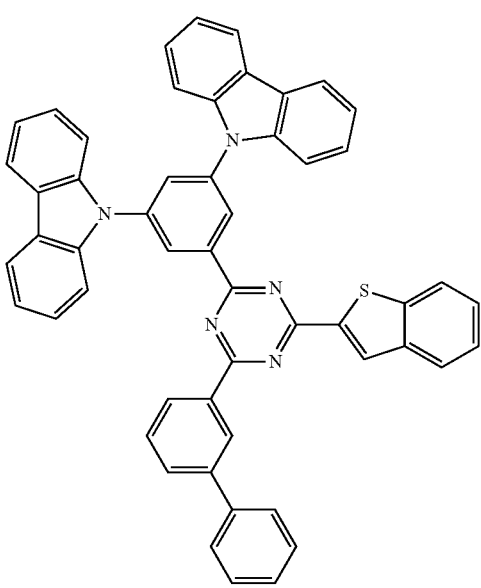
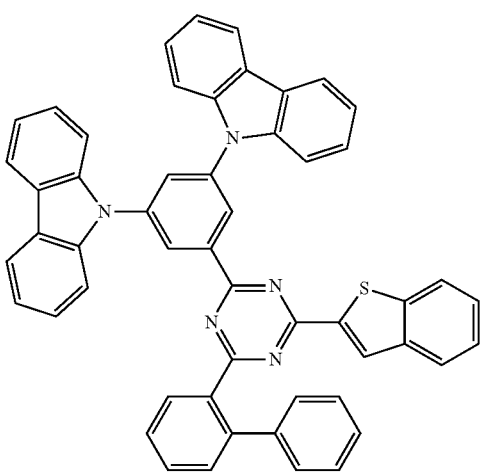
118
-continued
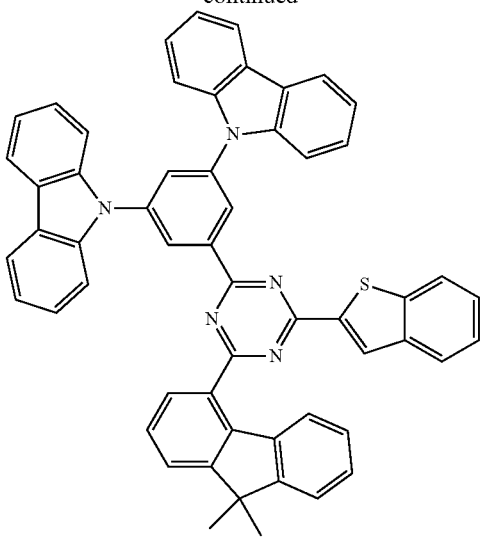

119
-continued
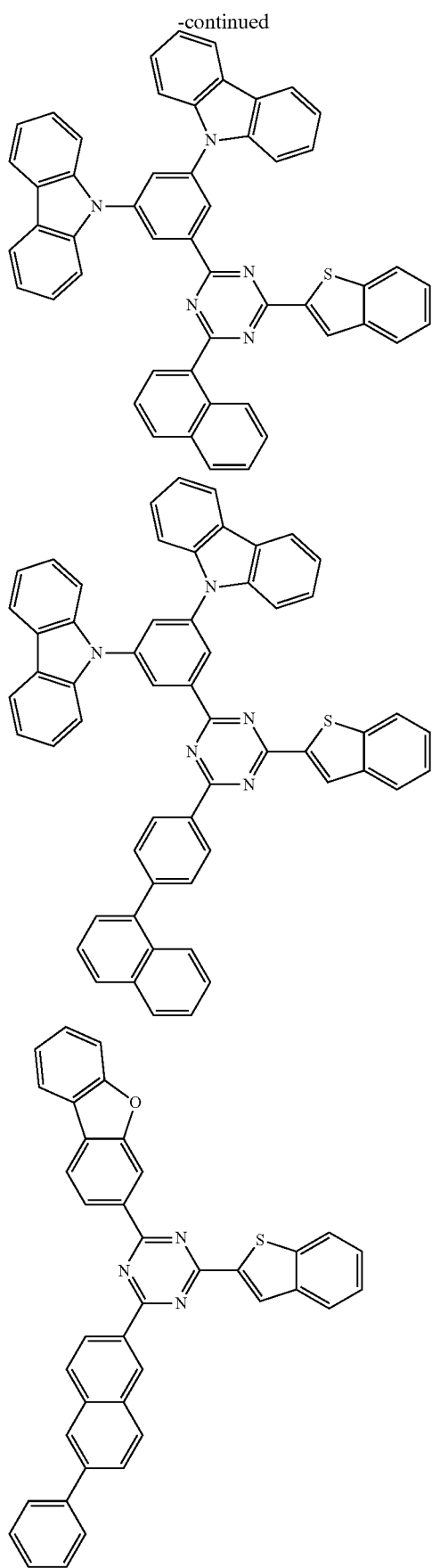
120
-continued
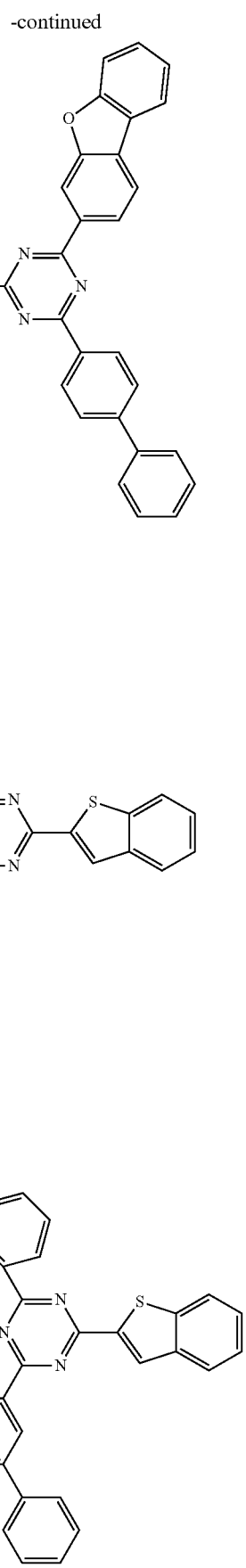

121
-continued
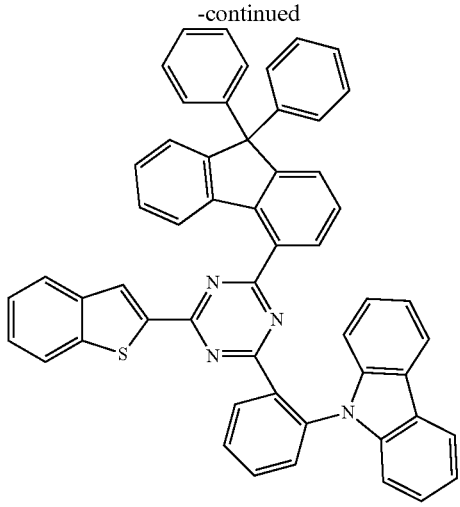
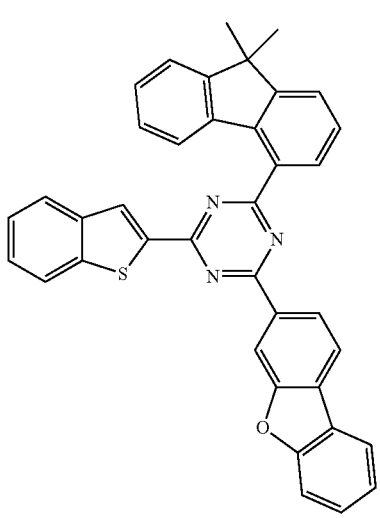
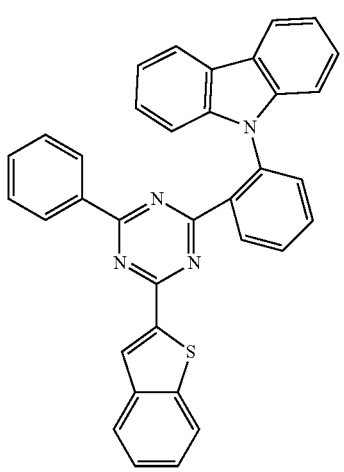
122
-continued
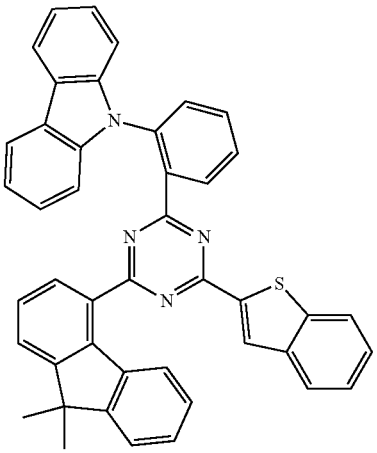
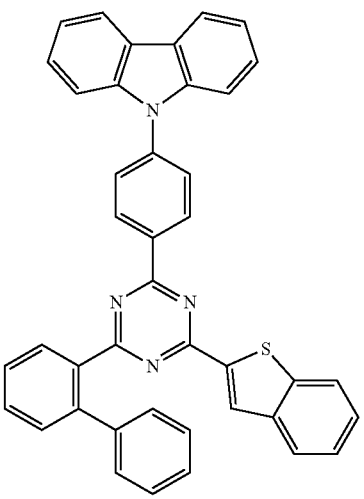

123
-continued
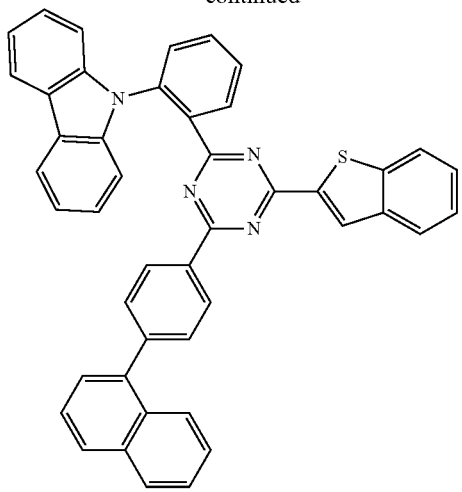
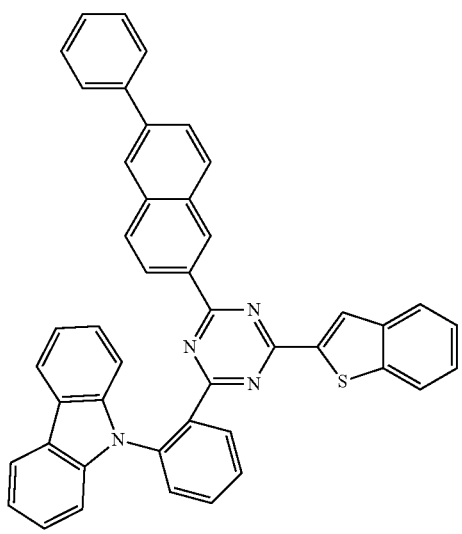
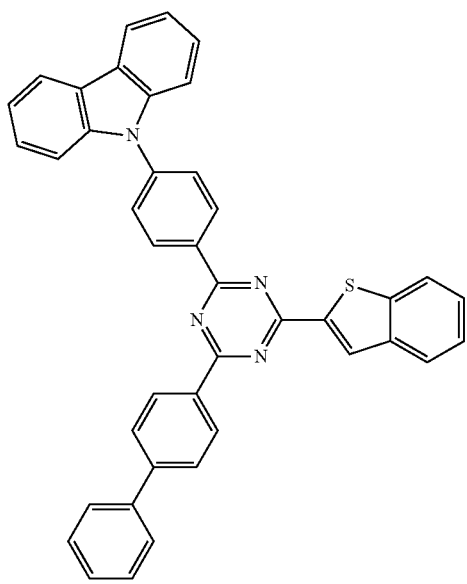
124
-continued
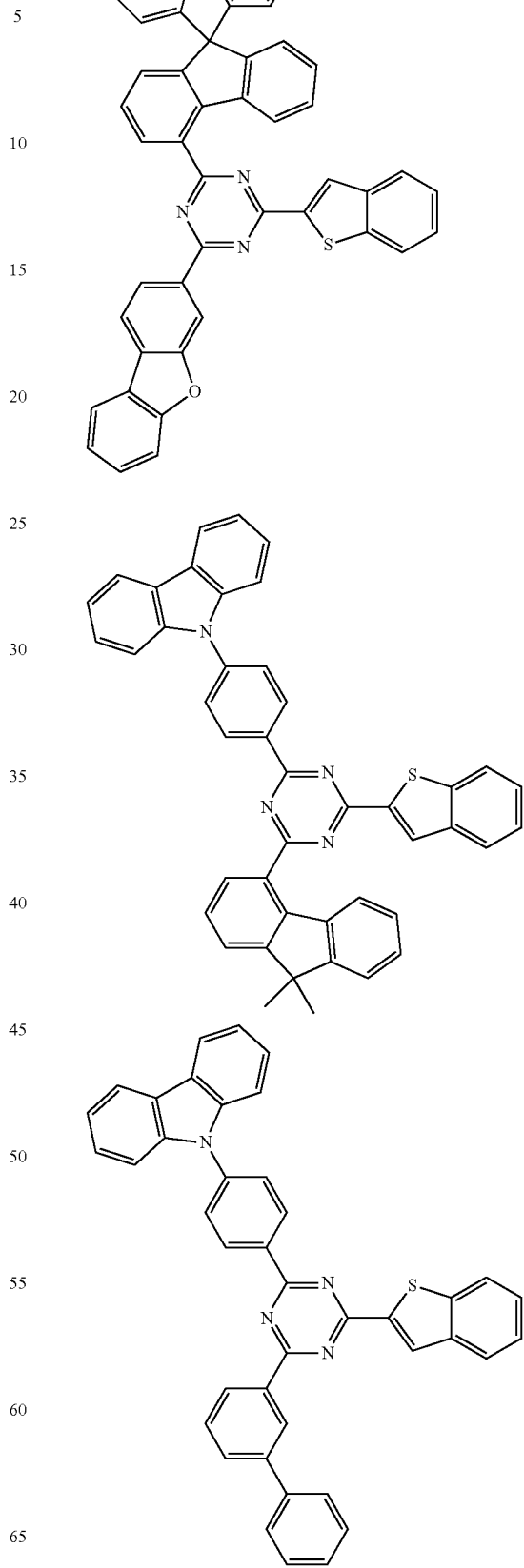

125
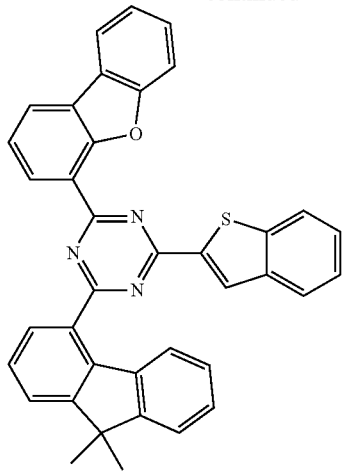
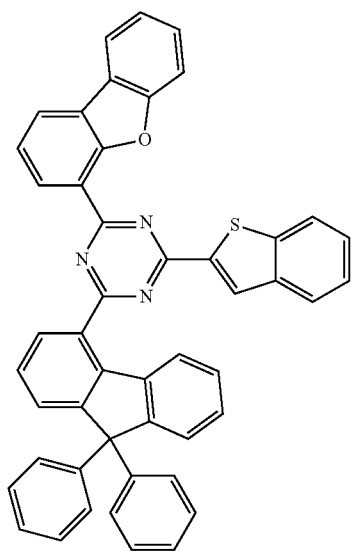
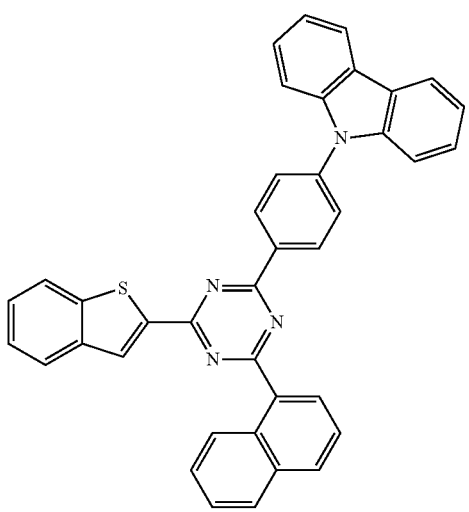
126
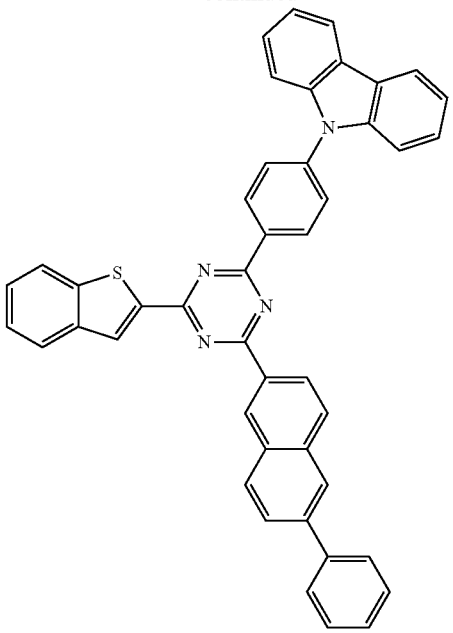
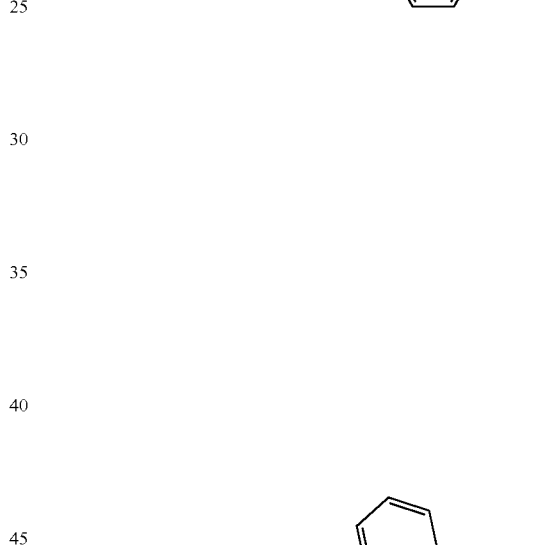
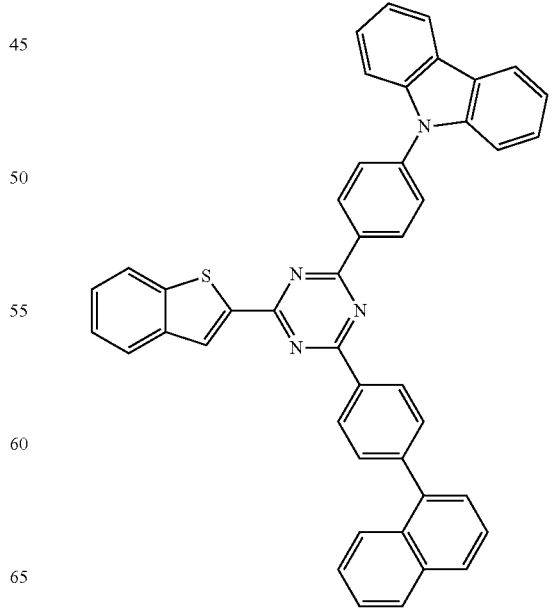

127
-continued
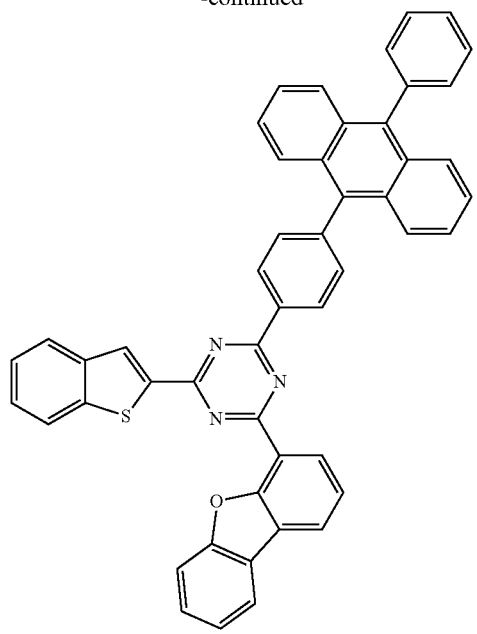
128
-continued
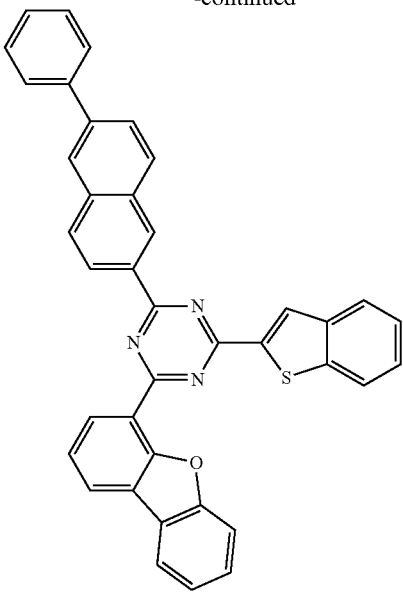
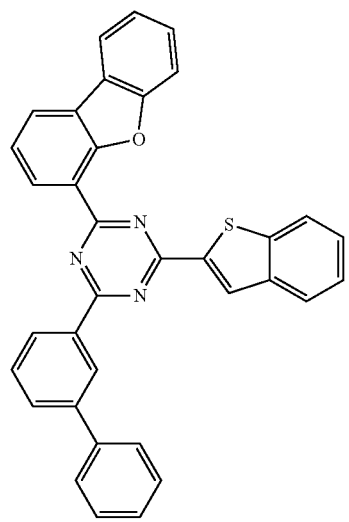
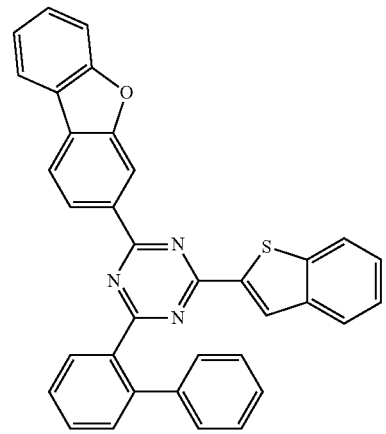

129
-continued
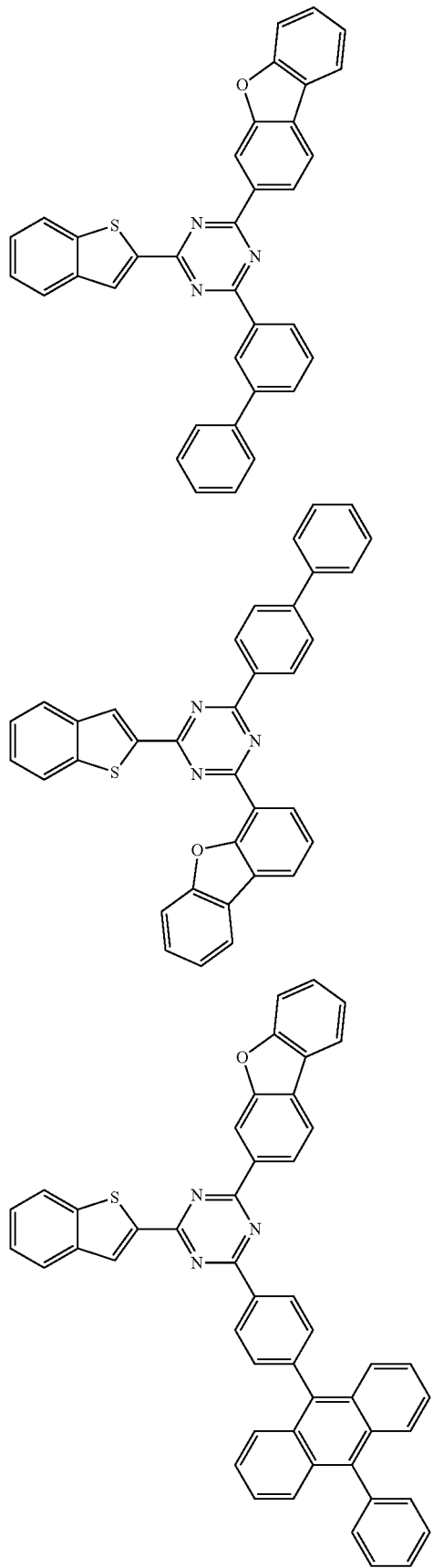
130
-continued
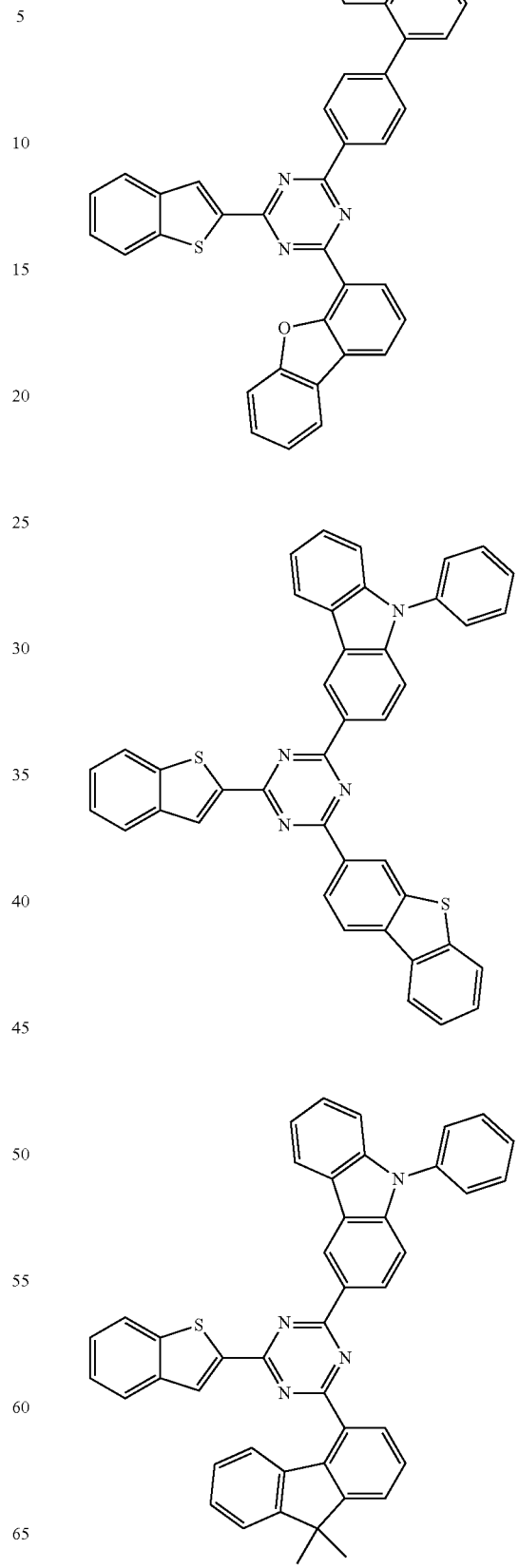

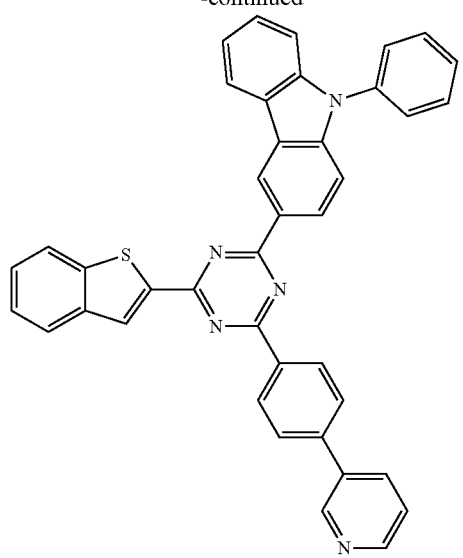
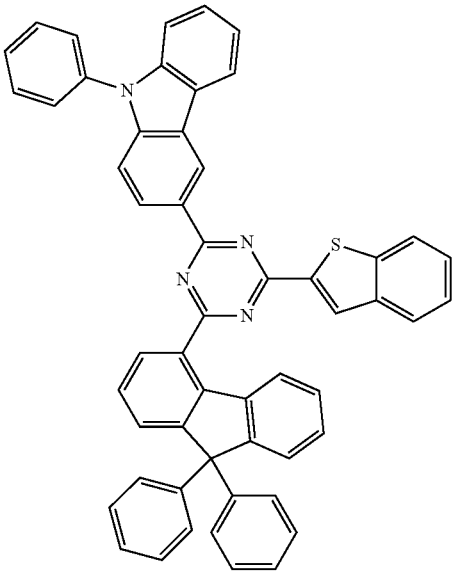
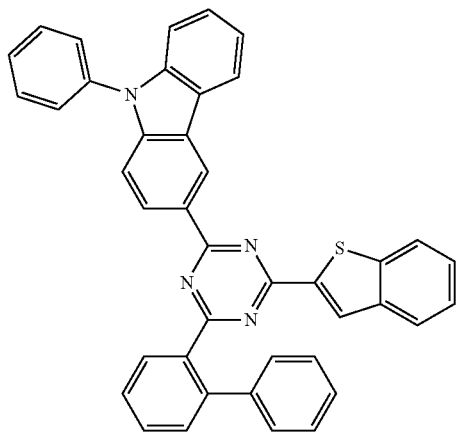
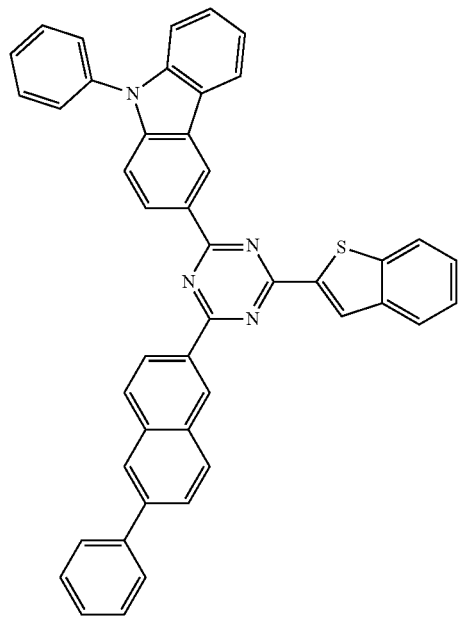
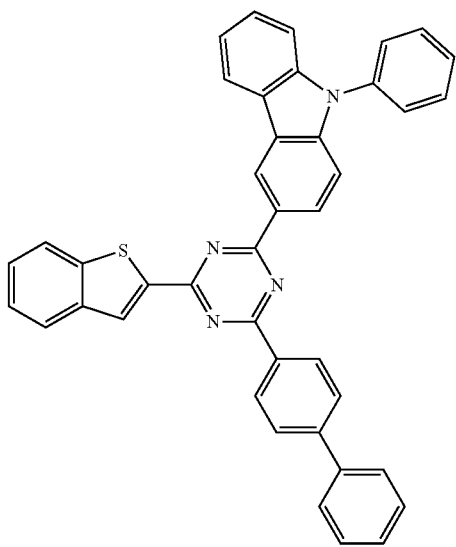

133
-continued
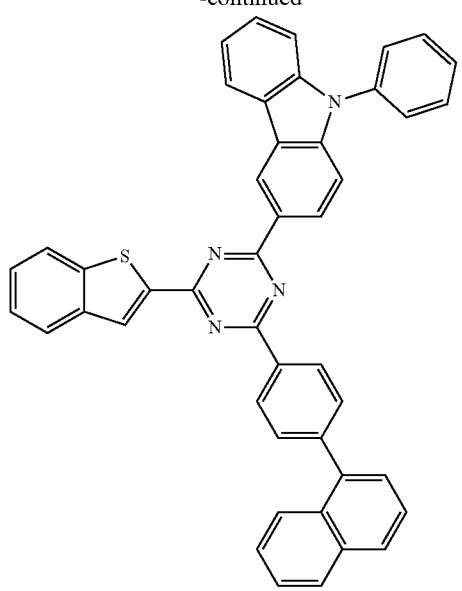
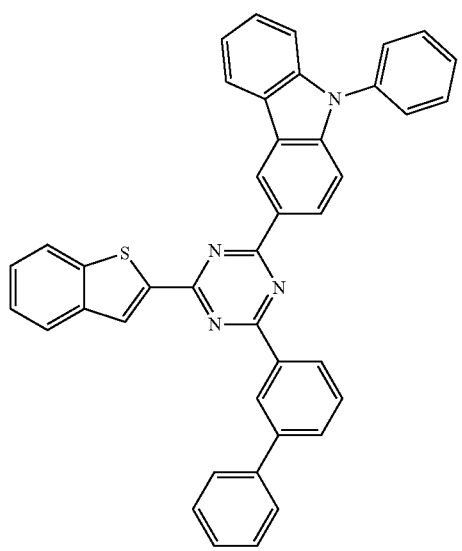
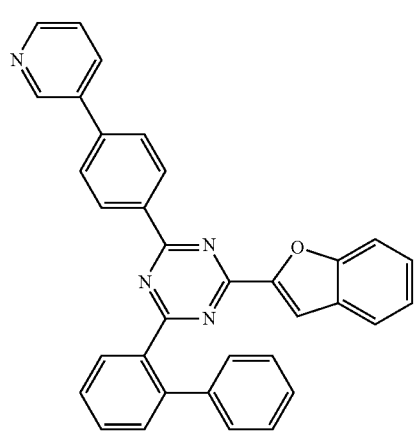
134
-continued
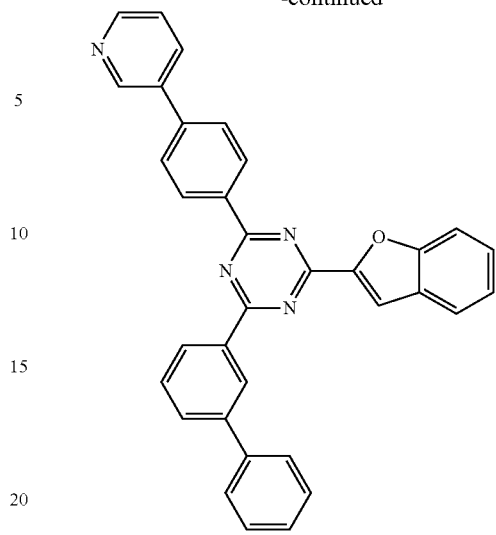
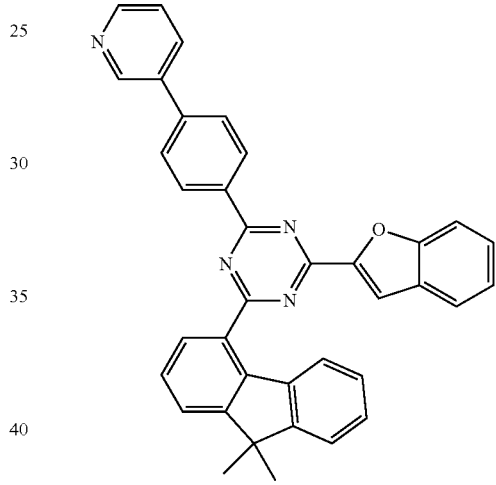
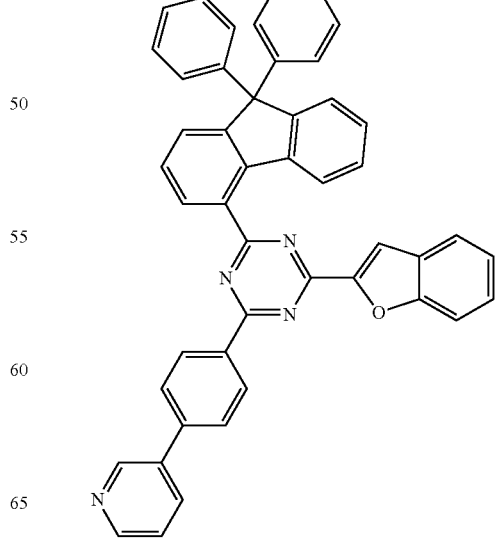

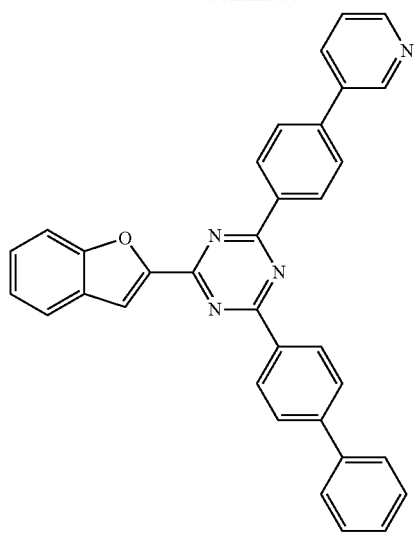
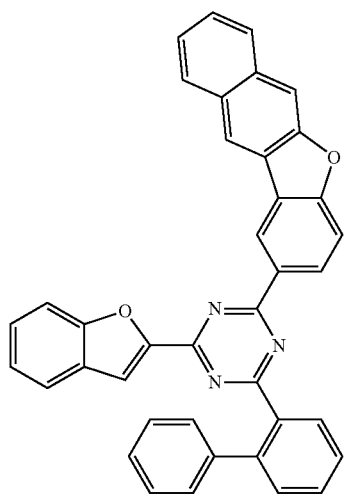
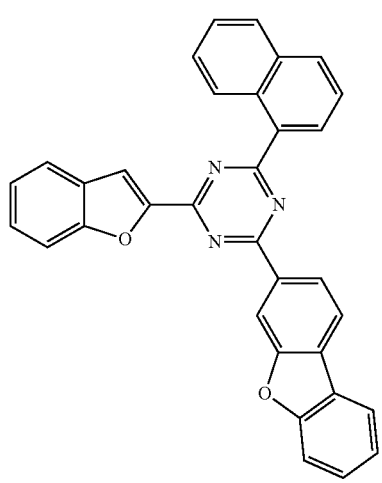
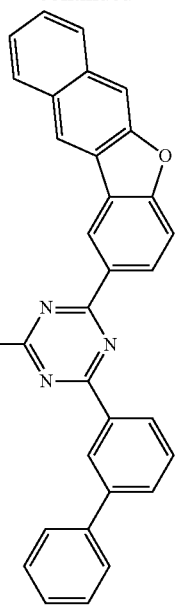
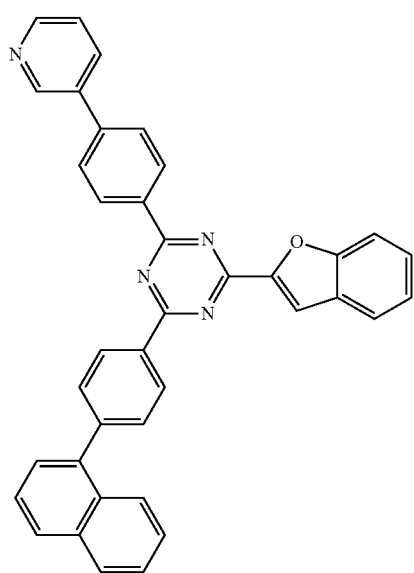

137
-continued
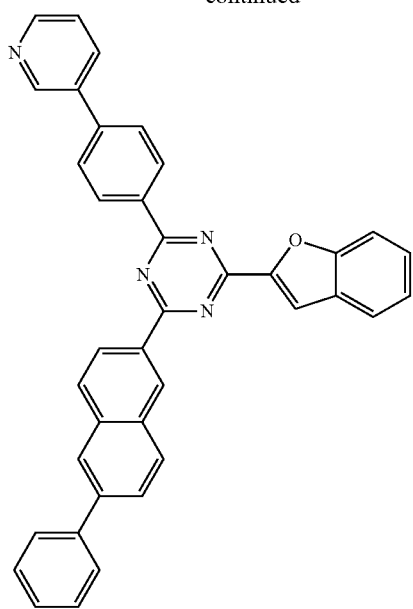
138
-continued
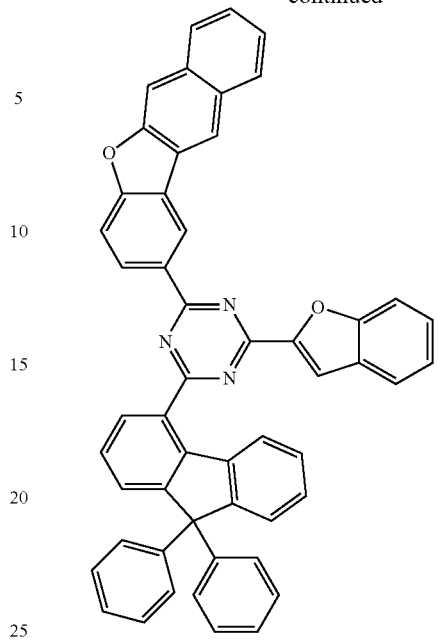
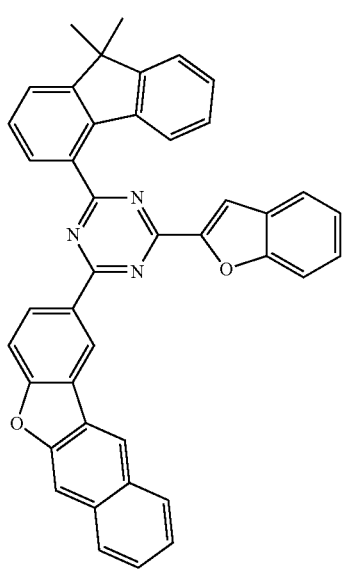
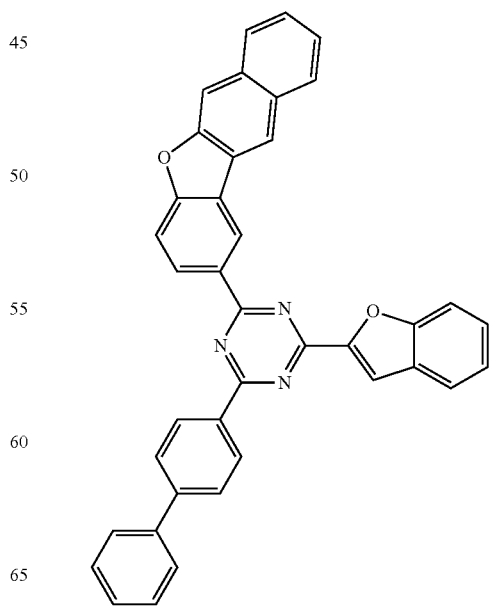

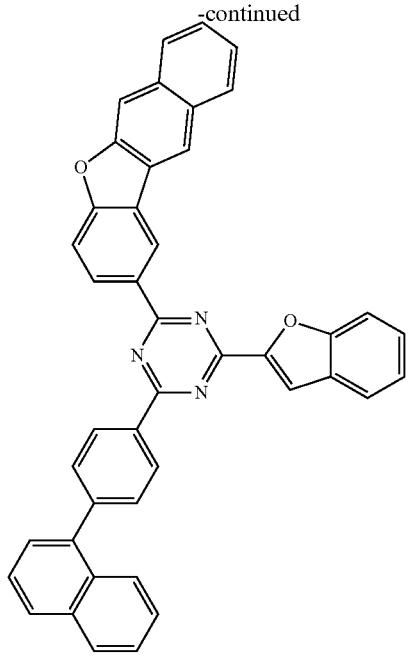
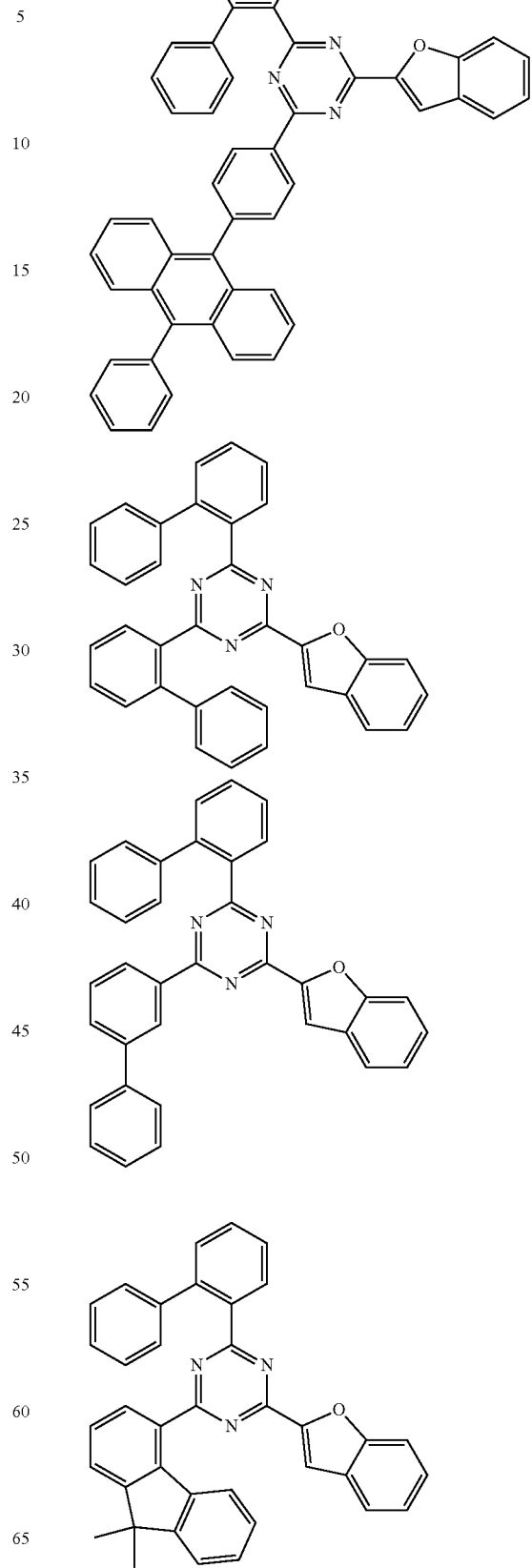

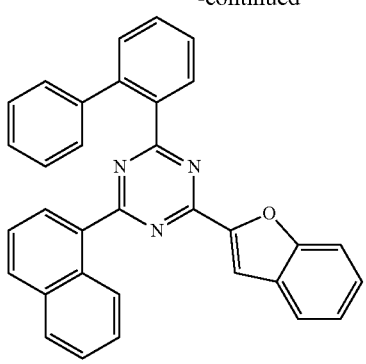
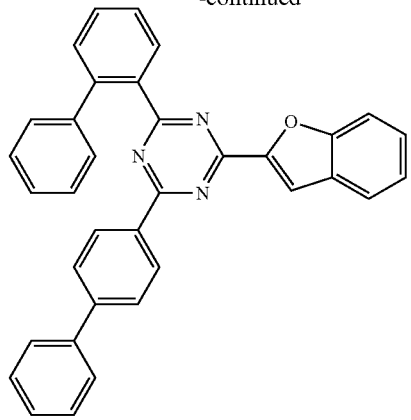
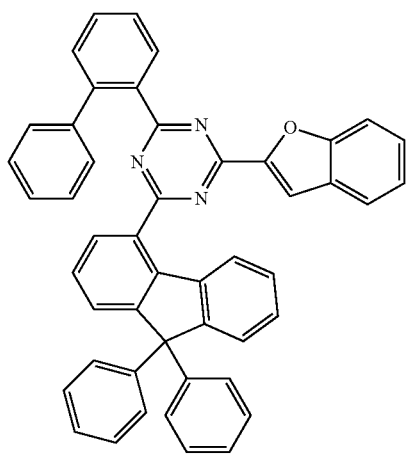
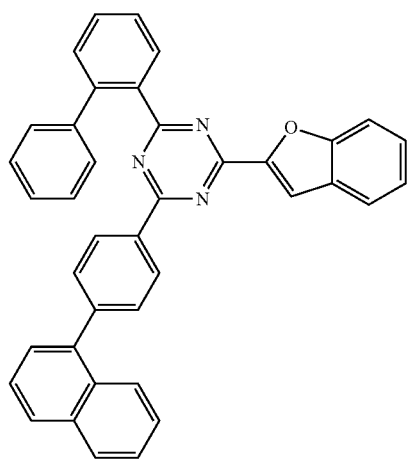
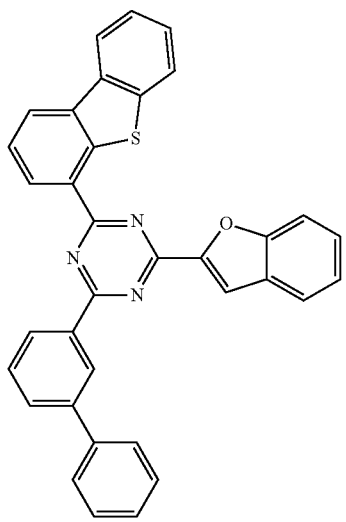
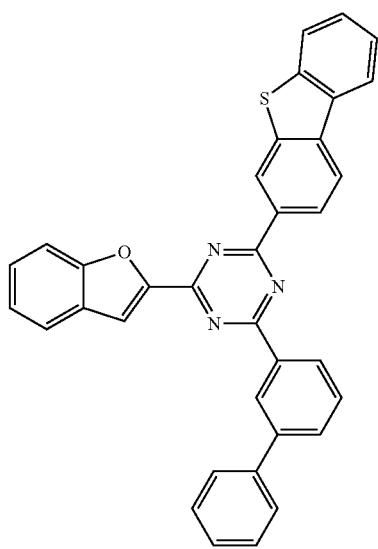

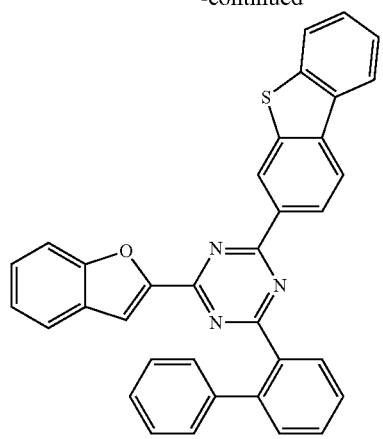
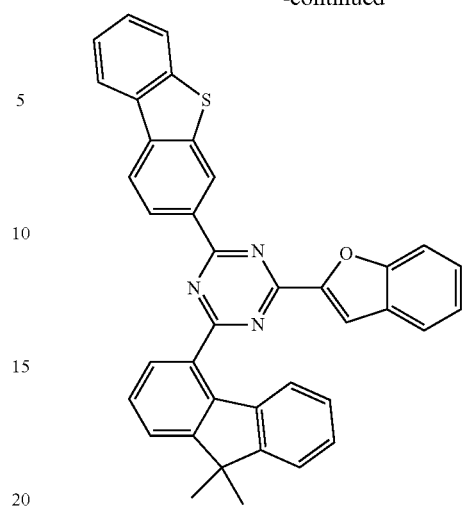
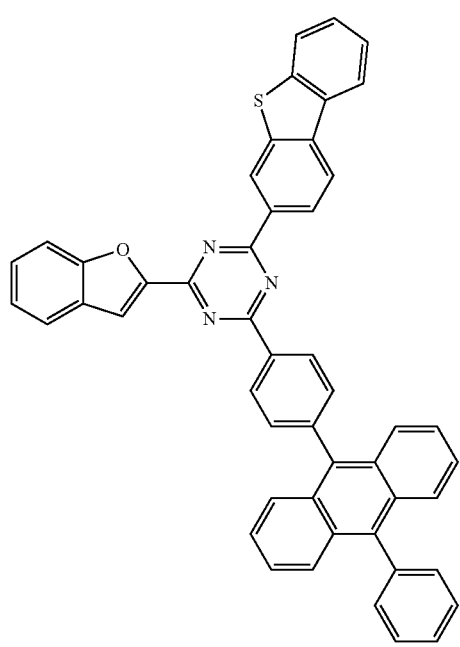
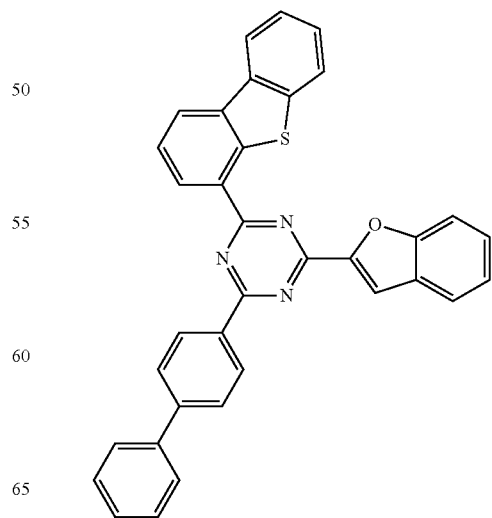
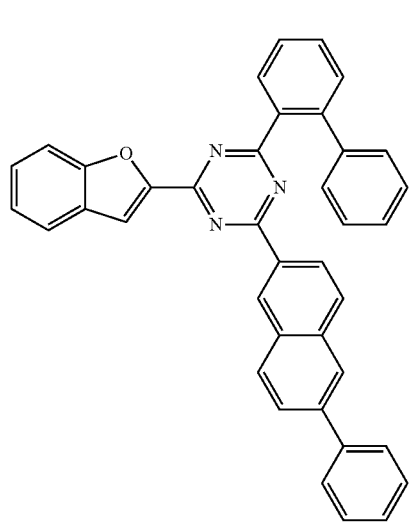

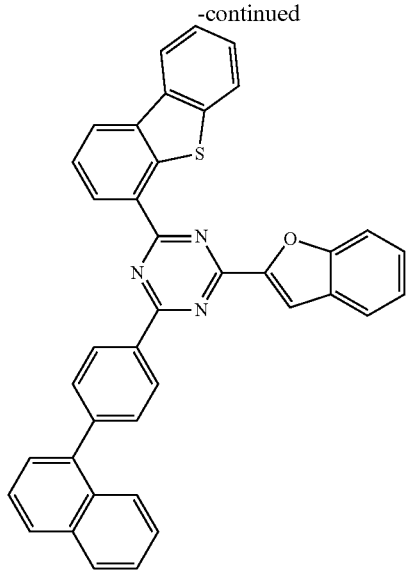
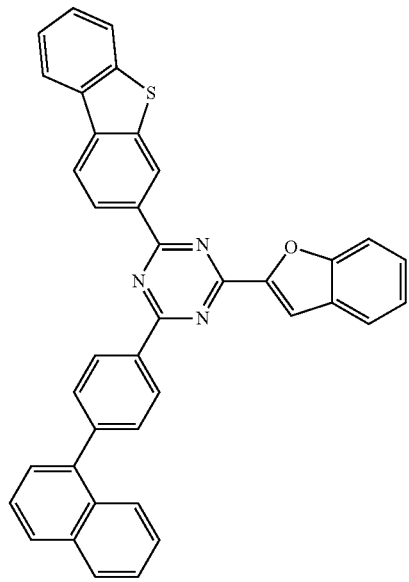
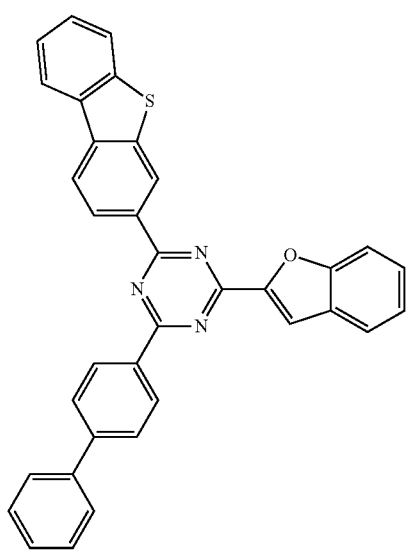
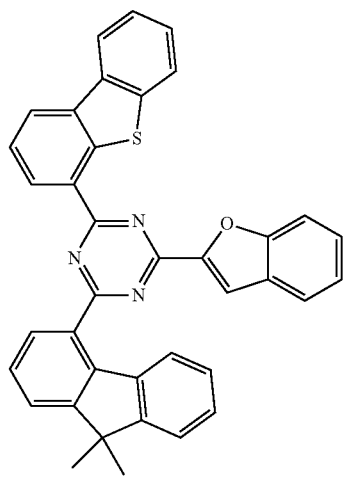
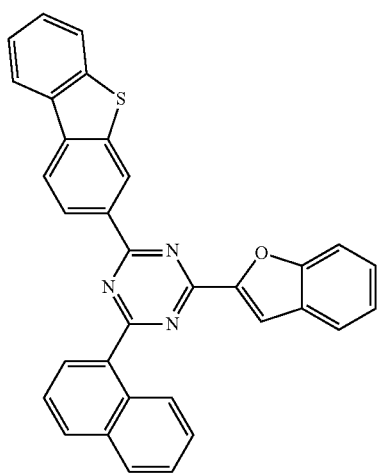
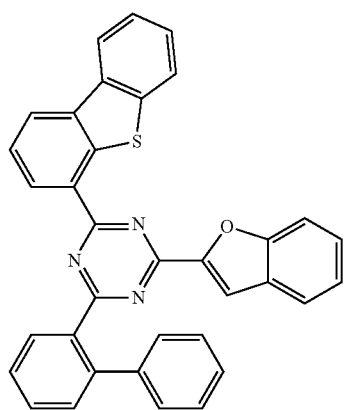

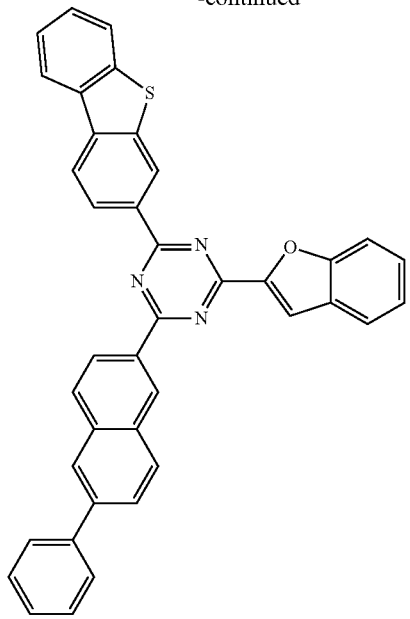
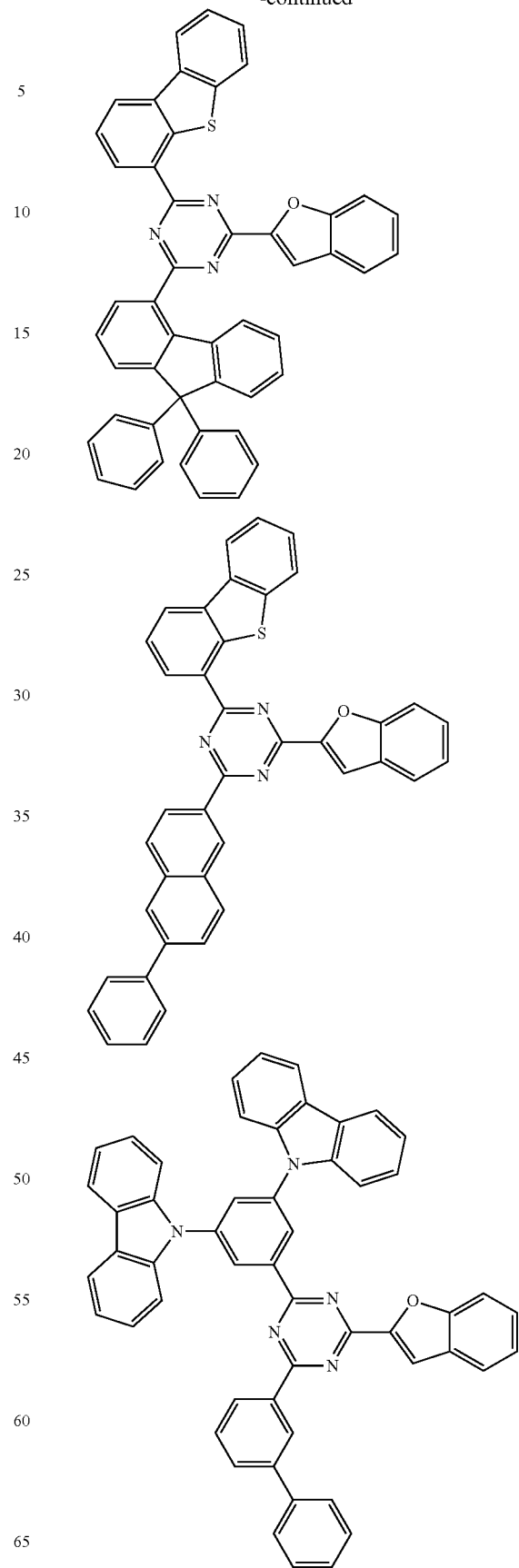

149
-continued
150
-continued
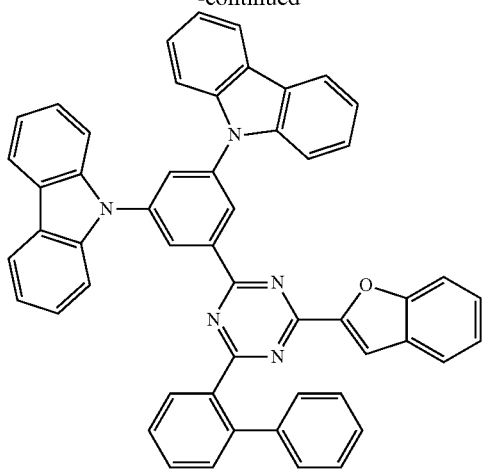
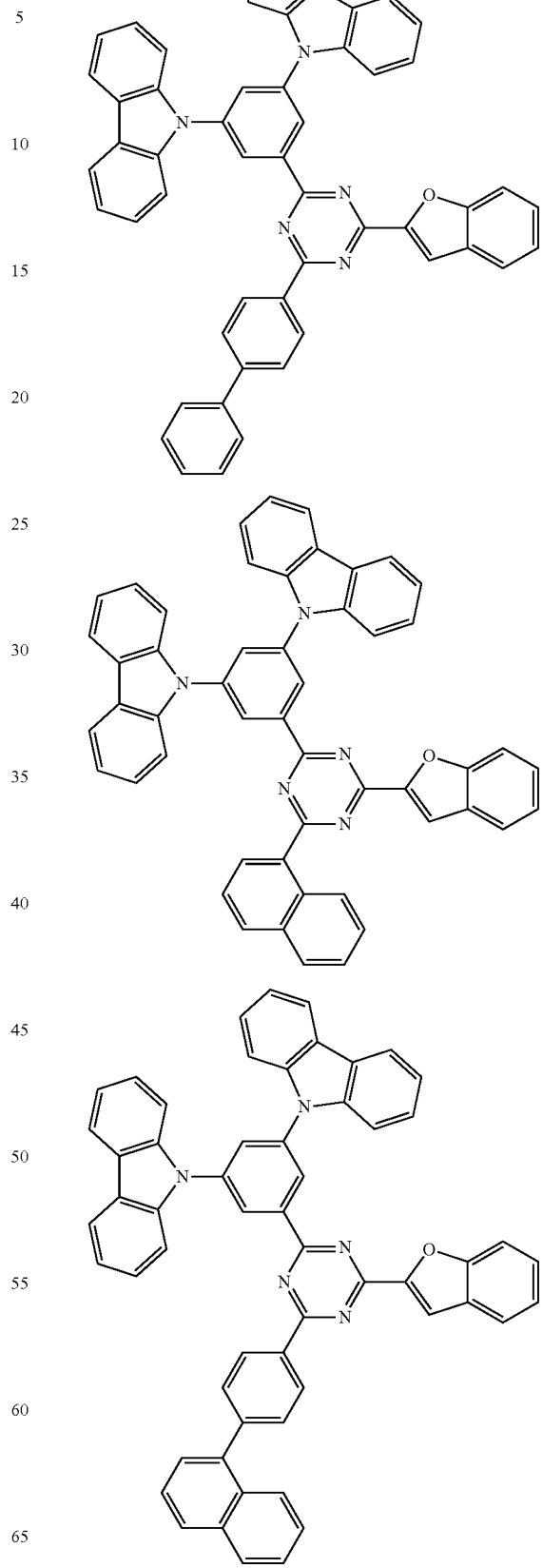

151
-continued
152
-continued
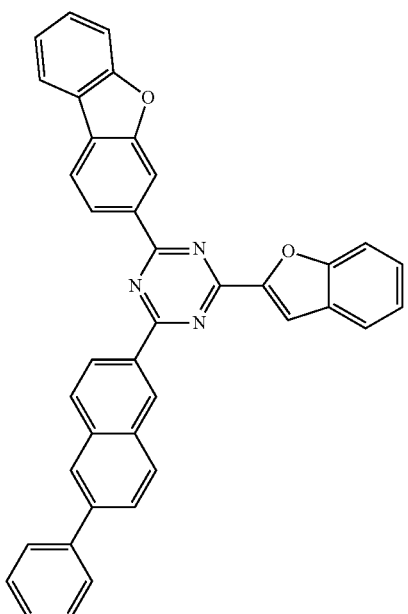
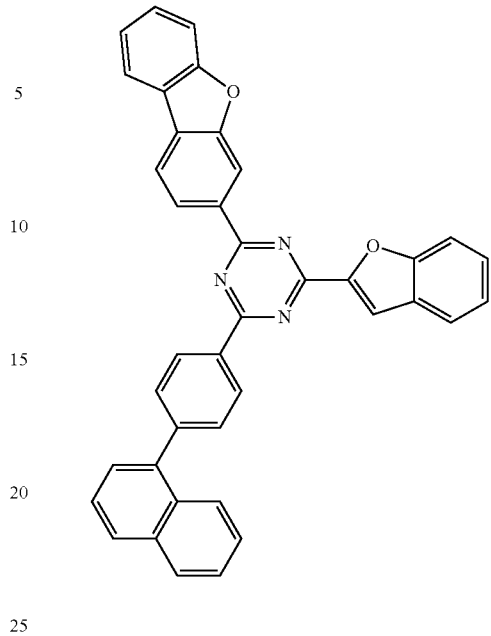
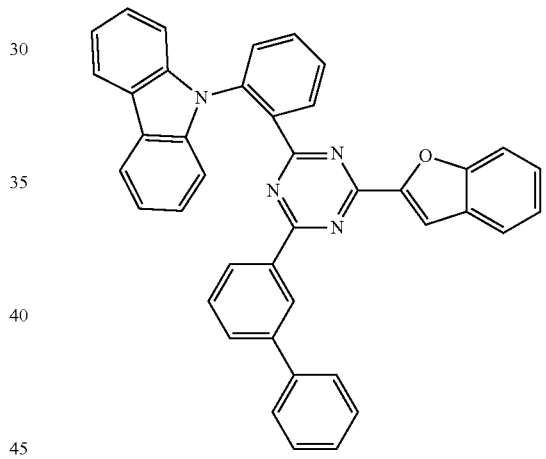
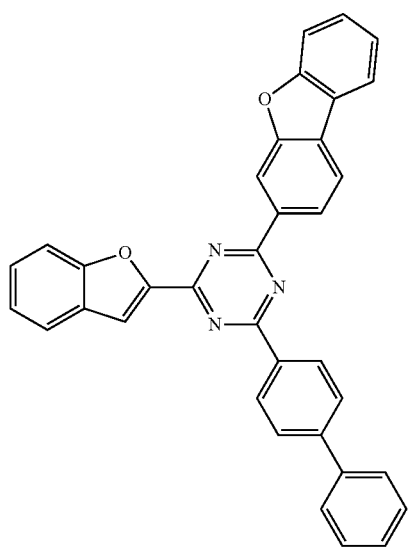
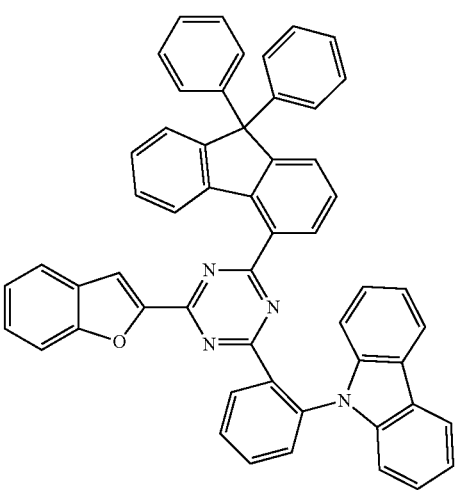

153
-continued
154
-continued
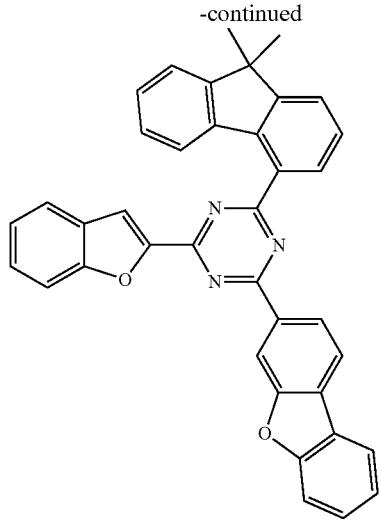
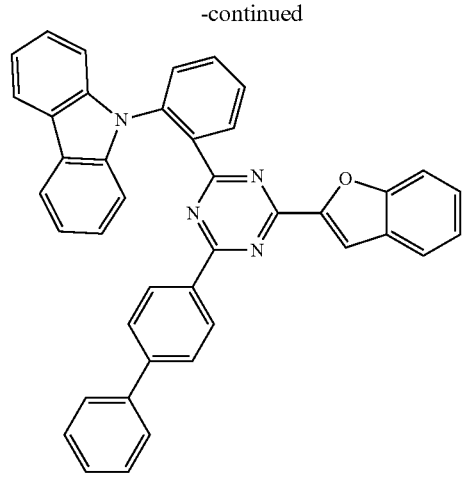
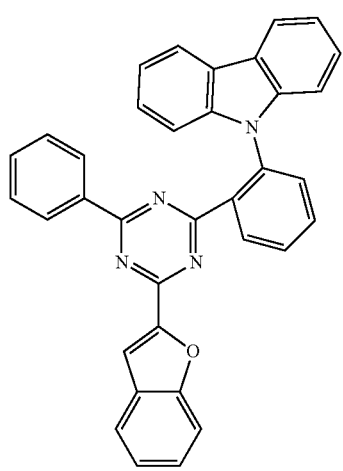
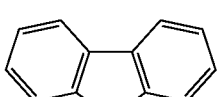
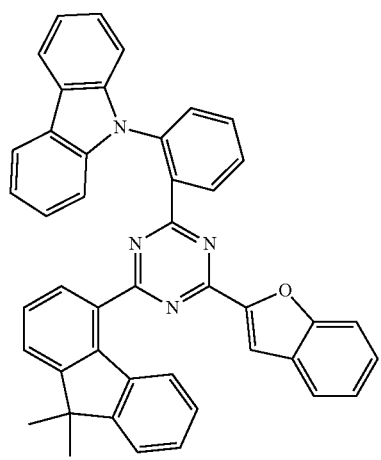
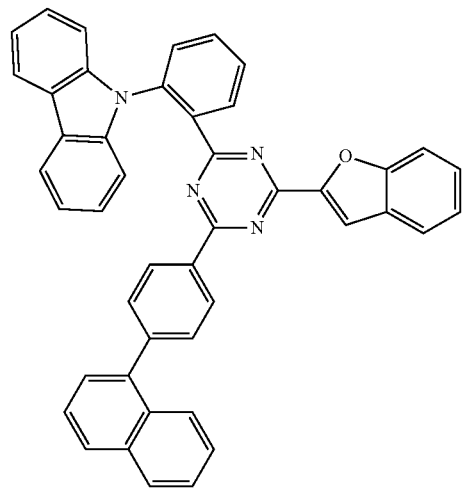

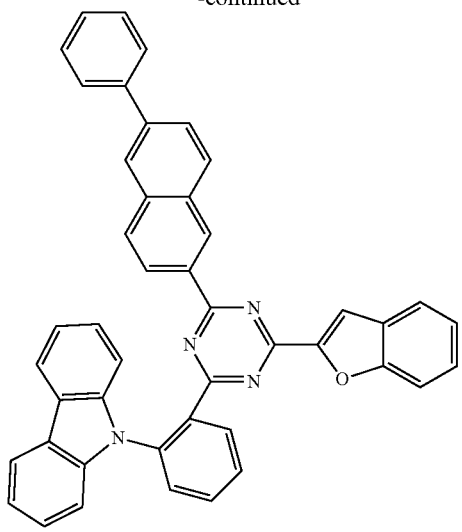
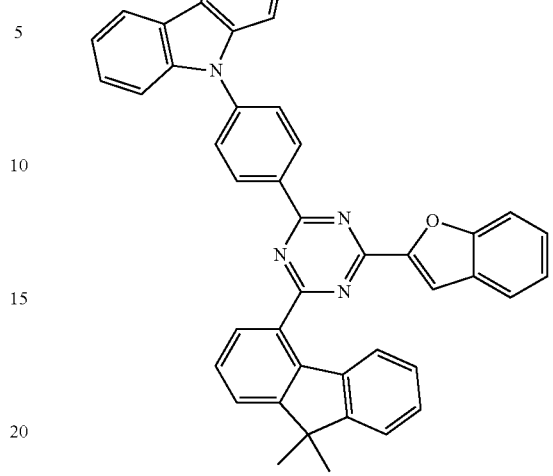
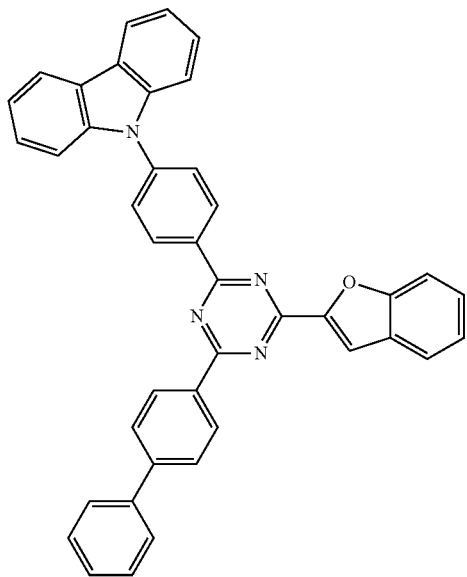
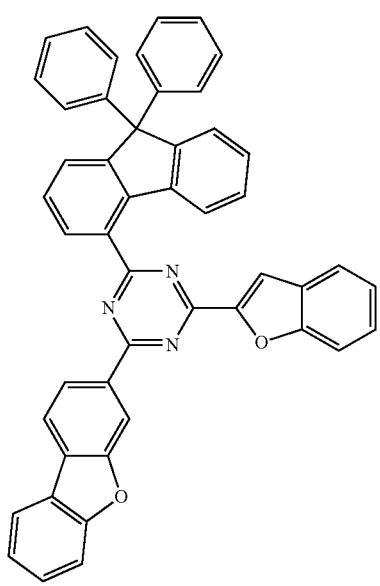

157
-continued
158
-continued
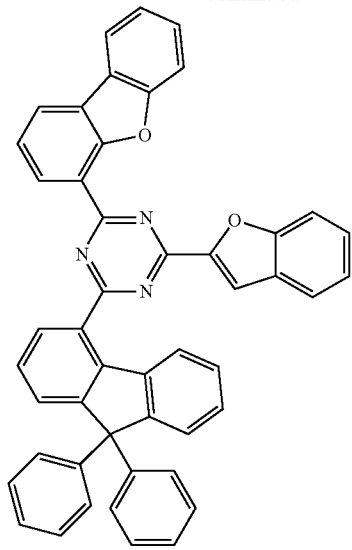
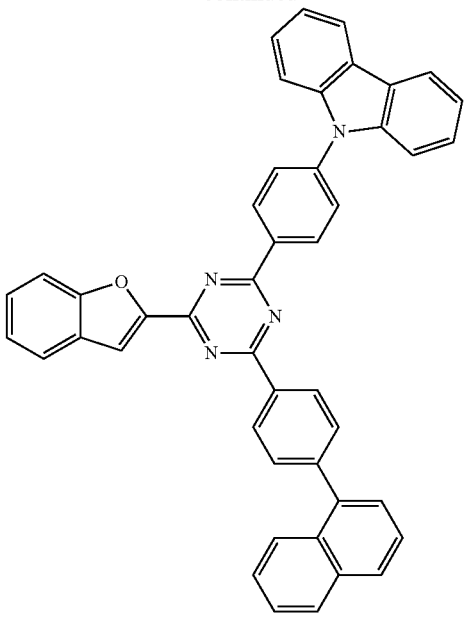
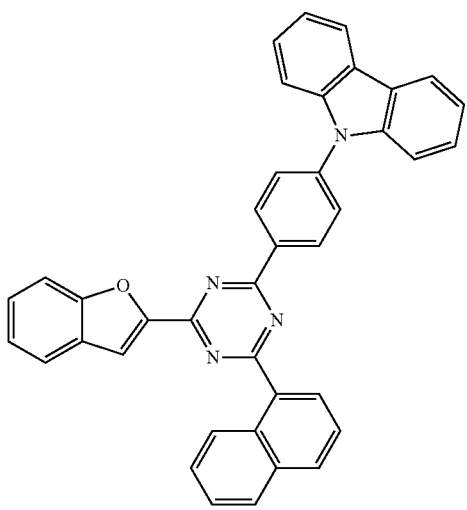
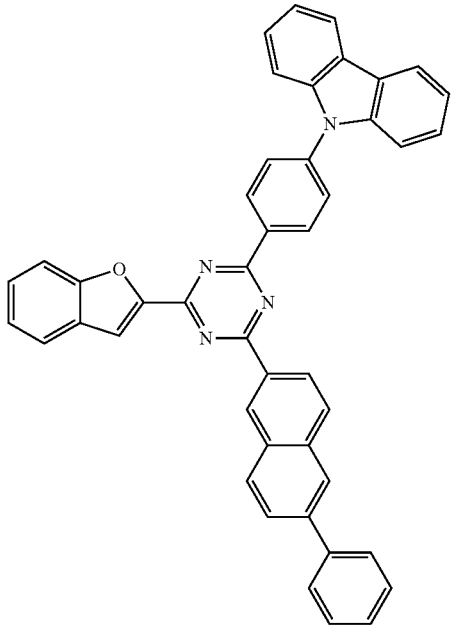

159
-continued
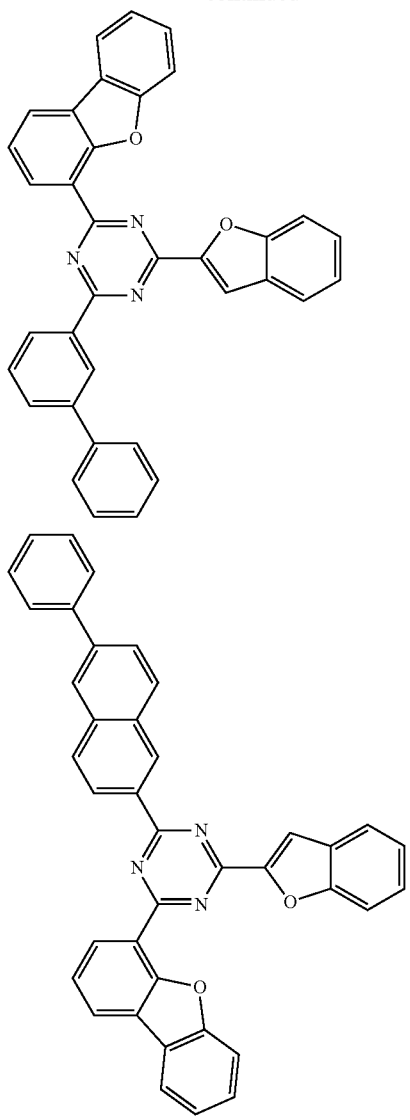
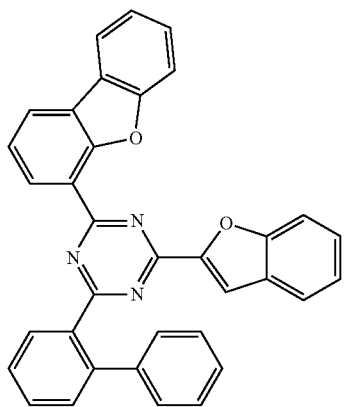
160
-continued
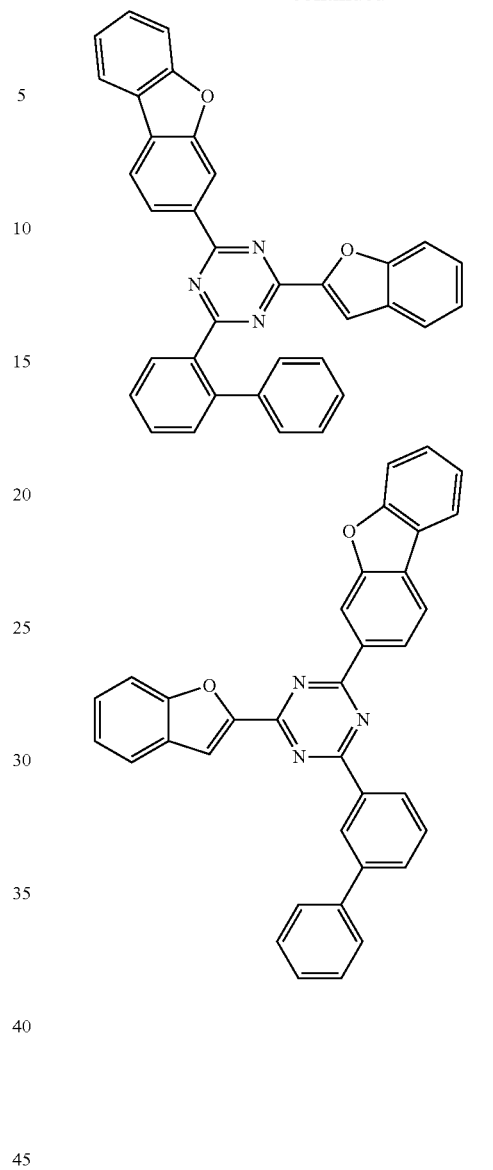

161
-continued
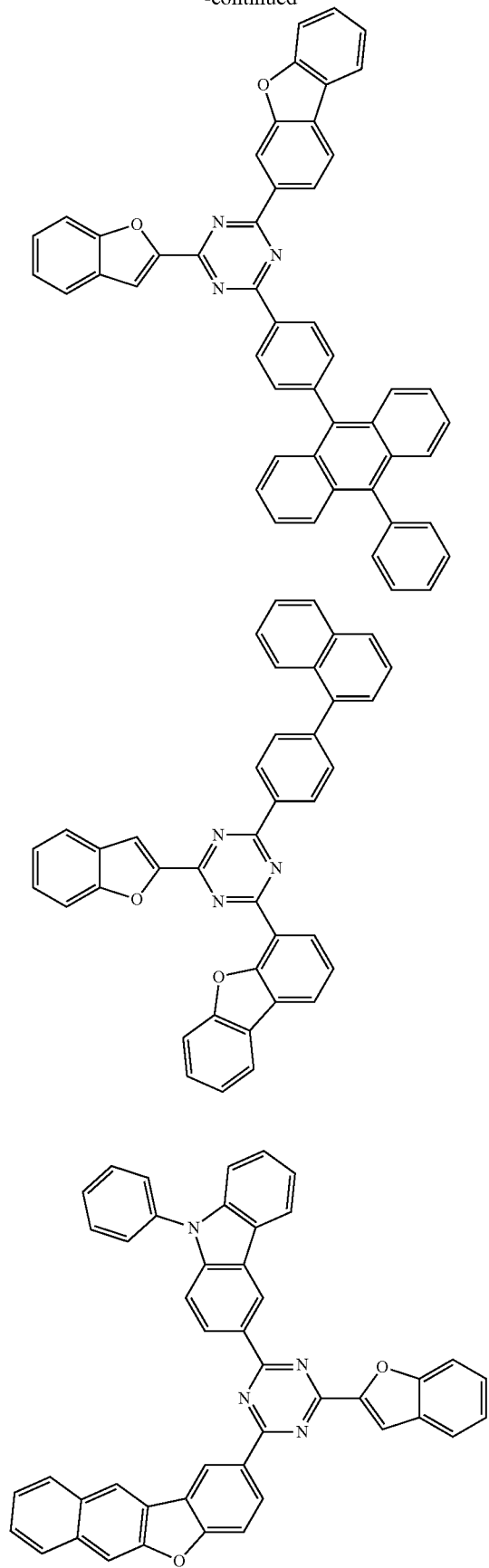
162
-continued
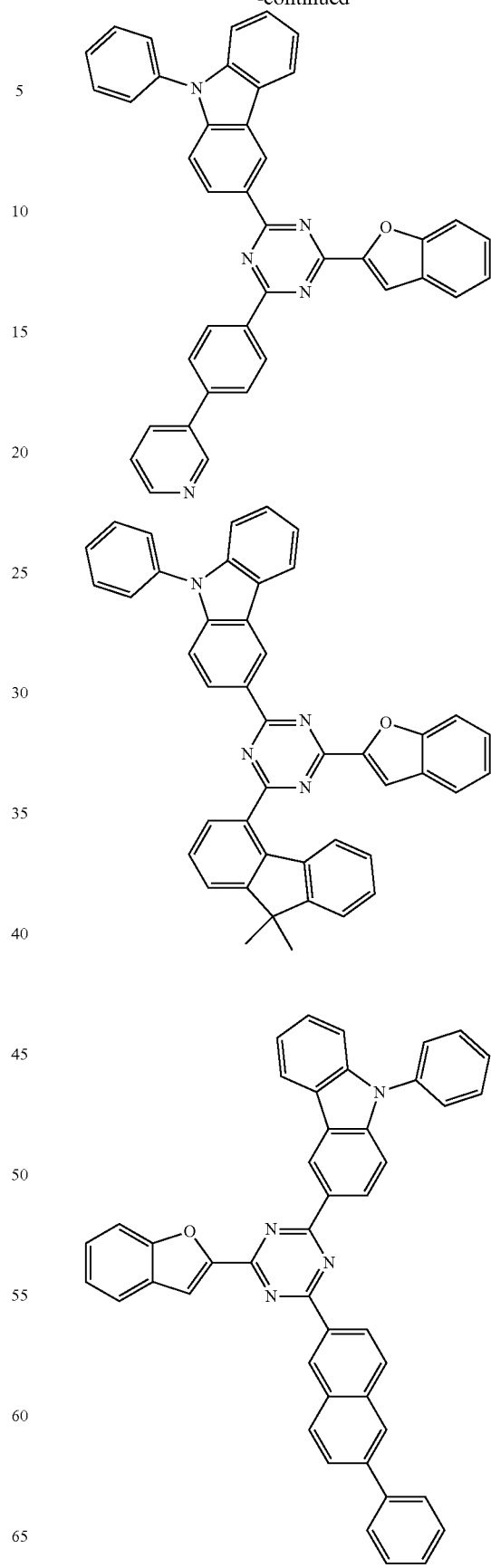

-continued
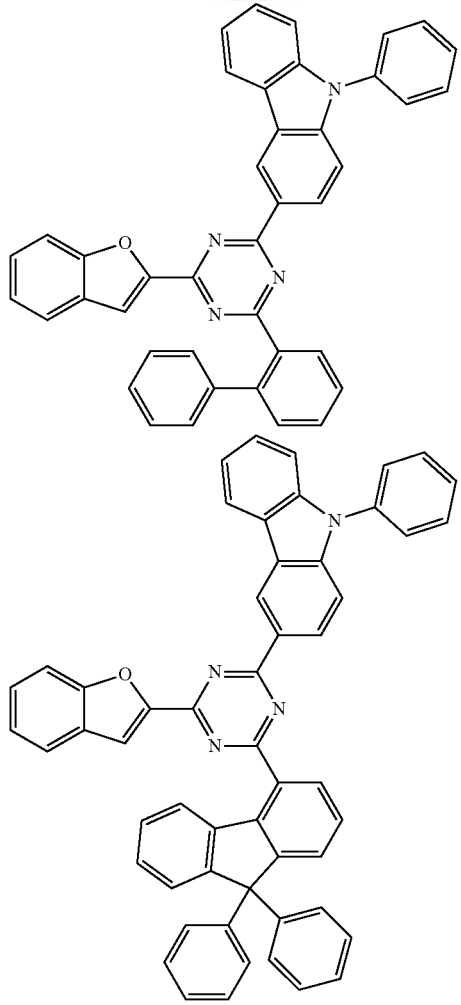
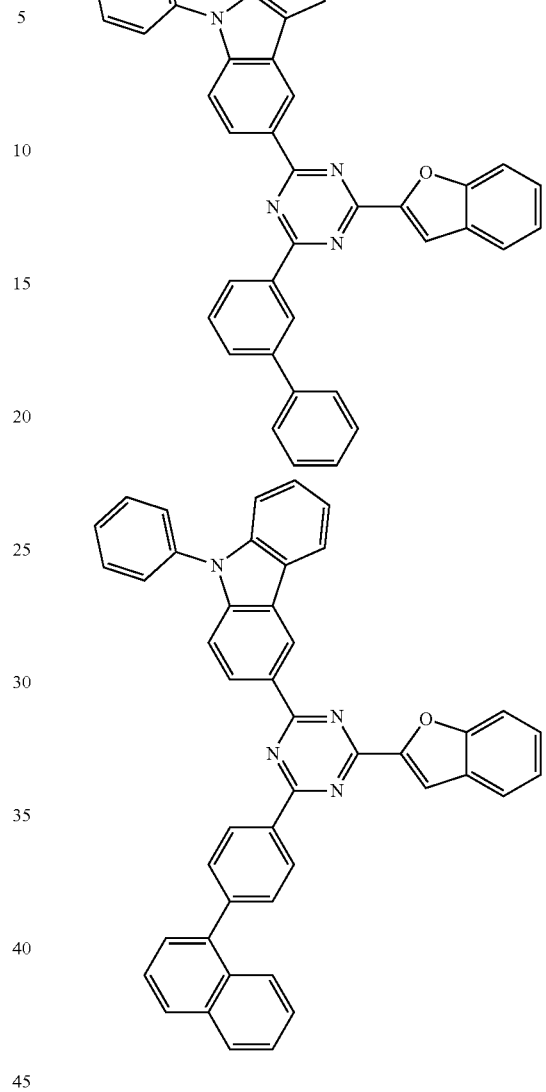
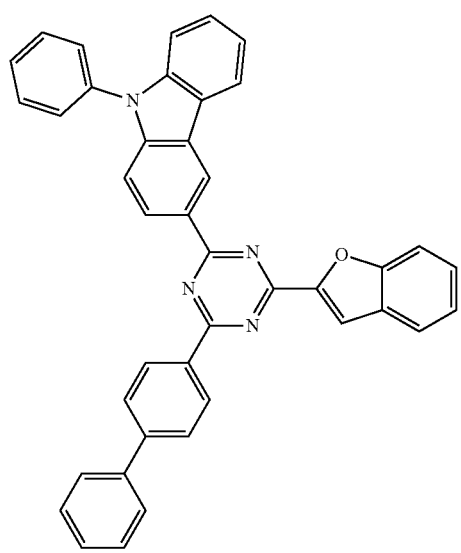
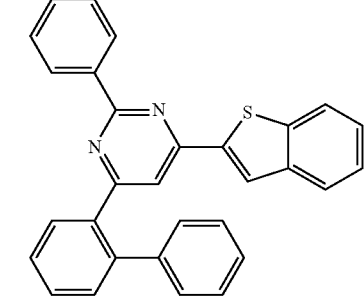

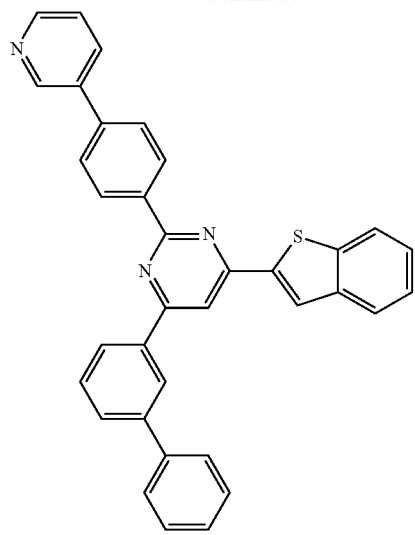
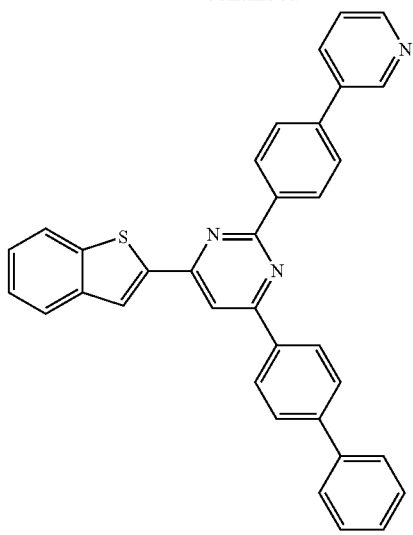
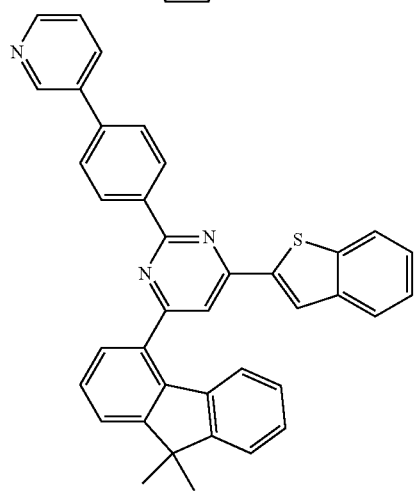
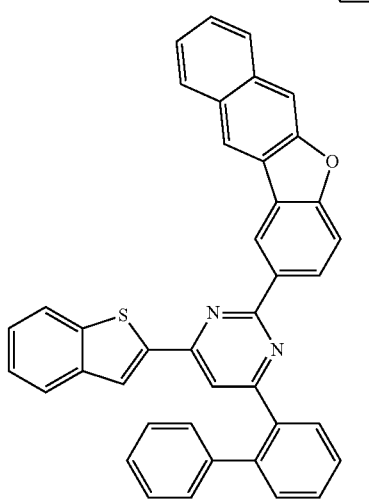
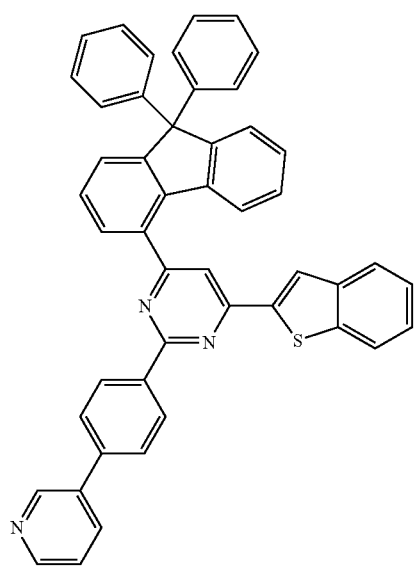
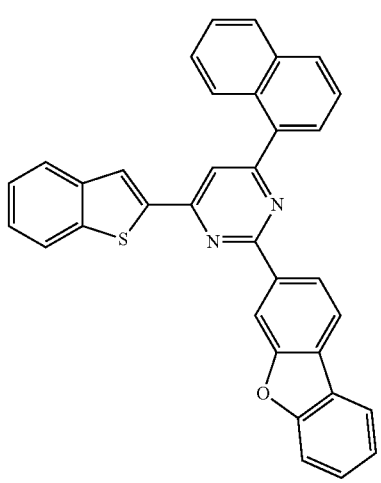

167
-continued
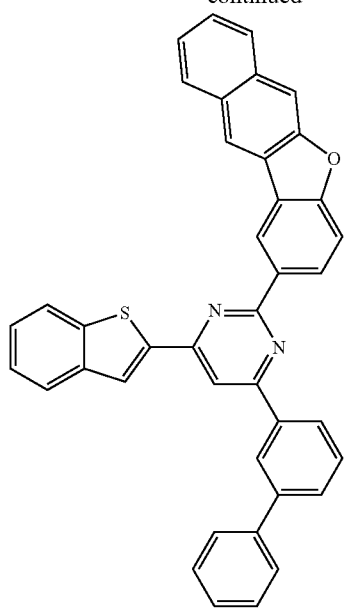
168
-continued
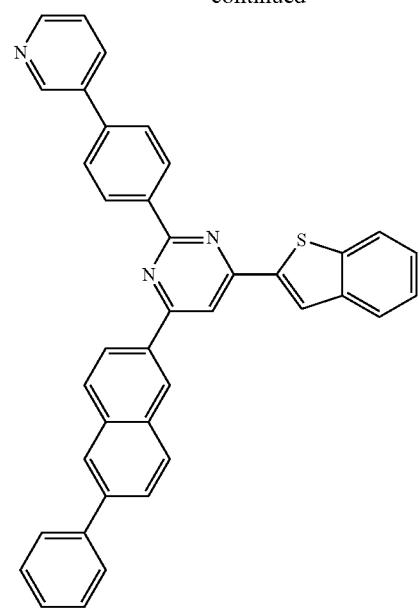
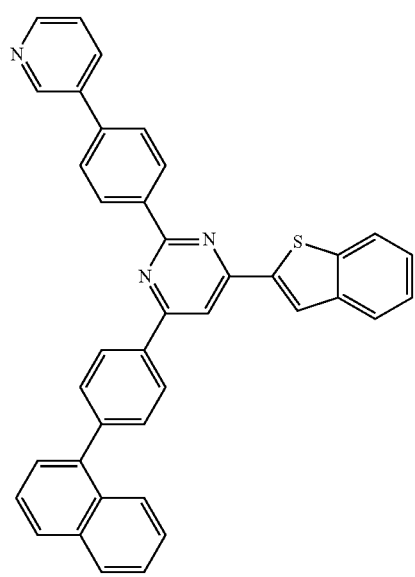
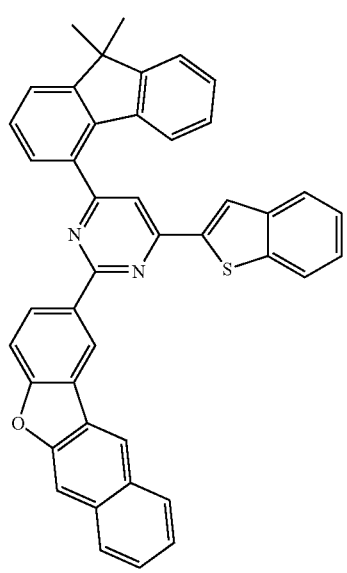

169
-continued
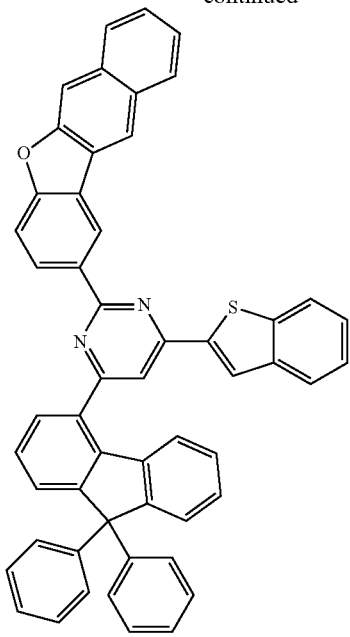
170
-continued
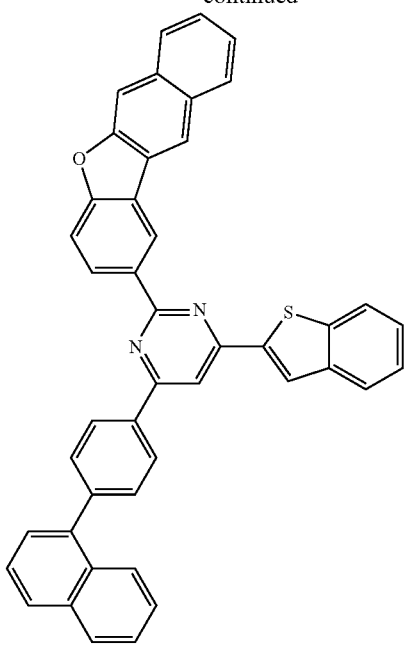
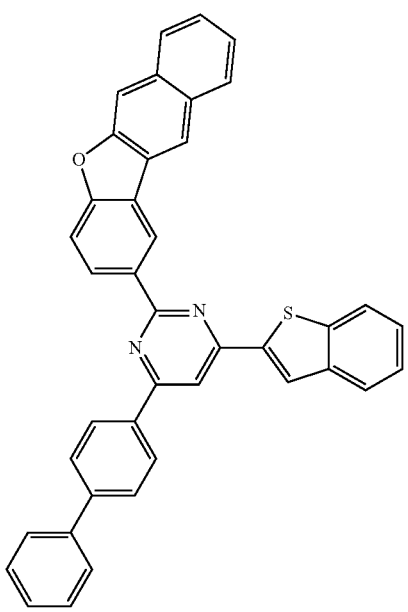
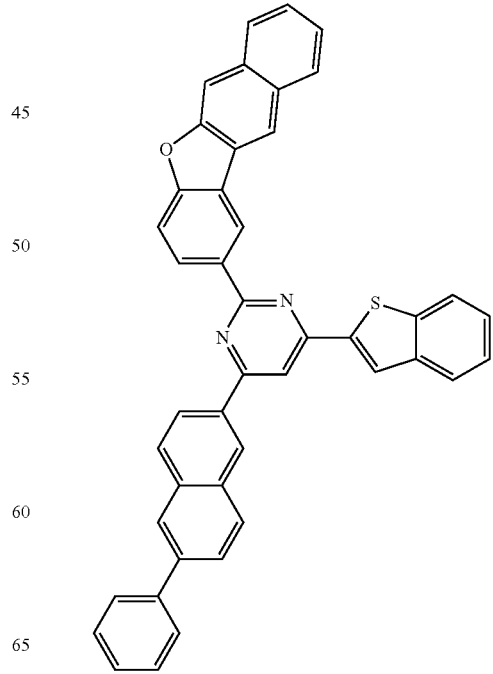

171
-continued
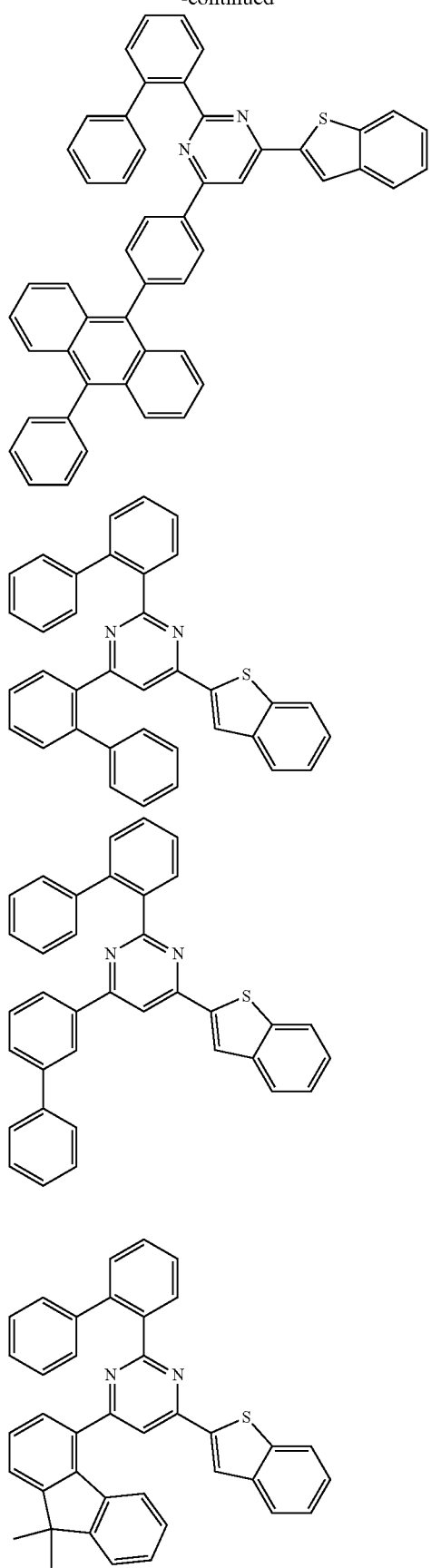
172
-continued
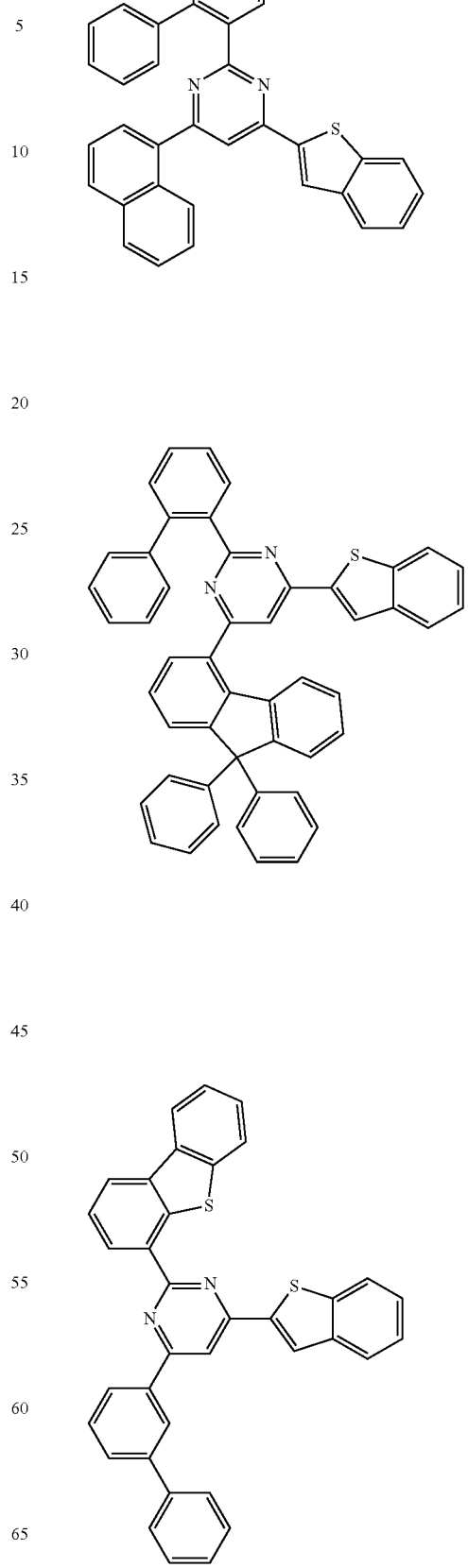

173
-continued
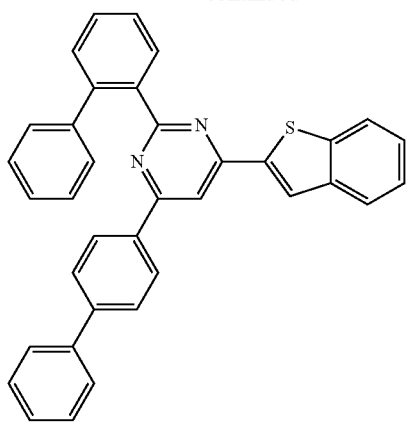
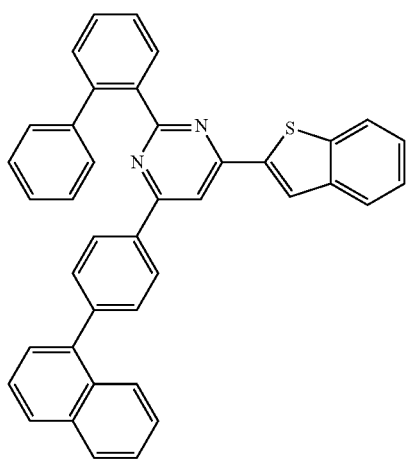
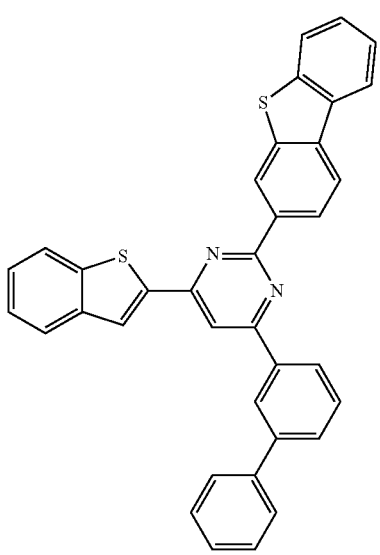
174
-continued
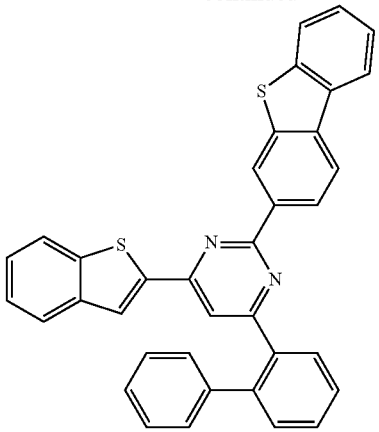
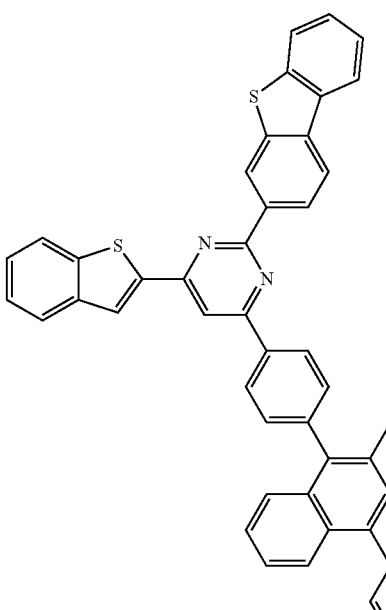
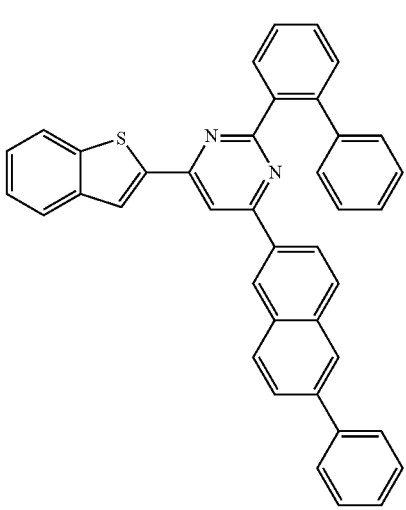

175
-continued
176
-continued
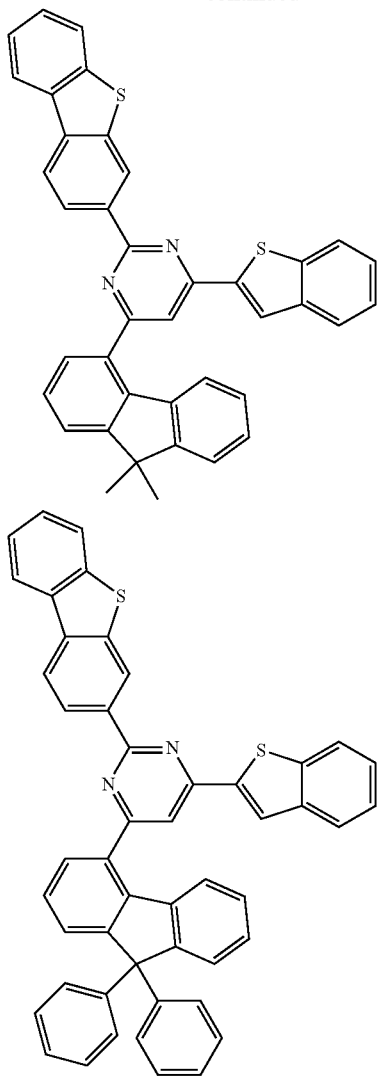
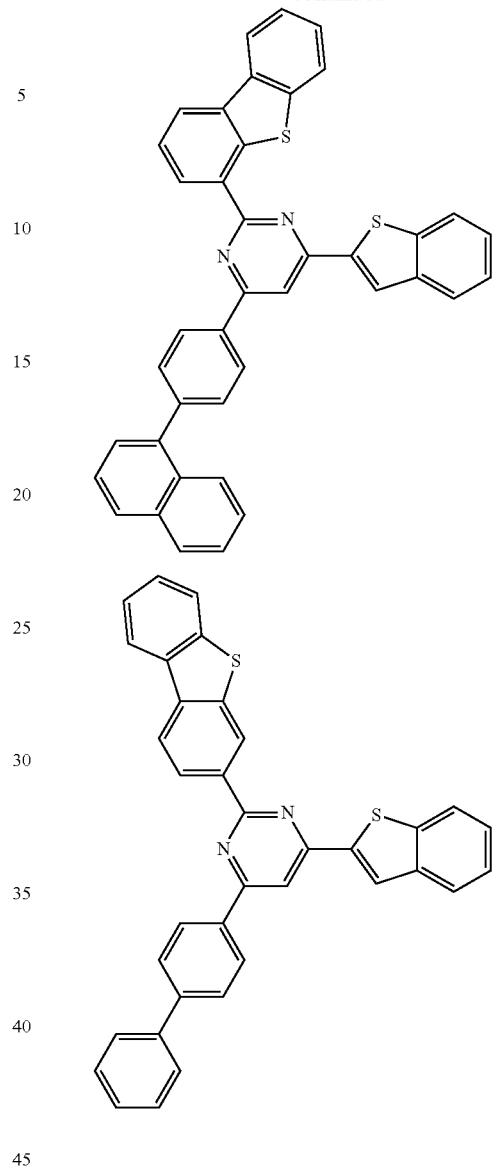
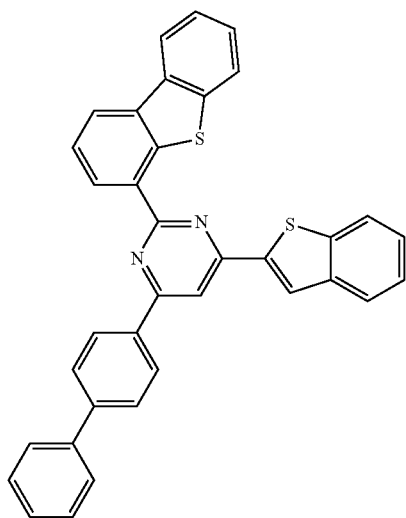

177
-continued
178
-continued
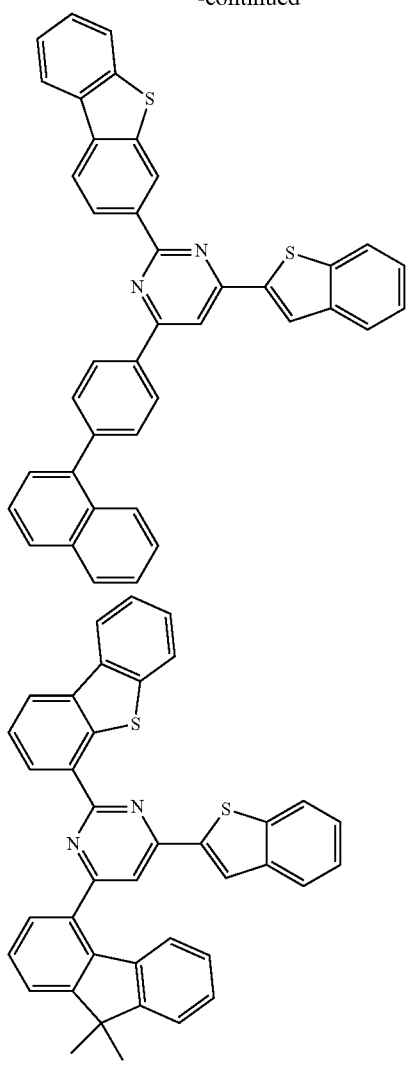
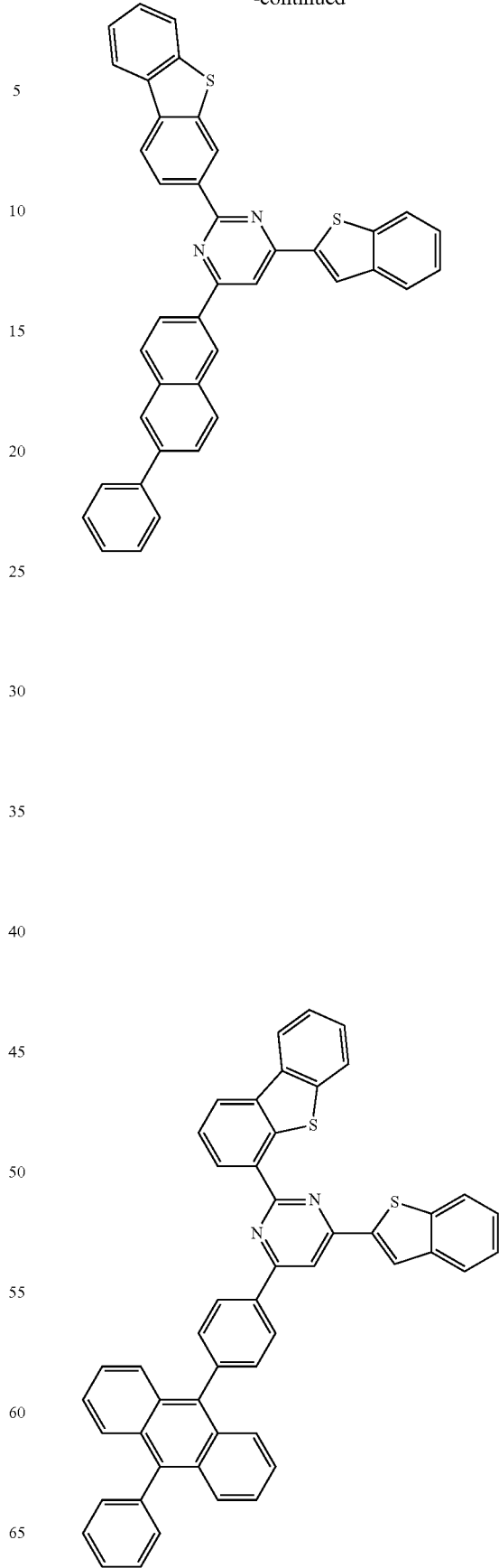

179
-continued
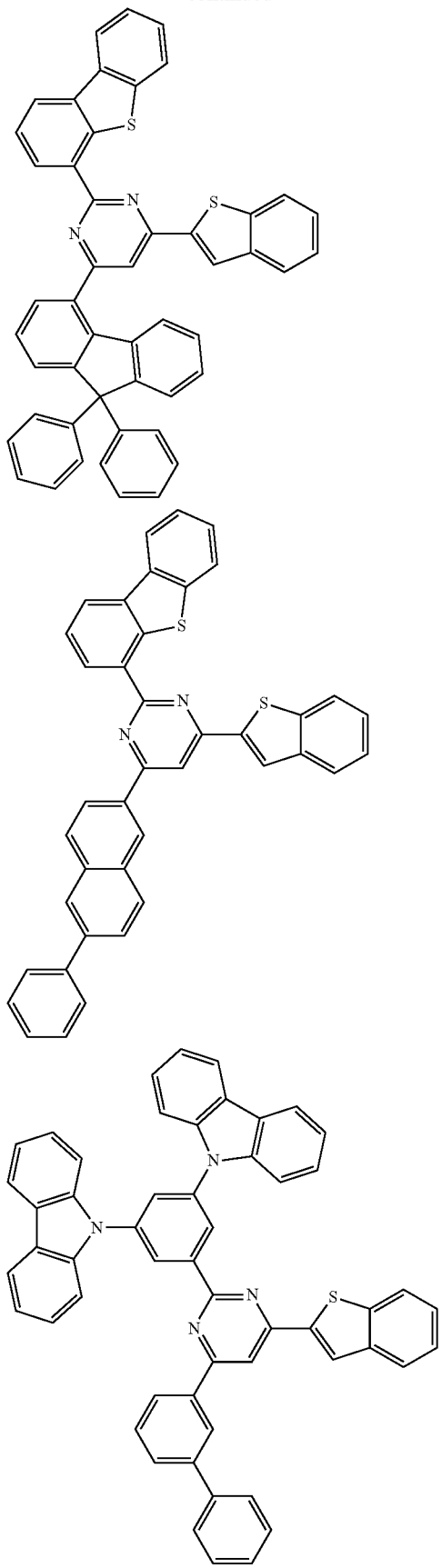
180
-continued
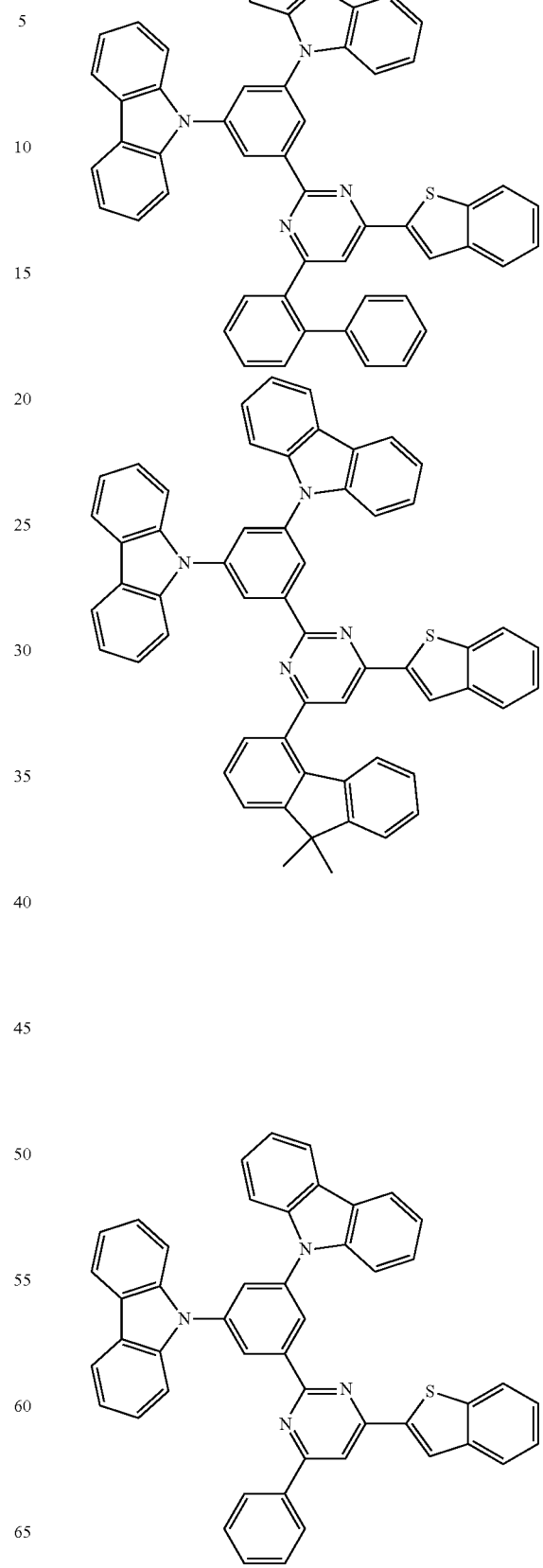

-continued
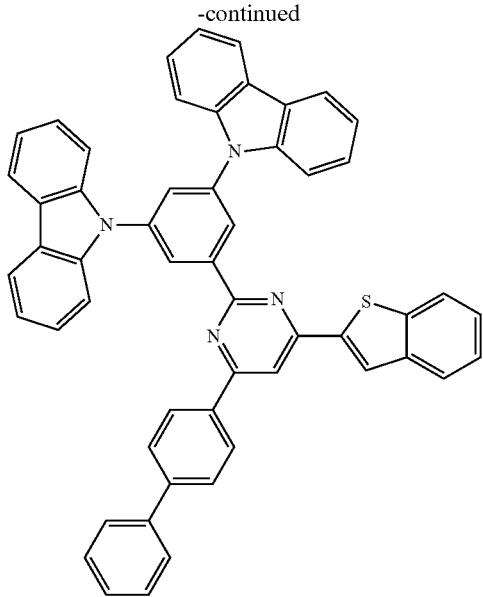
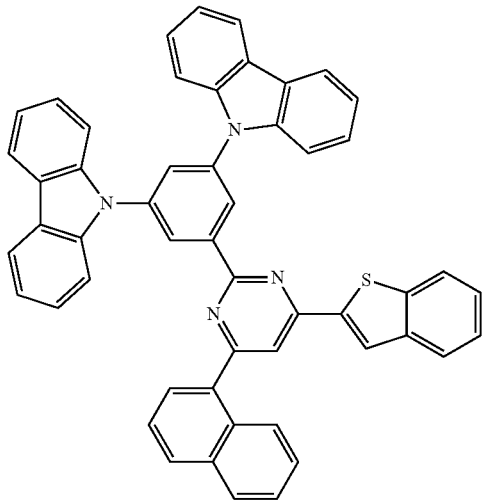
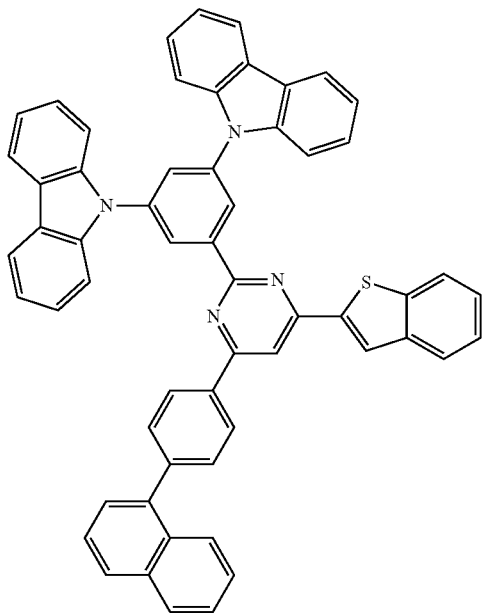
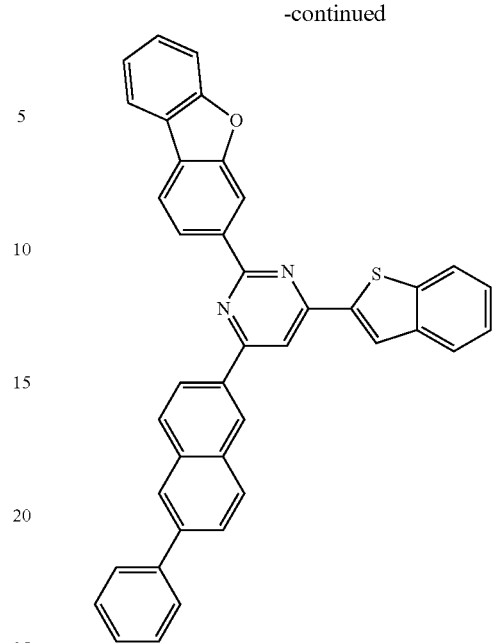
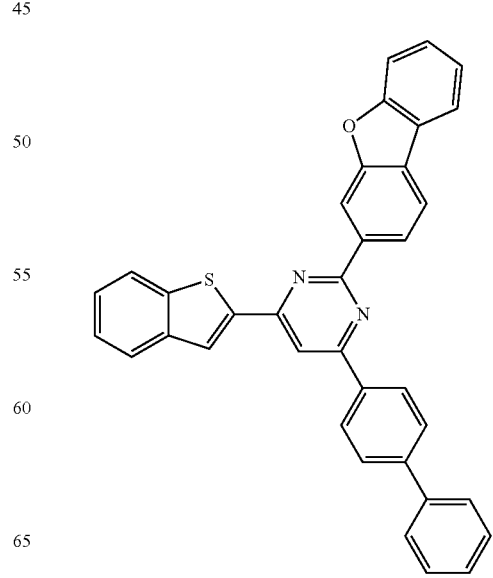

183
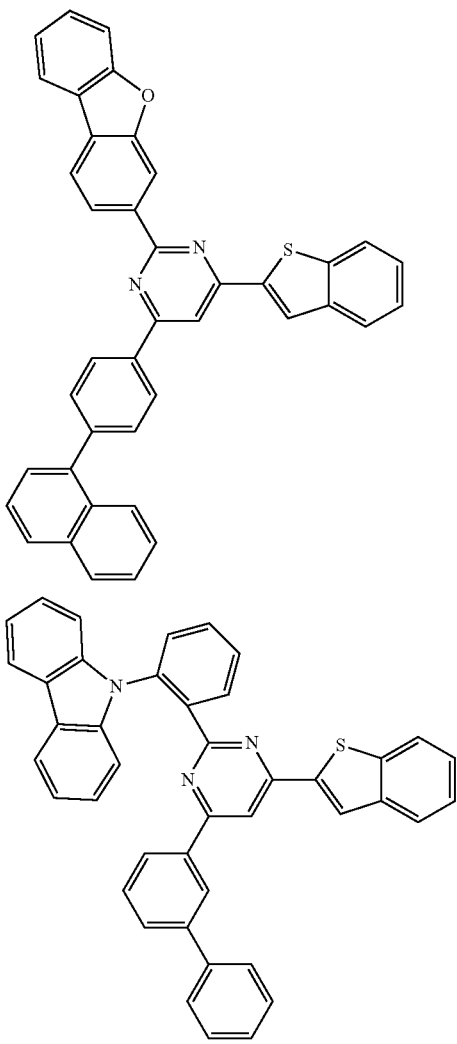
184
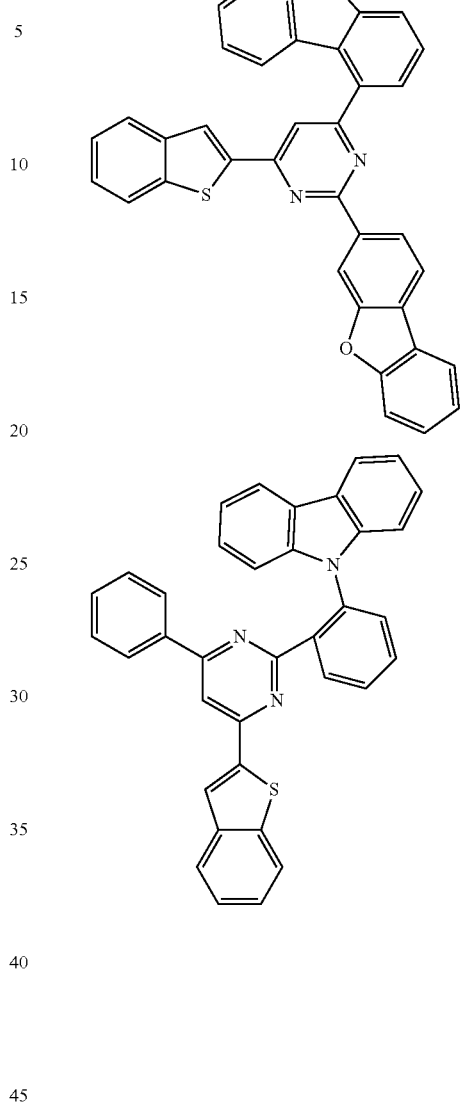
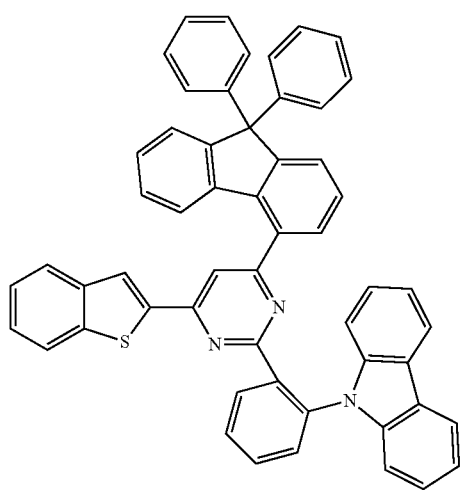
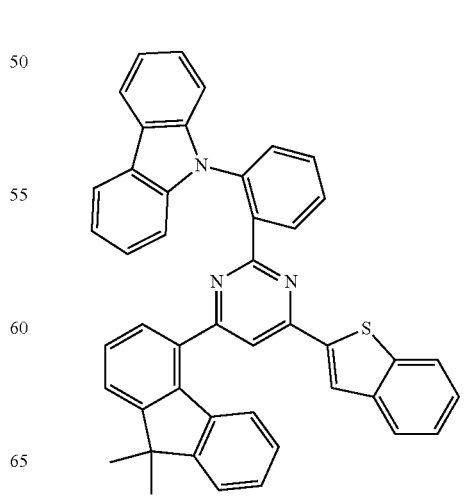

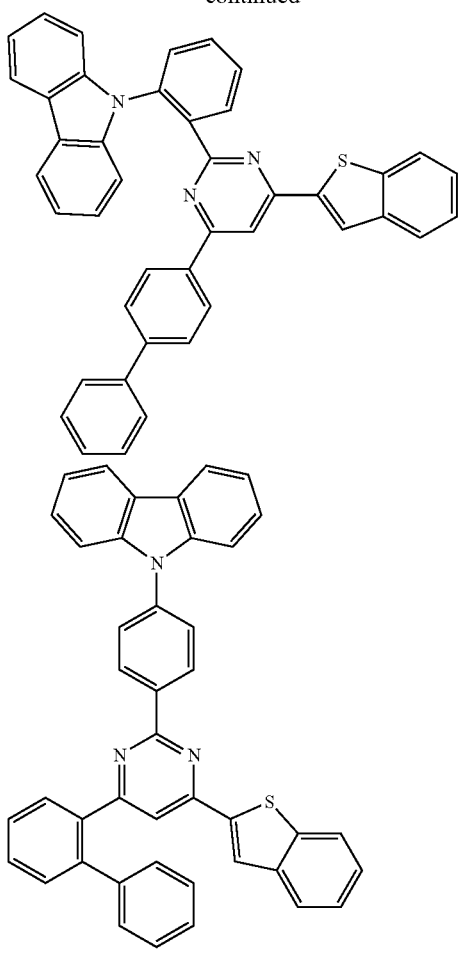
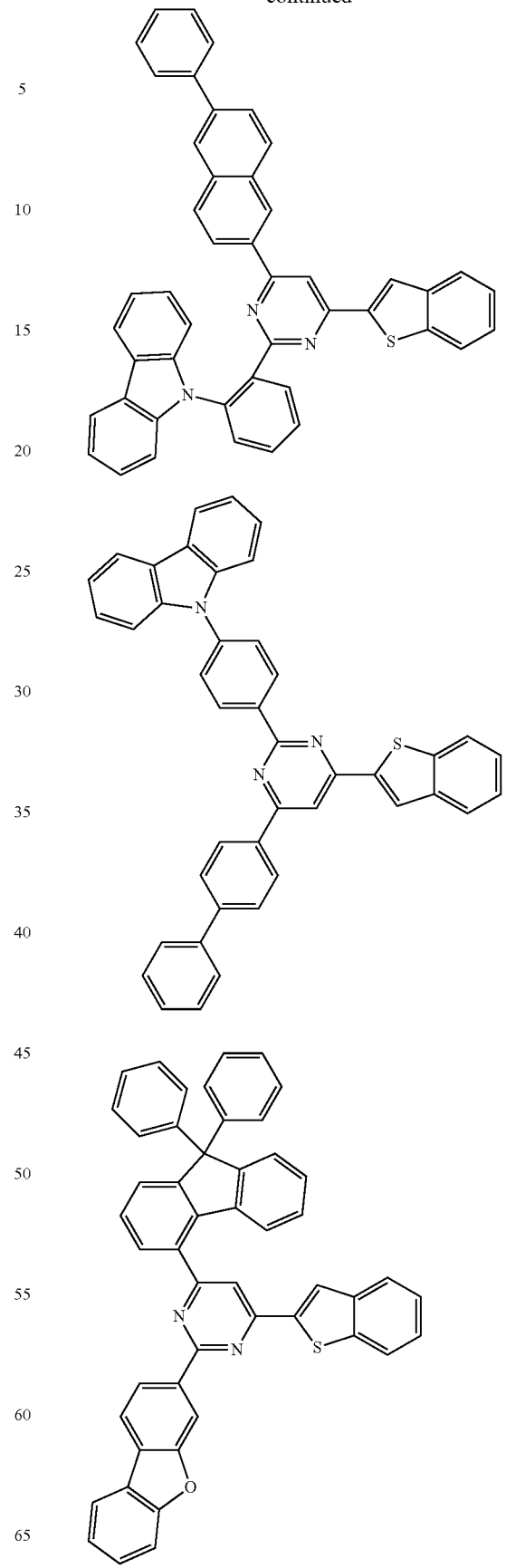

187
-continued
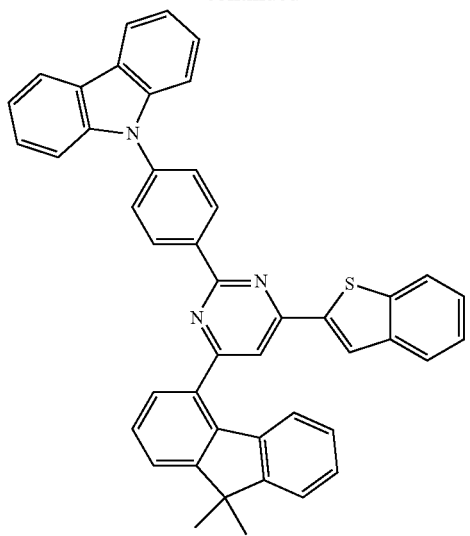
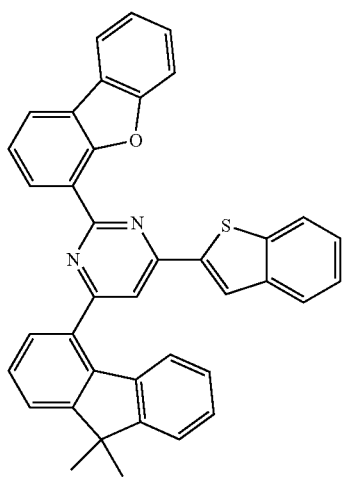
188
-continued
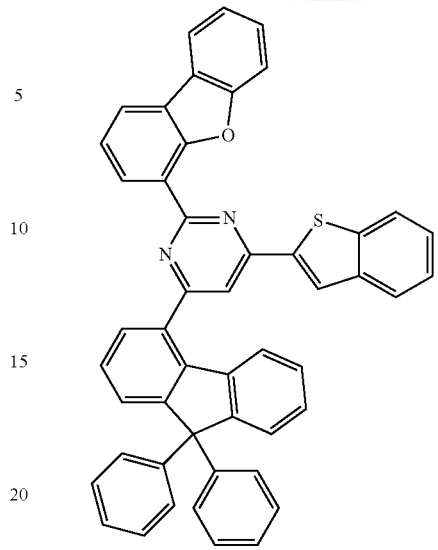
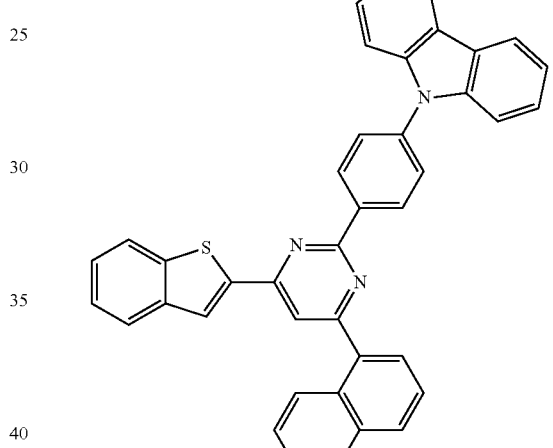
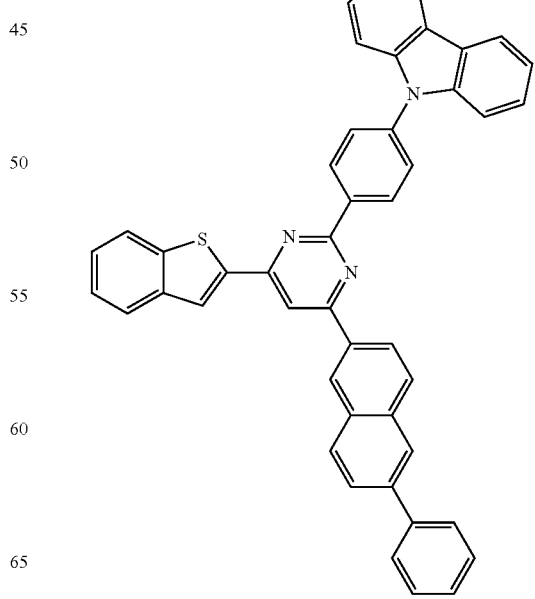

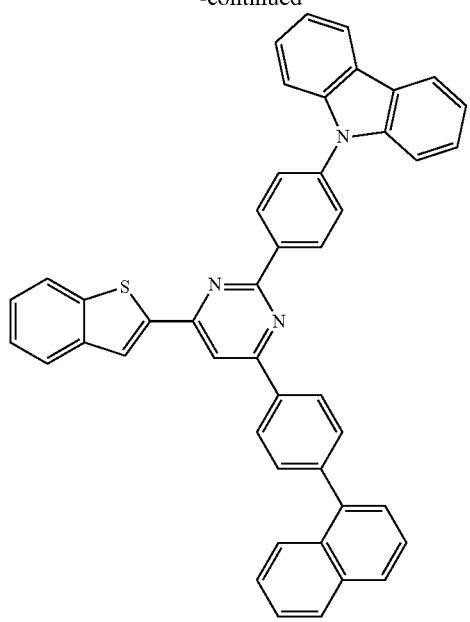
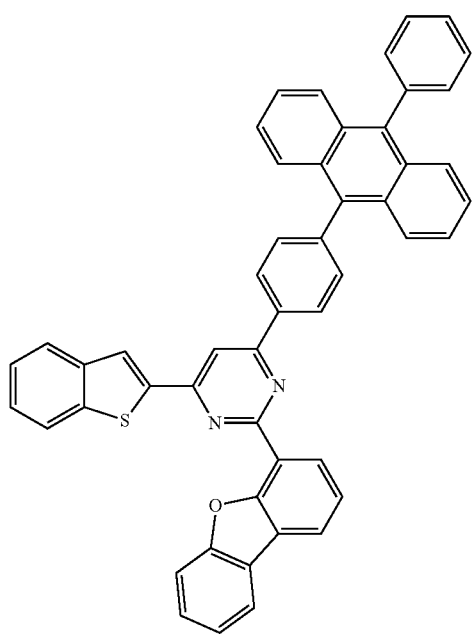
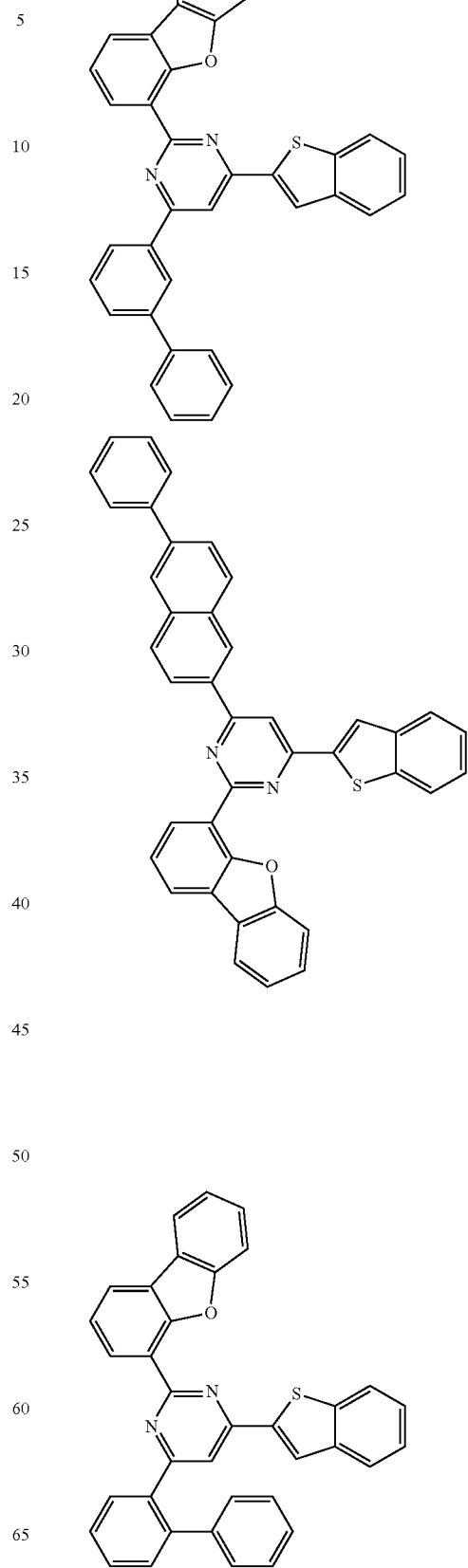

191
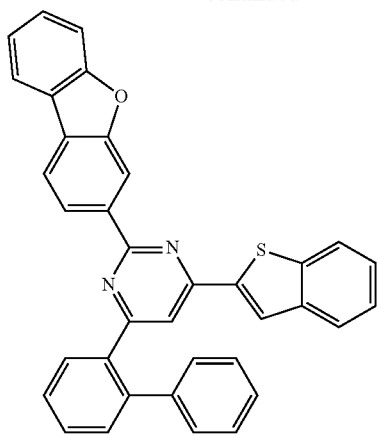
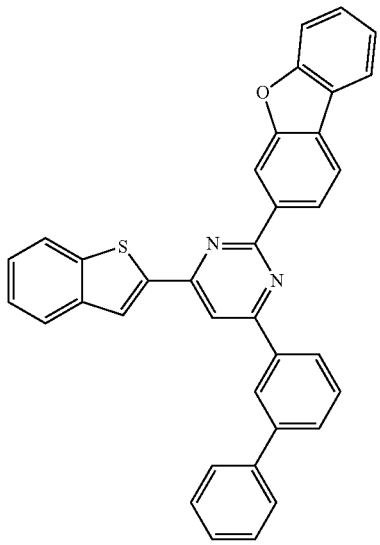
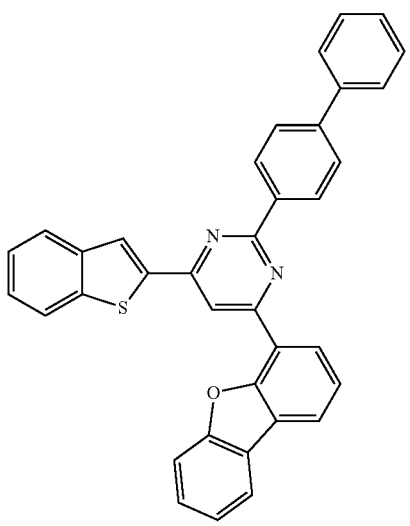
192
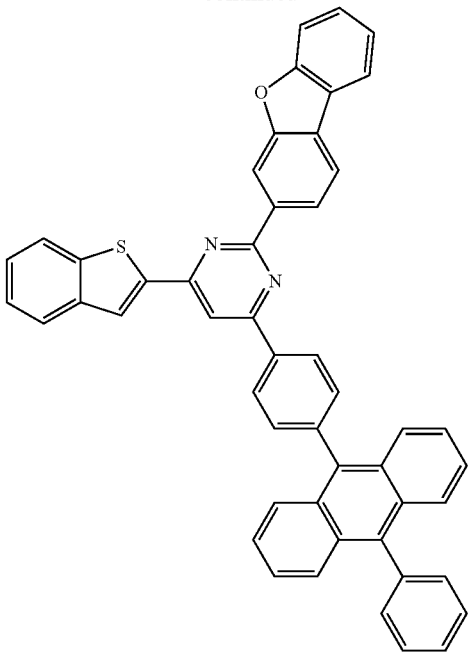
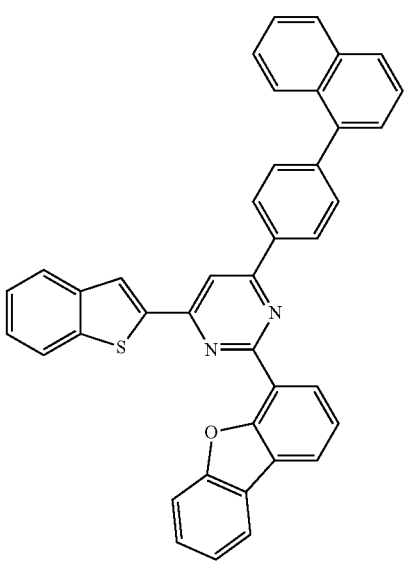

193
-continued
194
-continued
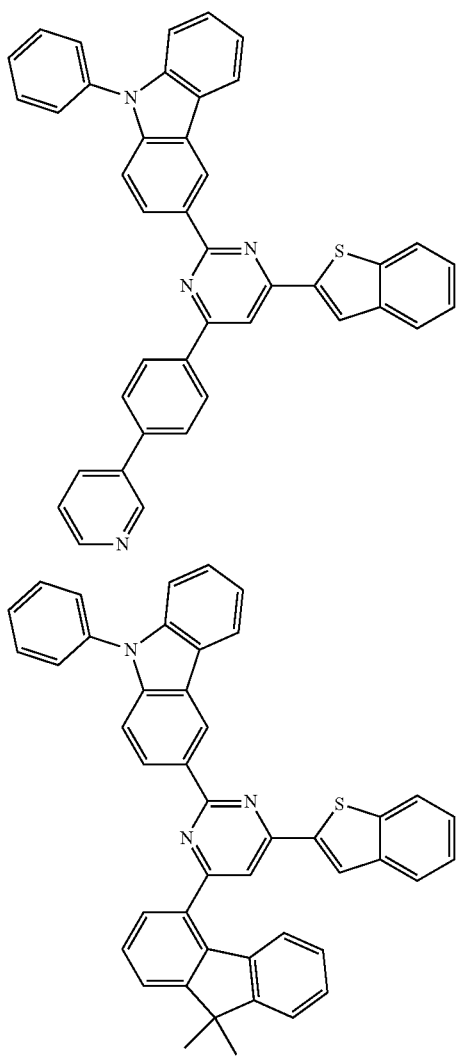
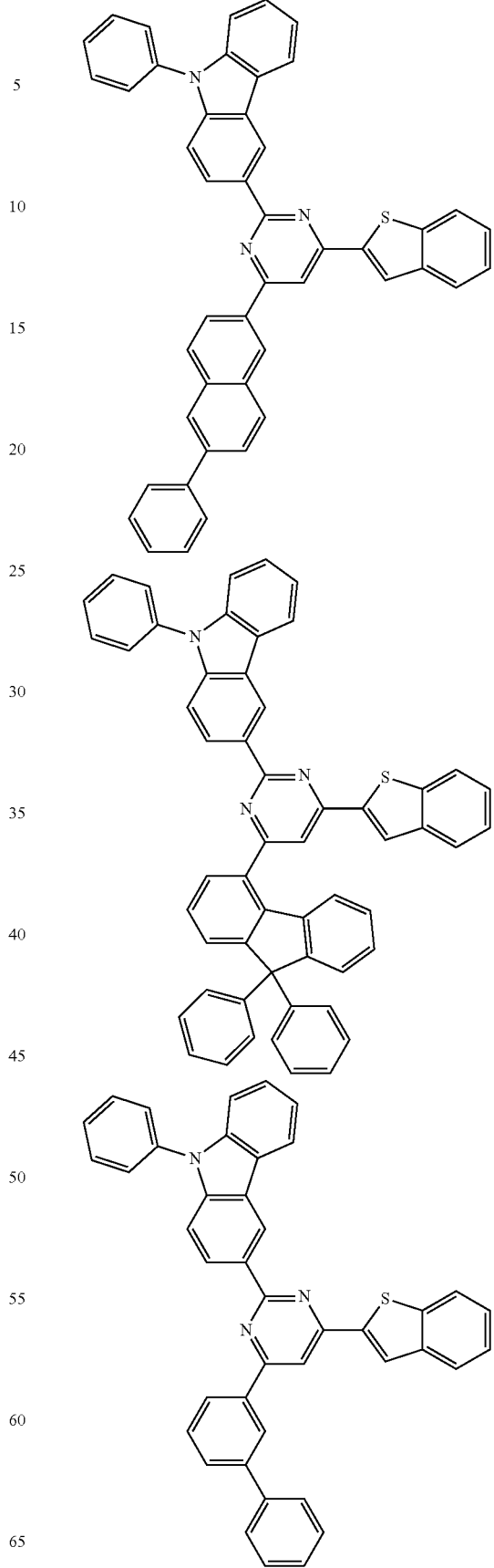

-continued
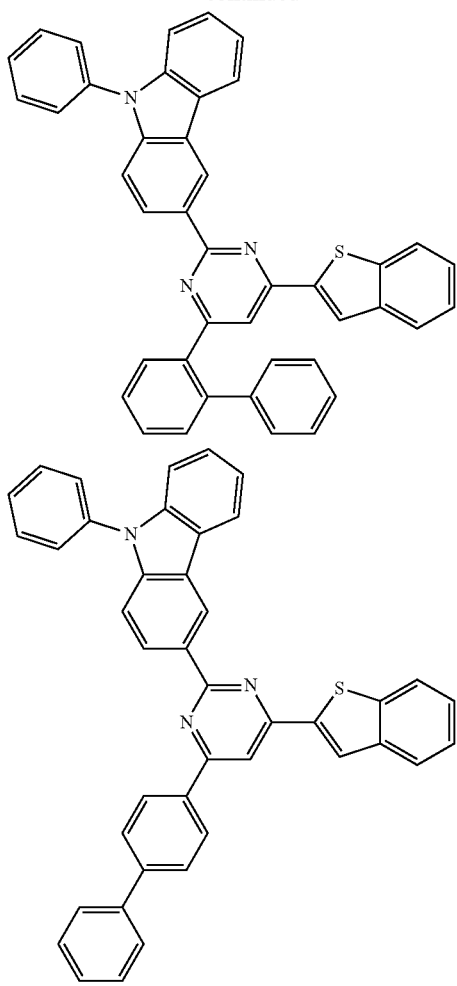
-continued
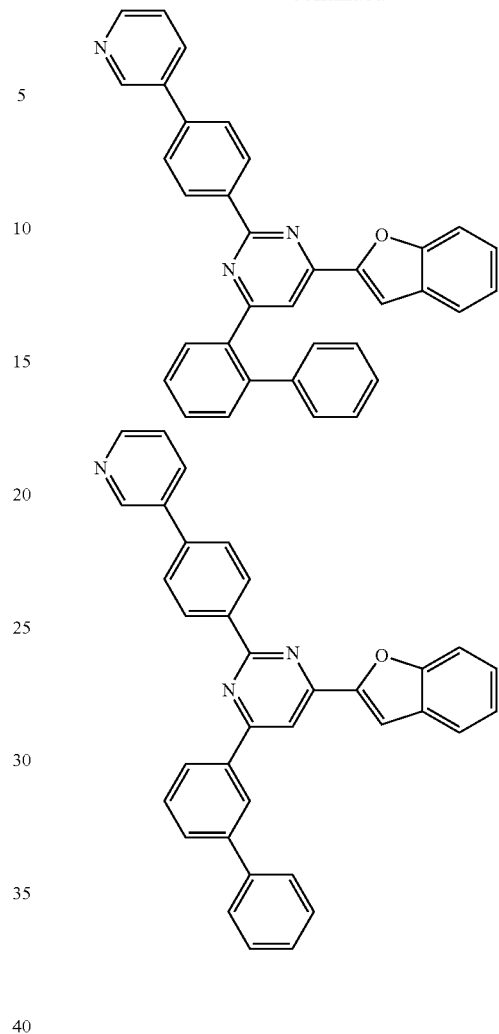
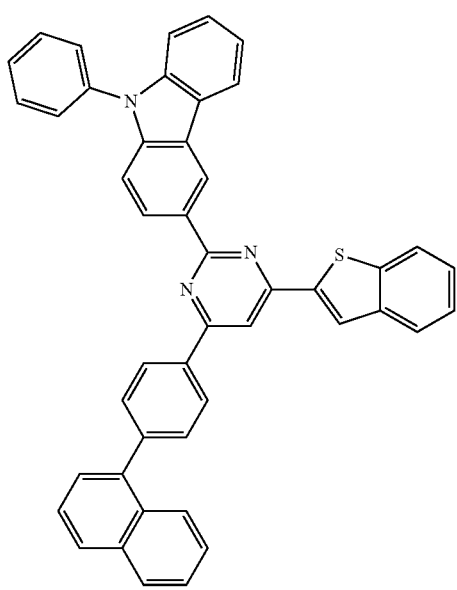
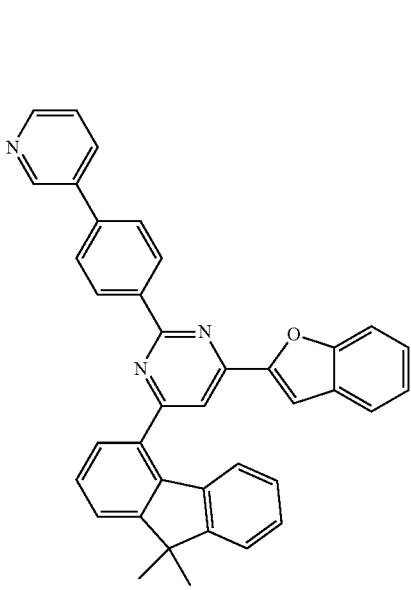

197
-continued
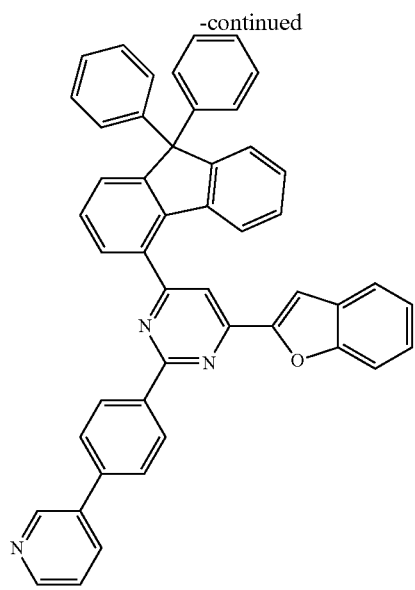
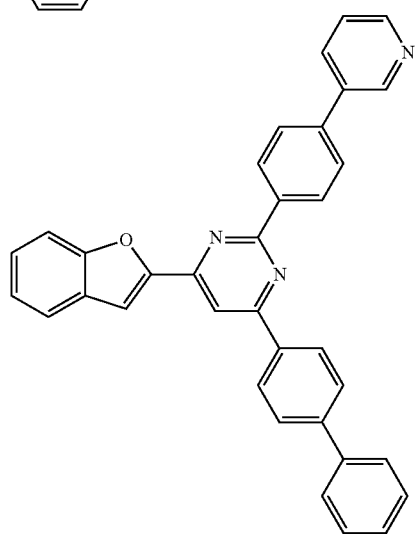
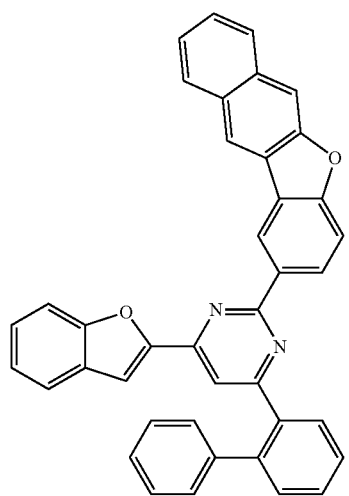
198
-continued
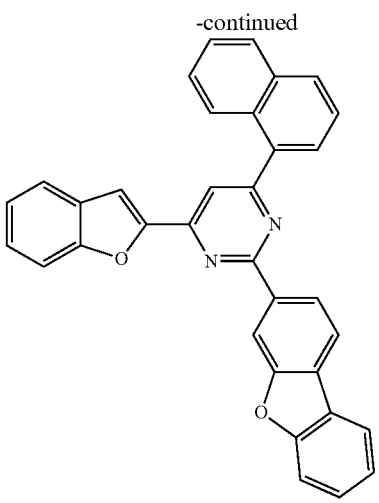
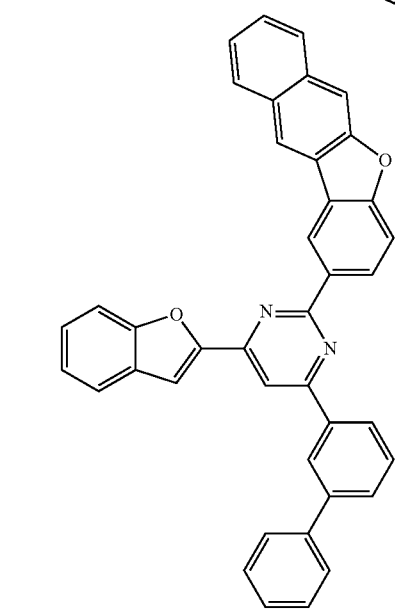
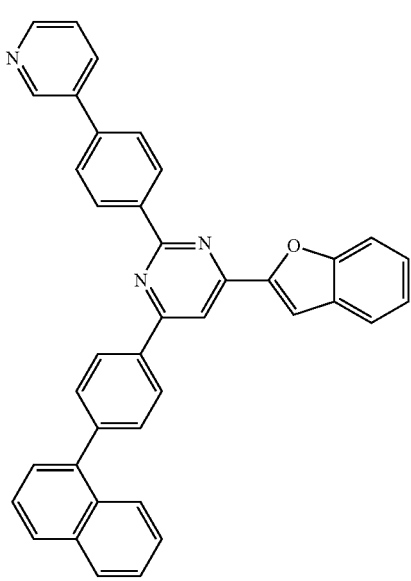

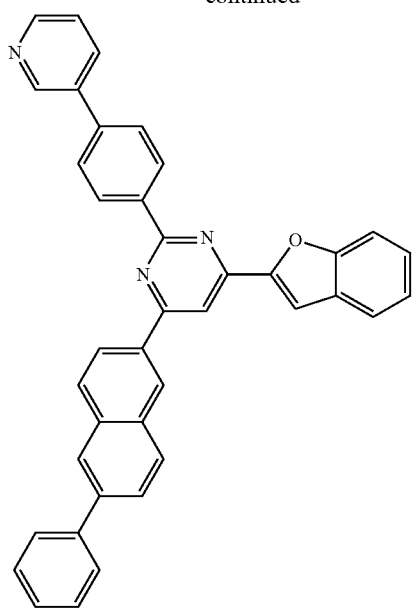
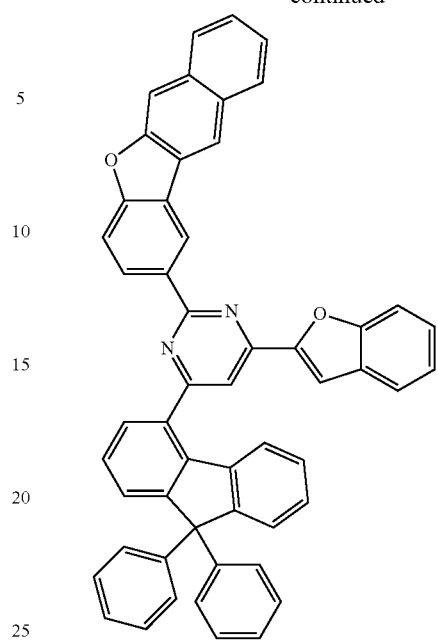
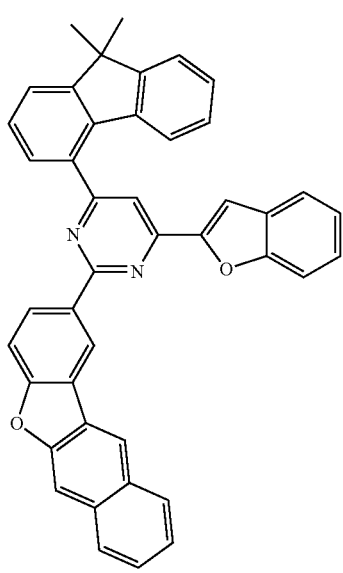
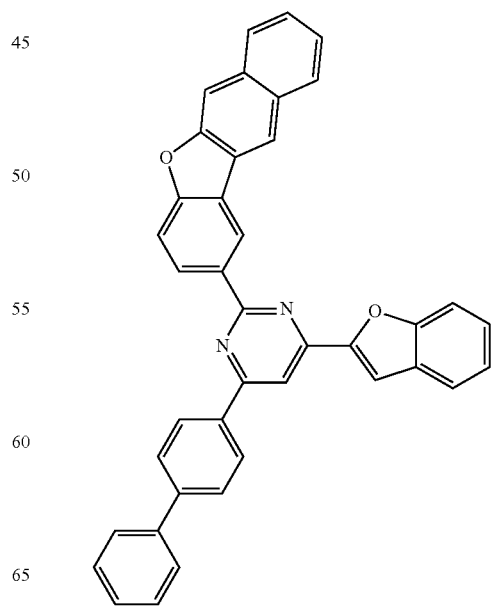

201
-continued
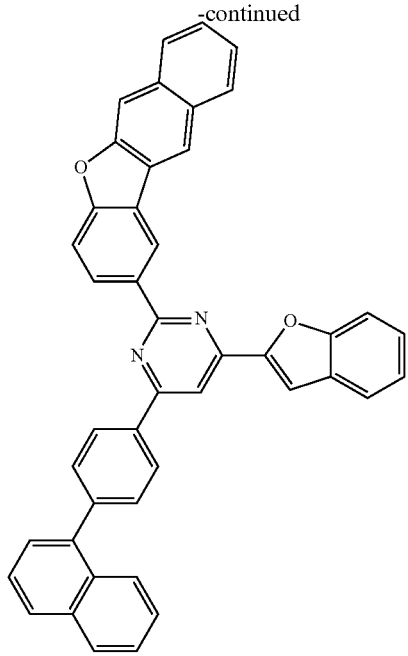
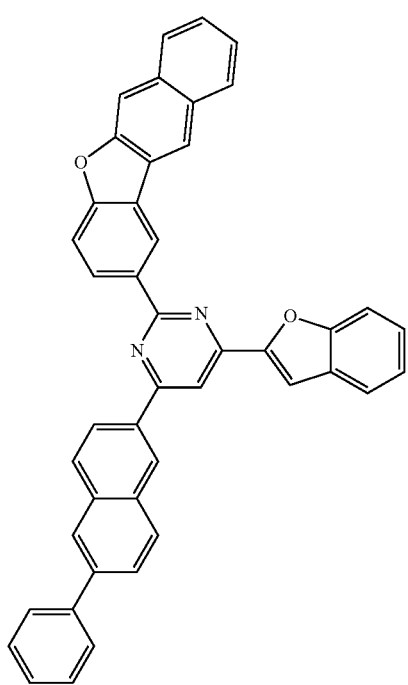
202
-continued
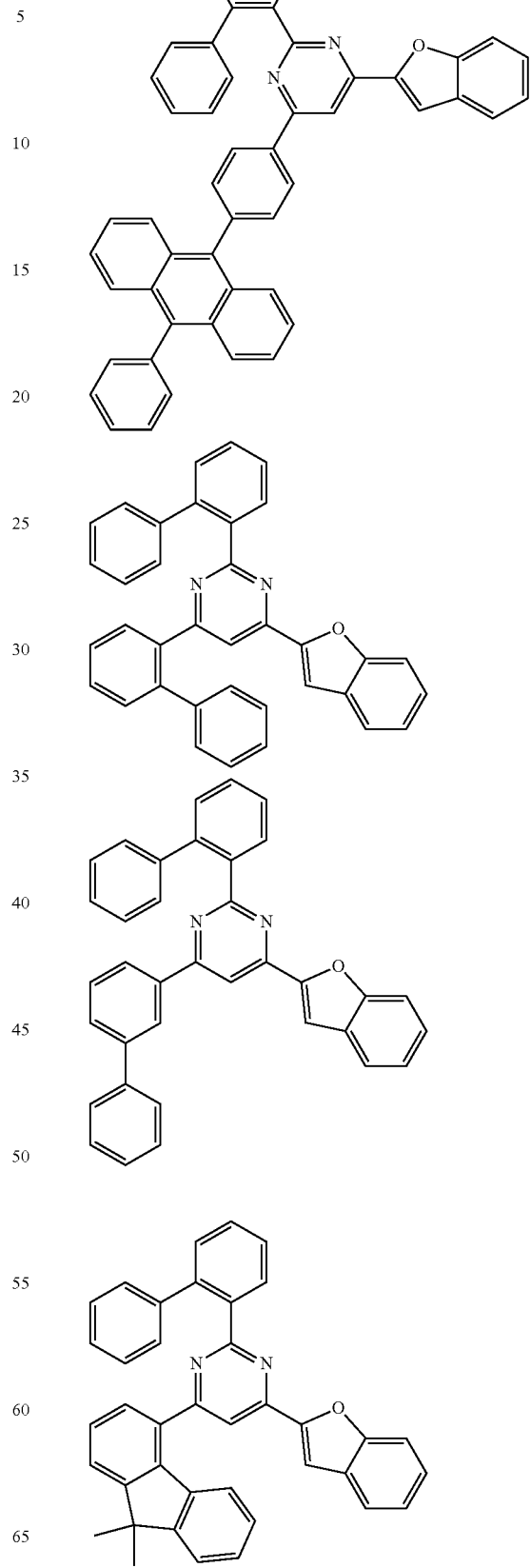

203
-continued
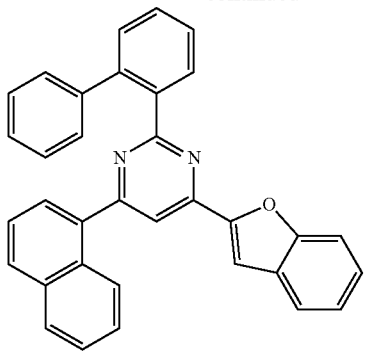
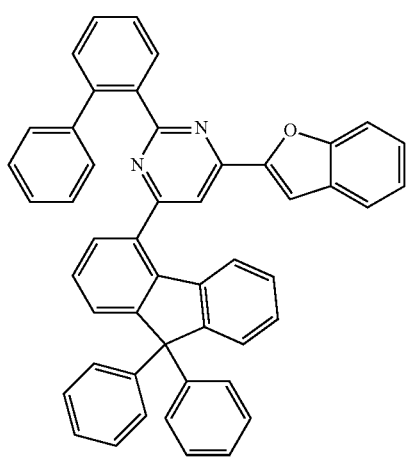
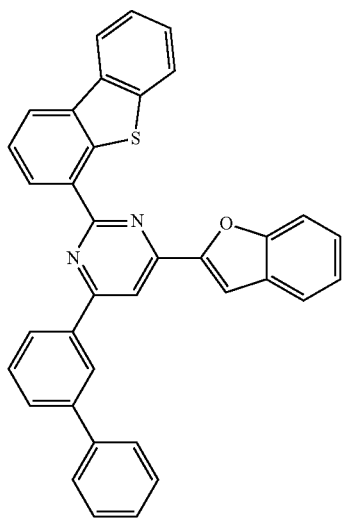
204
-continued
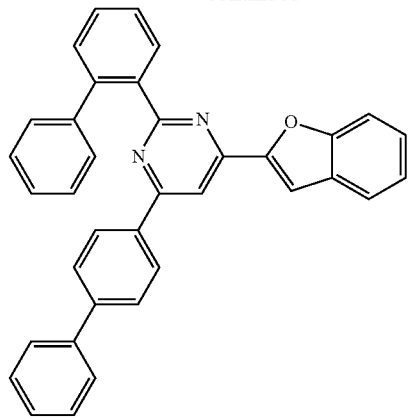
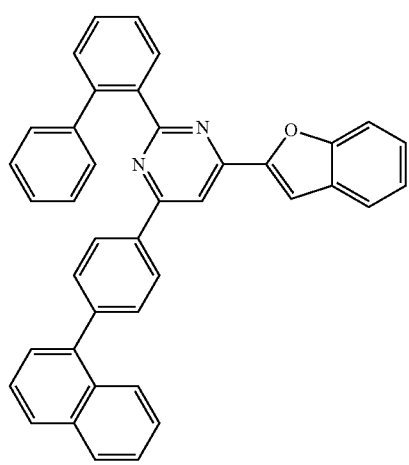
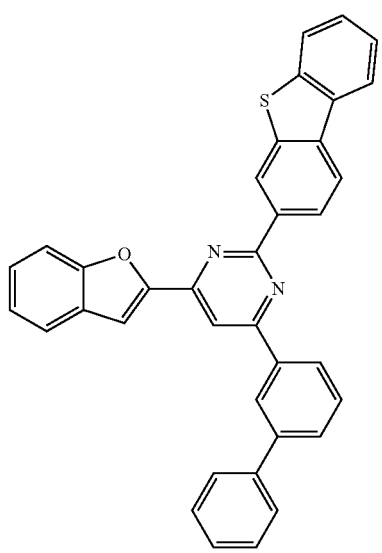

205
-continued
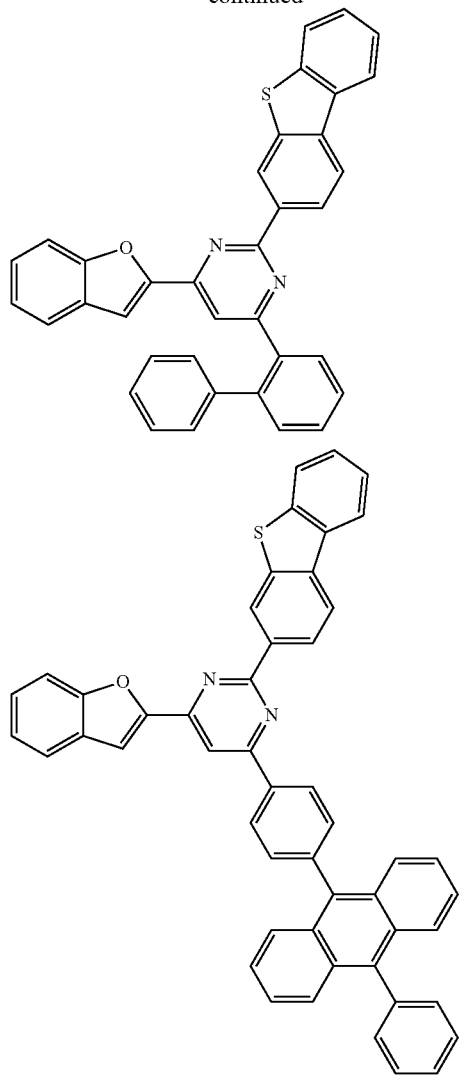
206
-continued
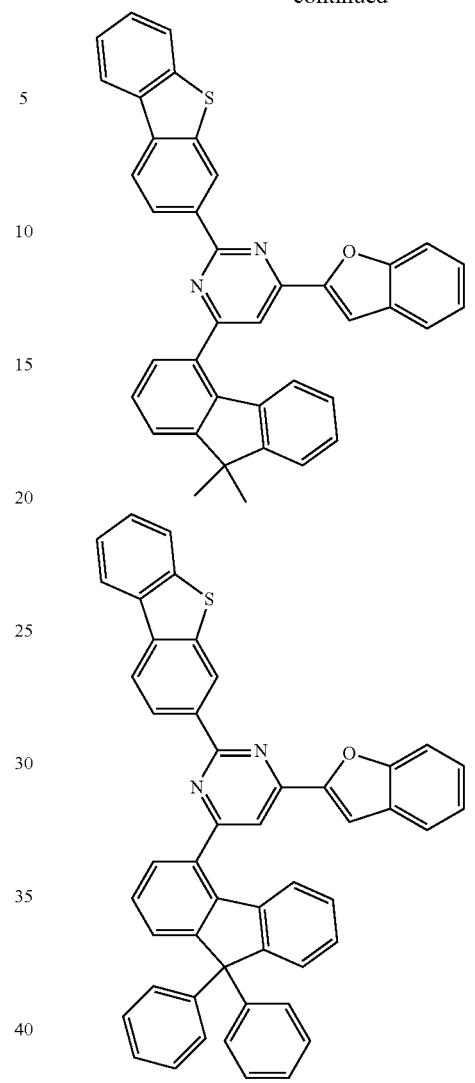
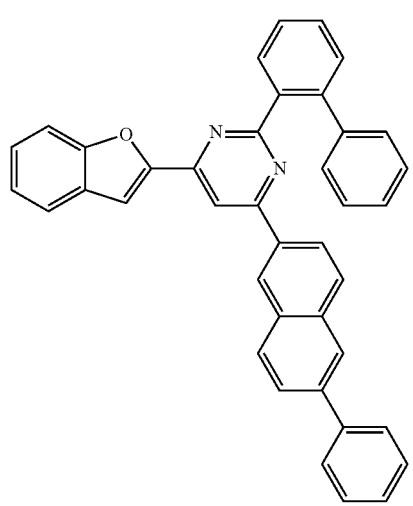
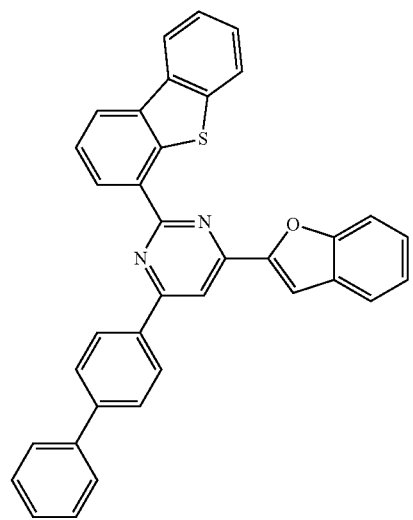

207
-continued
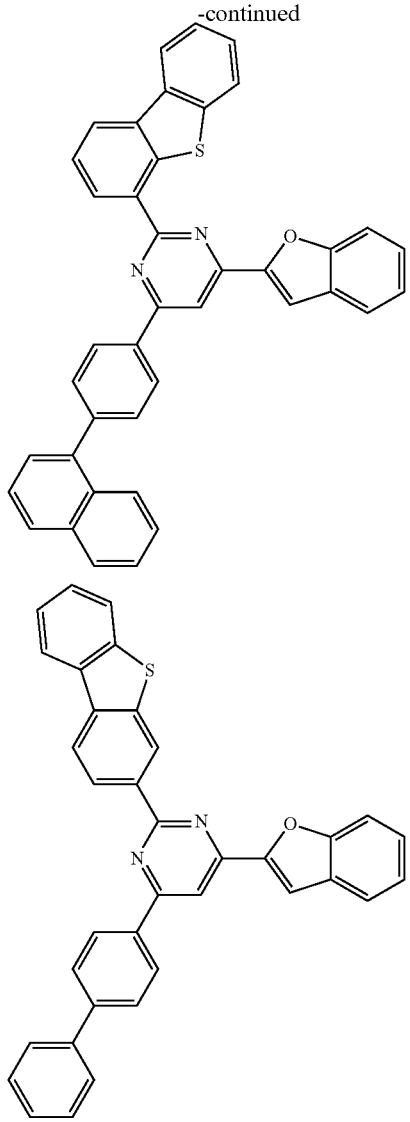
208
-continued
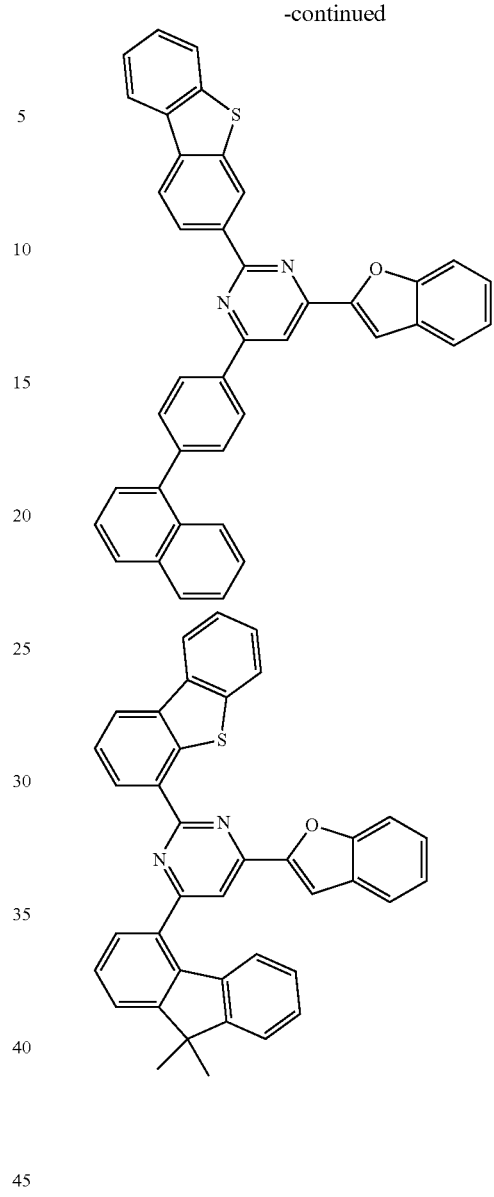
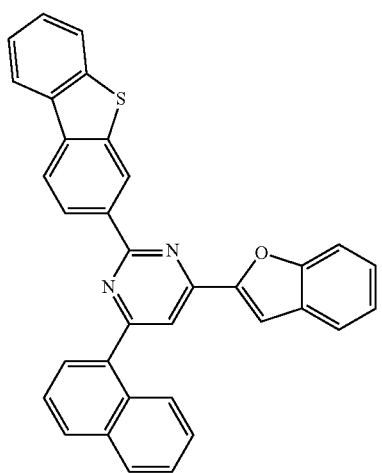

209
-continued
210
-continued
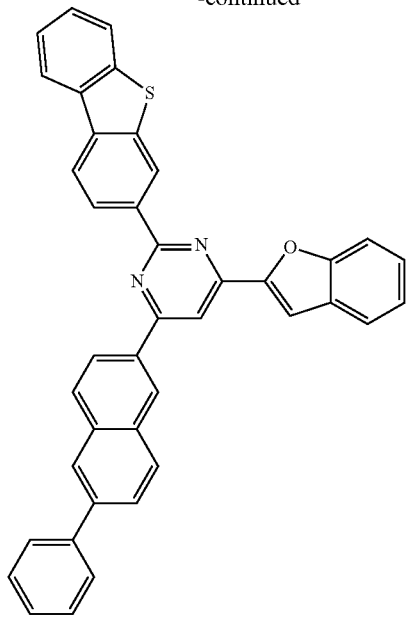
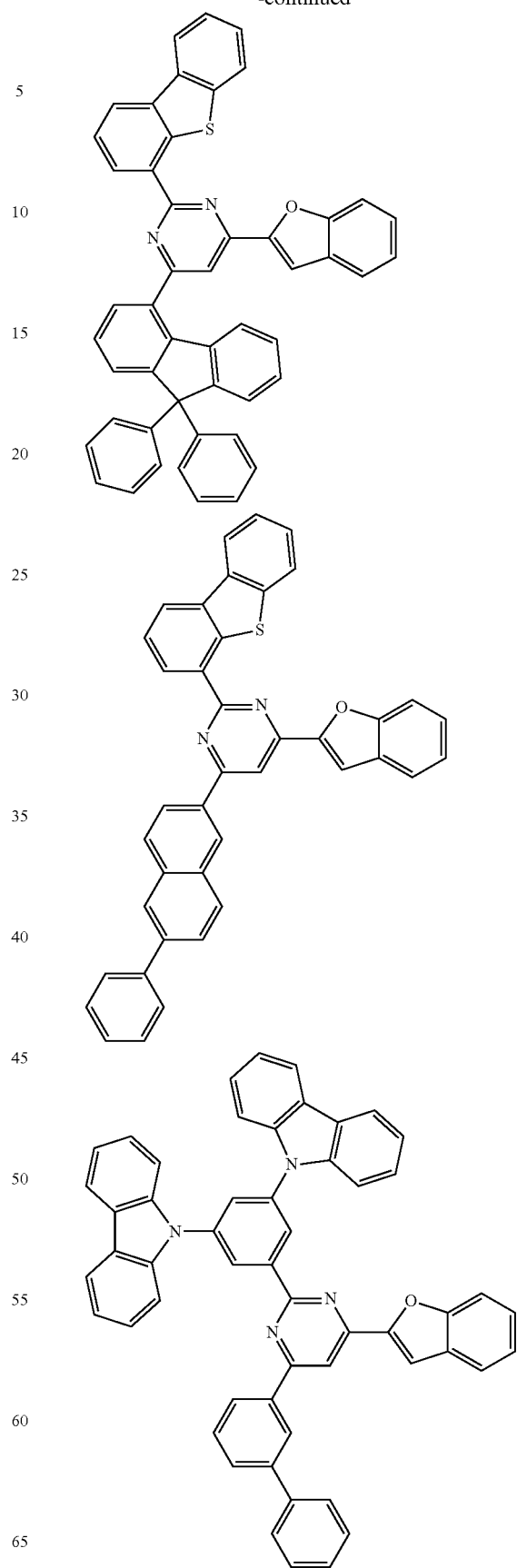

211
-continued
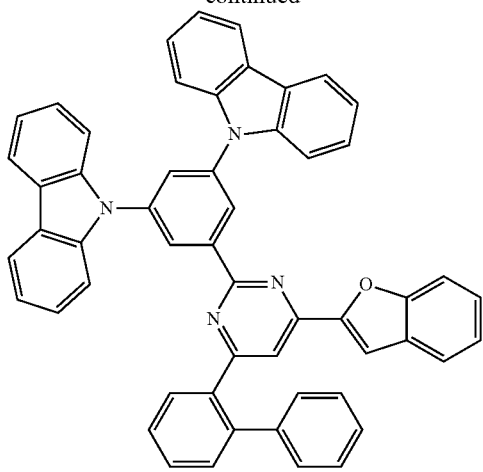
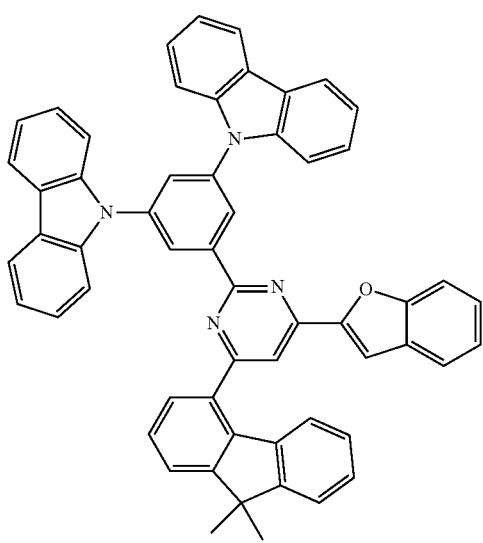
212
-continued
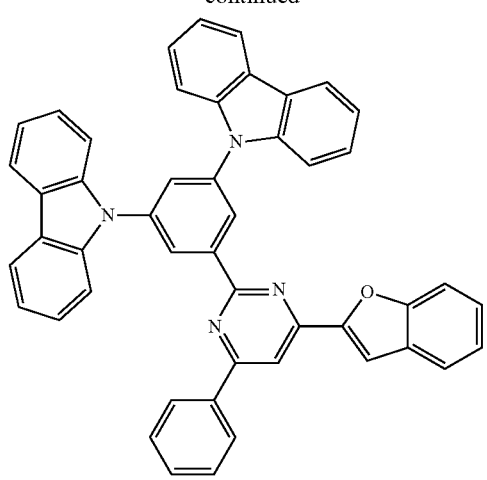
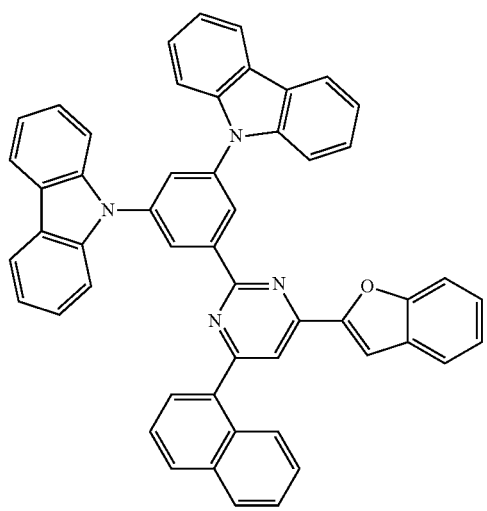

213
-continued
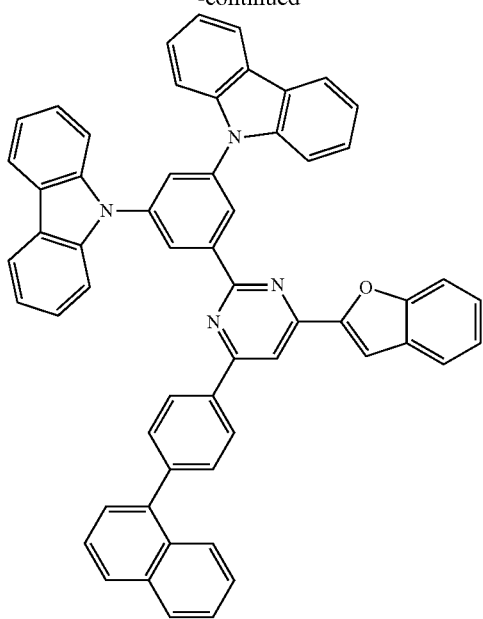
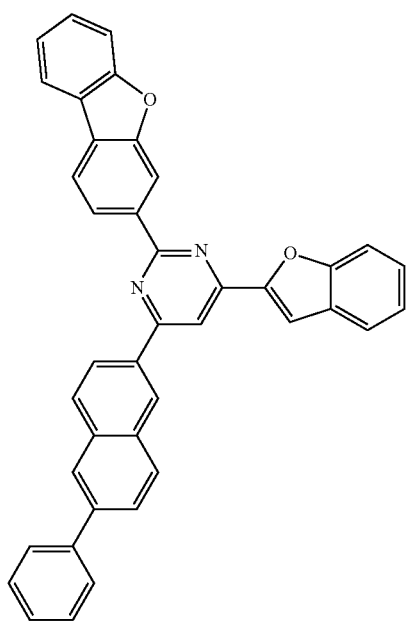
214
-continued
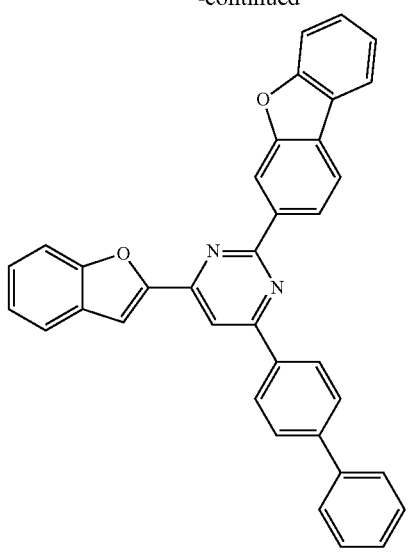
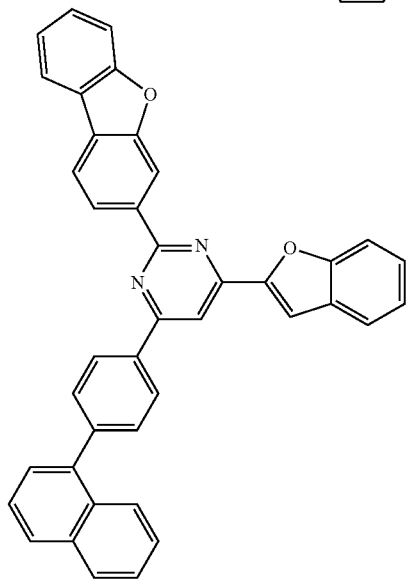
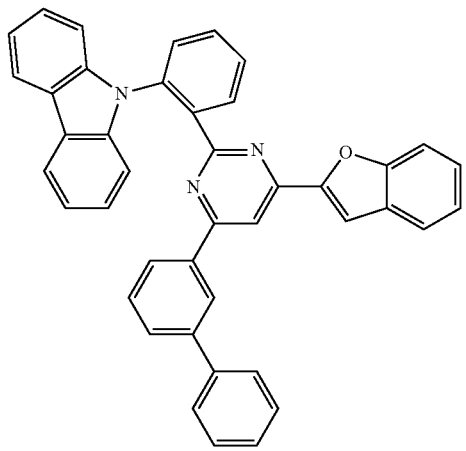

215
-continued
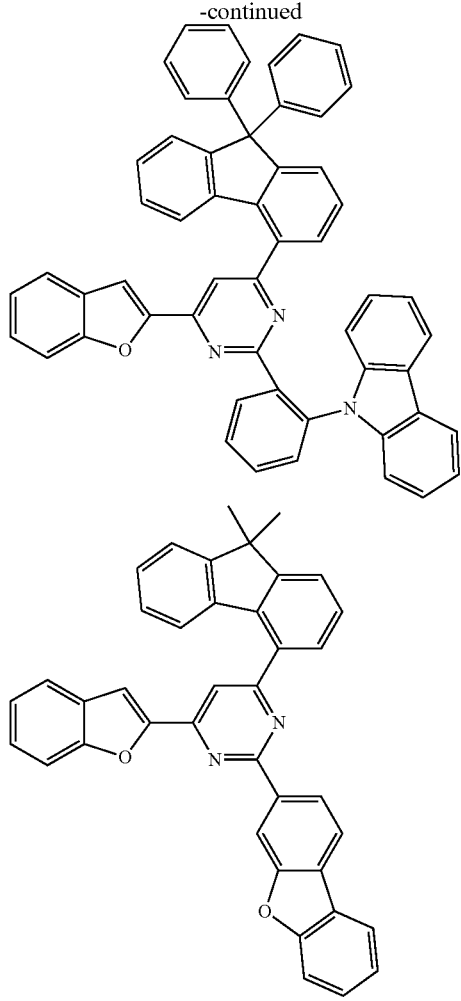
216
-continued
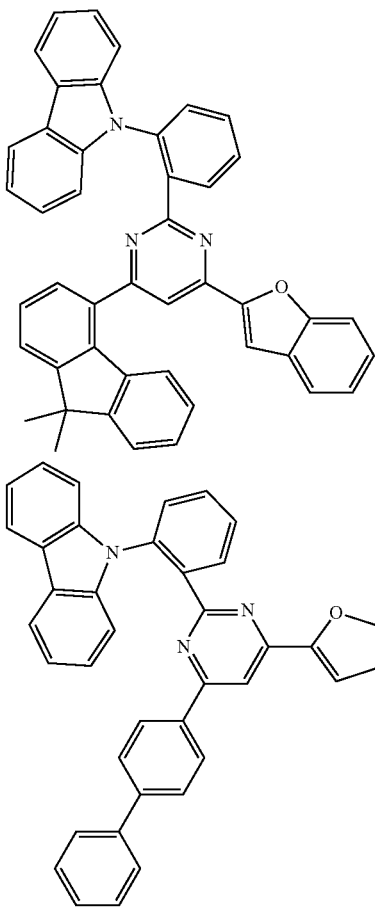
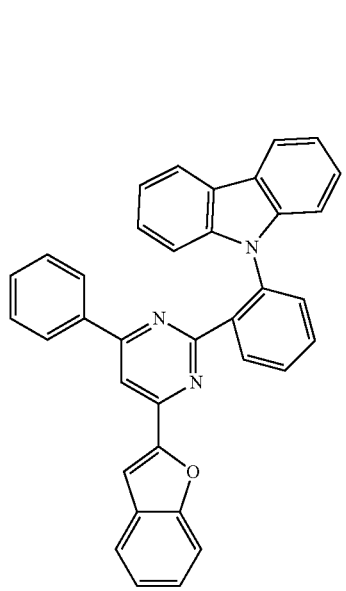
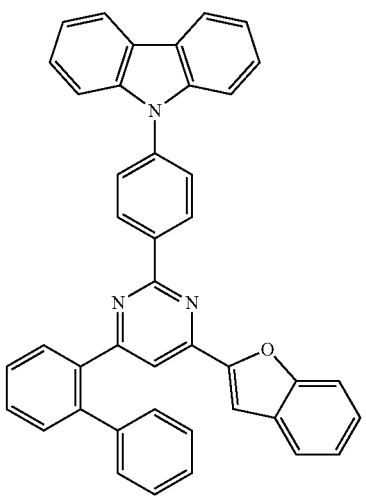

217
-continued
218
-continued
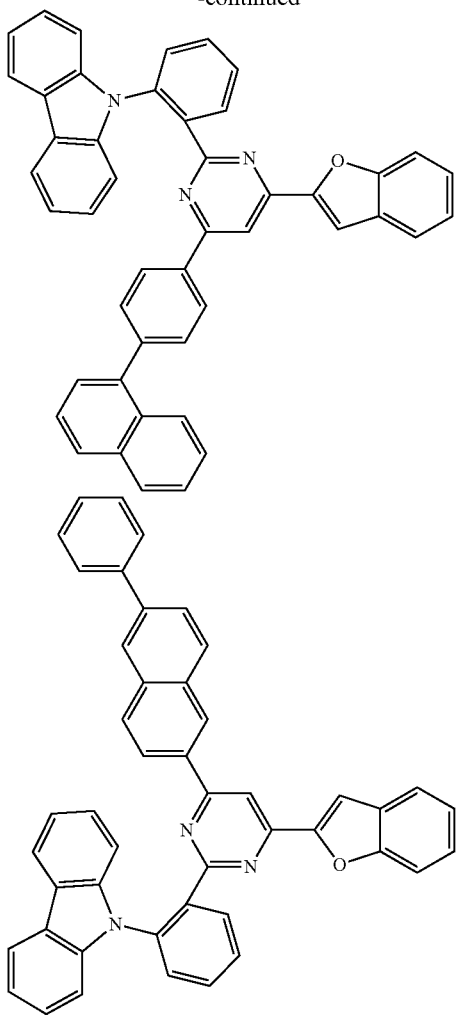
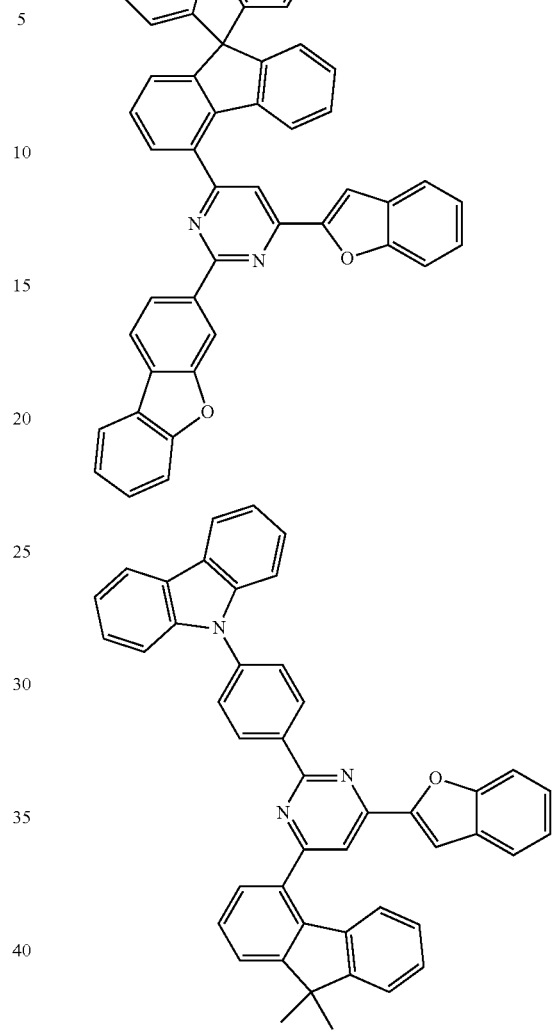
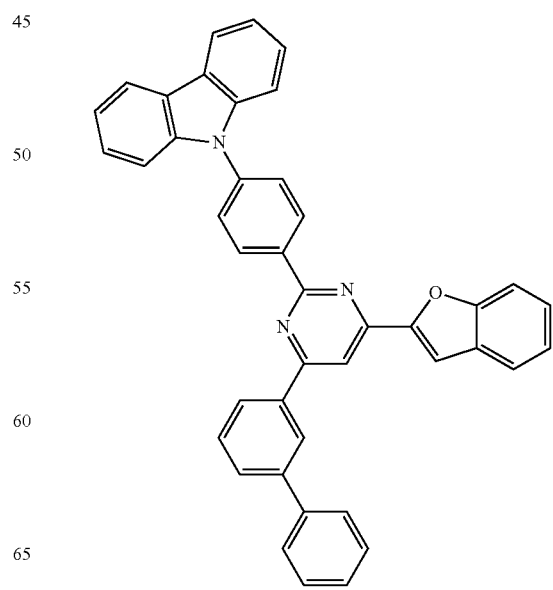

219
-continued
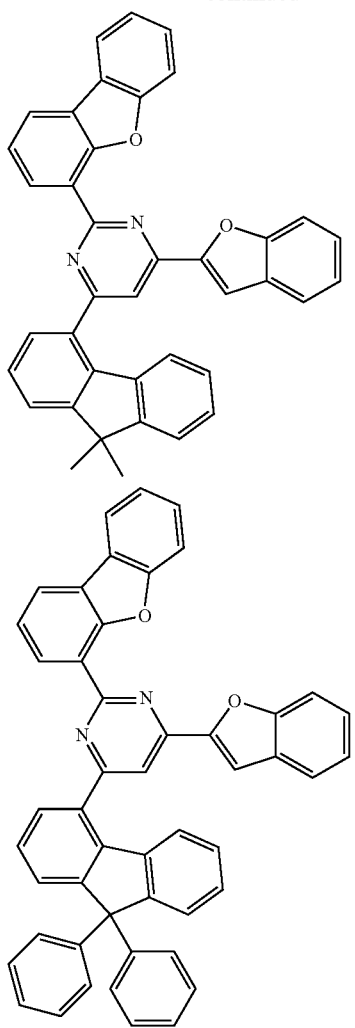
220
-continued
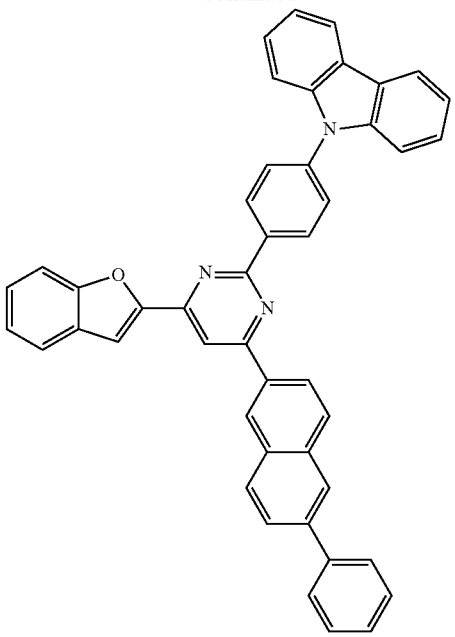
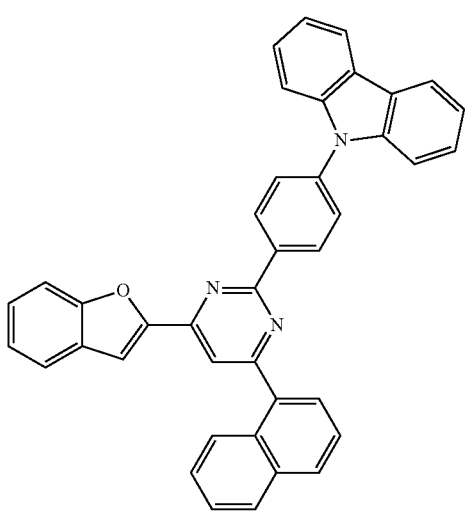
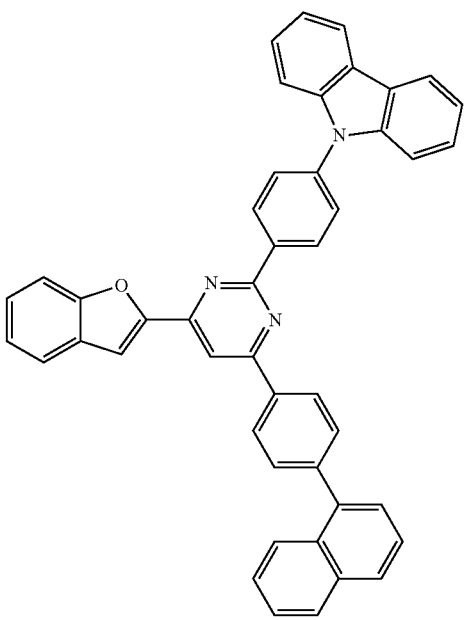

221
-continued
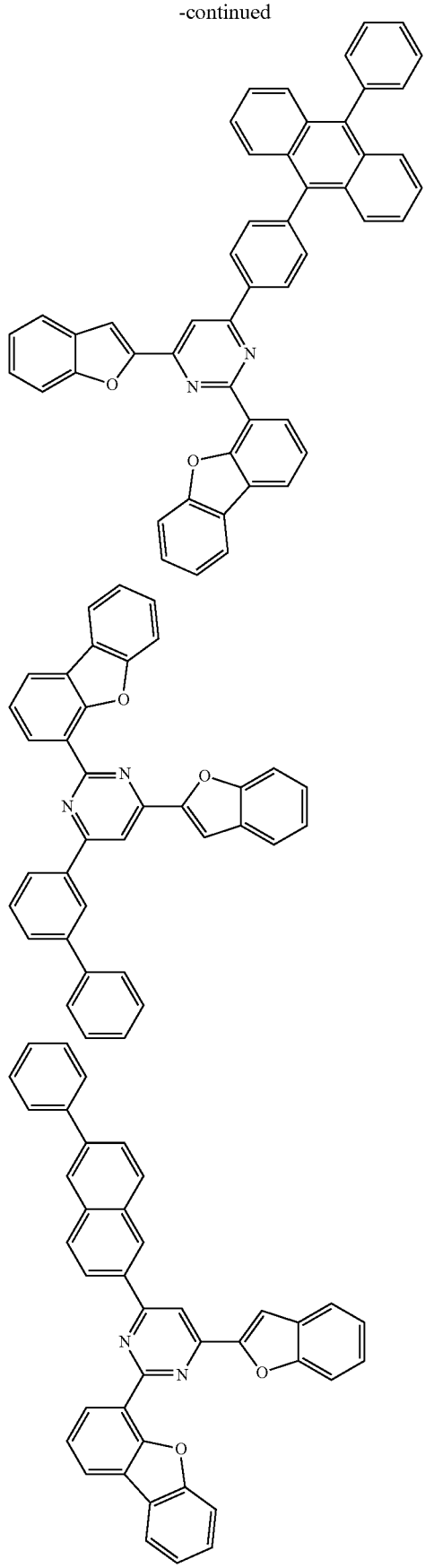
222
-continued
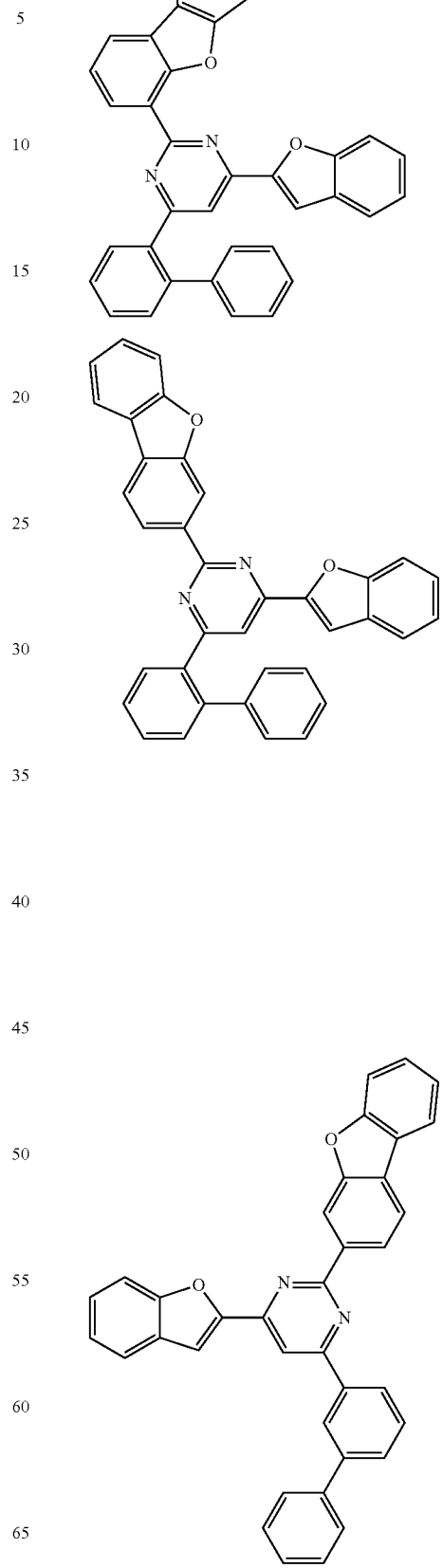

223
-continued
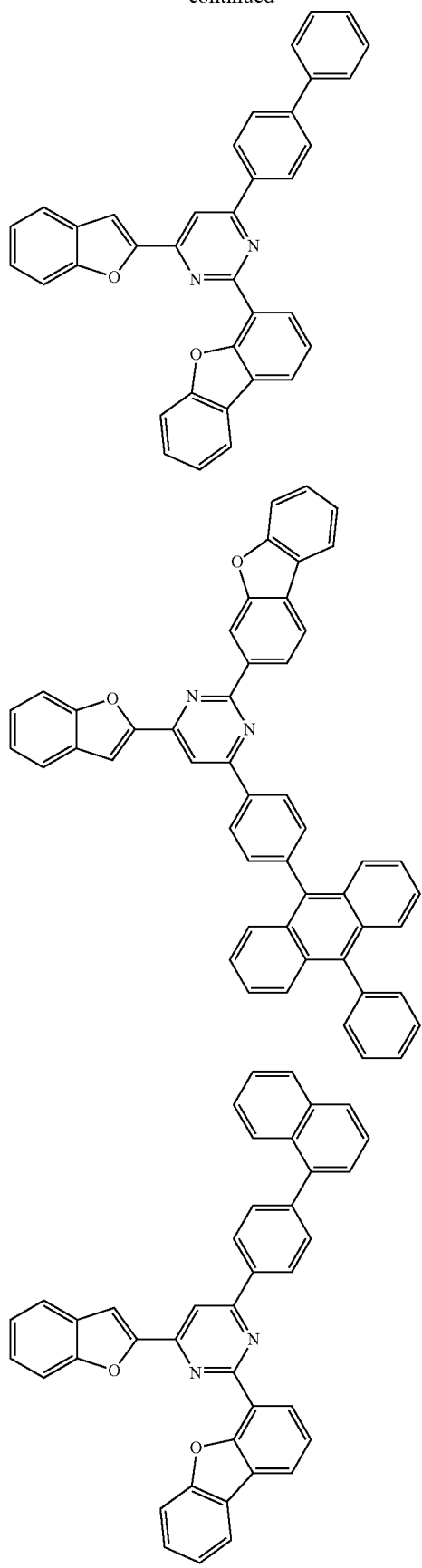
224
-continued
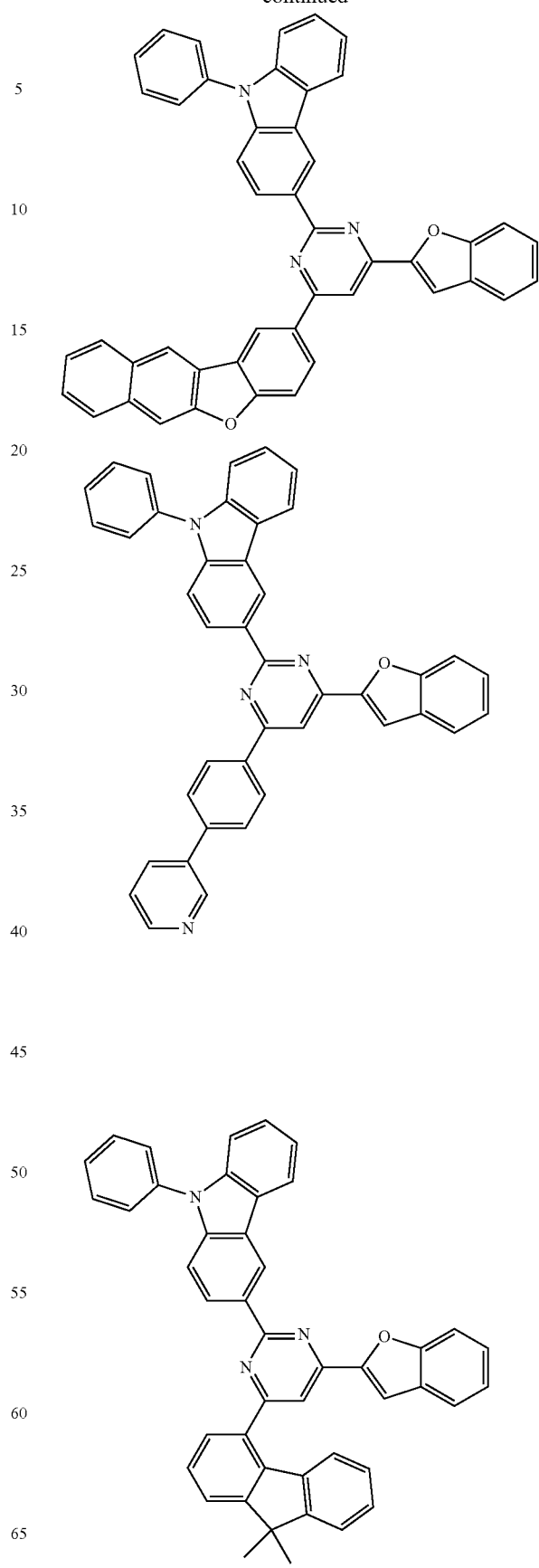

225
-continued
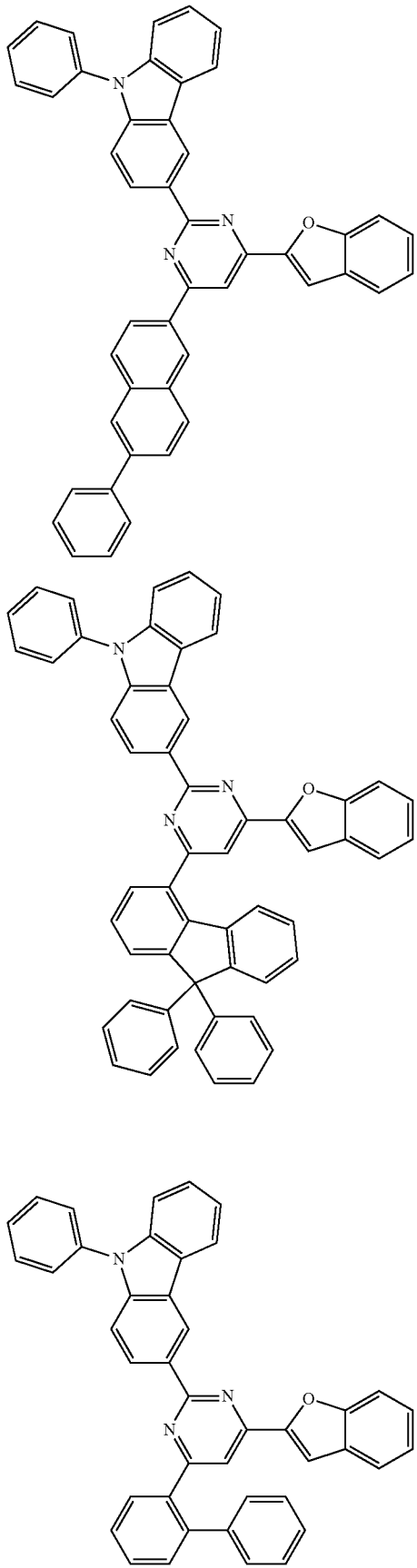
226
-continued
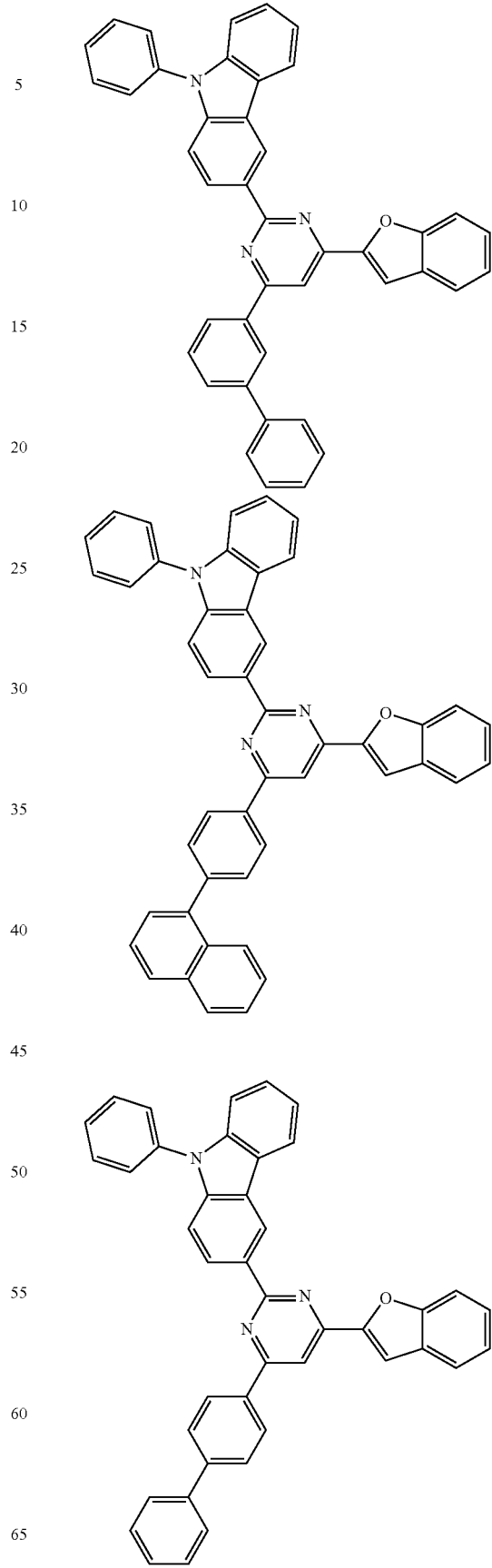

227
-continued
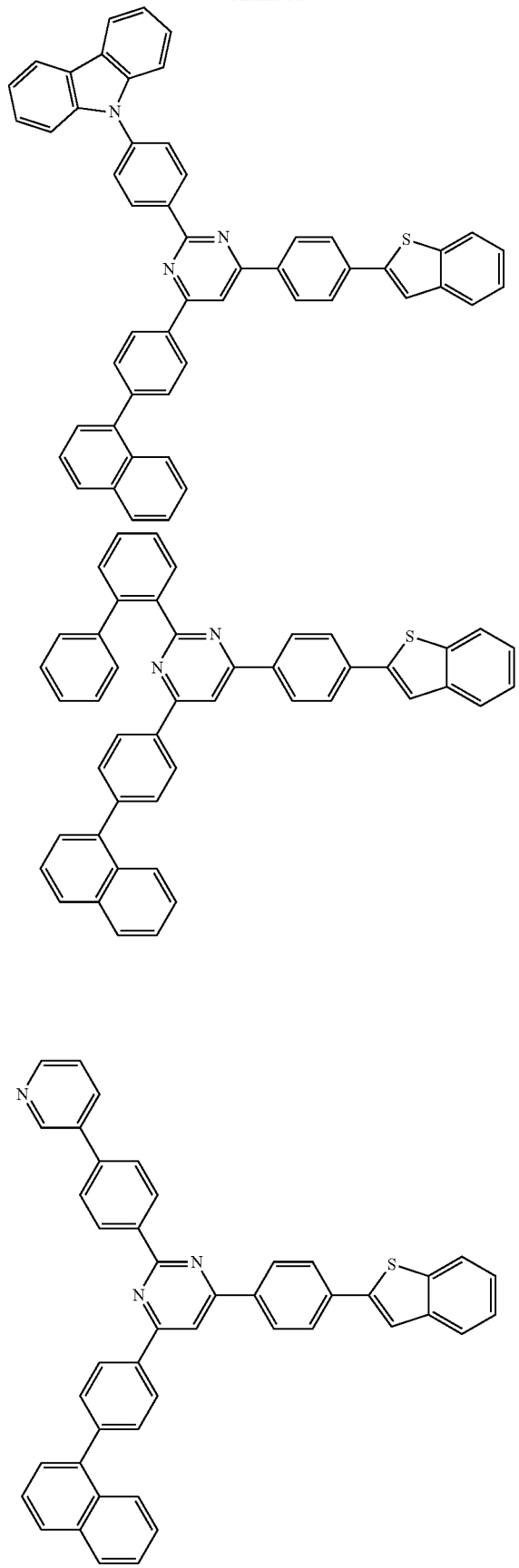
228
-continued
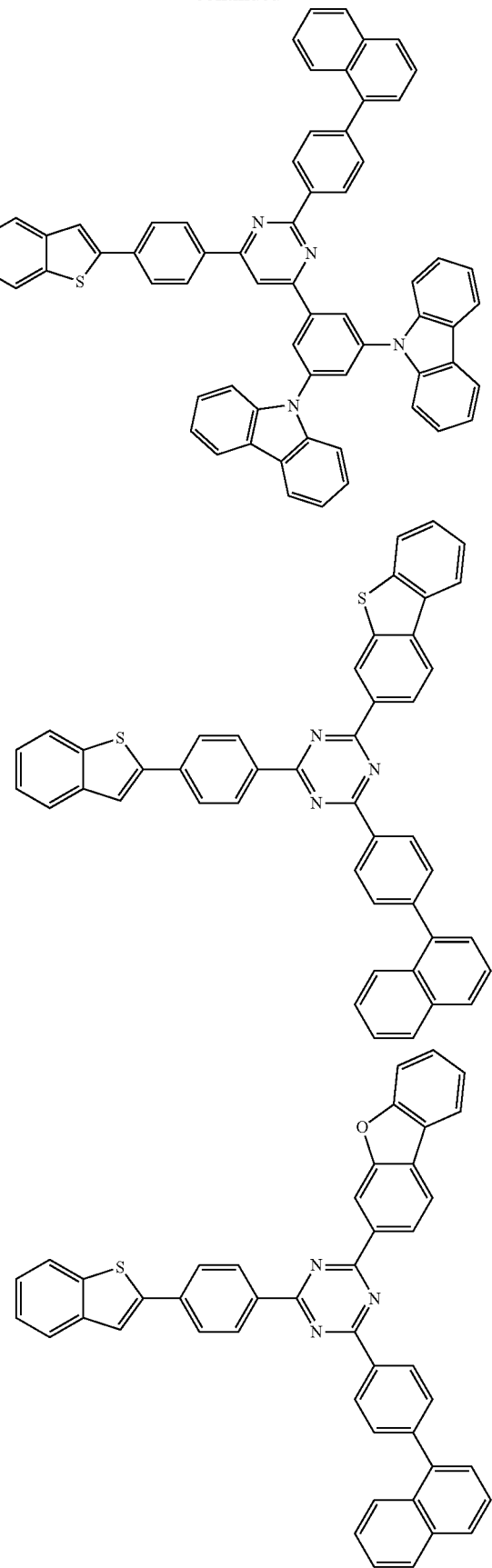

229
-continued
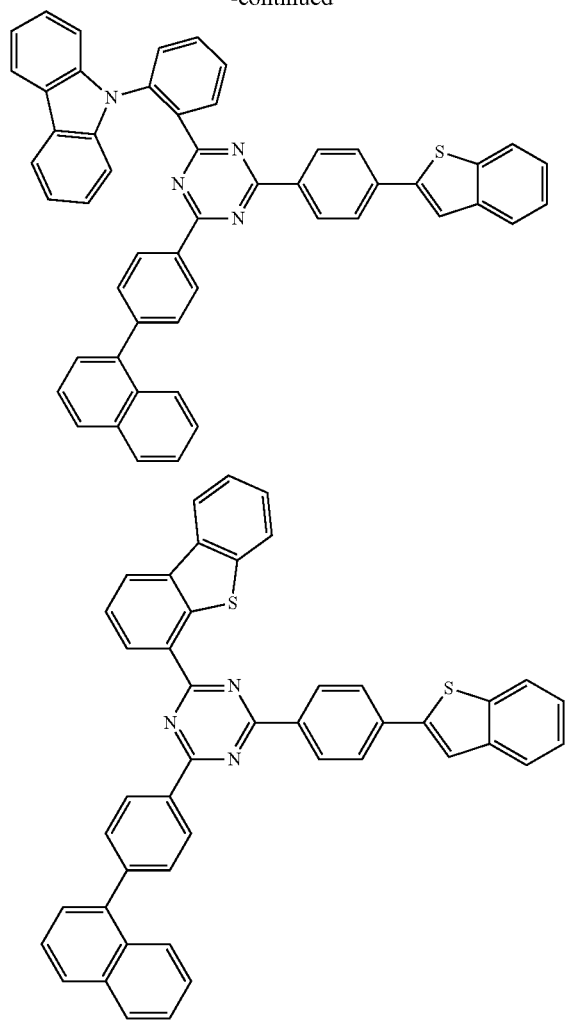
230
-continued
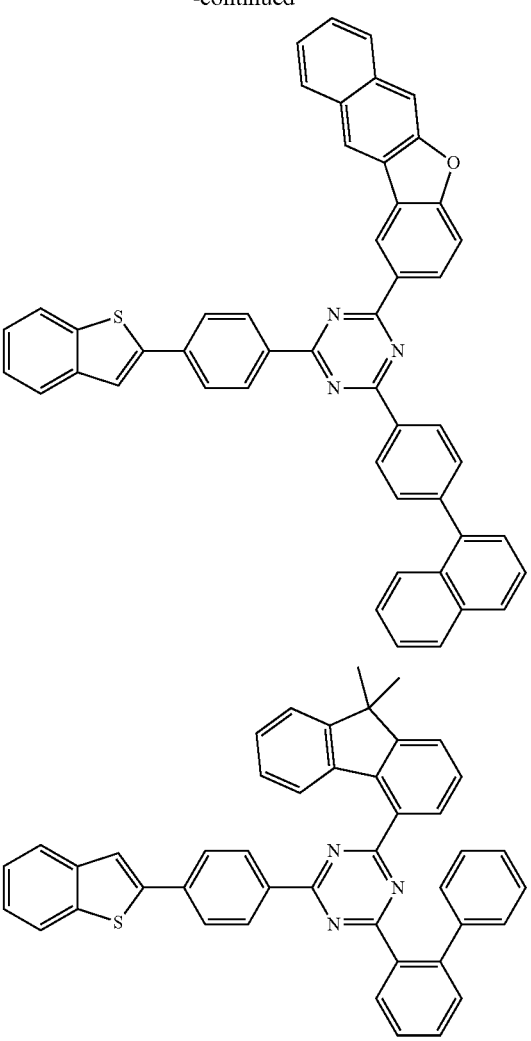
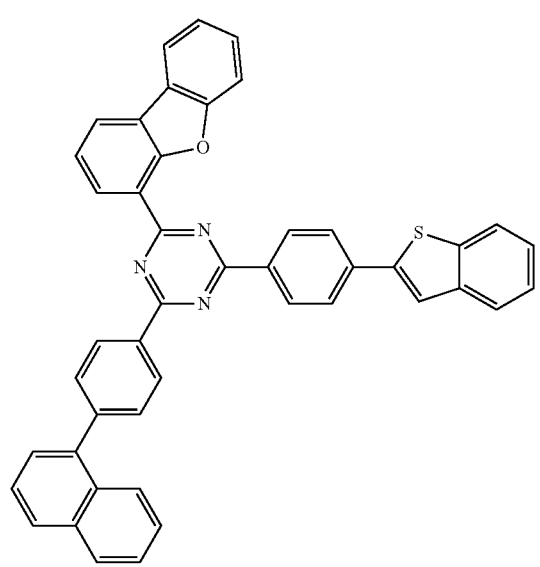
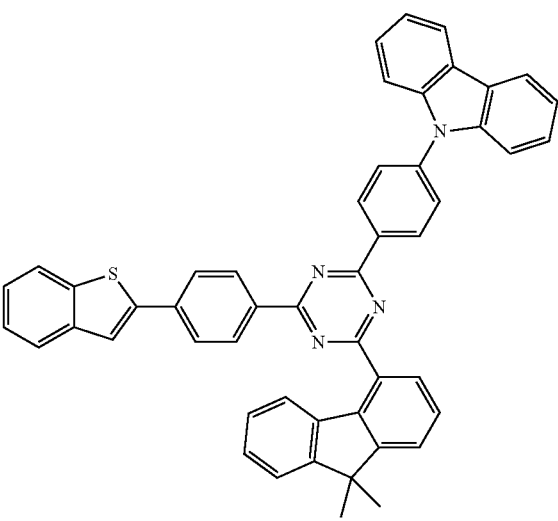

231
-continued
232
-continued
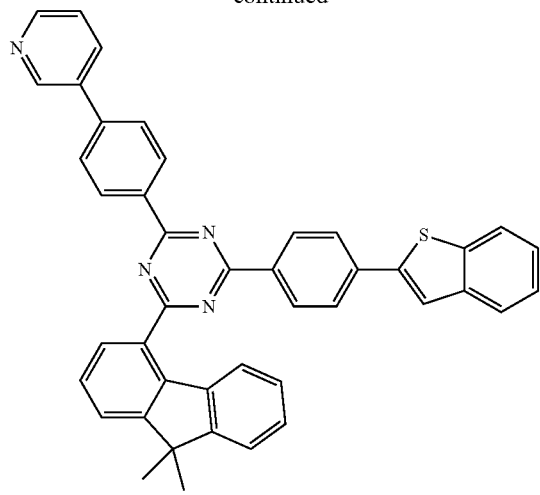
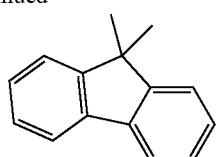
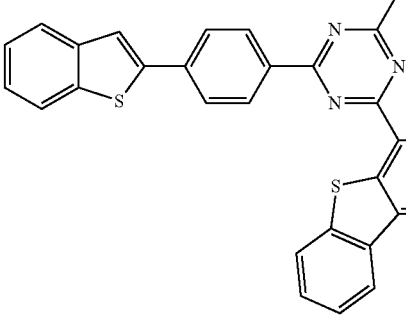
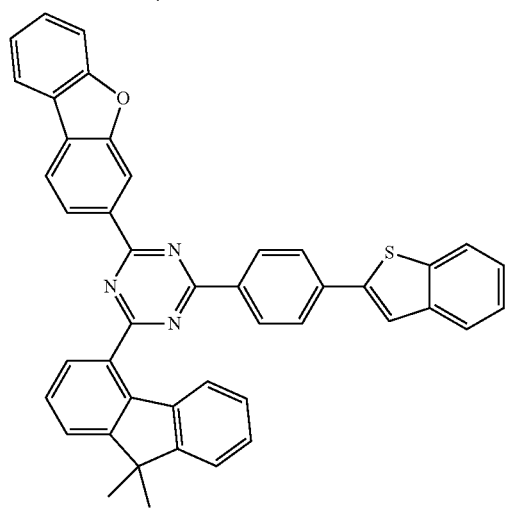
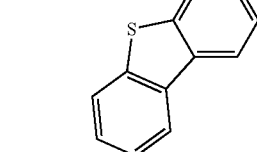
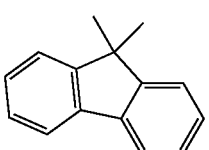
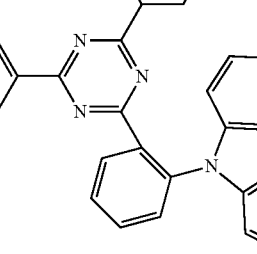
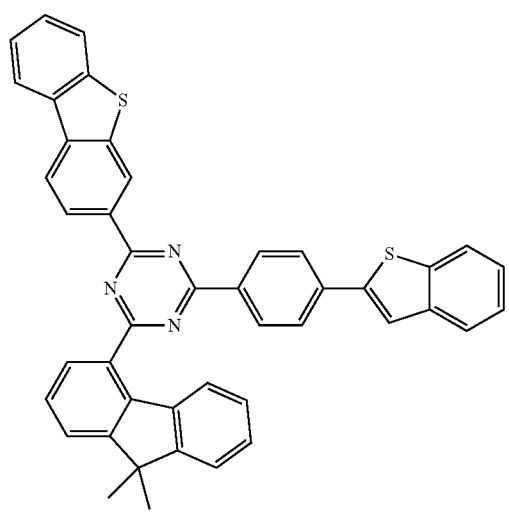
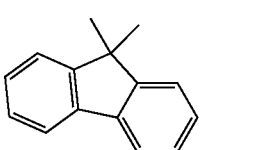
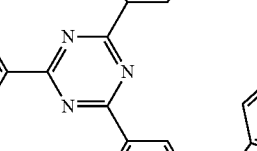
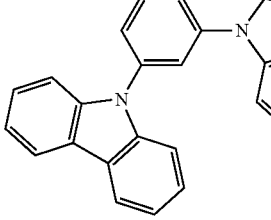

233
-continued
234
-continued
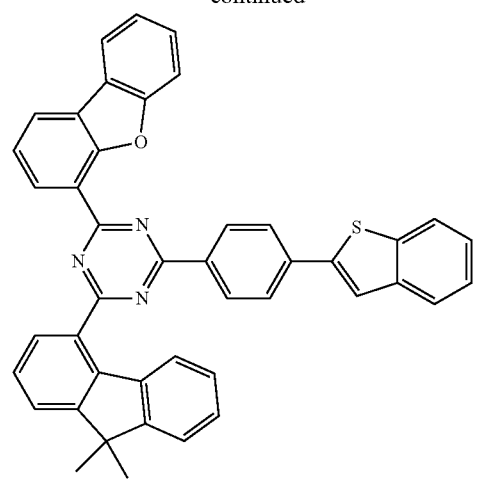
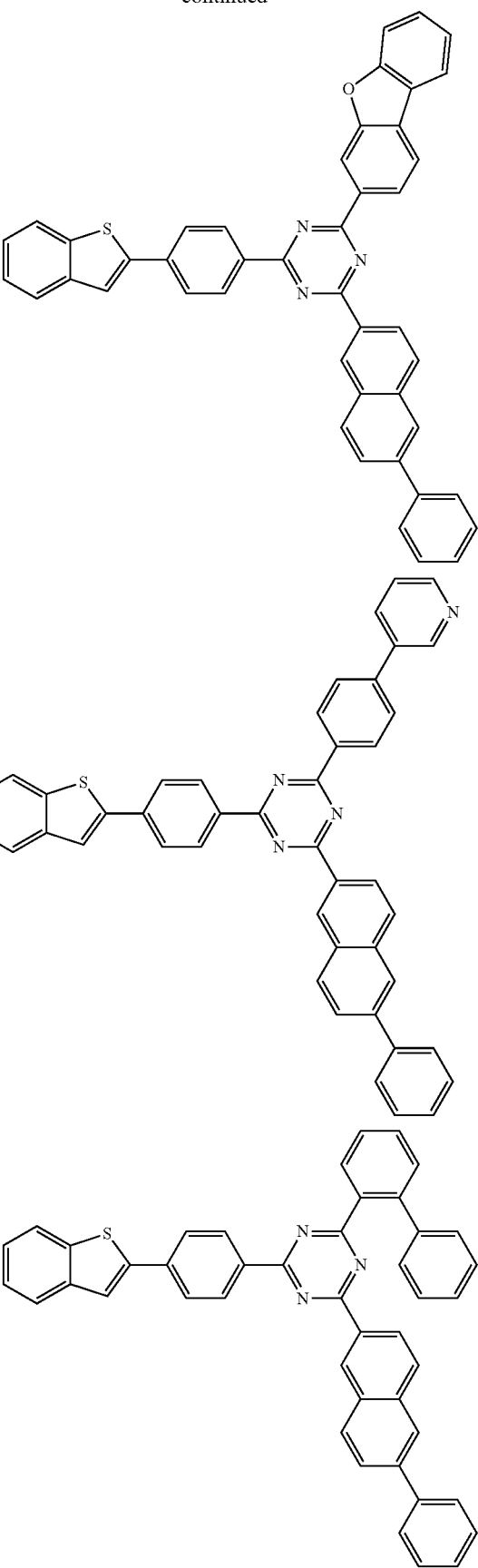

235
-continued
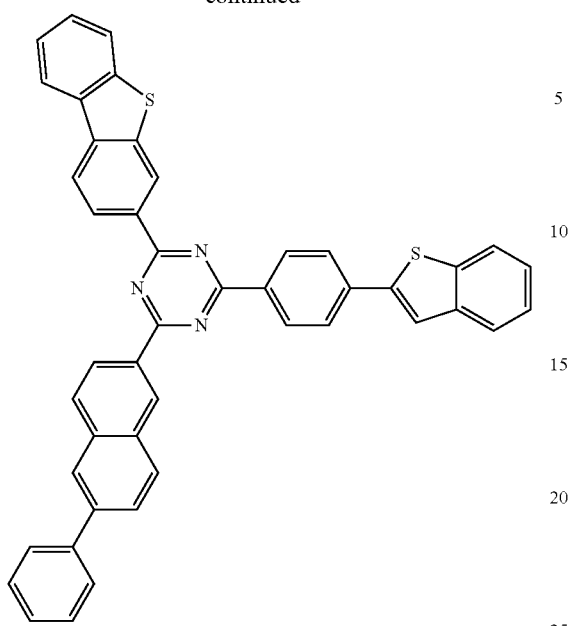
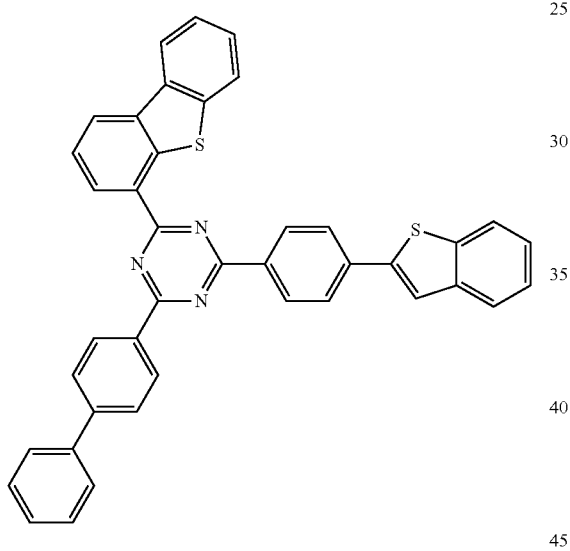
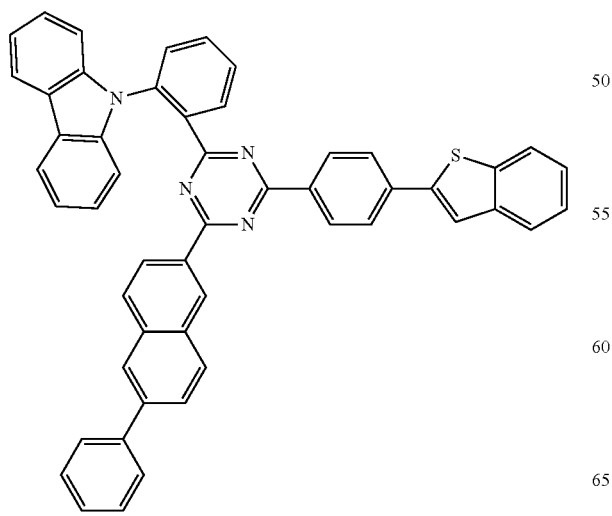
236
-continued
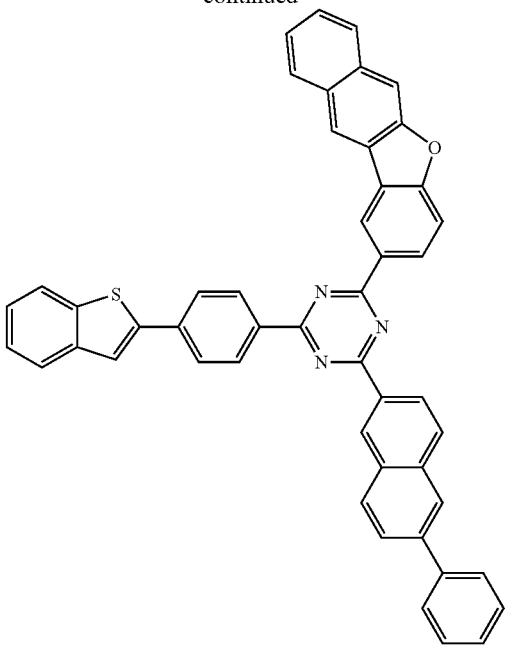
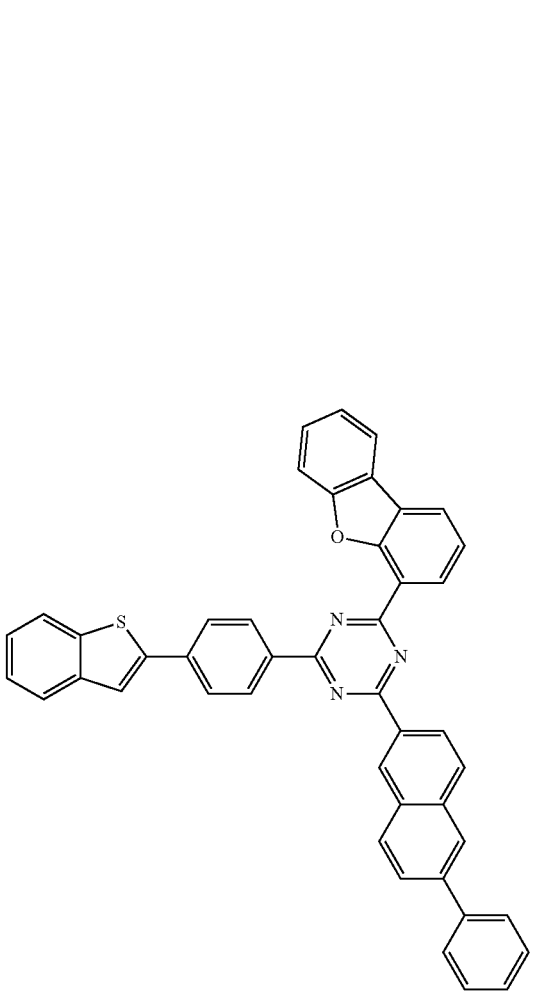

-continued
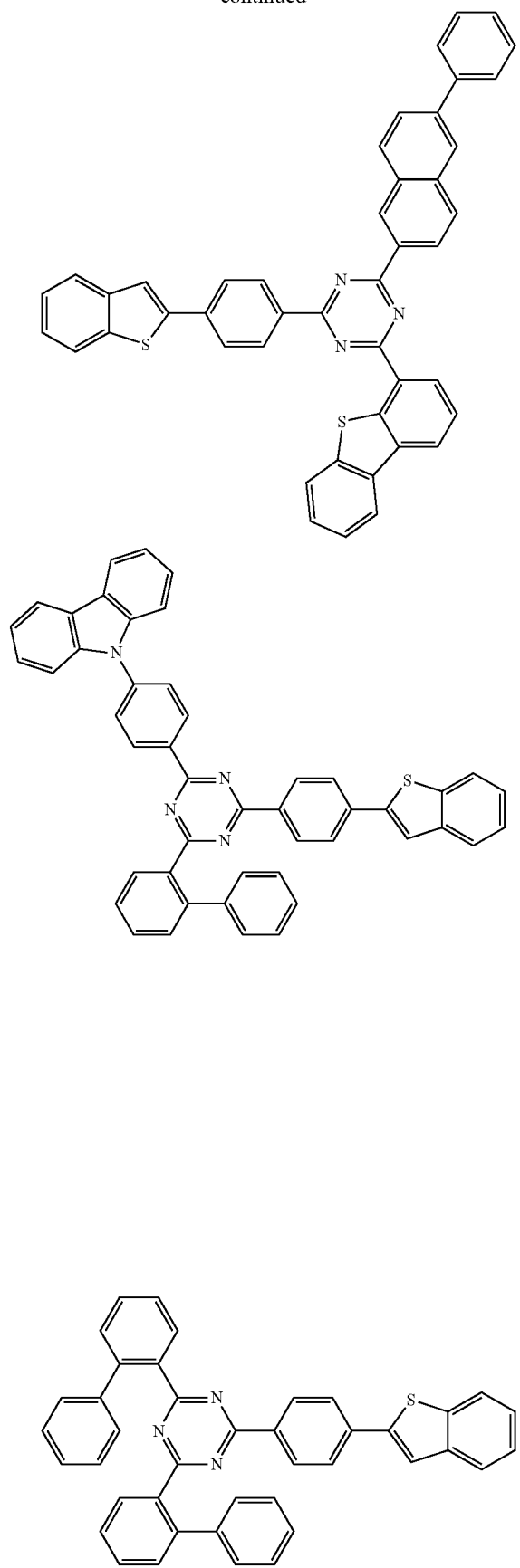
-continued
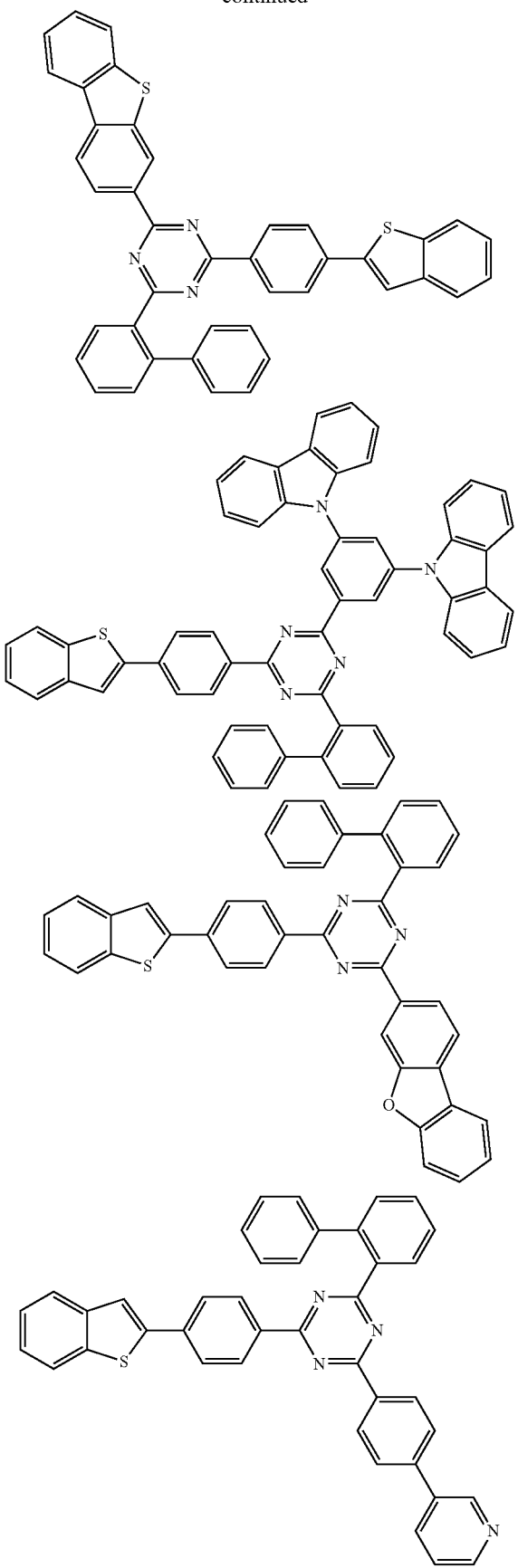

239
-continued
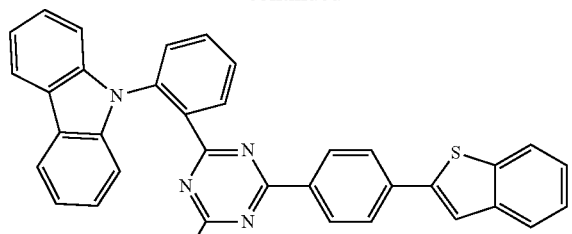
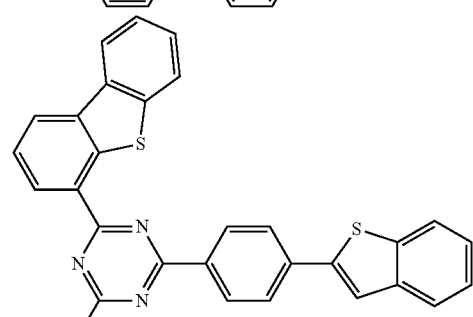
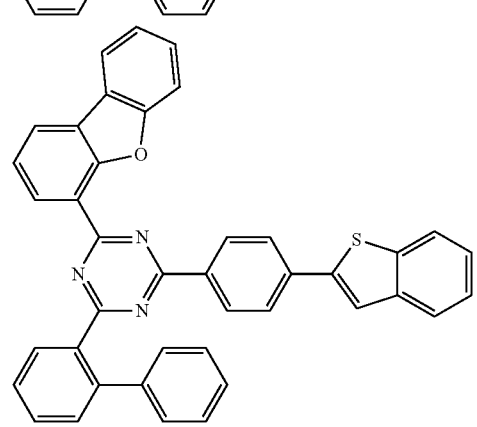
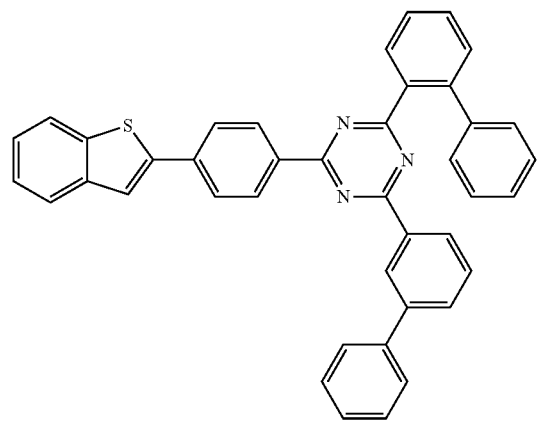
240
-continued
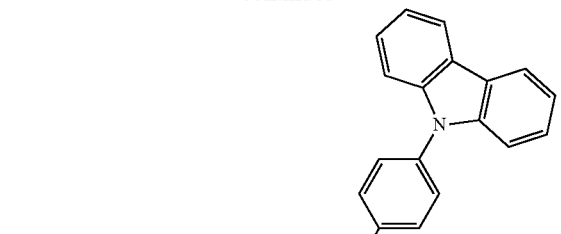
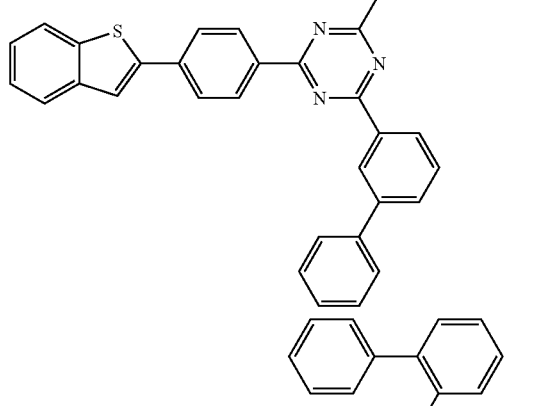
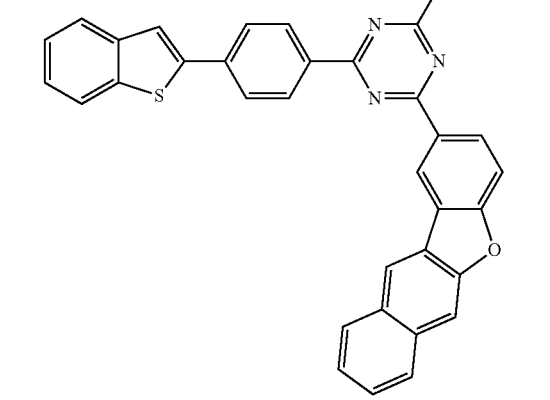
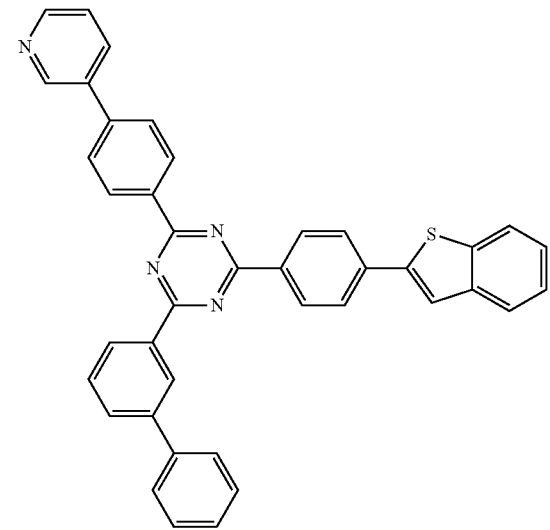

241
-continued
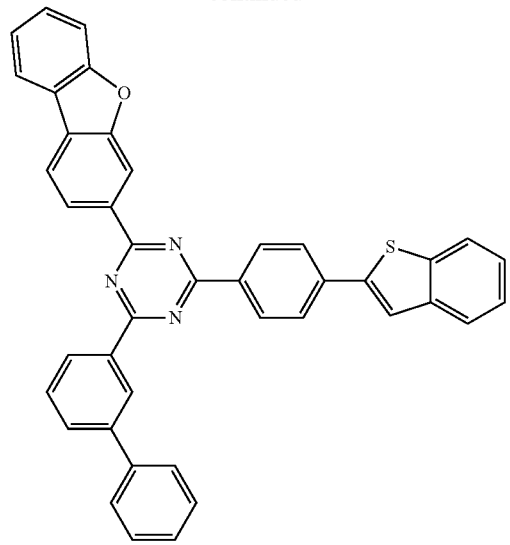
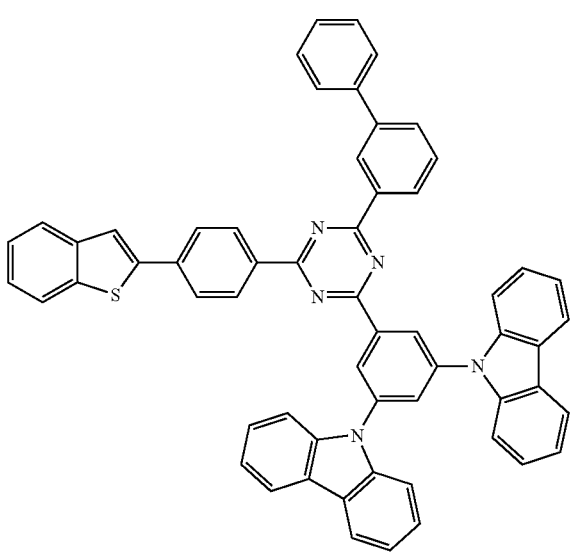
242
-continued
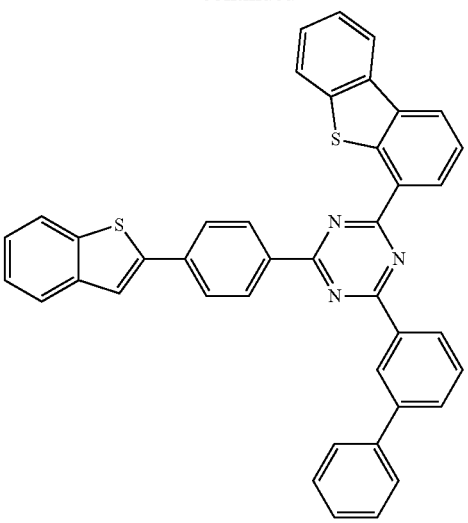
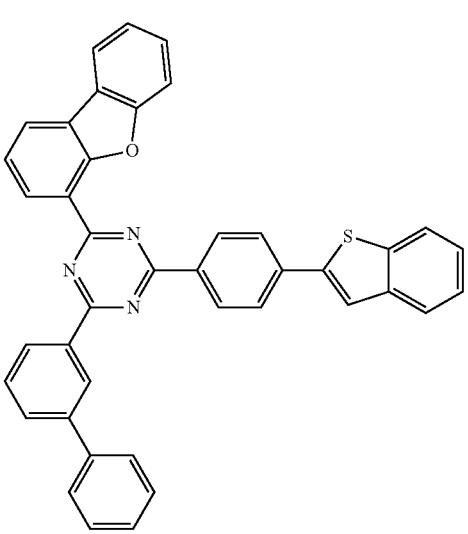

243
-continued
244
-continued
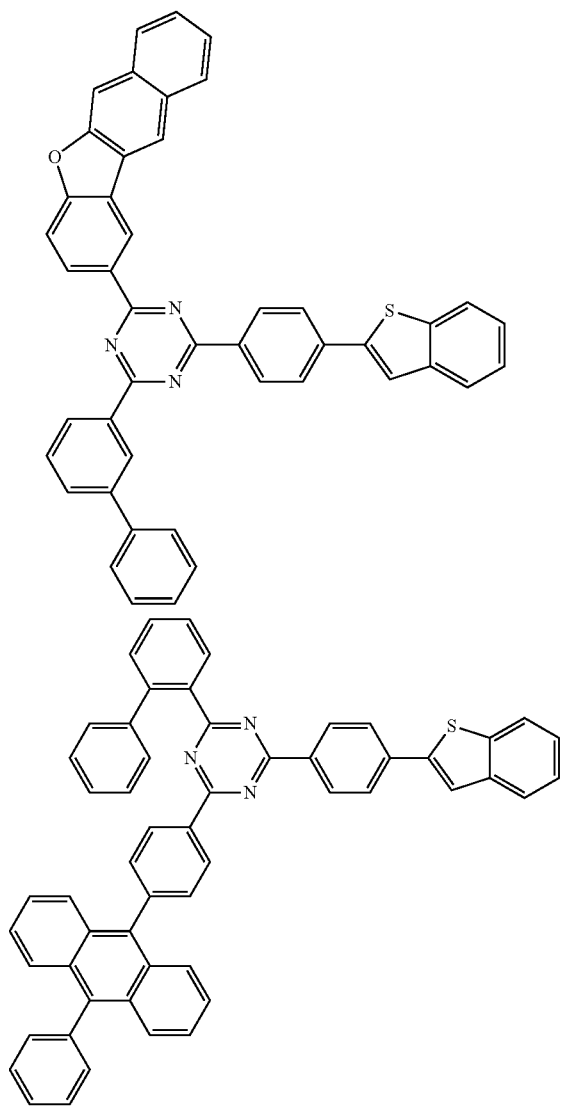
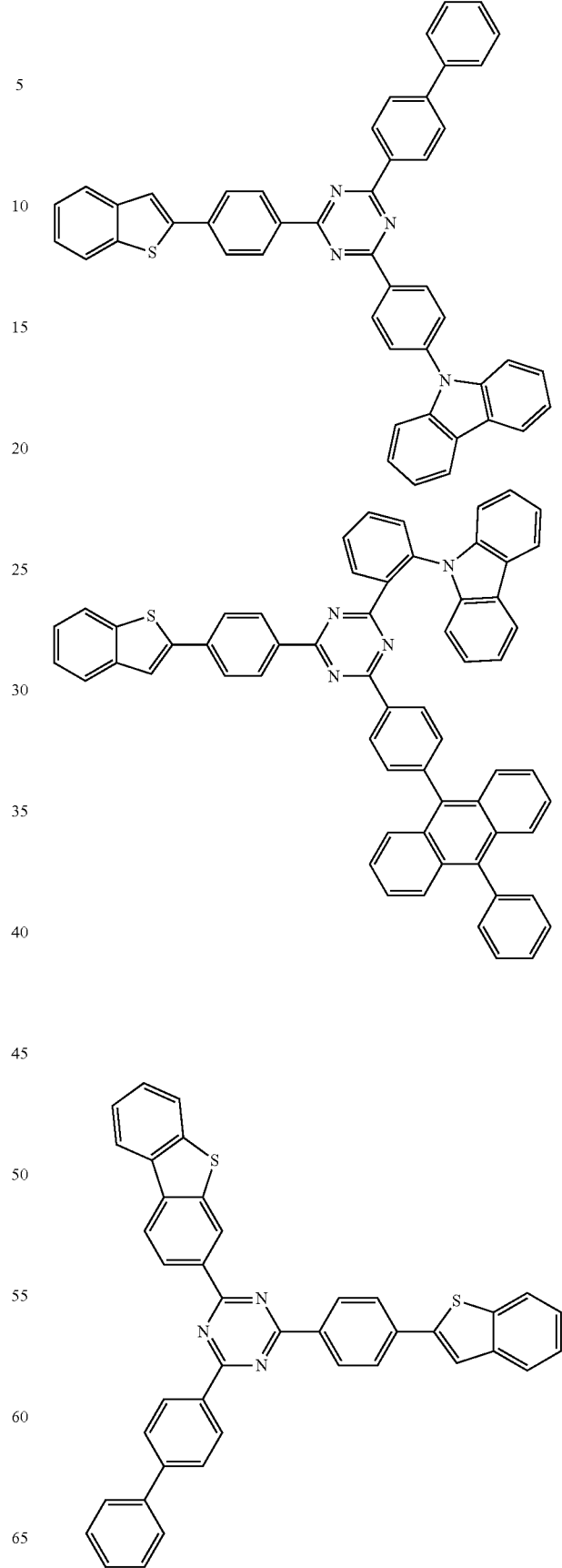

245
-continued
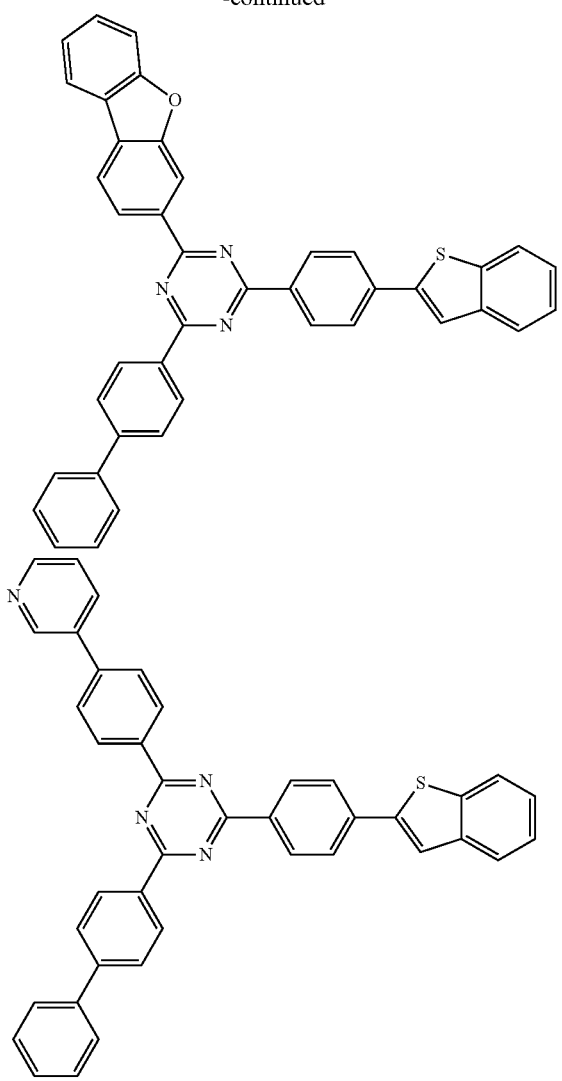
246
-continued
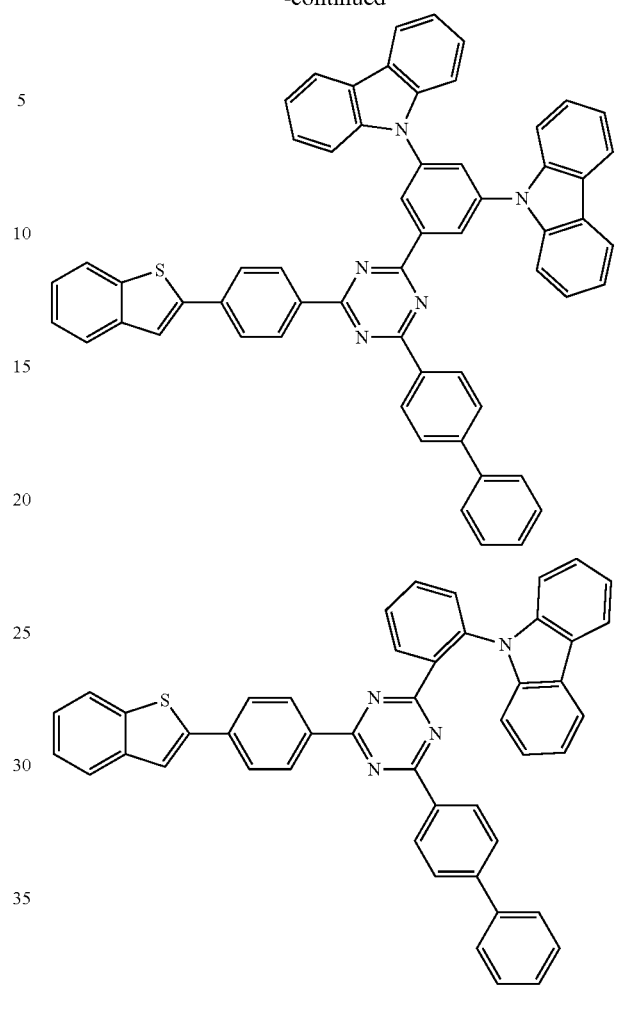
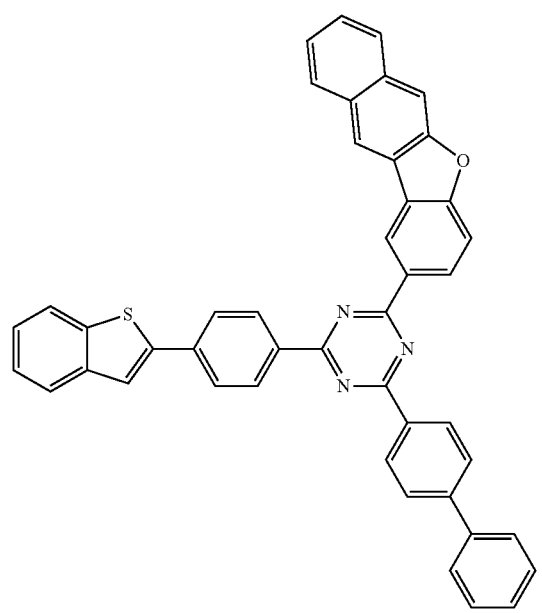

247
-continued
248
-continued
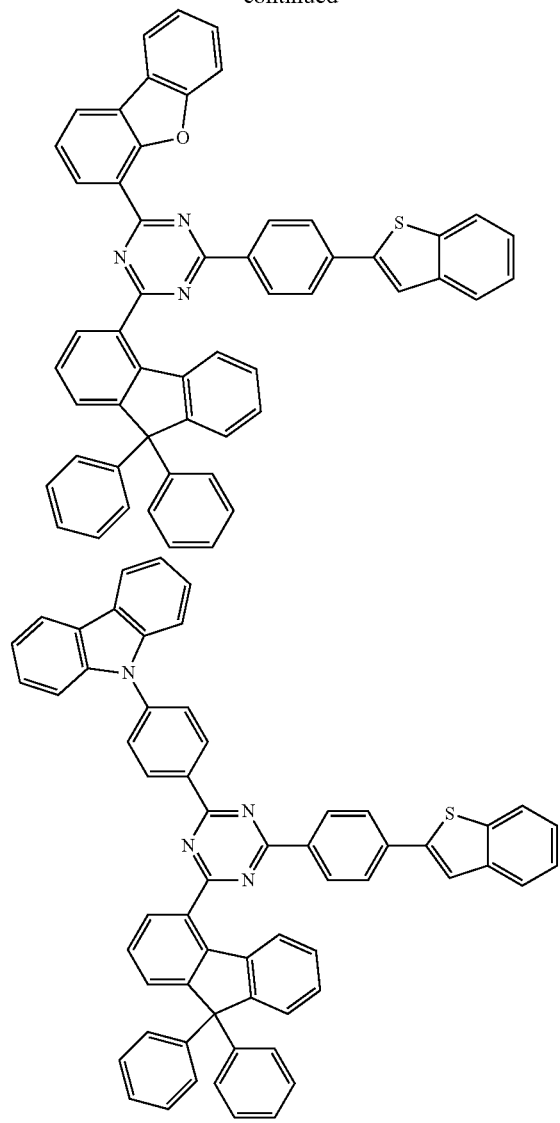
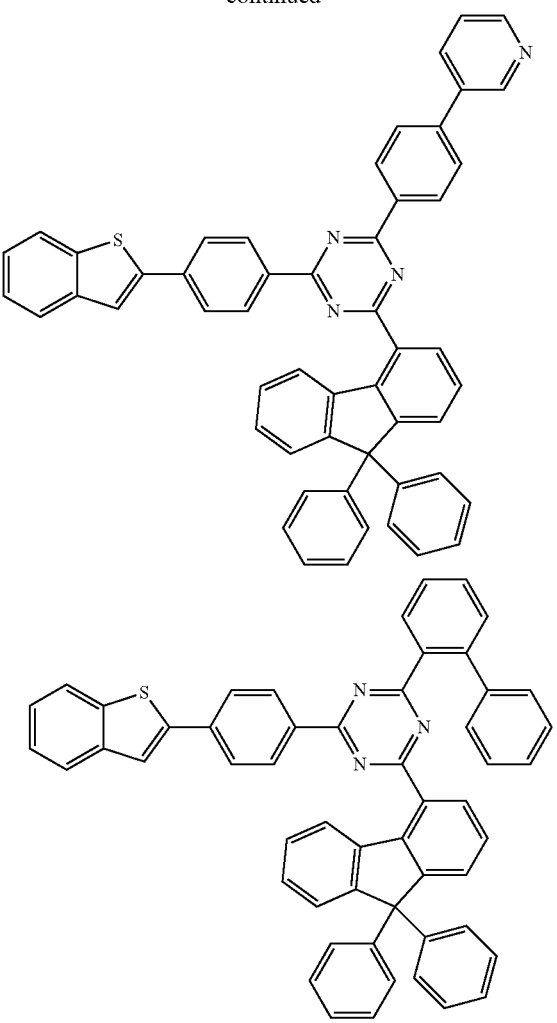
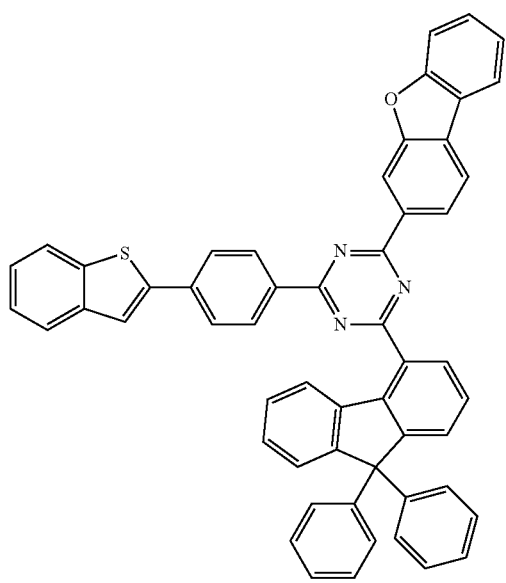

249
-continued
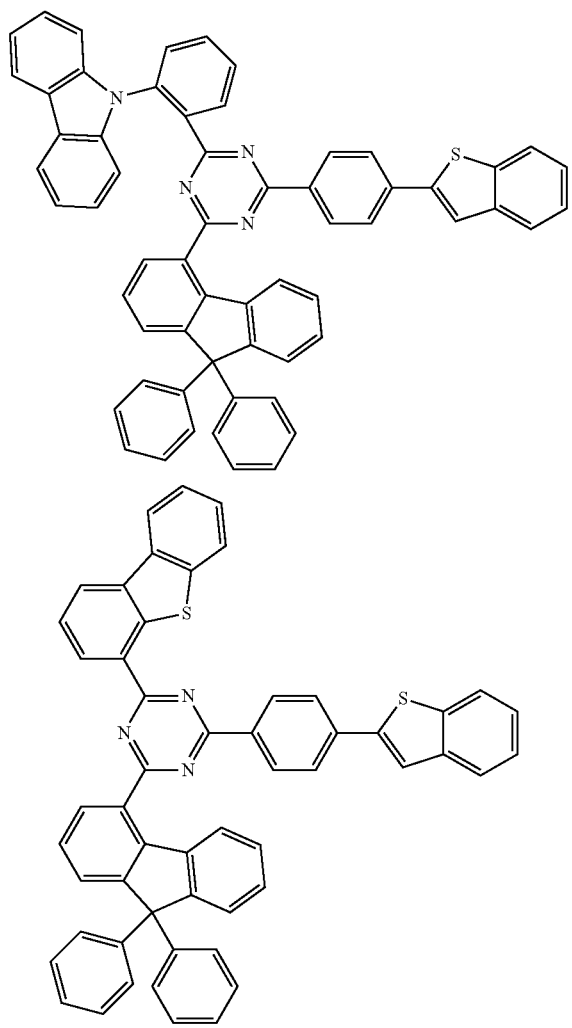
250
-continued
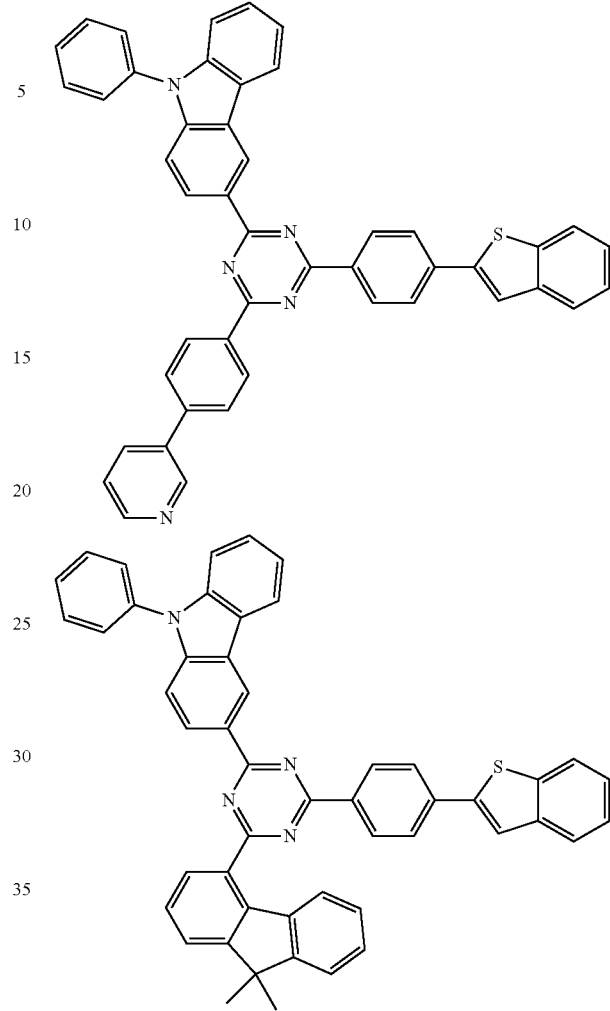
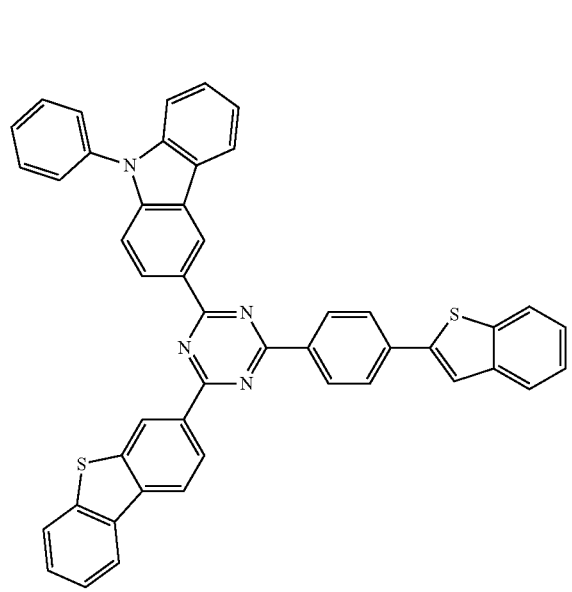
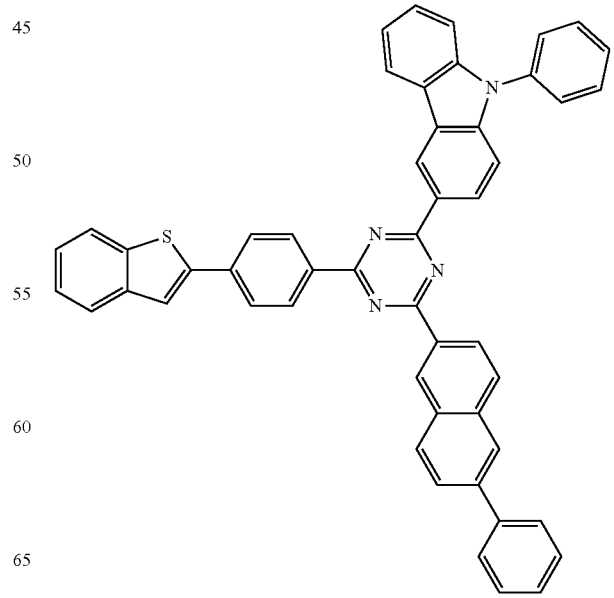

251
-continued
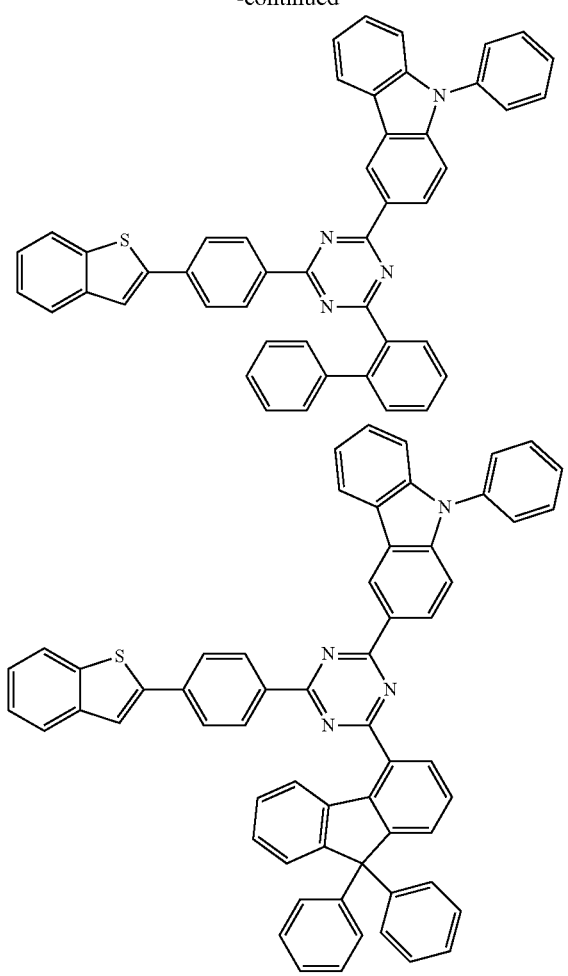
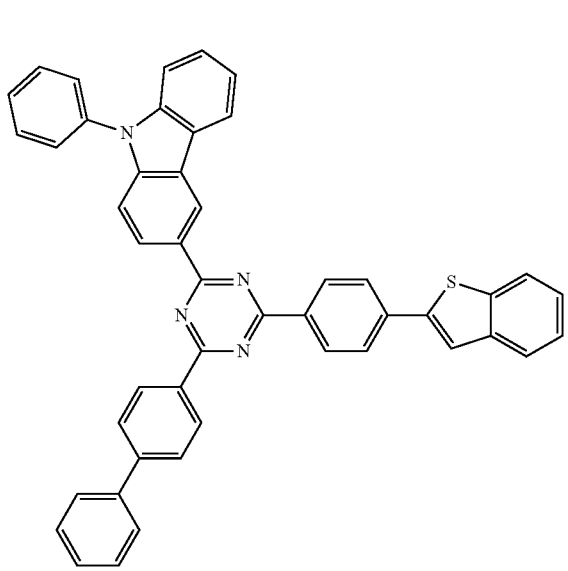
252
-continued
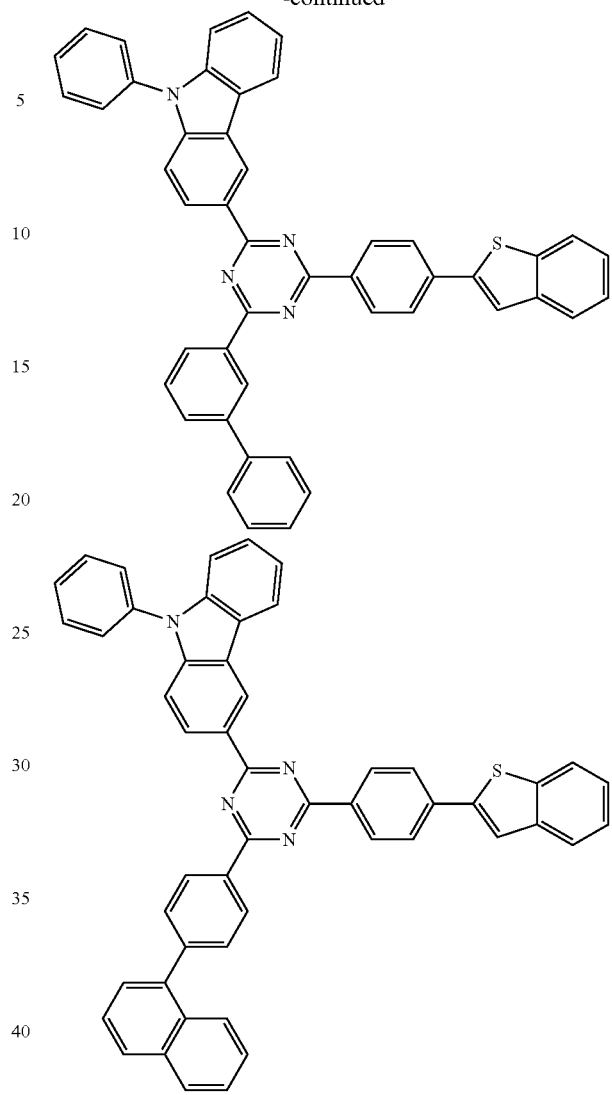
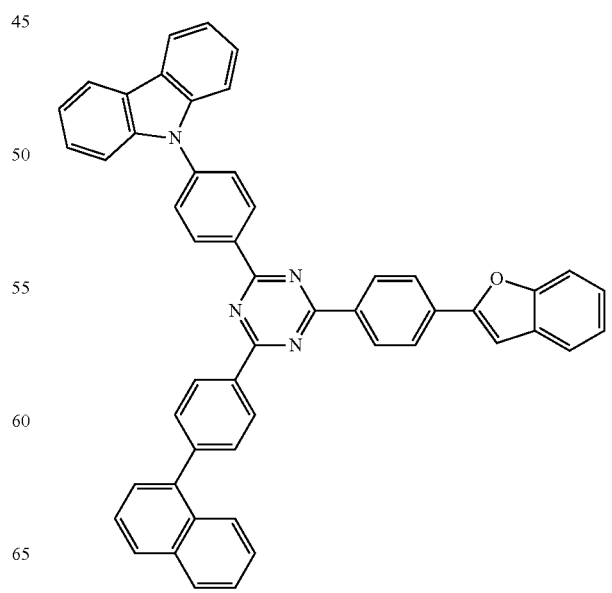

253
-continued
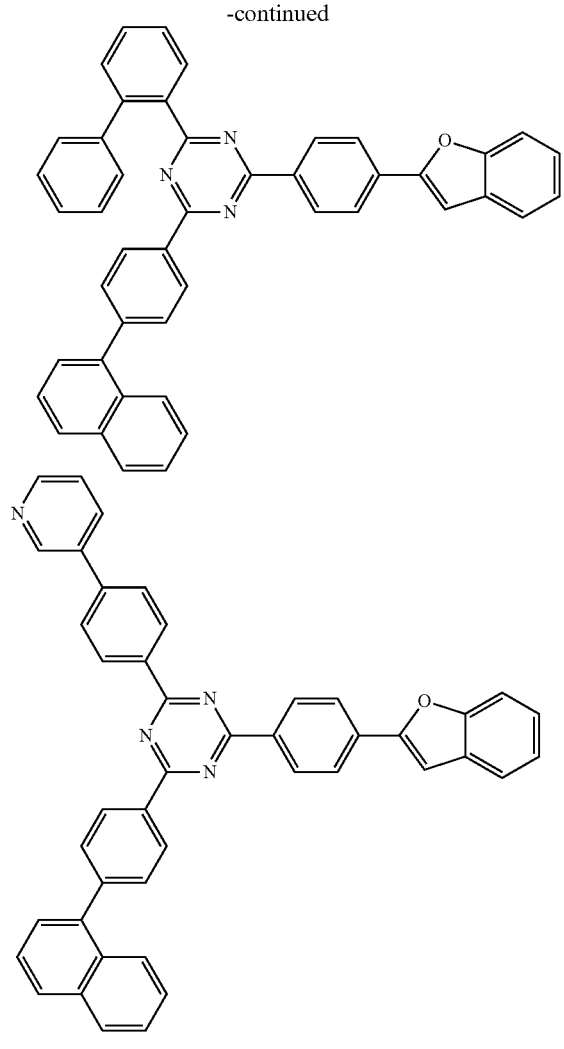
254
-continued
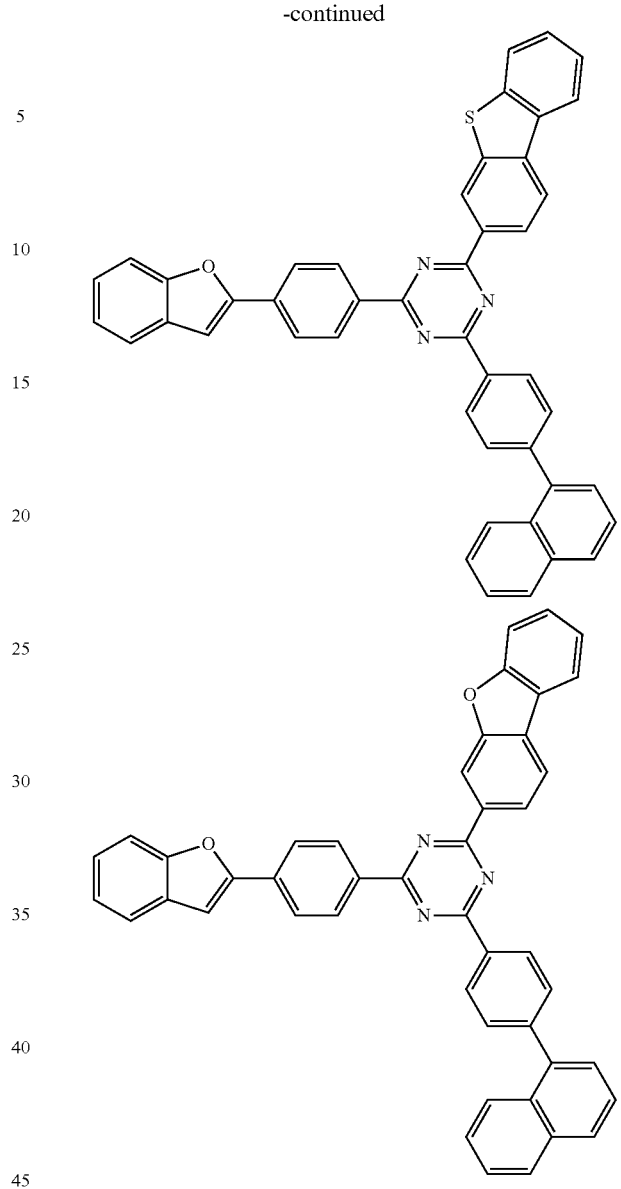
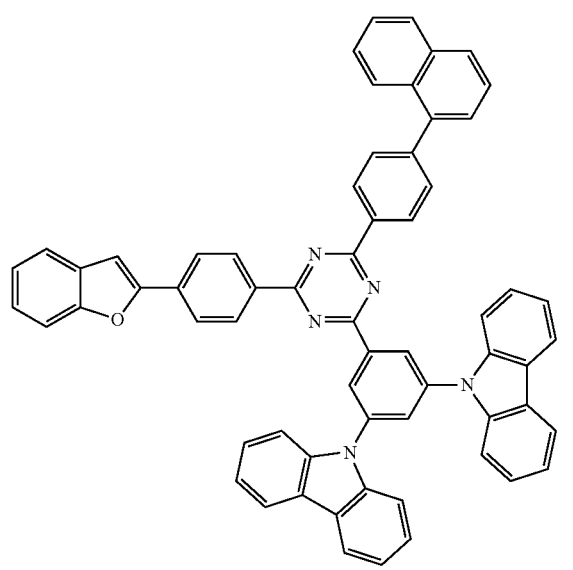
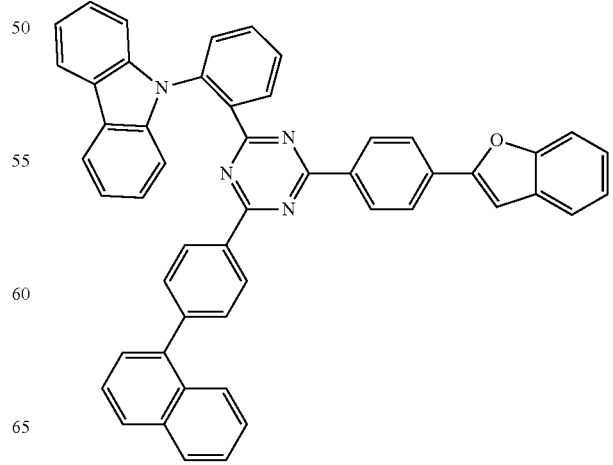

255
-continued
256
-continued
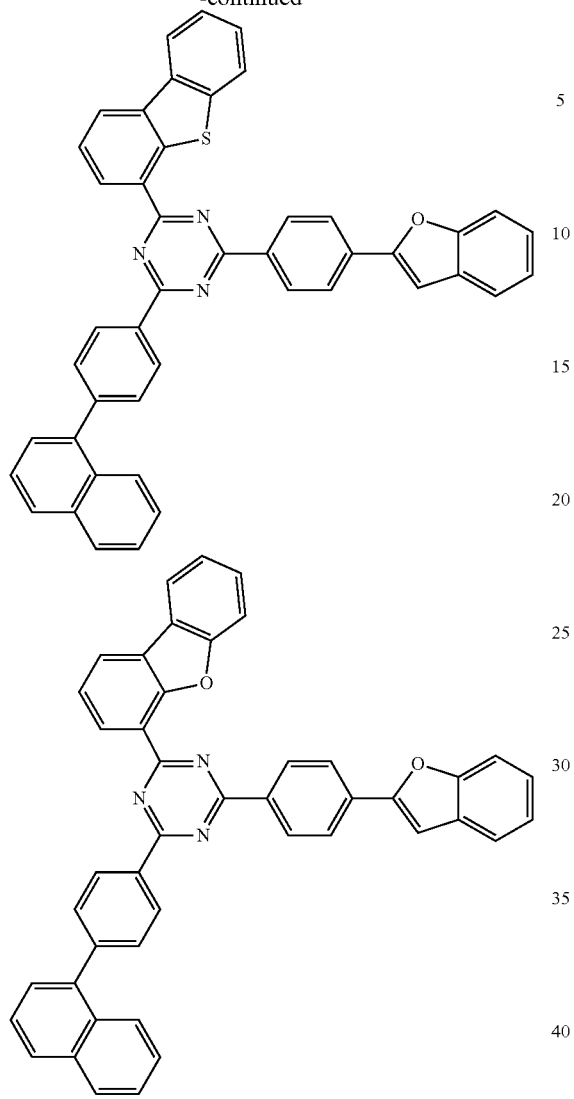
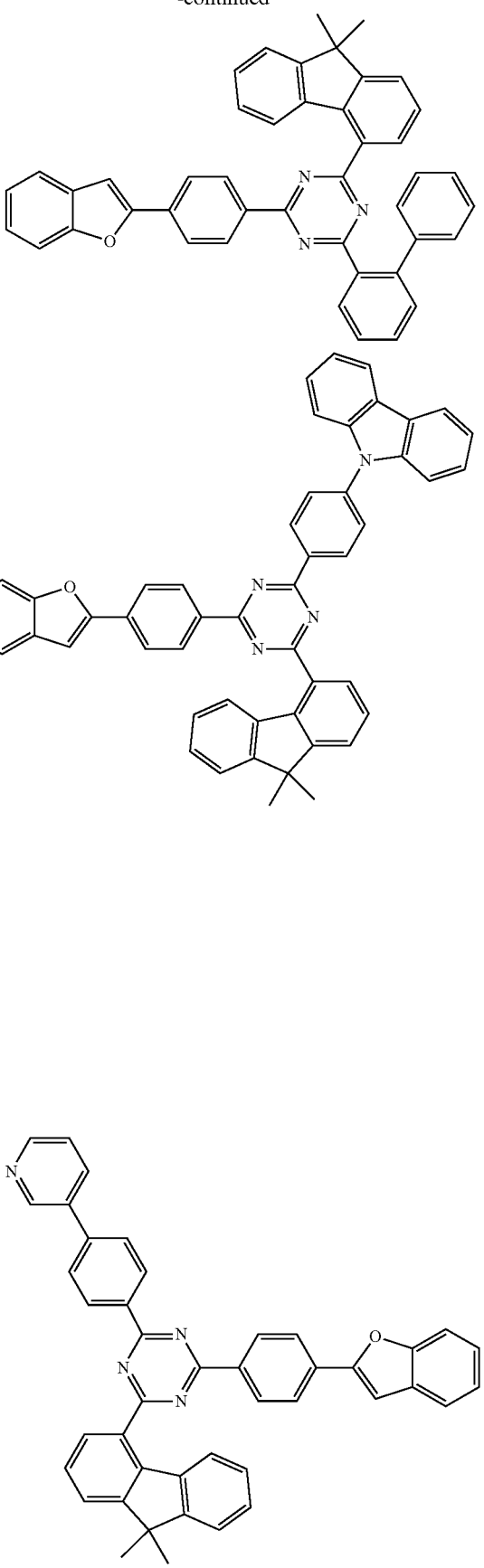

257
-continued
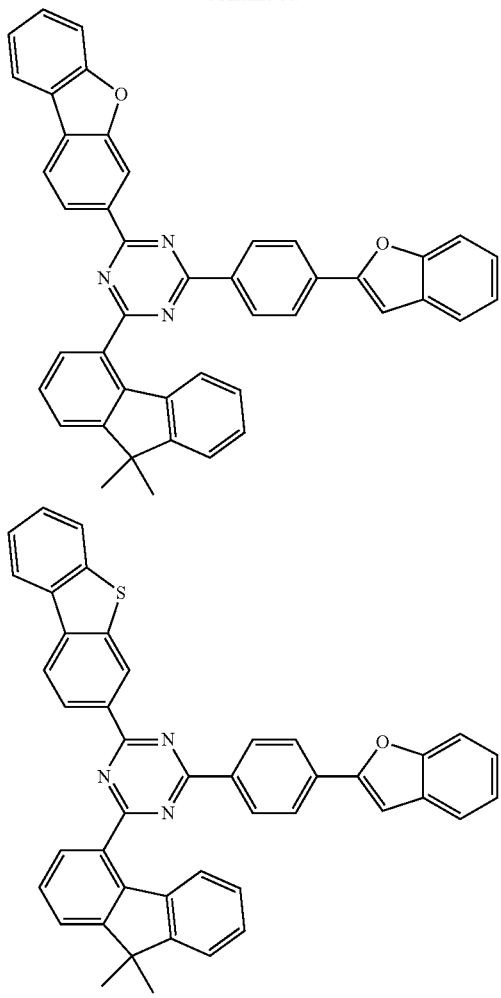
258
-continued
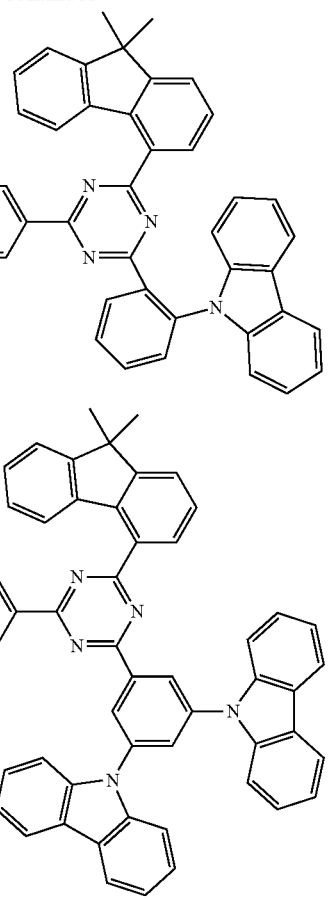
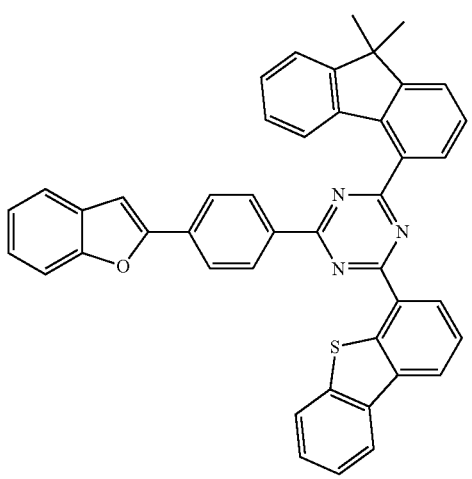

259
-continued
260
-continued
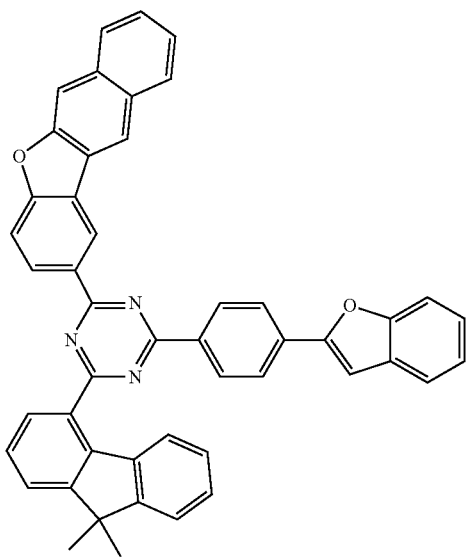
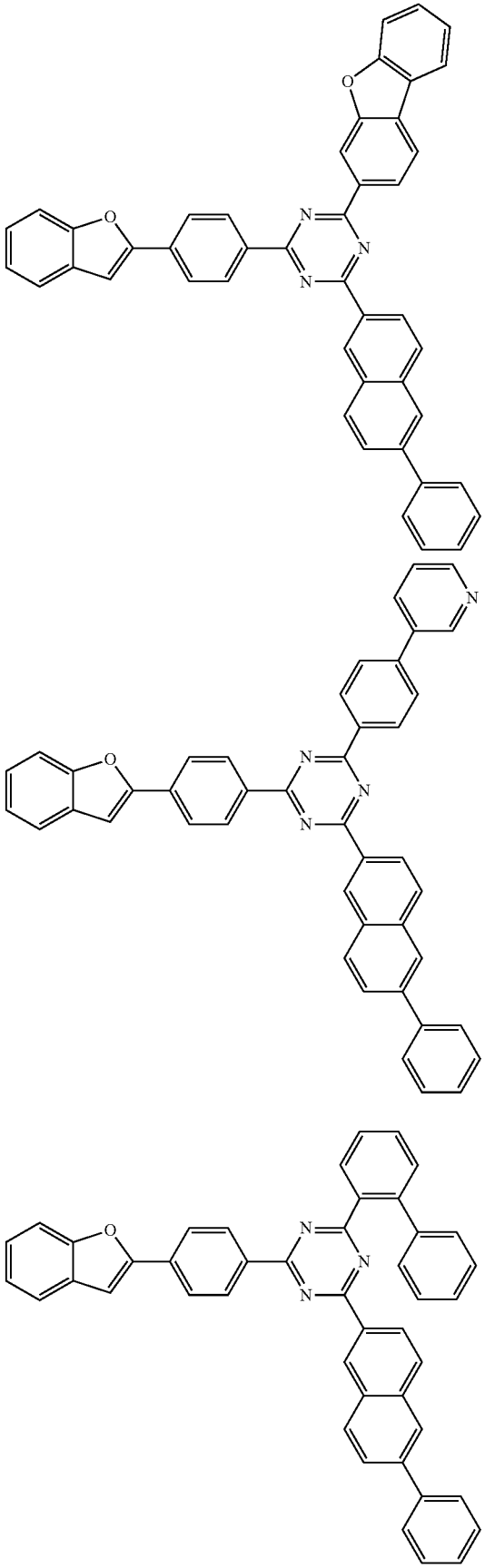
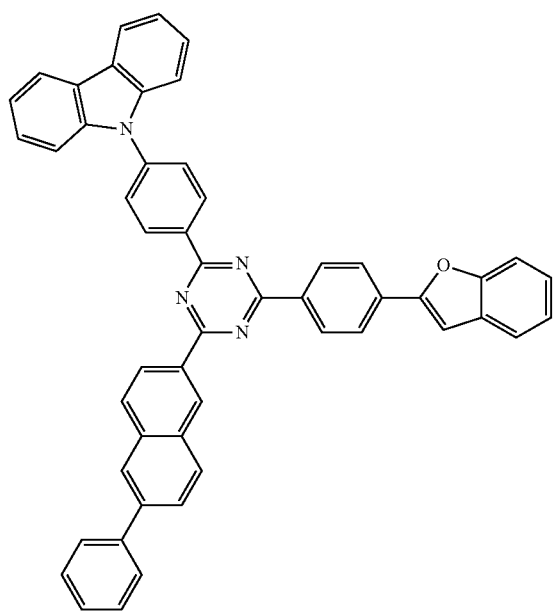

261
-continued
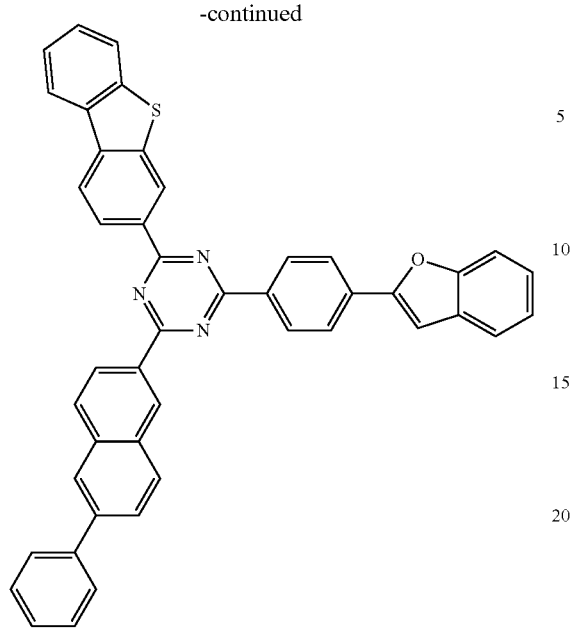
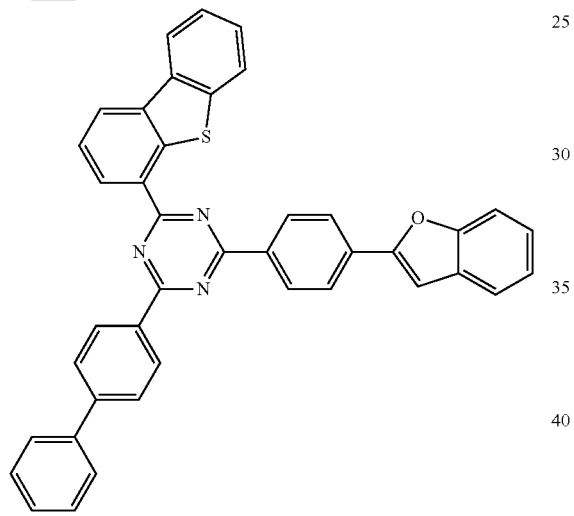
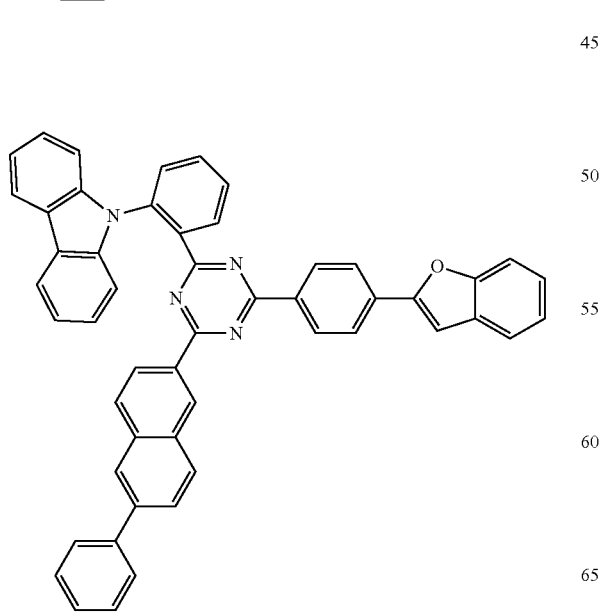
262
-continued
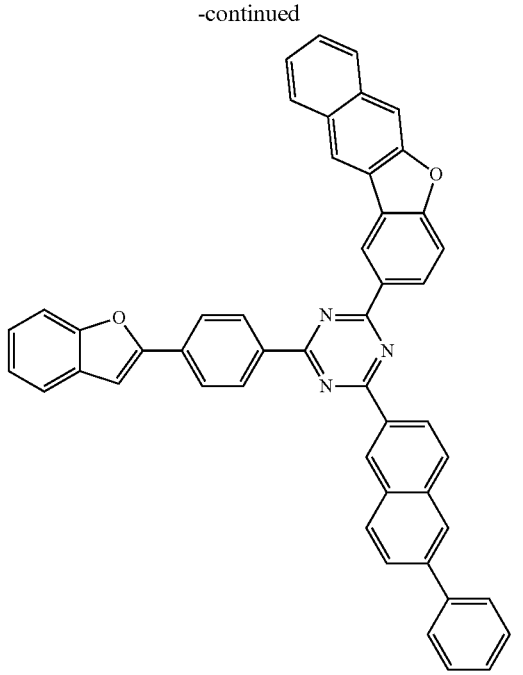
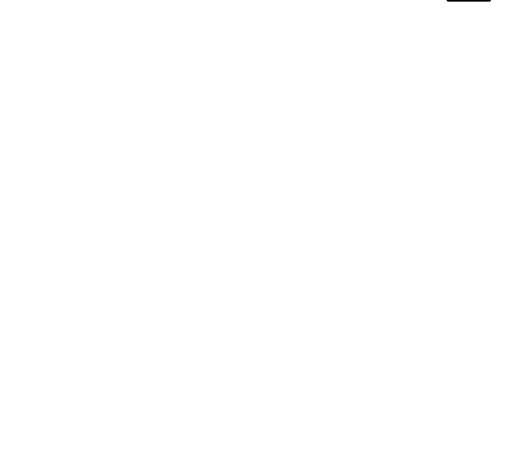
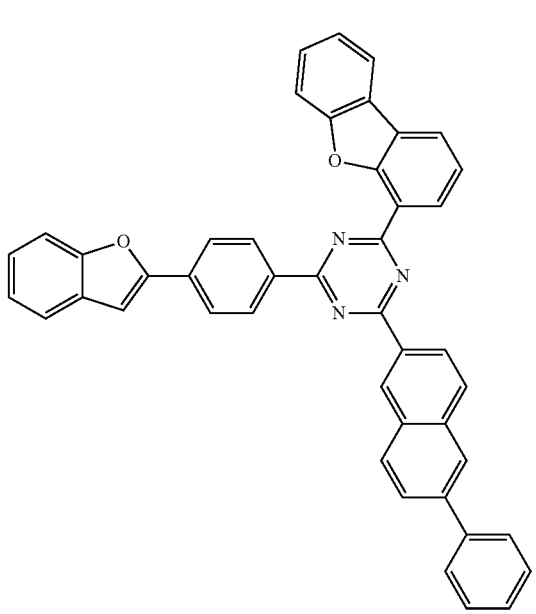

263
-continued
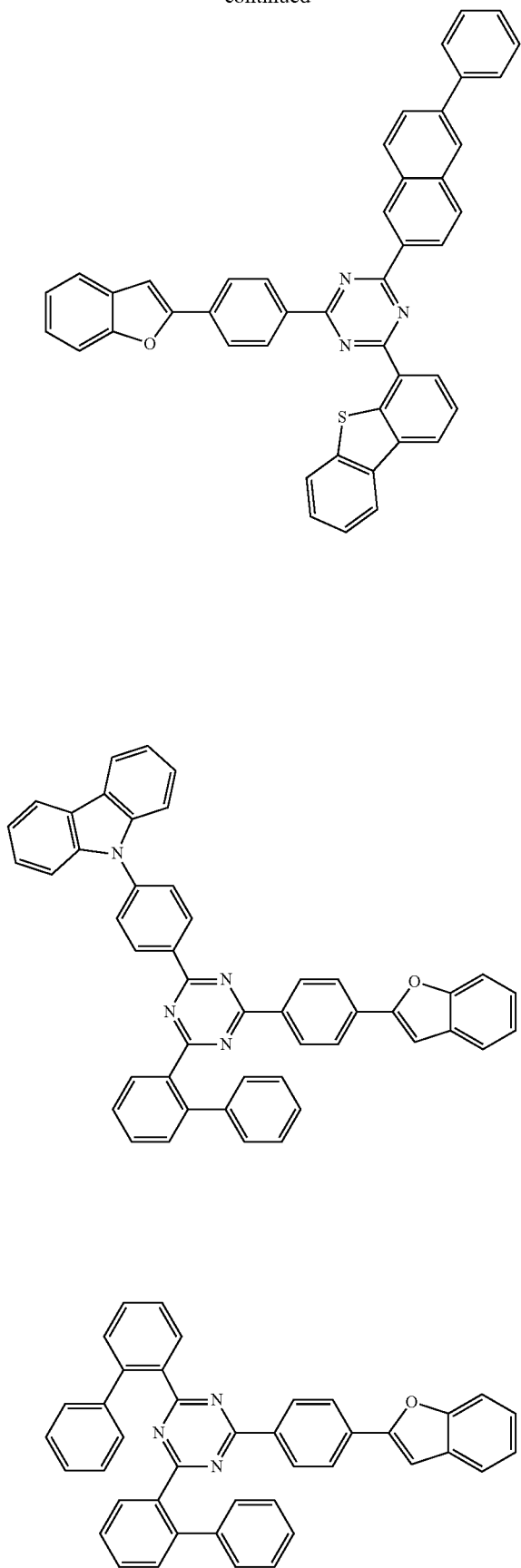
264
-continued
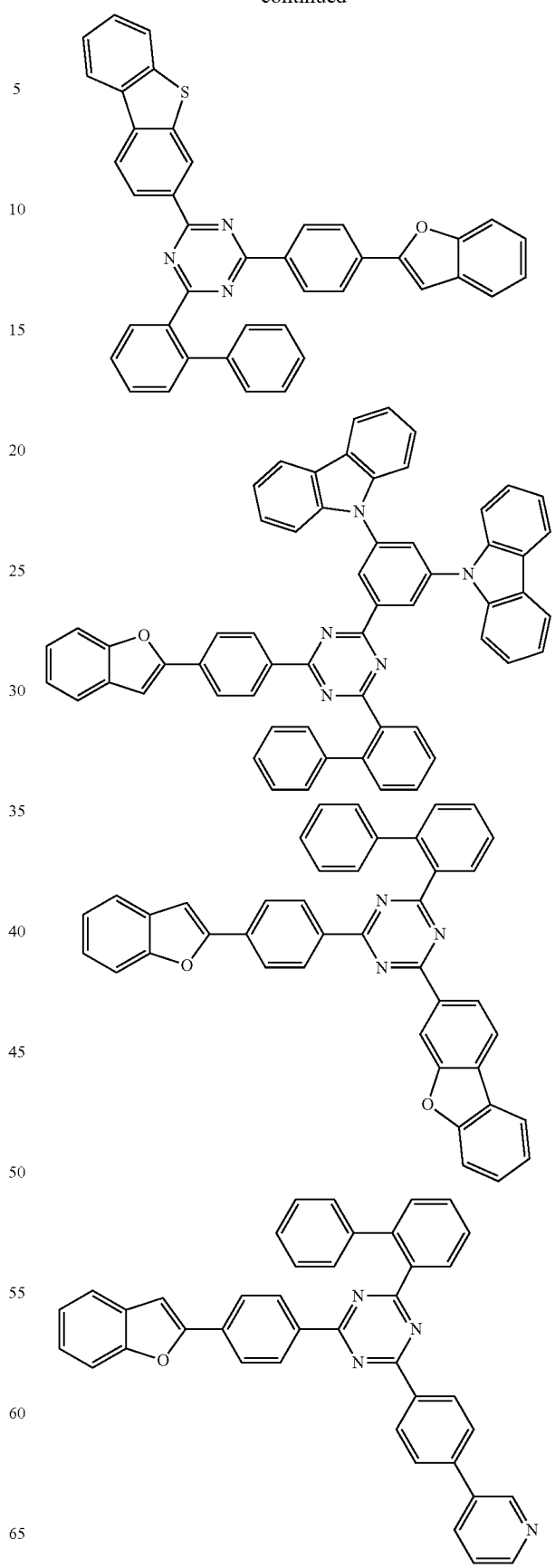

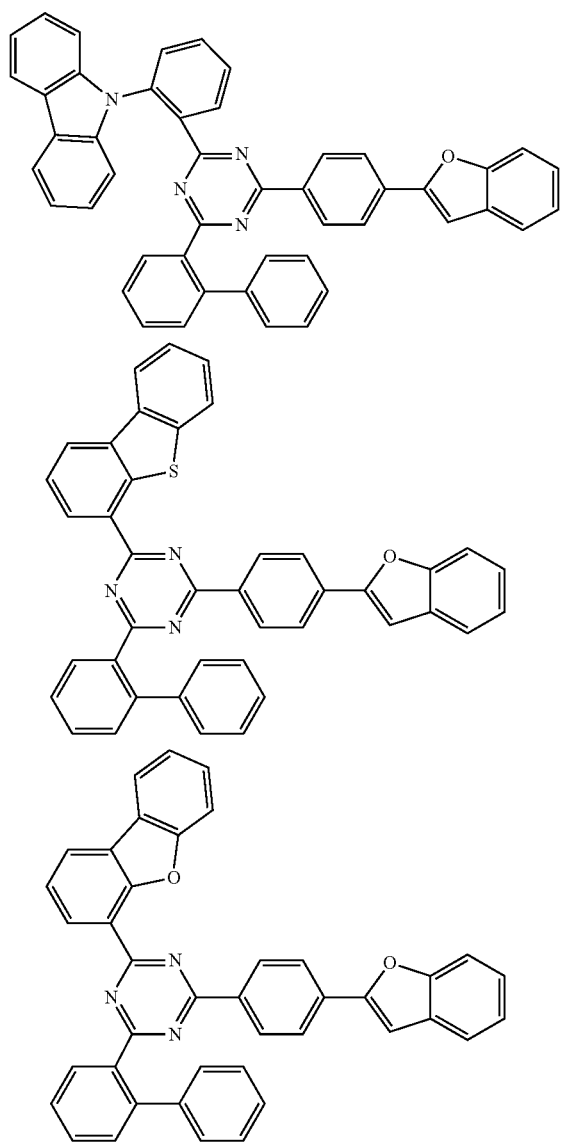
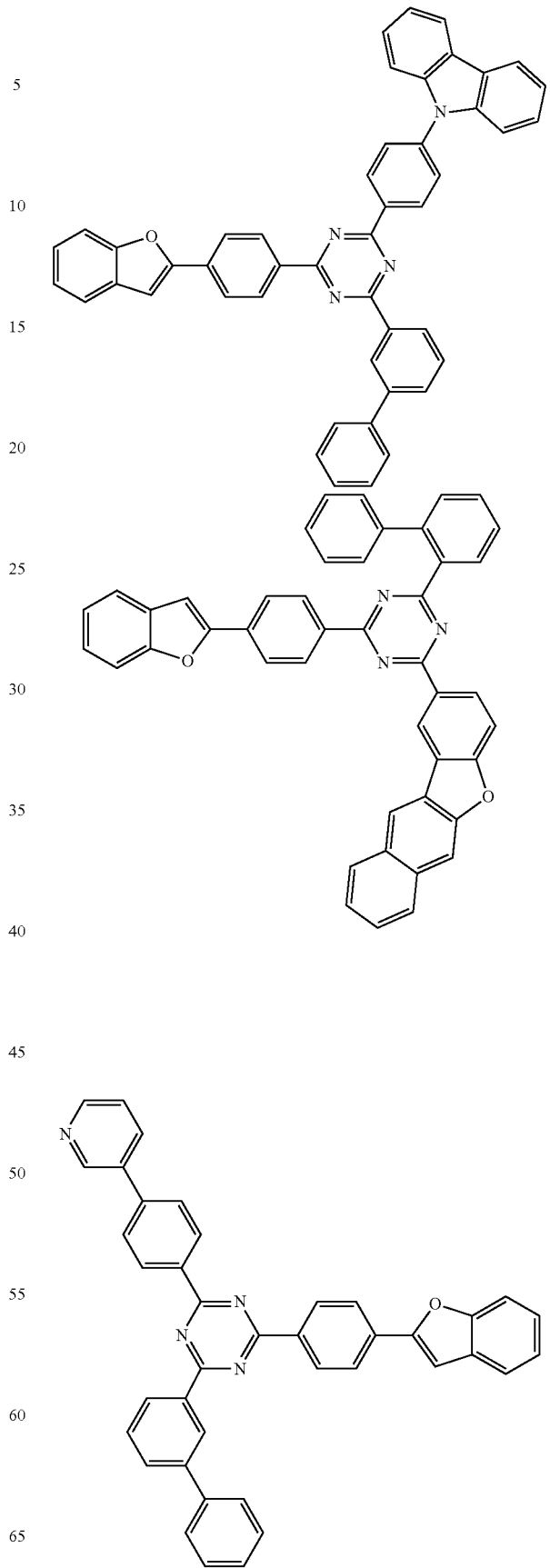

267
-continued
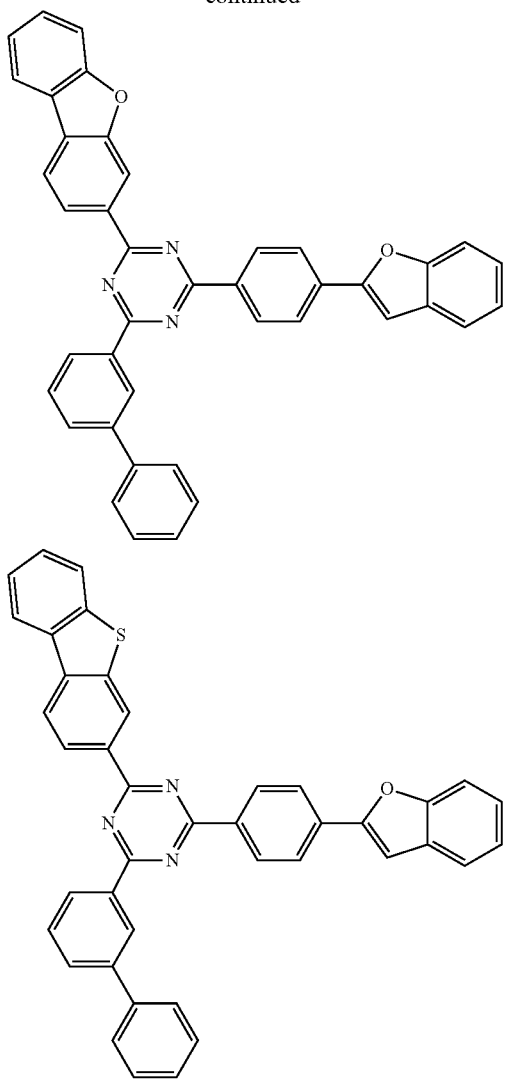
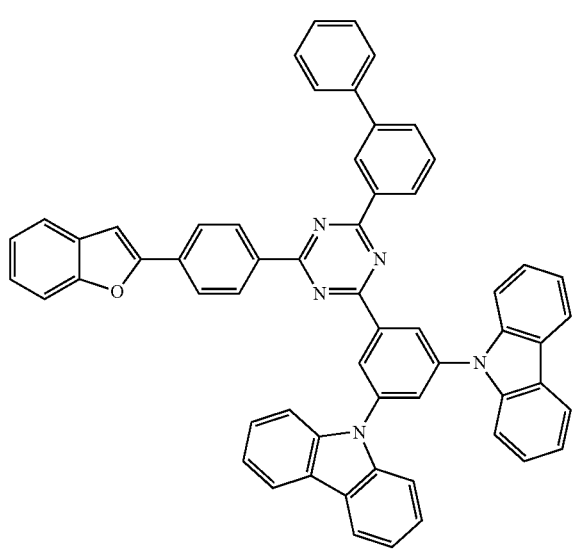
268
-continued
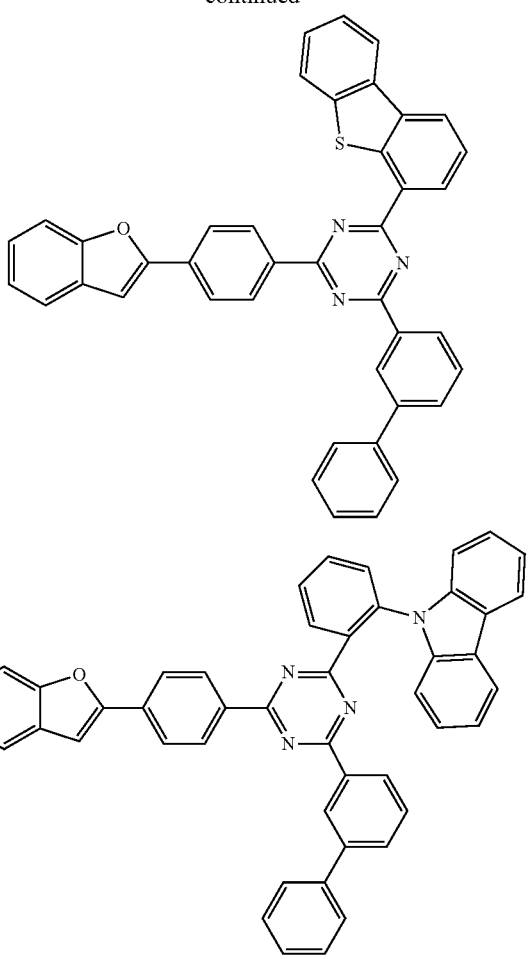
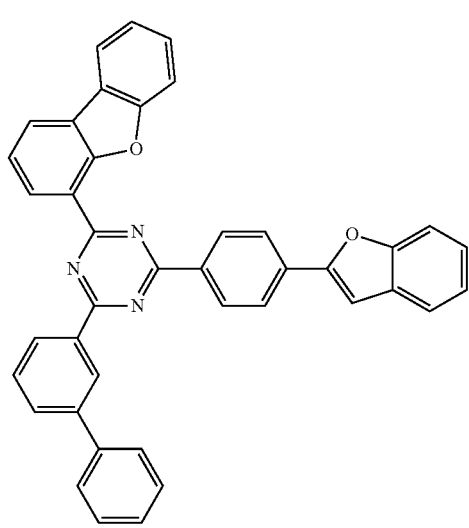

269
-continued
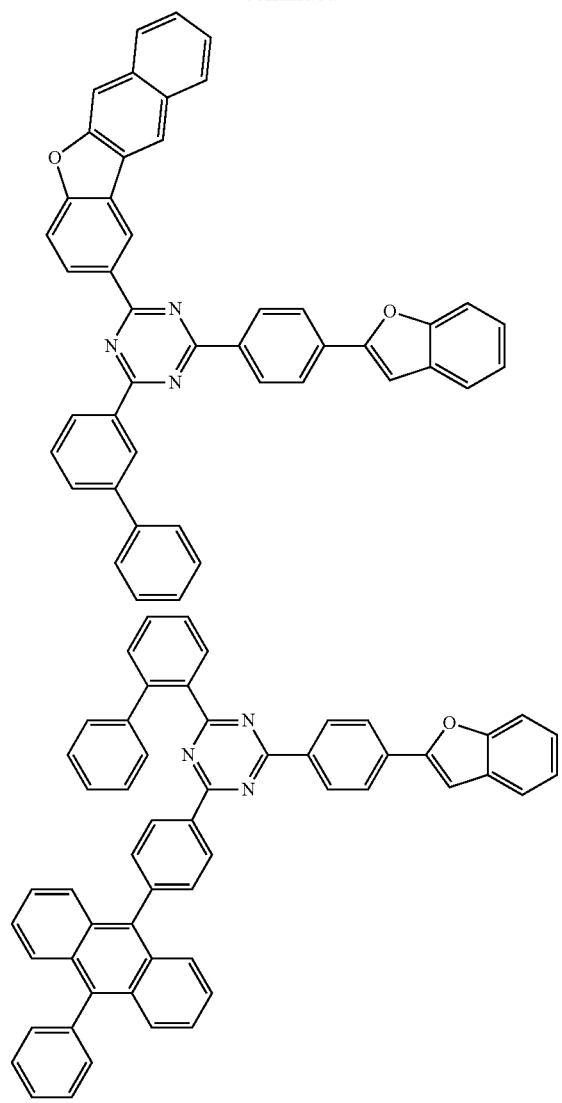
270
-continued
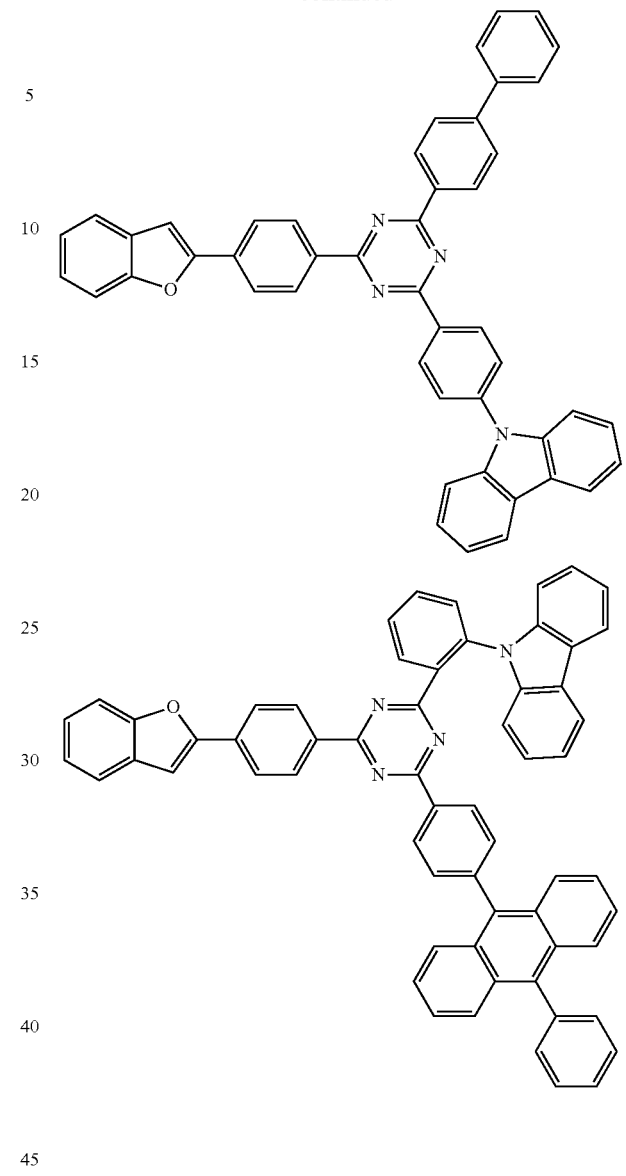
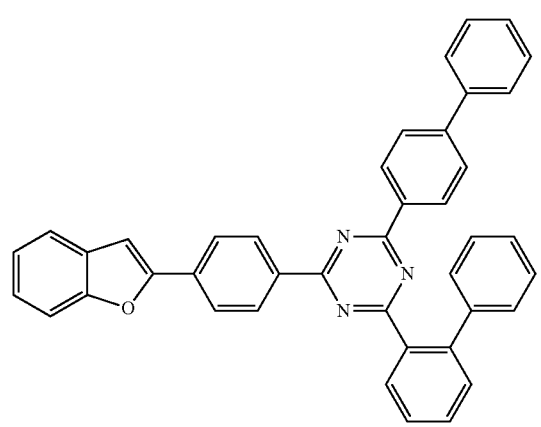
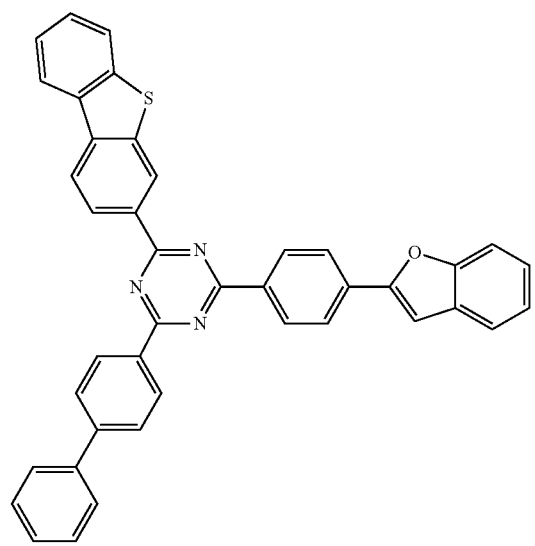

271
-continued
272
-continued
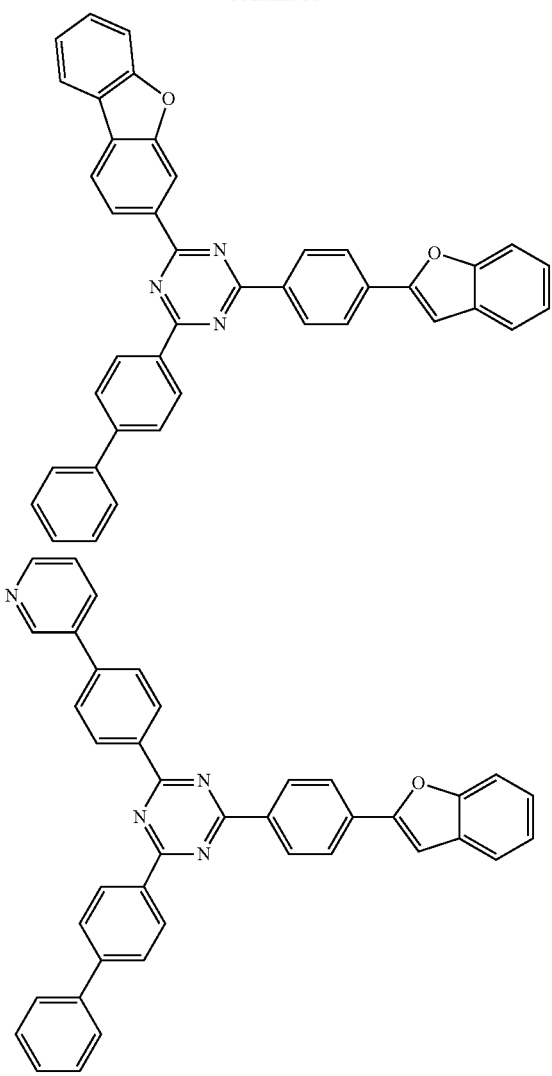
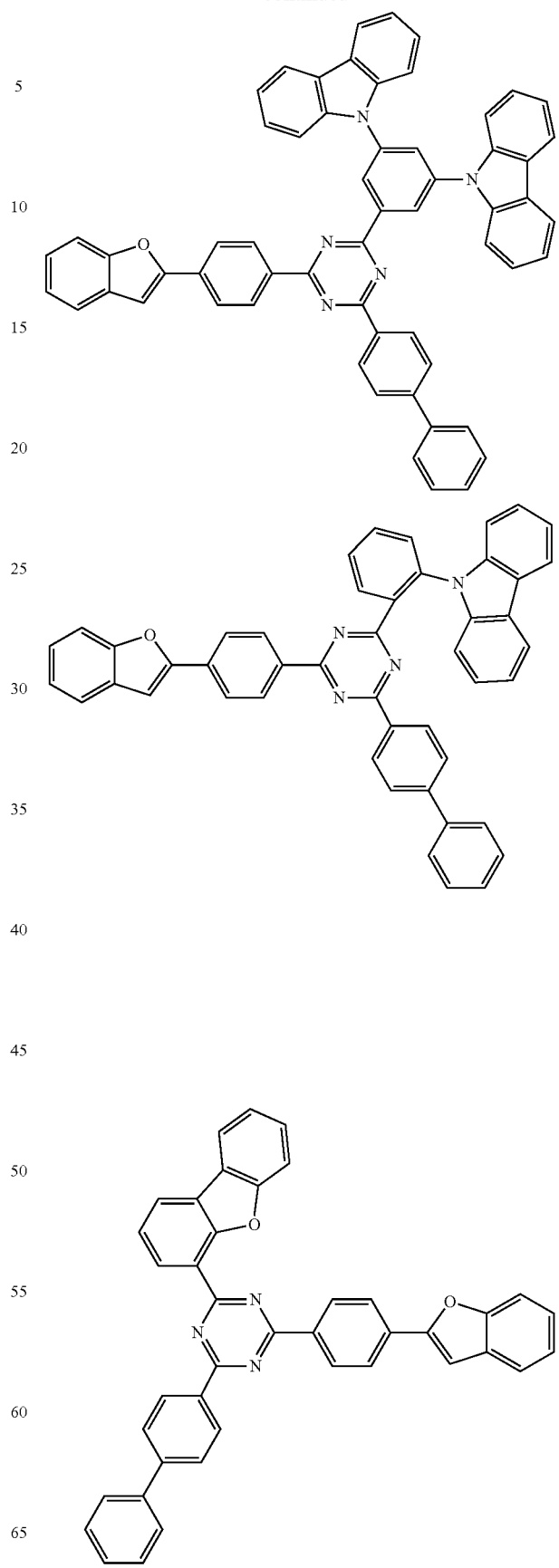

273
-continued
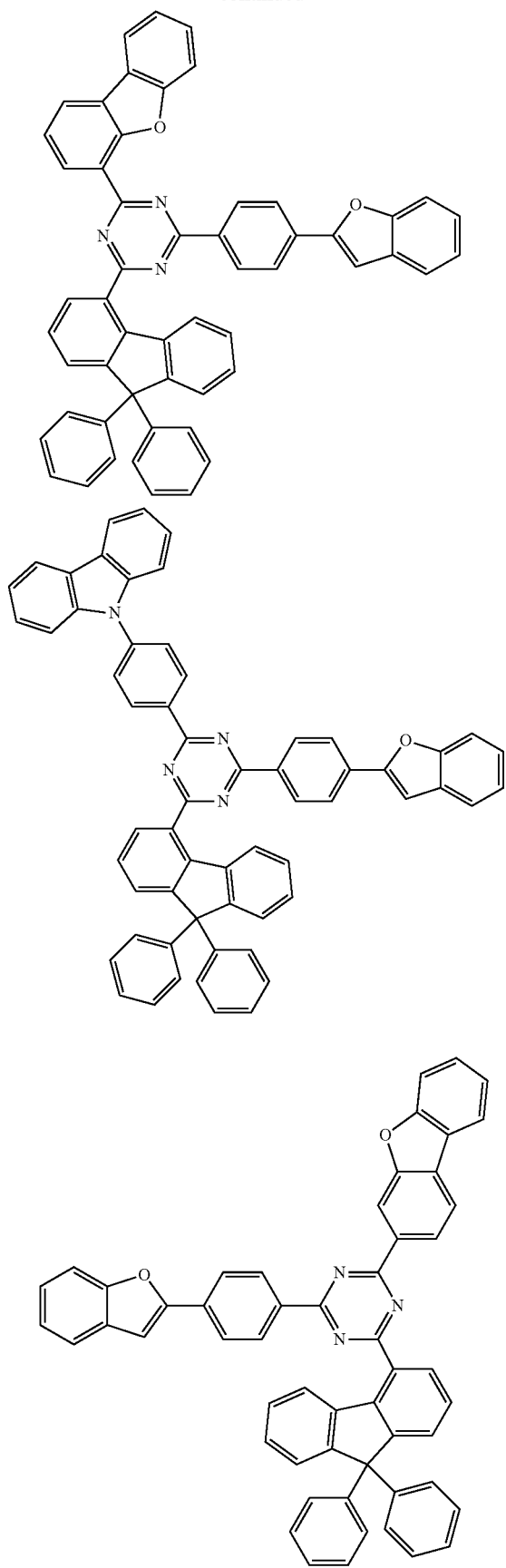
274
-continued
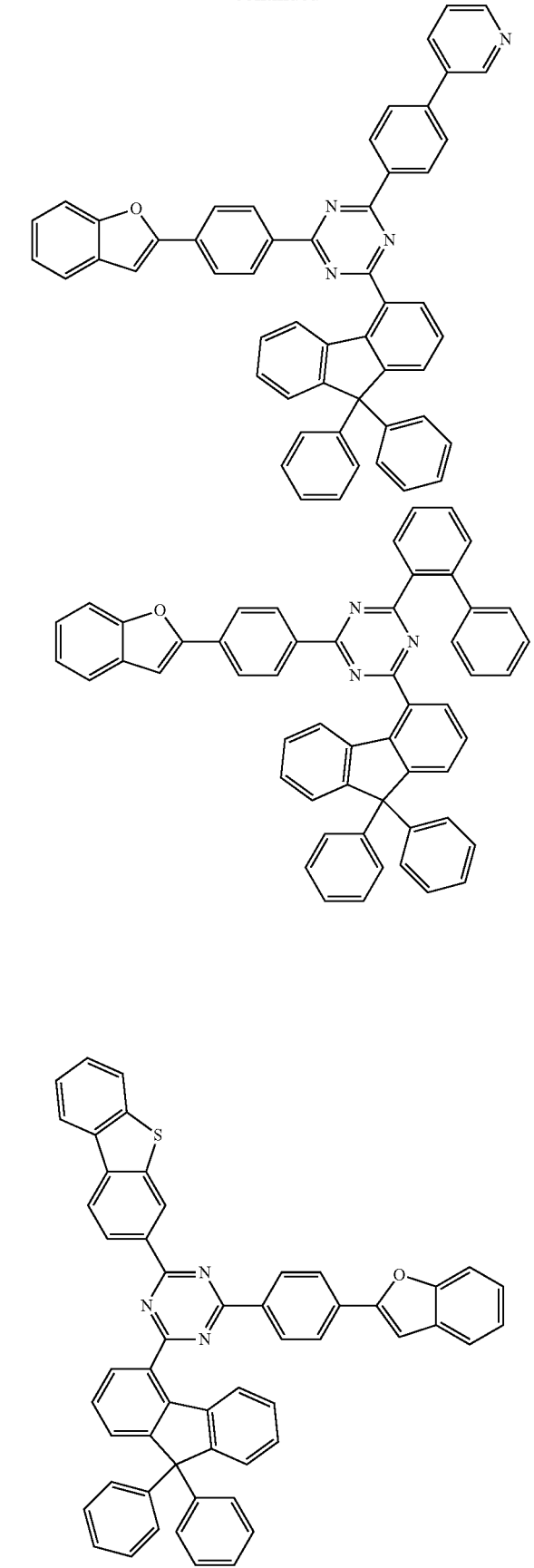

275
-continued
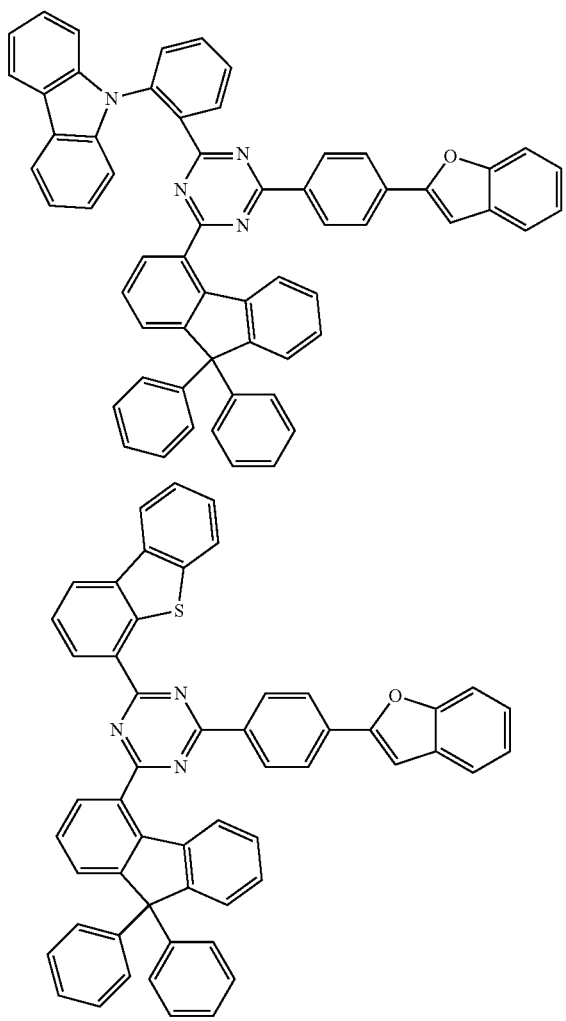
276
-continued
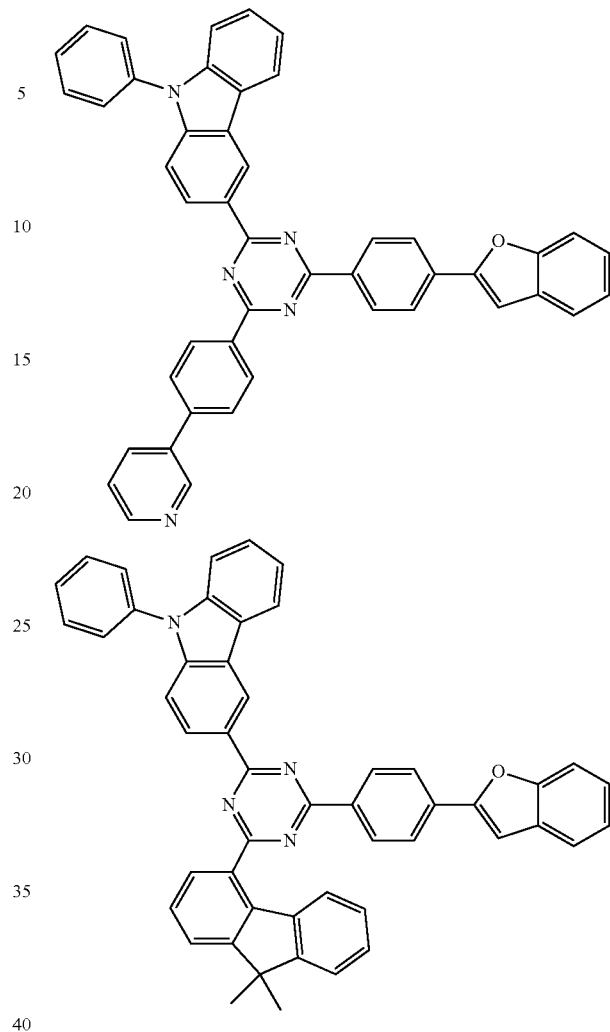
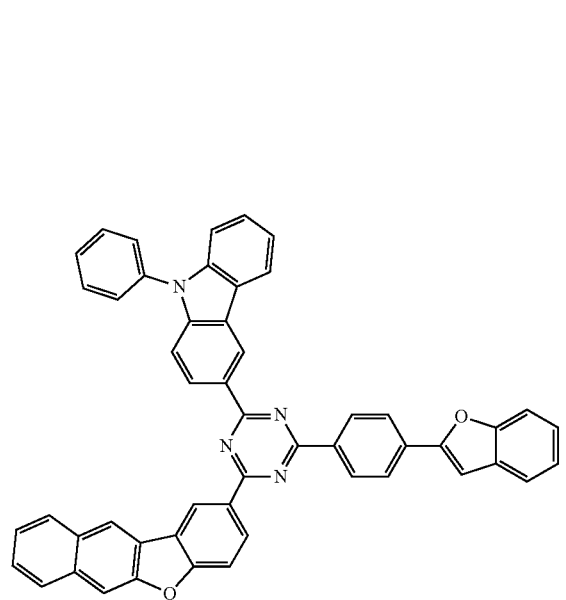
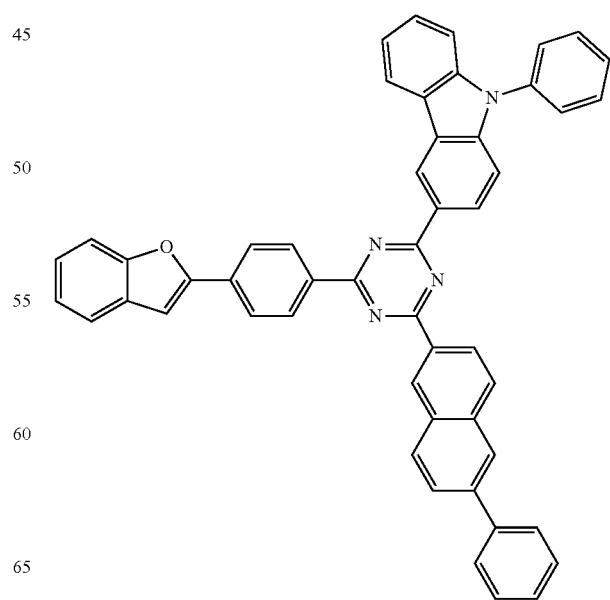

277
-continued
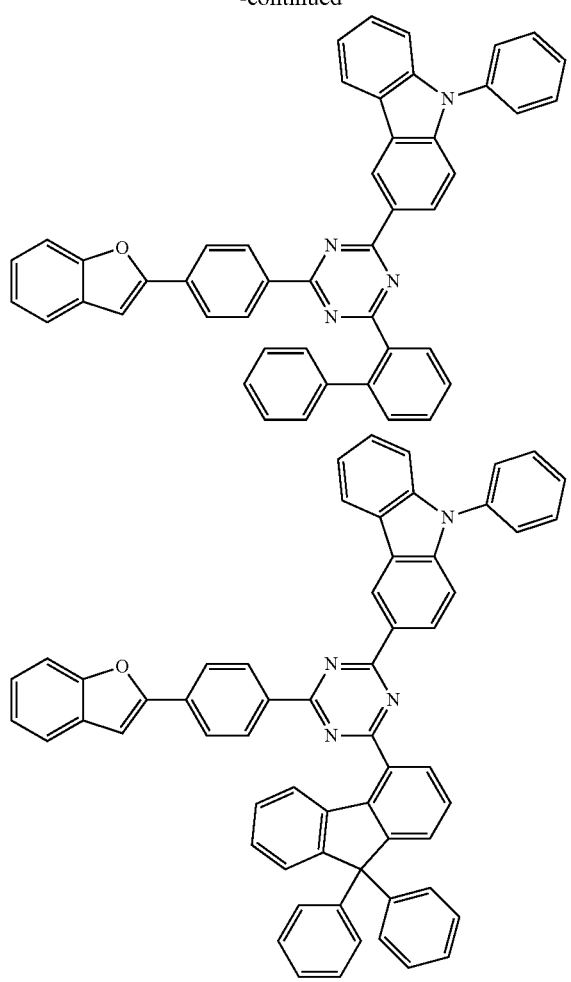
278
-continued
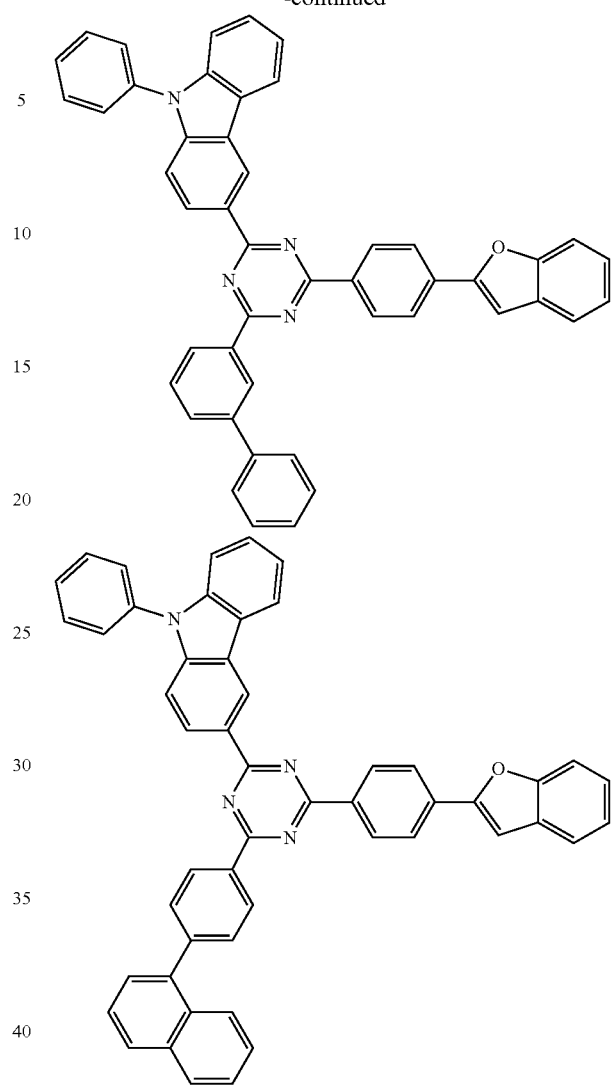
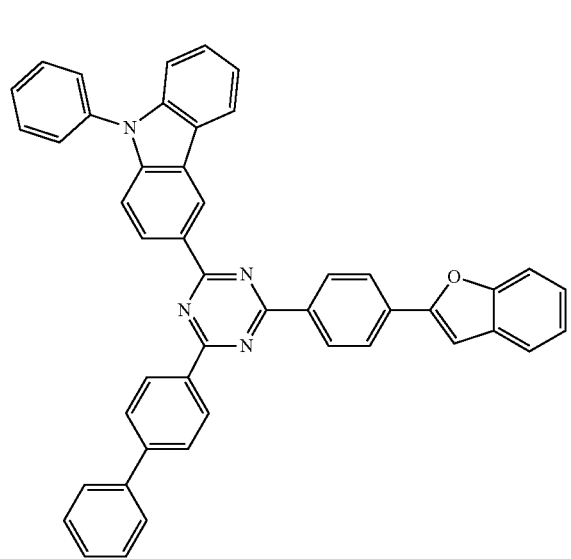
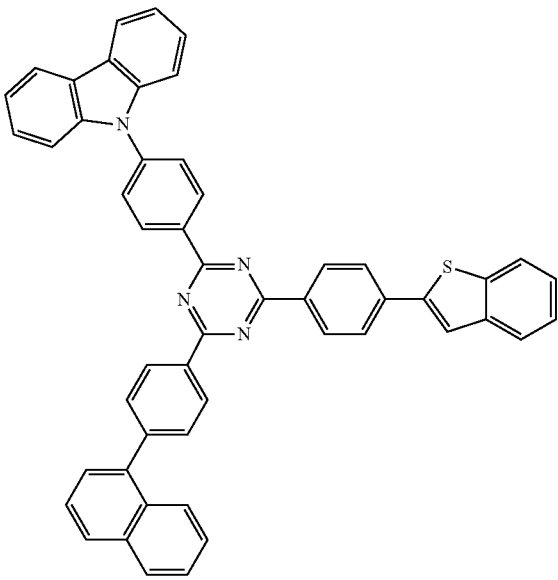

279
-continued
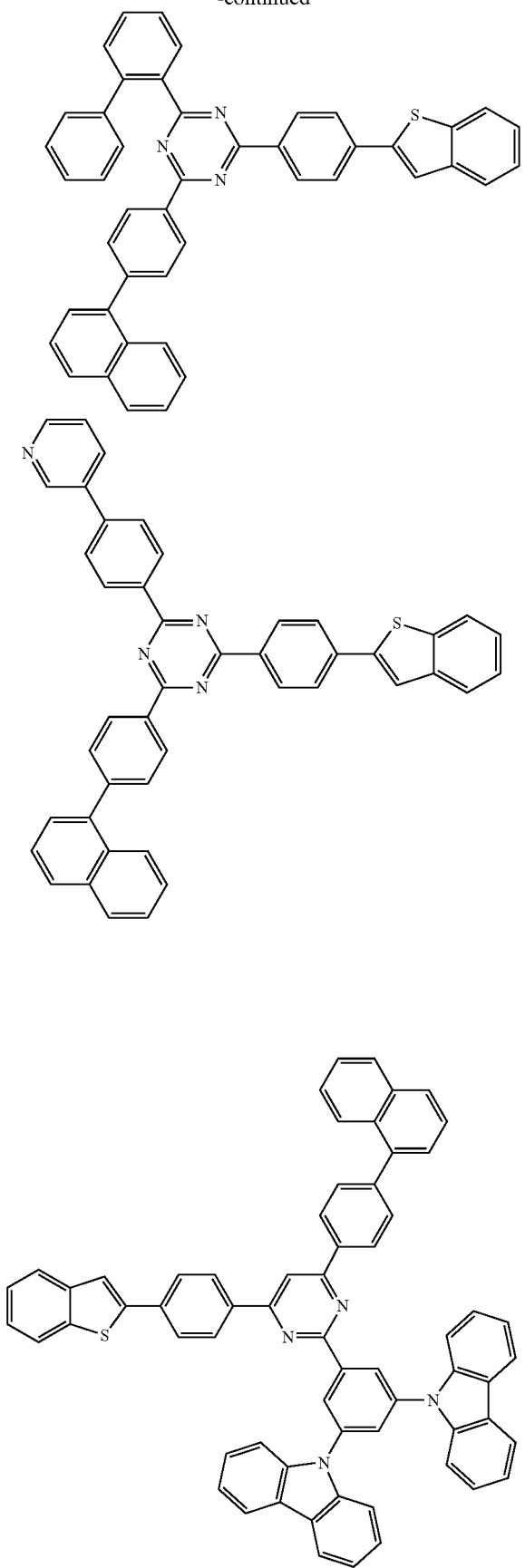
280
-continued
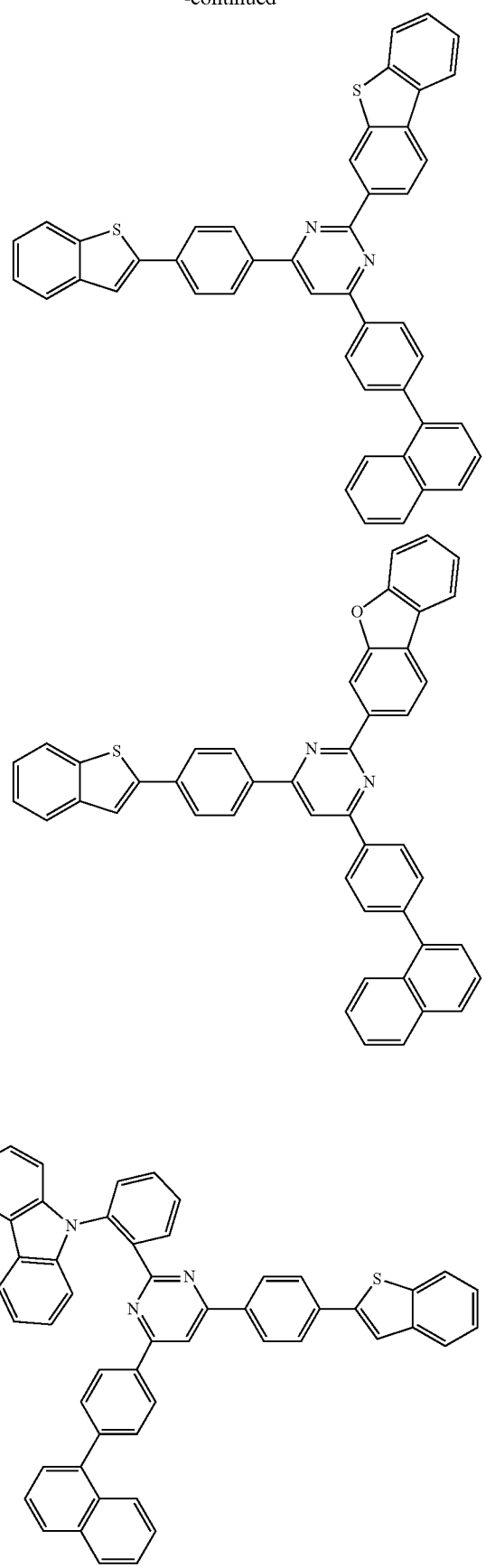

281
-continued
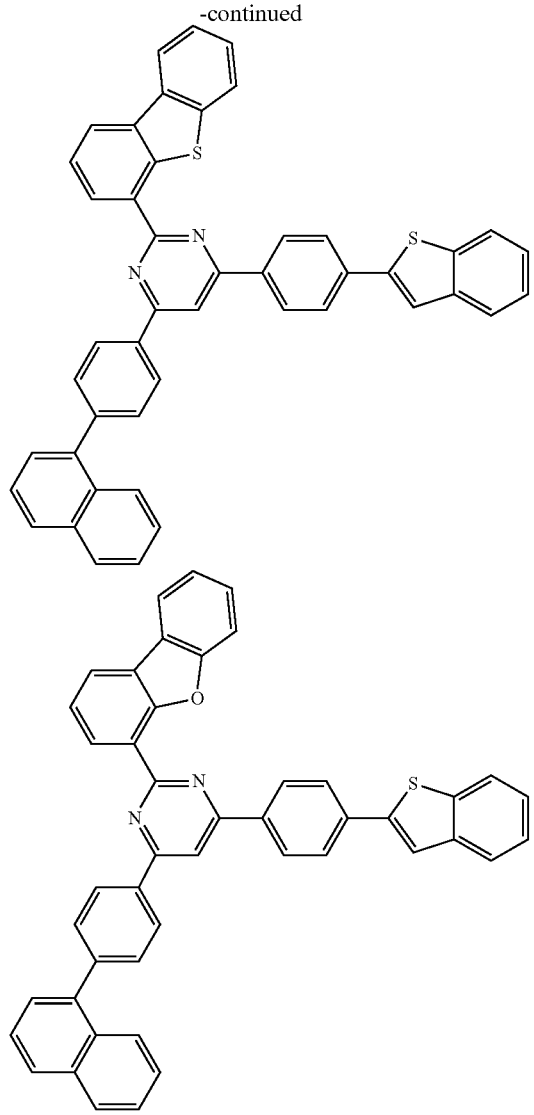
282
-continued
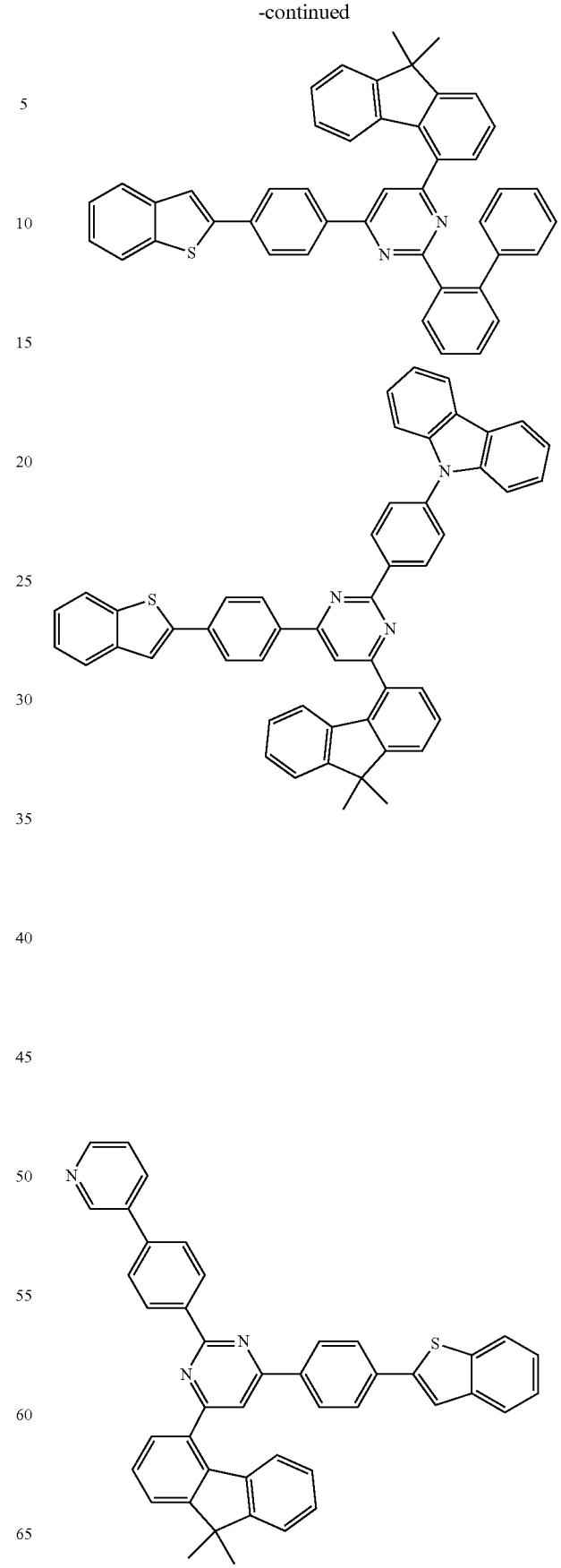

283
-continued
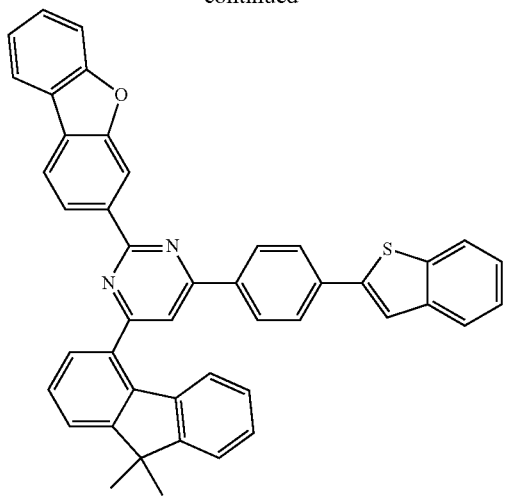
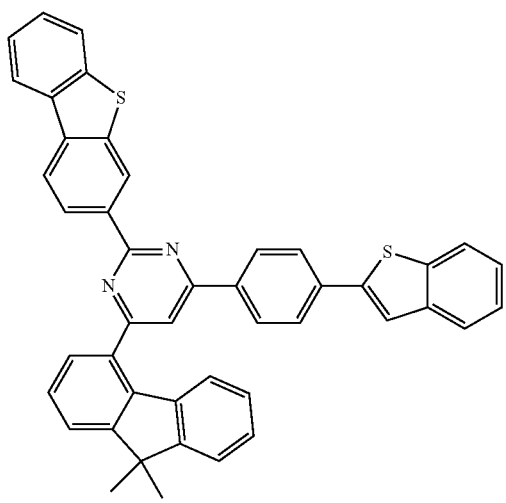
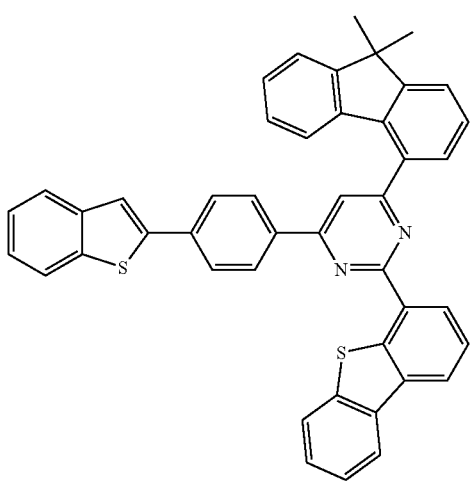
284
-continued
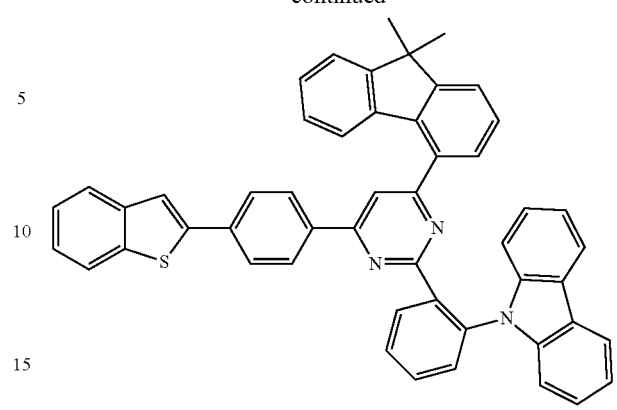
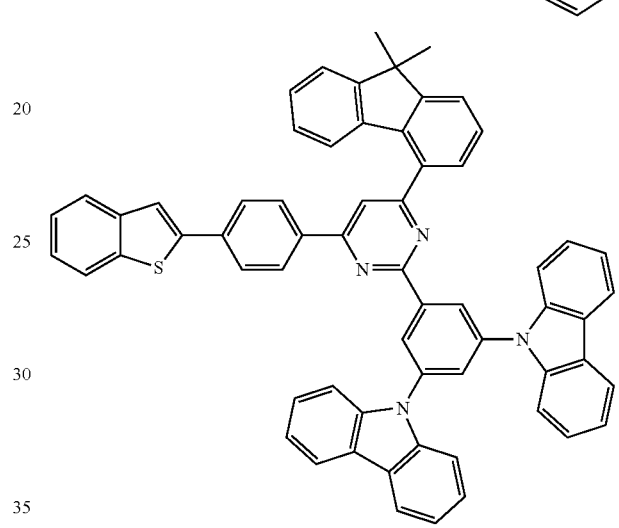
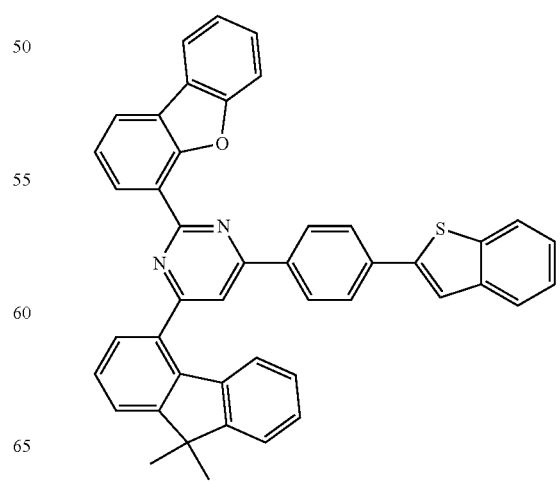

285
-continued
286
-continued
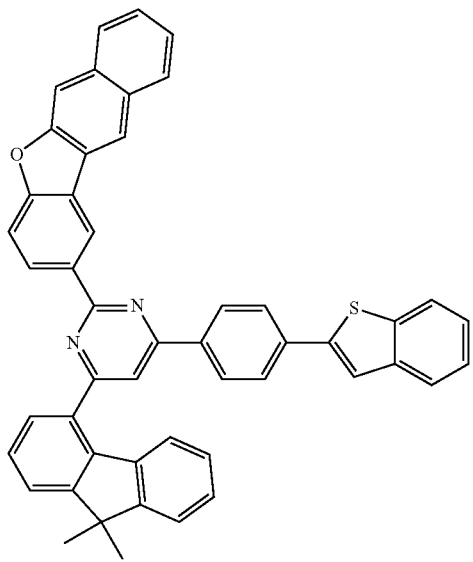
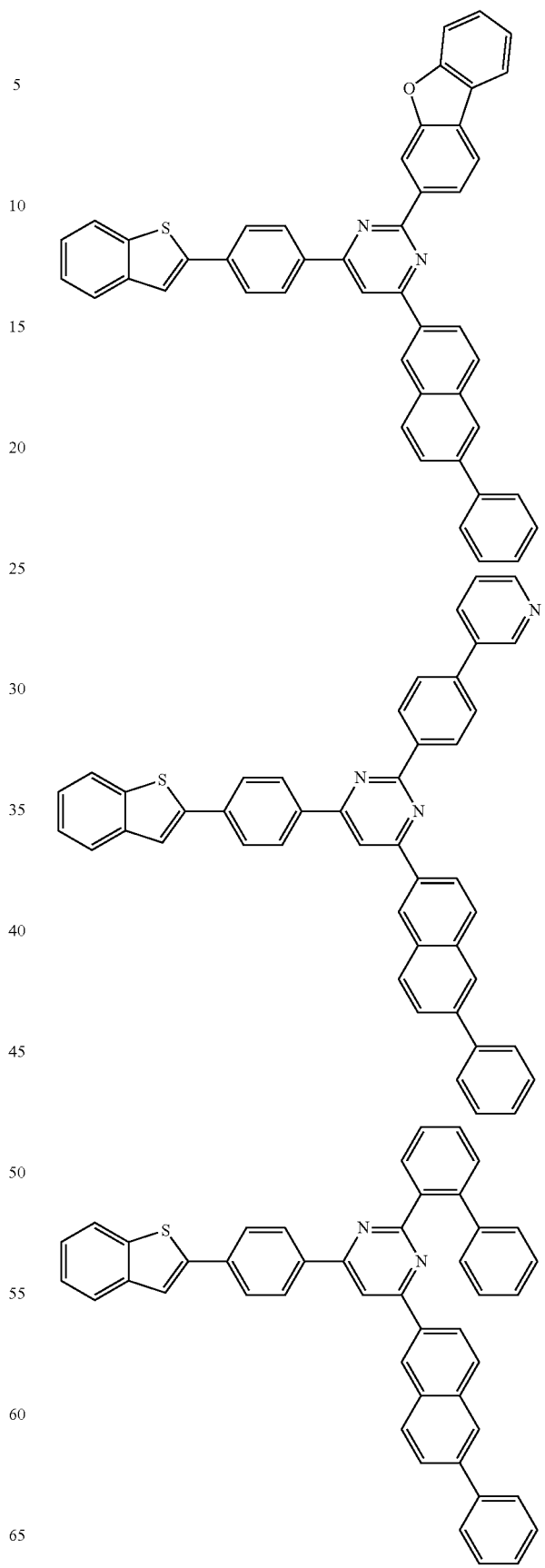

287
-continued
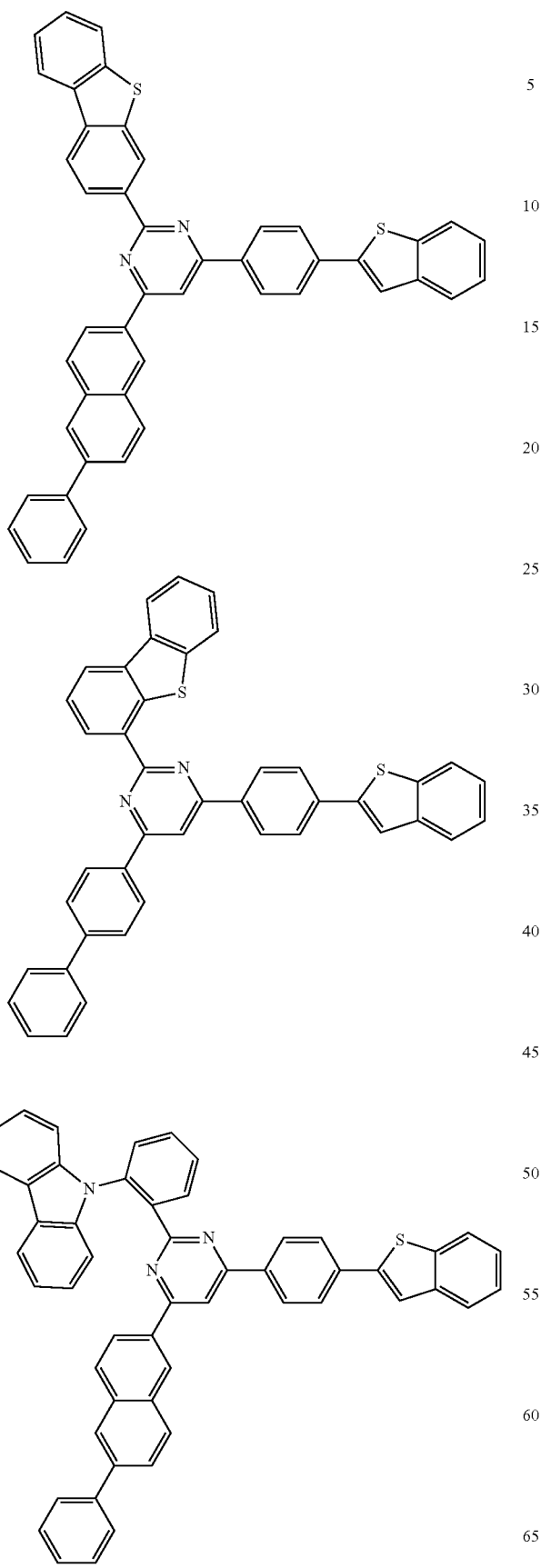
288
-continued
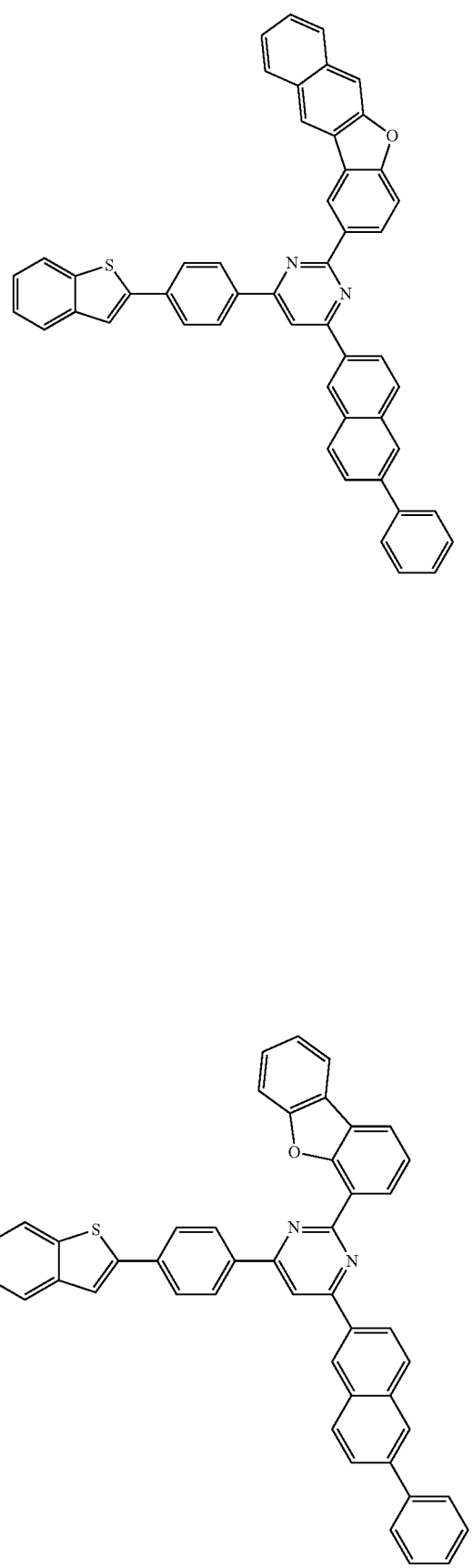

289
-continued
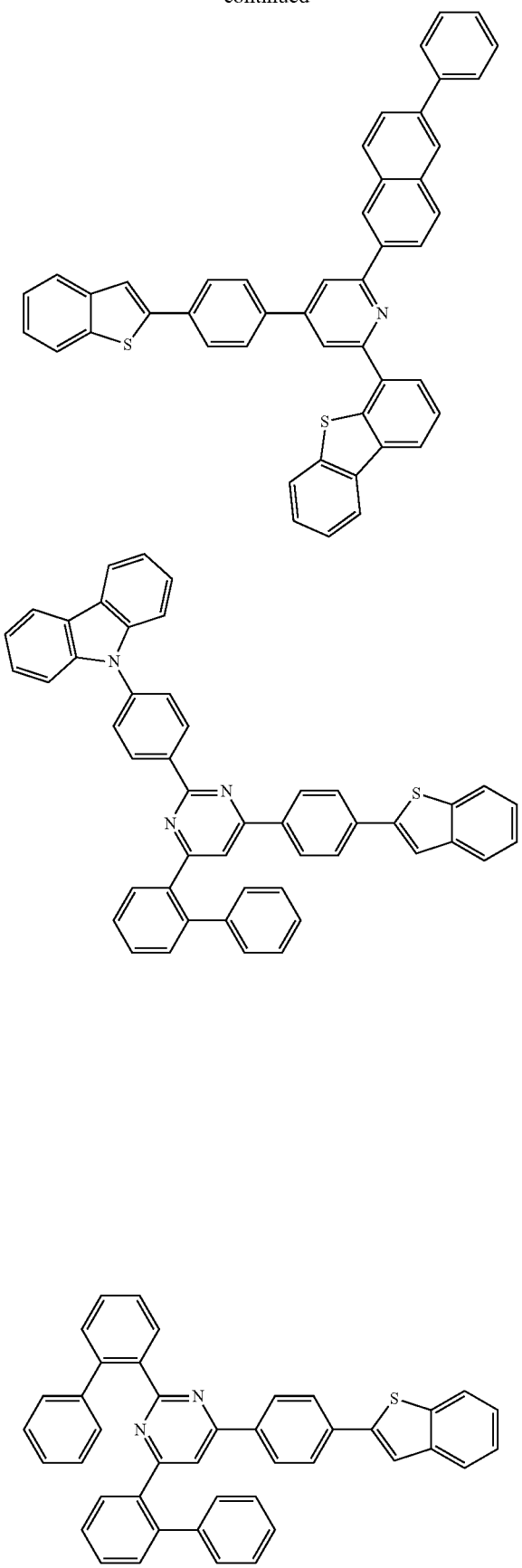
290
-continued
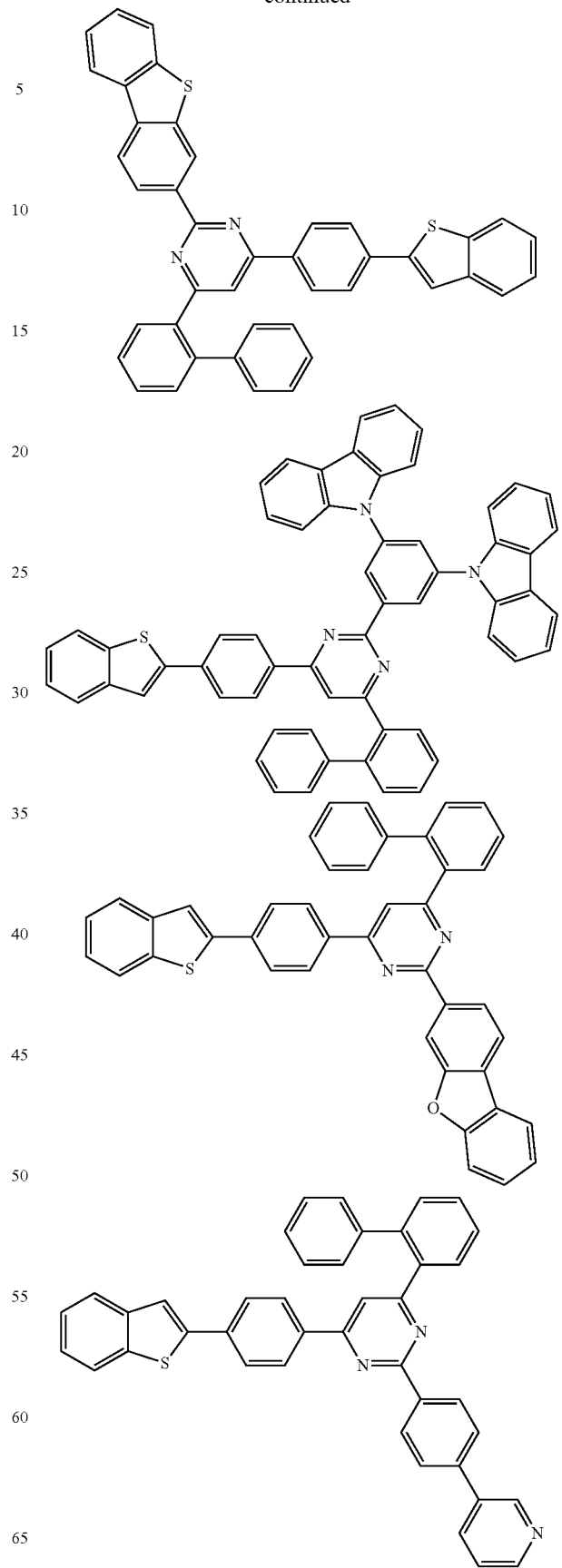

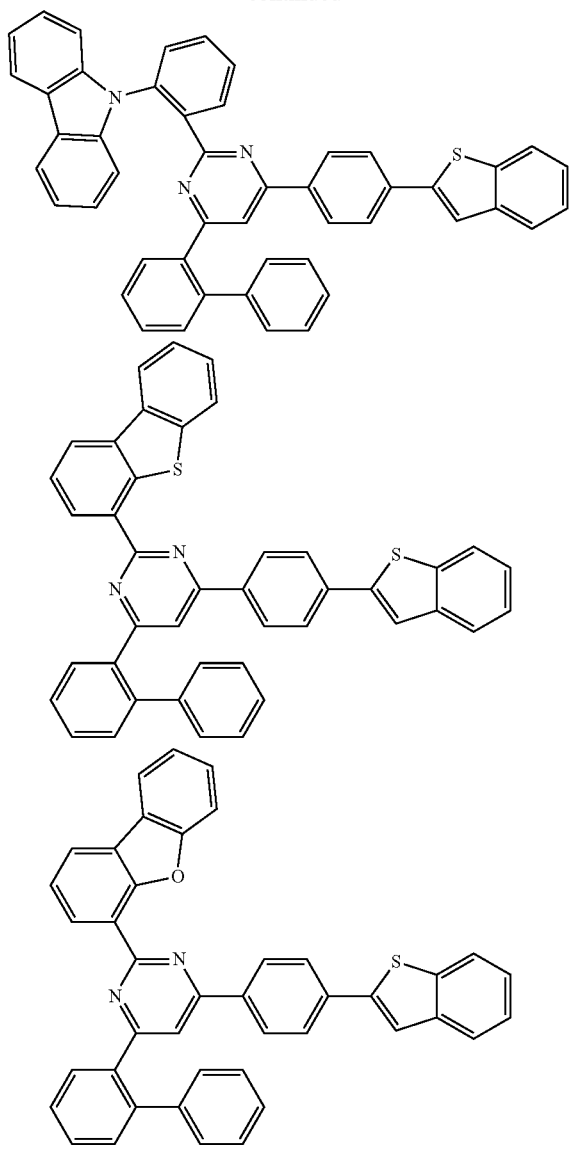
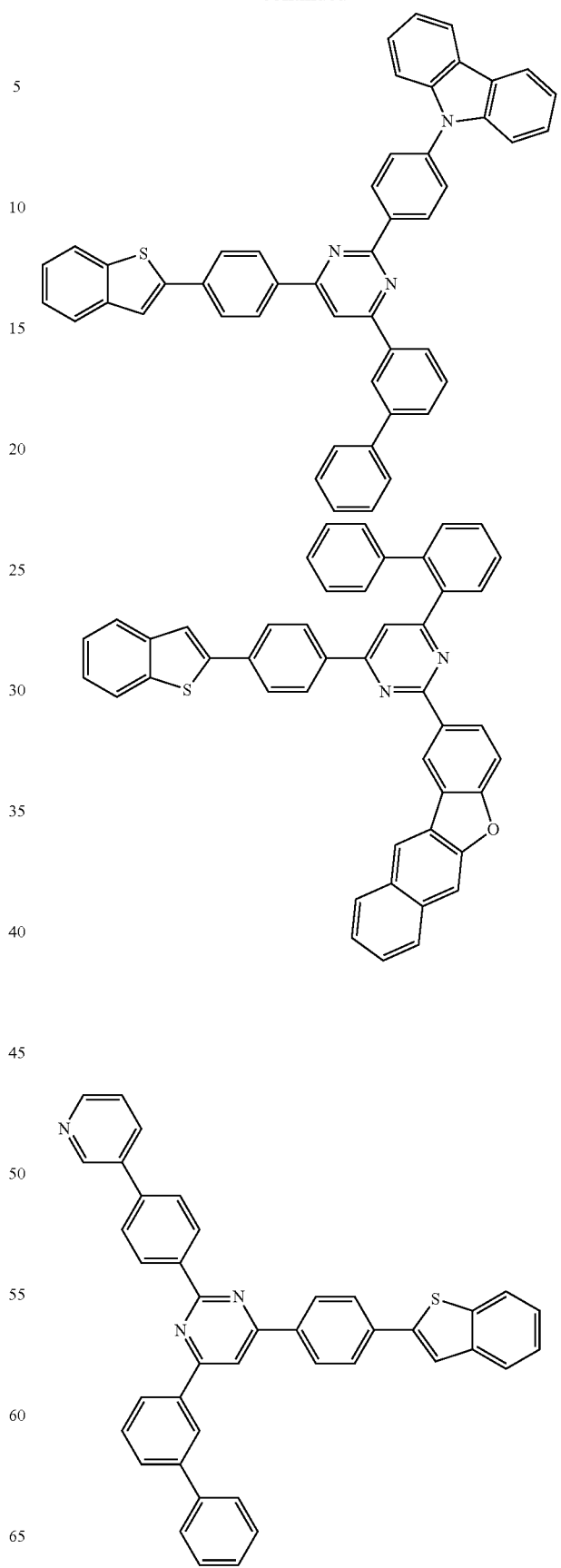

293
-continued
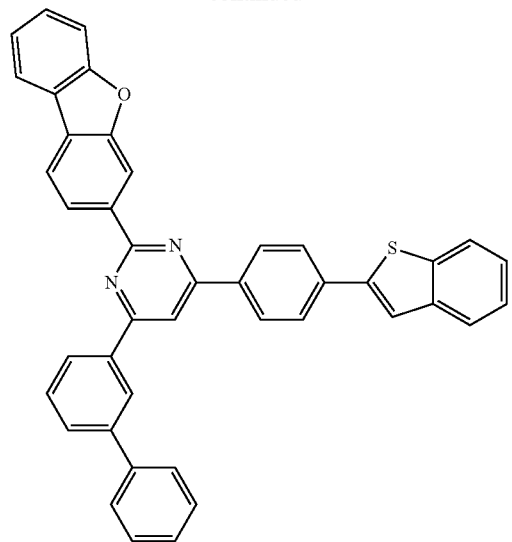
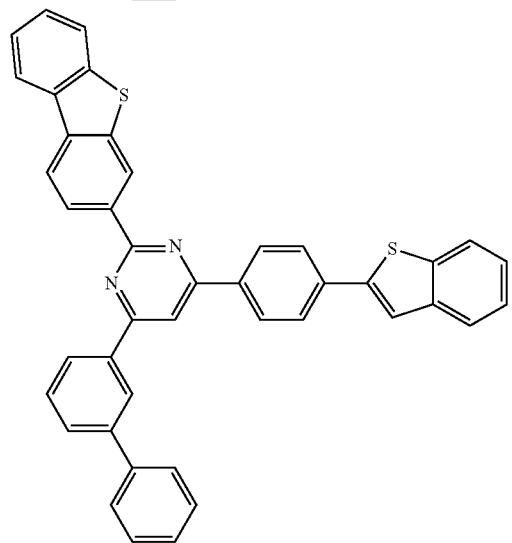
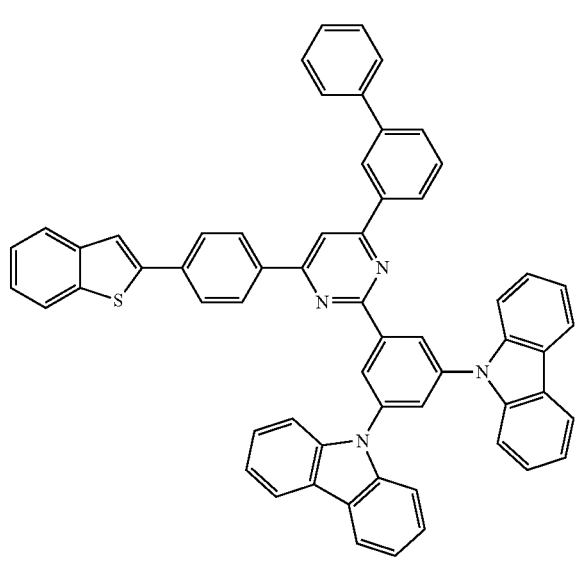
294
-continued
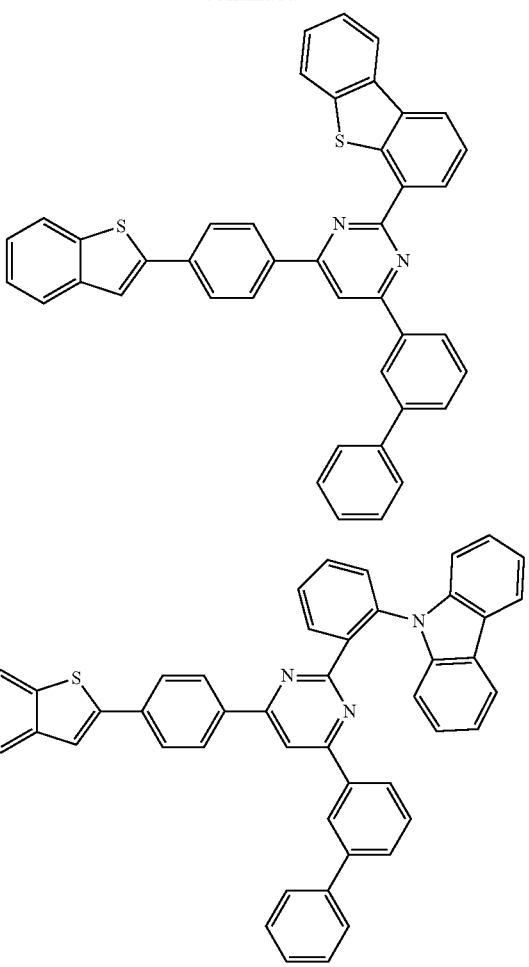
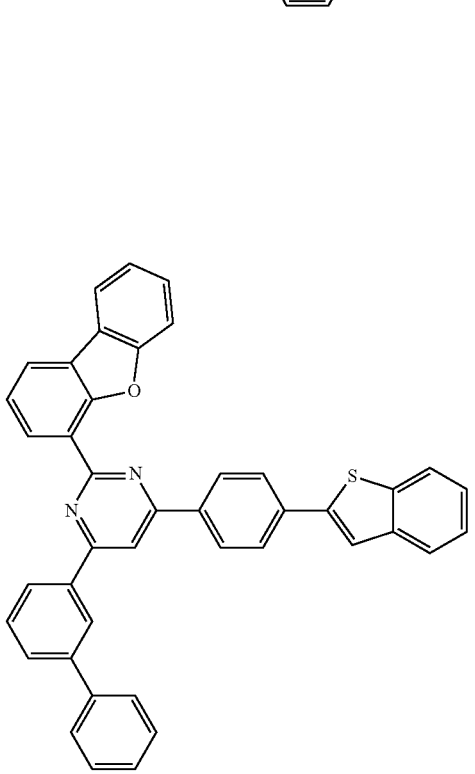

295
-continued
296
-continued
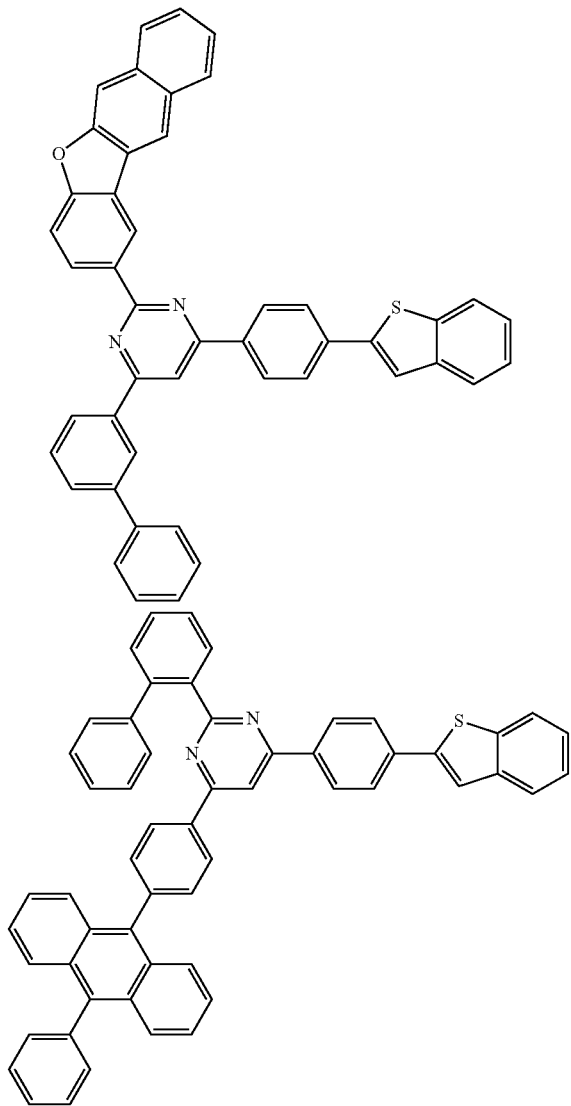
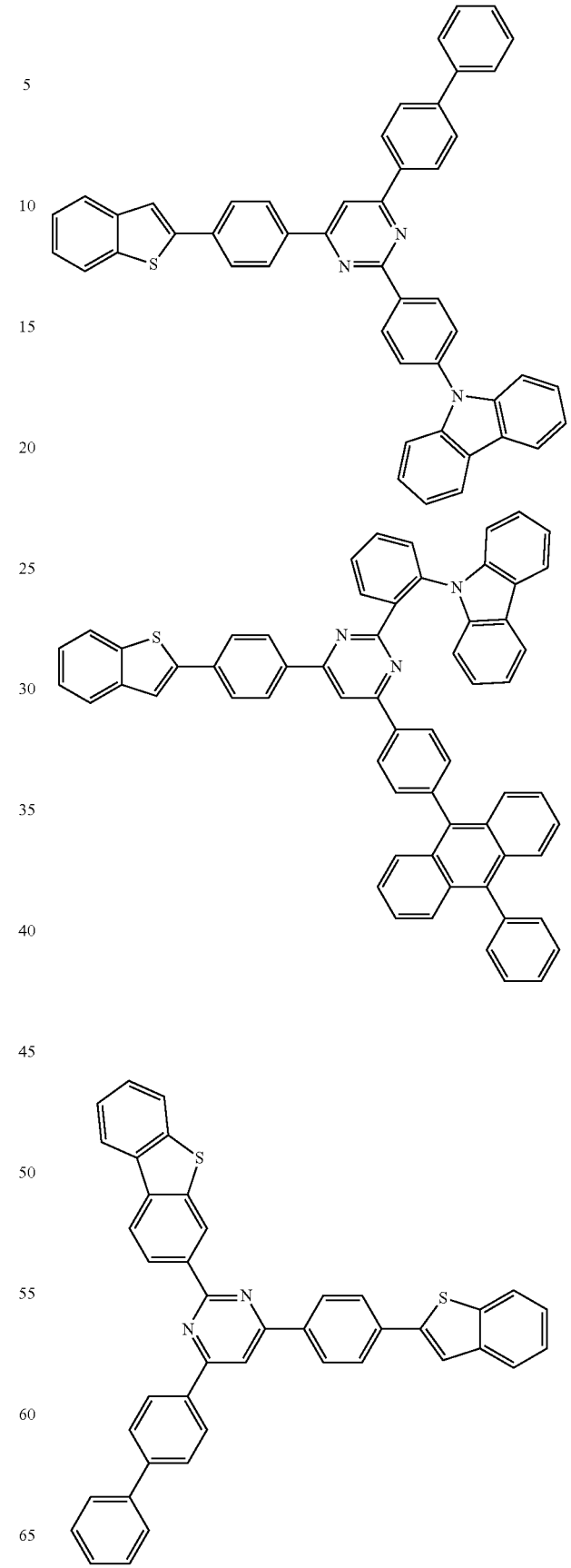

297
-continued
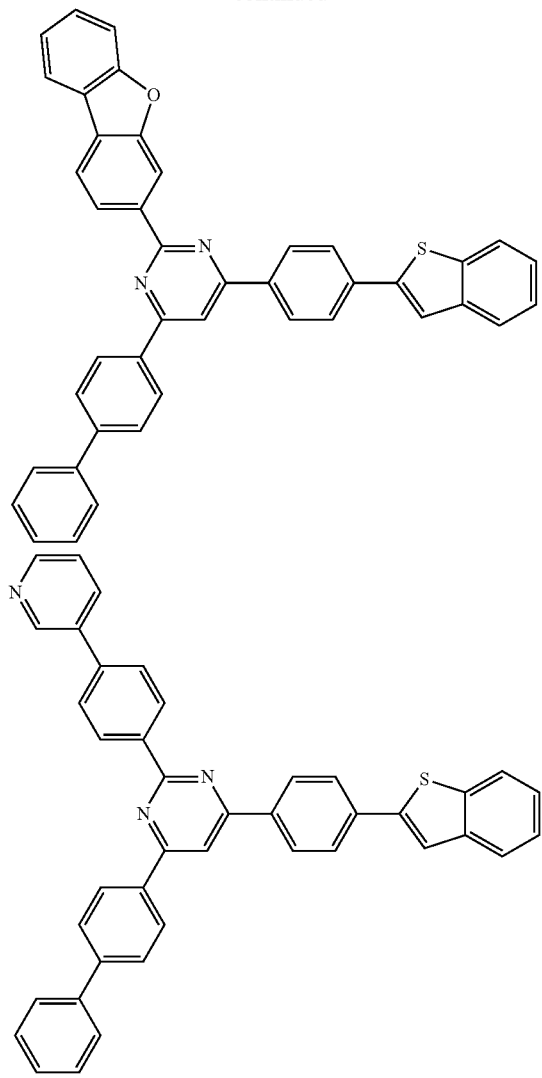
298
-continued
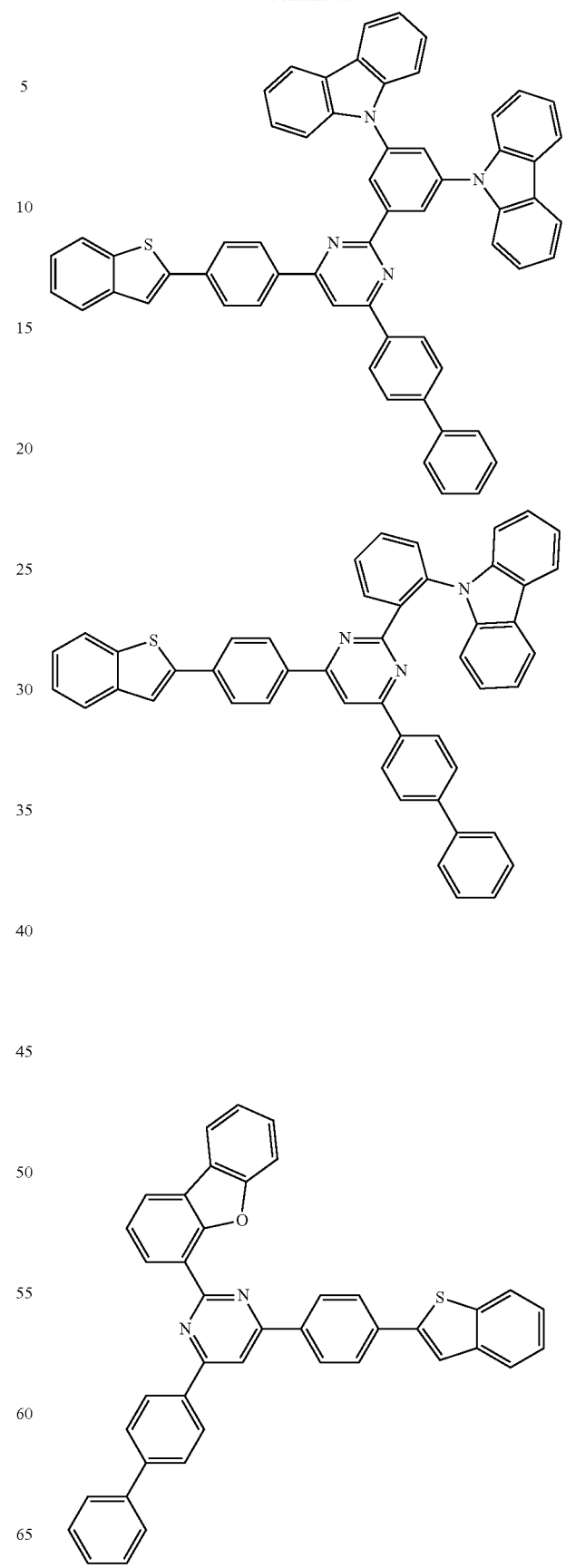

299
-continued
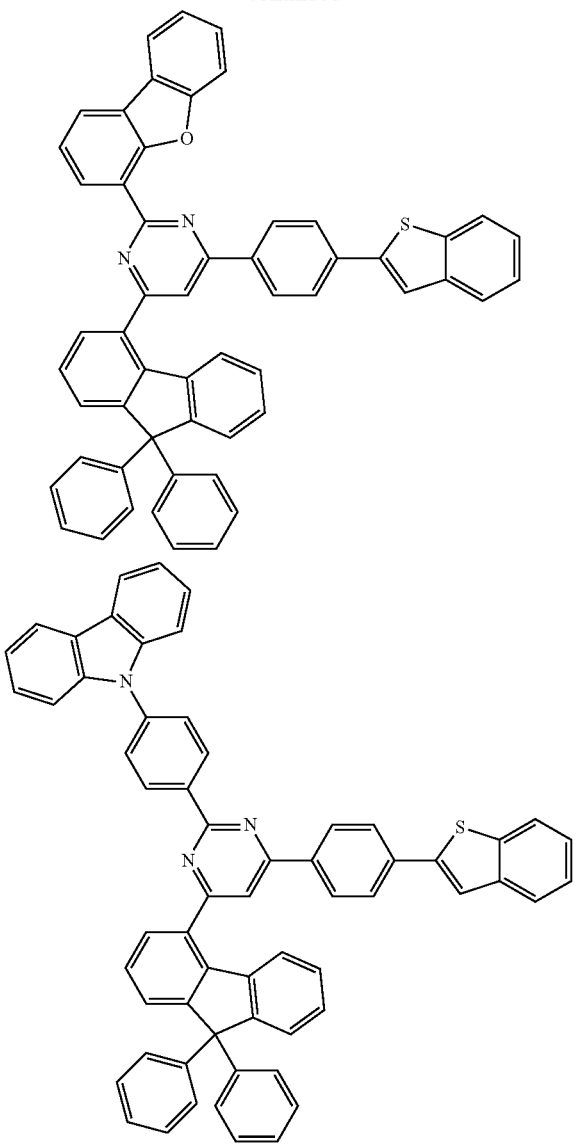
300
-continued

301
-continued
302
-continued
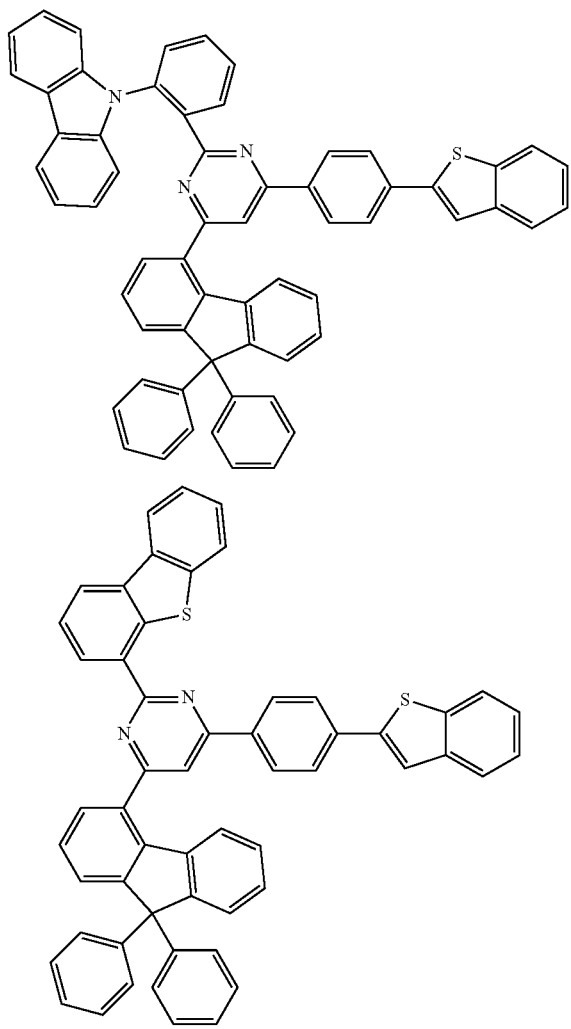
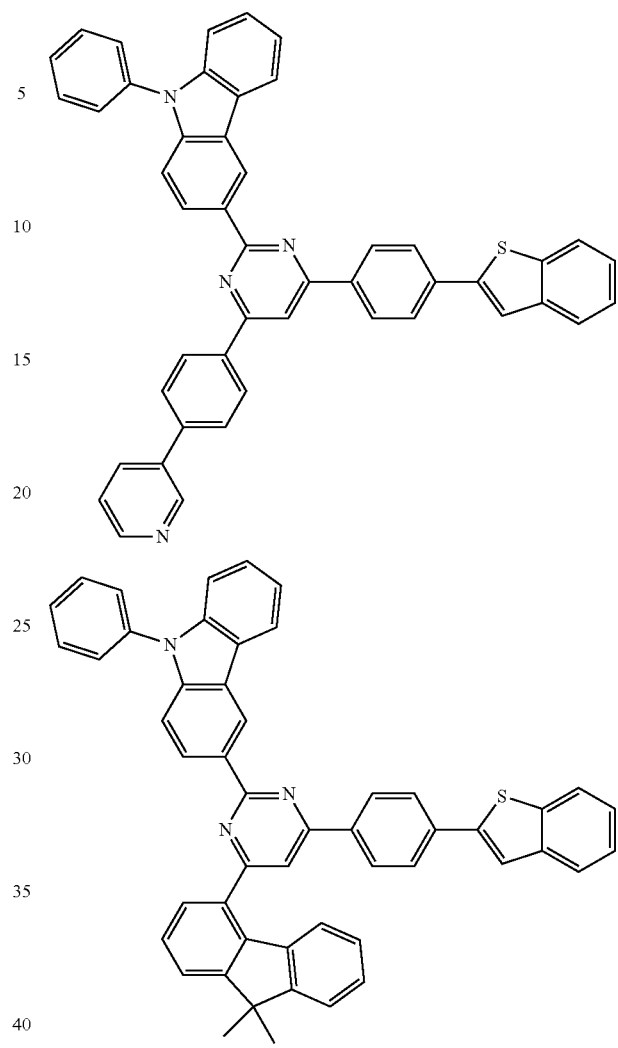
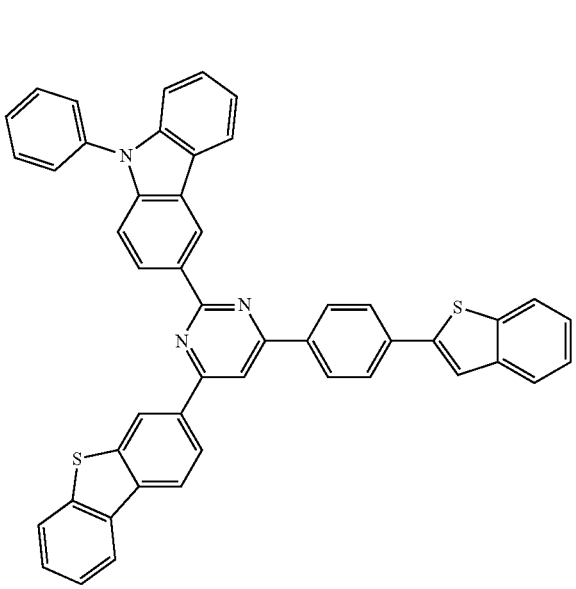
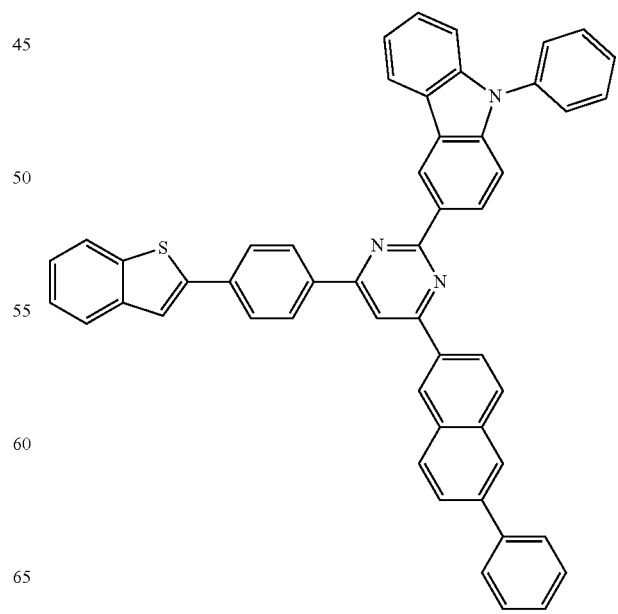

303
-continued
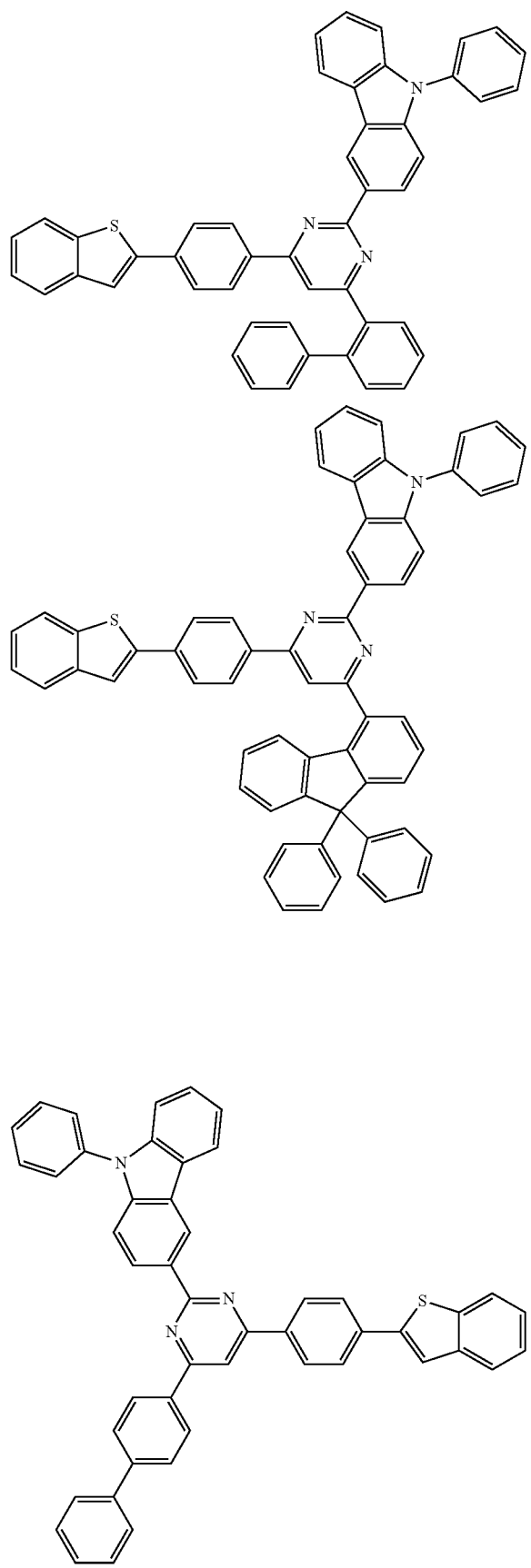
304
-continued
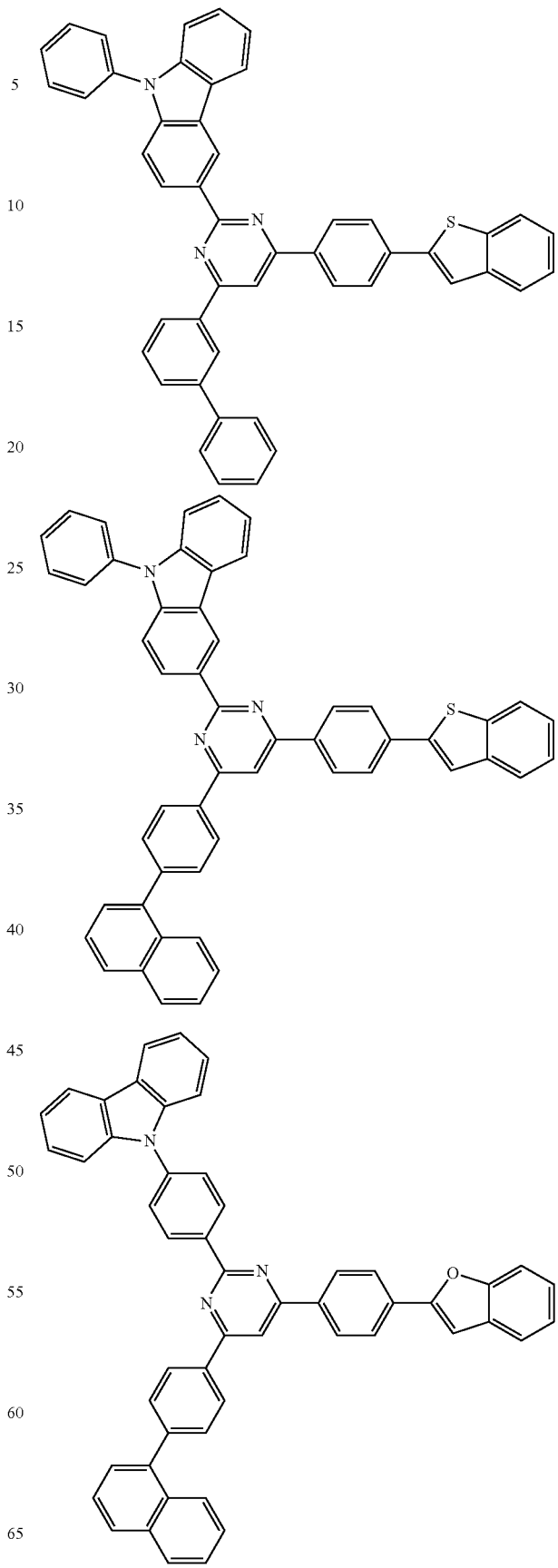

305
-continued
306
-continued
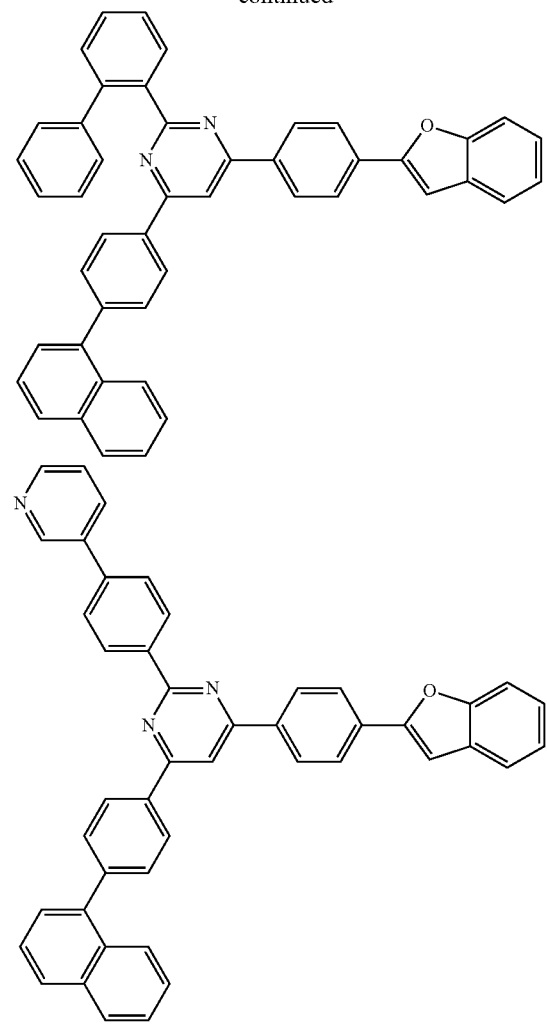
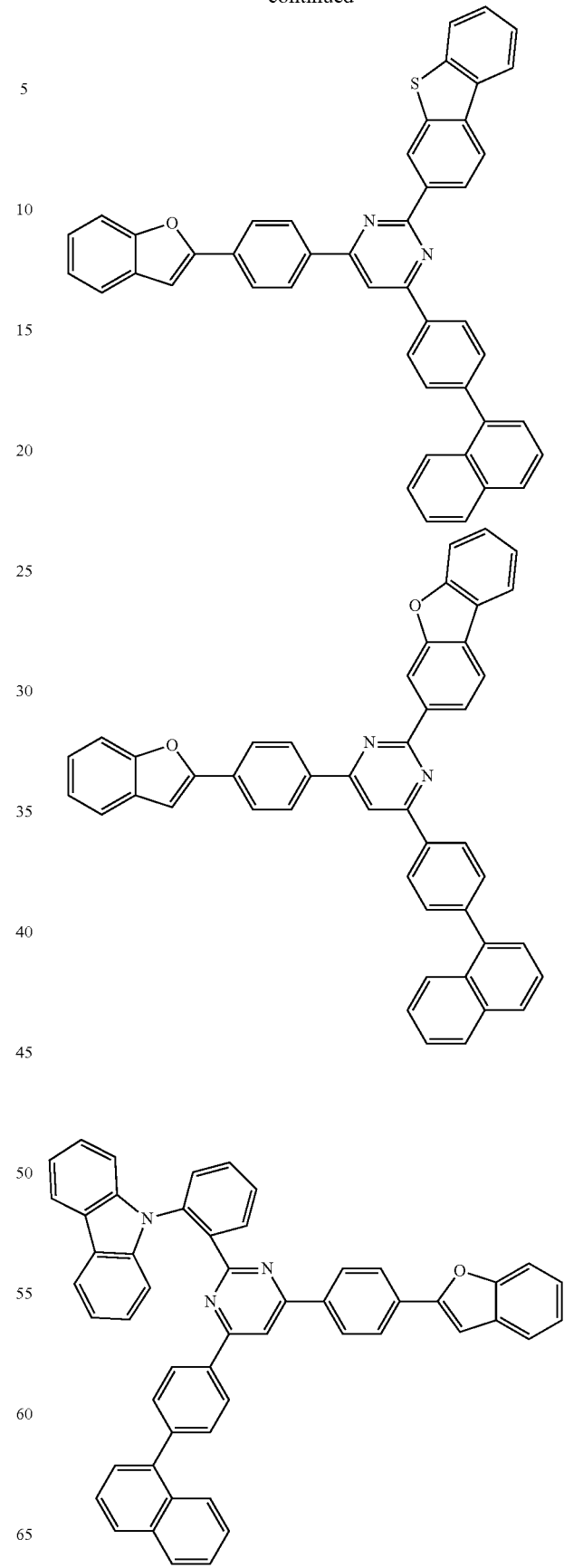

307
-continued
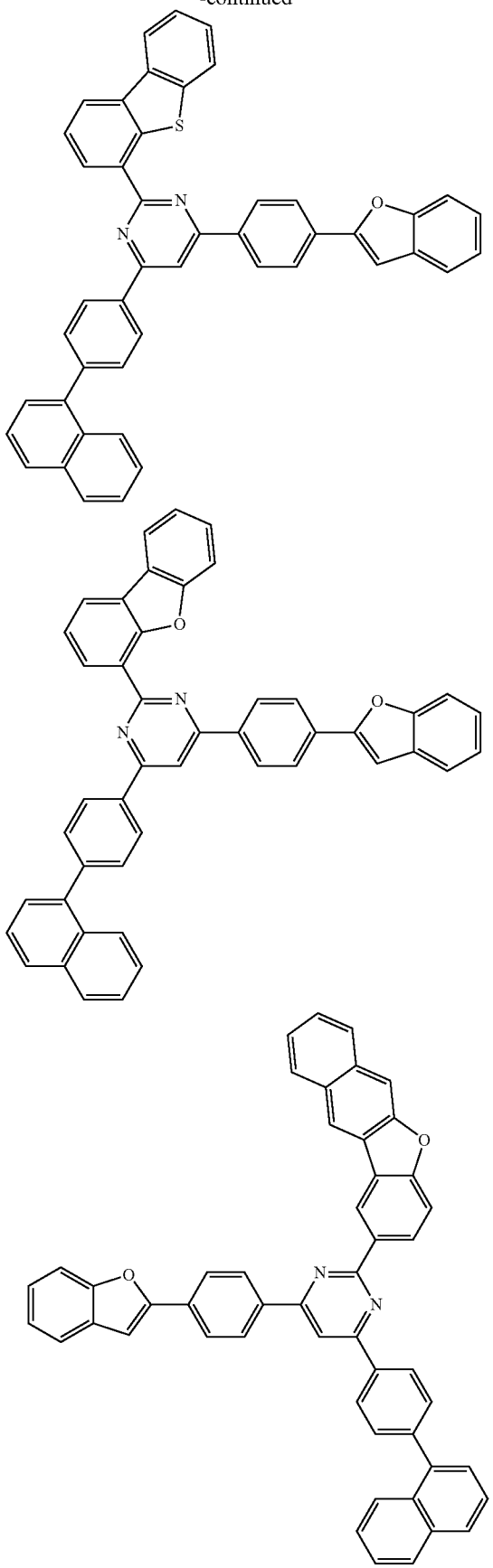
308
-continued
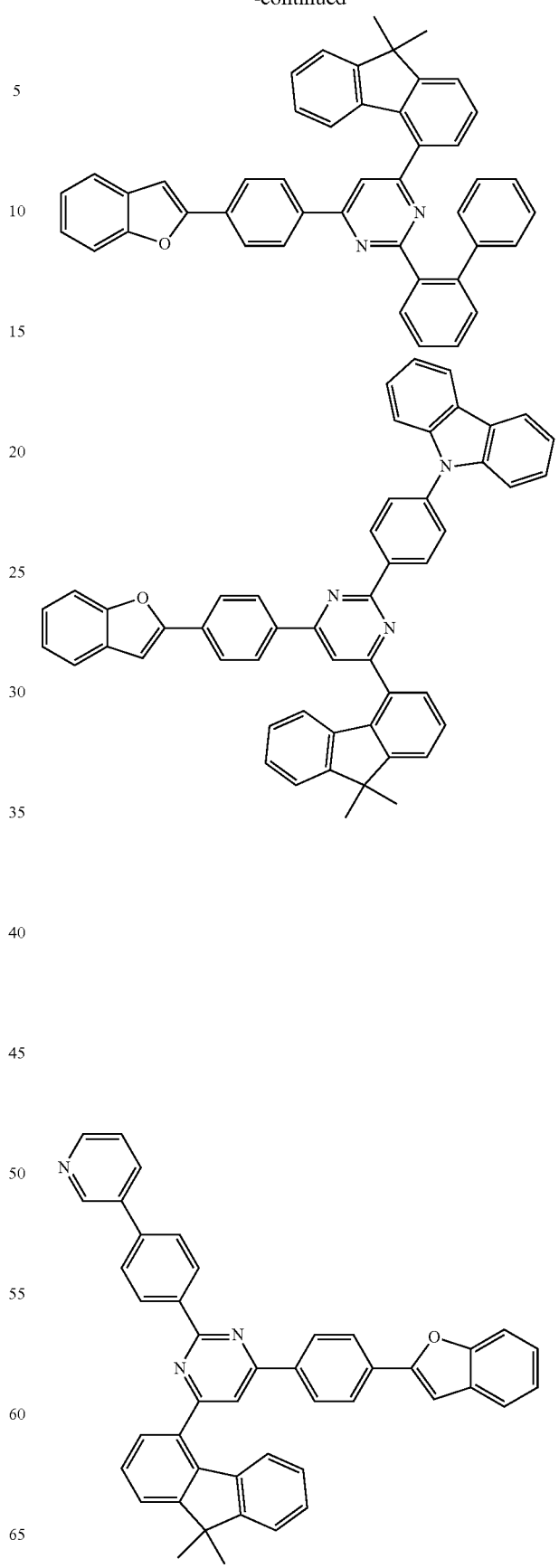

309
-continued
310
-continued
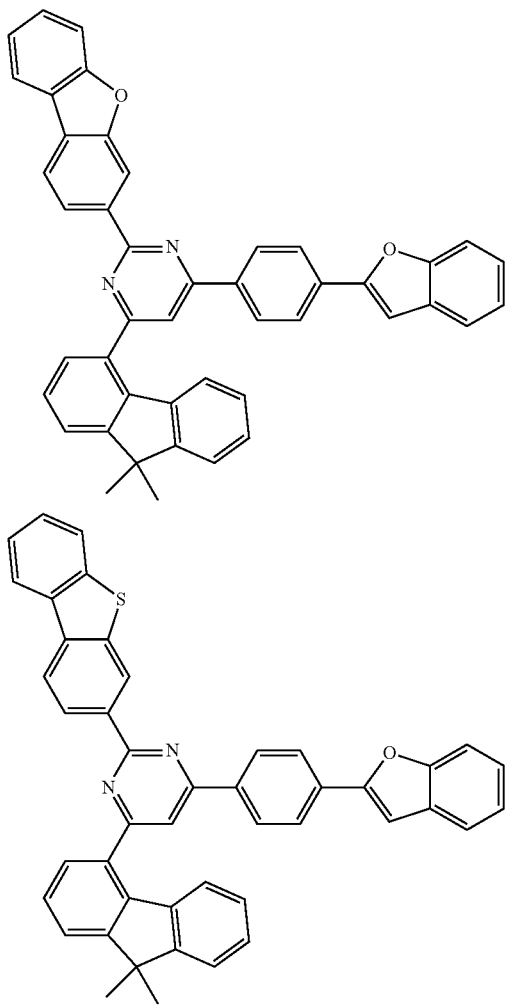
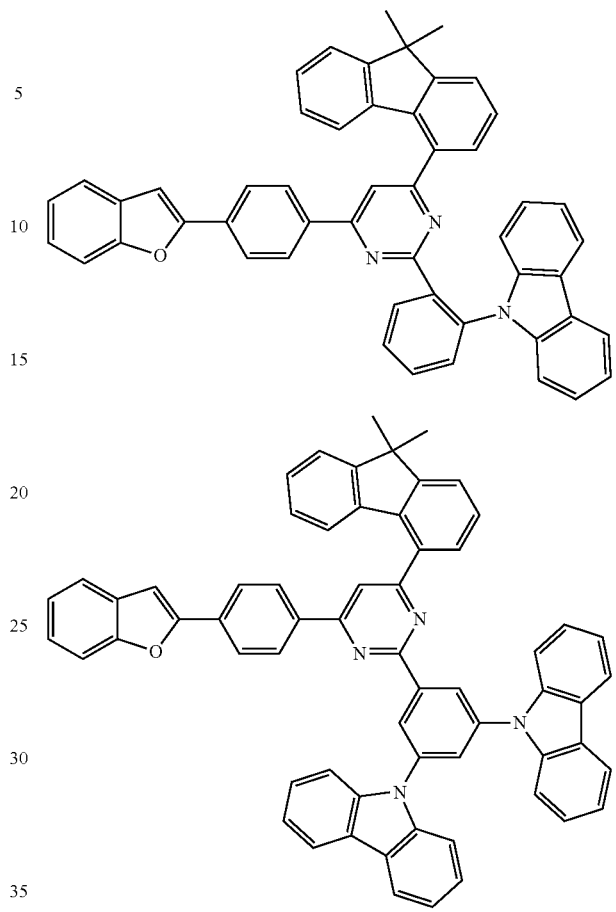
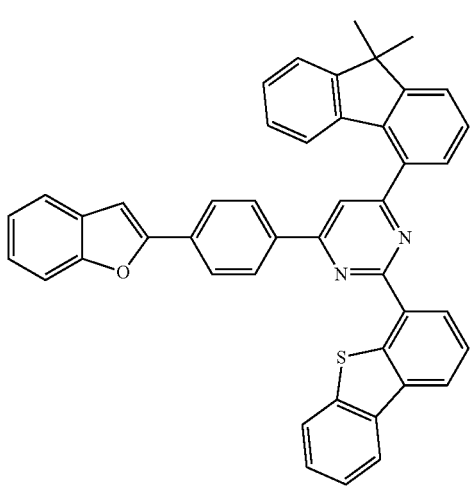
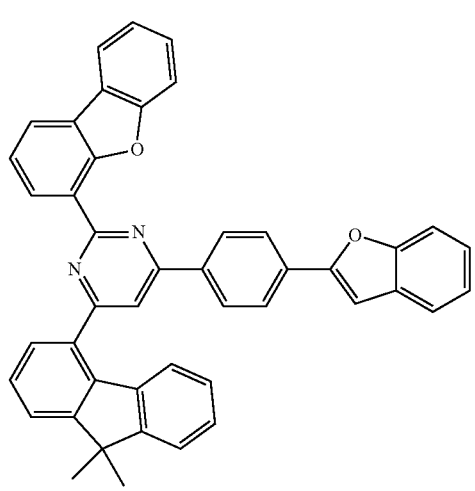

311
-continued
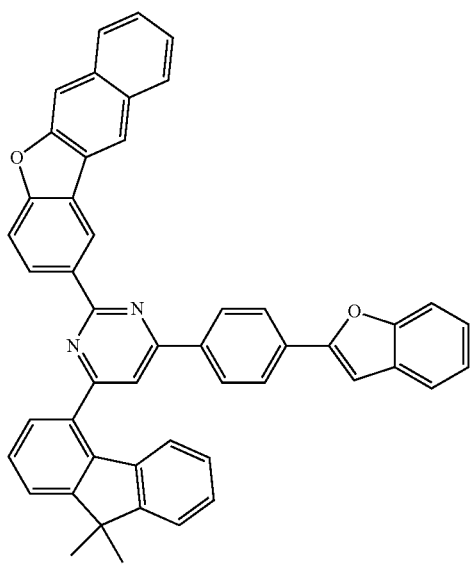
312
-continued
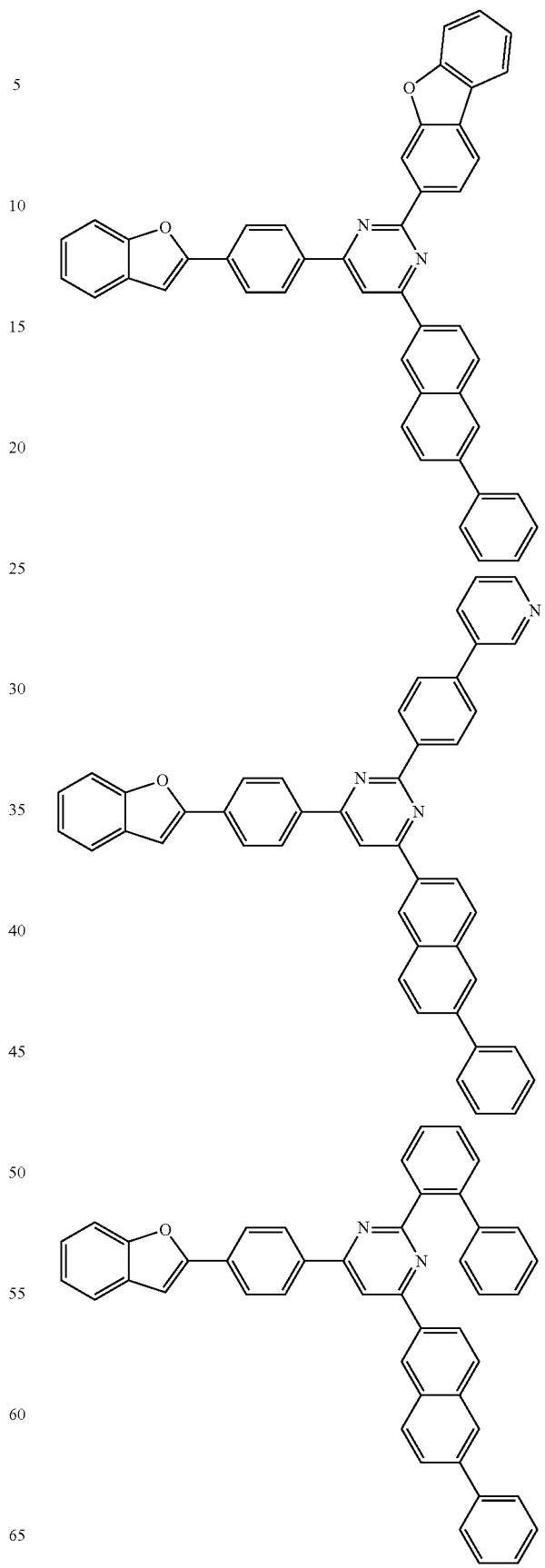
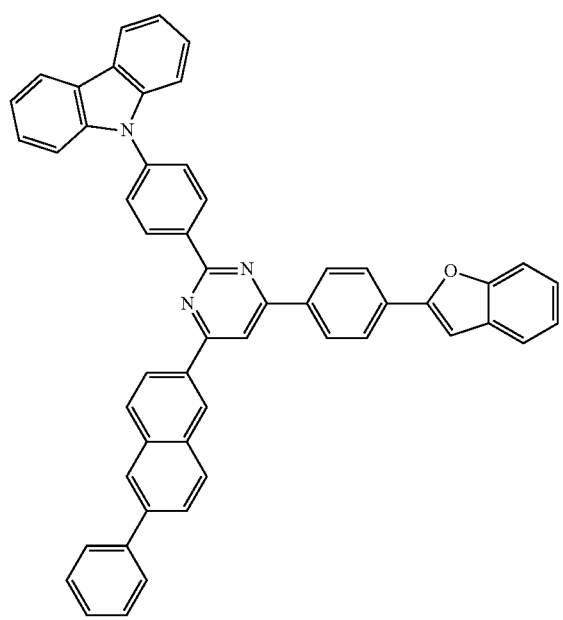

313
-continued
314
-continued
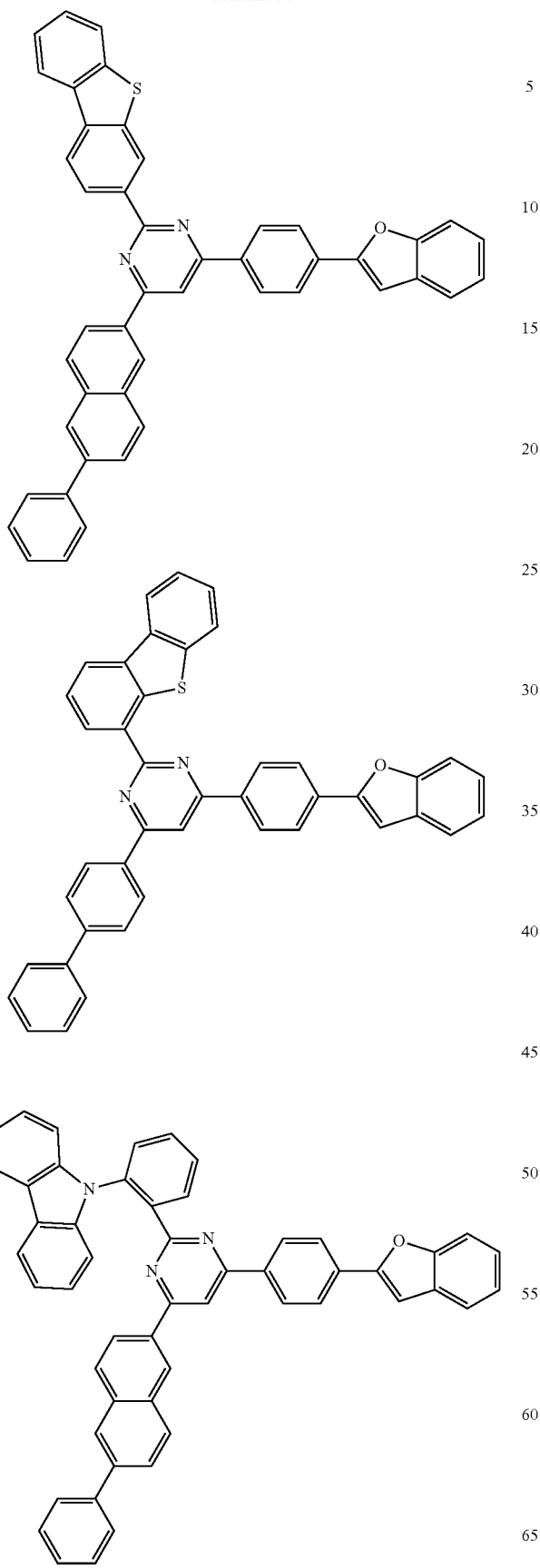
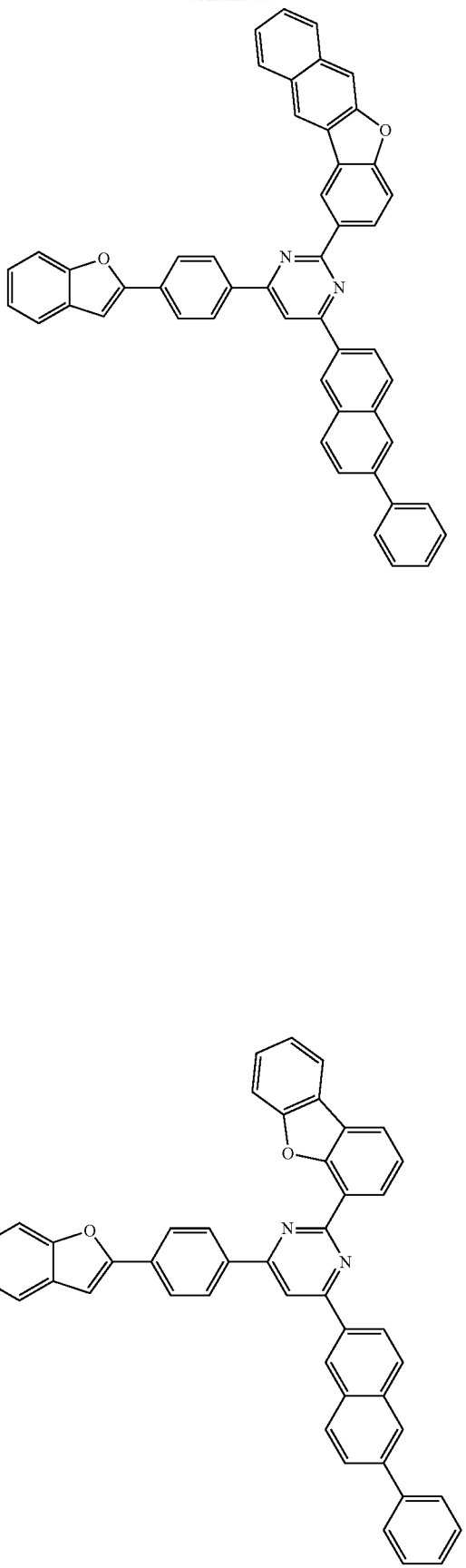

315
-continued
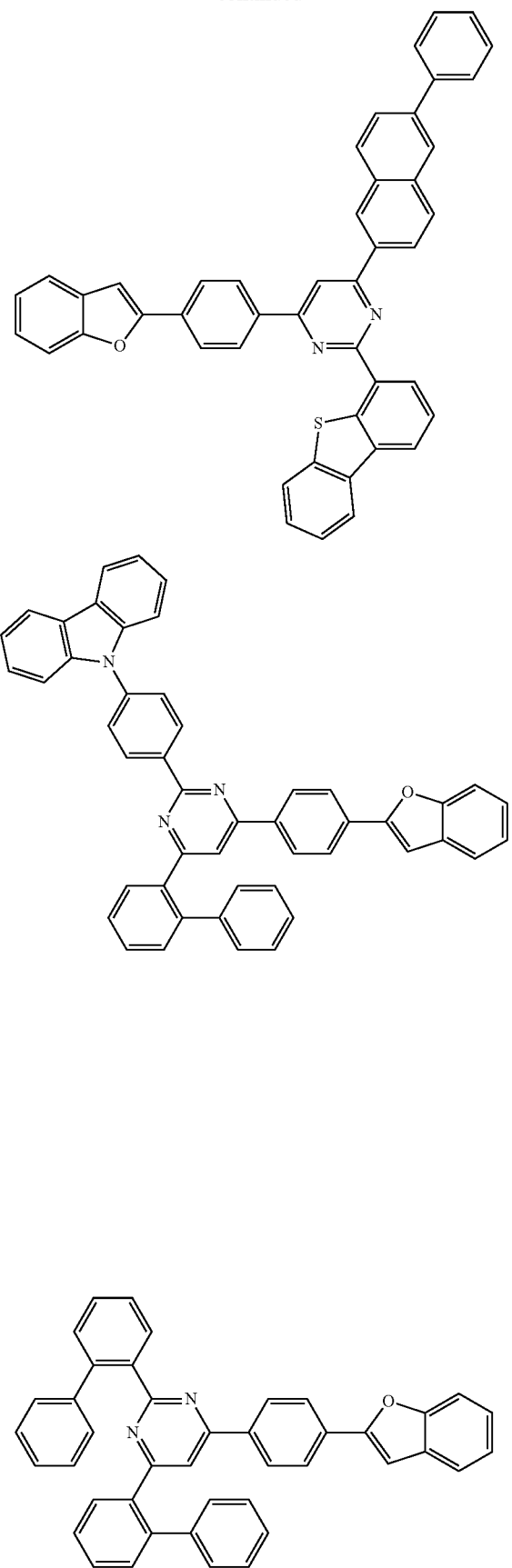
316
-continued
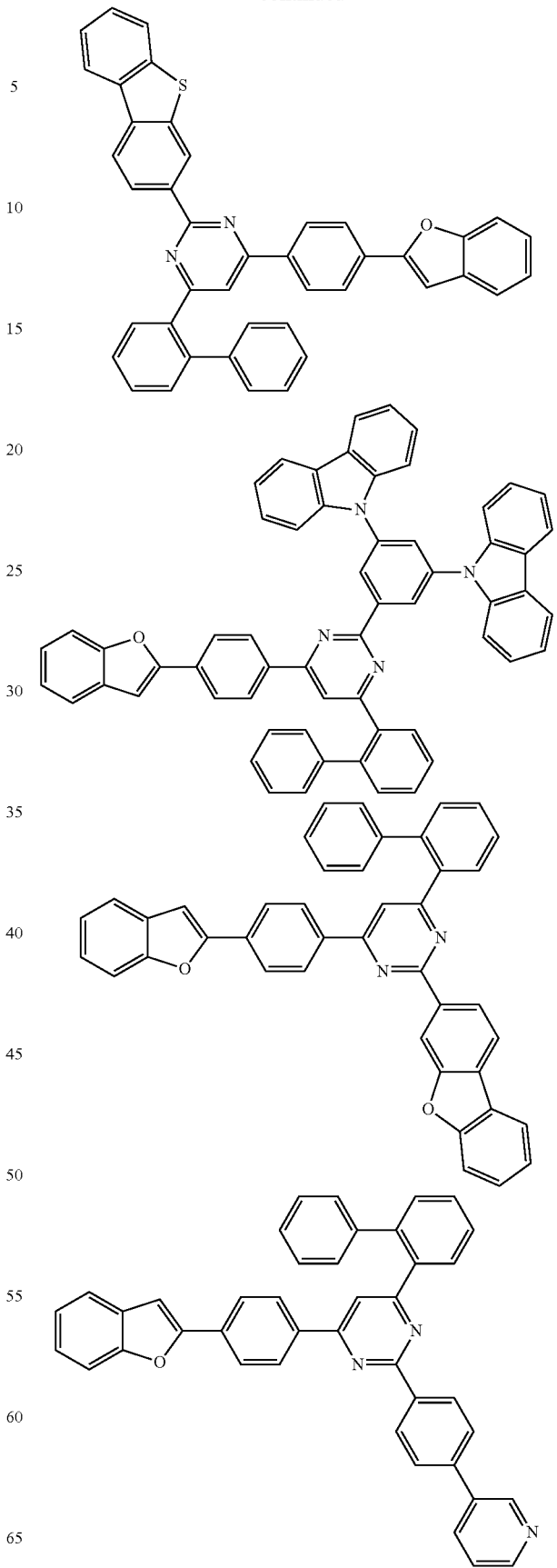

317
-continued
318
-continued
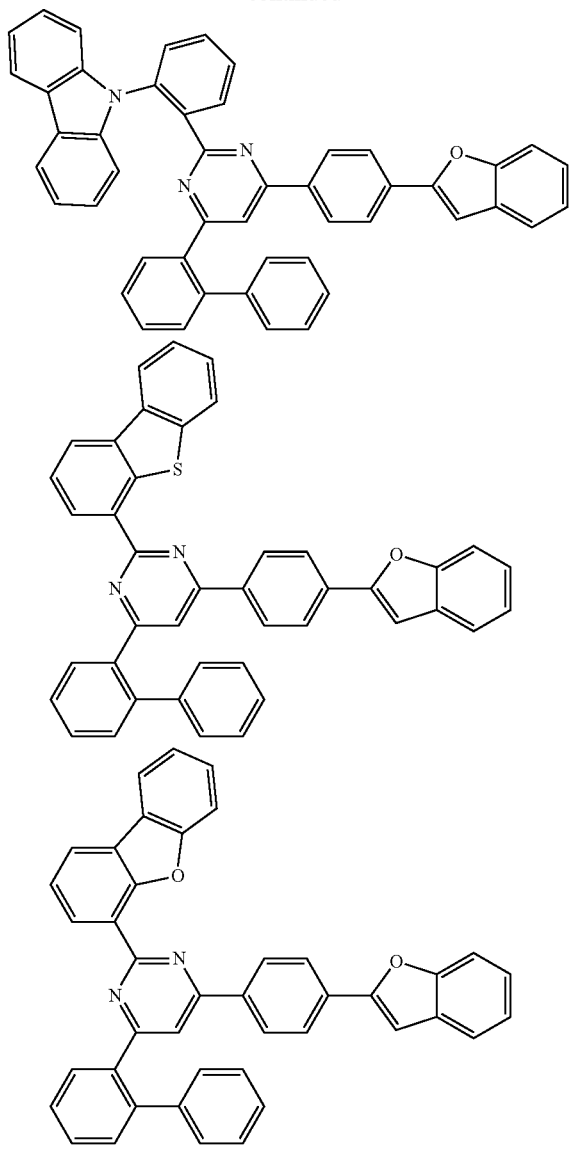
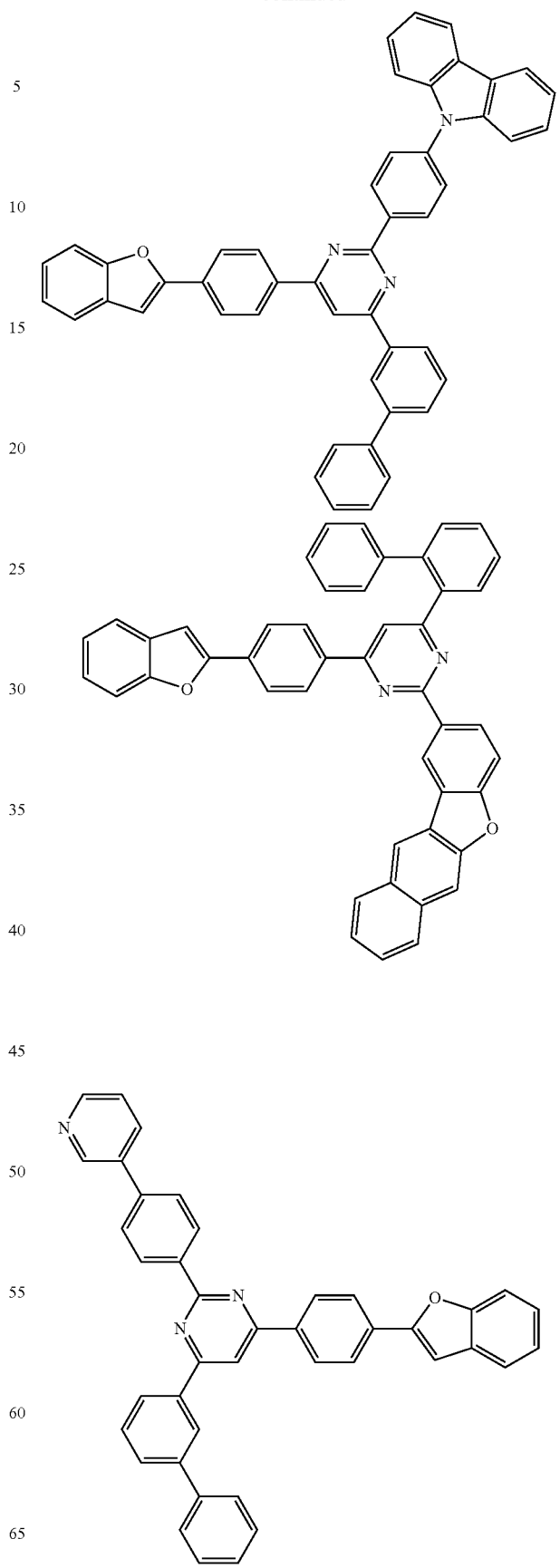

319
-continued
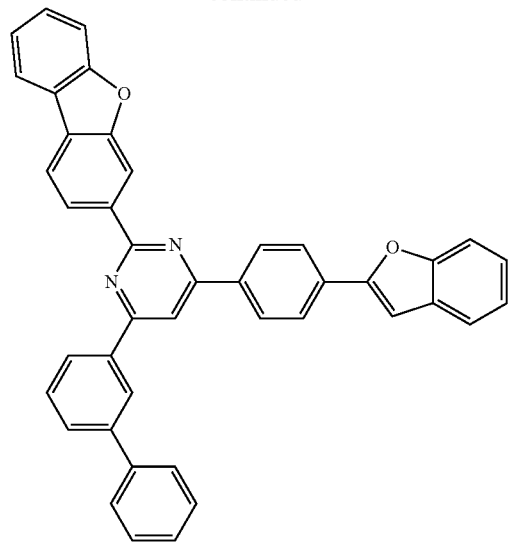
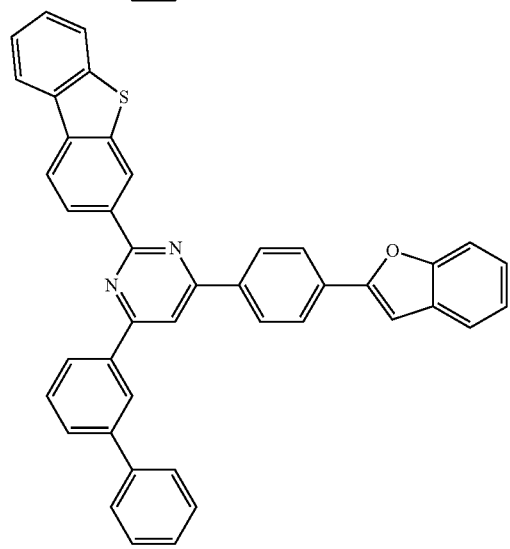
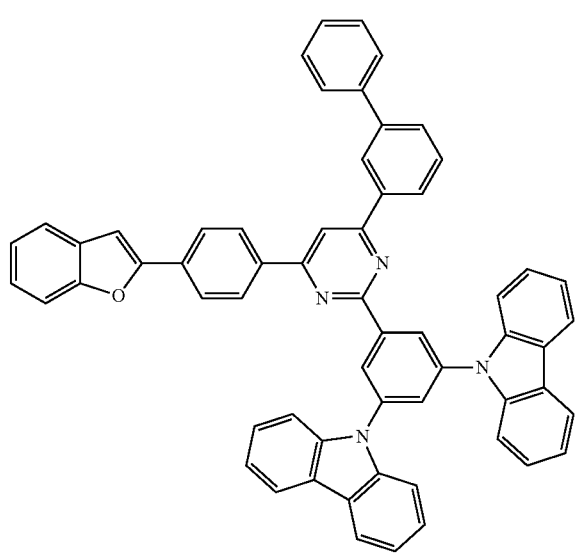
320
-continued
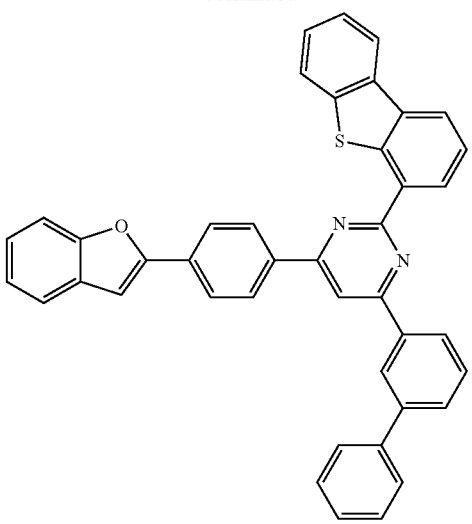
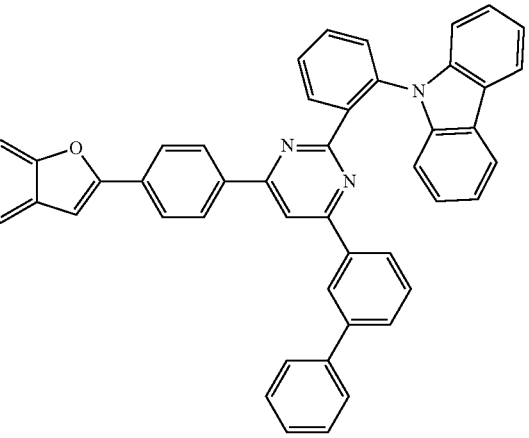
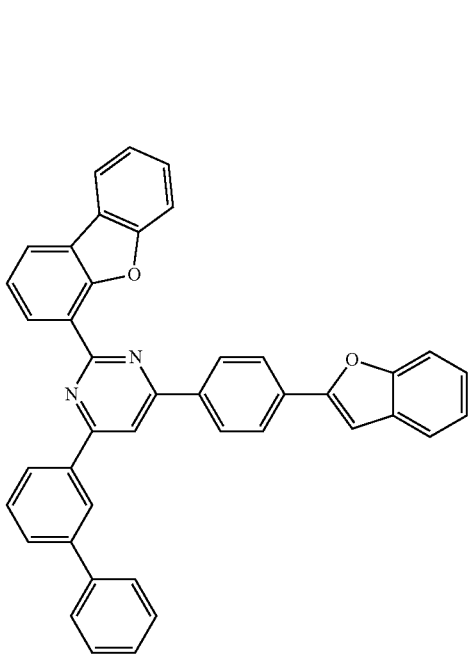

321
-continued
322
-continued
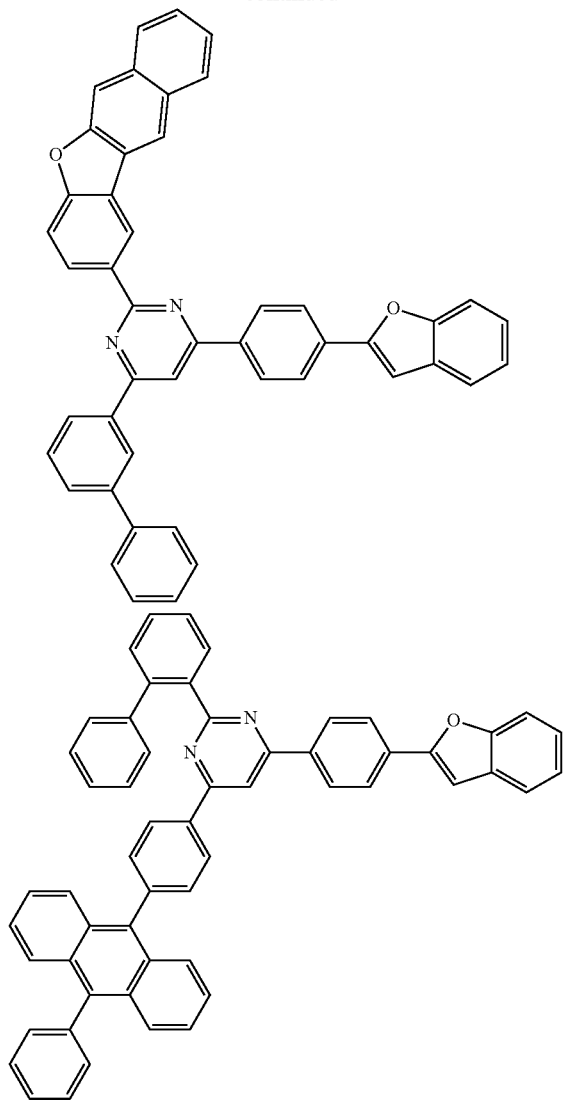
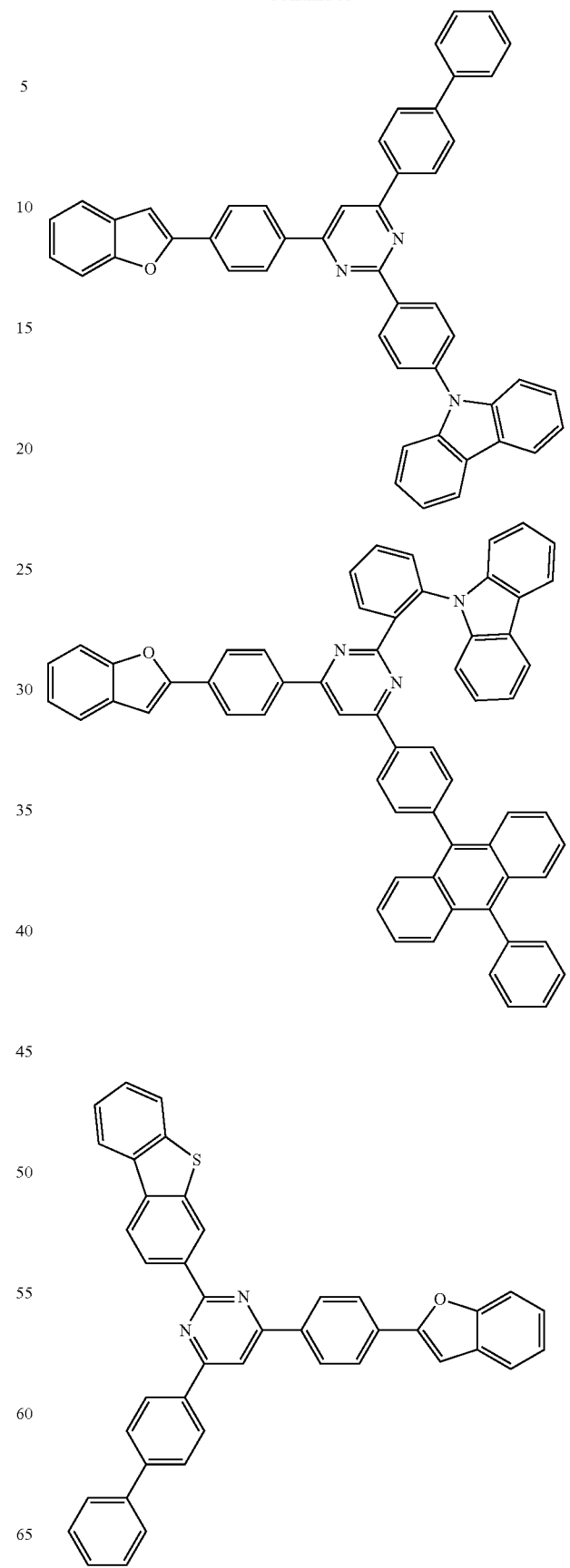

323
-continued
324
-continued
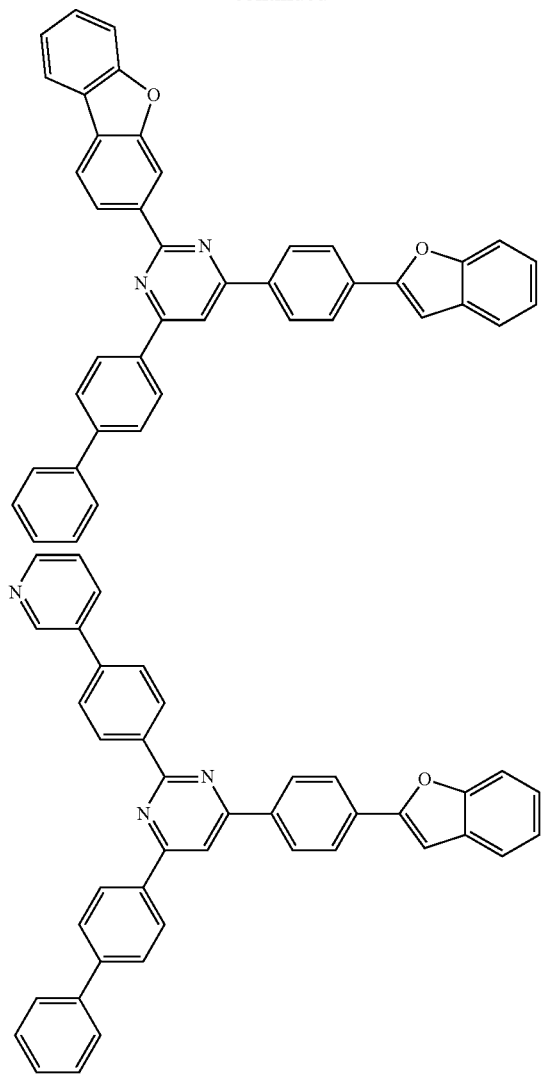
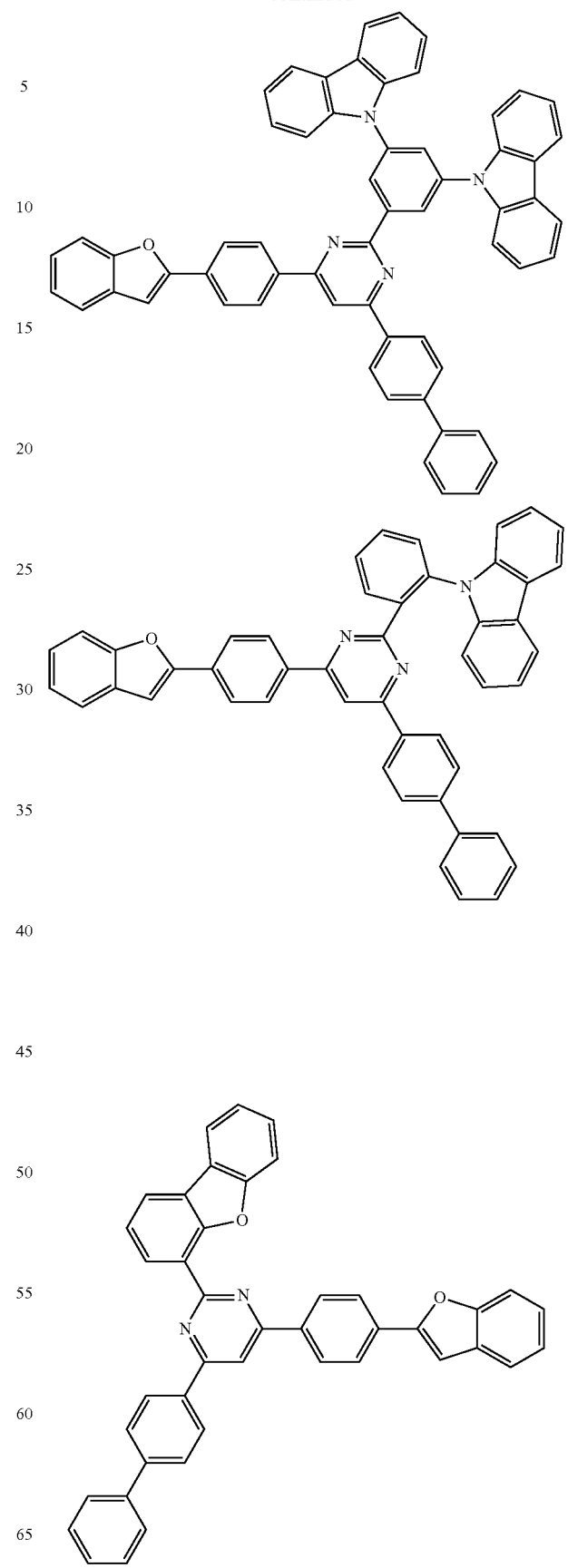

325
-continued
326
-continued
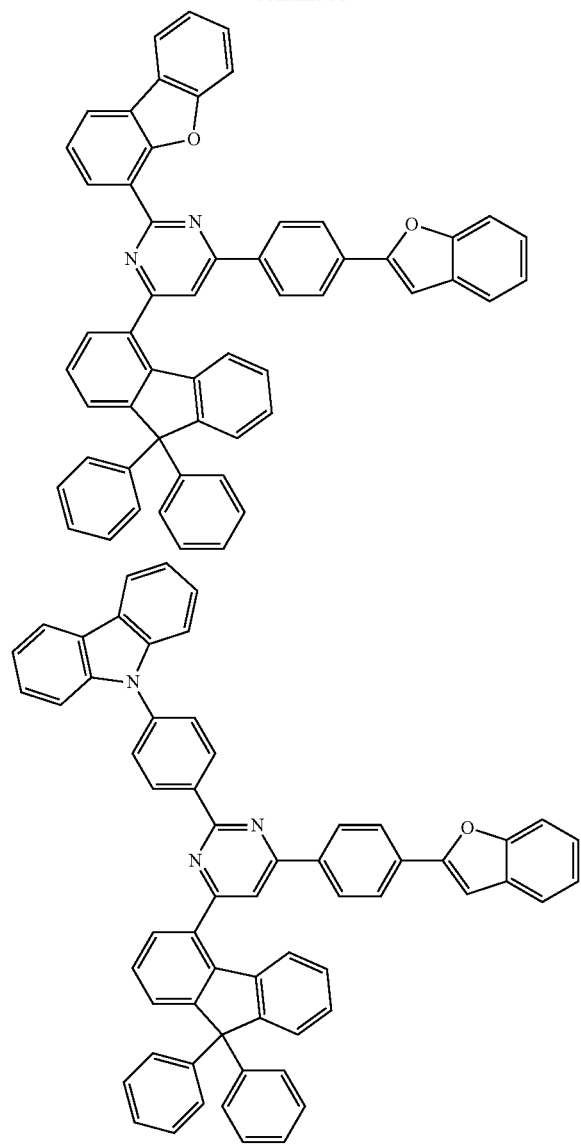
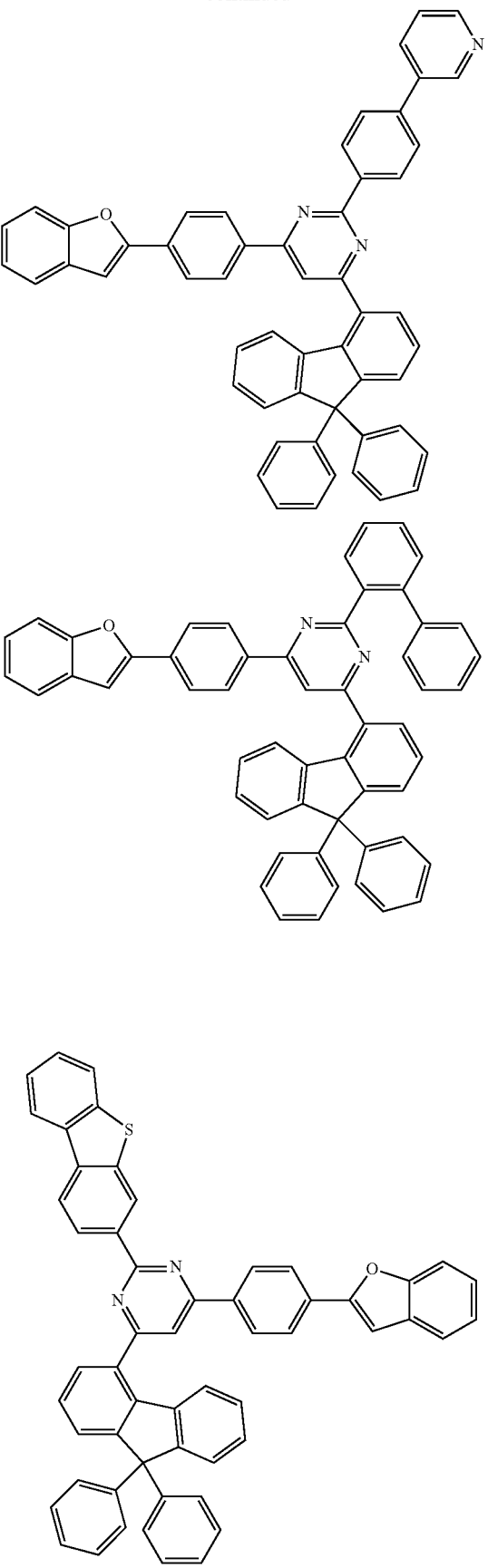

327
-continued
328
-continued
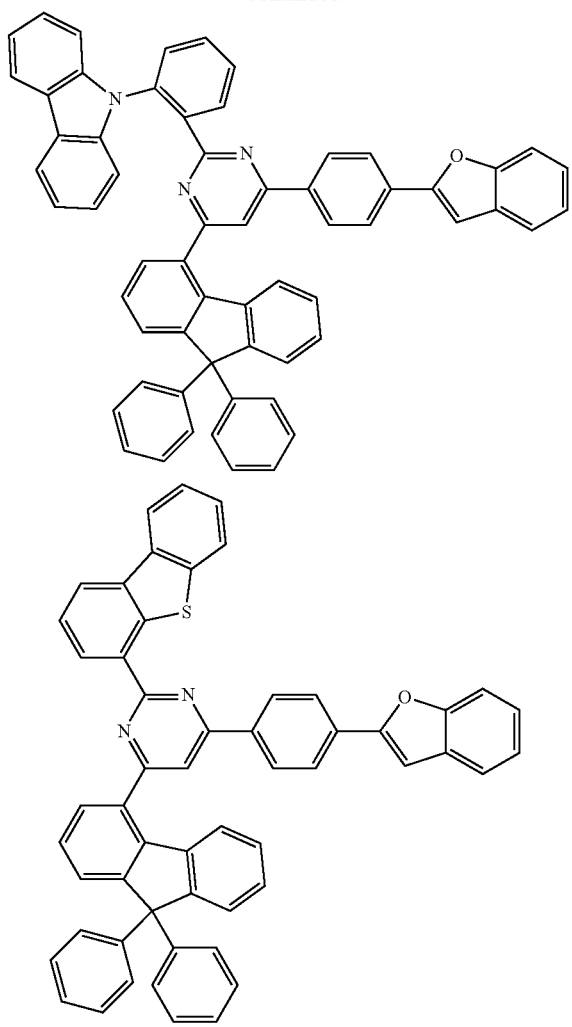
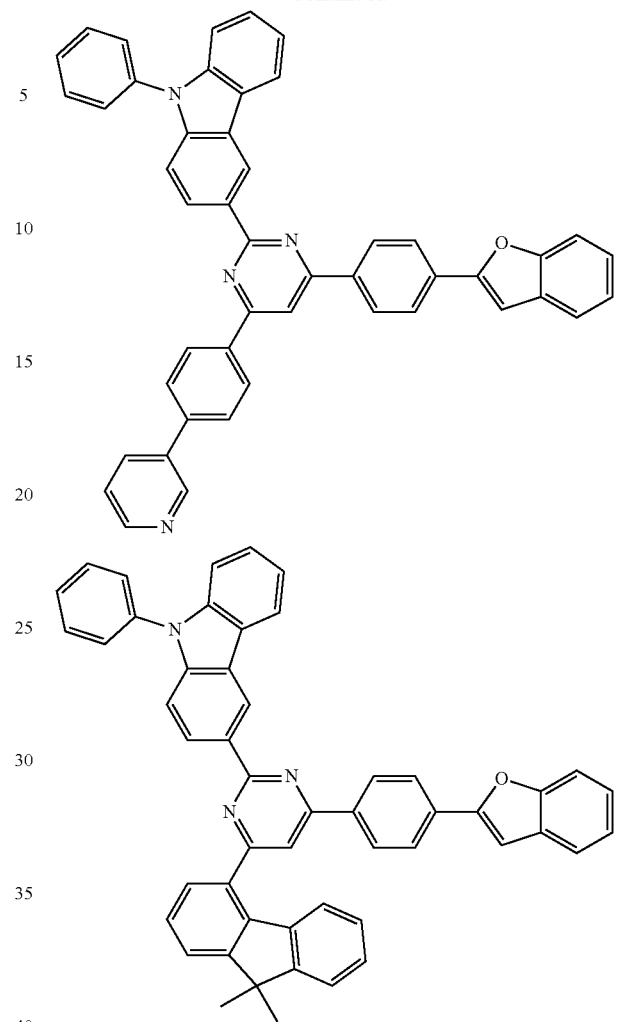
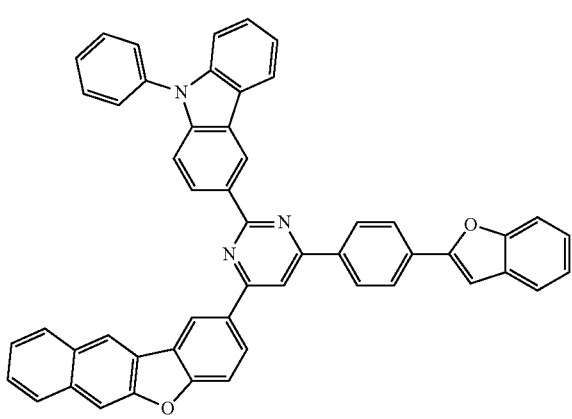
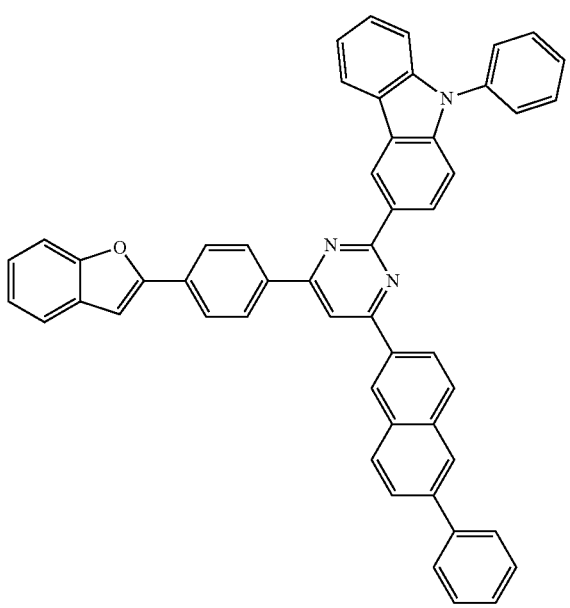

329
-continued

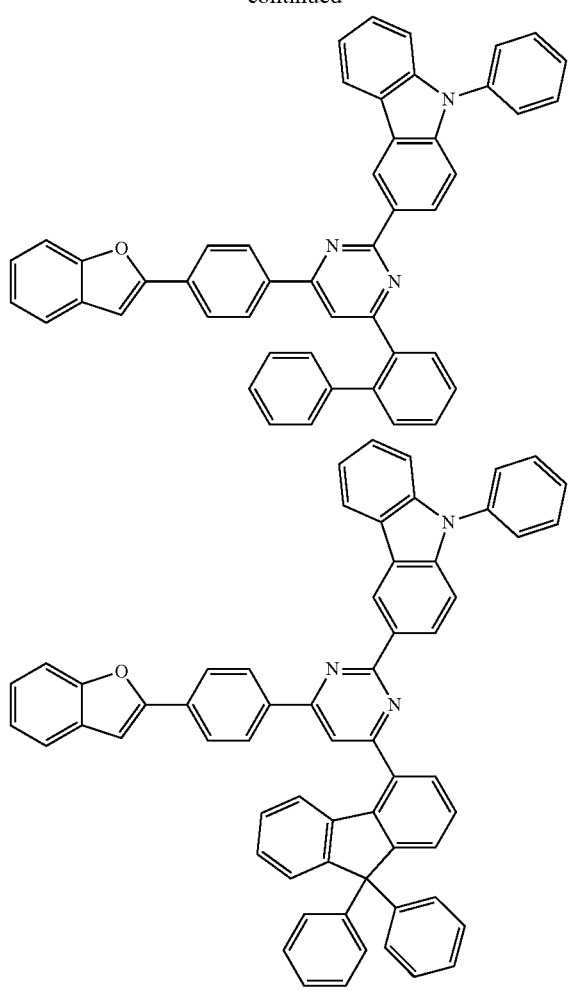

330
-continued

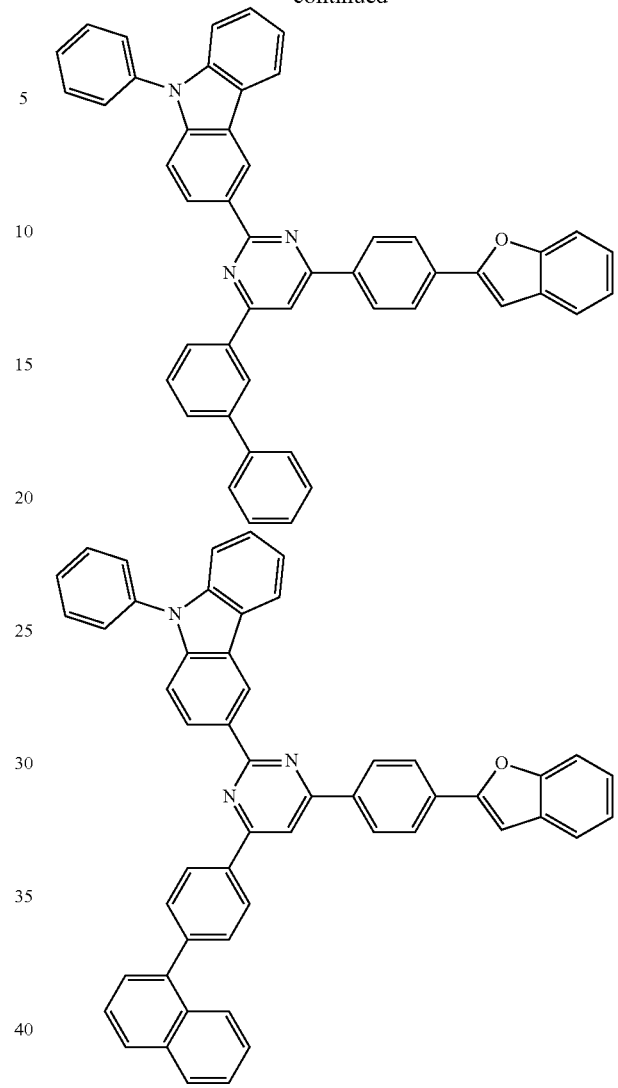

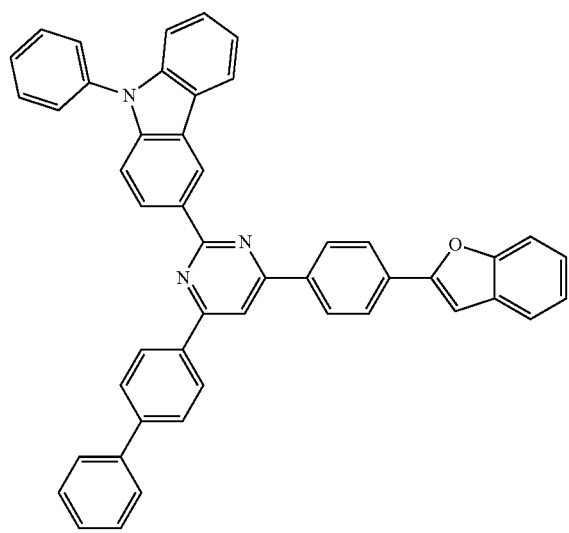

A method of producing the compound (1) is not particularly limited, and those skilled in the art may easily perform production by a method described in the following Examples, or by a method obtained by modifying the method with reference to a known synthesis method.

Material for Organic EL Device

The material for the organic EL device of the present invention contains the compound (1). The content of the compound (1) in the material for the organic EL device of the present invention is not particularly limited, and is, for example, 1% by mass or more (including 100%), preferably 10% by mass or more (including 100%), more preferably 50% by mass or more (including 100%), further preferably 80% by mass or more (including 100%), and particularly preferably 90% by mass or more (including 100%). The material for the organic EL device of the present invention is useful in producing the organic EL device.

Organic EL Device

Next, the organic EL device of the present invention will be described.

The organic EL device includes a cathode, an anode, and organic layers between the cathode and the anode. The organic layers include a light emitting layer, and at least one layer among the organic layers contains the compound (1). Examples of the organic layer containing the compound (1) may include a hole transporting zone (a hole injecting layer, a hole transporting layer, an electron blocking layer, an exciton blocking layer, etc.) provided between the anode and the light emitting layer, the light emitting layer, a space layer, an electron transporting zone (an electron injecting layer, an electron transporting layer, a hole blocking layer, etc.) provided between the cathode and the light emitting layer, and the like, but are not limited thereto. The compound (1) is preferably used as a material for the electron transporting zone or the light emitting layer in a fluorescent or phosphorescent EL device, more preferably as a material for the electron transporting zone, further preferably as a material for the electron transporting layer.

The organic EL device of the present invention may be a fluorescent or phosphorescent light emission-type monochromatic light emitting device or a fluorescent/phosphorescent hybrid-type white light emitting device, and may be a simple type having a single light emitting unit or a tandem type having a plurality of light emitting units. Among these, the fluorescent light emission-type device is preferred. The "light emitting unit" referred to herein refers to a minimum unit that emits light by recombination of injected holes and electrons, which includes organic layers among which at least one layer is a light emitting layer.

For example, as a representative device configuration of the simple type organic EL device, the following device configuration may be exemplified.

(1) Anode/Light Emitting Unit/Cathode

Also, the light emitting unit may be a stacked-type having a plurality of phosphorescent light emitting layers or fluorescent light emitting layers. In this case, a space layer may be provided between the light emitting layers for the purpose of preventing excitons generated in the phosphorescent light emitting layer from diffusing into the fluorescent light emitting layer. Representative layer configurations of the simple type light emitting unit are described below. Layers in parentheses are optional.

- (a) (hole injecting layer/) hole transporting layer/fluorescent light emitting layer (/electron transporting layer/electron injecting layer)
- (b) (hole injecting layer/) hole transporting layer/phosphorescent light emitting layer (/electron transporting layer/electron injecting layer)
- (c) (hole injecting layer/) hole transporting layer/first fluorescent light emitting layer/second fluorescent light emitting layer (/electron transporting layer/electron injecting layer)
- (d) (hole injecting layer/) hole transporting layer/first phosphorescent light emitting layer/second phosphorescent light emitting layer (/electron transporting layer/electron injecting layer)
- (e) (hole injecting layer/) hole transporting layer/phosphorescent light emitting layer/space layer/fluorescent light emitting layer (/electron transporting layer/electron injecting layer)
- (f) (hole injecting layer/) hole transporting layer/first phosphorescent fight emitting layer/second phosphorescent fight emitting layer/space layer/fluorescent fight emitting layer (/electron transporting layer/electron injecting layer)
- (g) (hole injecting layer/) hole transporting layer/first phosphorescent fight emitting layer/space layer/second phosphorescent light emitting layer/space layer/fluorescent fight emitting layer (/electron transporting layer/electron injecting layer)
- (h) (hole injecting layer/) hole transporting layer/phosphorescent light emitting layer/space layer/first fluorescent light emitting layer/second fluorescent light emitting layer (/electron transporting layer/electron injecting layer)
- (i) (hole injecting layer/) hole transporting layer/electron blocking layer/fluorescent light emitting layer (/electron transporting layer/electron injecting layer)
- (j) (hole injecting layer/) hole transporting layer/electron blocking layer/phosphorescent light emitting layer (/electron transporting layer/electron injecting layer)
- (k) (hole injecting layer/) hole transporting layer/exciton blocking layer/fluorescent light emitting layer (/electron transporting layer/electron injecting layer)
- (l) (hole injecting layer/) hole transporting layer/exciton blocking layer/phosphorescent light emitting layer (/electron transporting layer/electron injecting layer)
- (m) (hole injecting layer/) first hole transporting layer/second hole transporting layer/fluorescent light emitting layer (/electron transporting layer/electron injecting layer)
- (n) (hole injecting layer/) first hole transporting layer/second hole transporting layer/phosphorescent light emitting layer (/electron transporting layer/electron injecting layer)
- (o) (hole injecting layer/) first hole transporting layer/second hole transporting layer/fluorescent light emitting layer/first electron transporting layer/second electron transporting layer (/electron injecting layer)
- (p) (hole injecting layer/) first hole transporting layer/second hole transporting layer/phosphorescent light emitting layer/first electron transporting layer/second electron transporting layer (/electron injecting layer)
- (q) (hole injecting layer/) hole transporting layer/fluorescent light emitting layer/hole blocking layer (/electron transporting layer/electron injecting layer)
- (r) (hole injecting layer/) hole transporting layer/phosphorescent fight emitting layer/hole blocking layer (/electron transporting layer/electron injecting layer)
- (s) (hole injecting layer/) hole transporting layer/fluorescent light emitting layer/exciton blocking layer (/electron transporting layer/electron injecting layer)
- (t) (hole injecting layer/) hole transporting layer/phosphorescent light emitting layer/exciton blocking layer (/electron transporting layer/electron injecting layer)

The phosphorescent and fluorescent light emitting layers may emit emission colors different from each other, respectively. Specifically, in the stacked light emitting unit (f), a layer configuration such as (hole injecting layer/) hole transporting layer/first phosphorescent light emitting layer (red light emission)/second phosphorescent light emitting layer (green light emission)/space layer/fluorescent light emitting layer (blue light emission)/electron transporting layer may be exemplified.

An electron blocking layer may be properly provided between each fight emitting layer and the hole transporting layer or the space layer. Also, a hole blocking layer may be properly provided between each light emitting layer and the electron transporting layer. The employment of the electron blocking layer or the hole blocking layer allows to improve the emission efficiency by confining electrons or holes within the light emitting layer and increasing the probability of charge recombination in the light emitting layer.

As a representative device configuration of the tandem type organic EL device, the following device configuration may be exemplified.

(2) Anode/First Light Emitting Unit/Intermediate Layer/Second Light Emitting Unit/Cathode Here, for example, each of the first light emitting unit and second light emitting unit may be independently selected from the above-described light emitting units.

The intermediate layer is also generally referred to as an intermediate electrode, an intermediate conductive layer, a charge generation layer, an electron withdrawing layer, a connecting layer, or an intermediate insulating layer, and a known material configuration may be used, in which electrons are supplied to the first light emitting unit, and holes are supplied to the second light emitting unit.

FIG. 1 is a schematic view illustrating an example of a configuration of the organic EL device of the present invention. The organic EL device 1 includes a substrate 2, an anode 3, a cathode 4, and a light emitting unit 10 disposed between the anode 3 and the cathode 4. The light emitting unit 10 includes a fight emitting layer 5. A hole transporting zone 6 (a hole injecting layer, a hole transporting layer, etc.) is provided between the light emitting layer 5 and the anode 3, and an electron transporting zone 7 (an electron injecting layer, an electron transporting layer, etc.) is provided between the light emitting layer 5 and the cathode 4. Also, an electron blocking layer (not illustrated) may be provided on the anode 3 side of the light emitting layer 5, and a hole blocking layer (not illustrated) may be provided on the cathode 4 side of the light emitting layer 5, respectively. These structure allows to further increase the generation efficiency of excitons in the light emitting layer 5 by confining electrons or holes in the fight emitting layer 5.

Figure 2:
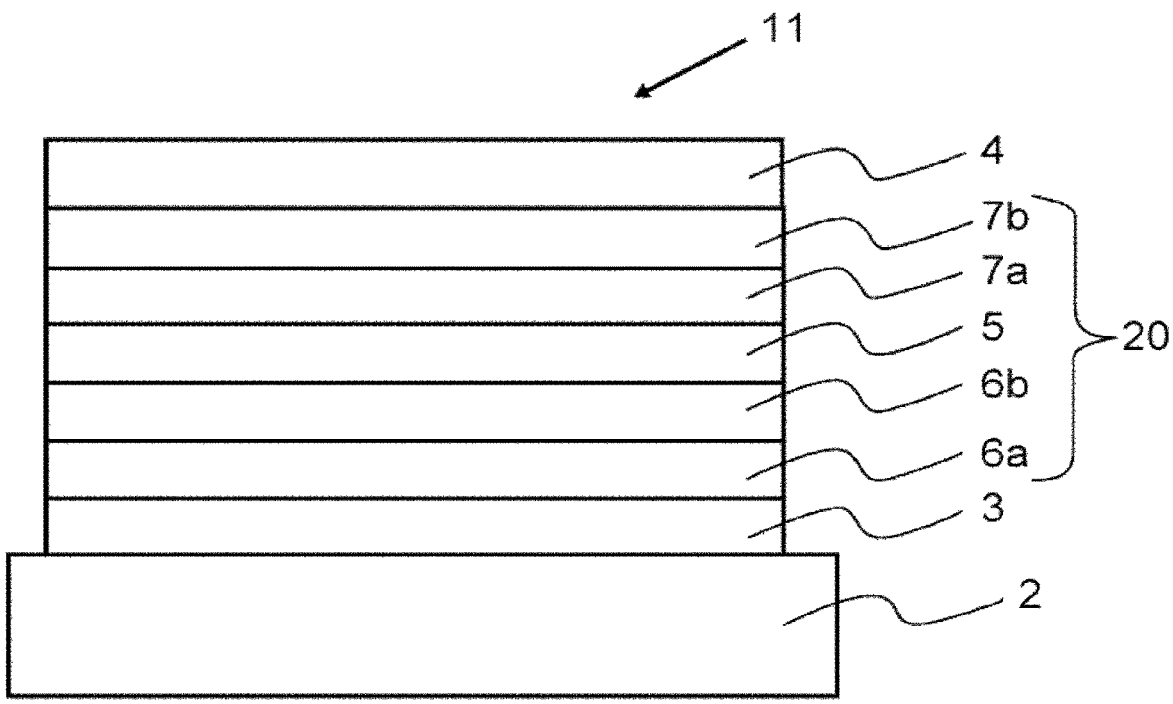
FIG. 2 is a schematic view illustrating another example of a layer configuration of the organic EL device according to the embodiment of the present invention.

FIG. 2 is a schematic view illustrating another configuration of the organic EL device of the present invention. An organic EL device 11 includes the substrate 2, the anode 3, the cathode 4, and a light emitting unit 20 disposed between the anode 3 and the cathode 4. The light emitting unit 20 includes the light emitting layer 5. A hole transporting zone disposed between the anode 3 and the light emitting layer 5 is formed of a first hole transporting layer 6a and a second hole transporting layer 6b. Also, an electron transporting zone disposed between the light emitting layer 5 and the cathode 4 is formed of a first electron transporting layer 7a and a second electron transporting layer 7b.

In the present invention, a host combined with a fluorescent dopant (a fluorescent emitting material) is called a fluorescent host, and a host combined with a phosphorescent dopant is called a phosphorescent host. The fluorescent host and the phosphorescent host are not distinguished from each other merely by their molecular structures. That is, the phosphorescent host means a material that forms a phosphorescent light emitting layer containing a phosphorescent dopant, but does not mean unavailability as a material that forms a fluorescent light emitting layer. The same also applies to the fluorescent host.

Substrate

The substrate is used as a support of the organic EL device. Examples of the substrate include a plate of glass, quartz, and plastic. Also, a flexible substrate may be used. Examples of the flexible substrate include a plastic substrate made of polycarbonate, polyarylate, polyether sulfone, polypropylene, polyester, polyvinyl fluoride, or polyvinyl chloride. Also, an inorganic vapor deposition film may be used.

Anode

It is preferable that a metal, an alloy, an electrically conductive compound, or a mixture thereof which has a high work function (specifically 4.0 eV or more) is used for the anode formed on the substrate. Specific examples thereof include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the metals (for example, titanium nitride) may be exemplified.

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide and 0.1 to 1 wt % of zinc oxide with respect to indium oxide. Besides, the manufacturing may be performed by a vacuum vapor deposition method, a coating method, an inkjet method, a spin coating method, etc.

The hole injecting layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table of the elements).

It is also possible to use elements belonging to Group 1 or 2 of the periodic table of the elements, which are materials having low work functions, that is, alkali metals such as lithium (Li) and cesium (Cs), alkaline earth metals such as magnesium (Mg), calcium (Ca), and strontium (Sr), and alloys containing these (for example, MgAg, AlLi), and rare earth metals such as europium (Eu), and ytterbium (Yb) and alloys containing these. When the anode is formed by using the alkali metals, the alkaline earth metals, and alloys containing these, a vacuum vapor deposition method or a sputtering method may be used. Further, when a silver paste or the like is used, a coating method, an inkjet method, etc. may be used.

Hole Injecting Layer

The hole injecting layer is a layer containing a material having a high hole injection ability (a hole injecting material). The hole injecting materials may be used alone or in combination in the hole injecting layer.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Examples of the hole injecting layer material also include aromatic amine compounds as low molecular organic compounds, such as 4,4',4"-tris(N,N-diphenylamino)triphenylamine (abbreviation: TDATA), 4,4', 4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High molecular compounds (oligomers, dendrimers, polymers, etc.) may also be used. Examples thereof include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). In addition, high molecular compounds to which an acid is added, such as poly(3,4-ethylenedioxythiophene)/poly (styrene sulfonic acid) (PEDOT/PSS), and polyaniline/poly (styrenesulfonic acid) (PAni/PSS), may also be used.

Also, it is also preferable to use an acceptor material such as a hexaazatriphenylene (HAT) compound represented by formula (K), in combination with another compound.

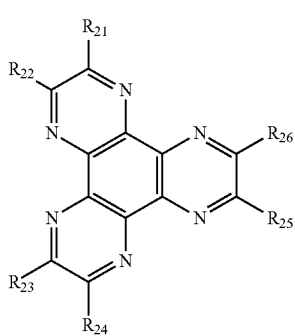

(K)

(In formula (K), each of $R_{21}$ to $R_{26}$ independently represents a cyano group, —$CONH_2$, a carboxy group, or —$COOR_{27}$ ($R_{27}$ represents an alkyl group having 1 to 20 carbon atoms or a cycloalkyl group having 3 to 20 carbon atoms). Also, adjacent two selected from $R_{24}$ and $R_{22}$, $R_{23}$ and $R_{24}$, and $R_{25}$ and $R_{20}$ may be bonded to each other to form a group represented by —CO—O—CO) Examples of $R_{27}$ include a methyl group, an ethyl group, an n-propyl group, an isopropyl group, an n-butyl group, an isobutyl group, a t-butyl group, a cyclopentyl group, and a cyclohexyl group.

Hole Transporting Layer

The hole transporting layer is a layer containing a material having a high hole transporting ability (a hole transporting material). The hole transporting materials may be used alone or in combination. Examples of the hole transporting material include an aromatic amine compound, a carbazole derivative, and an anthracene derivative.

Examples of the aromatic amine compound include 4,4'-bis[N-(1-naphthyl)-N-phenylamino]biphenyl (abbreviation: NPB) or N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TD ATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). These aromatic amine compounds have a hole mobility of $10^{-6}$ cm$^2$/Vs or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA). Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

Examples thereof also include high molecular compounds such as poly(N-vinylcarbazole) (abbreviation: PVK) or poly (4-vinyltriphenylamine) (abbreviation: PVTPA).

Meanwhile, compounds other than the above may also be used as long as they are compounds high in the hole transporting ability rather than in the electron transporting ability.

The hole transporting layer may have a single-layer structure, or a multi-layer structure including two or more layers. For example, the hole transporting layer may have a two-layer structure including a first hole transporting layer (anode side) and a second hole transporting layer (cathode side).

Dopant Material of Light Emitting Layer

The light emitting layer is a layer containing a material having a high light emitting property (a dopant material), and various materials may be used. For example, a fluorescent emitting material or a phosphorescent emitting material may be used as the dopant material. The fluorescent emitting material is a compound that emits light from a singlet excited state, and the phosphorescent emitting material is a compound that emits from a light triplet excited state.

Examples of a blue-based fluorescent emitting material that may be used for the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

Examples of a green-based fluorescent emitting material that may be used for the light emitting layer include an aromatic amine derivative. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylene diamine (abbreviation: 2DPABPhA), N-[9,10-bis(1,1'-biphenyl-2-yl)]-N-[4-(9H-carbazole-9-yl)phenyl]N-phenylanthracene-2-amine (abbreviation: 2YGABPhA), and N,N,9-triphenylanthracene-9-amine (abbreviation: DPhAPhA).

Examples of a red-based fluorescent emitting material that may be used for the light emitting layer include a tetracene derivative and a diamine derivative. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

Examples of a blue-based phosphorescent emitting material that may be used for the light emitting layer include a metal complex such as an iridium complex, an osmium complex, and a platinum complex. Specific examples thereof include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium (III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III)acetylacetonate (abbreviation: FIracac).

Examples of a green-based phosphorescent emitting material that may be used for the light emitting layer include an iridium complex. Examples thereof include tris(2-phenylpyridinato-N,C2')iridium(III) (abbreviation: Ir(ppy)3), bis(2-phenylpyridinato-N,C2')iridium(III)acetylacetonate (abbreviation: Ir(ppy)2(acac)), bis(1,2-diphenyl-1H-benzoimidazolato)iridium(III)acetylacetonate (abbreviation: Ir(pbi)2(acac)), and bis(benzo[h]quinolinato)iridium(III) acetylacetonate (abbreviation: Ir(bzq)2(acac)).

Examples of a red-based phosphorescent emitting material that may be used for the light emitting layer include a metal complex such as an iridium complex, a platinum complex, a terbium complex, and a europium complex. Specific examples thereof include organic metal complexes such as bis[2-(2'-benzo[4,5a]thienyl)pyridinato-N,C3'] iridium(III)acetylacetonate (abbreviation: Ir(btp)2(acac)), bis(1-phenylisoquinolinato-N,C2')iridium(III)acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrinplatinum(II) (abbreviation: PtOEP).

Also, rare earth metal complexes such as tris(acetylacetonate) (monophenanthrohne)terbium(III) (abbreviation: Tb(acac)3(Phen)), tris(1,3-diphenyl-1,3-propandionato) (monophenanthrohne)europium(III) (abbreviation: Eu(DBM)3(Phen)), and tris[1-(2-thenoyl)-3,3,3-trifluoroacetonate](monophenanthroline)europium(III) (abbreviation: Eu(TTA)3(Phen)) emit light from rare earth metal ions (electron transition between different multiplicities), and thus may be used as the phosphorescent emitting material.

Host Material of Light Emitting Layer

The light emitting layer may have a configuration in which the above-described dopant material is dispersed in another material (a host material). The host material is preferably a material that has a higher lowest unoccupied orbital level (LUMO level) and a lower highest occupied orbital level (HOMO level) than the dopant material.

Examples of the host material include:
(1) a metal complex such as an aluminum complex, a beryllium complex, or a zinc complex,
(2) a heterocyclic compound such as an oxadiazole derivative, a benzoimidazole derivative, or a phenanthroline derivative,
(3) a fused aromatic compound such as a carbazole derivative, an anthracene derivative, a phenanthrene derivative, a pyrene derivative, or a chrysene derivative, or
(4) an aromatic amine compound such as a triarylamine derivative or a fused polycyclic aromatic amine derivative.

For example, metal complexes such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc (II) (abbreviation: Znq), bis[2-(2-benzoxazolyl)phenolato] zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzoimidazole) (abbreviation: TPBI), and bathophenanthroline (abbreviation: BPhen), bathocuproine (abbreviation: BCP); fused aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5'-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl) tripyrene (abbreviation: TPB3), 9,10-diphenylanthracene (abbreviation: DPAnth), and 6,12-dimethoxy-5,11-diphenylchrysene; and aromatic amine compounds such as N,N-diphenyl-9-[4-(10-phenyl-9-anthryl)phenyl]-9H-carbazole-3-amine (abbreviation: CzA1PA), 4-(10-phenyl-9-anthryl) triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis [N-(1 naphthyl)-N-phenylamino]biphenyl (abbreviation: NPB or crNPD), N,N'-bis(3-methylphenyl)-N,N'-diphenyl-[1,1'-biphenyl]-4,4'diamine (abbreviation: TPD), 4,4'bis[N-(9,9-dimethylfluorene-2-yl)-N-phenylamino]biphenyl (abbreviation: DFLDPBi), and 4,4'-bis[N-(spiro-9,9'bifluorene-2-yl)-N-phenylamino]biphenyl (abbreviation: BSPB) may be used. A plurality of types of host materials may be used.

In particular, in the case of a blue fluorescent device, it is preferable to use the following anthracene compounds as the host material.

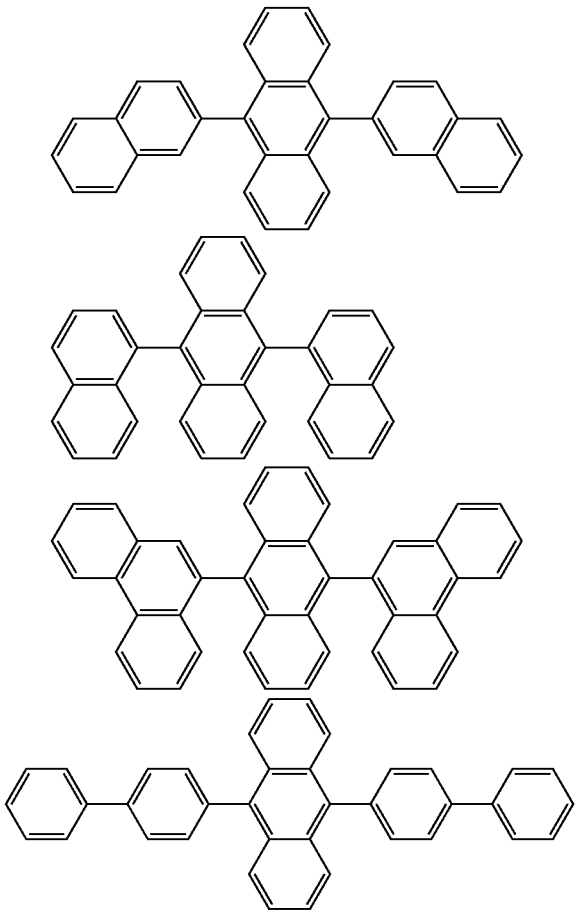

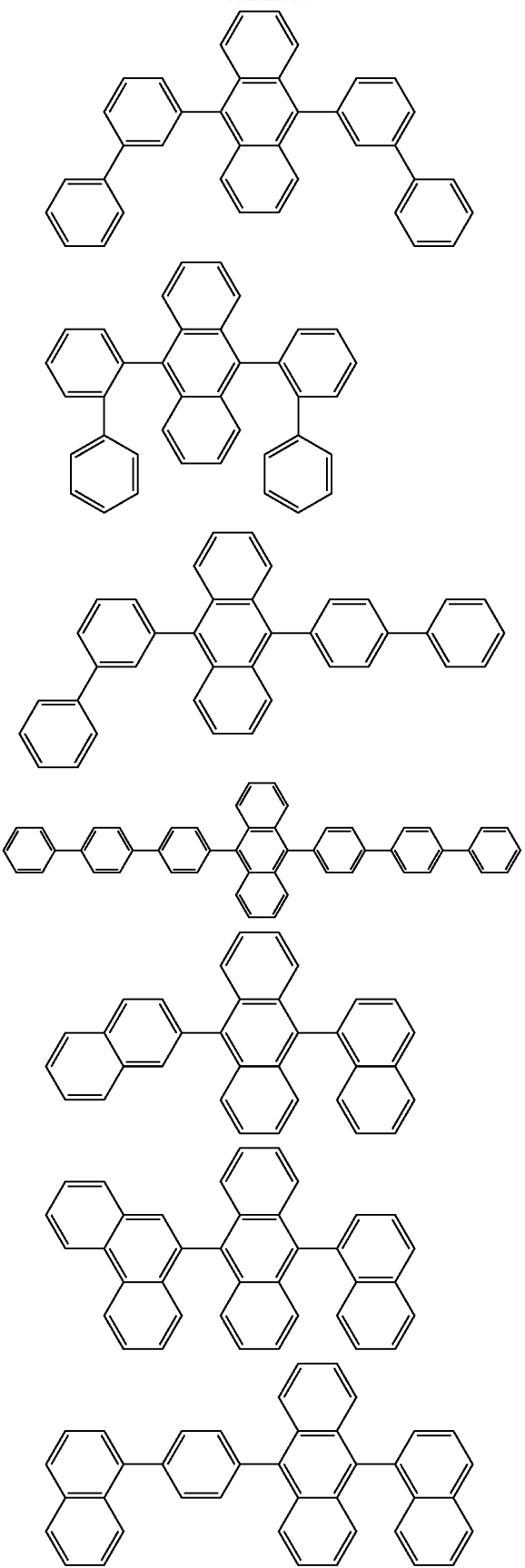

341
-continued
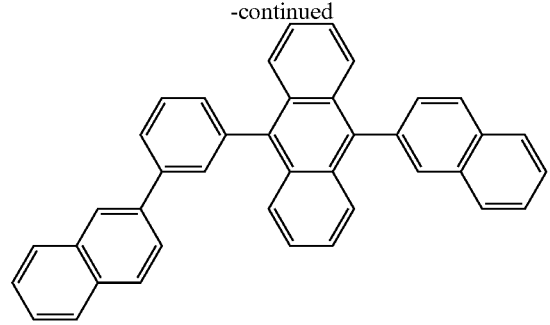
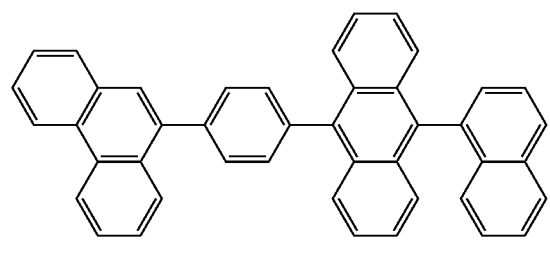
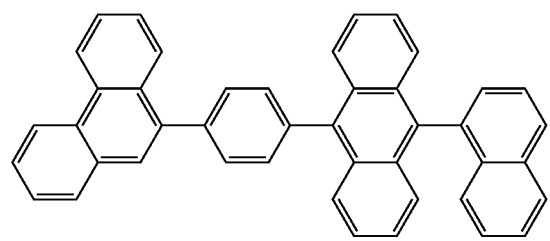
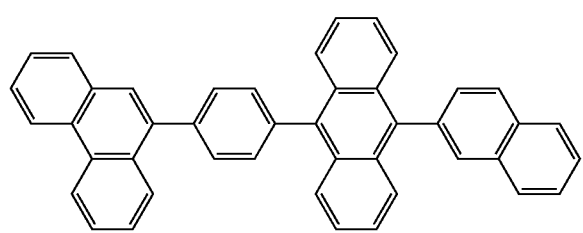
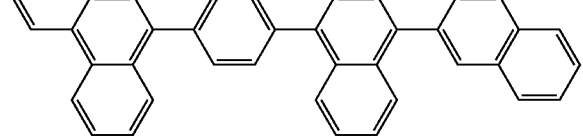
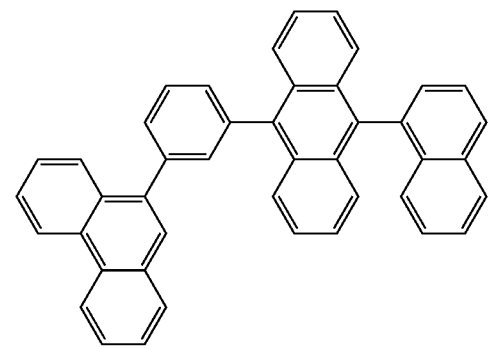
342
-continued
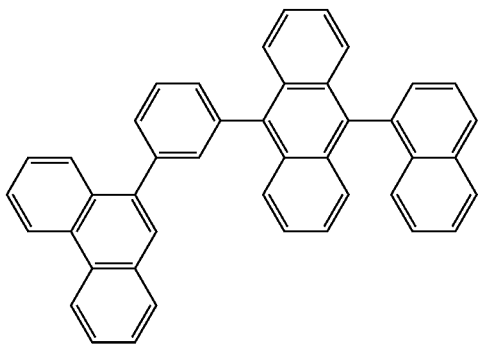
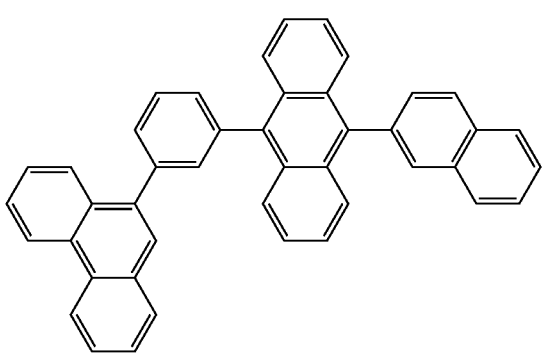
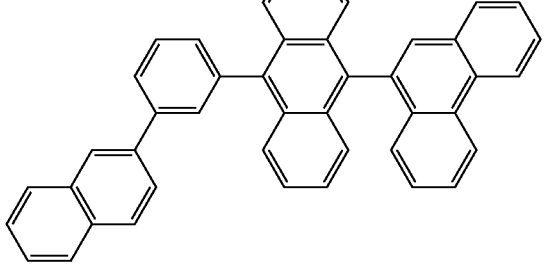
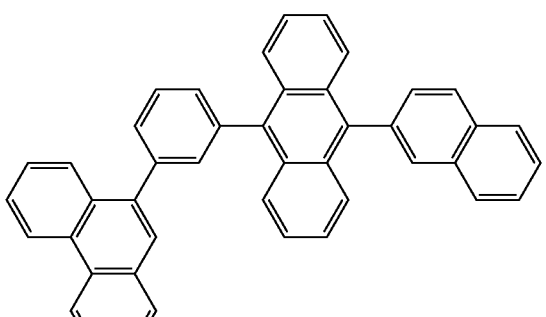
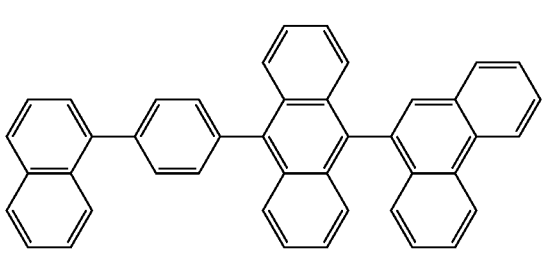

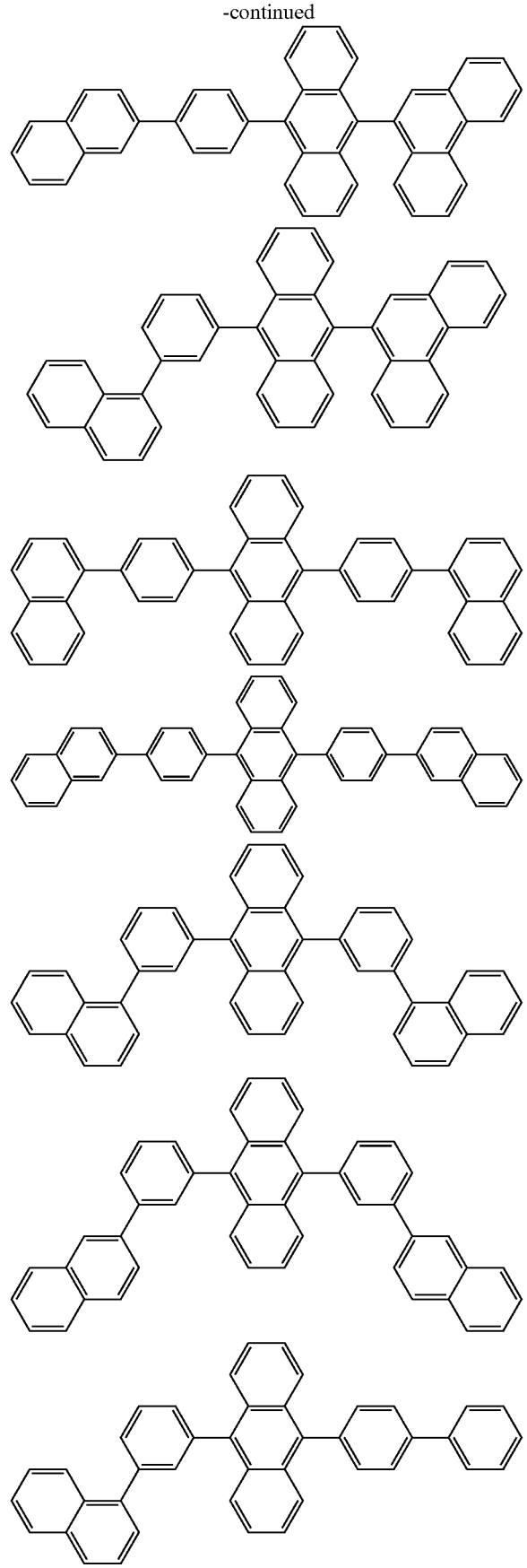
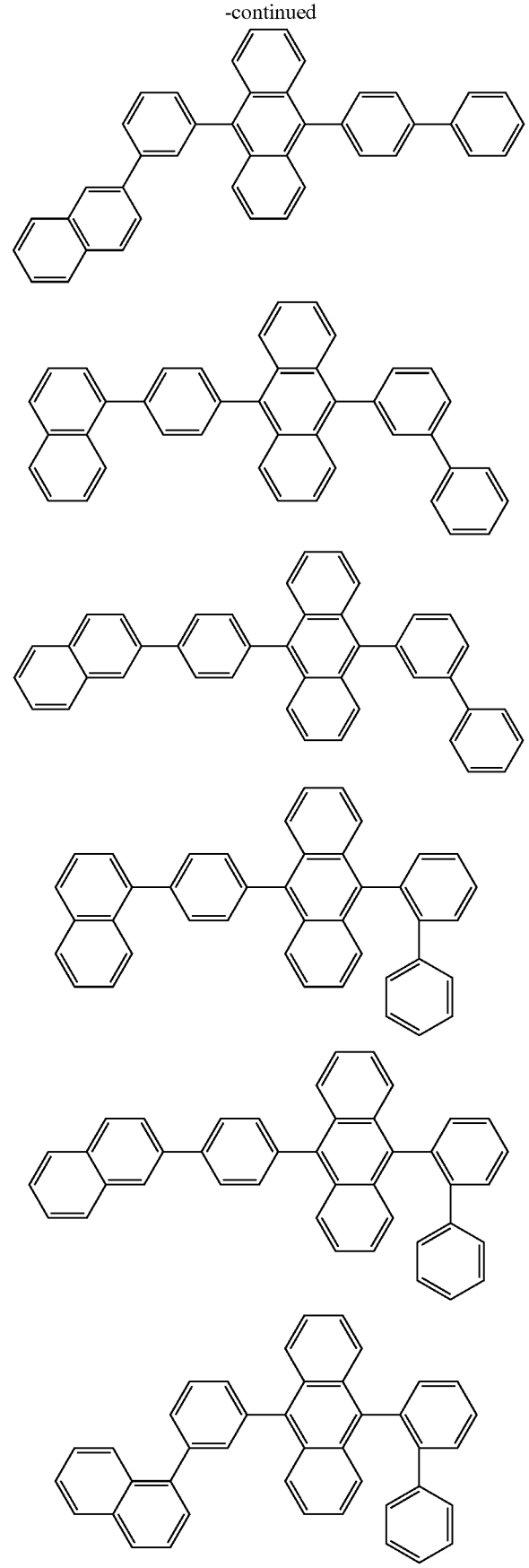

345
-continued
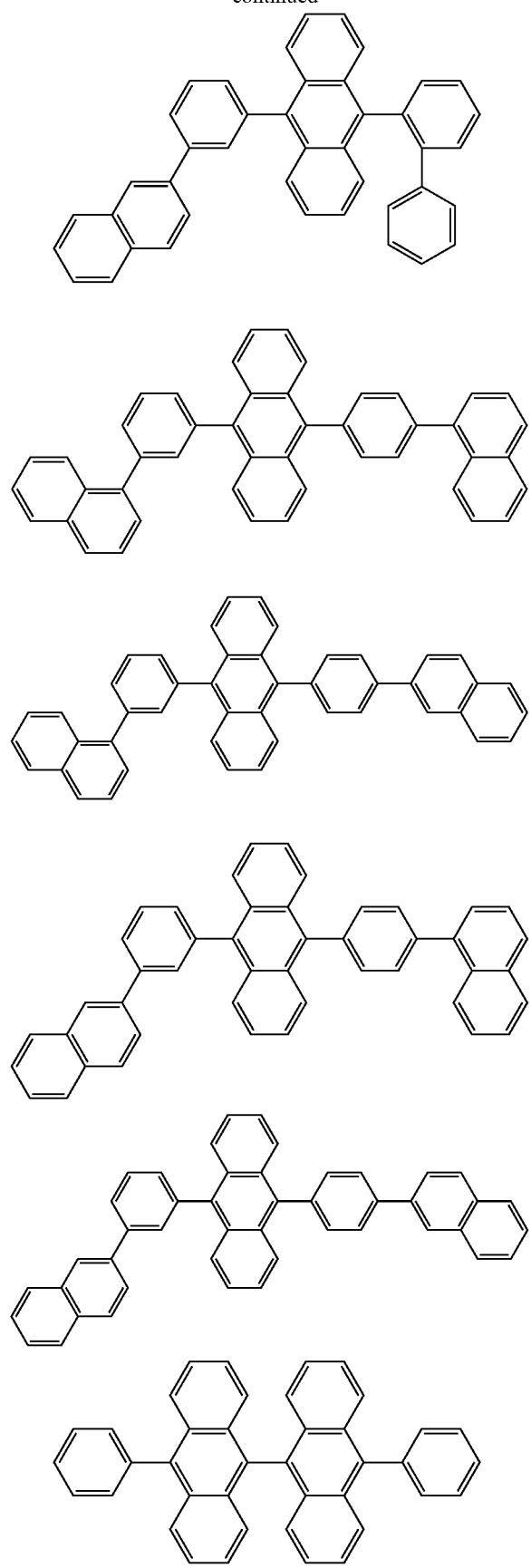
346
-continued
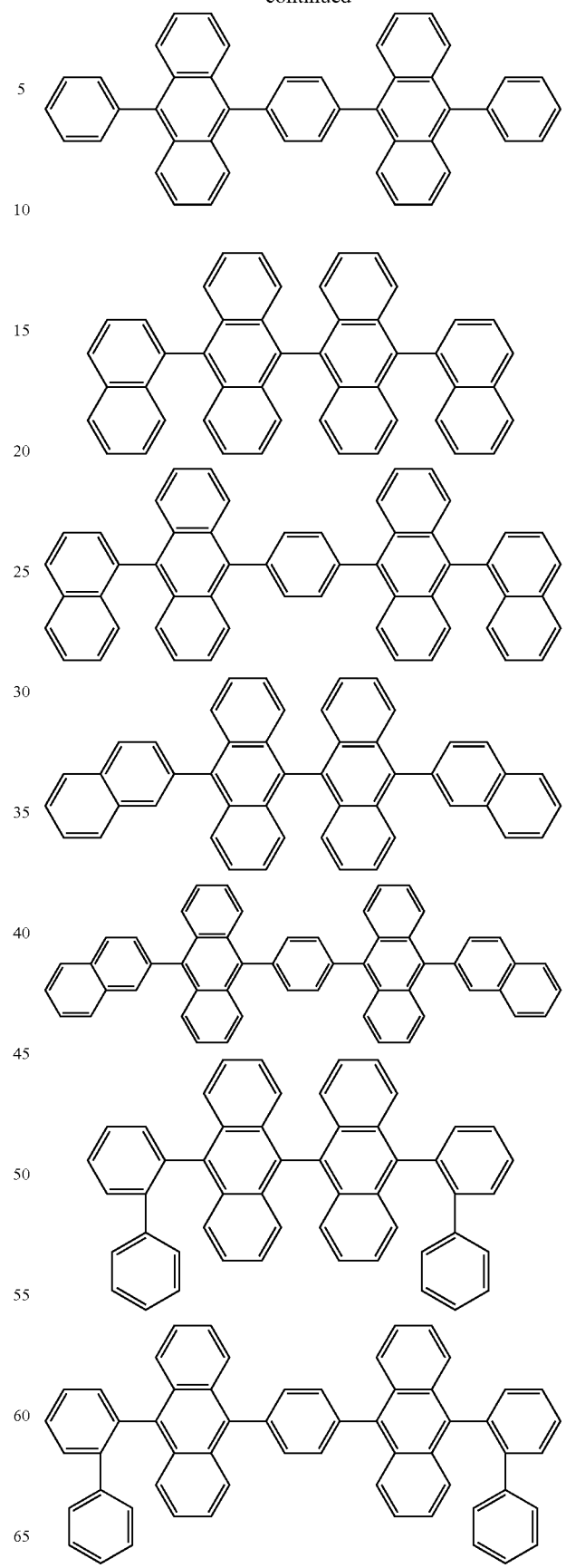

347
-continued
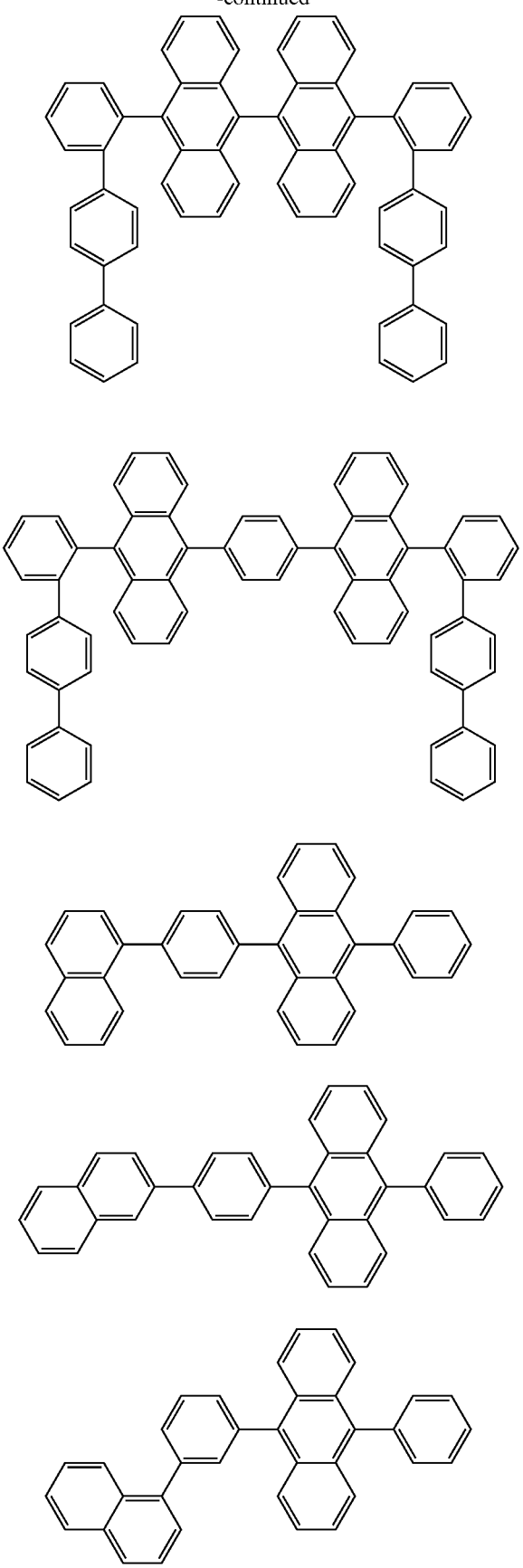
348
-continued
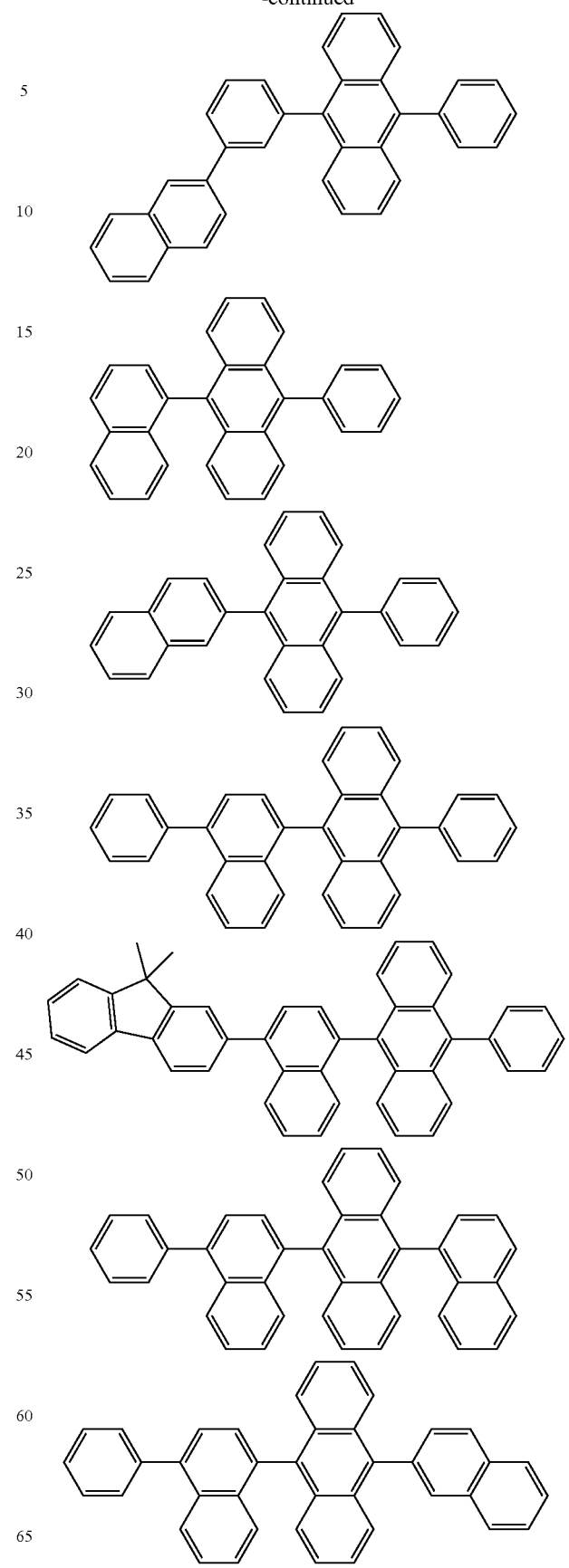

349
-continued
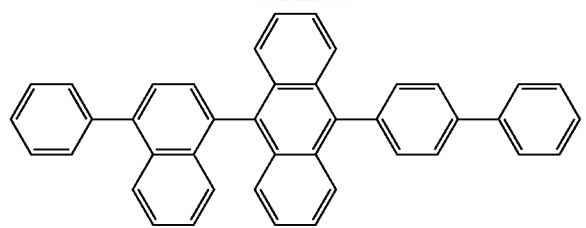
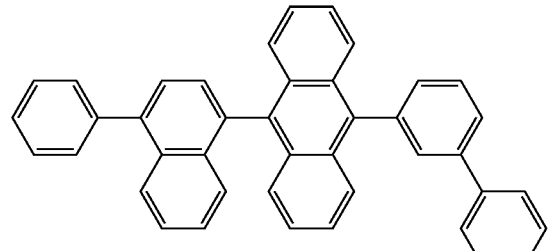
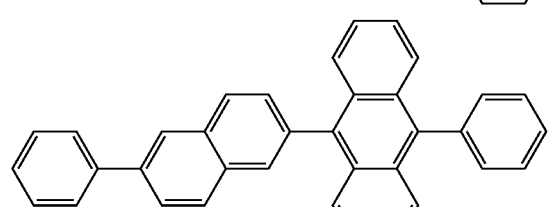
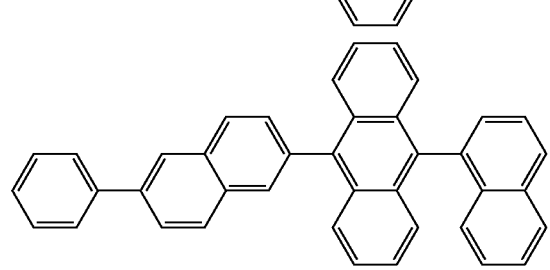
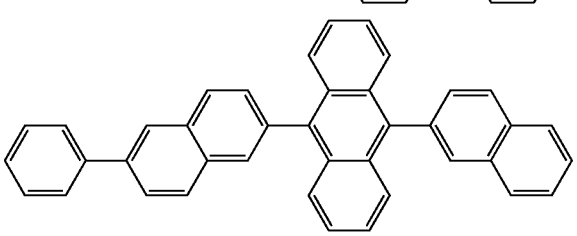
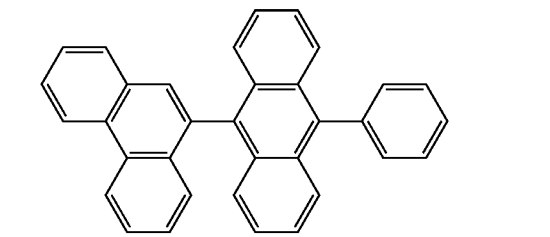
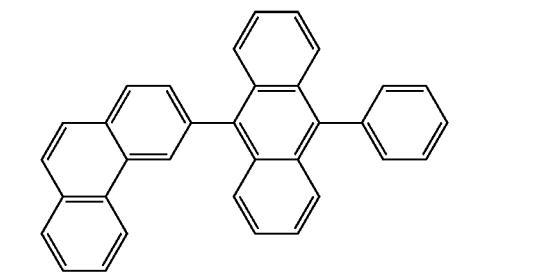
350
-continued
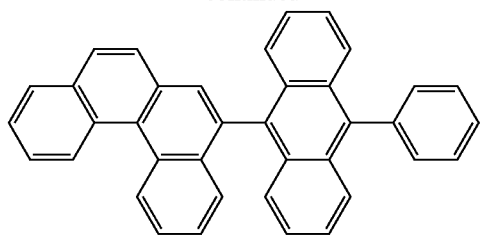
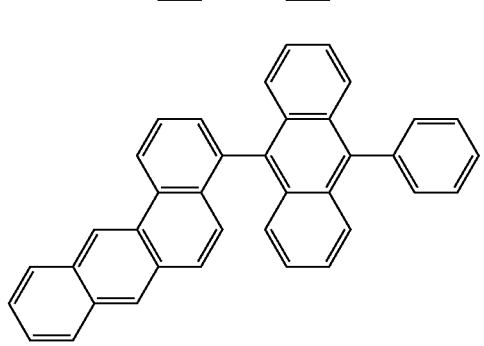
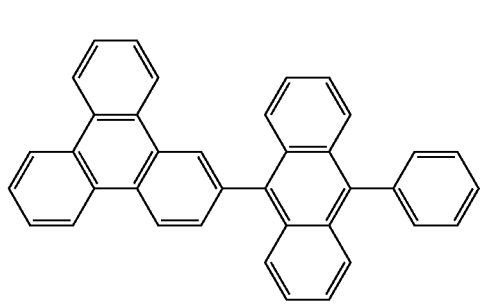
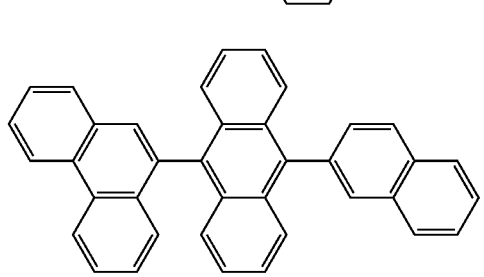
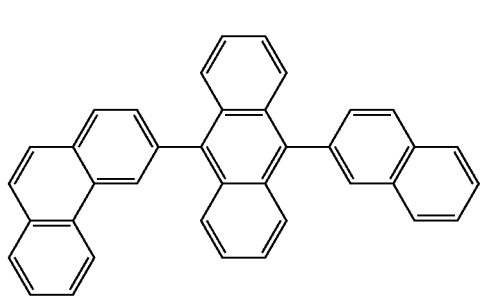
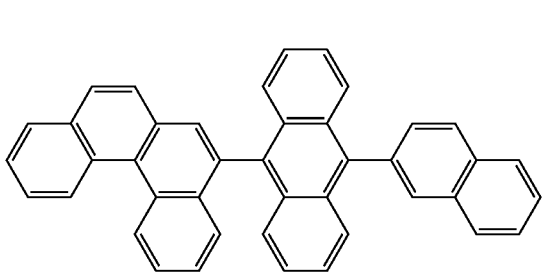

351
-continued
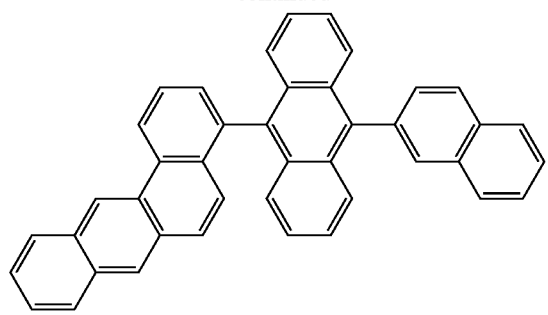
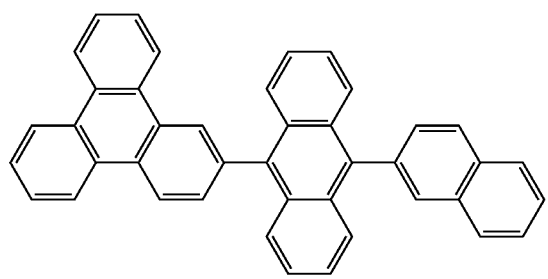
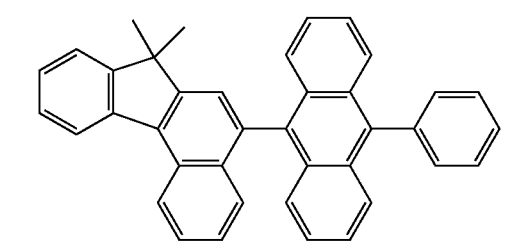
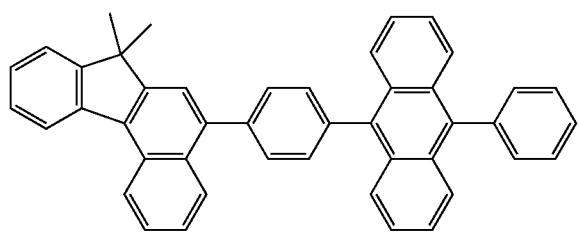
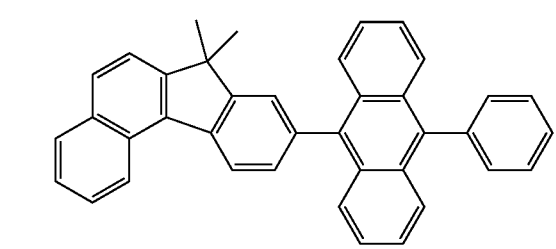
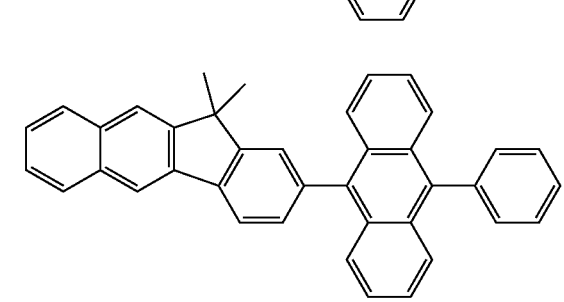
352
-continued
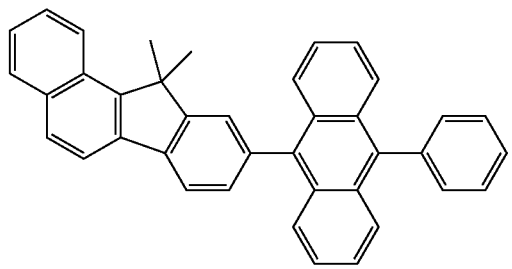
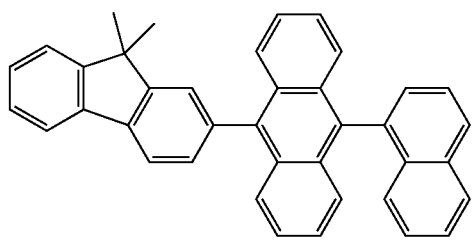
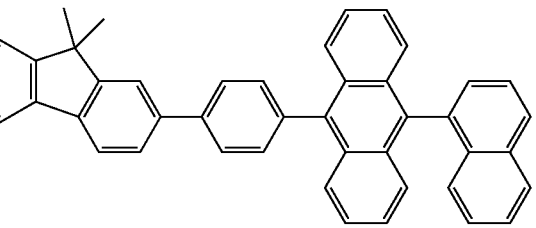
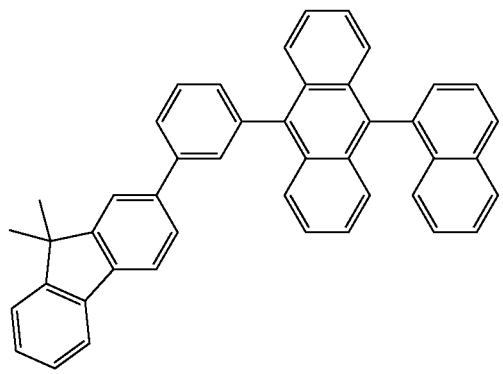
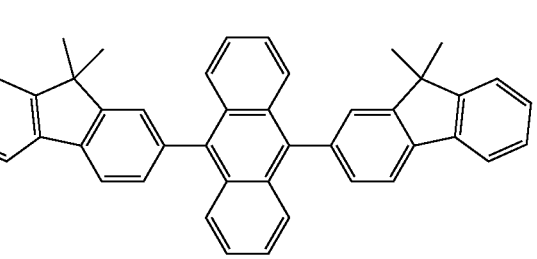
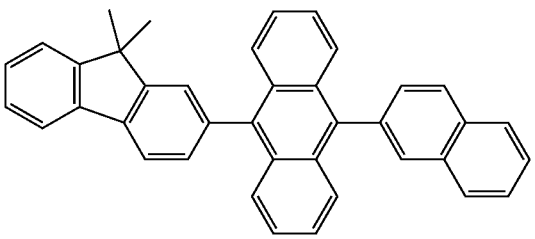

353
-continued
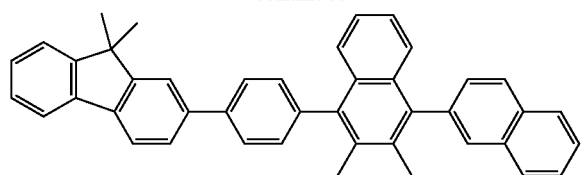
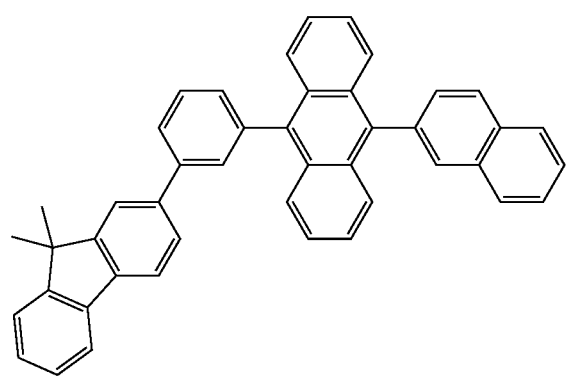
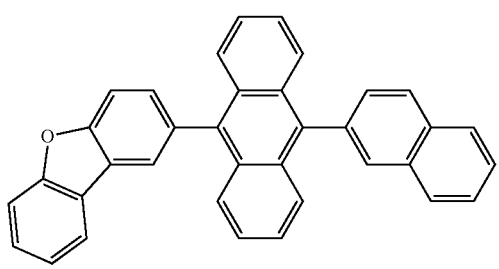
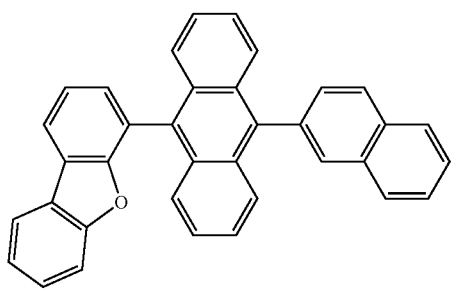
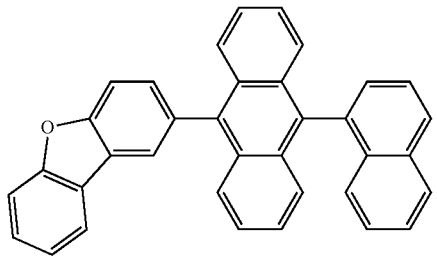
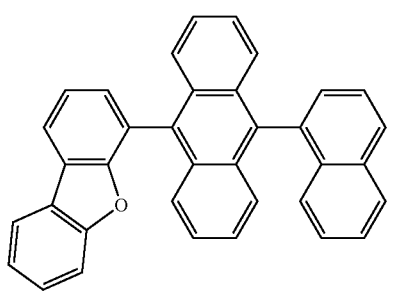
354
-continued
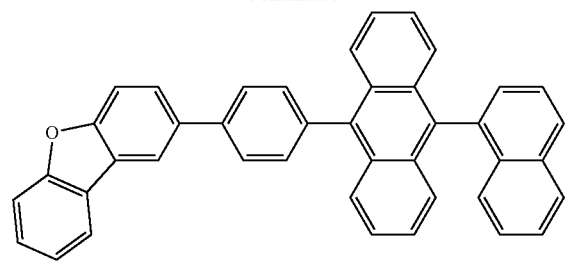
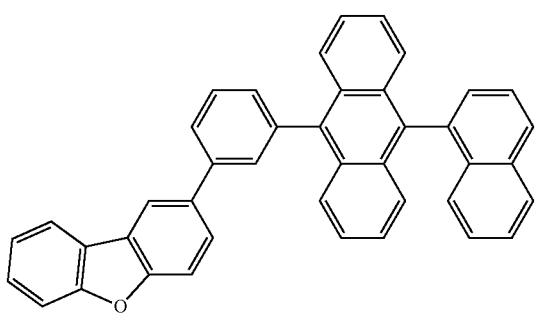
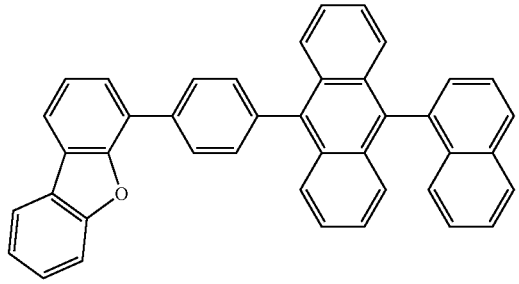
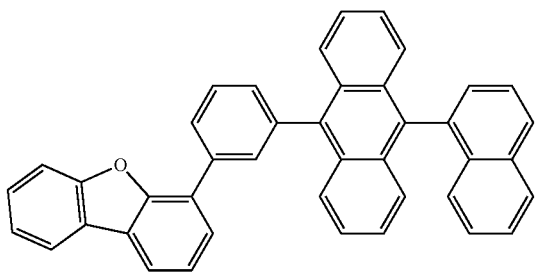
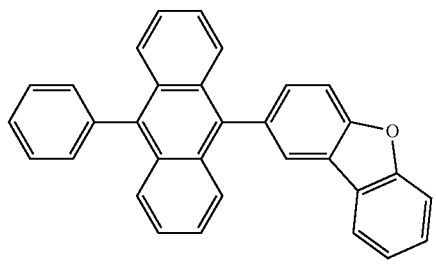
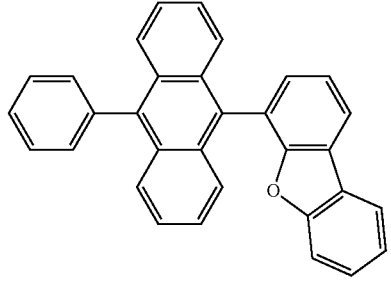

355
-continued
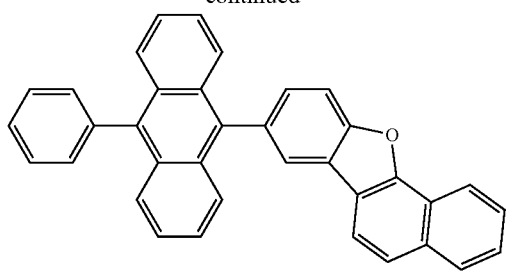
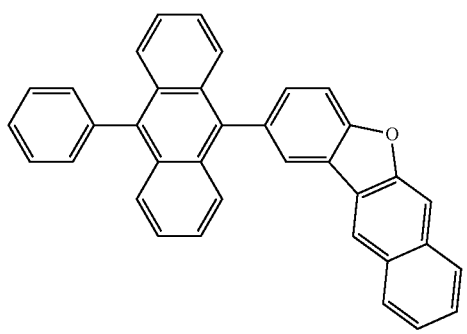
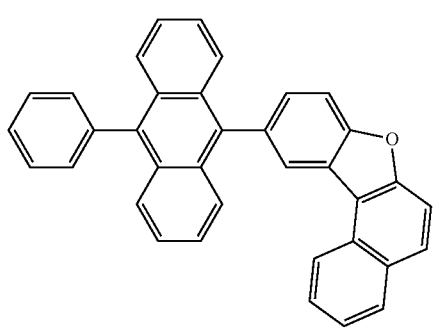
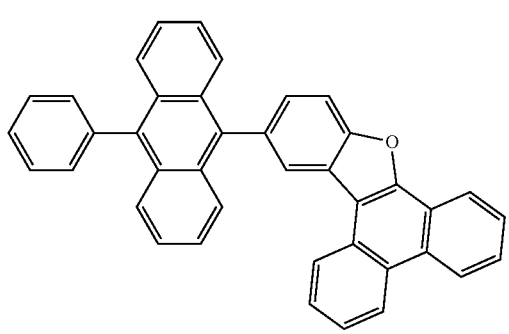
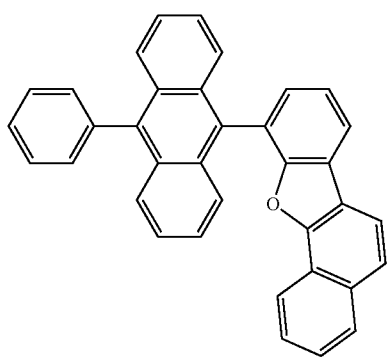
356
-continued
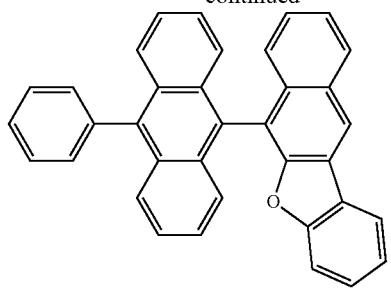
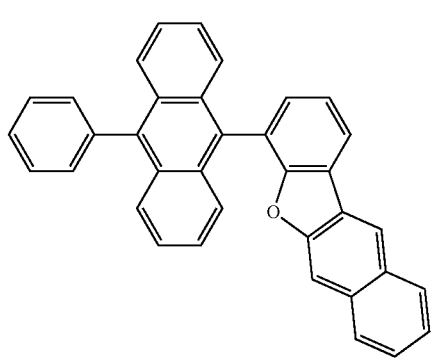
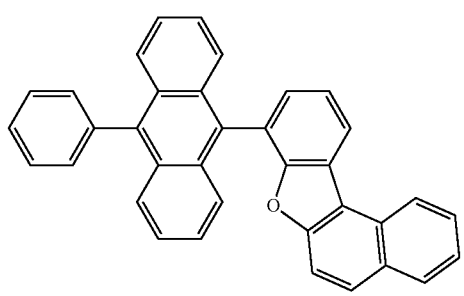
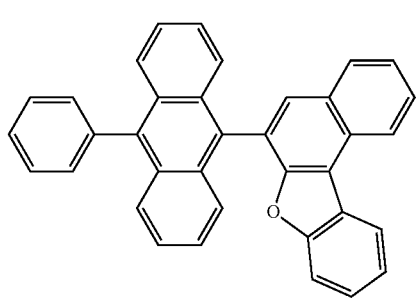
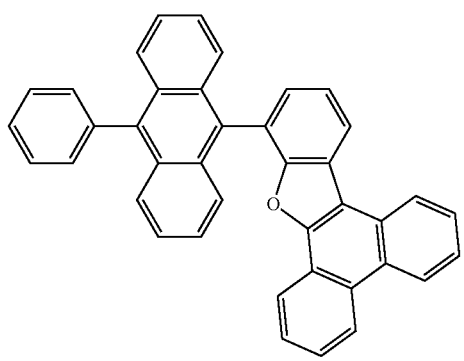

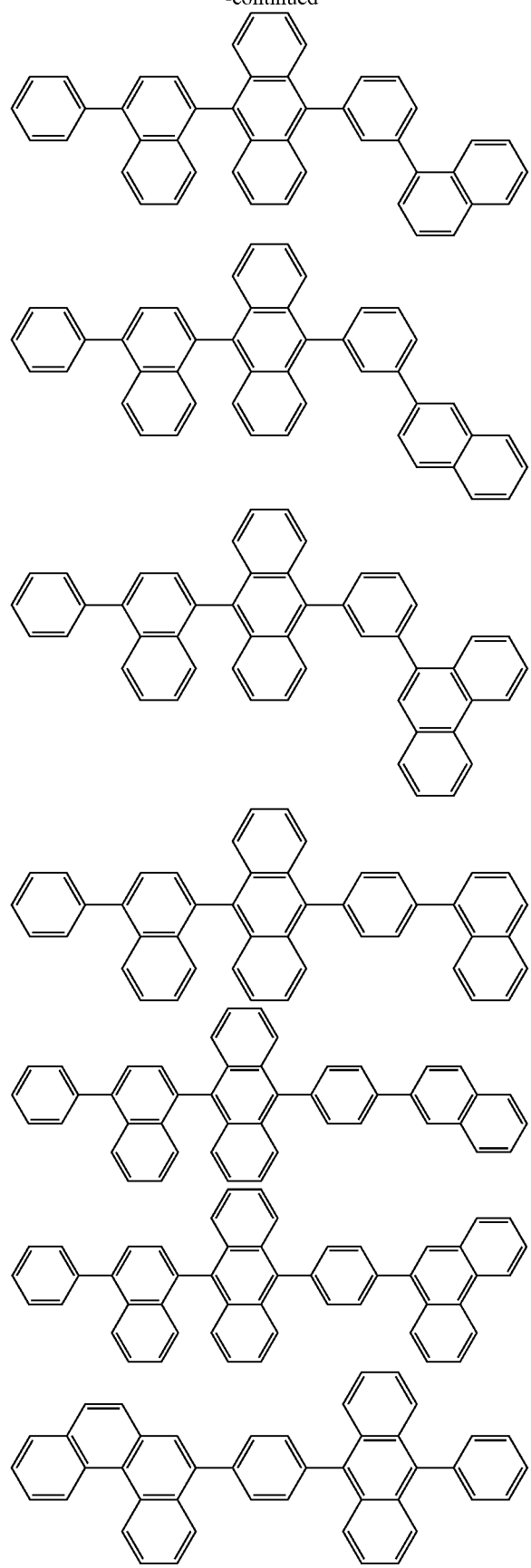
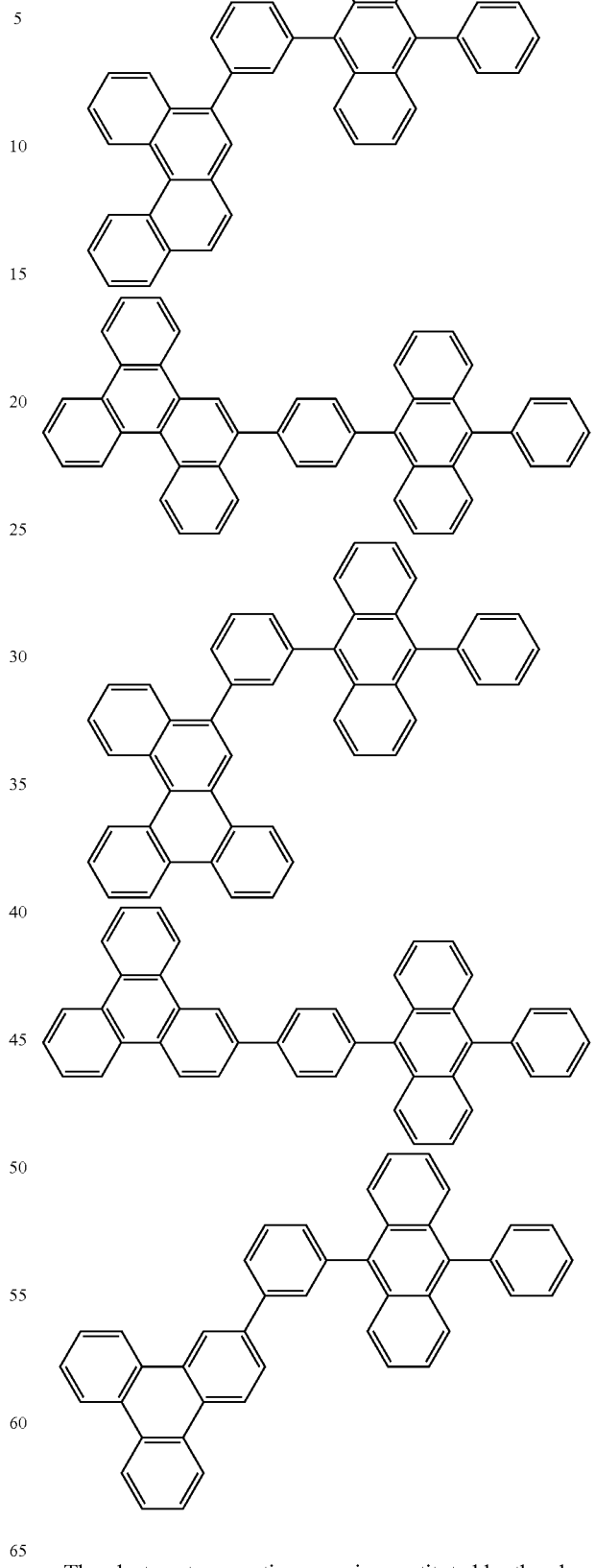
The electron transporting zone is constituted by the electron injecting layer, the electron transporting layer, the hole blocking layer, etc. It is preferable that any one of these layers contains the compound (1), and particularly, it is more preferable that the electron transporting layer contains the compound (1). Also, any one of the layers in the electron transporting zone, particularly, the electron transporting layer preferably contains one or more selected from the group of an alkali metal, an alkaline earth metal, a rare earth metal, oxide of the alkali metal, an alkali metal halide, oxide of the alkaline earth metal, an alkaline earth metal halide, oxide of the rare earth metal, a rare earth metal halide, an organic complex containing the alkali metal, an organic complex containing the alkaline earth metal, and an organic complex containing the rare earth metal.

Electron Transporting Layer

The electron transporting layer is a layer containing a material having a high electron transporting ability (an electron transporting material). For the electron transporting layer, the compound (1) or a combination of the compound (1) with another electron transporting material may be used. Examples of another electron transporting material include:
(1) a metal complex such as an aluminum complex, a beryllium complex, or a zinc complex,
(2) a heteroaromatic compound such as an imidazole derivative, a benzoimidazole derivative, an azine derivative, a carbazole derivative, or a phenanthroline derivative, or
(3) a high molecular compound.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: BeBq$_2$), bis(2-methyl-8-quinolinolato)(4-phenylphenolato)aluminum (III) (abbreviation: BAlq), bis(8-quinolinolato)zinc(II) (abbreviation: Znq), bis[2-(2-benzoxazolyl)phenolato]zinc (II) (abbreviation: ZnPBO), and bis[2-(2-benzothiazolyl)phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs).

Examples of the high molecular compound include poly [(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy).

The materials are materials having an electron mobility of $10^{-6}$ cm$^2$/Vs or more. Materials other than the above may also be used in the electron transporting layer as long as they are materials high in the electron transporting ability rather than in the hole transporting ability.

The electron transporting layer may be a single-layer, or a multi-layer including two or more layers. For example, the electron transporting layer may be a layer including a first electron transporting layer (anode side) and a second electron transporting layer (cathode side). Each of the two or more electron transporting layers is formed by the electron transporting material.

In the electron transporting layer having a two-layer structure, the compound (1) may be contained in either or both of the first electron transporting layer and the second electron transporting layer. Meanwhile, the compound (1) contained in the first electron transporting layer is different from the compound (1) contained in the second electron transporting layer.

In one embodiment of the present invention, the compound (1) is preferably contained in the second electron transporting layer, in another embodiment, the compound (1) is preferably contained in the first electron transporting layer, and in a still another embodiment, the compound (1) is preferably contained in the first electron transporting layer and the second electron transporting layer.

Electron Injecting Layer

The electron injecting layer is a layer containing a material having a high electron injection ability. In the electron injecting layer, alkali metals, alkaline earth metals, or compounds thereof such as lithium (Li), cesium (Cs), calcium (Ca), lithium fluoride (LiF), cesium fluoride (CsF), calcium fluoride (CaFv), or lithium oxide (LiO$_x$) may be used. Besides, a material having an electron transporting ability, in which an alkali metal, an alkaline earth metal, or a compound thereof is contained, specifically Alq in which magnesium (Mg) is contained may be used. In this case, electron injection from the cathode may be more efficiently performed.

Otherwise, in the electron injecting layer, a composite material obtained by mixing an organic compound with an electron donor may be used. Such a composite material is excellent in the electron injection ability and the electron transporting ability because the organic compound receives electrons from the electron donor. In this case, the organic compound is preferably a material excellent in transporting received electrons, and specific examples thereof include a material constituting the electron transporting layer as described above (a metal complex, a heteroaromatic compound, etc.). As the electron donor, a material having an electron donation property for the organic compound may be used. Specifically, alkali metals, alkaline earth metals and rare earth metals are preferred, and examples thereof include lithium, cesium, magnesium, calcium, erbium, and ytterbium. Also, alkali metal oxide or alkaline earth metal oxide is preferred, and examples thereof include lithium oxide, calcium oxide, and barium oxide. Also, a Lewis base such as magnesium oxide may also be used. Further, an organic compound such as tetrathiafulvalene (abbreviation: TTF) may also be used.

Cathode

It is preferable that a metal, an alloy, an electrically conductive compound, or a mixture thereof which has a low work function (specifically 3.8 eV or less) is used for the cathode. Specific examples of such a cathode material include elements belonging to group 1 or 2 of the periodic table of the elements, that is, alkali metals such as lithium (Li) and cesium (Cs), alkaline earth metals such as magnesium (Mg), calcium (Ca), and strontium (Sr), and alloys containing these (for example, MgAg, and AlLi), and rare earth metals such as europium (Eu), and ytterbium (Yb) and alloys containing these.

When the cathode is formed by using the alkali metals, the alkaline earth metals, and the alloys containing these, a vacuum vapor deposition method or a sputtering method may be used. Also, when a silver paste or the like is used, a coating method, an inkjet method, etc. may be used.

By providing the electron injecting layer, the cathode may be formed using various conductive materials such as Al, Ag, ITO, graphene, and indium oxide-tin oxide containing silicon or silicon oxide regardless of the magnitude of a work function. Such a conductive material may be deposited by using a sputtering method, an inkjet method, a spin coating method or the like.

Insulating Layer

The organic EL device applies an electric field to an ultrathin film, and thus pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of these may also be used.

Space Layer

The space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. The space layer may also be provided between the plurality of phosphorescent light emitting layers. The "carrier" mentioned herein means a charge carrier in a substance.

Since the space layer is provided between the light emitting layers, a material having both an electron transporting ability and a hole transporting ability is preferred. Also, one having a triplet energy of 2.6 eV or more is preferred in order to prevent triplet energy diffusion in the adjacent phosphorescent light emitting layer. Examples of the material used for the space layer include the same as those used for the hole transporting layer as described above.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transporting layer, and the hole blocking layer is a layer that prevents holes from leaking from the light emitting layer to the electron transporting layer. The exciton blocking layer has a function of preventing excitons generated in the light emitting layer from diffusing into the surrounding layers, and confining the excitons within the light emitting layer.

Each layer of the organic EL device may be formed by a conventionally known vapor deposition method, a coating method, etc. For example, formation may be performed by a known method using a vapor deposition method such as a vacuum vapor deposition method, or a molecular beam vapor deposition method (MBE method), or a coating method using a solution of a compound for forming a layer, such as a dipping method, a spin coating method, a casting method, a bar-coating method, or a roll coating method.

The film thickness of each layer is not particularly limited, but is usually 5 nm to 10 μm, more preferably 10 nm to 0.2 μm because in general, when the film thickness is too small, defects such as pinholes are likely to occur, and conversely, when the film thickness is too large, a high driving voltage is required and the efficiency decreases.

The organic EL device may be used for electronic devices, such as display components of organic EL panel modules, etc., display devices of televisions, mobile phones, personal computers, etc., and light emitting devices of lightings and vehicular lamps.

EXAMPLES

Hereinafter, the present invention will be described in more detail by using Examples, but the present invention is not limited to the following Examples.

<Calculation 1 of Af Value of Compound>

Regarding chemical structural formulas of Example Compounds 1 to 10 (compounds mentioned in the above specific examples, as reposted below), and the following Comparative Compounds C1 to C6, an electron affinity (Af) was calculated by using a quantum chemical calculation program (Gaussian 09, Revision E (Gaussian Inc.); calculation method: B3LYP/6-31G* (it means B3LYP is used as a theory and 6-31G* is used for a basis function)). The results are noted in Table 1.

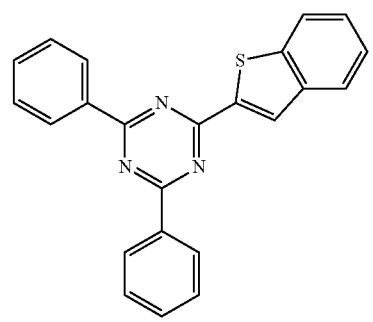

1

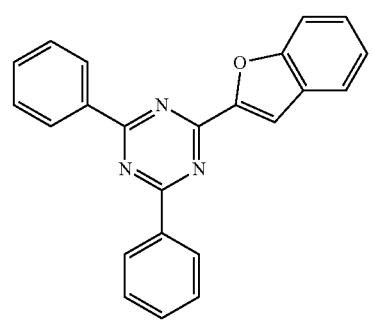

2

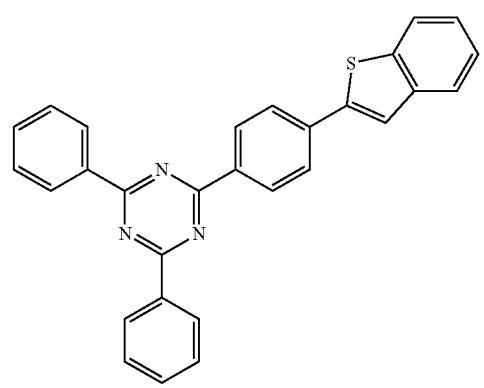

3

363
-continued
4
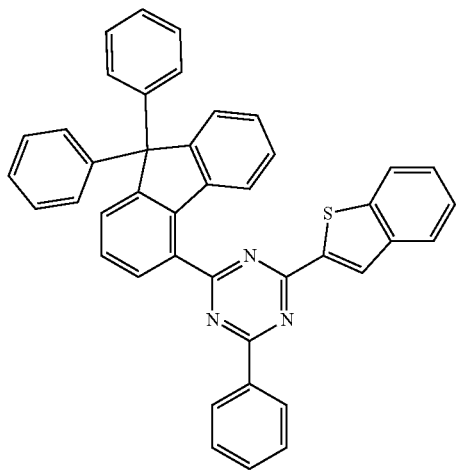
5
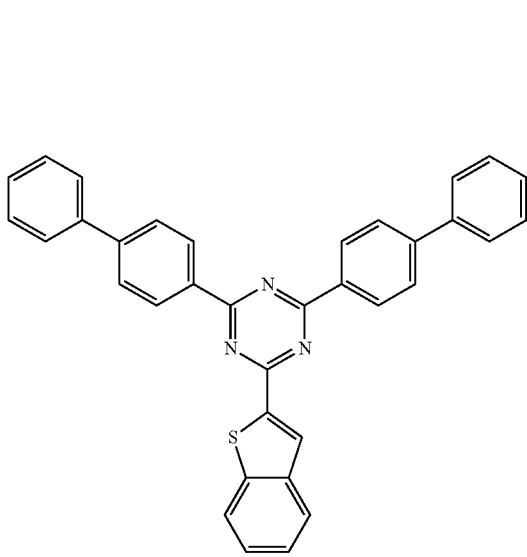
6
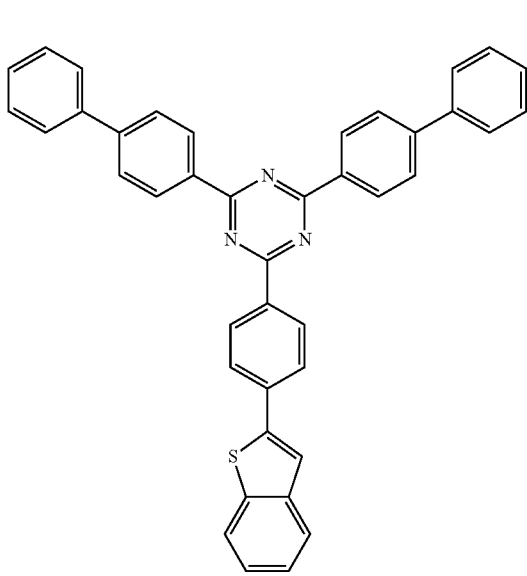
364
-continued
7
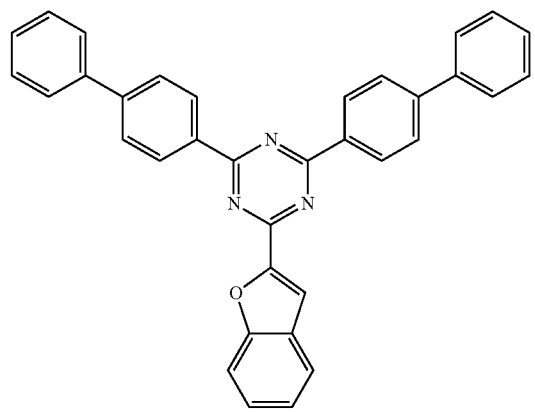
8
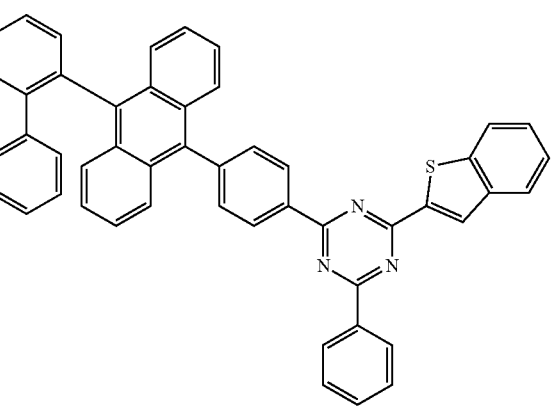
9
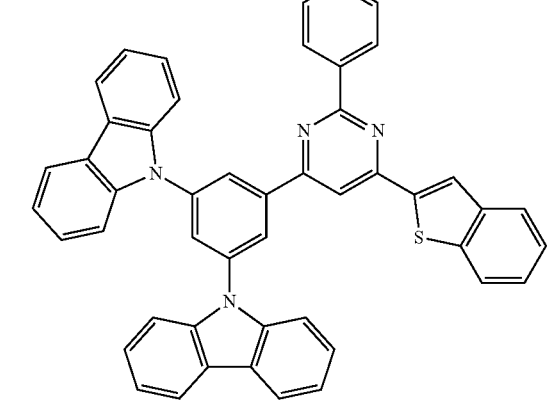
10
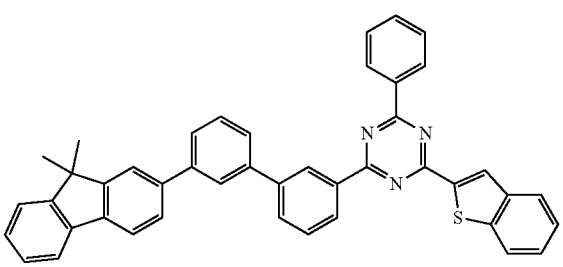

C1
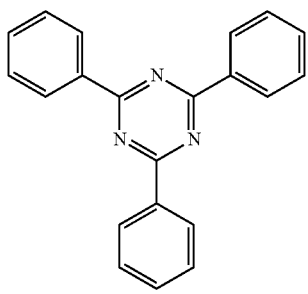

C2
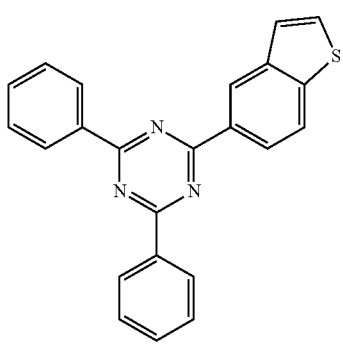

C3
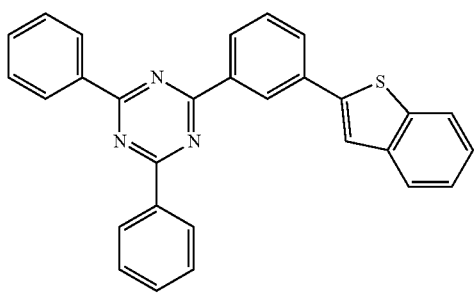

C4
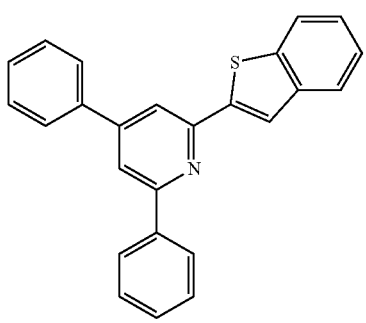

C5
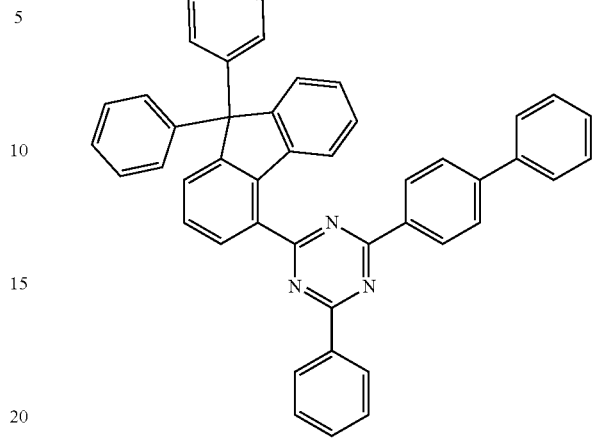

C6
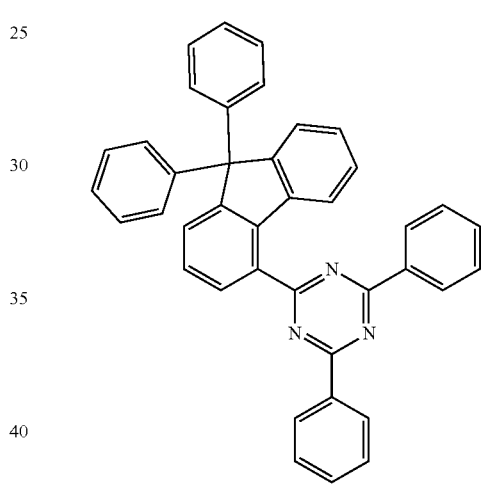

TABLE 1

|  | Compound Name | Calculated Af [eV] |
|---|---|---|
| Example 1 | Compound 1 | 2.04 |
| Example 2 | Compound 2 | 2.00 |
| Example 3 | Compound 3 | 2.05 |
| Example 4 | Compound 4 | 2.05 |
| Example 5 | Compound 5 | 2.04 |
| Example 6 | Compound 6 | 2.04 |
| Example 7 | Compound 7 | 2.00 |
| Example 8 | Compound 8 | 2.05 |
| Example 9 | Compound 9 | 2.13 |
| Example 10 | Compound 10 | 2.07 |
| Comparative Example 1 | Comparative Compound C1 | 1.80 |
| Comparative Example 2 | Comparative Compound C2 | 1.89 |
| Comparative Example 3 | Comparative Compound C3 | 1.91 |
| Comparative Example 4 | Comparative Compound C4 | 1.55 |
| Comparative Example 5 | Comparative Compound C5 | 1.90 |
| Comparative Example 6 | Comparative Compound C6 | 1.82 |

It can be found that the Compounds 1 to 10 of Examples 1 to 10 have larger electron affinity (Af) values than Comparative Compounds C1 to C6 of Comparative Examples 1 to 6. By linking a fused ring including a 5-membered ring (that contains sulfur or oxygen having a higher electronegativity than carbon) and a benzene ring, to a triazine skeleton or a pyrimidine skeleton directly or via a p phenylene group, it is possible to generally deepen the electron affinity of the entire compound molecule. Also, it is presumed that when the triazine skeleton or the pyrimidine skeleton is disposed in the vicinity of sulfur or oxygen in the fused ring, the electron affinity of the compound may be further deepened. In particular, when $R^6$ in formula (1) is bonded to *a, the electron affinity may be further deepened. As the electron affinity is deepened, electron injection into the light emitting layer is suppressed. As a result, it may be thought that a device life may be improved.

Synthesis of Compound

Synthesis Example 1 (Synthesis of Compound 4)

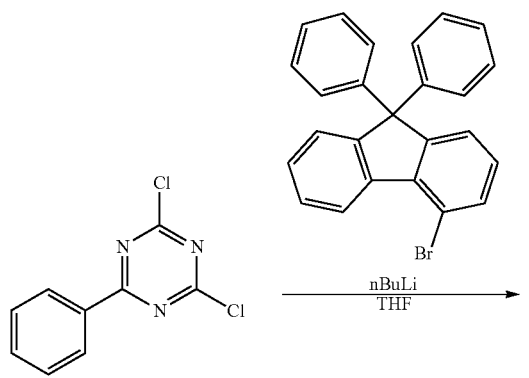

Intermediate A

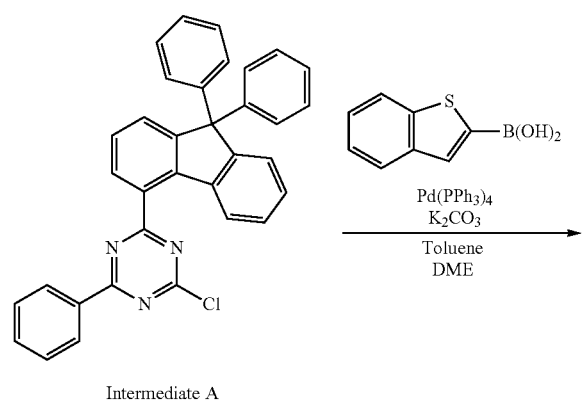

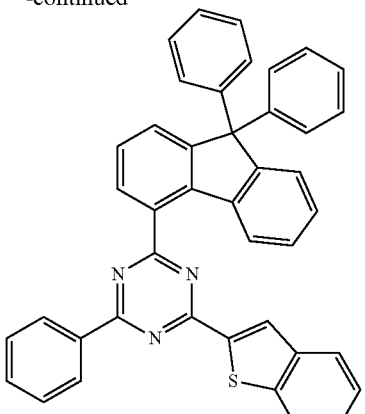

Compound 4

(1-1) Synthesis of Intermediate A

Under argon atmosphere, a tetrahydrofuran solution of 9,9-diphenyl-4-bromofluorene (10 g) was cooled to −78° C. 1.6 M n-butyllithium solution (16 mL) was added dropwise for 30 min, followed by stirring at −78° C. for 1 h. This solution was added dropwise to a tetrahydrofuran solution of 1-phenyl-3,5-dichlorotriazine (5.7 g) cooled to −78° C., for 1 h, followed by stirring at −78° C. for 3 h. After the temperature was returned to room temperature, water (50 mL) was added. In the reaction solution, the solvent was removed through evaporation under reduced pressure, and the obtained solid was washed with dichloromethane (80 mL) to obtain an Intermediate A (6.1 g, yield 48%).

(1-2) Synthesis of Compound 4

Under argon atmosphere, the Intermediate A (3.0 g) obtained in (1-1), benzo[b]thiophene-2-boronic acid (2.1 g), 2N potassium carbonate aqueous solution (5.0 mL), tetrakis (triphenylphosphine)palladium (0.07 g), and toluene (20 mL) were added to dimethoxyethane (50 mL), and heated under reflux for 2 h. The reaction solution was cooled to room temperature, and extracted with toluene. Then, the organic layer was washed with saturated brine, and dried over anhydrous magnesium sulfate. The solvent was removed through evaporation under reduced pressure. The obtained residue was purified by silica gel chromatography to obtain Compound 4 (1.6 g, yield 43%), which was identified as Compound 4 because the molecular weight of Compound 4 was 605.76, and the mass spectrum analysis result of the obtained compound was m/z (ratio of mass to charge)=606.

Synthesis Example 2 (Synthesis of Compound 5)

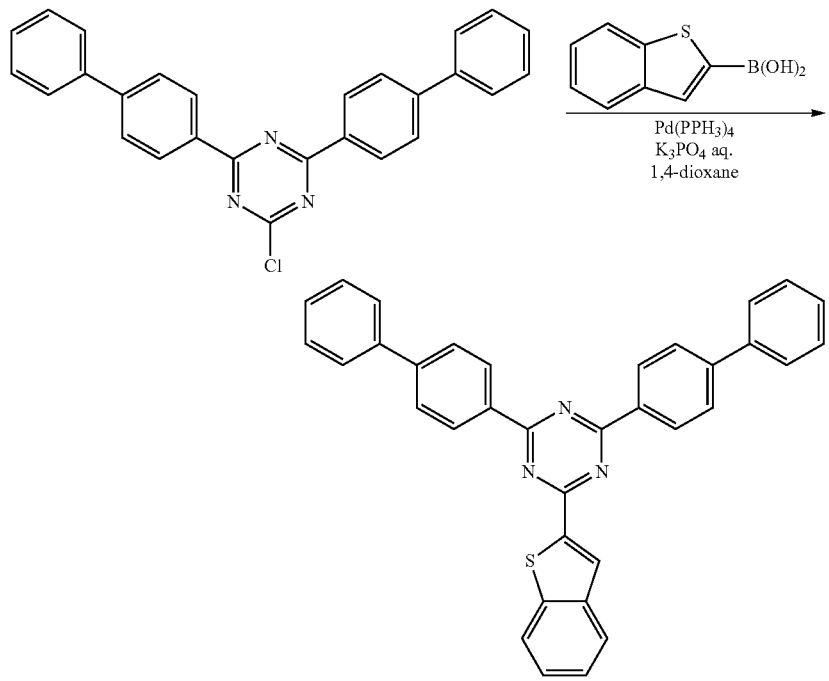

Under argon atmosphere, 2,4-bis(1,1'-biphenyl-4-yl)-6-chloro-1,3,5-triazine (synthesized by the method described in Japanese Patent 5795896B2) (8.6 g), benzo[b]thiophene-2-boronic acid (3.8 g), 2M tripotassium phosphate aqueous solution (26 mL), and tetrakis(triphenylphosphine)palladium (1.19 g) were added to 1,4-dioxane (215 mL), and heated under reflux for 7 h. The reaction solution was cooled to room temperature and a precipitated solid was collected through filtration. The solid was purified by silica gel chromatography to obtain Compound 5 (8.7 g, yield 82%), which was identified as Compound 5 because the molecular weight of Compound 5 was 517.65, and the mass spectrum analysis result of the obtained compound was m/z (ratio of mass to charge)=517.

Synthesis Example 3 (Synthesis of Compound 6)

(1) Synthesis of Intermediate B

Under argon atmosphere, 2-(4-bromophenyl)benzo[b]thiophene (8.0 g), bis(pinacolato)diboron (7.4 g), potassium acetate (5.4 g), and Pd(dppf)$_2$Cl$_2$·CH$_2$Cl$_2$. (1.1 g) were added to 1,4-dioxane (80 mL), and heated under reflux for 4 h. The reaction solution was extracted with dichloromethane (400 mL), and the solvent was removed through evaporation under reduced pressure. The obtained residue was purified by silica gel column chromatography to obtain an Intermediate B (8.4 g, yield 90%).

(2) Synthesis of Compound 6

Compound 6 represented by the above structural formula was synthesized in the same manner as in Compound 5, by changing benzo[b]thiophene-2-boronic acid to the Intermediate B (yield 87%), which was identified as Compound 6 because the molecular weight of Compound 6 was 593.75, and the mass spectrum analysis result of the obtained compound was m/z (ratio of mass to charge)=593.

Synthesis Example 4 (Synthesis of Compound 7)

Compound 7 represented by the above structural formula was synthesized in the same manner as in Compound 5, by changing benzo[b]thiophene-2-boronic acid to benzo[b]furan-2-boronic acid (yield 93%), which was identified as Compound 7 because the molecular weight of Compound 7 was 501.59, and the mass spectrum analysis result of the obtained compound was m/z (ratio of mass to charge)=501.

Synthesis Example 5 (Synthesis of Compound 8)

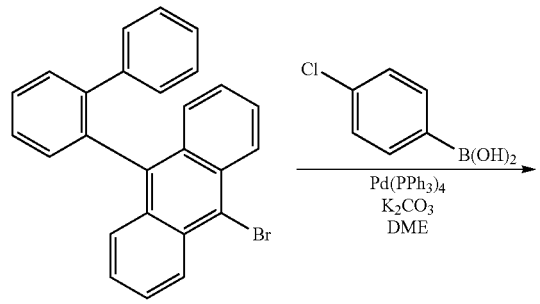

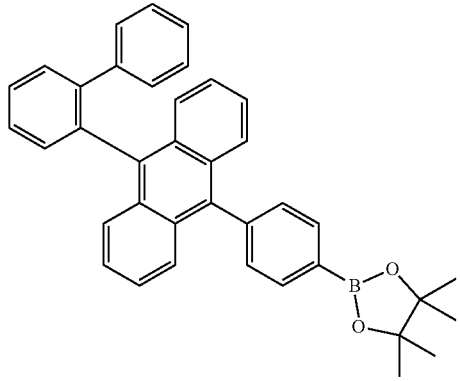

Intermediate D

Under argon atmosphere, the Intermediate C (11 g), bis(pinacolato)diboron (6.2 g), tris(dibenzyhdeneacetone)dipalladium (0.9 g), XPhos (0.96 g) and potassium acetate (7.2 g) were added to 1,4-dioxane (250 mL), and heated under reflux for 3 h. The solvent was removed through evaporation under reduced pressure, and the obtained residue was subjected to column chromatography to obtain an Intermediate D (13 g, yield 100%).

(3) Synthesis of Intermediate E

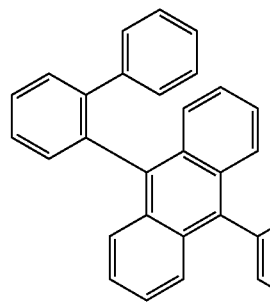

Intermediate C

Under argon atmosphere, 9-(1,1'-biphenyl)-2-yl-10-bromoanthracene (10 g), 4-chlorophenylboronic acid (4.4 g), tetrakis(triphenylphosphine)palladium (0.57 g), and 2M potassium carbonate aqueous solution (37 mL) were added to dimethoxyethane (200 mL), and heated under reflux for 10 h. The reaction solution was returned to room temperature, and the solvent was removed through evaporation under reduced pressure. The obtained residue was washed with methanol, and an Intermediate C was obtained (10 g, yield 89%).

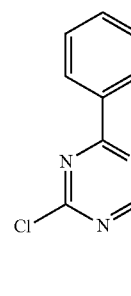

Intermediate E

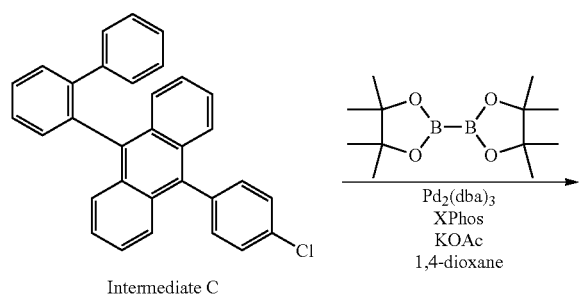

Intermediate C 2,4-dichloro-6-phenyl-1,3,5-triazine (10.0 g), benzo[b]thiophene-2-boronic acid (8.7 g), and dichlorobis(triphenylphosphine)palladium (310 mg) were added, and the inside of the container was replaced with argon. To this, toluene (221 mL), and sodium carbonate aqueous solution (2M, 55 mL) were added, followed by heating with stirring for 5.5 h at 60° C. under argon atmosphere. The reaction solution was returned to room temperature, water was added, and the precipitated solid was collected through filtration. The obtained solid was subjected to column chromatography to obtain an Intermediate E (7.6 g, yield 53%).

(4) Synthesis of Compound 8
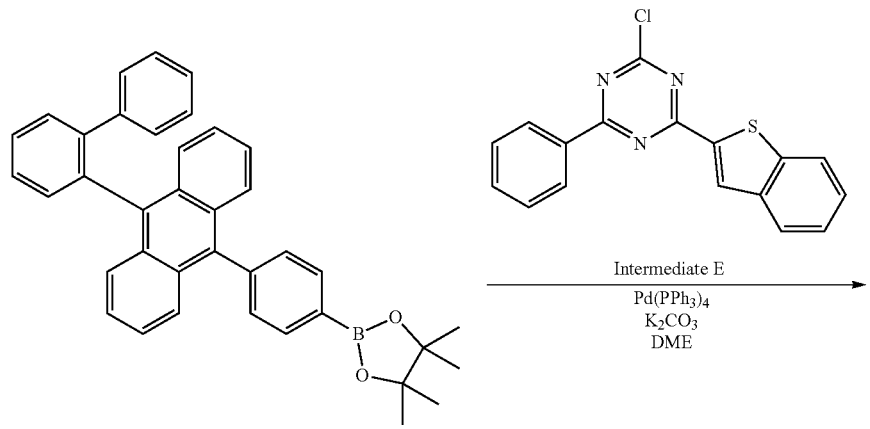
Intermediate D
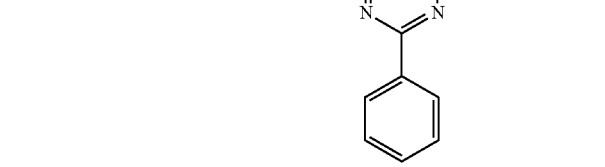
Compound 8

Under argon atmosphere, the Intermediate D (2.4 g), the Intermediate E (1.2 g), tetrakis(triphenylphosphine)palladium (0.09 g), and 2M potassium carbonate aqueous solution (11 mL) were added to dimethoxyethane (50 mL), and heated under reflux for 3 h. The solvent was removed through evaporation under reduced pressure, and the residue was subjected to column chromatography to obtain Compound 8 (2.3 g, yield 89%), which was identified as Compound 8 because the molecular weight of Compound 8 was 693.87, and the mass spectrum analysis result of the obtained compound was m/z (ratio of mass to charge)=693.

Synthesis Example 6 (Synthesis of Compound 9)

(1) Synthesis of Intermediate F 2-acetylbenzo[b]thiophene (5.0 g) and 3,5-difluorobenzaldehyde (4.0 g) were added and argon replacement was performed. Next, ethanol (280 mL) and sodium hydroxide (2.8 g) were added, and stirred at room temperature for 3 h under argon atmosphere. Next, benzamidine-hydrochloride (4.4 g), and sodium hydroxide (1.4 g) were added, followed by heating for 3 h at 80° C. The reaction solution was returned to room temperature, and the precipitated solid was collected through filtration, and washed with water, methanol, and n-hexane to obtain an Intermediate F (4.2 g, yield 37%).

(2) Synthesis of Compound 9

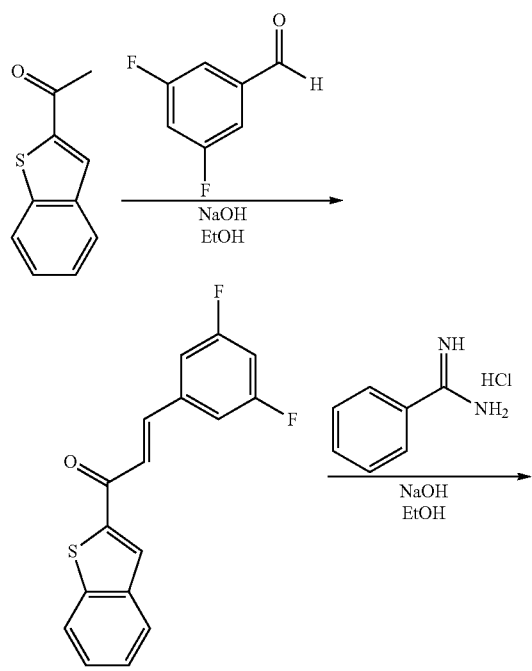

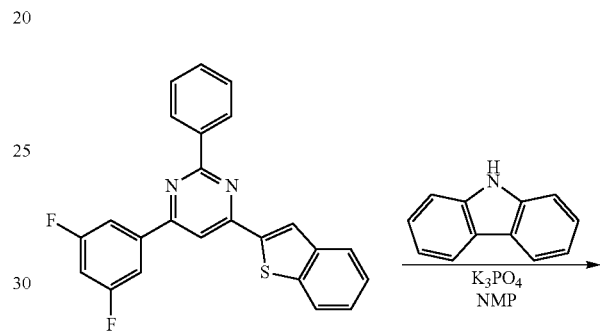

Intermediate F

Intermediate F

Compound 9

The Intermediate F (3.7 g), carbazole (6.2 g), and tripotassium phosphate (7.8 g) were added and argon replacement was performed. N methylpyrrolidone (185 mL) was added, followed by heating with stirring for 11 h at 180° C. The reaction solution was returned to room temperature, water was added, and the precipitated solid was collected through filtration. The obtained solid was subjected to column chromatography to obtain Compound 8 (4.5 g, yield 70%), which was identified as Compound 9 because the molecular weight of Compound 9 was 694.86, and the mass spectrum analysis result of the obtained compound was m/z (ratio of mass to charge)=694.

Synthesis Example 7 (Synthesis of Compound 10)

(1) Synthesis of Intermediate G

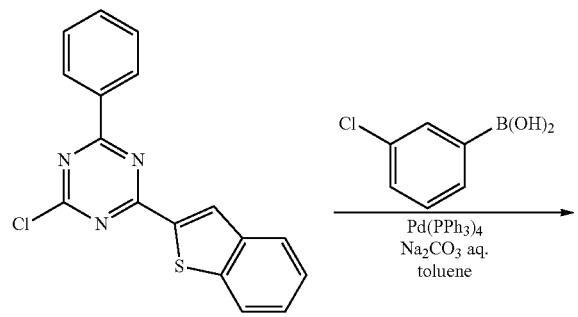

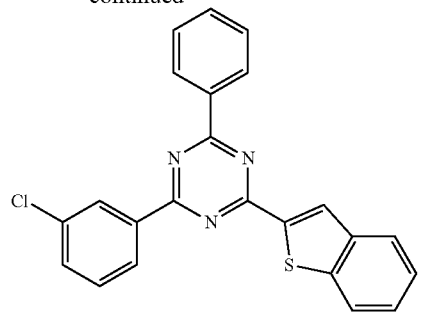

Intermediate G

The Intermediate E (3.5 g), 3-chlorophenylboronic acid (2.5 g), and tetrakis(triphenylphosphine)palladium (250 mg) were added, and the inside of the container was replaced with argon. Next, toluene (108 mL), and sodium carbonate aqueous solution (2M, 13.5 mL) were added, followed by heating with stirring under argon atmosphere for 4.5 h at 70° C. The reaction solution was concentrated, methanol was added, and the precipitated solid was collected through filtration and washed with water and methanol. The obtained solid was subjected to column chromatography to obtain an Intermediate G (4.0 g, yield 93%).

(3) Synthesis of Compound 10

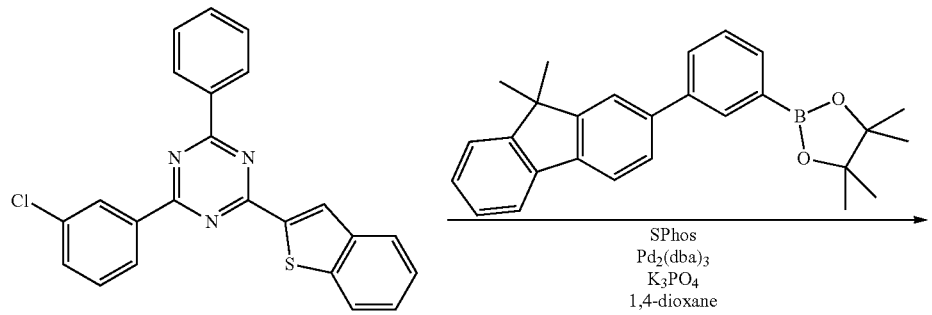

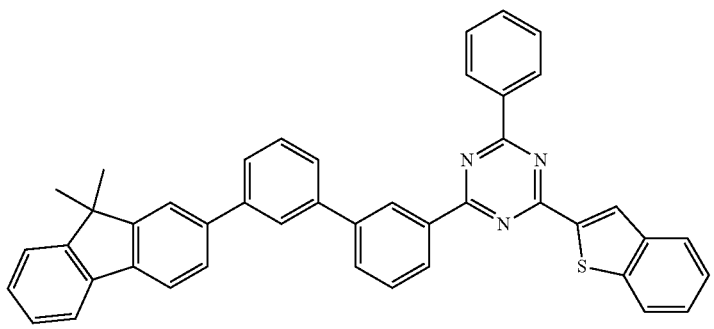

Compound 10

The Intermediate G (3.0 g), 2-[3-(9,9-dimethyl-9H-fluorene-2-yl)phenyl]-4,4,5,5,-tetramethyl-1,3,2-dioxaborolane (3.3 g), 2-dicyclohexylphosphino-2',6'-dimethoxybiphenyl (0.49 g), tris(dibenzylideneacetone)dipalladium (0.28 g), and tripotassium phosphate (9.6 g) were added, and the inside of the container was replaced with argon. Then, 1,4-dioxane (75 mL) was added, followed by heating under reflux for 7 h under argon atmosphere. The reaction solution was returned to room temperature, water was added, and the precipitated solid was collected through filtration and washed with water and methanol. The obtained solid was subjected to column chromatography to obtain Compound 9 (3.3 g, yield 72%), which was identified as Compound 10 because the molecular weight of Compound 9 was 633.81, and the mass spectrum analysis result of the obtained compound was m/z (ratio of mass to charge)=633.

<Production of Organic EL Device>

An Organic EL Device was Produced as Follows.

Production Example 1

A glass substrate (25 mm×75 mm×1.1 mm) provided with an ITO transparent electrode (manufactured by GEOMATEC Co., Ltd.) was ultrasonically cleaned in isopropyl alcohol for 5 min, and then was subjected to UV ozone cleaning for 30 min. The thickness of the ITO transparent electrode was 130 nm.

The cleaned glass substrate provided with the ITO transparent electrode was mounted on a substrate holder of a vacuum vapor deposition apparatus. First, the following Compound HT-1 and the following Compound HI were co deposited so as to cover the ITO transparent electrode to form a hole injecting layer with a film thickness of 10 nm. The concentration of Compound HI in the hole injecting layer was 3.0% by mass.

Next, on the hole injecting layer, the following compound HT-1 (a first hole transporting layer material) was vapor-deposited so as to form a first hole transporting layer with a film thickness of 80 nm.

Next, on the first hole transporting layer, the following compound HT-2 (a second hole transporting layer material) was vapor-deposited so as to form a second hole transporting layer with a film thickness of 5 nm.

Next, on the second hole transporting layer, the following compound BH (a host material) and the following Compound BD (a dopant material) were co-deposited so as to form a light emitting layer with a film thickness of 25 nm. The concentration of Compound BD in the light emitting layer was 4.0% by mass.

Next, on the light emitting layer, the following compound ET-1 was vapor-deposited so as to form a first electron transporting layer with a film thickness of 5 nm.

Next, on the first electron transporting layer, Compound 4 synthesized in Synthesis Example 1 (a second electron transporting layer material) and the following compound Liq were co-deposited so as to form a second electron transporting layer with a film thickness of 20 nm. The concentration of Compound 4 and Liq in the second electron transporting layer was 50.0% by mass.

Next, on the second electron transporting layer, LiF was vapor-deposited so as to form an electron injecting electrode (cathode) with a film thickness of 1 nm.

Then, on the LiF film, metal Al was vapor-deposited to form a metal Al cathode with a film thickness of 80 nm.

A device configuration of Production Example 1 is schematically illustrated as follows.

ITO (130)/HT-1:HI (10:3%)/HT-1 (80)/HT-2 (5)/BH:BD (25:4%)/ET-1 (5)/Compound 4:Liq (20:50%)/LiF (1)/Al (80)

Numbers in parentheses indicate a film thickness (unit: nm). Similarly, in parentheses, numbers expressed as a percentage indicate the ratio (% by mass) of a compound described on the right, in the layer. The same also applies to the corresponding descriptions in the following Comparative Production Examples 1 and 2.

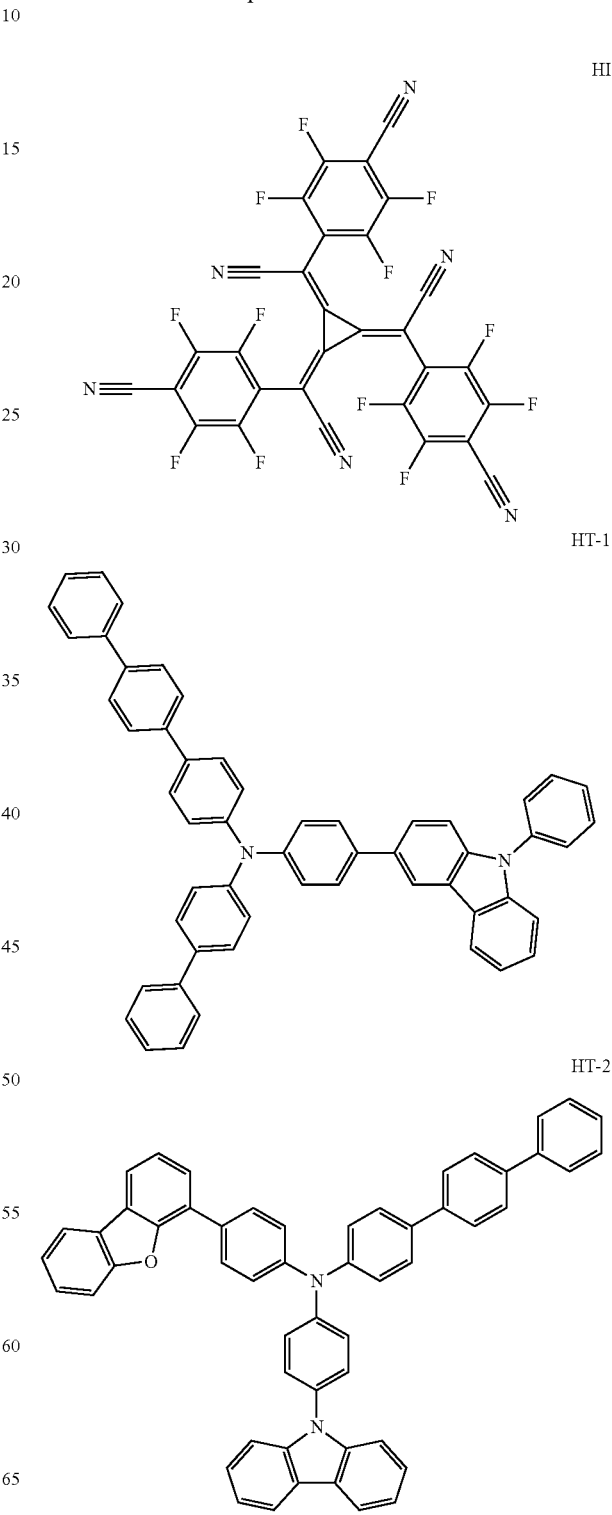

-continued

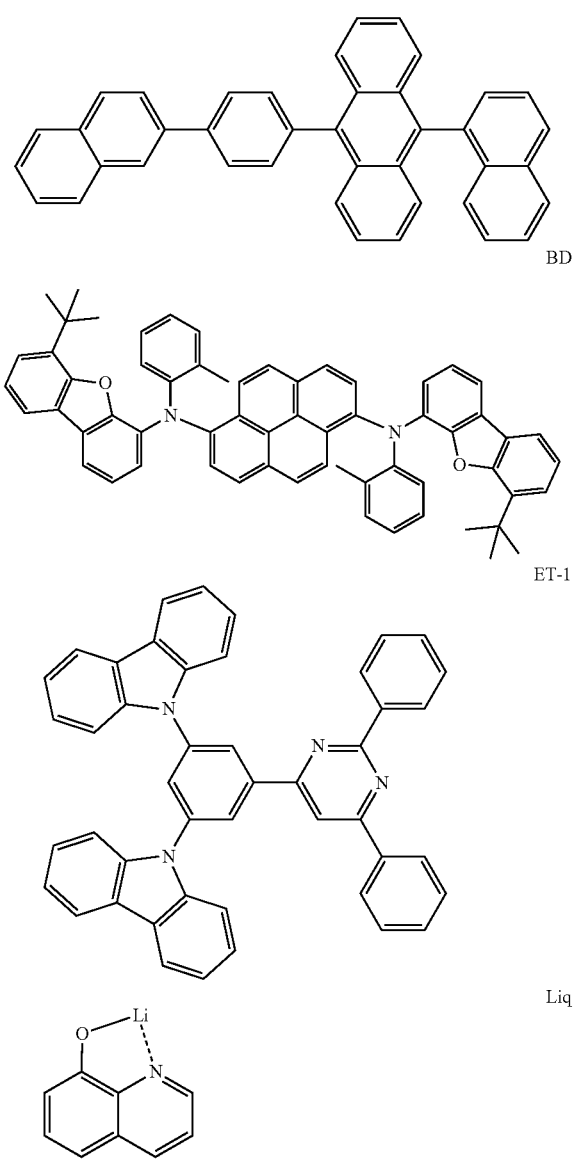

Production Example 2

An organic EL device was produced in the same manner as in Production Example 1 except that instead of Compound 4 used for the second electron transporting layer in Production Example 1, Compound 5 was used as the second electron transporting layer material.

A device configuration of Production Example 2 is schematically illustrated as follows.

ITO (130)/HT-1:HI (10:3%)/HT-1 (80)/HT-2 (5)/BH:BD (25:4%)/ET-1 (5)/Compound 5:Liq (20:50%)/LiF (1)/Al (80)

Production Example 3

An organic EL device was produced in the same manner as in Production Example 1 except that instead of Compound 4 used for the second electron transporting layer in Production Example 1, Compound 6 was used as the second electron transporting layer material.

A device configuration of Production Example 3 is schematically illustrated as follows.

ITO (130)/HT-1:HI (10:3%)/HT-1 (80)/HT-2 (5)/BH:BD (25:4%)/ET-1 (5)/Compound 6:Liq (20:50%)/LiF (1)/Al (80)

Production Example 4

An organic EL device was produced in the same manner as in Production Example 1 except that instead of Compound 4 used for the second electron transporting layer in Production Example 1, Compound 7 was used as the second electron transporting layer material.

A device configuration of Production Example 4 is schematically illustrated as follows.

ITO (130)/HT-1:HI (10:3%)/HT-1 (80)/HT-2 (5)/BH:BD (25:4%)/ET-1 (5)/Compound 7:Liq (20:50%)/LiF (1)/Al (80)

Production Example 5

An organic EL device was produced in the same manner as in Production Example 1 except that instead of Compound 4 used for the second electron transporting layer in Production Example 1, Compound 8 was used as the second electron transporting layer material.

A device configuration of Production Example 5 is schematically illustrated as follows.

ITO (130)/HT-1:HI (10:3%)/HT-1 (80)/HT-2 (5)/BH:BD (25:4%)/ET-1 (5)/Compound 8:Liq (20:50%)/LiF (1)/Al (80)

Comparative Production Example 1

An organic EL device was produced in the same manner as in Production Example 1 except that instead of Compound 4 used for the second electron transporting layer in Production Example 1, Comparative Compound C5 was used as the second electron transporting layer material.

A device configuration of Comparative Production Example 1 is schematically illustrated as follows.

ITO (130)/HT-1:HI (10:3%)/HT-1 (80)/HT-2 (5)/BH:BD (25:4%)/ET-1 (5)/Comparative Compound C5:Liq (20:50%)/LiF (1)/Al (80)

Comparative Production Example 2

An organic EL device was produced in the same manner as in Production Example 1 except that instead of Compound 4 used for the second electron transporting layer in Production Example 1, Comparative Compound C6 was used as the second electron transporting layer material.

A device configuration of Comparative Production Example 2 is schematically illustrated as follows.

ITO(130)/HT-1:HI (10:3%)/HT-1 (80)/HT-2 (5)/BH:BD (25:4%)/ET-1 (5)/Comparative Compound C6:Liq (20:50%)/LiF (1)/Al (80)

<Evaluation of Organic EL Device>

For the produced organic EL device, a voltage was applied to the organic EL device so that the current density was 10 mA/cm², and the external quantum efficiency was evaluated. Also, a voltage was applied to the organic EL device so that a current density was 50 mA/cm², and 90% lifetime (LT90) was evaluated. Here, the 90% lifetime (LT90) refers to a time (hr) until the luminance is reduced to 90% of the initial luminance during constant current driving.
<Evaluation of Compound>

The electron affinity (Af) of a compound can be calculated from the redox potential of each compound obtained by various electrochemical measurements. Af may be calculated by the following mathematical expression (A), in accordance with the procedure described in Djulovich, Mayo, Forrest, Thompson, Organic Electronics, 10 (2009) p. 515-520, from a first reduction potential (Ere[V]) of a compound measured in a dimethylformamide (DMF) solvent, and a first oxidation potential (Efc[V]) of ferrocene measured similarly as the internal standard.

$$Af[eV]=-(-1.19\times(Ere-Efc)-4.78) \quad (A)$$

Here, the redox potential may be measured by a method such as cyclic voltammetry (CV) or differential pulse voltammetry (DPV). In the present application, the redox potential of each compound was measured by DPV measurement in accordance with the procedure described below.

In the DPV measurement, an electrochemical analyzer (manufactured by ALS Co., Ltd., product number: ALS 852D) was used. The solution for the DPV measurement was prepared as follows. Tetrabutylammonium hexafluorophosphoric acid as a supporting electrolyte was dissolved in DMF as a solvent, to a concentration of 100 mmol/L, a compound as a measurement target was dissolved to a concentration of 1.0 mmol/L, and ferrocene as the internal standard was dissolved to a concentration of 1.0 mmol/L, so as to prepare a solution for DPV measurement.

In the DPV measurement, a platinum electrode was used for an auxiliary electrode, a glassy carbon electrode was used for a working electrode, and a silver/silver chloride electrode was used for a reference electrode. The measurement conditions of the DPV measurement were a voltage increase by 0.01 V in each step, a pulse voltage of 0.025 V, a pulse width of 0.05 sec, a pulse time of 0.2 sec, and a potential measurement time of 0.02 sec.

Af of each compound was calculated using the above mathematical expression (A), where Ere is a first reduction potential of the compound as a measurement target, and Efc is a first oxidation potential of ferrocene, which were measured under the above measurement conditions.

The results are noted in Table 2.

TABLE 2

| | Material of second electron transporting layer | External quantum efficiency % | LT90 [h] | Measured AF [eV] | Calculated AF [eV] |
|---|---|---|---|---|---|
| Production Example 1 | Compound 4 | 10 | 414 | 2.54 | 2.04 |
| Production Example 2 | Compound 5 | 11 | 430 | 2.52 | 2.04 |
| Production Example 3 | Compound 6 | 11 | 445 | 2.50 | 2.04 |
| Production Example 4 | Compound 7 | 10 | 360 | 2.51 | 2.00 |
| Production Example 5 | Compound 8 | 10 | 363 | 2.52 | 2.05 |
| Production Comparative Example 1 | Comparative Compound C5 | 10 | 277 | 2.41 | 1.80 |
| Production Comparative Example 2 | Comparative Compound C6 | 10 | 318 | 2.38 | 1.89 |

As is clear from Table 2, it can be found that when Compounds 4 to 8 of Production Examples 1 to 5, which are included in formula (1) having a specific structure, are used as electron transporting materials of organic EL devices, it is possible to obtain organic EL devices capable of achieving a long lifetime while maintaining a high external quantum efficiency, which cannot be realized in Comparative Compounds C5 and C6 of Comparative Production Examples 1 and 2.

It may be thought that in the material of the present invention, unlike in Comparative Compound C5, a group linked to a triazine skeleton is not an aryl group, but a fused ring including a 5-membered ring (that contains sulfur or oxygen) and a benzene ring so that the electron affinity of the entire compound molecule is deepened, and as a result, the lifetime is improved. The smaller the absolute value of the actually measured electron affinity Af, the more significantly the lifetime of the device is reduced, which meets the result of the electron affinity calculated by software on the basis of a chemical structure.

<Calculation 2 of Af Value of Compound>

The electron affinity (Af) was calculated on Compounds 1, 2, and 4 to 10 in which the benzothiophene skeleton or the benzofuran skeleton is changed to a benzene ring, by using the above-described quantum chemical calculation program. The results are noted in Table 3 together with the calculated values of Af of Compounds 1, 2, and 4 to 10.

TABLE 3

| Compound Name | Calculated Af [eV] | Calculated Af of Corresponding Comparative Compound [eV] |
|---|---|---|
| Compound 1 | 2.04 | 1.80 |
| Compound 2 | 2.00 | 1.80 |
| Compound 4 | 2.05 | 1.82 |
| Compound 5 | 2.04 | 1.90 |
| Compound 6 | 2.04 | 1.89 |
| Compound 7 | 2.00 | 1.90 |
| Compound 8 | 2.05 | 1.86 |
| Compound 9 | 2.13 | 1.94 |
| Compound 10 | 2.07 | 1.82 |

Compound 1 (Reposted)

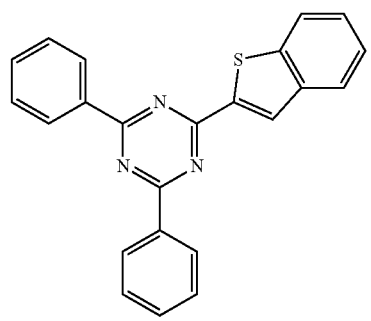

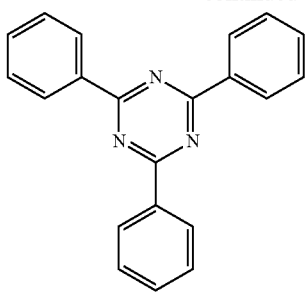
Corresponding Comparative Compound
Compound 2 (Reposted)
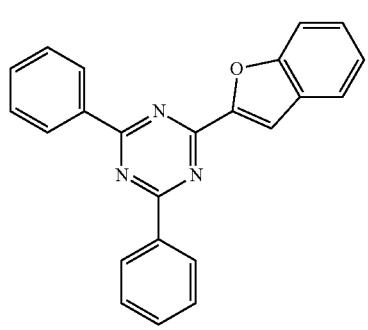
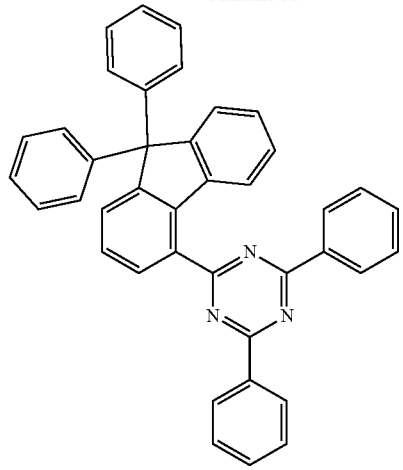
Corresponding Comparative Compound
Compound 5 (Reposted)
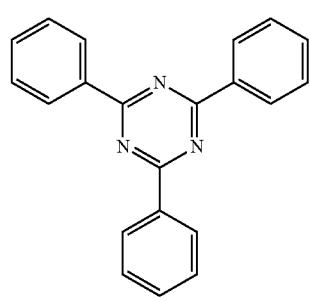
Corresponding Comparative Compound
Compound 4 (Reposted)
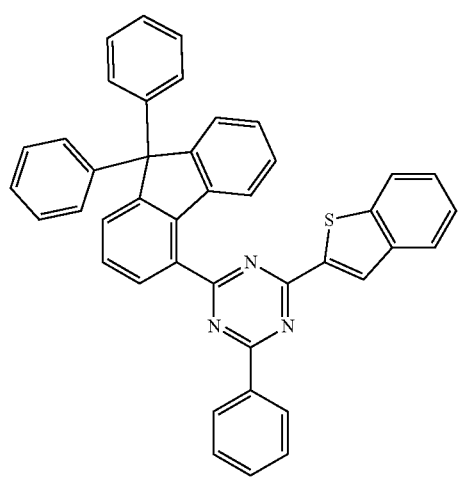
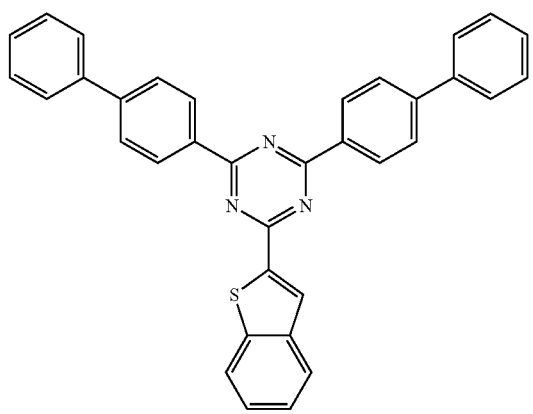
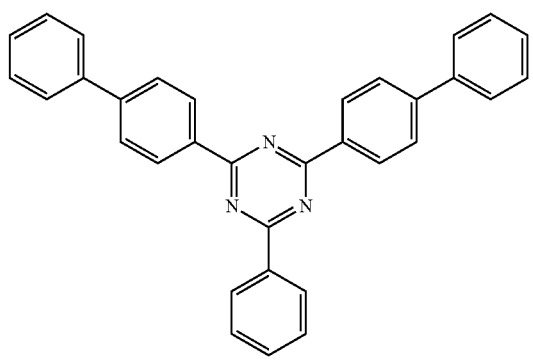
Corresponding Comparative Compound Compound 6 (Reposted)
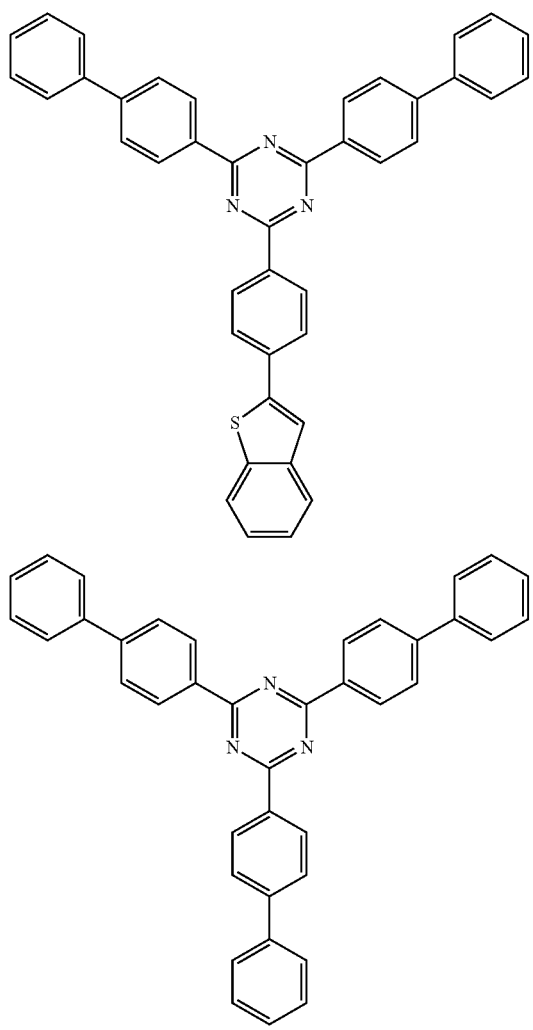
Corresponding Comparative Compound
Compound 7 (Reposted)
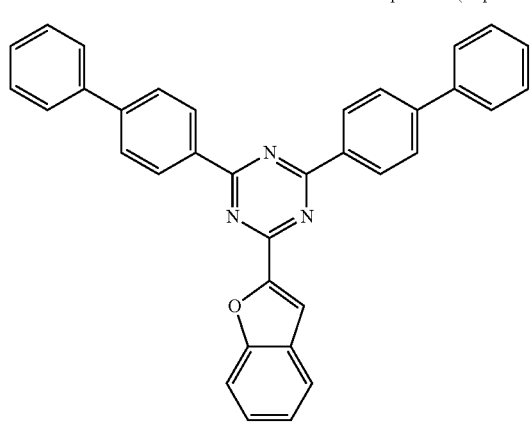
Corresponding Comparative Compound
Compound 8 (Reposted)
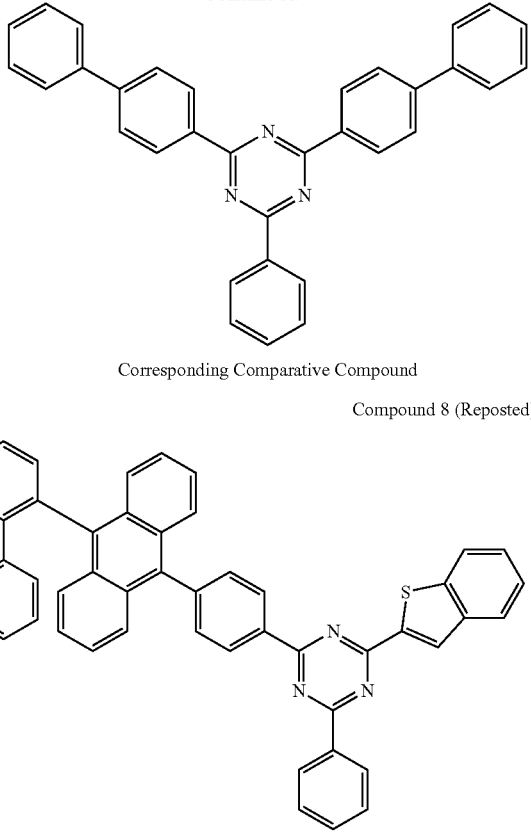
Corresponding Comparative Compound
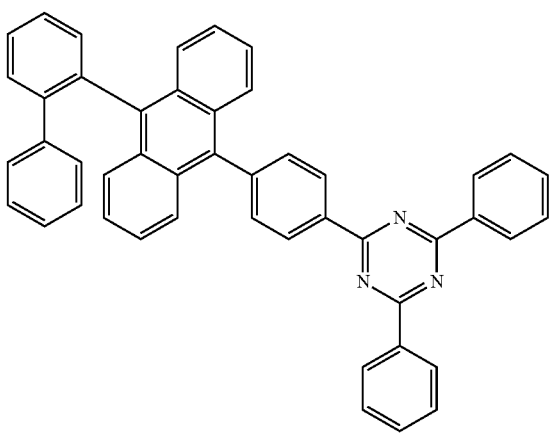

Compound 9 (Reposted)

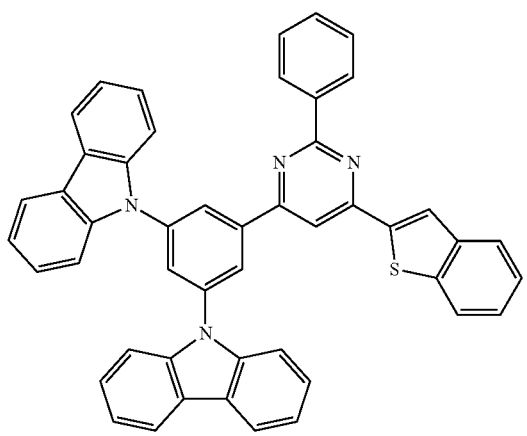

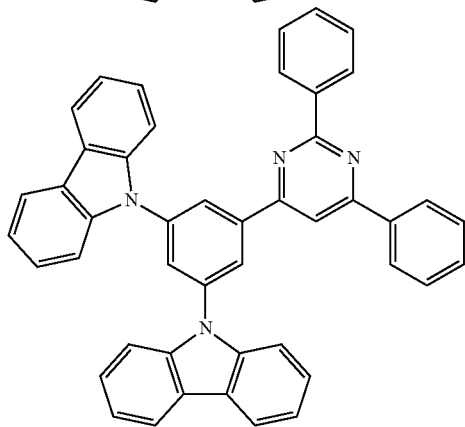

Corresponding Comparative Compound

Compound 10 (Reposted)

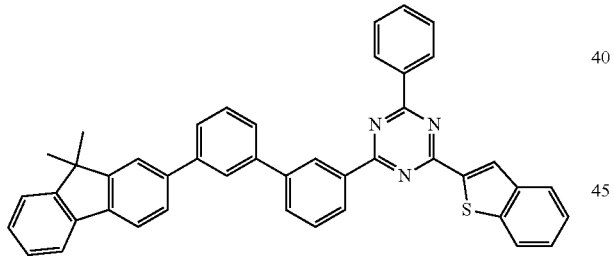

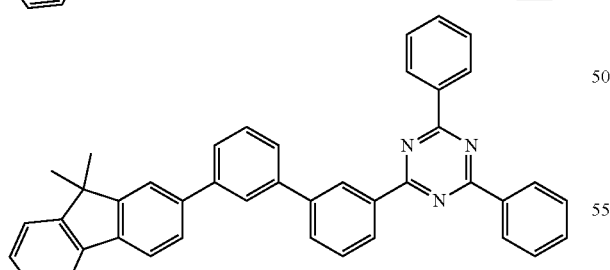

Corresponding Comparative Compound

As is clear from Table 3, it can be found that in all compounds, a compound having a benzothiophene skeleton or a benzofuran skeleton has a deeper electron affinity of the entire compound by 0.1 eV or more (an absolute value is increased) than a compound having a benzene ring at the same position.

REFERENCE SIGNS LIST

1,11: organic EL device
2: substrate
3: anode
4: cathode
5: light emitting layer
6: hole transporting zone (hole transporting layer)
6a: first hole transporting layer
6b: second hole transporting layer
7: electron transporting zone (electron transporting layer)
7a: first electron transporting layer
7b: second electron transporting layer
10, 20: light emitting unit

The invention claimed is:

1. A compound selected from the group consisting of:

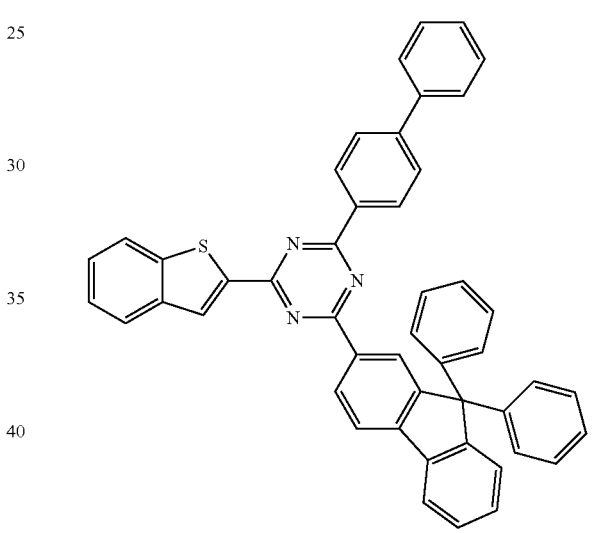

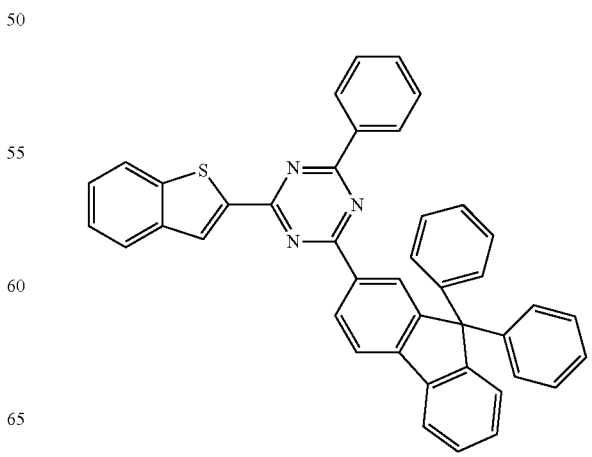

391
-continued
392
-continued
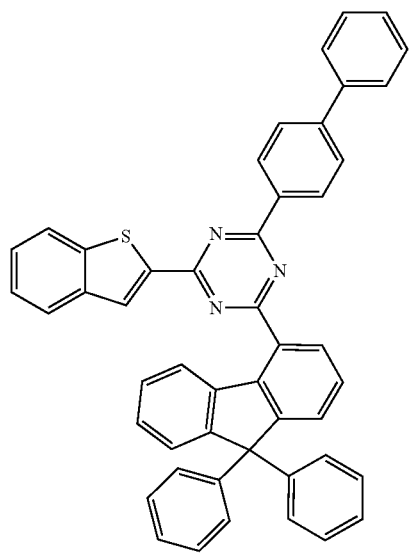
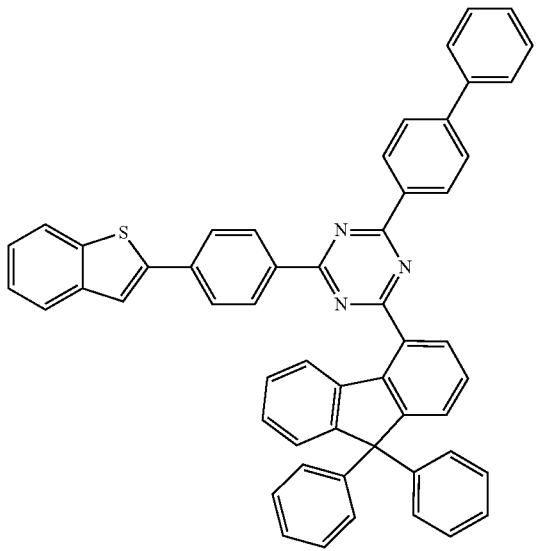
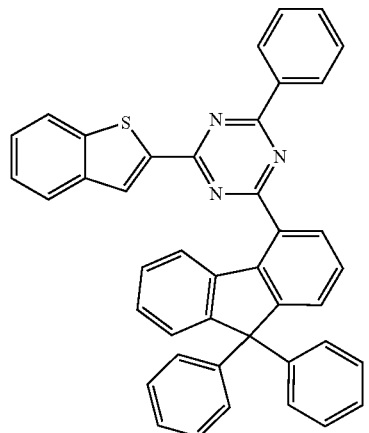
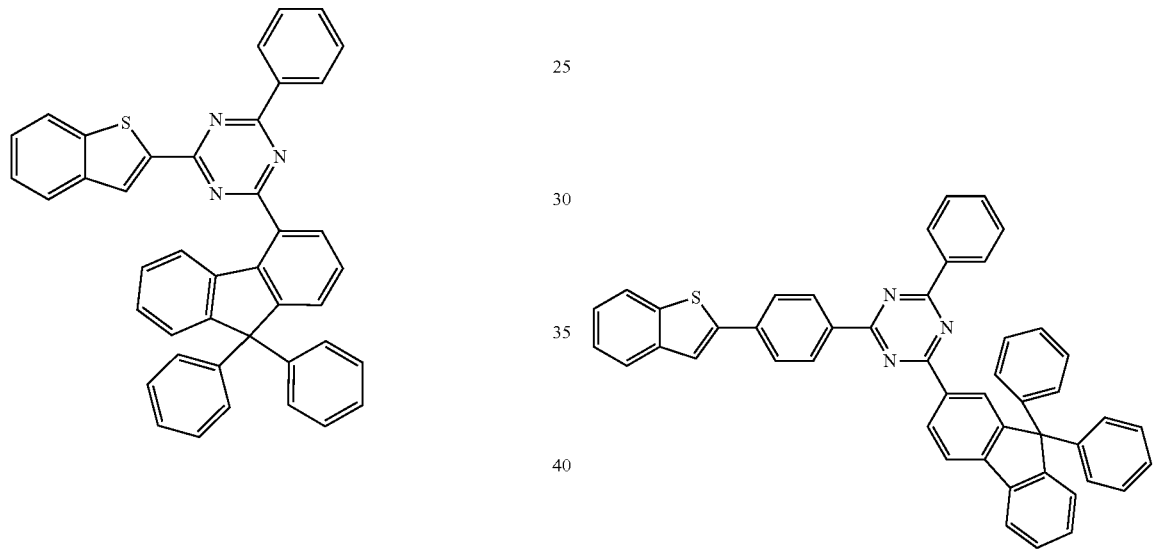
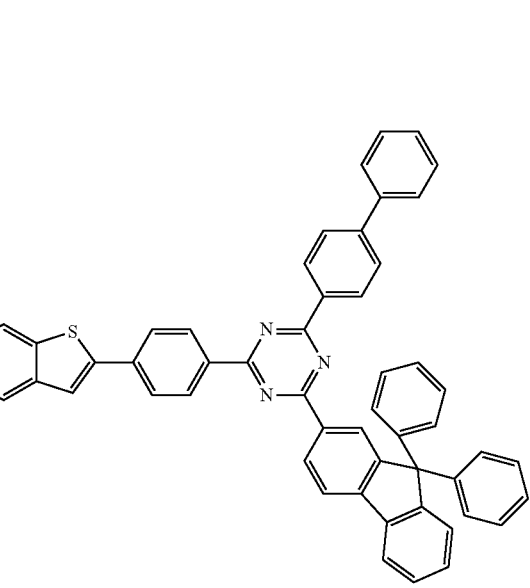
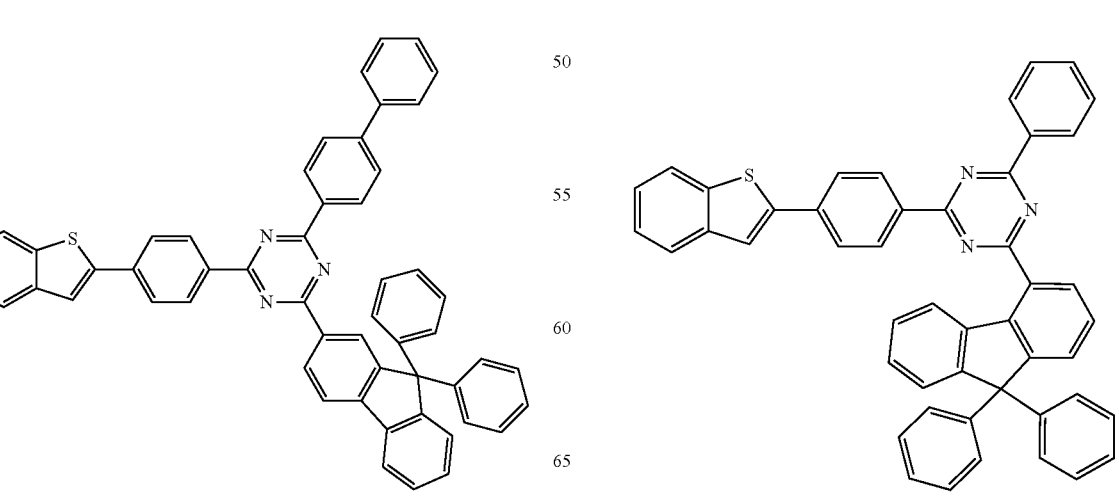

393
-continued
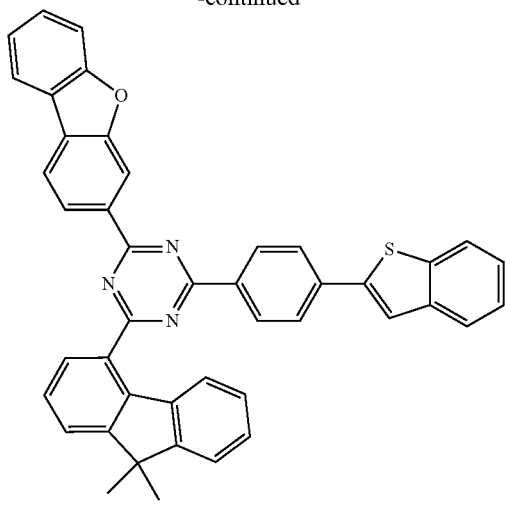
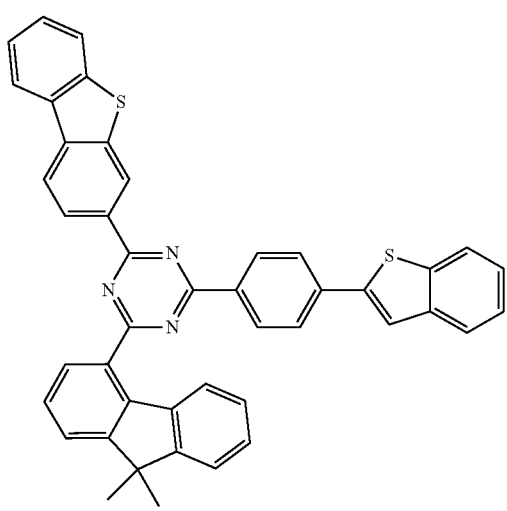
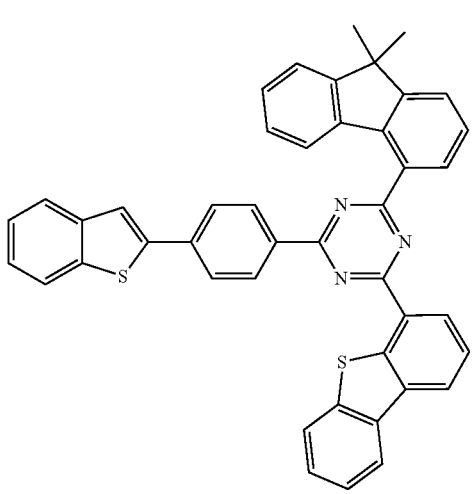
394
-continued
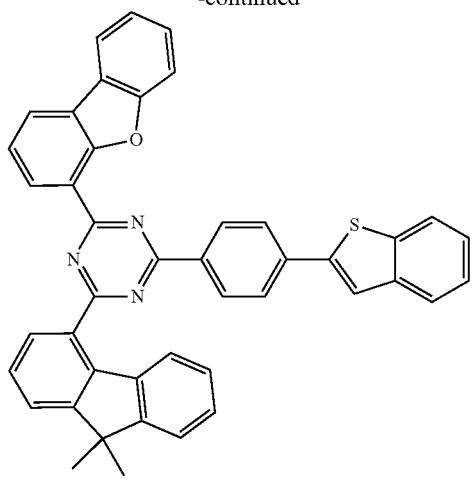
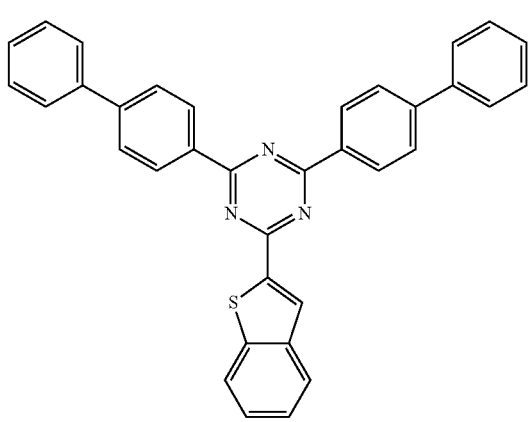
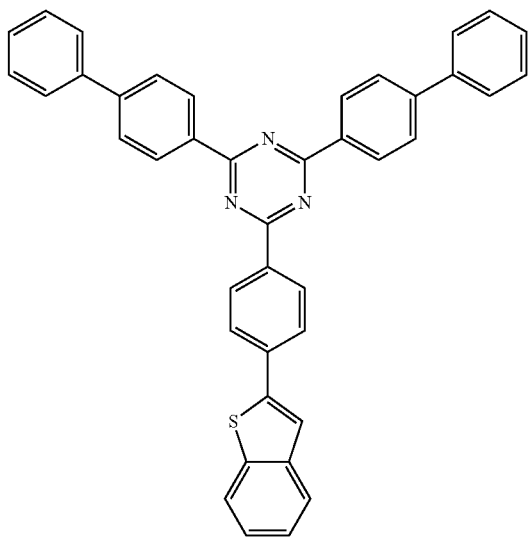

-continued
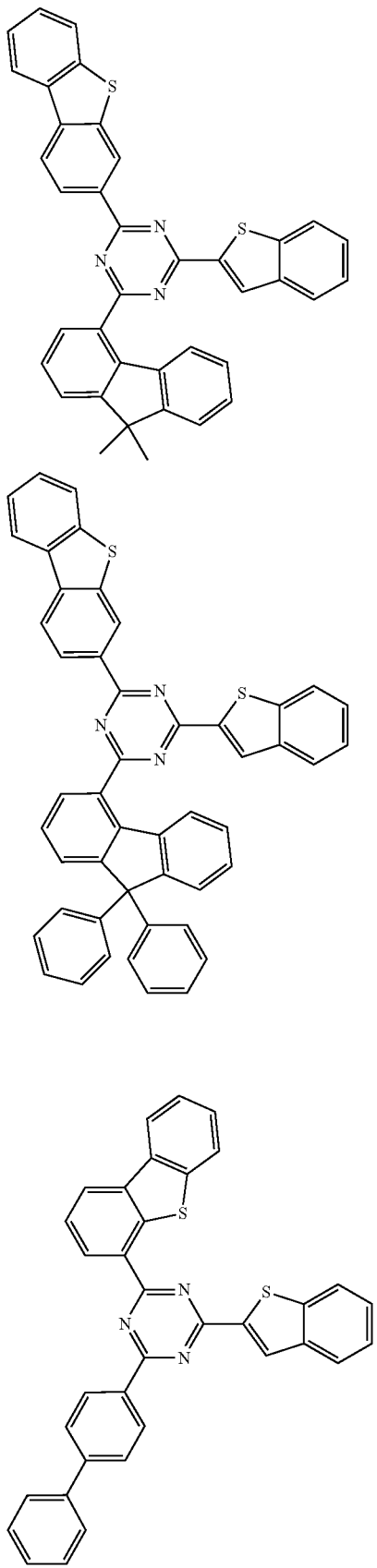
2. A compound selected from the group consisting of:
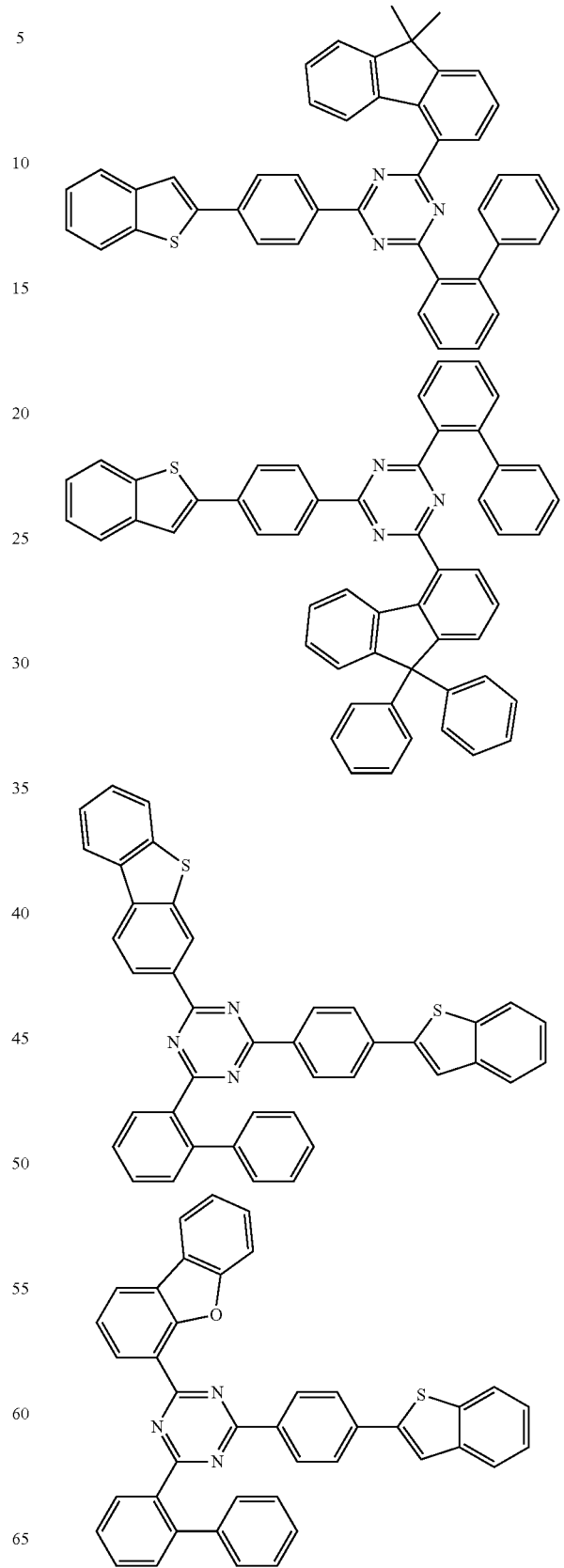

397
-continued
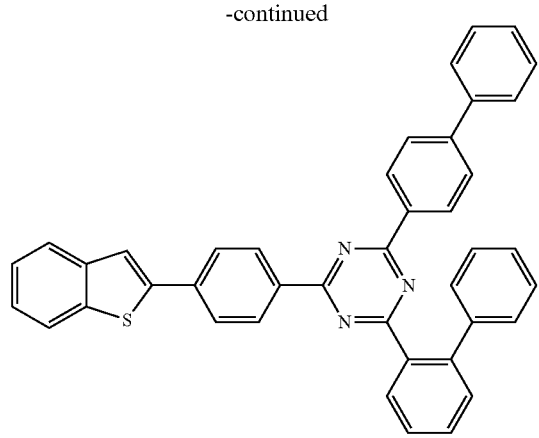
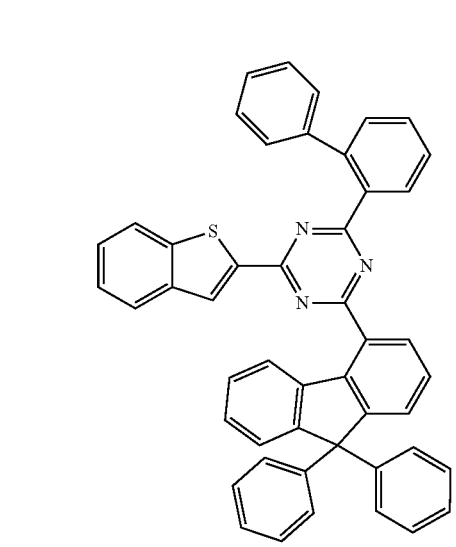
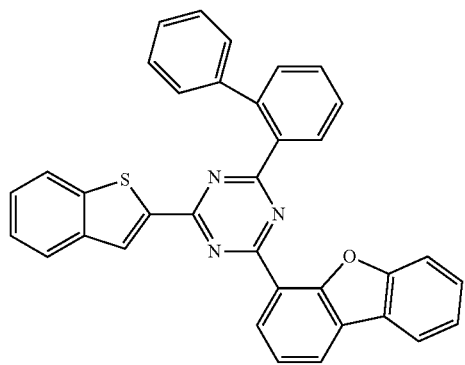
398
-continued
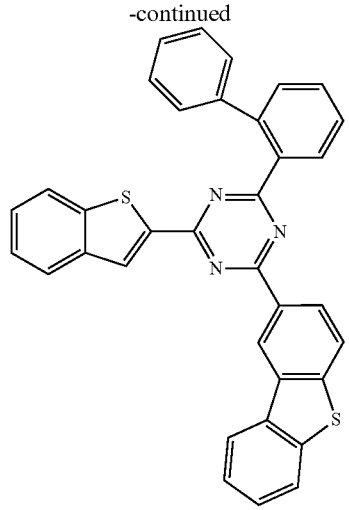
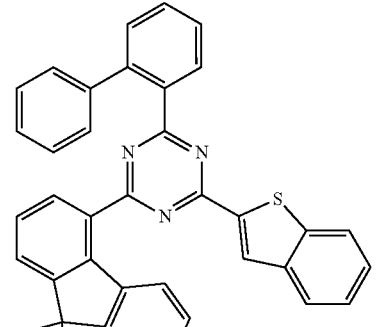
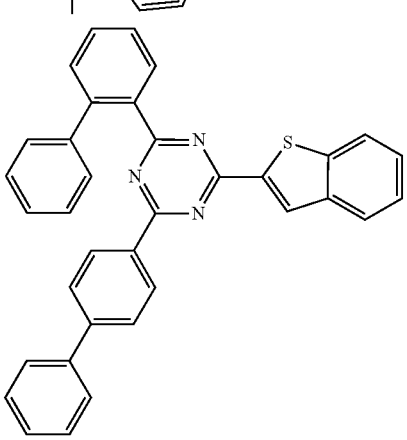
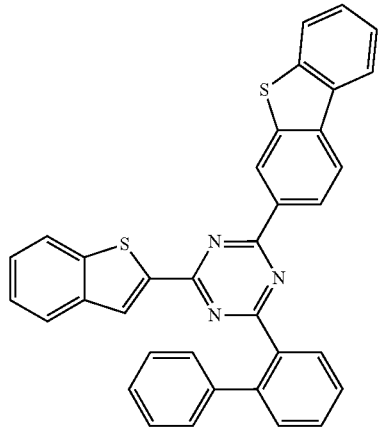

3. A compound selected from the group consisting of:

-continued

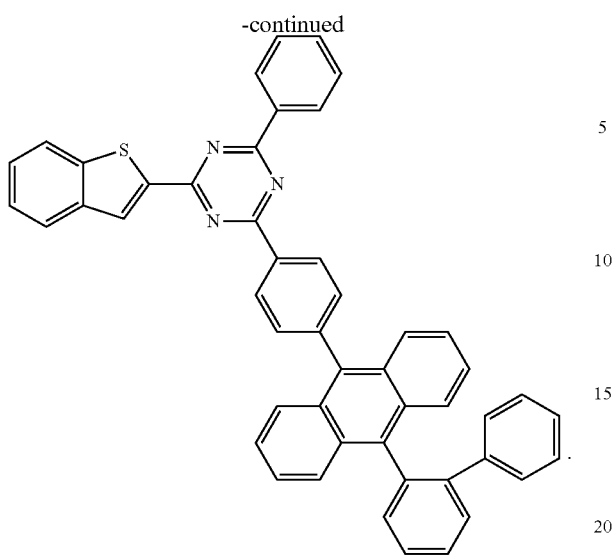

4. A material, comprising:
the compound of claim 1,
wherein the material is suitable for an organic electroluminescent element.

5. An organic electroluminescent element, comprising:
an anode;
a cathode; and
organic layers between the anode and the cathode,
wherein the organic layers comprise a light emitting layer, and
at least one layer in the organic layers comprises the compound of claim 1.

6. The organic electroluminescent element of claim 5, comprising an electron transporting zone between the cathode and the light emitting layer,
wherein the electron transporting zone comprises the compound.

7. The organic electroluminescent element of claim 6, wherein the electron transporting zone further comprises one or more selected from the group consisting of an alkali metal, an alkaline earth metal, a rare earth metal, oxide of the alkali metal, an alkali metal halide, oxide of the alkaline earth metal, an alkaline earth metal halide, oxide of the rare earth metal, a rare earth metal halide, an organic complex comprising the alkali metal, an organic complex comprising the alkaline earth metal, and an organic complex containing the rare earth metal.

8. The organic electroluminescent element of claim 6, wherein the electron transporting zone comprises a first electron transporting layer and a second electron transporting layer, and either or both of the first electron transporting layer and the second electron transporting layer comprise the compound.

9. An electronic device, comprising:
the organic electroluminescent element of claim 5.

10. An organic electroluminescent element, comprising:
an anode;
a cathode; and
organic layers between the anode and the cathode,
wherein the organic layers comprise a light emitting layer, and
at least one layer in the organic layers comprises the compound of claim 2.

11. An organic electroluminescent element, comprising:
an anode;
a cathode; and
organic layers between the anode and the cathode,
wherein the organic layers comprise a light emitting layer, and
at least one layer in the organic layers comprises the compound of claim 3.

12. The compound of claim 1, which is:

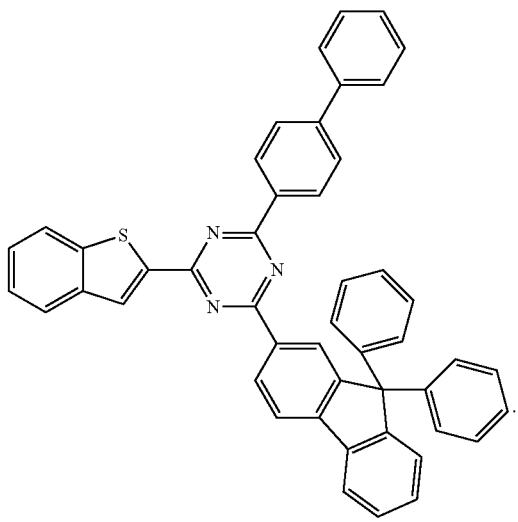 [SMILES: c1ccc(-c2ccc(-c3nc(-c4ccc5c(c4)C(c4ccccc4)(c4ccccc4)c4ccccc4-5)nc(-c4cc5ccccc5s4)n3)cc2)cc1]

13. The compound of claim 1, which is:

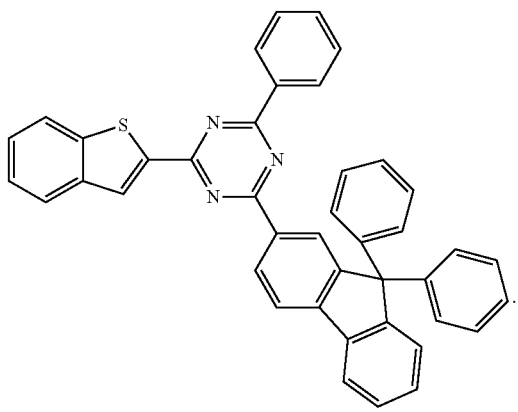 [SMILES: c1ccc(-c2nc(-c3ccc4c(c3)C(c3ccccc3)(c3ccccc3)c3ccccc3-4)nc(-c3cc4ccccc4s3)n2)cc1]

14. The compound of claim 1, which is:
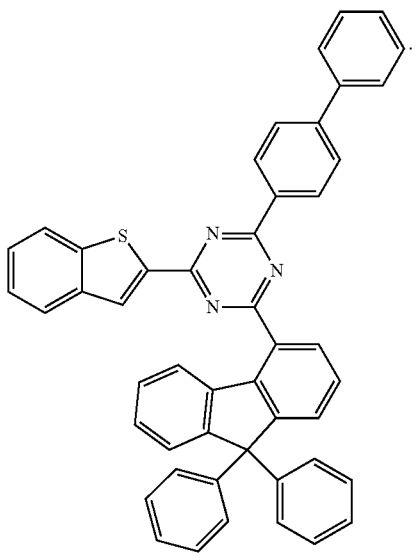 [SMILES: c1ccc(-c2ccc(-c3nc(-c4cc5ccccc5s4)nc(-c4cccc5c4-c4ccccc4C5(c4ccccc4)c4ccccc4)n3)cc2)cc1]
15. The compound of claim 1, which is:
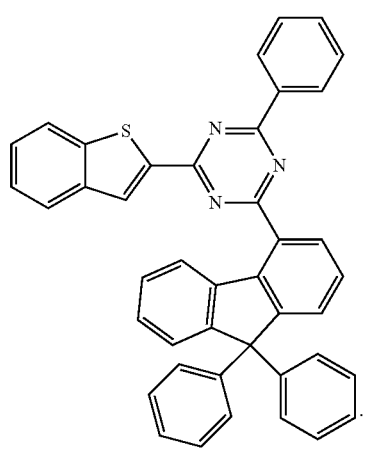 [SMILES: c1ccc(-c2nc(-c3cc4ccccc4s3)nc(-c3cccc4c3-c3ccccc3C4(c3ccccc3)c3ccccc3)n2)cc1]
16. The compound of claim 1, which is:
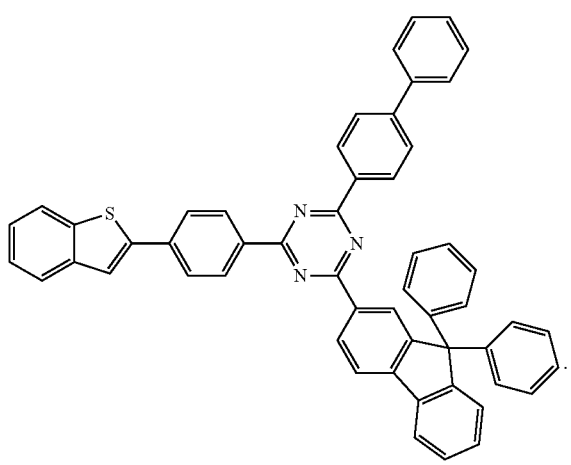 [SMILES: c1ccc(-c2ccc(-c3nc(-c4ccc(-c5cc6ccccc6s5)cc4)nc(-c4ccc5c(c4)C(c4ccccc4)(c4ccccc4)c4ccccc4-5)n3)cc2)cc1]
17. The compound of claim 1, which is:
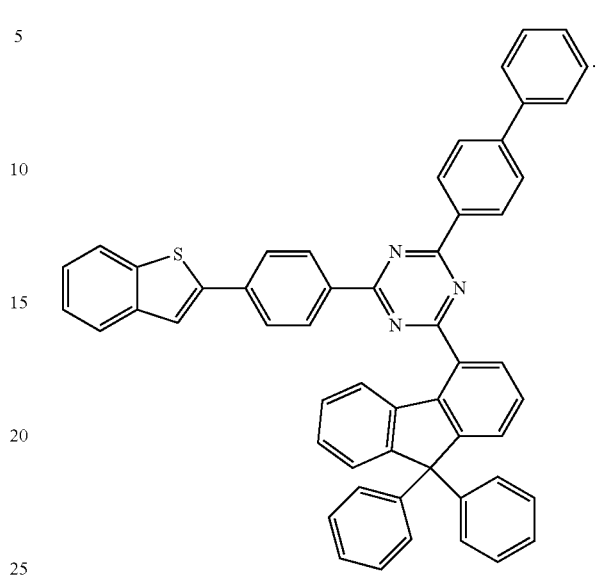
18. The compound of claim 1, which is:
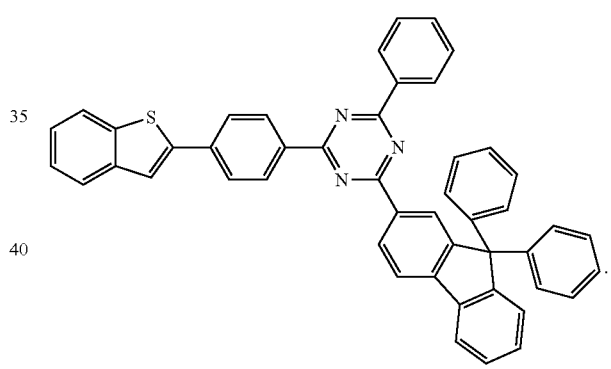
19. The compound of claim 1, which is:
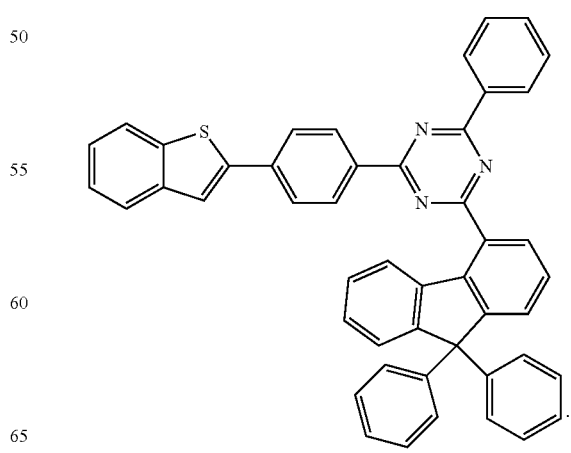

20. The compound of claim 1, which is:
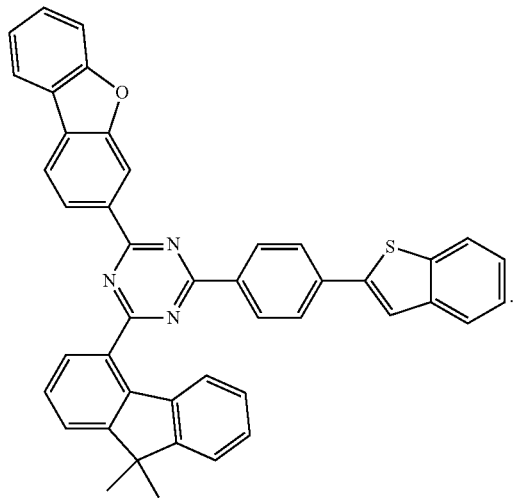 [SMILES: CC1(C)c2ccccc2-c2c(-c3nc(-c4ccc(-c5cc6ccccc6s5)cc4)nc(-c4ccc5c(c4)oc4ccccc45)n3)cccc21]
21. The compound of claim 1, which is:
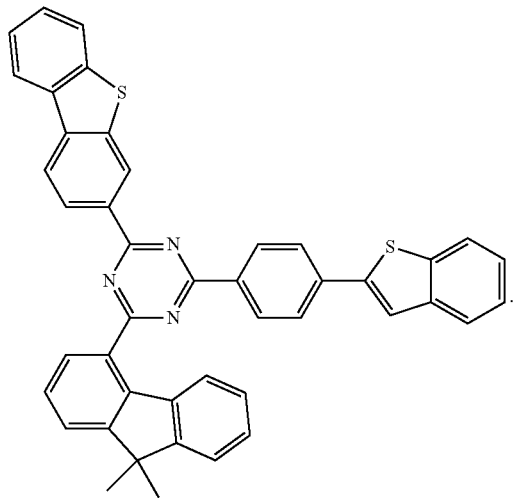 [SMILES: CC1(C)c2ccccc2-c2c(-c3nc(-c4ccc(-c5cc6ccccc6s5)cc4)nc(-c4ccc5c(c4)sc4ccccc45)n3)cccc21]
22. The compound of claim 1, which is:
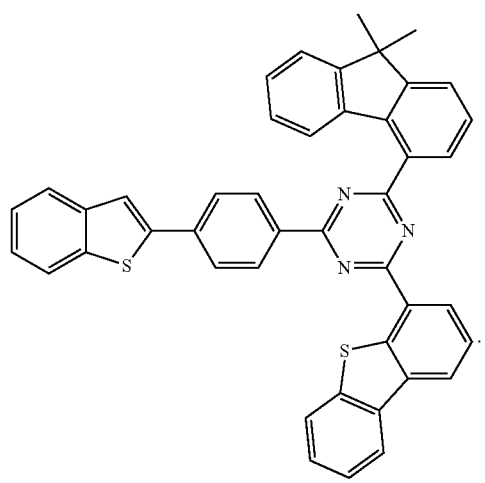 [SMILES: CC1(C)c2ccccc2-c2c(-c3nc(-c4ccc(-c5cc6ccccc6s5)cc4)nc(-c4cccc5c4sc4ccccc45)n3)cccc21]
23. The compound of claim 1, which is:
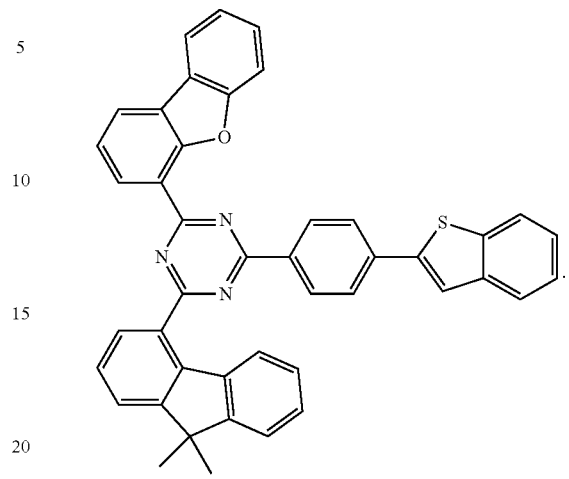
24. The compound of claim 1, which is:
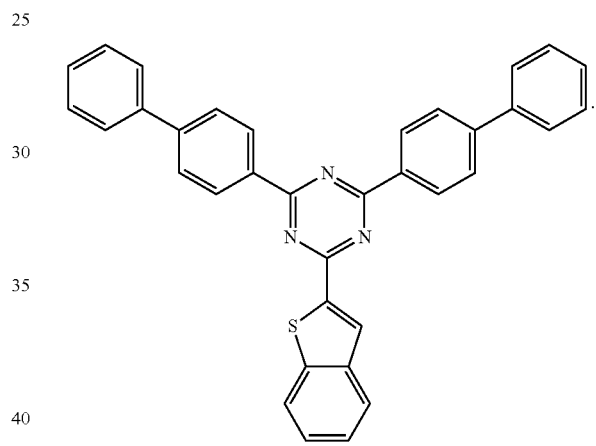
25. The compound of claim 1, which is:
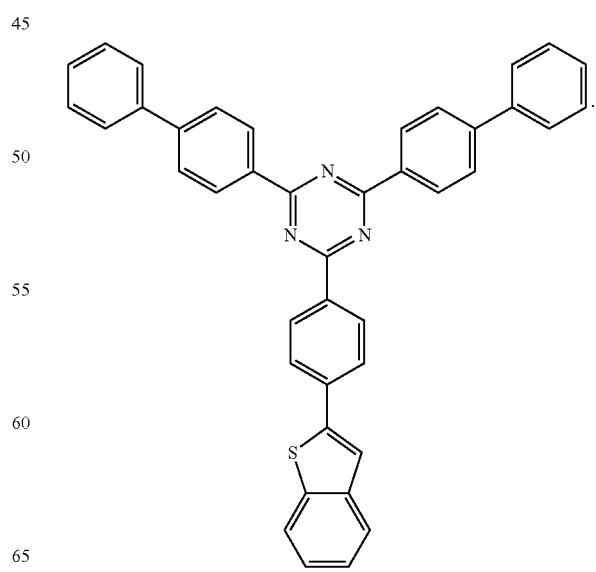

26. The compound of claim 1, which is:
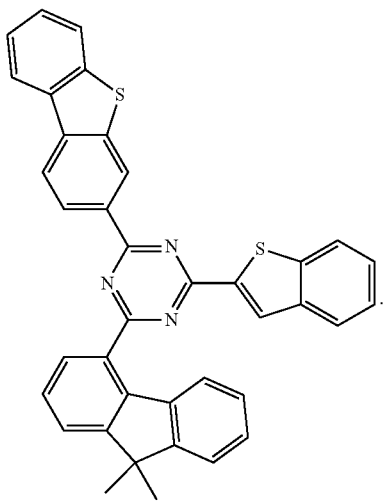 [SMILES: CC1(C)c2ccccc2-c2c(-c3nc(-c4ccc5c(c4)sc4ccccc45)nc(-c4cc5ccccc5s4)n3)cccc21]
27. The compound of claim 1, which is:
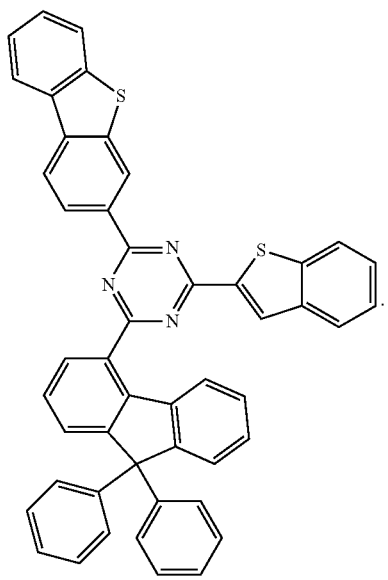 [SMILES: c1ccc(C2(c3ccccc3)c3ccccc3-c3c(-c4nc(-c5ccc6c(c5)sc5ccccc56)nc(-c5cc6ccccc6s5)n4)cccc32)cc1]
28. The compound of claim 1, which is:
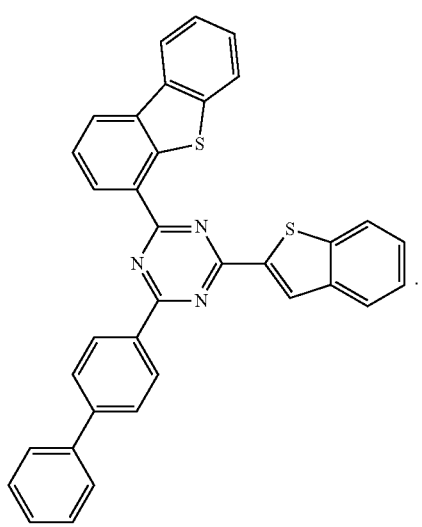 [SMILES: c1ccc(-c2ccc(-c3nc(-c4cc5ccccc5s4)nc(-c4cccc5c4sc4ccccc45)n3)cc2)cc1]
29. The compound of claim 2, which is:
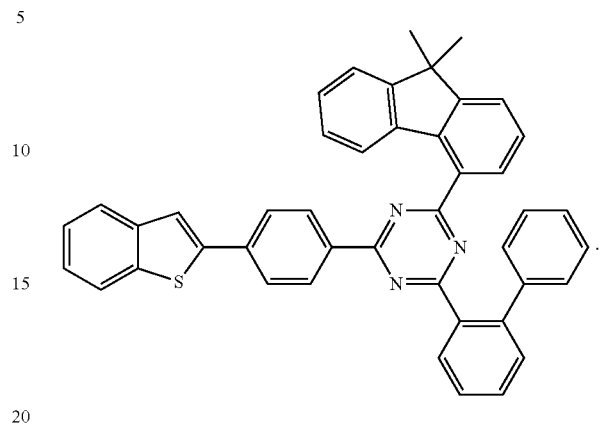
30. The compound of claim 2, which is:
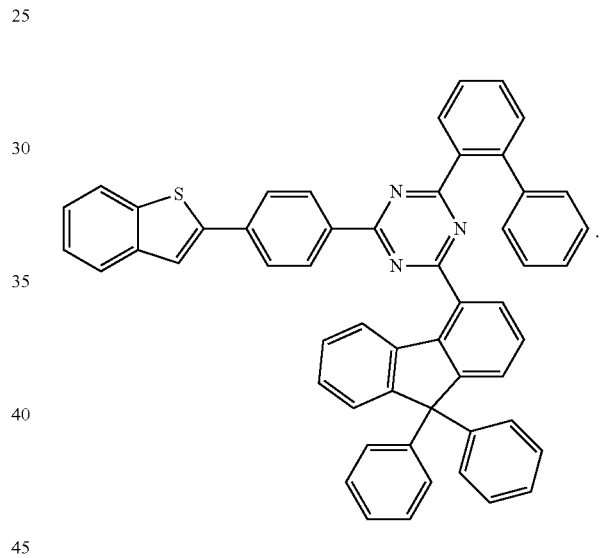
31. The compound of claim 2, which is:
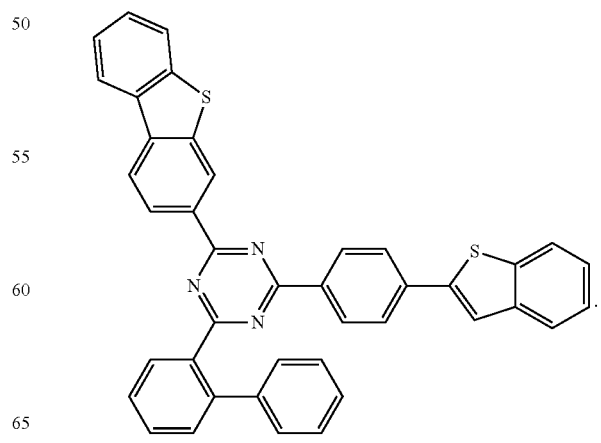

32. The compound of claim 2, which is:
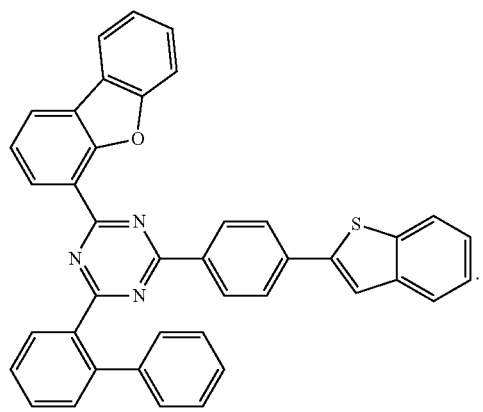 [SMILES: c1ccc(-c2ccccc2-c2nc(-c3ccc(-c4cc5ccccc5s4)cc3)nc(-c3cccc4c3oc3ccccc34)n2)cc1]
33. The compound of claim 2, which is:
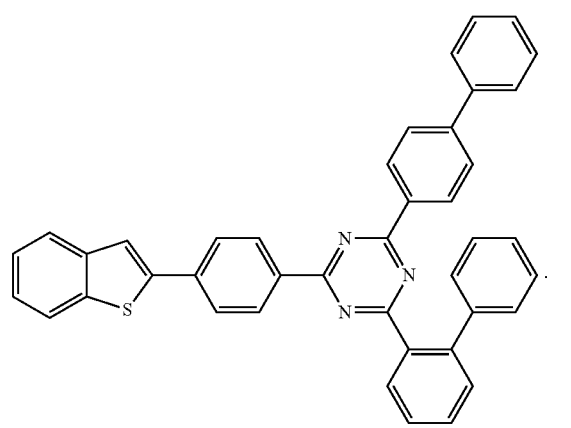 [SMILES: c1ccc(-c2ccc(-c3nc(-c4ccc(-c5cc6ccccc6s5)cc4)nc(-c4ccccc4-c4ccccc4)n3)cc2)cc1]
34. The compound of claim 2, which is:
35. The compound of claim 2, which is:
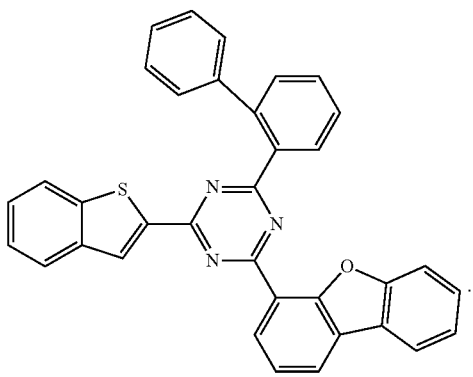 [SMILES: c1ccc(-c2ccccc2-c2nc(-c3cc4ccccc4s3)nc(-c3cccc4c3oc3ccccc34)n2)cc1]
36. The compound of claim 2, which is:
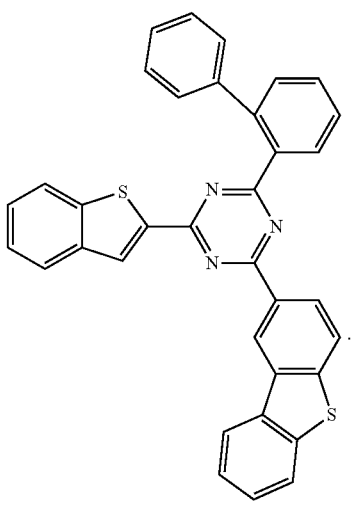 [SMILES: c1ccc(-c2ccccc2-c2nc(-c3ccc4sc5ccccc5c4c3)nc(-c3cc4ccccc4s3)n2)cc1]
37. The compound of claim 2, which is:
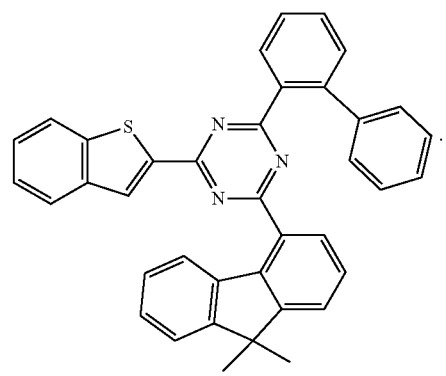 [SMILES: CC1(C)c2ccccc2-c2c(-c3nc(-c4cc5ccccc5s4)nc(-c4ccccc4-c4ccccc4)n3)cccc21]

38. The compound of claim 2, which is:
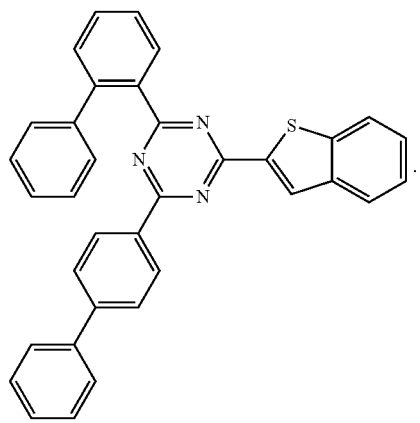 [SMILES: c1ccc(-c2ccc(-c3nc(-c4cc5ccccc5s4)nc(-c4ccccc4-c4ccccc4)n3)cc2)cc1]
39. The compound of claim 2, which is:
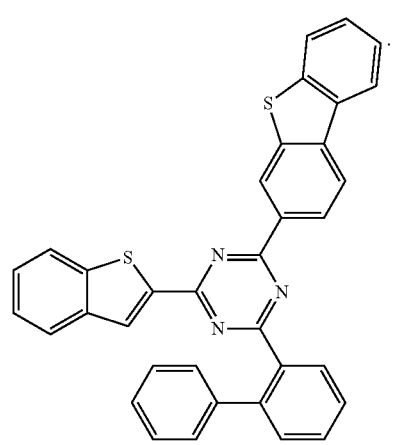 [SMILES: c1ccc(-c2ccccc2-c2nc(-c3ccc4c(c3)sc3ccccc34)nc(-c3cc4ccccc4s3)n2)cc1]
40. The compound of claim 2, which is:
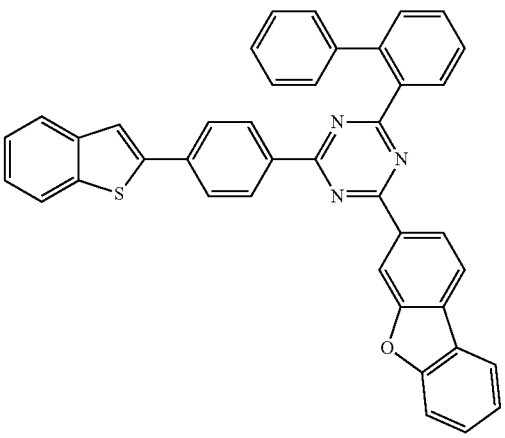
41. The compound of claim 2, which is:
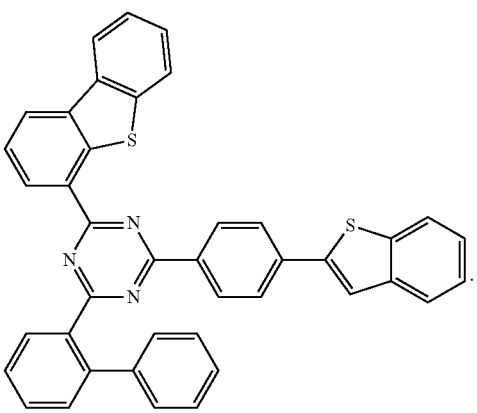 [SMILES: c1ccc(-c2ccccc2-c2nc(-c3ccc(-c4cc5ccccc5s4)cc3)nc(-c3cccc4c3sc3ccccc34)n2)cc1]
* * * * *